US011028407B2

(12) United States Patent
Lu et al.

(10) Patent No.: US 11,028,407 B2
(45) Date of Patent: Jun. 8, 2021

(54) INSECTICIDAL COMBINATIONS OF POLYPEPTIDES HAVING IMPROVED ACTIVITY SPECTRUM AND USES THEREOF

(71) Applicants: PIONEER HI-BRED INTERNATIONAL, INC., Johnston, IA (US); E. I. DU PONT DE NEMOURS AND COMPANY, Wilmington, DE (US)

(72) Inventors: Albert L Lu, West Des Moines, IA (US); Gusui Wu, Foster City, CA (US)

(73) Assignees: PIONEER HI-BRED INTERNATIONAL, INC.; E. I. DU PONT DE NEMOURS AND COMPANY

( * ) Notice: Subject to any disclaimer, the term of this patent is extended or adjusted under 35 U.S.C. 154(b) by 0 days.

(21) Appl. No.: 16/092,341

(22) PCT Filed: Apr. 19, 2017

(86) PCT No.: PCT/US2017/028258

§ 371 (c)(1),
(2) Date: Oct. 9, 2018

(87) PCT Pub. No.: WO2017/184673

PCT Pub. Date: Oct. 26, 2017

(65) Prior Publication Data

US 2020/0140882 A1 May 7, 2020

Related U.S. Application Data

(60) Provisional application No. 62/324,652, filed on Apr. 19, 2016.

(51) Int. Cl.
*C12N 15/82* (2006.01)
*C07K 14/325* (2006.01)

(52) U.S. Cl.
CPC ........ *C12N 15/8286* (2013.01); *C07K 14/325* (2013.01); *Y02A 40/146* (2018.01)

(58) Field of Classification Search
None
See application file for complete search history.

(56) References Cited

U.S. PATENT DOCUMENTS

2016/0347799 A1* 12/2016 Barry ..................... A01N 37/46
2017/0166921 A1* 6/2017 Barry ................... C07K 14/415
2017/0226164 A1 8/2017 Izumi Wilcoxon et al.

FOREIGN PATENT DOCUMENTS

WO 2015120270 A1 8/2015
WO 2015120276 A1 8/2015
WO WO 2015/120270 A1 * 8/2015
WO WO 2015/120276 A1 * 8/2015

OTHER PUBLICATIONS

Pardo-Lopez et al. (2009) Peptides 30:589-595.*
Abdul-Rauf & Ellar (1999) Curr Microbiol 39:94-98.*
Wagner, Lucena et al: "Molecular Approaches to Improve the Insecticidal Activity of Bacillus Thuringiensis Cry Toxins", Toxins, Aug. 2004 (Aug. 13, 2014), vol. 6, No. 8, pp. 2393-2423.
Deguchi et al: "Mycoplasma Genitalium: Another Important Pathogen of Nongonococcal Urethritis", Journal of Urology, Mar. 1, 2002 (Mar. 1, 2002), vol. 167, No. 3, pp. 1210-1217.
International Search Report and Written Opinion, International Application No. PCT/US2017/028258 dated Aug. 23, 2017.

* cited by examiner

*Primary Examiner* — Russell T Boggs

(57) ABSTRACT

The disclosure provides nucleic acids, and variants and fragments thereof, derived from strains of *Bacillus thuringiensis* encoding variant polypeptides having increased pesticidal activity against insect pests, including Lepidoptera and Coleopteran. Particular embodiments of the disclosure provide isolated nucleic acids encoding pesticidal proteins, pesticidal compositions, DNA constructs, and transformed microorganisms and plants comprising a nucleic acid of the embodiments. These compositions find use in methods for controlling pests, especially plant pests.

10 Claims, 17 Drawing Sheets

Specification includes a Sequence Listing.

Fig. 1a

```
                 1                                                50
   Cry1Bd   (1)  MTSNRKNENEIINALSIPAVSNHSAQMDLSLDARIEDSLCIAEGNNINPL
 IP1B-B1    (1)  MPSNRKNENEIIN-----AVSNHSAQMDLSLDARIEDSLCVAEVNNIDPF
    MP258   (1)  M[illegible]SNRKNENEIINALSIPAVSNHSAQMDLSPDARIEDSLCIAEGNNINPL
 IP1B-B21   (1)  MPSNRKNENEIINALSIPAVSNHSAQMDLSLDARIEDSLCIAEGNNINPL
 IP1B-B22   (1)  MPSNRKNENGIINALSIPAVSNHSAQMDLSPDARIEDSLCVAEVNNIDPF
 IP1B-B23   (1)  MPSNRKNENEIIN-----AVSNHSAQMDLSPDARIEDSLCVAEVNNIDPF
 IP1B-B24   (1)  MPSNRKNENEIINALSIPAVSNHSAQMDLSLDARIEDSLCIAEGNNINPL
 IP1B-B25   (1)  MPSNRKNENEIINALSIPAVSNHSAQMDLSLDARIEDSLCIAEGNNINPL
 IP1B-B26   (1)  MPSNRKNENEIINALSIPAVSNHSAQMDLSLDARIEDSLCIAEGNNINPL
 IP1B-B27   (1)  MPSNRKNENEIINALSIPAVSNHSAQMDLSLDARIEDSLCIAEGNNINPL
 IP1B-B28   (1)  MPSNRKNENEIINALSIPAVSNHSAQMDLSLDARIEDSLCIAEGNNINPL
 IP1B-B29   (1)  MPSNRKNENEIINALSIPAVSNHSAQMDLSLDARIEDSLCIAEGNNINPL
 IP1B-B40   (1)  MPSNRKNENEIINALSIPAVSNHSAQMDLSLDARIEDSLCIAEGNNINPL
 IP1B-B41   (1)  MPSNRKNENEIINALSIPAVSNHSAQMDLSLDARIEDSLCIAEGNNINPL
 IP1B-B42   (1)  MPSNRKNENEIINALSIPAVSNHSAQMDLSLDARIEDSLCIAEGNNINPL
 IP1B-B43   (1)  MPSNRKNENEIINALSIPAVSNHSAQMDLSLDARIEDSLCIAEGNNINPL
 IP1B-B44   (1)  MPSNRKNENEIINALSIPAVSNHSAQMDLSLDARIEDSLCIAEGNNINPL
 IP1B-B45   (1)  MPSNRKNENEIINALSIPAVSNHSAQMDLSLDARIEDSLCIAEGNNINPL
 IP1B-B46   (1)  MPSNRKNENEIINALSIPAVSNHSAQMDLSLDARIEDSLCIAEGNNINPL
 IP1B-B47   (1)  MPSNRKNENEIINALSIPAVSNHSAQMDLSLDARIEDSLCIAEGNNINPL
 IP1B-B31   (1)  MPSNRKNENEIIN-----AVSNHSAQMDLSLDARIEDSLCVAEVNNIDPF
 IP1B-B32   (1)  MPSNRKNENEIIN-----AVSNHSAQMDLSLDARIEDSLCVAEVNNIDPF
 IP1B-B33   (1)  MPSNRKNENEIIN-----AVSNHSAQMDLSLDARIEDSLCVAEVNNIDPF
 IP1B-B34   (1)  MPSNRKNENEIIN-----AVSNHSAQMDLSLDARIEDSLCVAEVNNIDPF
    GS060   (1)  MPSNRKNENEIINALSIPAVSNHSAQMDLSPDARIEDSLCVAEGNNIDPF

                 51                                               100
   Cry1Bd  (51)  VSASTVQTGINIAGRILGVLGVPFAGQLASFYSFLVGELWPSGRDPWEIF
 IP1B-B1   (46)  VSASTVQTGISIAGRILGVLGVPFAGQLASFYSFLVGELWPSGRDPWEIF
    MP258  (51)  VSASTVQTGINIAGRILGVLGVPFAGQLASFYSFIVGELWPSGRDPWEIF
 IP1B-B21  (51)  VSASTVQTGINIAGRILGVLGVPFAGQLASFYSFIVGELWPSGRDPWEIF
 IP1B-B22  (51)  VSASTVQTGINIAGRILGVLGVPFAGQLASFYSFIVGELWPSGRDPWEIF
 IP1B-B23  (46)  VSASTVQTGINIAGRILGVLGVPFAGQLASFYSFLVGELWPSGRDPWEIF
 IP1B-B24  (51)  VSASTVQTGINIAGRILGVLGVPFAGQLASFYSFIVGELWPSGRDPWEIF
 IP1B-B25  (51)  VSASTVQTGINIAGRILGVLGVPFAGQLASFYSFIVGELWPSGRDPWEIF
 IP1B-B26  (51)  VSASTVQTGINIAGRILGVLGVPFAGQLASFYSFIVGELWPSGRDPWEIF
 IP1B-B27  (51)  VSASTVQTGINIAGRILGVLGVPFAGQLASFYSFIVGELWPSGRDPWEIF
 IP1B-B28  (51)  VSASTVQTGINIAGRILGVLGVPFAGQLASFYSFIVGELWPSGRDPWEIF
 IP1B-B29  (51)  VSASTVQTGINIAGRILGVLGVPFAGQLASFYSFIVGELWPSGRDPWEIF
 IP1B-B40  (51)  VSASTVQTGINIAGRILGVLGVPFAGQLASFYSFIVGELWPSGRDPWEIF
 IP1B-B41  (51)  VSASTVQTGINIAGRILGVLGVPFAGQLASFYSFIVGELWPSGRDPWEIF
 IP1B-B42  (51)  VSASTVQTGINIAGRILGVLGVPFAGQLASFYSFIVGELWPSGRDPWEIF
 IP1B-B43  (51)  VSASTVQTGINIAGRILGVLGVPFAGQLASFYSFIVGELWPSGRDPWEIF
 IP1B-B44  (51)  VSASTVQTGINIAGRILGVLGVPFAGQLASFYSFIVGELWPSGRDPWEIF
 IP1B-B45  (51)  VSASTVQTGINIAGRILGVLGVPFAGQLASFYSFIVGELWPSGRDPWEIF
 IP1B-B46  (51)  VSASTVQTGINIAGRILGVLGVPFAGQLASFYSFIVGELWPSGRDPWEIF
 IP1B-B47  (51)  VSASTVQTGINIAGRILGVLGVPFAGQLASFYSFIVGELWPSGRDPWEIF
 IP1B-B31  (46)  VSASTVQTGISIAGRILGVLGVPFAGQLASFYSFLVGELWPSGRDPWEIF
 IP1B-B32  (46)  VSASTVQTGISIAGRILGVLGVPFAGQLASFYSFLVGELWPSGRDPWEIF
 IP1B-B33  (46)  VSASTVQTGINIAGRILGVLGVPFAGQLASFYSFLVGELWPSGRDPWEIF
 IP1B-B34  (46)  VSASTVQTGISIAGRILGVLGVPFAGQLASFYSFLVGELWPSGRDPWEIF
    GS060  (51)  VSASTVQTGISIAGRILGVLGVPFAGQLASFYSFLVGELWPSGRDPWEIF
```

Fig. 1b

```
                  101                                              150
   Cry1Bd  (101)  LEHVEQLIRQQVTENTRNTAIARLEGLGRGYRSYQQALETWLDNRNDARS
   IP1B-B1  (96)  MEHVEQIVRQQITDSVRDTAIARLEGLGRGYRSYQQALETWLDNRNDARS
    MP258  (101)  LEHVEQLVRQQITENARNTALARLQGLGASFRAYQQSLEDWLENRDDART
 IP1B-B21  (101)  MEHVEQLVRQQITENARNTALARLQGLGASFRAYQQSLEDWLENRDNART
 IP1B-B22  (101)  LEHVEQLVRQQITENARNTALARLQGLGASFRAYQQSLEDWLENRDDART
 IP1B-B23   (96)  MEHVEQIVRQQITENARNTALARLQGLGASFRAYQQSLEDWLENRDDART
 IP1B-B24  (101)  MEHVEQLVRQQITENARNTALARLQGLGASFRAYQQSLEDWLENRDNART
 IP1B-B25  (101)  MEHVEQLVRQQITENARNTALARLQGLGASFRAYQQSLEDWLENRDNART
 IP1B-B26  (101)  MEHVEQLVRQQITENARNTALARLQGLGASFRAYQQSLEDWLENRDNART
 IP1B-B27  (101)  MEHVEQLVRQAITLNARNTALARLQGLGASFRAYQQSLEDWLENRDNART
 IP1B-B28  (101)  MEHVEQLVRQAITLNARNTALARLQGLGASFRAYQQSLEDWLENRDNART
 IP1B-B29  (101)  MEHVEQLVRQAITLNARNTALARLQGLGASFRAYQQSLEDWLENRDNART
 IP1B-B40  (101)  MEHVEQLVRQHITENARNTALARLQGLGASFRAYQQSLEDWLENRDNART
 IP1B-B41  (101)  MEHVEQLVRQHITENARNTALARLQGLGASFRAYQQSLEDWLENRDNART
 IP1B-B42  (101)  MEHVEQLVRQMITLNARNTALARLQGLGASFRAYQQSLEDWLENRDNART
 IP1B-B43  (101)  MEHVEQLVRQMITMNARNTALARLQGLGASFRAYQQSLEDWLENRDNART
 IP1B-B44  (101)  MEHVEQLVRQMITHNARNTALARLQGLGASFRAYQQSLEDWLENRDNART
 IP1B-B45  (101)  MEHVEQLVRQHITMNARNTALARLQGLGASFRAYQQSLEDWLENRDNART
 IP1B-B46  (101)  MEHVEQLVRQMITHNARNTALARLQGLGASFRAYQQSLEDWLENRDNART
 IP1B-B47  (101)  MEHVEQLVRQHITMNARNTALARLQGLGASFRAYQQSLEDWLENRDNART
 IP1B-B31   (96)  MEHVEQIVRQQITDSVRDTAIARLEGLGRGYRSYQQALETWLDNRNDARS
 IP1B-B32   (96)  MEHVEQIVRQQITDSVRDTAIARLEGLGRGYRSYQQALETWLDNRNDARS
 IP1B-B33   (96)  MEHVEQIVRQQITDSVRDTAIARLEGLGRGYRSYQQALETWLDNRNDARS
 IP1B-B34   (96)  LEHVEQLIRQQVTENTRNTAIARLEGLGRGYRSYQQALETWLDNRNDARS
    GS060  (101)  MEHVEQIVRQQITDSVRDTAIARLEGLGRGYRSYQQALETWLDNRNDARS

                  151                                              200
   Cry1Bd  (151)  RSIILERYVALELDITTAIPLFRIRNEEVPLLMVYAQAANLHLLLLRDAS
   IP1B-B1 (146)  RSIIRERYIALELDITTAIPLFSIRNQEVPLLMVYAQAANLHLLLLRDAS
    MP258  (151)  RSVLYTQYIALELDFLNAMPLFAINNQQVPLLMVYAQAANLHLLLLRDAS
 IP1B-B21  (151)  RSVLYTQYIALELDFLNAMPLFAINNQQVPLLMVYAQAANLHLLLLRDAS
 IP1B-B22  (151)  RSVLYTQYIALELDFLNAMPLFAINNQRVPLLMVYAQAANLHLLLLRDAS
 IP1B-B23  (146)  RSVLYTQYIALELDFLNAMPLFAINNQQVPLLMVYAQAANLHLLLLRDAS
 IP1B-B24  (151)  RSVLYTQYIALELDFLNAMPLFAINNQQVPLLMVYAQAANLHLLLLRDAS
 IP1B-B25  (151)  RSVLYTQYIALELDFLNAMPLFAINNQQVPLLMVYAQAANLHLLLLRDAS
 IP1B-B26  (151)  RSVLYTQYIALELDFLNAMPLFAINNQQVPLLMVYAQAANLHLLLLRDAS
 IP1B-B27  (151)  RSVLYTQYIALELDFLNAMPLFAINNQQVPLLMVYAQAANLHLLLLRDAS
 IP1B-B28  (151)  RSVLYTQYIALELDFLNAMPLFAINNQQVPLLMVYAQAANLHLLLLRDAS
 IP1B-B29  (151)  RSVLYTQYIALELDFLNAMPLFAINNQQVPLLMVYAQAANLHLLLLRDAS
 IP1B-B40  (151)  RSVLYTQYIALELDFLNAMPLFAINNQQVPLLMVYAQAANLHLLLLRDAS
 IP1B-B41  (151)  RSVLYTQYIALELDFLNAMPLFAINNQQVPLLMVYAQAANLHLLLLRDAS
 IP1B-B42  (151)  RSVLYTQYIALELDFLNAMPLFAINNQQVPLLMVYAQAANLHLLLLRDAS
 IP1B-B43  (151)  RSVLYTQYIALELDFLNAMPLFAINNQQVPLLMVYAQAANLHLLLLRDAS
 IP1B-B44  (151)  RSVLYTQYIALELDFLNAMPLFAINNQQVPLLMVYAQAANLHLLLLRDAS
 IP1B-B45  (151)  RSVLYTQYIALELDFLNAMPLFAINNQQVPLLMVYAQAANLHLLLLRDAS
 IP1B-B46  (151)  RSVLYTQYIALELDFLNAMPLFAINNQQVPLLMVYAQAANLHLLLLRDAS
 IP1B-B47  (151)  RSVLYTQYIALELDFLNAMPLFAINNQQVPLLMVYAQAANLHLLLLRDAS
 IP1B-B31  (146)  RSIIRERYIALELDITTAIPLFSIRNQEVPLLMVYAQAANLHLLLLRDAS
 IP1B-B32  (146)  RSIIRERYIALELDITTAIPLFSIRNQEVPLLMVYAQAANLHLLLLRDAS
 IP1B-B33  (146)  RSIILERYIALELDITTAIPLFSIRNQEVPLLMVYAQAANLHLLLLRDAS
 IP1B-B34  (146)  RSIILERYVALELDITTAIPLFSIRNQEVPLLMVYAQAANLHLLLLRDAS
    GS060  (151)  RSIIRERYIALELDITTAIPLFSIRNQEVPLLMVYAQAANLHLLLLRDAS
```

Fig. 1c

| | | 201 … 250 |
|---|---|---|
| Cry1Bd | (201) | LFGSEWGMASSDVNQYYQEQIRYTEEYSNHCVQWYNTGLNNLRGTNAESW |
| IP1B-B1 | (196) | LFGSEWGMSSSDVNQYYQEQIRYTEEYSNHCVQWYNTGLNNLRGTNAESW |
| MP258 | (201) | LFGSEFGLTSQEIQRYYERQAEKTREYSDYCARWYNTGLNNLRGTNAESW |
| IP1B-B21 | (201) | LFGSEFGLTSQEIQRYYERQAEKTREYSDYCARWYNTGLNNLRGTNAESW |
| IP1B-B22 | (201) | LFGSEFGLTSQEIQRYYERQAEKTREYSDYCARWYNTGLNNLRGTNAESW |
| IP1B-B23 | (196) | LFGSEFGLTSQEIQRYYERQAEKTREYSDYCARWYNTGLNNLRGTNAESW |
| IP1B-B24 | (201) | LFGSEFGLTSQEIQRYYERQAEKTREYSDYCARWYNTGLNNLRGTNAESW |
| IP1B-B25 | (201) | LFGSEFGLTSQEIQRYYERQAEKTREYSDYCARWYNTGLNNLRGTNAESW |
| IP1B-B26 | (201) | LFGSEFGLTSQEIQRYYERQAEKTREYSDYCARWYNTGLNNLRGTNAESW |
| IP1B-B27 | (201) | LFGSEFGLTSQEIQRYYERQAEKTREYSDYCARWYNTGLNNLRGTNAESW |
| IP1B-B28 | (201) | LFGSEFGLTSQEIQRYYERQAEKTREYSDYCARWYNTGLNNLRGTNAESW |
| IP1B-B29 | (201) | LFGSEFGLTSQEIQRYYERQAEKTREYSDYCARWYNTGLNNLRGTNAESW |
| IP1B-B40 | (201) | LFGSEFGLTSQEIQRYYERQAEKTREYSDYCARWYNTGLNNLRGTNAESW |
| IP1B-B41 | (201) | LFGSEFGLTSQEIQRYYERQAEKTREYSDYCARWYNTGLNNLRGTNAESW |
| IP1B-B42 | (201) | LFGSEFGLTSQEIQRYYERQAEKTREYSDYCARWYNTGLNNLRGTNAESW |
| IP1B-B43 | (201) | LFGSEFGLTSQEIQRYYERQAEKTREYSDYCARWYNTGLNNLRGTNAESW |
| IP1B-B44 | (201) | LFGSEFGLTSQEIQRYYERQAEKTREYSDYCARWYNTGLNNLRGTNAESW |
| IP1B-B45 | (201) | LFGSEFGLTSQEIQRYYERQAEKTREYSDYCARWYNTGLNNLRGTNAESW |
| IP1B-B46 | (201) | LFGSEFGLTSQEIQRYYERQAEKTREYSDYCARWYNTGLNNLRGTNAESW |
| IP1B-B47 | (201) | LFGSEFGLTSQEIQRYYERQAEKTREYSDYCARWYNTGLNNLRGTNAESW |
| IP1B-B31 | (196) | LFGSEWGMSSSDVNQYYQEQIRYTEEYSNHCVQWYNTGLNNLRGTNAESW |
| IP1B-B32 | (196) | LFGSEWGMSSSDVNQYYQEQIRYTEEYSNHCVQWYNTGLNNLRGTNAESW |
| IP1B-B33 | (196) | LFGSEWGMASSDVNQYYQEQIRYTEEYSNHCVQWYNTGLNNLRGTNAESW |
| IP1B-B34 | (196) | LFGSEWGMSSADVNQYYQEQIRYTEEYSNHCVQWYNTGLNNLRGTNAESW |
| GS060 | (201) | LFGSEWGMSSADVNQYYQEQIRYTEEYSNHCVQWYNTGLNRLRGTTAESW |

| | | 251 … 300 |
|---|---|---|
| Cry1Bd | (251) | LRYNQFRRDLTLGVLDLVALFPSYDTRTYPINTSAQLTREIYTDPIGRTN |
| IP1B-B1 | (246) | LRYNQFRRDLTLGVLDLVALFPSYDTRVYPMNTSAQLTREIYTDPIGRTN |
| MP258 | (251) | LRYNQFRRDLTLGVLDLVALFPSYDTRIYPINTSAQLTREIYTDPIGRTN |
| IP1B-B21 | (251) | LRYNQFRRDLTLGVLDLVALFPSYDTRIYPINTSAQLTREIYTDPIGRTN |
| IP1B-B22 | (251) | LRYNQFRRDLTLGVLDLVALFPSYDTRVYPINTSAQLTREIYTDPIGRTN |
| IP1B-B23 | (246) | LRYNQFRRDLTLGVLDLVALFPSYDTRIYPINTSAQLTREIYTDPIGRTN |
| IP1B-B24 | (251) | LRYNQFRRDLTLGVLDLVALFPSYDTRIYPINTSAQLTREIYTDPIGRTN |
| IP1B-B25 | (251) | LRYNQFRRDLTLGVLDLVALFPSYDTRIYPINTSAQLTREIYTDPIGRTN |
| IP1B-B26 | (251) | LRYNQFRRDLTLGVLDLVALFPSYDTRIYPINTSAQLTREIYTDPIGRTN |
| IP1B-B27 | (251) | LRYNQFRRDLTLGVLDLVALFPSYDTRIYPINTSAQLTREIYTDPIGRTN |
| IP1B-B28 | (251) | LRYNQFRRDLTLGVLDLVALFPSYDTRIYPINTSAQLTREIYTDPIGRTN |
| IP1B-B29 | (251) | LRYNQFRRDLTLGVLDLVALFPSYDTRIYPINTSAQLTREIYTDPIGRTN |
| IP1B-B40 | (251) | LRYNQFRRDLTLGVLDLVALFPSYDTRIYPINTSAQLTREIYTDPIGRTN |
| IP1B-B41 | (251) | LRYNQFRRDLTLGVLDLVALFPSYDTRIYPINTSAQLTREIYTDPIGRTN |
| IP1B-B42 | (251) | LRYNQFRRDLTLGVLDLVALFPSYDTRIYPINTSAQLTREIYTDPIGRTN |
| IP1B-B43 | (251) | LRYNQFRRDLTLGVLDLVALFPSYDTRIYPINTSAQLTREIYTDPIGRTN |
| IP1B-B44 | (251) | LRYNQFRRDLTLGVLDLVALFPSYDTRIYPINTSAQLTREIYTDPIGRTN |
| IP1B-B45 | (251) | LRYNQFRRDLTLGVLDLVALFPSYDTRIYPINTSAQLTREIYTDPIGRTN |
| IP1B-B46 | (251) | LRYNQFRRDLTLGVLDLVALFPSYDTRIYPINTSAQLTREIYTDPIGRTN |
| IP1B-B47 | (251) | LRYNQFRRDLTLGVLDLVALFPSYDTRIYPINTSAQLTREIYTDPIGRTN |
| IP1B-B31 | (246) | LRYNQFRRDLTLGVLDLVALFPSYDTRVYPMNTSAQLTREIYTDPIGRTN |
| IP1B-B32 | (246) | LRYNQFRRDLTLGVLDLVALFPSYDTRTYPINTSAQLTREIYTDPIGRTN |
| IP1B-B33 | (246) | LRYNQFRRDLTLGVLDLVALFPSYDTRTYPINTSAQLTREIYTDPIGRTN |
| IP1B-B34 | (246) | LRYNQFRRDLTLGVLDLVALFPSYDTRTYPINTSAQLTREIYTDPIGRTN |
| GS060 | (251) | VRYNQFRRDLTLGVLDLVALFPSYDTRTYPIPTTAQLTREVYTDPNGVVA |

Fig. 1d

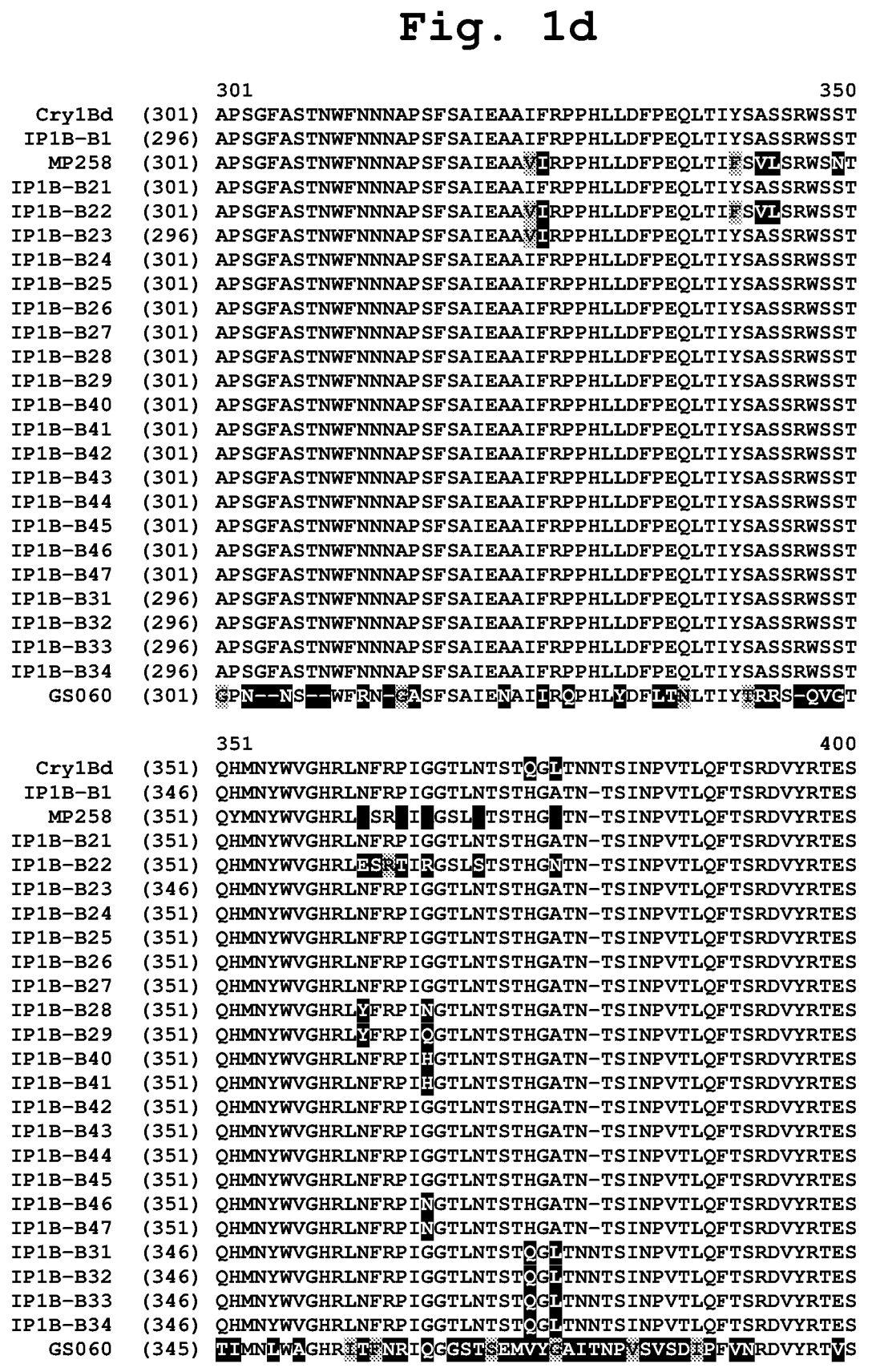

```
                301                                              350
   Cry1Bd  (301) APSGFASTNWFNNNAPSFSAIEAAIFRPPHLLDFPEQLTIYSASSRWSST
  IP1B-B1  (296) APSGFASTNWFNNNAPSFSAIEAAIFRPPHLLDFPEQLTIYSASSRWSST
    MP258  (301) APSGFASTNWFNNNAPSFSAIEAAVIRPPHLLDFPEQLTIFSVLSRWSNT
 IP1B-B21  (301) APSGFASTNWFNNNAPSFSAIEAAIFRPPHLLDFPEQLTIYSASSRWSST
 IP1B-B22  (301) APSGFASTNWFNNNAPSFSAIEAAVIRPPHLLDFPEQLTIFSVLSRWSST
 IP1B-B23  (296) APSGFASTNWFNNNAPSFSAIEAAVIRPPHLLDFPEQLTIYSASSRWSST
 IP1B-B24  (301) APSGFASTNWFNNNAPSFSAIEAAIFRPPHLLDFPEQLTIYSASSRWSST
 IP1B-B25  (301) APSGFASTNWFNNNAPSFSAIEAAIFRPPHLLDFPEQLTIYSASSRWSST
 IP1B-B26  (301) APSGFASTNWFNNNAPSFSAIEAAIFRPPHLLDFPEQLTIYSASSRWSST
 IP1B-B27  (301) APSGFASTNWFNNNAPSFSAIEAAIFRPPHLLDFPEQLTIYSASSRWSST
 IP1B-B28  (301) APSGFASTNWFNNNAPSFSAIEAAIFRPPHLLDFPEQLTIYSASSRWSST
 IP1B-B29  (301) APSGFASTNWFNNNAPSFSAIEAAIFRPPHLLDFPEQLTIYSASSRWSST
 IP1B-B40  (301) APSGFASTNWFNNNAPSFSAIEAAIFRPPHLLDFPEQLTIYSASSRWSST
 IP1B-B41  (301) APSGFASTNWFNNNAPSFSAIEAAIFRPPHLLDFPEQLTIYSASSRWSST
 IP1B-B42  (301) APSGFASTNWFNNNAPSFSAIEAAIFRPPHLLDFPEQLTIYSASSRWSST
 IP1B-B43  (301) APSGFASTNWFNNNAPSFSAIEAAIFRPPHLLDFPEQLTIYSASSRWSST
 IP1B-B44  (301) APSGFASTNWFNNNAPSFSAIEAAIFRPPHLLDFPEQLTIYSASSRWSST
 IP1B-B45  (301) APSGFASTNWFNNNAPSFSAIEAAIFRPPHLLDFPEQLTIYSASSRWSST
 IP1B-B46  (301) APSGFASTNWFNNNAPSFSAIEAAIFRPPHLLDFPEQLTIYSASSRWSST
 IP1B-B47  (301) APSGFASTNWFNNNAPSFSAIEAAIFRPPHLLDFPEQLTIYSASSRWSST
 IP1B-B31  (296) APSGFASTNWFNNNAPSFSAIEAAIFRPPHLLDFPEQLTIYSASSRWSST
 IP1B-B32  (296) APSGFASTNWFNNNAPSFSAIEAAIFRPPHLLDFPEQLTIYSASSRWSST
 IP1B-B33  (296) APSGFASTNWFNNNAPSFSAIEAAIFRPPHLLDFPEQLTIYSASSRWSST
 IP1B-B34  (296) APSGFASTNWFNNNAPSFSAIEAAIFRPPHLLDFPEQLTIYSASSRWSST
    GS060  (301) GPN--NS--WFRN-GASFSAIENAIIRQPHLYDFLTNLTIYTRRS-QVGT

                351                                              400
   Cry1Bd  (351) QHMNYWVGHRLNFRPIGGTLNTSTQGLTNNTSINPVTLQFTSRDVYRTES
  IP1B-B1  (346) QHMNYWVGHRLNFRPIGGTLNTSTHGATN-TSINPVTLQFTSRDVYRTES
    MP258  (351) QYMNYWVGHRL[illegible]SR[illegible]I[illegible]GSL[illegible]TSTHG[illegible]TN-TSINPVTLQFTSRDVYRTES
 IP1B-B21  (351) QHMNYWVGHRLNFRPIGGTLNTSTHGATN-TSINPVTLQFTSRDVYRTES
 IP1B-B22  (351) QHMNYWVGHRLESRTIRGSLSTSTHGNTN-TSINPVTLQFTSRDVYRTES
 IP1B-B23  (346) QHMNYWVGHRLNFRPIGGTLNTSTHGATN-TSINPVTLQFTSRDVYRTES
 IP1B-B24  (351) QHMNYWVGHRLNFRPIGGTLNTSTHGATN-TSINPVTLQFTSRDVYRTES
 IP1B-B25  (351) QHMNYWVGHRLNFRPIGGTLNTSTHGATN-TSINPVTLQFTSRDVYRTES
 IP1B-B26  (351) QHMNYWVGHRLNFRPIGGTLNTSTHGATN-TSINPVTLQFTSRDVYRTES
 IP1B-B27  (351) QHMNYWVGHRLNFRPIGGTLNTSTHGATN-TSINPVTLQFTSRDVYRTES
 IP1B-B28  (351) QHMNYWVGHRLYFRPINGTLNTSTHGATN-TSINPVTLQFTSRDVYRTES
 IP1B-B29  (351) QHMNYWVGHRLYFRPIQGTLNTSTHGATN-TSINPVTLQFTSRDVYRTES
 IP1B-B40  (351) QHMNYWVGHRLNFRPIHGTLNTSTHGATN-TSINPVTLQFTSRDVYRTES
 IP1B-B41  (351) QHMNYWVGHRLNFRPIHGTLNTSTHGATN-TSINPVTLQFTSRDVYRTES
 IP1B-B42  (351) QHMNYWVGHRLNFRPIGGTLNTSTHGATN-TSINPVTLQFTSRDVYRTES
 IP1B-B43  (351) QHMNYWVGHRLNFRPIGGTLNTSTHGATN-TSINPVTLQFTSRDVYRTES
 IP1B-B44  (351) QHMNYWVGHRLNFRPIGGTLNTSTHGATN-TSINPVTLQFTSRDVYRTES
 IP1B-B45  (351) QHMNYWVGHRLNFRPIGGTLNTSTHGATN-TSINPVTLQFTSRDVYRTES
 IP1B-B46  (351) QHMNYWVGHRLNFRPINGTLNTSTHGATN-TSINPVTLQFTSRDVYRTES
 IP1B-B47  (351) QHMNYWVGHRLNFRPINGTLNTSTHGATN-TSINPVTLQFTSRDVYRTES
 IP1B-B31  (346) QHMNYWVGHRLNFRPIGGTLNTSTQGLTNNTSINPVTLQFTSRDVYRTES
 IP1B-B32  (346) QHMNYWVGHRLNFRPIGGTLNTSTQGLTNNTSINPVTLQFTSRDVYRTES
 IP1B-B33  (346) QHMNYWVGHRLNFRPIGGTLNTSTQGLTNNTSINPVTLQFTSRDVYRTES
 IP1B-B34  (346) QHMNYWVGHRLNFRPIGGTLNTSTQGLTNNTSINPVTLQFTSRDVYRTES
    GS060  (345) TIMNLWAGHRITFNRIQGGSTSEMVYGAITNPVSVSDIPFVNRDVYRTVS
```

Fig. 1e

```
                  401                                               450
   Cry1Bd  (401)  NAGTNILFTTPVNGVPWARFNFINPQNIYERGATTYSQPYQGVGIQLFDS
  IP1B-B1  (395)  FAGTNILFTTPVNGVPWARFNFINPQNIYERGATTYSQPYQGVGIQLFDS
    MP258  (400)  YAGINILLTTPVNGVPWARFNWRNPLNSLR-GSLLYTIGYTGVGTQLFDS
 IP1B-B21  (400)  YAGINILLTTPVNGVPWARFNWRNPLNSLR-GSLLYTIGYTGVGTQLFDS
 IP1B-B22  (400)  YAGINILLTTPVNGVPWARFNWRNPLNSLR-GSLLYTIGYTGVGTQLFDS
 IP1B-B23  (395)  YAGINILLTTPVNGVPWARFNWRNPLNSLR-GSLLYTIGYTGVGIQLFDS
 IP1B-B24  (400)  YAGINILLTTPVNGVPWARFNWRNPLNSLR-GSLLYTIGYTGVGTQLFDS
 IP1B-B25  (400)  YAGINILLTTPVNGVPWARFNWRNPLNSLR-GSLLYTIGYTGVGTQLFDS
 IP1B-B26  (400)  YAGINILLTTPVNGVPWARFNWRNPLNSLR-GSLLYTIGYTGVGTQLFDS
 IP1B-B27  (400)  YAGINILLTTPVNGVPWARFNWRNPLNSLR-GSLLYTIGYTGVGTQLFDS
 IP1B-B28  (400)  YAGINILLTTPVNGVPWARFNWRNPLNSLR-GSLLYTIGYTGVGTQLFDS
 IP1B-B29  (400)  YAGINILLTTPVNGVPWARFNWRNPLNSLR-GSLLYTIGYTGVGTQLFDS
 IP1B-B40  (400)  YAGINILLTTPVNGVPWARFNWRNPLNSLR-GSLLYTIGYTGVGTQLFDS
 IP1B-B41  (400)  YAGINILLTTPVNGVPWARFNWRNPLNSLR-GSLLYTIGYTGVGTQLFDS
 IP1B-B42  (400)  YAGINILLTTPVNGVPWARFNWRNPLNSLR-GSLLYTIGYTGVGTQLFDS
 IP1B-B43  (400)  YAGINILLTTPVNGVPWARFNWRNPLNSLR-GSLLYTIGYTGVGTQLFDS
 IP1B-B44  (400)  YAGINILLTTPVNGVPWARFNWRNPLNSLR-GSLLYTIGYTGVGTQLFDS
 IP1B-B45  (400)  YAGINILLTTPVNGVPWARFNWRNPLNSLR-GSLLYTIGYTGVGTQLFDS
 IP1B-B46  (400)  YAGINILLTTPVNGVPWARFNWRNPLNSLR-GSLLYTIGYTGVGTQLFDS
 IP1B-B47  (400)  YAGINILLTTPVNGVPWARFNWRNPLNSLR-GSLLYTIGYTGVGTQLFDS
 IP1B-B31  (396)  NAGTNILFTTPVNGVPWARFNFINPQNIYERGATTYSQPYQGVGIQLFDS
 IP1B-B32  (396)  NAGTNILFTTPVNGVPWARFNFINPQNIYERGATTYSQPYQGVGIQLFDS
 IP1B-B33  (396)  NAGTNILFTTPVNGVPWARFNFINPQNIYERGATTYSQPYQGVGIQLFDS
 IP1B-B34  (396)  NAGTNILFTTPVNGVPWARFNFINPQNIYERGATTYSQPYQGVGIQLFDS
    GS060  (395)  LAGGLGSLSGIRYGLTRVDFDMIFRNHPDIVTGLFYHPGHAGIATQVKDS

                  451                                               500
   Cry1Bd  (451)  ETELPPETTERPNYESYSHRLSHIGLIIGNTLRAPVYSWTHRSADRTNTI
  IP1B-B1  (445)  ETELPPETTERPNYESYSHRLSHIGLIIGNTLRAPVYSWTHRSADRTNTI
    MP258  (449)  ETELPPETTERPNYESYSHRLSNIRLISGNTLRAPVYSWTHRSADRTNTI
 IP1B-B21  (449)  ETELPPETTERPNYESYSHRLSNIRLIIGNTLRAPVYSWTHRSADRTNTI
 IP1B-B22  (449)  ETELPPETTERPNYESYSHRLSHIGLIIGNTLRAPVYSWTHRSADRTNTT
 IP1B-B23  (444)  ETELPPETTERPNYESYSHRLSNIRLISGNTLRAPVYSWTHRSADRTNTI
 IP1B-B24  (449)  ETELPPETTERPNYESYSHRLSNIRLIIGNTLRAPVYSWTHRSADRTNTI
 IP1B-B25  (449)  ETELPPETTERPNYESYSHRLSNIRLIIGNTLRAPVYSWTHRSADRTNTI
 IP1B-B26  (449)  ETELPPETTERPNYESYSHRLSNIRLIISNTLRAPVYSWTHRSADRTNTI
 IP1B-B27  (449)  ETELPPETTERPNYESYSHRLSNIRLIISGTLRAPVYSWTHRSADRTNTI
 IP1B-B28  (449)  ETELPPETTERPNYESYSHRLSNIRLIIGNTLRAPVYSWTHRSADRTNTI
 IP1B-B29  (449)  ETELPPETTERPNYESYSHRLSNIRLIIGNTLRAPVYSWTHRSADRTNTI
 IP1B-B40  (449)  ETELPPETTERPNYESYSHRLSNIRLIISNTLRAPVYSWTHRSADRTNTI
 IP1B-B41  (449)  ETELPPETTERPNYESYSHRLSNIRLIIGNTLRAPVYSWTHRSADRTNTI
 IP1B-B42  (449)  ETELPPETTERPNYESYSHRLSNIRLIIGGTLRAPVYSWTHRSADRTNTI
 IP1B-B43  (449)  ETELPPETTERPNYESYSHRLSNIRLIIGGTLRAPVYSWTHRSADRTNTI
 IP1B-B44  (449)  ETELPPETTERPNYESYSHRLSNIRLIIGGTLRAPVYSWTHRSADRTNTI
 IP1B-B45  (449)  ETELPPETTERPNYESYSHRLSNIRLIIGGTLRAPVYSWTHRSADRTNTI
 IP1B-B46  (449)  ETELPPETTERPNYESYSHRLSNIRLIIGNTLRAPVYSWTHRSADRTNTI
 IP1B-B47  (449)  ETELPPETTERPNYESYSHRLSNIRLIIGNTLRAPVYSWTHRSADRTNTI
 IP1B-B31  (446)  ETELPPETTERPNYESYSHRLSHIGLIIGNTLRAPVYSWTHRSATLTNTI
 IP1B-B32  (446)  ETELPPETTERPNYESYSHRLSHIGLIIGNTLRAPVYSWTHRSATLTNTI
 IP1B-B33  (446)  ETELPPETTERPNYESYSHRLSHIGLIIGNTLRAPVYSWTHRSATLTNTI
 IP1B-B34  (446)  ETELPPETTERPNYESYSHRLSHIGLIIGNTLRAPVYSWTHRSATLTNTI
    GS060  (445)  ETELPPETTEQPNYRAFSHLLSHISMGPTTQDVPPVYSWTHQSADRTNTI
```

Fig. 1f

```
                501                                               550
   Cry1Bd (501) GPNRITQIPAVKGRFLFNG-SVISGPGFTGGDVVRLNRNNGNIQNRGYIE
  IP1B-B1 (495) GPNRITQIPAVKGRFLFNG-SVISGPGFTGGDVVRLNRNNGNIQNRGYIE
    MP258 (499) ATNIITQIPAVKGNFLFNG-SVISGPGFTGGDLVRLNNSGNNIQNRGYLE
 IP1B-B21 (499) ATNIITQIPAVKGNFLFNG-SVISGPGFTGGDLVRLNNSGNNIQNRGYIE
 IP1B-B22 (499) GPNRITQIPAVKGNFLFNG-SVISGPGFTGGDLVRLNNSGNNIQNRGYLE
 IP1B-B23 (494) ATNIITQIPAVKGNFLFNG-SVTSGPGFTGGDLVRLNNSGNNIQNRGYLE
 IP1B-B24 (499) ATNIITQIPAVKGNFLFNG-SVISGPGFTGGDLVRLNNSGNNIQNRGYIE
 IP1B-B25 (499) ATNIITQIPAVKGNFLFNG-SVISGPGFTGGDLVRLNNSGNNIQNRGYIE
 IP1B-B26 (499) ATNIITQIPAVKGNFLFNG-SVISGPGFTGGDLVRLNNSGNNIQNRGYIE
 IP1B-B27 (499) ATNIITQIPAVKGNFLFNG-SVISGPGFTGGDLVRLNNSGNNIQNRGYIE
 IP1B-B28 (499) ATNIITQIPAVKGNFLFNG-SVISGPGFTGGDLVRLNNSGNNIQNRGYIE
 IP1B-B29 (499) ATNIITQIPAVKGNFLFNG-SVISGPGFTGGDLVRLNNSGNNIQNRGYIE
 IP1B-B40 (499) ATNIITQIPAVKGNFLFNG-SVISGPGFTGGDLVRLNNSGNNIYNRGYIE
 IP1B-B41 (499) ATNIITQIPAVKGNFLFNG-SVISGPGFTGGDLVRLNNSGNNIYNRGYIE
 IP1B-B42 (499) ATNIITQIPAVKGNFLFNG-SVISGPGFTGGDLVRLNNSGNNIQNRGYIE
 IP1B-B43 (499) ATNIITQIPAVKGNFLFNG-SVISGPGFTGGDLVRLNNSGNNIQNRGYIE
 IP1B-B44 (499) ATNIITQIPAVKGNFLFNG-SVISGPGFTGGDLVRLNNSGNNIQNRGYIE
 IP1B-B45 (499) ATNIITQIPAVKGNFLFNG-SVISGPGFTGGDLVRLNNSGNNIQNRGYIE
 IP1B-B46 (499) ATNIITQIPAVKGNFLFNG-SVISGPGFTGGDLVRLNNSGNNIQNRGYIE
 IP1B-B47 (499) ATNIITQIPAVKGNFLFNG-SVISGPGFTGGDLVRLNNSGNNIQNRGYIE
 IP1B-B31 (496) DPERINQIPLVKGFRVWGGTSVITGPGFTGGDILRRNTFGDFVSLQVNIN
 IP1B-B32 (496) DPERINQIPLVKGFRVWGGTSVITGPGFTGGDILRRNTFGDFVSLQVNIN
 IP1B-B33 (496) DPERINQIPLVKGFRVWGGTSVITGPGFTGGDILRRNTFGDFVSLQVNIN
 IP1B-B34 (496) DPERINQIPLVKGFRVWGGTSVITGPGFTGGDILRRNTFGDFVSLQVNIN
    GS060 (495) NSDRITQIPLVKAHTLQSGTTVVKGPGFTGGDILRRTSGGPFAFSNVNLD

                551                                               600
   Cry1Bd (550) VPIQFTSTSTRYRVRVRYASVTSIELNVNLGNSS-------IFTNTLPAT
  IP1B-B1 (544) VPIQFTSTSTRYRVRVRYASVTSIELNVNLGNSS-------IFTNTLPAT
    MP258 (548) VPIQFISTSTRYRVRVRYASVTPIQLSVNWGNSN-------IFSSIVPAT
 IP1B-B21 (548) VPIQFISTSTRYRVRVRYASVTPIQLSVNWGNSN-------IFSSIVPAT
 IP1B-B22 (548) VPIQFISTSTRYRVRVRYASVTPIQLSVNWGNSN-------IFSSIVPAT
 IP1B-B23 (543) VPIQFISTSTRYRVRVRYASVTPIQLSVNWGNSN-------IFSSIVPAT
 IP1B-B24 (548) VPIQFISTSTRYRVRVRYASVTPIQLSVNWGNSN-------IFSRIVPAT
 IP1B-B25 (548) VPIQFISTSTRYRVRVRYASVTPIRLSVNWGNSN-------IFSSIVPAT
 IP1B-B26 (548) VPIQFISTSTRYRVRVRYASVTPIRLSVNWGNSN-------IFSSIVPAT
 IP1B-B27 (548) VPIQFISTSTRYRVRVRYASVTPIRLSVNWGNSN-------IFSSIVPAT
 IP1B-B28 (548) VPIQFISTSTRYRVRVRYASVTPIRLSVNWGNSN-------IFSSIVPAT
 IP1B-B29 (548) VPIQFISTSTRYRVRVRYASVTPIRLSVNWGNSN-------IFSSIVPAT
 IP1B-B40 (548) VPIQFISTSTRYRVRVRYASVTPIRLSVNWGNSN-------IFSSIVPAT
 IP1B-B41 (548) VPIQFISTSTRYRVRVRYASVTPIRLSVNWGNSN-------IFSTIVPAT
 IP1B-B42 (548) VPIQFISTSTRYRVRVRYASVTPIRLSVNWGNSN-------IFSSIVPAT
 IP1B-B43 (548) VPIQFISTSTRYRVRVRYASVTPIRLSVNWGNSN-------IFSSIVPAT
 IP1B-B44 (548) VPIQFISTSTRYRVRVRYASVTPIRLSVNWGNSN-------IFSSIVPAT
 IP1B-B45 (548) VPIQFISTSTRYRVRVRYASVTPIRLSVNWGNSN-------IFSSIVPAT
 IP1B-B46 (548) VPIQFISTSTRYRVRVRYASVTPIRLSVNWGNSN-------IFSSIVPAT
 IP1B-B47 (548) VPIQFISTSTRYRVRVRYASVTPIRLSVNWGNSN-------IFSSIVPAT
 IP1B-B31 (546) SPIT-----QRYRLRFRYASSRDARVIVLTGAASTGVGGQVSVNMPIQKT
 IP1B-B32 (546) SPIT-----QRYRLRFRYASSRDARVIVLTGAASTGVGGQVSVNMPIQKT
 IP1B-B33 (546) SPIT-----QRYRLRFRYASSRDARVIVLTGAASTGVGGQVSVNMPIQKT
 IP1B-B34 (546) SPIT-----QRYRLRFRYASSRDARVIVLTGAASTGVGGQVSVNMPIQKT
    GS060 (545) FNLS-----QRYRARIRYASTTNLRIYVTVAGER-------IFAGQFDKT
```

Fig. 1g

```
                601                                               650
    Cry1Bd (593) AASLDNLQSGDFGYVEINNAFTS---ATGNIVGARN-------FSANAEV
    IP1B-B1 (587) AASLDNLQSGDFGYVEINNAFTS---ATGNIVGARN-------FSANAEV
     MP258 (591) ATSLDNLQSRDFGYFESTNAFTS---ATGNVVGVRN-------FSENAGV
  IP1B-B21 (591) ATSLDNLQSRNFGYFESTNAFTS---ATGNVVGVRN-------FSENAGV
  IP1B-B22 (591) ATSLDNLQSRDFGYFESTNAFTS---ATGNVVGVRN-------FSENAGV
  IP1B-B23 (586) ATSLDNLQSRDFGYFESTNAFTS---ATGNVVGVRN-------FSENAGV
  IP1B-B24 (591) AYSLDNLQSRNFGYFESTNAFTS---ATGNVVGVRN-------FSENAGV
  IP1B-B25 (591) ATSLDNLQSRNFGYFESRNAFTS---ATGNVVGVRN-------FSENAGV
  IP1B-B26 (591) ATSLDNLQSRNFGYFESRNAFTS---ATGNVVGVRN-------FSENAGV
  IP1B-B27 (591) ATSLDNLQSRNFGYFESRNAFTS---ATGNVVGVRN-------FSENAGV
  IP1B-B28 (591) ATSLDNLQSRNFGYFESRNAFTS---ATGNVVGVRN-------FSENAGV
  IP1B-B29 (591) ATSLDNLQSRNFGYFESRNAFTS---ATGNVVGVRN-------FSENAGV
  IP1B-B40 (591) ATSLDNLQSRNFGYFESRNAFTS---ATGNVVGVRN-------FSENAGV
  IP1B-B41 (591) ATSLDNLQSRNFGYFESRNAFTS---ATGNVVGVRN-------FSENAGV
  IP1B-B42 (591) ATSLDNLQSRNFGYFESRNAFTS---ATGNVVGVRN-------FSENAGV
  IP1B-B43 (591) ATSLDNLQSRNFGYFESRNAFTS---ATGNVVGVRN-------FSENAGV
  IP1B-B44 (591) ATSLDNLQSRNFGYFESRNAFTS---ATGNVVGVRN-------FSENAGV
  IP1B-B45 (591) ATSLDNLQSRNFGYFESRNAFTS---ATGNVVGVRN-------FSENAGV
  IP1B-B46 (591) ATSLDNLQSRNFGYFESRNAFTS---ATGNVVGVRN-------FSENAGV
  IP1B-B47 (591) ATSLDNLQSRNFGYFESRNAFTS---ATGNVVGVRN-------FSENAGV
  IP1B-B31 (591) MEIGENLTSRTFRYTDFSNPFSFR--ANPDIIGISEQPLFGAGSISSGEL
  IP1B-B32 (591) MEIGENLTSRTFRYTDFSNPFSFR--ANPDIIGISEQPLFGAGSISSGEL
  IP1B-B33 (591) MEIGENLTSRTFRYTDFSNPFSFR--ANPDIIGISEQPLFGAGSISSGEL
  IP1B-B34 (591) MEIGENLTSRTFRYTDFSNPFSFR--ANPDIIGISEQPLFGAGSISSGEL
     GS060 (583) MDAGAPLTFQSFSYATINTAFTFPERSSSLTVGADT-------FSSGNEV

                651                      675
    Cry1Bd (633) IIDRFEFIPVTATFEAEYDLERAQK
    IP1B-B1 (627) IIDRFEFIPVTATFEAEYDLERAQK
     MP258 (631) IIDRFEFIPVTATFEAEYDLERAQE
  IP1B-B21 (631) IIDRFEFIPVTATFEAEYDLERAQE
  IP1B-B22 (631) IIDRFEFIPVTATFEAEYDLERAQE
  IP1B-B23 (626) IIDRFEFIPVTATFEAEYDLERAQE
  IP1B-B24 (631) IIDRFEFIPVTATFEAEYDLERAQE
  IP1B-B25 (631) IIDRFEFIPVTATFEAEYDLERAQE
  IP1B-B26 (631) IIDRFEFIPVTATFEAEYDLERAQE
  IP1B-B27 (631) IIDRFEFIPVTATFEAEYDLERAQE
  IP1B-B28 (631) IIDRFEFIPVTATFEAEYDLERAQE
  IP1B-B29 (631) IIDRFEFIPVTATFEAEYDLERAQE
  IP1B-B40 (631) IIDRFEFIPVTATFEAEYDLERAQE
  IP1B-B41 (631) IIDRFEFIPVTATFEAEYDLERAQE
  IP1B-B42 (631) IIDRFEFIPVTATFEAEYDLERAQE
  IP1B-B43 (631) IIDRFEFIPVTATFEAEYDLERAQE
  IP1B-B44 (631) IIDRFEFIPVTATFEAEYDLERAQE
  IP1B-B45 (631) IIDRFEFIPVTATFEAEYDLERAQE
  IP1B-B46 (631) IIDRFEFIPVTATFEAEYDLERAQE
  IP1B-B47 (631) IIDRFEFIPVTATFEAEYDLERAQE
  IP1B-B31 (639) YIDKIEIILADATFEAESDLERAQK
  IP1B-B32 (639) YIDKIEIILADATFEAESDLEGARK
  IP1B-B33 (639) YIDKIEIILADATFEAESDLEKAQK
  IP1B-B34 (639) YIDKIEIILADATFEAESDLERAQK
     GS060 (626) YVDRFELIPVTATFEAESDLERARK
```

Fig. 2a

Met Thr Ser Asn Arg Lys Asn Glu Asn Glu Ile Ile Asn Ala Leu Ser
1 5 10 15
***************************************************************

Ile Pro Ala Val Ser Asn His Ser Ala Gln Met Asp Leu Ser Pro Asp
20 25 30
****************************************************************

Ala Arg Ile Glu Asp Ser Leu Cys Ile Ala Glu Gly Asn Asn Ile Asn
35 40 45
*******########################################################

Pro Leu Val Ser Ala Ser Thr Val Gln Thr Gly Ile Asn Ile Ala Gly
50 55 60
#########################################################

Arg Ile Leu Gly Val Leu Gly Val Pro Phe Ala Gly Gln Leu Ala Ser
65 70 75 80
#########################################################

Phe Tyr Ser Phe Ile Val Gly Glu Leu Trp Pro Ser Gly Arg Asp Pro
85 90 95
#########################################################

Trp Glu Ile Phe Leu Glu His Val Glu Gln Leu Val Arg Gln Gln Ile
100 105 110
#########################################################

Thr Glu Asn Ala Arg Asn Thr Ala Leu Ala Arg Leu Gln Gly Leu Gly
115 120 125
#########################################################

Ala Ser Phe Arg Ala Tyr Gln Gln Ser Leu Glu Asp Trp Leu Glu Asn
130 135 140
#########################################################

Fig.2b

```
Arg Asp Asp Ala Arg Thr Arg Ser Val Leu Tyr Thr Gln Tyr Ile Ala
145                 150                 155                 160
################################################################

Leu Glu Leu Asp Phe Leu Asn Ala Met Pro Leu Phe Ala Ile Asn Asn
                165                 170                 175
################################################################

Gln Gln Val Pro Leu Leu Met Val Tyr Ala Gln Ala Ala Asn Leu His
            180                 185                 190
################################################################

Leu Leu Leu Leu Arg Asp Ala Ser Leu Phe Gly Ser Glu Phe Gly Leu
        195                 200                 205
################################################################

Thr Ser Gln Glu Ile Gln Arg Tyr Tyr Glu Arg Gln Ala Glu Lys Thr
    210                 215                 220
################################################################

Arg Glu Tyr Ser Asp Tyr Cys Ala Arg Trp Tyr Asn Thr Gly Leu Asn
225                 230                 235                 240
################################################################

Asn Leu Arg Gly Thr Asn Ala Glu Ser Trp Leu Arg Tyr Asn Gln Phe
                245                 250                 255
################################################################

Arg Arg Asp Leu Thr Leu Gly Val Leu Asp Leu Val Ala Leu Phe Pro
            260                 265                 270
################################################################

Ser Tyr Asp Thr Arg Ile Tyr Pro Ile Asn Thr Ser Ala Gln Leu Thr
        275                 280                 285
###############&&&&&&&&&&&&&&&&&&&&&&&&&&&&&&&&&&&&&&&&&&&&&&&&&
```

Fig. 2c

```
Arg Glu Ile Tyr Thr Asp Pro Ile Gly Arg Thr Asn Ala Pro Ser Gly
    290                 295                 300
&&&&&&&&&&&&&&&&&&&&&&&&&&&&&&&&&&&&&&&&&&&&&&&&&&&&&&&&&&&&&&&&

Phe Ala Ser Thr Asn Trp Phe Asn Asn Asn Ala Pro Ser Phe Ser Ala
305                 310                 315                 320
&&&&&&&&&&&&&&&&&&&&&&&&&&&&&&&&&&&&&&&&&&&&&&&&&&&&&&&&&&&&&&&&

Ile Glu Ala Ala Val Ile Arg Pro Pro His Leu Leu Asp Phe Pro Glu
                325                 330                 335
&&&&&&&&&&&&&&&&&&&&&&&&&&&&&&&&&&&&&&&&&&&&&&&&&&&&&&&&&&&&&&&&

Gln Leu Thr Ile Phe Ser Val Leu Ser Arg Trp Ser Asn Thr Gln Tyr
            340                 345                 350
&&&&&&&&&&&&&&&&&&&&&&&&&&&&&&&&&&&&&&&&&&&&&&&&&&&&&&&&&&&&&&&&

Met Asn Tyr Trp Val Gly His Arg Leu Glu Ser Arg Thr Ile Arg Gly
        355                 360                 365
&&&&&&&&&&&&&&&&&&&&&&&&&&&&&&&&&&&&&&&&&&&&&&&&&&&&&&&&&&&&&&&&

Ser Leu Ser Thr Ser Thr His Gly Asn Thr Asn Thr Ser Ile Asn Pro
    370                 375                 380
&&&&&&&&&&&&&&&&&&&&&&&&&&&&&&&&&&&&&&&&&&&&&&&&&&&&&&&&&&&&&&&&

Val Thr Leu Gln Phe Thr Ser Arg Asp Val Tyr Arg Thr Glu Ser Tyr
385                 390                 395                 400
&&&&&&&&&&&&&&&&&&&&&&&&&&&&&&&&&&&&&&&&&&&&&&&&&&&&&&&&&&&&&&&&

Ala Gly Ile Asn Ile Leu Leu Thr Thr Pro Val Asn Gly Val Pro Trp
                405                 410                 415
&&&&&&&&&&&&&&&&&&&&&&&&&&&&&&&&&&&&&&&&&&&&&&&&&&&&&&&&&&&&&&&&

Ala Arg Phe Asn Trp Arg Asn Pro Leu Asn Ser Leu Arg Gly Ser Leu
            420                 425                 430
&&&&&&&&&&&&&&&&&&&&&&&&&&&&&&&&&&&&&&&&&&&&&&&&&&&&&&&&&&&&&&&&
```

Fig. 2d

```
Leu Tyr Thr Ile Gly Tyr Thr Gly Val Gly Thr Gln Leu Phe Asp Ser
        435                 440                 445
&&&&&&&&&&&&&&&&&&&&&&&&&&&&&&&&&&&&&&&&&&&&&&&&&&&&&&&&&&&&&&&

Glu Thr Glu Leu Pro Pro Glu Thr Thr Glu Arg Pro Asn Tyr Glu Ser
    450                 455                 460
&&&&&&&&&&&&&&&&&&&&&&&&&&&&&&&&&&&&&&&&&&&&&&&&&&&&&&&&&&&&&&&

Tyr Ser His Arg Leu Ser Asn Ile Arg Leu Ile Ser Gly Asn Thr Leu
465                 470                 475                 480
&&&&&&&&&&&&&&&&&&&&&&&&&&&&&&&&&&&&&&&&&&&&&&&&&&&&&&&&&&&&&&&

Arg Ala Pro Val Tyr Ser Trp Thr His Arg Ser Ala Asp Arg Thr Asn
                485                 490                 495
&&&&&&&&&&&&&&&&&&&&&&&&&&&&&&&&&&&&&&&&&&&&&&&&&&&!!!!!!!!!!!!

Thr Ile Ala Thr Asn Ile Ile Thr Gln Ile Pro Ala Val Lys Gly Asn
            500                 505                 510
!!!!!!!!!!!!!!!!!!!!!!!!!!!!!!!!!!!!!!!!!!!!!!!!!!!!!!!!!!!!!!!

Phe Leu Phe Asn Gly Ser Val Ile Ser Gly Pro Gly Phe Thr Gly Gly
        515                 520                 525
!!!!!!!!!!!!!!!!!!!!!!!!!!!!!!!!!!!!!!!!!!!!!!!!!!!!!!!!!!!!!!!

Asp Leu Val Arg Leu Asn Asn Ser Gly Asn Asn Ile Gln Asn Arg Gly
    530                 535                 540
!!!!!!!!!!!!!!!!!!!!!!!!!!!!!!!!!!!!!!!!!!!!!!!!!!!!!!!!!!!!!!!

Tyr Leu Glu Val Pro Ile Gln Phe Ile Ser Thr Ser Thr Arg Tyr Arg
545                 550                 555                 560
!!!!!!!!!!!!!!!!!!!!!!!!!!!!!!!!!!!!!!!!!!!!!!!!!!!!!!!!!!!!!!!

Val Arg Val Arg Tyr Ala Ser Val Thr Pro Ile Gln Leu Ser Val Asn
                565                 570                 575
!!!!!!!!!!!!!!!!!!!!!!!!!!!!!!!!!!!!!!!!!!!!!!!!!!!!!!!!!!!!!!!
```

Fig. 2e

```
Trp Gly Asn Ser Asn Ile Phe Ser Ser Ile Val Pro Ala Thr Ala Thr
            580                 585                 590
!!!!!!!!!!!!!!!!!!!!!!!!!!!!!!!!!!!!!!!!!!!!!!!!!!!!!!!!!!!!!!!!

Ser Leu Asp Asn Leu Gln Ser Arg Asp Phe Gly Tyr Phe Glu Ser Thr
        595                 600                 605
!!!!!!!!!!!!!!!!!!!!!!!!!!!!!!!!!!!!!!!!!!!!!!!!!!!!!!!!!!!!!!!!

Asn Ala Phe Thr Ser Ala Thr Gly Asn Val Val Gly Val Arg Asn Phe
    610                 615                 620
!!!!!!!!!!!!!!!!!!!!!!!!!!!!!!!!!!!!!!!!!!!!!!!!!!!!!!!!!!!!!!!!

Ser Glu Asn Ala Gly Val Ile Ile Asp Arg Phe Glu Phe Ile Pro Val
625                 630                 635                 640
!!!!!!!!!!!!!!!!!!!!!!!!!!!!!!!!!!!!!!!!!!!!!!!!!!!!!!!!!!!!!!!!

Thr Ala Thr Phe Glu Ala Glu Tyr Asp Leu Glu Arg Ala Gln Glu
                645                 650                 655
!!!!!!!!!!!!!!!!!!!!!!!!!!!!!!!!!!!!!!!!!!!!!!!!!!!!!!!!!!!!
```

Fig. 3

```
                           1                                                  50
Cry1Be Dom I    (1)  IEDSLCIAEGNNIDPFVSASTVQTGINIAGRILGVLGVPFAGQIASFYSF
 MP258 Dom I    (1)  IEDSLCIAEGNNINPLVSASTVQTGINIAGRILGVLGVPFAGQLASFYSF

                     51                                                100
Cry1Be Dom I   (51)  LVGELWPRGRDPWEIFLEHVEQLIRQQVTENTRDTALARLQGLGNSFRAY
 MP258 Dom I   (51)  IVGELWPSGRDPWEIFLEHVEQLVRQQITENARNTALARLQGLGASFRAY

                     101                                               150
Cry1Be Dom I  (101)  QQSLEDWLENRDDARTRSVLYTQYIALELDFLNAMPLFAIRNQEVPLLMV
 MP258 Dom I  (101)  QQSLEDWLENRDDARTRSVLYTQYIALELDFLNAMPLFAINNQQVPLLMV

                     151                                               200
Cry1Be Dom I  (151)  YAQAANLHLLLLRDASLFGSEFGLTSQEIQRYYERQVEKTREYSDYCARW
 MP258 Dom I  (151)  YAQAANLHLLLLRDASLFGSEFGLTSQEIQRYYERQAEKTREYSDYCARW

                     201
Cry1Be Dom I  (201)  YNTGLNNLRGTNAESWLRYNQFRRDLTLGVLDLVALFPSYD
 MP258 Dom I  (201)  YNTGLNNLRGTNAESWLRYNQFRRDLTLGVLDLVALFPSYD
                     251
```

Fig. 4

```
                    1                                                50
Cry1Ah D3     (1)   -NNIIASDSITQIPAVKGNFLFNGSVISGPGFTGGDLVRLNSSGNNIQNR
Cry1Bd D3     (1)   RTNTIGPNRITQIPAVKGRFLFNGSVISGPGFTGGDVVRLNRNNGNIQNR
Cry1Bh D3     (1)   RTNTIGPNRITQIPAVKGRFLFNGSVISGPGFTGGDVVRLNRNNGNIQNR
Cry1Bi D3     (1)   RTNTIGPNRITQIPAVKGNLLFNGSVISGPGFTGGDLVRLNNSGNNIQNR
 MP258 D3     (1)   RTNTIATNIITQIPAVKGNFLFNGSVISGPGFTGGDLVRLNNSGNNIQNR

                    51                                              100
Cry1Ah D3    (50)   GYIEVPIHFPSTSTRYRVRVRYASVTPIHLNVNWGNSSIFSNTVPATATS
Cry1Bd D3    (51)   GYIEVPIQFTSTSTRYRVRVRYASVTSIELNVNLGNSSIFTNTLPATAAS
Cry1Bh D3    (51)   GYIEVPIQFTSTSTRYRVRVRYASVTSIELNVNWGNSSIFTNTLPATAAS
Cry1Bi D3    (51)   GYLEVPIQFTSTSTRYRVRVRYASVTPIHLSVNWGNSNIFSSTVPATAAS
 MP258 D3    (51)   GYLEVPIQFISTSTRYRVRVRYASVTPIQLSVNWGNSNIFSSIVPATATS

                    101                                             150
Cry1Ah D3   (100)   LDNLQSSDFGYFESANAFTSSLGNIVGVRNFSGTAGVIIDRFEFIPVTAT
Cry1Bd D3   (101)   LDNLQSGDFGYVEINNAFTSATGNIVGARNFSANAEVIIDRFEFIPVTAT
Cry1Bh D3   (101)   LDNLQSGDFGYVEINNAFTSATGNIVGVRNFSANAEVIIDRFEFIPVTAT
Cry1Bi D3   (101)   LDNLQSRDFGYFESTNAFTSVTGNVVGVRNFSENARVIIDRFEFIPVTAT
 MP258 D3   (101)   LDNLQSRDFGYFESTNAFTSATGNVVGVRNFSENAGVIIDRFEFIPVTAT

                    151       162
Cry1Ah D3   (150)   LEAEYNLERAQK
Cry1Bd D3   (151)   FEAEYDLERAQK
Cry1Bh D3   (151)   FEAKYDLERAQK
Cry1Bi D3   (151)   FEAEYDLERAQE
 MP258 D3   (151)   FEAEYDLERAQE
```

Fig. 5a

```
                        1                                                50
 MP258 D1&2     (1)  IEDSLCIAEGNNINPLVSASTVQTGINIAGRILGVLGVPFAGQLASFYSF
Cry1Be D1&2     (1)  IEDSLCIAEGNNIDPFVSASTVQTGINIAGRILGVLGVPFAGQIASFYSF
Cry1Bi D1&2     (1)  IEDGLCIAEGEYIDPFVSASTVQTGISIAGRILGVLGVPFAGQLASFYSF
Cry1Bg D1&2     (1)  IEDGLCIAEGEYIDPFVSASTVQTGISIAGRILGVLGVPFAGQLASFYSF
Cry1Bf D1&2     (1)  IEDSLCIAEGNNINPLVSASTVQTGINIAGRILGVLGVPFAGQIASFYSF
Cry1Ba D1&2     (1)  IEDSLCIAEGNNIDPFVSASTVQTGINIAGRILGVLGVPFAGQLASFYSF
Cry1Bh D1&2     (1)  IEDSLCVAEVNNIDPFVSASTVQTGINIAGRILGVLGVPFAGQLASFYSF
Cry1Bd D1&2     (1)  IEDSLCIAEGNNINPLVSASTVQTGINIAGRILGVLGVPFAGQLASFYSF
Cry1Bb D1&2     (1)  IEDSLCVAEVNNIDPFVSASTVQTGINIAGRILGVLGVPFAGQLASFYSF
Cry1Bc D1&2     (1)  IEDSLCVAEVNNIDPFVSASTVQTGINIAGRILGVLGVPFAGQLASFYSF

                     51                                               100
 MP258 D1&2    (51)  IVGELWPSGRDPWEIFLEHVEQLVRQQITENARNTALARLQGLGASFRAY
Cry1Be D1&2    (51)  LVGELWPRGRDPWEIFLEHVEQLIRQQVTENTRDTALARLQGLGNSFRAY
Cry1Bi D1&2    (51)  IVGELWPKGRDQWEIFMEHVEQLVRQQITANARNTALARLQGLGDSFRAY
Cry1Bg D1&2    (51)  IVGELWPKGRDQWEIFMEHVEQLVRQQITANARNTALARLQGLGDSFRAY
Cry1Bf D1&2    (51)  LVGELWPRGRDQWEIFLEHVEQLINQQITENARNTALARLQGLGDSFRAY
Cry1Ba D1&2    (51)  LVGELWPRGRDQWEIFLEHVEQLINQQITENARNTALARLQGLGDSFRAY
Cry1Bh D1&2    (51)  LVGELWPSGRDPWEIFLEHVEQLIRQQVTENTRNTAIARLEGLGRGYRSY
Cry1Bd D1&2    (51)  LVGELWPSGRDPWEIFLEHVEQLIRQQVTENTRNTAIARLEGLGRGYRSY
Cry1Bb D1&2    (51)  LVGELWPSGRDPWEIFLEHVEQLIRQQVTENTRNTAIARLEGLGRGYRSY
Cry1Bc D1&2    (51)  LVGELWPSGRDPWEIFLEHVEQLIRQQVTENTRNTAIARLEGLGRGYRSY

                     101                                              150
 MP258 D1&2   (101)  QQSLEDWLENRDDARTRSVLYTQYIALELDFLNAMPLFAINNQQVPLLMV
Cry1Be D1&2   (101)  QQSLEDWLENRDDARTRSVLYTQYIALELDFLNAMPLFAIRNQEVPLLMV
Cry1Bi D1&2   (101)  QQSLEDWLENRNDARTRSVLYTQYIALELDFLNAMPLFAIREQEVPLLMV
Cry1Bg D1&2   (101)  QQSLEDWLENRNDARTRSVLYTQYIALELDFLNAMPLFAIREQEVPLLMV
Cry1Bf D1&2   (101)  QQSLEDWLENRDDARTRSVLYTQYIALELDFLNAMPLFAIRNQEVPLLMV
Cry1Ba D1&2   (101)  QQSLEDWLENRDDARTRSVLYTQYIALELDFLNAMPLFAIRNQEVPLLMV
Cry1Bh D1&2   (101)  QQALETWLDNRNDARSRSIILERYVALELDITTAIPLFRIRNQEVPLLMV
Cry1Bd D1&2   (101)  QQALETWLDNRNDARSRSIILERYVALELDITTAIPLFRIRNEEVPLLMV
Cry1Bb D1&2   (101)  QQALETWLDNRNDARSRSIILERYVALELDITTAIPLFRIRNEEVPLLMV
Cry1Bc D1&2   (101)  QQALETWLDNRNDARSRSIILERYVALELDITTAIPLFRIRNEEVPLLMV

                     151                                              200
 MP258 D1&2   (151)  YAQAANLHLLLLRDASLFGSEFGLTSQEIQRYYERQAEKTREYSDYCARW
Cry1Be D1&2   (151)  YAQAANLHLLLLRDASLFGSEFGLTSQEIQRYYERQVEKTREYSDYCARW
Cry1Bi D1&2   (151)  YAQAANLHLLLLRDASLYGREFGLTSQEIQRYYERQVERTRDYSDHCVQW
Cry1Bg D1&2   (151)  YAQAANLHLLLLRDASLYGREFGLTSQEIQRYYERQVERTRDYSDHCVQW
Cry1Bf D1&2   (151)  YAQAANLHLLLLRDASLFGSEFGLTSQEIQRYYERQVEQTRDYSDYCVEW
Cry1Ba D1&2   (151)  YAQAANLHLLLLRDASLFGSEFGLTSQEIQRYYERQVERTRDYSDYCVEW
Cry1Bh D1&2   (151)  YAQAANLHLLLLRDASLFGSEWGTASSDVNQYYQEQIRYTEEYSNHCVQW
Cry1Bd D1&2   (151)  YAQAANLHLLLLRDASLFGSEWGMASSDVNQYYQEQIRYTEEYSNHCVQW
Cry1Bb D1&2   (151)  YAQAANLHLLLLRDASLFGSEWGMASSDVNQYYQEQIRYTEEYSNHCVQW
Cry1Bc D1&2   (151)  YAQAANLHLLLLRDASLFGSEWGMASSDVNQYYQEQIRYTEEYSNHCVQW
```

Fig. 5b

```
                         201                                                250
 MP258 D1&2     (201)    YNTGLNNLRGTNAESWLRYNQFRRDLTLGVLDLVALFPSYDTRIYPINTS
Cry1Be D1&2     (201)    YNTGLNNLRGTNAESWLRYNQFRRDLTLGVLDLVALFPSYDTRVYPMNTS
Cry1Bi D1&2     (201)    YNTGLNNLRGTNAESWVRYNQFRRDLTLGVLDLVALFPSYDTRTYPINTS
Cry1Bg D1&2     (201)    YNTGLNNLRGTNAESWVRYNQFRRDLTLGVLDLVALFPSYDTRTYPINTS
Cry1Bf D1&2     (201)    YNTGLNSLRGTNAASWVRYNQFRRDLTLGVLDLVALFPSYDTRTYPINTS
Cry1Ba D1&2     (201)    YNTGLNSLRGTNAASWVRYNQFRRDLTLGVLDLVALFPSYDTRTYPINTS
Cry1Bh D1&2     (201)    YNTGLNNLRGTNAESWVRYNQFRRDLTLGVLDLVALFPSYDTRTYPINTS
Cry1Bd D1&2     (201)    YNTGLNNLRGTNAESWLRYNQFRRDLTLGVLDLVALFPSYDTRTYPINTS
Cry1Bb D1&2     (201)    YNTGLNNLRGTNAESWLRYNQFRRDLTLGVLDLVALFPSYDTRTYPINTS
Cry1Bc D1&2     (201)    YNTGLNNLRGTNAESWLRYNQFRRDLTLGVLDLVALFPSYDTRTYPINTS

                         251                                                300
 MP258 D1&2     (251)    AQLTREIYTDPIGRTNAPSGFASTNWFNNNAPSFSAIEAAVIRPPHLLDF
Cry1Be D1&2     (251)    AQLTREIYTDPIGRTNAPSGFASTNWFNNNAPSFSAIEAAVIRPPHLLDF
Cry1Bi D1&2     (251)    AQLTREVYTDAIGATGVN--MASMNWYNNNAPSFSAIETAVIRSPHLLDF
Cry1Bg D1&2     (251)    AQLTREVYTDAIGATGVN--MASMNWYNNNAPSFSAIETAVIRSPHLLDF
Cry1Bf D1&2     (251)    AQLTREVYTDAIGATGVN--MASMNWYNNNAPSFSAIETAVIRSPHLLDF
Cry1Ba D1&2     (251)    AQLTREVYTDAIGATGVN--MASMNWYNNNAPSFSAIEAAAIRSPHLLDF
Cry1Bh D1&2     (251)    AQLTREVYTDAIGTVHPSQAFASTTWFNNNAPSFSAIEAAVIRPPHLLDF
Cry1Bd D1&2     (251)    AQLTREIYTDPIGRTNAPSGFASTNWFNNNAPSFSAIEAAIFRPPHLLDF
Cry1Bb D1&2     (251)    AQLTREIYTDPIGRTNAPSGFASTNWFNNNAPSFSAIEAAIFRPPHLLDF
Cry1Bc D1&2     (251)    AQLTREIYTDPIGRTNAPSGFASTNWFNNNAPSFSAIEAAIFRPPHLLDF

                         301                                                350
 MP258 D1&2     (301)    PEQLTIFSVLSRWSNTQYMNYWVGHRLESRTIRGSLSTSTHGNTN-TSIN
Cry1Be D1&2     (301)    PEQLTIFSVLSRWSNTQYMNYWVGHRLESRTIRGSLSTSTHGNTN-TSIN
Cry1Bi D1&2     (299)    LEQLKIFSASSRWSNTRHMTYWRGHTIQSRPIRGALITSTHGNTN-TSIN
Cry1Bg D1&2     (299)    LEQLKIFSASSRWSNTRHMTYWRGHTIQSRPIRGALITSTHGNTN-TSIN
Cry1Bf D1&2     (299)    LEQLTIFSTSSRWSATRHMTYWRGHTIQSRPIGGGLNTSTHGSTN-TSIN
Cry1Ba D1&2     (299)    LEQLTIFSASSRWSNTRHMTYWRGHTIQSRPIGGGLNTSTHGATN-TSIN
Cry1Bh D1&2     (301)    PEQLTIYSTLSRWSNTQFMNIWAGHRLESRPIAGSLNTSTQGSTN-TSIN
Cry1Bd D1&2     (301)    PEQLTIYSASSRWSSTQHMNYWVGHRLNFRPIGGTLNTSTQGLTNNTSIN
Cry1Bb D1&2     (301)    PEQLTIYSASSRWSSTQHMNYWVGHRLNFRPIGGTLNTSTQGLTNNTSIN
Cry1Bc D1&2     (301)    PEQLTIYSASSRWSSTQHMNYWVGHRLNFRPIGGTLNTSTQGLTNNTSIN

                         351                                                400
 MP258 D1&2     (350)    PVTLQFTSRDVYRTESYAGINIL--LTTPVNGVPWARFNWRNPLNSLR-G
Cry1Be D1&2     (350)    PVTLQFTSRDVYRTESFAGINIL--LTTPVNGVPWARFNWRNPLNSLR-G
Cry1Bi D1&2     (348)    PVTFQFPSRDVYRTESYAGVLLWGIYLEPIHGVPTVRFNFRNPQNTFERG
Cry1Bg D1&2     (348)    PVTFQFPSRDVYRTESYAGVLLWGIYLEPIHGVPTVRFNFRNPQNTFERG
Cry1Bf D1&2     (348)    PVRLSFFSRDVYWTESYAGVLLWGIYLEPIHGVPTVRFNFRNPQNTFERG
Cry1Ba D1&2     (348)    PVTLRFASRDVYRTESYAGVLLWGIYLEPIHGVPTVRFNFTNPQNISDRG
Cry1Bh D1&2     (350)    PVTLQFTSRDIYRTESLAGLNIF--ITQPVNGVPWVRFNWRNPLNSLR-G
Cry1Bd D1&2     (351)    PVTLQFTSRDVYRTESNAGTNIL--FTTPVNGVPWARFNFINPQNIYERG
Cry1Bb D1&2     (351)    PVTLQFTSRDVYRTESNAGTNIL--FTTPVNGVPWARFNFINPQNIYERG
Cry1Bc D1&2     (351)    PVTLQFTSRDVYRTESNAGTNIL--FTTPVNGVPWARFNFINPQNIYERG
```

Fig. 5c

```
                      401                                              450
 MP258 D1&2   (397)  SLLYTIGYTGVGTQLFDSETELPPETTERPNYESYSHRLSNIRLISGNTL
Cry1Be D1&2   (397)  SLLYTIGYTGVGTQLFDSETELPPETTERPNYESYSHRLSNIRLISGNTL
Cry1Bi D1&2   (398)  TANYSQPYESPGLQLKDSETELPPETTERPNYESYSHRLSHIGIILQTRL
Cry1Bg D1&2   (398)  TANYSQPYESPGLQLKDSETELPPETTERPNYESYSHRLSHIGIILQTRL
Cry1Bf D1&2   (398)  TANYSQPYESPGLQLKDSETELPPETTERPNYESYSHRLSHIGLISQSRV
Cry1Ba D1&2   (398)  TANYSQPYESPGLQLKDSETELPPETTERPNYESYSHRLSHIGIILQSRV
Cry1Bh D1&2   (397)  SLLYTIGYTGVGTQLQDSETELPPETTERPNYESYSHRLSHIGLISSSHV
Cry1Bd D1&2   (399)  ATTYSQPYQGVGIQLFDSETELPPETTERPNYESYSHRLSHIGLIIGNTL
Cry1Bb D1&2   (399)  ATTYSQPYQGVGIQLFDSETELPPETTERPNYESYSHRLSHIGLIIGNTL
Cry1Bc D1&2   (399)  ATTYSQPYQGVGIQLFDSETELPPETTERPNYESYSHRLSHIGLIIGNTL

                      451          464
 MP258 D1&2   (447)  RAPVYSWTHRSAD-
Cry1Be D1&2   (447)  RAPVYSWTHRSADR
Cry1Bi D1&2   (448)  NVPVYSWTHRSADR
Cry1Bg D1&2   (448)  NVPVYSWTHRSADR
Cry1Bf D1&2   (448)  HVPVYSWTHRSADR
Cry1Ba D1&2   (448)  NVPVYSWTHRSADR
Cry1Bh D1&2   (447)  RALVYSWTHRSADR
Cry1Bd D1&2   (449)  RAPVYSWTHRSADR
Cry1Bb D1&2   (449)  RAPVYSWTHRSADR
Cry1Bc D1&2   (449)  RAPVYSWTHRSADR
```

INSECTICIDAL COMBINATIONS OF POLYPEPTIDES HAVING IMPROVED ACTIVITY SPECTRUM AND USES THEREOF

CROSS-REFERENCE TO RELATED APPLICATIONS

This application claims priority to International Patent Application PCT/US2017/28258 filed on Apr. 19, 2017, which claims priority to U.S. Provisional Application No. 62/324,652, filed Apr. 19, 2016, which is hereby incorporated herein in its entirety by reference.

REFERENCE TO SEQUENCE LISTING SUBMITTED ELECTRONICALLY

A sequence listing having the file name "7116WOPCT_SequenceListing.txt" created on Apr. 15, 2016 and having a size of 266 kilobytes is filed in computer readable form concurrently with the specification. The sequence listing is part of the specification and is herein incorporated by reference in its entirety.

FIELD

The present disclosure relates to recombinant nucleic acids that encode pesticidal polypeptides having insecticidal activity against corn earworm and/or fall armyworm and/or an improved spectrum of pesticidal activity against insect pests. Compositions and methods of the disclosure utilize the disclosed nucleic acids, and their encoded pesticidal polypeptides, to control plant pests.

BACKGROUND

Insect pests are a major factor in the loss of the world's agricultural crops. For example, armyworm feeding, black cutworm damage, or European corn borer damage can be economically devastating to agricultural producers. Insect pest-related crop loss from European corn borer attacks on field and sweet corn alone has reached about one billion dollars a year in damage and control expenses.

Traditionally, the primary method for impacting insect pest populations is the application of broad-spectrum chemical insecticides. However, consumers and government regulators alike are becoming increasingly concerned with the environmental hazards associated with the production and use of synthetic chemical pesticides. Because of such concerns, regulators have banned or limited the use of some of the more hazardous pesticides. Thus, there is substantial interest in developing alternative pesticides.

Biological control of insect pests of agricultural significance using a microbial agent, such as fungi, bacteria, or another species of insect affords an environmentally friendly and commercially attractive alternative to synthetic chemical pesticides. Generally speaking, the use of biopesticides presents a lower risk of pollution and environmental hazards, and biopesticides provide greater target specificity than is characteristic of traditional broad-spectrum chemical insecticides. In addition, biopesticides often cost less to produce and thus improve economic yield for a wide variety of crops.

Certain species of microorganisms of the genus *Bacillus* are known to possess pesticidal activity against a broad range of insect pests including Lepidoptera, Diptera, Coleoptera, Hemiptera, and others. *Bacillus thuringiensis* (Bt) and *Bacillus papilliae* are among the most successful biocontrol agents discovered to date. Insect pathogenicity has also been attributed to strains of *B. larvae, B. lentimorbus, B. sphaericus* (Harwook, ed., ((1989) *Bacillus* (Plenum Press), 306), and *B. cereus* (WO 96/10083). Pesticidal activity appears to be concentrated in parasporal crystalline protein inclusions, although pesticidal proteins have also been isolated from the vegetative growth stage of *Bacillus*. Several genes encoding these pesticidal proteins have been isolated and characterized (see, for example, U.S. Pat. Nos. 5,366,892 and 5,840,868).

Microbial insecticides, particularly those obtained from *Bacillus* strains, have played an important role in agriculture as alternatives to chemical pest control. Recently, agricultural scientists have developed crop plants with enhanced insect resistance by genetically engineering crop plants to produce pesticidal proteins from *Bacillus*. For example, corn and cotton plants have been genetically engineered to produce pesticidal proteins isolated from strains of Bt (see, e.g., Aronson (2002) *Cell Mol. Life Sci.* 59(3):417-425; Schnepf et al. (1998) *Microbiol Mol Biol Rev.* 62(3):775-806). These genetically engineered crops are now widely used in American agriculture and have provided the farmer with an environmentally friendly alternative to traditional insect-control methods. In addition, potatoes genetically engineered to contain pesticidal Cry toxins have been sold to the American farmer. While they have proven to be very successful commercially, these genetically engineered, insect-resistant crop plants provide resistance to only a narrow range of the economically important insect pests.

Accordingly, there remains a need for new Bt toxins with an improved spectrum of insecticidal activity against insect pests, e.g., toxins which are improved active against insects from the order Lepidoptera and/or Coleoptera. In addition, there remains a need for biopesticides having activity against a variety of insect pests and for biopesticides which have improved insecticidal activity.

SUMMARY

Compositions and methods are provided for impacting insect pests. More specifically, the embodiments of the present disclosure relate to methods of impacting insects utilizing nucleotide sequences encoding insecticidal peptides to produce transformed microorganisms and plants that express an insecticidal polypeptide of the embodiments. In some embodiments, the nucleotide sequences encode polypeptides that are pesticidal for at least one insect belonging to the order Lepidoptera.

In some aspects nucleic acid molecules and fragments and variants thereof are provided, which encode polypeptides that possess pesticidal activity against insect pests (e.g. SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, and SEQ ID NO: 46, and encoding the polypeptide of SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43 or SEQ ID NO: 45, respectively). The wild-type (e.g., naturally occurring) nucleotide sequence of the embodiments, which was obtained from Bt, encodes an insecticidal peptide. The embodiments further provide fragments and variants of the disclosed nucleotide sequence that encode biologically active (e.g., insecticidal) polypeptides.

In another aspect variant Cry1B polypeptides are provided, encoded by a modified (e.g., mutagenized or manipulated) nucleic acid molecule of the embodiments. In particular examples, pesticidal proteins of the embodiments include fragments of full-length proteins and polypeptides that are produced from mutagenized nucleic acids designed to introduce particular amino acid sequences into the polypeptides of the embodiments. In particular embodiments, the polypeptides have enhanced pesticidal activity relative to the activity of the naturally occurring polypeptide from which they are derived.

In another aspect the nucleic acids of the embodiments can also be used to produce transgenic (e.g., transformed) monocot or dicot plants that are characterized by genomes that comprise at least one stably incorporated nucleotide construct comprising a coding sequence of the embodiments operably linked to a promoter that drives expression of the encoded pesticidal polypeptide. Accordingly, transformed plant cells, plant tissues, plants, and seeds thereof are also provided.

In another aspect transformed plant can be produced using a nucleic acid that has been optimized for increased expression in a host plant. For example, one of the pesticidal polypeptides of the embodiments can be back-translated to produce a nucleic acid comprising codons optimized for expression in a particular host, for example a crop plant such as a corn (*Zea mays*) plant. Expression of a coding sequence by such a transformed plant (e.g., dicot or monocot) will result in the production of a pesticidal polypeptide and confer increased insect resistance to the plant. Some embodiments provide transgenic plants expressing pesticidal polypeptides that find use in methods for impacting various insect pests.

In another aspect, pesticidal or insecticidal compositions containing the variant Cry1B polypeptides of the embodiments are provided and the composition can optionally comprise further insecticidal peptides. The embodiments encompass the application of such compositions to the environment of insect pests in order to impact the insect pests.

Compositions and methods for stacking a Cry1B variant polypeptide with a PtIP-83 polypeptide as disclosed in US Patent Application Publication Number US2016/0347799, and/or a PtIP-50 and a PtIP-65 polypeptide as disclosed in PCT Publication Number WO2015/120270 are contemplated by the disclosure. In a further embodiment, compositions and methods for stacking a polynucleotide encoding a Cry1B variant polypeptide with a polynucleotide encoding a PtIP-83 polypeptide and/or a polynucleotide encoding a PtIP-50 and a PtIP-65 polypeptide are also contemplated by the disclosure In one embodiment, methods and compositions are contemplated that comprise polynucleotide sequences encoding a Cry1B variant polypeptide disclosed herein, in combination with a polynucleotide encoding a PtIP-83Aa (SEQ ID NO: 62), a PtIP-83Cb (SEQ ID NO: 64) or a PtIP-83Gb (SEQ ID NO: 66), and/or a polynucleotide encoding a PtIP-50 (SEQ ID NOs: 88-115) and a PtIP-65 (SEQ ID NOs: 67-87) polypeptide.

BRIEF DESCRIPTION OF THE FIGURES

FIG. 1*a*-1*g* shows an amino acid sequence alignment, using the ALIGNX® module of the Vector NTI® suite, of Cry1Bd (SEQ ID NO: 1), IP1B-B1 (SEQ ID NO: 3), IP1B-B21 (SEQ ID NO: 5), IP1B-B22 (SEQ ID NO: 7), IP1B-B23 (SEQ ID NO: 9), IP1B-B24 (SEQ ID NO: 11), IP1B-B25 (SEQ ID NO: 13), IP1B-B26 (SEQ ID NO: 15), IP1B-B27 (SEQ ID NO: 17), IP1B-B28 (SEQ ID NO: 19), IP1B-B29 (SEQ ID NO: 21), IP1B-B31 (SEQ ID NO: 23), IP1B-B32 (SEQ ID NO: 25), IP1B-B33 (SEQ ID NO: 27), IP1B-B34 (SEQ ID NO: 29), IP1B-B40 (SEQ ID NO: 31), IP1B-B41 (SEQ ID NO: 33), IP1B-B42 (SEQ ID NO: 35), IP1B-B43 (SEQ ID NO: 37), IP1B-B44 (SEQ ID NO: 39), IP1B-B45 (SEQ ID NO: 41), IP1B-B46 (SEQ ID NO: 43), IP1B-B47 (SEQ ID NO: 45), MP258 (SEQ ID NO: 47), and GS060 (SEQ ID NO: 49). The amino acid sequence diversity between the Cry1B polypeptides is highlighted.

FIG. 2*a*-2*e* shows the amino acid sequence of MP258 (SEQ ID NO: 47) with the leader region (*), Domain I (#), Domain II (&), and Domain III (!) indicated below the sequence.

FIG. 3 shows an amino acid sequence alignment, using the ALIGNX® module of the Vector NTI® suite, of the Cry1Be type Domain I of Cry1Be (amino acids 35-276 of SEQ ID NO: 58) and the Cry1Be type Domain I of MP258 (amino acids 36-276 of SEQ ID NO: 47). The amino acid sequence diversity between Domains I of the Cry1B polypeptides is highlighted.

FIG. 4 shows an amino acid sequence alignment, using the ALIGNX® module of the Vector NTI® suite, of Domain III of Cry1Ah (SEQ ID NO: 61), Cry1Bd, Cry1Bh (SEQ ID NO: 52), Cry1Bi (SEQ ID NO: 54), and MP258 (SEQ ID NO: 47). The amino acid sequence diversity between Domain III the Cry1B polypeptides is highlighted.

FIG. 5*a*-5*c* shows an amino acid sequence alignment, using the ALIGNX® module of the Vector NTI® suite, of Domain I and Domain II of MP258 (SEQ ID NO: 47), Cry1Be (SEQ ID NO: 58), Cry1Bi (SEQ ID NO: 54), Cry1Bg (SEQ ID NO: 60), Cry1Bf (SEQ ID NO: 59), Cry1Ba (SEQ ID NO: 55), Cry1Bh (SEQ ID NO: 52), Cry1Bd (SEQ ID NO: 1), Cry1Bb (SEQ ID NO: 56), and Cry1Bc (SEQ ID NO: 57). The amino acid sequence diversity between Domain I and Domain II of the Cry1B polypeptides is highlighted.

DETAILED DESCRIPTION

The embodiments of the disclosure are drawn to compositions and methods for impacting insect pests, particularly plant pests. More specifically, the isolated nucleic acid of the embodiments, and fragments and variants thereof, comprise nucleotide sequences that encode pesticidal polypeptides (e.g., proteins). The disclosed pesticidal proteins are biologically active (e.g., pesticidal) against insect pests such as, but not limited to, insect pests of the order Lepidoptera and/or Coleoptera.

The compositions of the embodiments comprise isolated nucleic acids, and fragments and variants thereof, which encode pesticidal polypeptides, expression cassettes comprising nucleotide sequences of the embodiments, isolated pesticidal proteins, and pesticidal compositions. Some embodiments provide modified pesticidal polypeptides having improved insecticidal activity against Lepidopterans relative to the pesticidal activity of the corresponding wild-type protein. The embodiments further provide plants and microorganisms transformed with these novel nucleic acids, and methods involving the use of such nucleic acids, pesticidal compositions, transformed organisms, and products thereof in impacting insect pests.

The nucleic acids and nucleotide sequences of the embodiments may be used to transform any organism to produce the encoded pesticidal proteins. Methods are provided that involve the use of such transformed organisms to impact or control plant pests. The nucleic acids and nucleotide sequences of the embodiments may also be used to transform organelles such as chloroplasts (McBride et al. (1995) *Biotechnology* 13: 362-365; and Kota et al. (1999) *Proc. Natl. Acad. Sci. USA* 96: 1840-1845).

The embodiments further relate to the identification of fragments and variants of the naturally-occurring coding sequence that encode biologically active pesticidal proteins. The nucleotide sequences of the embodiments find direct use in methods for impacting pests, particularly insect pests such as pests of the order Lepidoptera. Accordingly, the embodiments provide new approaches for impacting insect pests that do not depend on the use of traditional, synthetic chemical insecticides. The embodiments involve the discovery of naturally-occurring, biodegradable pesticides and the genes that encode them.

The embodiments further provide fragments and variants of the naturally occurring coding sequence that also encode biologically active (e.g., pesticidal) polypeptides. The nucleic acids of the embodiments encompass nucleic acid or nucleotide sequences that have been optimized for expression by the cells of a particular organism, for example nucleic acid sequences that have been back-translated (i.e., reverse translated) using plant-preferred codons based on the amino acid sequence of a polypeptide having enhanced pesticidal activity. The embodiments further provide mutations which confer improved or altered properties on the polypeptides of the embodiments. See, e.g. U.S. Pat. No. 7,462,760.

In the description that follows, a number of terms are used extensively. The following definitions are provided to facilitate understanding of the embodiments.

Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. The above-defined terms are more fully defined by reference to the specification as a whole.

As used herein, "nucleic acid" includes reference to a deoxyribonucleotide or ribonucleotide polymer in either single- or double-stranded form, and unless otherwise limited, encompasses known analogues (e.g., peptide nucleic acids) having the essential nature of natural nucleotides in that they hybridize to single-stranded nucleic acids in a manner similar to that of naturally occurring nucleotides.

As used herein, the terms "encoding" or "encoded" when used in the context of a specified nucleic acid mean that the nucleic acid comprises the requisite information to direct translation of the nucleotide sequence into a specified protein. The information by which a protein is encoded is specified by the use of codons. A nucleic acid encoding a protein may comprise non-translated sequences (e.g., introns) within translated regions of the nucleic acid or may lack such intervening non-translated sequences (e.g., as in cDNA).

As used herein, "full-length sequence" in reference to a specified polynucleotide or its encoded protein means having the entire nucleic acid sequence or the entire amino acid sequence of a native (non-synthetic), endogenous sequence. A full-length polynucleotide encodes the full-length, catalytically active form of the specified protein.

As used herein, the term "antisense" used in the context of orientation of a nucleotide sequence refers to a duplex polynucleotide sequence that is operably linked to a promoter in an orientation where the antisense strand is transcribed. The antisense strand is sufficiently complementary to an endogenous transcription product such that translation of the endogenous transcription product is often inhibited. Thus, where the term "antisense" is used in the context of a particular nucleotide sequence, the term refers to the complementary strand of the reference transcription product.

The terms "polypeptide," "peptide," and "protein" are used interchangeably herein to refer to a polymer of amino acid residues. The terms apply to amino acid polymers in which one or more amino acid residues is an artificial chemical analogue of a corresponding naturally occurring amino acid, as well as to naturally occurring amino acid polymers.

The terms "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass known analogues of natural amino acids that can function in a similar manner as naturally occurring amino acids.

Polypeptides of the embodiments can be produced either from a nucleic acid disclosed herein, or by the use of standard molecular biology techniques. For example, a protein of the embodiments can be produced by expression of a recombinant nucleic acid of the embodiments in an appropriate host cell, or alternatively by a combination of ex vivo procedures.

As used herein, the terms "isolated" and "purified" are used interchangeably to refer to nucleic acids or polypeptides or biologically active portions thereof that are substantially or essentially free from components that normally accompany or interact with the nucleic acid or polypeptide as found in its naturally occurring environment. Thus, an isolated or purified nucleic acid or polypeptide is substantially free of other cellular material or culture medium when produced by recombinant techniques, or substantially free of chemical precursors or other chemicals when chemically synthesized.

An "isolated" nucleic acid is generally free of sequences (such as, for example, protein-encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acids can contain less than about 5 kb, 4 kb, 3 kb, 2 kb, 1 kb, 0.5 kb, or 0.1 kb of nucleotide sequences that naturally flank the nucleic acids in genomic DNA of the cell from which the nucleic acid is derived.

As used herein, the term "isolated" or "purified" as it is used to refer to a polypeptide of the embodiments means that the isolated protein is substantially free of cellular material and includes preparations of protein having less than about 30%, 20%, 10%, or 5% (by dry weight) of contaminating protein. When the protein of the embodiments or biologically active portion thereof is recombinantly produced, culture medium represents less than about 30%, 20%, 10%, or 5% (by dry weight) of chemical precursors or non-protein-of-interest chemicals.

A "recombinant" nucleic acid molecule (or DNA) is used herein to refer to a nucleic acid sequence (or DNA) that is in a recombinant bacterial or plant host cell. In some embodiments, an "isolated" or "recombinant" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For purposes of the disclosure, "isolated" or "recombinant" when used to refer to nucleic acid molecules excludes isolated chromosomes.

As used herein a "non-genomic nucleic acid sequence" or "non-genomic nucleic acid molecule" refers to a nucleic acid molecule that has one or more change in the nucleic acid sequence compared to a native or genomic nucleic acid sequence. In some embodiments the change to a native or genomic nucleic acid molecule includes but is not limited to: changes in the nucleic acid sequence due to the degeneracy of the genetic code; codon optimization of the nucleic acid sequence for expression in plants; changes in the nucleic acid sequence to introduce at least one amino acid substitution, insertion, deletion and/or addition compared to the native or genomic sequence; removal of one or more intron associated with the genomic nucleic acid sequence; insertion of one or more heterologous introns; deletion of one or more upstream or downstream regulatory regions associated with the genomic nucleic acid sequence; insertion of one or more heterologous upstream or downstream regulatory regions; deletion of the 5' and/or 3' untranslated region associated with the genomic nucleic acid sequence; insertion of a heterologous 5' and/or 3' untranslated region; and modification of a polyadenylation site. In some embodiments the non-genomic nucleic acid molecule is a cDNA. In some embodiments the non-genomic nucleic acid molecule is a synthetic nucleic acid sequence.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps.

As used herein, the term "impacting insect pests" refers to effecting changes in insect feeding, growth, and/or behavior at any stage of development, including but not limited to: killing the insect; retarding growth; preventing reproductive capability; antifeedant activity; and the like.

As used herein, the terms "pesticidal activity" and "insecticidal activity" are used synonymously to refer to activity of an organism or a substance (such as, for example, a protein) that can be measured by, but is not limited to, pest mortality, pest weight loss, pest repellency, and other behavioral and physical changes of a pest after feeding and exposure for an appropriate length of time. Thus, an organism or substance having pesticidal activity adversely impacts at least one measurable parameter of pest fitness. For example, "pesticidal proteins" are proteins that display pesticidal activity by themselves or in combination with other proteins.

As used herein, the term "pesticidally effective amount" means a quantity of a substance or organism that has pesticidal activity when present in the environment of a pest. For each substance or organism, the pesticidally effective amount is determined empirically for each pest affected in a specific environment. Similarly, an "insecticidally effective amount" may be used to refer to a "pesticidally effective amount" when the pest is an insect pest.

As used herein, the term "recombinantly engineered" or "engineered" means the utilization of recombinant DNA technology to introduce (e.g., engineer) a change in the protein structure based on an understanding of the protein's mechanism of action and a consideration of the amino acids being introduced, deleted, or substituted.

As used herein, the term "mutant nucleotide sequence" or "mutation" or "mutagenized nucleotide sequence" means a nucleotide sequence that has been mutagenized or altered to contain one or more nucleotide residues (e.g., base pair) that is not present in the corresponding wild-type sequence. Such mutagenesis or alteration consists of one or more additions, deletions, or substitutions or replacements of nucleic acid residues. When mutations are made by adding, removing, or replacing an amino acid of a proteolytic site, such addition, removal, or replacement may be within or adjacent to the proteolytic site motif, so long as the object of the mutation is accomplished (i.e., so long as proteolysis at the site is changed).

A mutant nucleotide sequence can encode a mutant insecticidal toxin showing improved or decreased insecticidal activity, or an amino acid sequence which confers improved or decreased insecticidal activity on a polypeptide containing it. As used herein, the term "mutant" or "mutation" in the context of a protein a polypeptide or amino acid sequence refers to a sequence which has been mutagenized or altered to contain one or more amino acid residues that are not present in the corresponding wild-type sequence. Such mutagenesis or alteration consists of one or more additions, deletions, or substitutions or replacements of amino acid residues. A mutant polypeptide shows improved or decreased insecticidal activity, or represents an amino acid sequence which confers improved insecticidal activity on a polypeptide containing it. Thus, the term "mutant" or "mutation" refers to either or both of the mutant nucleotide sequence and the encoded amino acids. Mutants may be used alone or in any compatible combination with other mutants of the embodiments or with other mutants. A "mutant polypeptide" may conversely show a decrease in insecticidal activity. Where more than one mutation is added to a particular nucleic acid or protein, the mutations may be added at the same time or sequentially; if sequentially, mutations may be added in any suitable order.

As used herein, the term "improved insecticidal activity" or "improved pesticidal activity" refers to an insecticidal polypeptide of the embodiments that has enhanced insecticidal activity relative to the activity of its corresponding wild-type protein, and/or an insecticidal polypeptide that is effective against a broader range of insects, and/or an insecticidal polypeptide having specificity for an insect that is not susceptible to the toxicity of the wild-type protein. A finding of improved or enhanced pesticidal activity requires a demonstration of an increase of pesticidal activity of at least 10%, against the insect target, or at least 20%, 25%, 30%, 35%, 40%, 45%, 50%, 60%, 70%, 100%, 150%, 200%, or 300% or greater increase of pesticidal activity relative to the pesticidal activity of the wild-type insecticidal polypeptide determined against the same insect.

For example, an improved pesticidal or insecticidal activity is provided where a wider or narrower range of insects is impacted by the polypeptide relative to the range of insects that is affected by a wild-type Bt toxin. A wider range of impact may be desirable where versatility is desired, while a narrower range of impact may be desirable where, for example, beneficial insects might otherwise be impacted by use or presence of the toxin. While the embodiments are not bound by any particular mechanism of action, an improved pesticidal activity may also be provided by changes in one or more characteristics of a polypeptide; for example, the stability or longevity of a polypeptide in an insect gut may be increased relative to the stability or longevity of a corresponding wild-type protein.

The term "toxin" as used herein refers to a polypeptide showing pesticidal activity or insecticidal activity or improved pesticidal activity or improved insecticidal activity. "Bt" or "*Bacillus thuringiensis*" toxin is intended to include the broader class of Cry toxins found in various strains of Bt, which includes such toxins as, for example, Cry1s, Cry2s, or Cry3s. The terms "proteolytic site" or "cleavage site" refer to an amino acid sequence which confers sensitivity to a class of proteases or a particular protease such that a polypeptide containing the amino acid sequence is digested by the class of proteases or particular protease. A proteolytic site is said to be "sensitive" to the protease(s) that recognize that site. It is appreciated in the art that the efficiency of digestion will vary, and that a decrease in efficiency of digestion can lead to an increase in stability or longevity of the polypeptide in an insect gut. Thus, a proteolytic site may confer sensitivity to more than one protease or class of proteases, but the efficiency of digestion at that site by various proteases may vary. Proteolytic sites include, for example, trypsin sites, chymotrypsin sites, and elastase sites.

Research has shown that the insect gut proteases of Lepidopterans include trypsins, chymotrypsins, and elastases. See, e.g., Lenz et al. (1991) *Arch. Insect Biochem. Physiol.* 16: 201-212; and Hedegus et al. (2003) *Arch. Insect Biochem. Physiol.* 53: 30-47. For example, about 18 different trypsins have been found in the midgut of *Helicoverpa armigera* larvae (see Gatehouse et al. (1997) *Insect Biochem. Mol. Biol.* 27: 929-944). The preferred proteolytic substrate sites of these proteases have been investigated. See, e.g., Peterson et al. (1995) *Insect Biochem. Mol. Biol.* 25: 765-774.

Efforts have been made to understand the mechanism of action of Bt toxins and to engineer toxins with improved properties. It has been shown that insect gut proteases can affect the impact of Bt Cry proteins on the insect. Some proteases activate the Cry proteins by processing them from a "protoxin" form into a toxic form, or "toxin." See, Oppert (1999) *Arch. Insect Biochem. Phys.* 42: 1-12; and Carroll et al. (1997) *J. Invertebrate Pathology* 70: 41-49. This activation of the toxin can include the removal of the N- and C-terminal peptides from the protein and can also include internal cleavage of the protein. Other proteases can degrade the Cry proteins. See Oppert, ibid.

A comparison of the amino acid sequences of Cry toxins of different specificities reveals five highly-conserved sequence blocks. Structurally, the toxins comprise three distinct Domains which are, from the N- to C-terminus: a cluster of seven alpha-helices implicated in pore formation (referred to as "Domain I"), three anti-parallel beta sheets implicated in cell binding (referred to as "Domain 2"), and a beta sandwich (referred to as "Domain 3"). The location and properties of these Domains are known to those of skill in the art. See, for example, Li et al. (1991) *Nature,* 305:815-821 and Morse et al. (2001) *Structure,* 9:409-417. When reference is made to a particular domain, such as Domain I, it is understood that the exact endpoints of the domain with regard to a particular sequence are not critical so long as the sequence or portion thereof includes sequence that provides at least some function attributed to the particular domain. Thus, for example, when referring to "Domain I," it is intended that a particular sequence includes a cluster of seven alpha-helices, but the exact endpoints of the sequence used or referred to with regard to that cluster are not critical. One of skill in the art is familiar with the determination of such endpoints and the evaluation of such functions.

In an effort to improve Cry2B toxins, an effort was undertaken to identify the nucleotide sequences encoding the crystal proteins from the selected strains, which had improved activity compared to the native toxin. Depending upon the characteristics of a given preparation, it was recognized that the demonstration of pesticidal activity sometimes required trypsin pretreatment to activate the pesticidal proteins. Thus, it is understood that some pesticidal proteins require protease digestion (e.g., by trypsin, chymotrypsin, and the like) for activation, while other proteins are biologically active (e.g., pesticidal) in the absence of activation.

Such molecules may be altered by means described, for example, U.S. Pat. No. 7,462,760. In addition, nucleic acid sequences may be engineered to encode polypeptides that contain additional mutations that confer improved or altered pesticidal activity relative to the pesticidal activity of the naturally occurring polypeptide. The nucleotide sequences of such engineered nucleic acids comprise mutations not found in the wild type sequences.

The mutant polypeptides of the embodiments are generally prepared by a process that involves the steps of: obtaining a nucleic acid sequence encoding a Cry family polypeptide; analyzing the structure of the polypeptide to identify particular "target" sites for mutagenesis of the underlying gene sequence based on a consideration of the proposed function of the target domain in the mode of action of the toxin; introducing one or more mutations into the nucleic acid sequence to produce a desired change in one or more amino acid residues of the encoded polypeptide sequence; and assaying the polypeptide produced for pesticidal activity.

Many of the Bt insecticidal toxins are related to various degrees by similarities in their amino acid sequences and tertiary structure and means for obtaining the crystal structures of Bt toxins are well known. Exemplary high-resolution crystal structure solution of both the Cry3A and Cry3B polypeptides are available in the literature. The solved structure of Cry3A (Li et al. (1991) *Nature* 353:815-821) provides insight into the relationship between structure and function of the toxin. A combined consideration of the published structural analyses of Bt toxins and the reported function associated with particular structures, motifs, and the like indicates that specific regions of the toxin are correlated with particular functions and discrete steps of the mode of action of the protein. For example, many toxins isolated from Bt are generally described as comprising three domains: a seven-helix bundle that is involved in pore formation, a three-sheet domain that has been implicated in receptor binding, and a beta-sandwich motif (Li et al. (1991) *Nature* 305: 815-821).

As reported in U.S. Pat. Nos. 7,105,332, and 7,462,760, the toxicity of Cry proteins can be improved by targeting the region located between alpha helices 3 and 4 of Domain I of the toxin. This theory was premised on a body of knowledge concerning insecticidal toxins, including: 1) that alpha helices 4 and 5 of Domain I of Cry3A toxins had been reported to insert into the lipid bilayer of cells lining the midgut of susceptible insects (Gazit et al. (1998) *Proc. Natl. Acad. Sci. USA* 95: 12289-12294); 2) the inventors' knowledge of the location of trypsin and chymotrypsin cleavage sites within the amino acid sequence of the wild-type protein; 3) the observation that the wild-type protein was more active against certain insects following in vitro activation by trypsin or chymotrypsin treatment; and 4) reports that digestion of toxins from the 3' end resulted in decreased toxicity to insects.

A series of mutations may be created and placed in a variety of background sequences to create novel polypeptides having enhanced or altered pesticidal activity. See, e.g., U.S. Pat. No. 7,462,760. These mutants include, but are not limited to: the addition of at least one more protease-sensitive site (e.g., trypsin cleavage site) in the region located between helices 3 and 4 of Domain I; the replacement of an original protease-sensitive site in the wild-type sequence with a different protease-sensitive site; the addition of multiple protease-sensitive sites in a particular location; the addition of amino acid residues near protease-sensitive site(s) to alter folding of the polypeptide and thus enhance digestion of the polypeptide at the protease-sensitive site(s); and adding mutations to protect the polypeptide from degradative digestion that reduces toxicity (e.g., making a series of mutations wherein the wild-type amino acid is replaced by valine to protect the polypeptide from digestion). Mutations may be used singly or in any combination to provide polypeptides of the embodiments.

Homologous sequences were identified by similarity search on the non-redundant database (nr) of National Center for Bioinformatics Information (NCBI) using BLAST and PSI-BLAST. The homologous proteins were made up of Cry toxins primarily from *Bacillus thuringiensis*.

A mutation which is an additional or alternative protease-sensitive site may be sensitive to several classes of proteases such as serine proteases, which include trypsin and chymotrypsin, or enzymes such as elastase. Thus, a mutation which is an additional or alternative protease-sensitive site may be designed so that the site is readily recognized and/or cleaved by a category of proteases, such as mammalian proteases or insect proteases. A protease-sensitive site may also be designed to be cleaved by a particular class of enzymes or a particular enzyme known to be produced in an organism, such as, for example, a chymotrypsin produced by the corn earworm *Heliothis zea* (Lenz et al. (1991) *Arch. Insect Biochem. Physiol.* 16: 201-212). Mutations may also confer resistance to proteolytic digestion, for example, to digestion by chymotrypsin at the C-terminus of the peptide.

The presence of an additional and/or alternative protease-sensitive site in the amino acid sequence of the encoded polypeptide can improve the pesticidal activity and/or specificity of the polypeptide encoded by the nucleic acids of the embodiments. Accordingly, the nucleotide sequences of the embodiments can be recombinantly engineered or manipulated to produce polypeptides having improved or altered insecticidal activity and/or specificity compared to that of an unmodified wild-type toxin. In addition, the mutations disclosed herein may be placed in or used in conjunction with other nucleotide sequences to provide improved properties. For example, a protease-sensitive site that is readily cleaved by insect chymotrypsin, e.g., a chymotrypsin found in the bertha armyworm or the corn earworm (Hegedus et al. (2003) *Arch. Insect Biochem. Physiol.* 53: 30-47; and Lenz et al. (1991) *Arch. Insect Biochem. Physiol.* 16: 201-212), may be placed in a Cry background sequence to provide improved toxicity to that sequence. In this manner, the embodiments provide toxic polypeptides with improved properties.

For example, a mutagenized Cry nucleotide sequence can comprise additional mutants that comprise additional codons that introduce a second trypsin-sensitive amino acid sequence (in addition to the naturally occurring trypsin site) into the encoded polypeptide. An alternative addition mutant of the embodiments comprises additional codons designed to introduce at least one additional different protease-sensitive site into the polypeptide, for example, a chymotrypsin-sensitive site located immediately 5' or 3' of the naturally occurring trypsin site. Alternatively, substitution mutants may be created in which at least one codon of the nucleic acid that encodes the naturally occurring protease-sensitive site is destroyed and alternative codons are introduced into the nucleic acid sequence in order to provide a different (e.g., substitute) protease-sensitive site. A replacement mutant may also be added to a Cry sequence in which the naturally-occurring trypsin cleavage site present in the encoded polypeptide is destroyed and a chymotrypsin or elastase cleavage site is introduced in its place.

It is recognized that any nucleotide sequence encoding the amino acid sequences that are proteolytic sites or putative proteolytic sites (for example, sequences such as RR, or LKM) can be used and that the exact identity of the codons used to introduce any of these cleavage sites into a variant polypeptide may vary depending on the use, i.e., expression in a particular plant species. It is also recognized that any of the disclosed mutations can be introduced into any polynucleotide sequence of the embodiments that comprises the codons for amino acid residues that provide the native trypsin cleavage site that is targeted for modification. Accordingly, variants of either full-length toxins or fragments thereof can be modified to contain additional or alternative cleavage sites, and these embodiments are intended to be encompassed by the scope of the embodiments disclosed herein.

It will be appreciated by those of skill in the art that any useful mutation may be added to the sequences of the embodiments so long as the encoded polypeptides retain pesticidal activity. Thus, sequences may also be mutated so that the encoded polypeptides are resistant to proteolytic digestion by chymotrypsin. More than one recognition site can be added in a particular location in any combination, and multiple recognition sites can be added to or removed from the toxin. Thus, additional mutations can comprise three, four, or more recognition sites. It is to be recognized that multiple mutations can be engineered in any suitable polynucleotide sequence; accordingly, either full-length sequences or fragments thereof can be modified to contain additional or alternative cleavage sites as well as to be resistant to proteolytic digestion. In this manner, the embodiments provide Cry toxins containing mutations that improve pesticidal activity as well as improved compositions and methods for impacting pests using other Bt toxins.

Mutations may protect the polypeptide from protease degradation, for example by removing putative proteolytic sites such as putative serine protease sites and elastase recognition sites from different areas. Some or all of such putative sites may be removed or altered so that proteolysis at the location of the original site is decreased. Changes in proteolysis may be assessed by comparing a mutant polypeptide with wild-type toxins or by comparing mutant toxins which differ in their amino acid sequence. Putative proteolytic sites and proteolytic sites include, but are not limited to, the following sequences: RR, a trypsin cleavage site; LKM, a chymotrypsin site; and a trypsin site. These sites may be altered by the addition or deletion of any number and kind of amino acid residues, so long as the pesticidal activity of the polypeptide is increased. Thus, polypeptides encoded by nucleotide sequences comprising mutations will comprise at least one amino acid change or addition relative to the native or background sequence, or 2, 3, 4, 5, 6, 7, 8, 9, 10, 11, 12, 13, 14, 15, 16, 17, 18, 19, 20, 21, 22, 23, 24, 25, 26, 27, 28, 29, 30, 32, 35, 38, 40, 45, 47, 50, 60, 70, 80, 90, 100, 110, 120, 130, 140, 150, 160, 170, 180, 190, 200, 210, 220, 230, 240, 250, 260, 270, or 280 or more amino acid changes or additions. Pesticidal activity of a polypeptide may also be improved by truncation of the native or full-length sequence, as is known in the art.

Compositions of the embodiments include nucleic acids, and fragments and variants thereof that encode pesticidal polypeptides. In particular, the embodiments provide for isolated nucleic acid molecules comprising nucleotide sequences encoding the amino acid sequence of SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43 and SEQ ID NO: 45, or the nucleotide sequences encoding said amino acid sequence, for example the nucleotide sequence set forth in SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44 or SEQ ID NO: 46, and fragments and variants thereof.

In particular, the embodiments provide for isolated nucleic acid molecules encoding the amino acid sequence shown in SEQ ID NO: 4 or SEQ ID NO: 8, or the nucleotide sequences encoding said amino acid sequence, for example the nucleotide sequence set forth in SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, and SEQ ID NO: 46, and fragments and variants thereof.

Also of interest are optimized nucleotide sequences encoding the pesticidal proteins of the embodiments. As used herein, the phrase "optimized nucleotide sequences" refers to nucleic acids that are optimized for expression in a particular organism, for example a plant. Optimized nucleotide sequences may be prepared for any organism of interest using methods known in the art. See, for example, U.S. Pat. No. 7,462,760, which describes an optimized nucleotide sequence encoding a disclosed pesticidal protein. In this example, the nucleotide sequence was prepared by reverse-translating the amino acid sequence of the protein and changing the nucleotide sequence so as to comprise maize-preferred codons while still encoding the same amino acid sequence. This procedure is described in more detail by Murray et al. (1989) *Nucleic Acids Res.* 17:477-498. Optimized nucleotide sequences find use in increasing expression of a pesticidal protein in a plant, for example monocot plants of the Gramineae (Poaceae) family such as, for example, a maize or corn plant.

In some embodiments polypeptides are provided comprising an amino acid sequence set forth in SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43 or SEQ ID NO: 45 and fragments and variants thereof.

In some embodiments polypeptides are provided comprising an amino acid sequence set forth in SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 31, SEQ ID NO: 33, SEQ ID NO: 35, SEQ ID NO: 37, SEQ ID NO: 39, SEQ ID NO: 41, SEQ ID NO: 43 or SEQ ID NO: 45 and fragments and variants thereof.

In some embodiments polypeptides are provided comprising an amino acid sequence set forth in SEQ ID NO: 23, SEQ ID NO: 25, SEQ ID NO: 27 or SEQ ID NO: 29, and fragments and variants thereof.

In some embodiments variant Cry1B polypeptides having an amino acid substitution compared to the corresponding reference Cry1B polypeptide are provides that have increased insecticidal activity against corn earworm and/or fall armyworm compared to the "corresponding reference Cry1B polypeptide". By "corresponding reference Cry1B polypeptide" is meant a wild type or native Cry1B polypeptide or variant Cry1B polypeptide of the present embodiments, which can serve as the amino acid sequence that is mutagenized to create variant Cry1B polypeptide. In some embodiments the corresponding reference Cry1B polypeptide comprises a Cry1Be type Domain I and a Cry1Ah type Domain III. By "Cry1Be type Domain I" is meant an amino acid sequence comprising a Domain I, which comprises a cluster of seven alpha-helices, of a three domain Cry1 polypeptide, having at least 90%, at least 91%, at least 92% at least 93% at least 94%, at least 95% at least 96%, at least 97%, at least 98%, at least 99% or greater sequence identity to amino acids 36-276 of SEQ ID NO: 58 (Cry1Be) or amino acids 35-276 of SEQ ID NO: 47. An amino acid sequence alignment of Domain I of Cry1Be (SEQ ID NO: 58) and MP258 (SEQ ID NO: 47) is shown in FIG. 3. Similarly, other native Cry1B polypeptides can be aligned with Cry1Be (SEQ ID NO: 58) and MP258 (SEQ ID NO: 47) to identify other Cry1Be type Domain I regions. By "Cry1Ah type Domain III" is meant an amino acid sequence comprising a Domain III, of a three domain Cry1 polypeptide having at least 80%, at least 81%, at least 82%, at least 83%, at least 84%, at least 85%, at least 86%, at least 87%, at least 88%, at least 89%, at least 90%, at least 91%, at least 92% at least 93% at least 94%, at least 95% at least 96%, at least 97%, at least 98%, at least 99% or greater sequence identity to amino acids 483-643 of SEQ ID NO: 61 (Cry1Ah) or 494-655 of SEQ ID NO: 47. An amino acid sequence alignment of Domain III of Cry1Ah (SEQ ID NO: 61), Cry1Bd (SEQ ID NO: 1), Cry1Bh (SEQ ID NO: 52), Cry1Bi (SEQ ID NO: 54), and MP258 (SEQ ID NO: 47) is shown in FIG. 4. Similarly, other native Cry1B polypeptides can be aligned with Cry1Ah (SEQ ID NO: 61), Cry1Bd, Cry1Bh (SEQ ID NO: 52), Cry1Bi (SEQ ID NO: 54), and/or MP258 (SEQ ID NO: 47) to identify other Cry1Ah type Domain III regions. In some embodiments the corresponding reference Cry1B polypeptide comprises a Cry1Ba type Domain I and Domain II. By "Cry1Ba type Domain I and Domain II" is meant an amino acid sequence comprising a Domain I and Domain II, of a three domain Cry1B polypeptide, having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92% at least 93% at least 94%, at least 95% at least 96%, at least 97%, at least 98%, at least 99% or greater sequence identity to amino acids 30-489 of SEQ ID NO: 55 (Cry1Ba). An amino acid sequence alignment of Domain I and Domain II of MP258 (SEQ ID NO: 47), Cry1Be (SEQ ID NO: 58), Cry1Bi (SEQ ID NO: 54), Cry1Bg (SEQ ID NO: 60), Cry1Bf (SEQ ID NO: 59), Cry1Ba (SEQ ID NO: 55), Cry1Bh (SEQ ID NO: 52), Cry1Bd (SEQ ID NO: 1), Cry1Bb (SEQ ID NO: 56), and Cry1Bc (SEQ ID NO: 57) is shown in FIG. 5. Similarly, other native Cry1B polypeptides can be aligned with Cry1Ba (SEQ ID NO: 55) and MP258 (SEQ ID NO: 47) to identify other Cry1Ba type Domain I and Domain II regions.

In some embodiments the corresponding reference Cry1B polypeptide comprises a Cry1Be type Domain I and Domain II. By "Cry1Be type Domain I and Domain II" is meant an amino acid sequence comprising a Domain I and Domain II, of a three domain Cry1B polypeptide, having at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92% at least 93% at least 94%, at least 95% at least 96%, at least 97%, at least 98%, at least 99% or greater sequence identity to amino acids 35-494 of SEQ ID NO: 58 (Cry1Be) or amino acids 35-493 of SEQ ID NO: 47. An amino acid sequence alignment of Domain I and Domain II of MP258 (SEQ ID NO: 47), Cry1Be (SEQ ID NO: 58), Cry1Bi (SEQ ID NO: 54), Cry1Bg (SEQ ID NO: 60), Cry1Bf (SEQ ID NO: 59), Cry1Ba (SEQ ID NO: 55), Cry1Bh (SEQ ID NO: 52), Cry1Bd (SEQ ID NO: 1), Cry1Bb (SEQ ID NO: 56), and Cry1Bc (SEQ ID NO: 57) is shown in FIG. 5. Similarly, other native Cry1B polypeptides can be aligned with Cry1Be (SEQ ID NO: 58) and MP258 (SEQ ID NO: 47) to identify other Cry1Be type Domain I and Domain II regions.

By "improved activity" or "increased activity" is intended an increase of at least about 10%, at least about 15%, at least about 20%, at least about 25%, at least about 30%, at least about 35%, at least about 40%, at least about 50%, at least about 60%, at least about 70%, at least about 80%, at least about 90%, at least about 100%, at least about 110%, at least about 120%, at least about 130%, at least about 140%, at least about 150%, at least about 160%, at least about 170%, at least about 180%, at least about 190%, at least about 200%, at least about 210% at least about 220%, at least about 230%, at least about 240%, at least about 250%, at least about 260%, at least about 270%, at least about 280%, at least about 290%, at least about 300%, at least about 310%, at least about 320%, at least about 330%, at least about 340%, at least about 350%, at least about 360%, at least about 370%, at least about 380%, at least about 390%, at least about 400%, at least about 410%, at least about 420%, at least about 430%, at least about 440%, at least about 450%, at least about 460%, at least about 470%, at least about 480%, at least about 490%, at least about 500%, at least about 510%, at least about 520%, at least about 530%, at least about 540%, at least about 550%, at least about 560%, at least about 570%, at least about 580%, at least about 590%, at least about 600%, at least about 650%, at least about 700%, at least about 750%, at least about 800%, at least about 850%, at least about 900%, at least about 950%, at least about 1000% or higher or at least about 1.1-fold, at least about 1.2-fold, at least about 1.3-fold, at least about 1.4-fold or at least about 1.5-fold, at least about 1.6-fold, at least about 1.7-fold, at least about 1.8-fold, at least about 1.9-fold, at least about 2-fold, at least about 2.1-fold, at least about 2.2-fold, at least about 2.3-fold, at least about 2.4-fold, at least about 2.5-fold, at least about 2.6-fold, at least about 2.7-fold, at least about 2.8-fold, at least about 2.9-fold, at least about 3-fold, at least about 3.1-fold, at least about 3.2-fold, at least about 3.3-fold, at least about 3.4-fold, at least about 3.5-fold, at least about 3.6-fold, at least about 3.7-fold, at least about 3.8-fold, at least about 3.9-fold, at least about 4-fold, at least about 4.1-fold, at least about 4.2-fold, at least about 4.3-fold, at least about 4.4-fold, at least about 4.5-fold, at least about 4.6-fold, at least about 4.7-fold, at least about 4.8-fold, at least about 4.9-fold, at least about 5-fold, at least about 5.1-fold, at least about 5.2-fold, at least about 5.3-fold, at least about 5.4-fold, at least about 5.5-fold, at least about 5.6-fold, at least about 5.7-fold, at least about 5.8-fold, at least about 5.9-fold, at least about 6-fold, at least about 6.1-fold, at least about 6.2-fold, at least about 6.3-fold, at least about 6.4-fold, at least about 6.5-fold, at least about 6.6-fold, at least about 6.7-fold, at least about 6.8-fold, at least about 6.9-fold, at least about 7-fold, at least about 7.1-fold, at least about 7.2-fold, at least about 7.3-fold, at least about 7.4-fold, at least about 7.5-fold, at least about 7.6-fold, at least about 7.7-fold, at least about 7.8-fold, at least about 7.9-fold, at least about 8-fold, at least about 8.1-fold, at least about 8.2-fold, at least about 8.3-fold, at least about 8.4-fold, at least about 8.5-fold, at least about 8.6-fold, at least about 8.7-fold, at least about 8.8-fold, at least about 8.9-fold, at least about 9-fold, at least about 9.1-fold, at least about 9.2-fold, at least about 9.3-fold, at least about 9.4-fold, at least about 9.5-fold, at least about 9.6-fold, at least about 9.7-fold, at least about 9.8-fold, at least about 9.9-fold, at least about 10-fold or higher increase in the pesticidal activity of the variant protein compared to the activity of the corresponding reference Cry1B polypeptide.

In some embodiments, the improvement consists of a decrease in the EC50 of at least about 10%, at least about 15%, at least about 20%, at least about 25%, at least about 30%, at least about 35%, at least about 40%, at least about 50%, at least about 60%, at least about 70%, at least about 80%, at least about 90%, at least about 100%, at least about 110%, at least about 120%, at least about 130%, at least about 140%, at least about 150%, at least about 160%, at least about 170%, at least about 180%, at least about 190%, at least about 200%, at least about 210% at least about 220%, at least about 230%, at least about 240%, at least about 250%, at least about 260%, at least about 270%, at least about 280%, at least about 290%, at least about 300%, at least about 310%, at least about 320%, at least about 330%, at least about 340%, at least about 350%, at least about 360%, at least about 370%, at least about 380%, at least about 390%, at least about 400%, at least about 410%, at least about 420%, at least about 430%, at least about 440%, at least about 450%, at least about 460%, at least about 470%, at least about 480%, at least about 490%, at least about 500%, at least about 510%, at least about 520%, at least about 530%, at least about 540%, at least about 550%, at least about 560%, at least about 570%, at least about 580%, at least about 590%, at least about 600%, at least about 650%, at least about 700%, at least about 750%, at least about 800%, at least about 850%, at least about 900%, at least about 950%, at least about 1000% or higher or at least about 1.1-fold, at least about 1.2-fold, at least about 1.3-fold, at least about 1.4-fold or at least about 1.5-fold, at least about 1.6-fold, at least about 1.7-fold, at least about 1.8-fold, at least about 1.9-fold, at least about 2-fold, at least about 2.1-fold, at least about 2.2-fold, at least about 2.3-fold, at least about 2.4-fold, at least about 2.5-fold, at least about 2.6-fold, at least about 2.7-fold, at least about 2.8-fold, at least about 2.9-fold, at least about 3-fold, at least about 3.1-fold, at least about 3.2-fold, at least about 3.3-fold, at least about 3.4-fold, at least about 3.5-fold, at least about 3.6-fold, at least about 3.7-fold, at least about 3.8-fold, at least about 3.9-fold, at least about 4-fold, at least about 4.1-fold, at least about 4.2-fold, at least about 4.3-fold, at least about 4.4-fold, at least about 4.5-fold, at least about 4.6-fold, at least about 4.7-fold, at least about 4.8-fold, at least about 4.9-fold, at least about 5-fold, at least about 5.1-fold, at least about 5.2-fold, at least about 5.3-fold, at least about 5.4-fold, at least about 5.5-fold, at least about 5.6-fold, at least about 5.7-fold, at least about 5.8-fold, at least about 5.9-fold, at least about 6-fold, at least about 6.1-fold, at least about 6.2-fold, at least about 6.3-fold, at least about 6.4-fold, at least about 6.5-fold, at least about 6.6-fold, at least about 6.7-fold, at least about 6.8-fold, at least about 6.9-fold, at least about 7-fold, at least about 7.1-fold, at least about 7.2-fold, at least about 7.3-fold, at least about 7.4-fold, at least about 7.5-fold, at least about 7.6-fold, at least about 7.7-fold, at least about 7.8-fold, at least about 7.9-fold, at least about 8-fold, at least about 8.1-fold, at least about 8.2-fold, at least about 8.3-fold, at least about 8.4-fold, at least about 8.5-fold, at least about 8.6-fold, at least about 8.7-fold, at least about 8.8-fold, at least about 8.9-fold, at least about 9-fold, at least about 9.1-fold, at least about 9.2-fold, at least about 9.3-fold, at least about 9.4-fold, at least about 9.5-fold, at least about 9.6-fold, at least about 9.7-fold, at least about 9.8-fold, at least about 9.9-fold, at least about 10-fold or greater reduction in the EC50 of the variant Cry1B polypeptide relative to the pesticidal activity of the corresponding reference Cry1B polypeptide.

In some embodiments the EC50 of the variant Cry1B polypeptide is <100 ppm, <90 ppm, <80 ppm, <70 ppm, <60 ppm, <50 ppm, <45 ppm, <40 ppm, <35 ppm, <30 ppm, <25 ppm, <20 ppm, <19 ppm, <18 ppm, <17 ppm, <16 ppm, <15 ppm, <14 ppm, <13 ppm, <12 ppm, <11 ppm, <10 ppm, <9 ppm, <8 ppm, <7 ppm, <6 ppm, <5 ppm, <4 ppm, <3 ppm, <2 ppm, <1 ppm, <0.9 ppm, <0.8 ppm, <0.7 ppm, <0.6 ppm, <0.5 ppm, <0.4 ppm, <0.3 ppm, <0.2 ppm or <0.1 ppm.

In some embodiments, the improvement consists of an increase in the Mean FAE Index of at least about 10%, at least about 15%, at least about 20%, at least about 25%, at least about 30%, at least about 35%, at least about 40%, at least about 50%, at least about 60%, at least about 70%, at least about 80%, at least about 90%, at least about 100%, at least about 110%, at least about 120%, at least about 130%, at least about 140%, at least about 150%, at least about 160%, at least about 170%, at least about 180%, at least about 190%, at least about 200%, at least about 210% at least about 220%, at least about 230%, at least about 240%, at least about 250%, at least about 260%, at least about 270%, at least about 280%, at least about 290%, at least about 300%, at least about 310%, at least about 320%, at least about 330%, at least about 340%, at least about 350%, at least about 360%, at least about 370%, at least about 380%, at least about 390%, at least about 400%, at least about 410%, at least about 420%, at least about 430%, at least about 440%, at least about 450%, at least about 460%, at least about 470%, at least about 480%, at least about 490%, at least about 500%, at least about 510%, at least about 520%, at least about 530%, at least about 540%, at least about 550%, at least about 560%, at least about 570%, at least about 580%, at least about 590%, at least about 600%, at least about 650%, at least about 700%, at least about 750%, at least about 800%, at least about 850%, at least about 900%, at least about 950%, at least about 1000% or higher or at least about 1.1-fold, at least about 1.2-fold, at least about 1.3-fold, at least about 1.4-fold or at least about 1.5-fold, at least about 1.6-fold, at least about 1.7-fold, at least about 1.8-fold, at least about 1.9-fold, at least about 2-fold, at least about 2.1-fold, at least about 2.2-fold, at least about 2.3-fold, at least about 2.4-fold, at least about 2.5-fold, at least about 2.6-fold, at least about 2.7-fold, at least about 2.8-fold, at least about 2.9-fold, at least about 3-fold, at least about 3.1-fold, at least about 3.2-fold, at least about 3.3-fold, at least about 3.4-fold, at least about 3.5-fold, at least about 3.6-fold, at least about 3.7-fold, at least about 3.8-fold, at least about 3.9-fold, at least about 4-fold, at least about 4.1-fold, at least about 4.2-fold, at least about 4.3-fold, at least about 4.4-fold, at least about 4.5-fold, at least about 4.6-fold, at least about 4.7-fold, at least about 4.8-fold, at least about 4.9-fold, at least about 5-fold, at least about 5.1-fold, at least about 5.2-fold, at least about 5.3-fold, at least about 5.4-fold, at least about 5.5-fold, at least about 5.6-fold, at least about 5.7-fold, at least about 5.8-fold, at least about 5.9-fold, at least about 6-fold, at least about 6.1-fold, at least about 6.2-fold, at least about 6.3-fold, at least about 6.4-fold, at least about 6.5-fold, at least about 6.6-fold, at least about 6.7-fold, at least about 6.8-fold, at least about 6.9-fold, at least about 7-fold, at least about 7.1-fold, at least about 7.2-fold, at least about 7.3-fold, at least about 7.4-fold, at least about 7.5-fold, at least about 7.6-fold, at least about 7.7-fold, at least about 7.8-fold, at least about 7.9-fold, at least about 8-fold, at least about 8.1-fold, at least about 8.2-fold, at least about 8.3-fold, at least about 8.4-fold, at least about 8.5-fold, at least about 8.6-fold, at least about 8.7-fold, at least about 8.8-fold, at least about 8.9-fold, at least about 9-fold, at least about 9.1-fold, at least about 9.2-fold, at least about 9.3-fold, at least about 9.4-fold, at least about 9.5-fold, at least about 9.6-fold, at least about 9.7-fold, at least about 9.8-fold, at least about 9.9-fold, at least about 10-fold or higher increase in the Mean FAE Index of the variant Cry1B polypeptide relative to the pesticidal activity of the corresponding reference Cry1B polypeptide.

"Mean FAE Index" (MFI) refers to the mean of multiple FAEGN an arithmetic mean of FAEGN. As used herein, the "Mean Deviation Score" refers to the arithmetic mean of multiple Deviation Scores.

In some embodiments, the improvement consists of an increase in the Mean Deviation Score of at least about 10%, at least about 15%, at least about 20%, at least about 25%, at least about 30%, at least about 35%, at least about 40%, at least about 50%, at least about 60%, at least about 70%, at least about 80%, at least about 90%, at least about 100%, at least about 110%, at least about 120%, at least about 130%, at least about 140%, at least about 150%, at least about 160%, at least about 170%, at least about 180%, at least about 190%, at least about 200%, at least about 210% at least about 220%, at least about 230%, at least about 240%, at least about 250%, at least about 260%, at least about 270%, at least about 280%, at least about 290%, at least about 300%, at least about 310%, at least about 320%, at least about 330%, at least about 340%, at least about 350%, at least about 360%, at least about 370%, at least about 380%, at least about 390%, at least about 400%, at least about 410%, at least about 420%, at least about 430%, at least about 440%, at least about 450%, at least about 460%, at least about 470%, at least about 480%, at least about 490%, at least about 500%, at least about 510%, at least about 520%, at least about 530%, at least about 540%, at least about 550%, at least about 560%, at least about 570%, at least about 580%, at least about 590%, at least about 600%, at least about 650%, at least about 700%, at least about 750%, at least about 800%, at least about 850%, at least about 900%, at least about 950%, at least about 1000% or higher or at least about 1.1-fold, at least about 1.2-fold, at least about 1.3-fold, at least about 1.4-fold or at least about 1.5-fold, at least about 1.6-fold, at least about 1.7-fold, at least about 1.8-fold, at least about 1.9-fold, at least about 2-fold, at least about 2.1-fold, at least about 2.2-fold, at least about 2.3-fold, at least about 2.4-fold, at least about 2.5-fold, at least about 2.6-fold, at least about 2.7-fold, at least about 2.8-fold, at least about 2.9-fold, at least about 3-fold, at least about 3.1-fold, at least about 3.2-fold, at least about 3.3-fold, at least about 3.4-fold, at least about 3.5-fold, at least about 3.6-fold, at least about 3.7-fold, at least about 3.8-fold, at least about 3.9-fold, at least about 4-fold, at least about 4.1-fold, at least about 4.2-fold, at least about 4.3-fold, at least about 4.4-fold, at least about 4.5-fold, at least about 4.6-fold, at least about 4.7-fold, at least about 4.8-fold, at least about 4.9-fold, at least about 5-fold, at least about 5.1-fold, at least about 5.2-fold, at least about 5.3-fold, at least about 5.4-fold, at least about 5.5-fold, at least about 5.6-fold, at least about 5.7-fold, at least about 5.8-fold, at least about 5.9-fold, at least about 6-fold, at least about 6.1-fold, at least about 6.2-fold, at least about 6.3-fold, at least about 6.4-fold, at least about 6.5-fold, at least about 6.6-fold, at least about 6.7-fold, at least about 6.8-fold, at least about 6.9-fold, at least about 7-fold, at least about 7.1-fold, at least about 7.2-fold, at least about 7.3-fold, at least about 7.4-fold, at least about 7.5-fold, at least about 7.6-fold, at least about 7.7-fold, at least about 7.8-fold, at least about 7.9-fold, at least about 8-fold, at least about 8.1-fold, at least about 8.2-fold, at least about 8.3-fold, at least about 8.4-fold, at least about 8.5-fold, at least about 8.6-fold, at least about 8.7-fold, at least about 8.8-fold, at least about 8.9-fold, at least about 9-fold, at least about 9.1-fold, at least about 9.2-fold, at least about 9.3-fold, at least about 9.4-fold, at least about 9.5-fold, at least about 9.6-fold, at least about 9.7-fold, at least about 9.8-fold, at least about 9.9-fold, at least about 10-fold or higher increase in the Mean Deviation Score of the variant Cry1B polypeptide relative to the pesticidal activity of the corresponding reference Cry1B polypeptide.

In some embodiments the improved activity of the variant Cry1B polypeptide is relative to the pesticidal activity of SEQ ID NO: 1 (Cry1Bd), SEQ ID NO: 47 (MP258), SEQ ID NO: 52 (Cry1Bh), SEQ ID NO: 54 (Cry1B0, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 31, SEQ ID NO: 33, SEQ ID NO: 35, SEQ ID NO: 37, SEQ ID NO: 39, SEQ ID NO: 41, SEQ ID NO: 43 or SEQ ID NO: 45.

In particular embodiments, pesticidal proteins of the embodiments provide full-length insecticidal polypeptides, fragments of full-length insecticidal polypeptides, and variant polypeptides that are produced from mutagenized nucleic acids designed to introduce particular amino acid sequences into polypeptides of the embodiments. In particular embodiments, the amino acid sequences that are introduced into the polypeptides comprise a sequence that provides a cleavage site for an enzyme such as a protease.

It is known in the art that the pesticidal activity of Bt toxins is typically activated by cleavage of the peptide in the insect gut by various proteases. Because peptides may not always be cleaved with complete efficiency in the insect gut, fragments of a full-length toxin may have enhanced pesticidal activity in comparison to the full-length toxin itself. Thus, some of the polypeptides of the embodiments include fragments of a full-length insecticidal polypeptide, and some of the polypeptide fragments, variants, and mutations will have enhanced pesticidal activity relative to the activity of the naturally occurring insecticidal polypeptide from which they are derived, particularly if the naturally occurring insecticidal polypeptide is not activated in vitro with a protease prior to screening for activity. Thus, the present application encompasses truncated versions or fragments of the sequences.

Mutations may be placed into any background sequence, including such truncated polypeptides, so long as the polypeptide retains pesticidal activity. One of skill in the art can readily compare two or more proteins with regard to pesticidal activity using assays known in the art or described elsewhere herein. It is to be understood that the polypeptides of the embodiments can be produced either by expression of a nucleic acid disclosed herein, or by the use of standard molecular biology techniques.

It is recognized that the pesticidal proteins may be oligomeric and will vary in molecular weight, number of residues, component peptides, activity against particular pests, and other characteristics. However, by the methods set forth herein, proteins active against a variety of pests may be isolated and characterized. The pesticidal proteins of the embodiments can be used in combination with other Bt toxins or other insecticidal proteins to increase insect target range. Furthermore, the use of the pesticidal proteins of the embodiments in combination with other Bt toxins or other insecticidal principles of a distinct nature has particular utility for the prevention and/or management of insect resistance. Other insecticidal agents include protease inhibitors (both serine and cysteine types), α-amylase, and peroxidase.

Fragments and variants of the nucleotide and amino acid sequences and the polypeptides encoded thereby are also encompassed by the embodiments. As used herein the term "fragment" refers to a portion of a nucleotide sequence of a polynucleotide or a portion of an amino acid sequence of a polypeptide of the embodiments. Fragments of a nucleotide sequence may encode protein fragments that retain the biological activity of the native or corresponding full-length protein and hence possess pesticidal activity. Thus, it is acknowledged that some of the polynucleotide and amino acid sequences of the embodiments can correctly be referred to as both fragments and mutants.

It is to be understood that the term "fragment," as it is used to refer to nucleic acid sequences of the embodiments, also encompasses sequences that are useful as hybridization probes. This class of nucleotide sequences generally does not encode fragment proteins retaining biological activity. Thus, fragments of a nucleotide sequence may range from at least about 20 nucleotides, about 50 nucleotides, about 100 nucleotides, and up to the full-length nucleotide sequence encoding the proteins of the embodiments.

A fragment of a nucleotide sequence of the embodiments that encodes a biologically active portion of a pesticidal protein of the embodiments will encode at least 15, 25, 30, 50, 100, 200, 250 or 300 contiguous amino acids, or up to the total number of amino acids present in a pesticidal polypeptide of the embodiments (for example, 651 amino acids for SEQ ID NO: 3). Thus, it is understood that the embodiments also encompass polypeptides that are fragments of the exemplary pesticidal proteins of the embodiments and having lengths of at least 15, 25, 30, 50, 100, 200, 250 or 300 contiguous amino acids, or up to the total number of amino acids present in a pesticidal polypeptide of the embodiments (for example, 651 amino acids for SEQ ID NO: 3). Fragments of a nucleotide sequence of the embodiments that are useful as hybridization probes or PCR primers generally need not encode a biologically active portion of a pesticidal protein. Thus, a fragment of a nucleic acid of the embodiments may encode a biologically active portion of a pesticidal protein, or it may be a fragment that can be used as a hybridization probe or PCR primer using methods disclosed herein. A biologically active portion of a pesticidal protein can be prepared by isolating a portion of one of the nucleotide sequences of the embodiments, expressing the encoded portion of the pesticidal protein (e.g., by recombinant expression in vitro), and assessing the activity of the encoded portion of the pesticidal protein.

Nucleic acids that are fragments of a nucleotide sequence of the embodiments comprise at least 16, 20, 50, 75, 100, 150, 200, 250, 300, 350, 400, 450, 500, 600, 700, 800, 850, 900 or 950 nucleotides, or up to the number of nucleotides present in a nucleotide sequence disclosed herein (for example, 1953 nucleotides for SEQ ID NO: 4). Particular embodiments envision fragments derived from (e.g., produced from) a first nucleic acid of the embodiments, wherein the fragment encodes a truncated toxin having pesticidal activity. Truncated polypeptides encoded by the polynucleotide fragments of the embodiments are having pesticidal activity that is either equivalent to, or improved, relative to the activity of the corresponding full-length polypeptide encoded by the first nucleic acid from which the fragment is derived. It is envisioned that such nucleic acid fragments of the embodiments may be truncated at the 3' end of the native or corresponding full-length coding sequence. Nucleic acid fragments may also be truncated at both the 5' and 3' end of the native or corresponding full-length coding sequence.

The term "variants" is used herein to refer to substantially similar sequences. For nucleotide sequences, conservative variants include those sequences that, because of the degeneracy of the genetic code, encode the amino acid sequence of one of the pesticidal polypeptides of the embodiments. Those having ordinary skill in the art will readily appreciate that due to the degeneracy of the genetic code, a multitude of nucleotide sequences encoding of the present disclosure exist.

In some embodiments the nucleic acid molecule encoding the polypeptide is a non-genomic nucleic acid sequence. As used herein a "non-genomic nucleic acid sequence" or "non-genomic nucleic acid molecule" or "non-genomic polynucleotide" refers to a nucleic acid molecule that has one or more change in the nucleic acid sequence compared to a native or genomic nucleic acid sequence. In some embodiments the change to a native or genomic nucleic acid molecule includes but is not limited to: changes in the nucleic acid sequence due to the degeneracy of the genetic code; codon optimization of the nucleic acid sequence for expression in plants; changes in the nucleic acid sequence to introduce at least one amino acid substitution, insertion, deletion and/or addition compared to the native or genomic sequence; removal of one or more intron associated with the genomic nucleic acid sequence; insertion of one or more heterologous introns; deletion of one or more upstream or downstream regulatory regions associated with the genomic nucleic acid sequence; insertion of one or more heterologous upstream or downstream regulatory regions; deletion of the 5' and/or 3' untranslated region associated with the genomic nucleic acid sequence; insertion of a heterologous 5' and/or 3' untranslated region; and modification of a polyadenylation site. In some embodiments the non-genomic nucleic acid molecule is a cDNA. In some embodiments the non-genomic nucleic acid molecule is a synthetic nucleic acid sequence.

Where appropriate, a nucleic acid may be optimized for increased expression in the host organism. Thus, where the host organism is a plant, the synthetic nucleic acids can be synthesized using plant-preferred codons for improved expression. See, for example, Campbell and Gowri, (1990) *Plant Physiol.* 92:1-11 for a discussion of host-preferred codon usage. For example, although nucleic acid sequences of the embodiments may be expressed in both monocotyledonous and dicotyledonous plant species, sequences can be modified to account for the specific codon preferences and GC content preferences of monocotyledons or dicotyledons as these preferences have been shown to differ (Murray et al. (1989) *Nucleic Acids Res.* 17:477-498). Thus, the maize-preferred codon for a particular amino acid may be derived from known gene sequences from maize. Maize codon usage for 28 genes from maize plants is listed in Table 4 of Murray, et al., supra. Methods are available in the art for synthesizing plant-preferred genes. A *Zea maize* codon usage table can be also found at kazusa.or.jp/codon/cgi-bin/showcodon.cgi?species=4577, which can be accessed using the www prefix.

A *Glycine max* codon usage table is shown in Table 3 and can also be found at kazusa.or.jp/codon/cgi-bin/showcodon.cgi?species=3847&aa=1&style=N, which can be accessed using the www prefix.

The skilled artisan will further appreciate that changes can be introduced by mutation of the nucleic acid sequences thereby leading to changes in the amino acid sequence of the encoded polypeptides, without altering the biological activity of the proteins. Thus, variant nucleic acid molecules can be created by introducing one or more nucleotide substitutions, additions and/or deletions into the corresponding nucleic acid sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleic acid sequences are also encompassed by the present disclosure.

Naturally occurring allelic variants such as these can be identified with the use of well-known molecular biology techniques, such as, for example, polymerase chain reaction (PCR) and hybridization techniques as outlined herein.

In some embodiments the polynucleotide encoding the polypeptide of SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43 or SEQ ID NO: 45 is a non-genomic nucleic acid sequence.

Variant nucleotide sequences also include synthetically derived nucleotide sequences, such as those generated, for example, by using site-directed mutagenesis but which still encode a pesticidal protein of the embodiments, such as a mutant toxin. Generally, variants of a particular nucleotide sequence of the embodiments will have at least about 70%, 75%, 80%, 85%, 86%, 87%, 88%, 89%, 90%, 91%, 92%, 93%, 94%, 95%, 96%, 97%, 98%, 99%, or more sequence identity to that particular nucleotide sequence as determined by sequence alignment programs described elsewhere herein using default parameters. A variant of a nucleotide sequence of the embodiments may differ from that sequence by as few as 1-15 nucleotides, as few as 1-10, such as 6-10, as few as 5, as few as 4, 3, 2, or even 1 nucleotide.

Variants of a particular nucleotide sequence of the embodiments (i.e., an exemplary nucleotide sequence) can also be evaluated by comparison of the percent sequence identity between the polypeptide encoded by a variant nucleotide sequence and the polypeptide encoded by the reference nucleotide sequence. Thus, for example, isolated nucleic acids that encode a polypeptide with a given percent sequence identity to the polypeptides of SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43 or SEQ ID NO: 45 are disclosed. Percent sequence identity between any two polypeptides can be calculated using sequence alignment programs described elsewhere herein using default parameters. Where any given pair of polynucleotides of the embodiments is evaluated by comparison of the percent sequence identity shared by the two polypeptides they encode, the percent sequence identity between the two encoded polypeptides is at least about 40%, 45%, 50%, 55%, 60%, 65%, 70%, generally at least about 75%, 80%, 85%, at least about 90%, 91%, 92%, 93%, 94%, 95%, 96%, 97%, or at least about 98%, 99% or more sequence identity.

As used herein, the term "variant protein" encompasses polypeptides that are derived from a native protein by: deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Accordingly, the term "variant protein" encompasses biologically active fragments of a native protein that comprise a sufficient number of contiguous amino acid residues to retain the biological activity of the native protein, i.e., to have pesticidal activity. Such pesticidal activity may be different or improved relative to the native protein or it may be unchanged, so long as pesticidal activity is retained.

Variant proteins encompassed by the embodiments are biologically active, that is they continue to possess the desired biological activity of the native protein, that is, pesticidal activity as described herein. Such variants may result from, for example, genetic polymorphism or from human manipulation. Biologically active variants of a native pesticidal protein of the embodiments will have at least about 60%, 65%, 70%, 75%, 80%, 85%, 86%, 87%, 88%, 89%, 90%, 91%, 92%, 93%, 94%, 95%, 96%, 97%, 98%, 99%, or more sequence identity to the amino acid sequence for the native protein as determined by sequence alignment programs described elsewhere herein using default parameters. A biologically active variant of a protein of the embodiments may differ from that protein by as few as 1-15 amino acid residues, as few as 1-10, such as 6-10, as few as 5, as few as 4, 3, 2, or even 1 amino acid residue.

In some embodiment the insecticidal polypeptide has at least 60%, 65%, 70%, 75%, 80%, 85%, 86%, 87%, 88%, 89%, 90%, 91%, 92%, 93%, 94%, 95%, 96%, 97%, 98%, 99%, or more sequence identity to the amino acid sequence of SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43 or SEQ ID NO: 45.

In some embodiments the polypeptide has a modified physical property. As used herein, the term "physical property" refers to any parameter suitable for describing the physical-chemical characteristics of a protein. As used herein, "physical property of interest" and "property of interest" are used interchangeably to refer to physical properties of proteins that are being investigated and/or modified. Examples of physical properties include, but are not limited to net surface charge and charge distribution on the protein surface, net hydrophobicity and hydrophobic residue distribution on the protein surface, surface charge density, surface hydrophobicity density, total count of surface ionizable groups, surface tension, protein size and its distribution in solution, melting temperature, heat capacity, and second virial coefficient. Examples of physical properties also include, but are not limited to solubility, folding, stability, and digestibility. In some embodiments the polypeptide has increased digestibility of proteolytic fragments in an insect gut. In some embodiments the polypeptide has increased stability in an insect gut. Models for digestion by simulated gastric fluids are known to one skilled in the art (Fuchs, R. L. and J. D. Astwood. *Food Technology* 50: 83-88, 1996; Astwood, J. D., et al *Nature Biotechnology* 14: 1269-1273, 1996; Fu T J et al *J. Agric Food Chem.* 50: 7154-7160, 2002).

The embodiments further encompass a microorganism that is transformed with at least one nucleic acid of the embodiments, with an expression cassette comprising the nucleic acid, or with a vector comprising the expression cassette. In some embodiments, the microorganism is one that multiplies on plants. An embodiment of the disclosure relates to an encapsulated pesticidal protein which comprises a transformed microorganism capable of expressing at least one pesticidal protein of the embodiments.

The embodiments provide pesticidal compositions comprising a transformed microorganism of the embodiments. In such embodiments, the transformed microorganism is generally present in the pesticidal composition in a pesticidally effective amount, together with a suitable carrier. The embodiments also encompass pesticidal compositions comprising an isolated protein of the embodiments, alone or in combination with a transformed organism of the embodiments and/or an encapsulated pesticidal protein of the embodiments, in an insecticidally effective amount, together with a suitable carrier.

The embodiments further provide a method of increasing insect target range by using a pesticidal protein of the embodiments in combination with at least one other or "second" pesticidal protein. Any pesticidal protein known in the art can be employed in the methods of the embodiments. Such pesticidal proteins include, but are not limited to, Bt toxins, protease inhibitors, α-amylases, and peroxidases.

The embodiments also encompass transformed or transgenic plants comprising at least one nucleotide sequence of the embodiments. In some embodiments, the plant is stably transformed with a nucleotide construct comprising at least one nucleotide sequence of the embodiments operably linked to a promoter that drives expression in a plant cell. As used herein, the terms "transformed plant" and "transgenic plant" refer to a plant that comprises within its genome a heterologous polynucleotide. Generally, the heterologous polynucleotide is stably integrated within the genome of a transgenic or transformed plant such that the polynucleotide is passed on to successive generations. The heterologous polynucleotide may be integrated into the genome alone or as part of a recombinant expression cassette.

It is to be understood that as used herein the term "transgenic" includes any cell, cell line, callus, tissue, plant part, or plant the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

As used herein, the term "plant" includes whole plants, plant organs (e.g., leaves, stems, roots, etc.), seeds, plant cells, and progeny of same. Parts of transgenic plants are within the scope of the embodiments and comprise, for example, plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like, originating in transgenic plants or their progeny previously transformed with a DNA molecule of the embodiments and therefore consisting at least in part of transgenic cells. The class of plants that can be used in the methods of the embodiments is generally as broad as the class of higher plants amenable to transformation techniques, including both monocotyledonous and dicotyledonous plants.

While the embodiments do not depend on a particular biological mechanism for increasing the resistance of a plant to a plant pest, expression of the nucleotide sequences of the embodiments in a plant can result in the production of the pesticidal proteins of the embodiments and in an increase in the resistance of the plant to a plant pest. The plants of the embodiments find use in agriculture in methods for impacting insect pests. Certain embodiments provide transformed crop plants, such as, for example, maize plants, which find use in methods for impacting insect pests of the plant, such as, for example, Lepidopteran pests.

A "subject plant or plant cell" is one in which genetic alteration, such as transformation, has been affected as to a gene of interest, or is a plant or plant cell which is descended from a plant or cell so altered and which comprises the alteration. A "control" or "control plant" or "control plant cell" provides a reference point for measuring changes in phenotype of the subject plant or plant cell.

A control plant or plant cell may comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e., with a construct which has no known effect on the trait of interest, such as a construct comprising a marker gene); (c) a plant or plant cell which is a non-transformed segregant among progeny of a subject plant or plant cell; (d) a plant or plant cell genetically identical to the subject plant or plant cell but which is not exposed to conditions or stimuli that would induce expression of the gene of interest; or (e) the subject plant or plant cell itself, under conditions in which the gene of interest is not expressed.

One of skill in the art will readily acknowledge that advances in the field of molecular biology such as site-specific and random mutagenesis, polymerase chain reaction methodologies, and protein engineering techniques provide an extensive collection of tools and protocols suitable for use to alter or engineer both the amino acid sequence and underlying genetic sequences of proteins of agricultural interest.

Thus, the proteins of the embodiments may be altered in various ways including amino acid substitutions, deletions, truncations, and insertions. Methods for such manipulations are generally known in the art. For example, amino acid sequence variants of the pesticidal proteins can be prepared by introducing mutations into a synthetic nucleic acid (e.g., DNA molecule). Methods for mutagenesis and nucleic acid alterations are well known in the art. For example, designed changes can be introduced using an oligonucleotide-mediated site-directed mutagenesis technique. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York), and the references cited therein.

The mutagenized nucleotide sequences of the embodiments may be modified so as to change about 1, 2, 3, 4, 5, 6, 8, 10, 12 or more of the amino acids present in the primary sequence of the encoded polypeptide. Alternatively, even more changes from the native sequence may be introduced such that the encoded protein may have at least about 1% or 2%, or about 3%, 4%, 5%, 6%, 7%, 8%, 9%, 10%, 11%, 12%, or even about 13%, 14%, 15%, 16%, 17%, 18%, 19%, or 20%, 21%, 22%, 23%, 24%, or 25%, 30%, 35%, or 40% or more of the codons altered, or otherwise modified compared to the corresponding wild-type protein. In the same manner, the encoded protein may have at least about 1% or 2%, or about 3%, 4%, 5%, 6%, 7%, 8%, 9%, 10%, 11%, 12%, or even about 13%, 14%, 15%, 16%, 17%, 18%, 19%, or 20%, 21%, 22%, 23%, 24%, or 25%, 30%, 35%, or 40% or more additional codons compared to the corresponding wild-type protein. It should be understood that the mutagenized nucleotide sequences of the embodiments are intended to encompass biologically functional, equivalent peptides which have pesticidal activity, such as an improved pesticidal activity as determined by antifeedant properties against European corn borer larvae. Such sequences may arise as a consequence of codon redundancy and functional equivalency that are known to occur naturally within nucleic acid sequences and the proteins thus encoded.

One of skill in the art would recognize that amino acid additions and/or substitutions are generally based on the relative similarity of the amino acid side-chain substituents, for example, their hydrophobicity, charge, size, and the like. Exemplary amino acid substitution groups that take several of the foregoing characteristics into consideration are well known to those of skill in the art and include: arginine and lysine; glutamate and aspartate; serine and threonine; glutamine and asparagine; and valine, leucine, and isoleucine.

Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be made.

Thus, the genes and nucleotide sequences of the embodiments include both the naturally occurring sequences and mutant forms. Likewise, the proteins of the embodiments encompass both naturally occurring proteins and variations (e.g., truncated polypeptides) and modified (e.g., mutant) forms thereof. Such variants will continue to possess the desired pesticidal activity. Obviously, the mutations that will be made in the nucleotide sequence encoding the variant must not place the sequence out of reading frame and generally will not create complementary regions that could produce secondary mRNA structure. See, EP Patent Application Publication No. 75,444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays, such as insect-feeding assays. See, for example, Marrone et al. (1985) *J. Econ. Entomol.* 78: 290-293 and Czapla and Lang (1990) *J. Econ. Entomol.* 83: 2480-2485, herein incorporated by reference.

Variant nucleotide sequences and proteins also encompass sequences and proteins derived from a mutagenic and recombinogenic procedure such as DNA shuffling. With such a procedure, one or more different coding sequences can be manipulated to create a new pesticidal protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, full-length coding sequences, sequence motifs encoding a domain of interest, or any fragment of a nucleotide sequence of the embodiments may be shuffled between the nucleotide sequences of the embodiments and corresponding portions of other known Cry nucleotide sequences to obtain a new gene coding for a protein with an improved property of interest.

Properties of interest include, but are not limited to, pesticidal activity per unit of pesticidal protein, protein stability, and toxicity to non-target species particularly humans, livestock, and plants and microbes that express the pesticidal polypeptides of the embodiments. The embodiments are not bound by a particular shuffling strategy, only that at least one nucleotide sequence of the embodiments, or part thereof, is involved in such a shuffling strategy. Shuffling may involve only nucleotide sequences disclosed herein or may additionally involve shuffling of other nucleotide sequences known in the art. Strategies for DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

The nucleotide sequences of the embodiments can also be used to isolate corresponding sequences from other organisms, particularly other bacteria, and more particularly other *Bacillus* strains. In this manner, methods such as PCR, hybridization, and the like can be used to identify such sequences based on their sequence homology to the sequences set forth herein. Sequences that are selected based on their sequence identity to the entire sequences set forth herein or to fragments thereof are encompassed by the embodiments. Such sequences include sequences that are orthologs of the disclosed sequences. The term "orthologs" refers to genes derived from a common ancestral gene and which are found in different species as a result of speciation. Genes found in different species are considered orthologs when their nucleotide sequences and/or their encoded protein sequences share substantial identity as defined elsewhere herein. Functions of orthologs are often highly conserved among species.

In a PCR approach, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.), hereinafter "Sambrook". See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$ or any other detectable marker. Thus, for example, probes for hybridization can be made by labeling synthetic oligonucleotides based on the sequences of the embodiments. Methods for preparation of probes for hybridization and for construction of cDNA and genomic libraries are generally known in the art and are disclosed in Sambrook.

For example, an entire sequence disclosed herein, or one or more portions thereof, may be used as a probe capable of specifically hybridizing to corresponding sequences and messenger RNAs. To achieve specific hybridization under a variety of conditions, such probes include sequences that are unique to the sequences of the embodiments and are generally at least about 10 or 20 nucleotides in length. Such probes may be used to amplify corresponding Cry sequences from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook).

Hybridization of such sequences may be carried out under stringent conditions. The term "stringent conditions" or "stringent hybridization conditions" as used herein refers to conditions under which a probe will hybridize to its target sequence to a detectably greater degree than to other sequences (e.g., at least 2-fold, 5-fold, or 10-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 or 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37 C, and a wash in 0.5× to 1×SSC at 55 to 60° C. Exemplary high stringency conditions include hybridization in 50% formamide, 1 M NaCl, 1% SDS at 37° C., and a final wash in 0.1×SSC at 60 to 65° C. for at least about 20 minutes. Optionally, wash buffers may comprise about 0.1% to about 1% SDS. The duration of hybridization is generally less than about 24 hours, usually about 4 to about 12 hours.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11-17; the local alignment algorithm of Smith et al. (1981) *Adv. Appl. Math.* 2:482; the global alignment algorithm of Needleman and Wunsch (1970) *J. Mol. Biol.* 48:443-453; the search-for-local alignment method of Pearson and Lipman (1988) *Proc. Natl. Acad. Sci.* 85:2444-2448; the algorithm of Karlin and Altschul (1990) *Proc. Natl. Acad. Sci. USA* 872264, as modified in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins et al. (1988) *Gene* 73:237-244 (1988); Higgins et al. (1989) *CABIOS* 5:151-153; Corpet et al. (1988) *Nucleic Acids Res.* 16:10881-90; Huang et al. (1992) *CABIOS* 8:155-65; and Pearson et al. (1994) *Meth. Mol. Biol.* 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the embodiments. BLAST protein searches can be performed with the BLASTX program, score=50, wordlength=3, to obtain amino acid sequences homologous to a protein or polypeptide of the embodiments. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See the National Center for Biotechnology Information website on the world wide web at ncbi.hlm.nih.gov. Alignment may also be performed manually by inspection.

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70%. 80%, 90%, or 95% or more sequence identity when compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes generally means sequence identity of at least 60%, 70%, 80%, 90%, or 95% or more sequence identity.

Another indication that nucleotide sequences are substantially identical is if two molecules hybridize to each other under stringent conditions. Generally, stringent conditions are selected to be about 5° C. lower than the $T_m$ for the specific sequence at a defined ionic strength and pH. However, stringent conditions encompass temperatures in the range of about 1° C. to about 20° C. lower than the $T_m$, depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70%, 80%, 85%, 90%, 95%, or more sequence identity to a reference sequence over a specified comparison window. Optimal alignment for these purposes can be conducted using the global alignment algorithm of Needleman and Wunsch (1970) supra. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

The use of the term "nucleotide constructs" herein is not intended to limit the embodiments to nucleotide constructs comprising DNA. Those of ordinary skill in the art will recognize that nucleotide constructs, particularly polynucleotides and oligonucleotides composed of ribonucleotides and combinations of ribonucleotides and deoxyribonucleotides, may also be employed in the methods disclosed herein. The nucleotide constructs, nucleic acids, and nucleotide sequences of the embodiments additionally encompass all complementary forms of such constructs, molecules, and sequences. Further, the nucleotide constructs, nucleotide molecules, and nucleotide sequences of the embodiments encompass all nucleotide constructs, molecules, and sequences which can be employed in the methods of the embodiments for transforming plants including, but not limited to, those comprised of deoxyribonucleotides, ribonucleotides, and combinations thereof. Such deoxyribonucleotides and ribonucleotides include both naturally occurring molecules and synthetic analogues. The nucleotide constructs, nucleic acids, and nucleotide sequences of the embodiments also encompass all forms of nucleotide constructs including, but not limited to, single-stranded forms, double-stranded forms, hairpins, stem-and-loop structures, and the like.

A further embodiment relates to a transformed organism such as an organism selected from the group consisting of plant and insect cells, bacteria, yeast, baculovirus, protozoa, nematodes, and algae. The transformed organism comprises: a DNA molecule of the embodiments, an expression cassette comprising the said DNA molecule, or a vector comprising the said expression cassette, which may be stably incorporated into the genome of the transformed organism.

The sequences of the embodiments are provided in DNA constructs for expression in the organism of interest. The construct will include 5' and 3' regulatory sequences operably linked to a sequence of the embodiments. The term "operably linked" as used herein refers to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. The construct may additionally contain at least one additional gene to be cotransformed into the organism. Alternatively, the additional gene(s) can be provided on multiple DNA constructs.

Such a DNA construct is provided with a plurality of restriction sites for insertion of the Cry toxin sequence to be under the transcriptional regulation of the regulatory regions. The DNA construct may additionally contain selectable marker genes.

The DNA construct will include in the 5' to 3' direction of transcription: a transcriptional and translational initiation region (i.e., a promoter), a DNA sequence of the embodiments, and a transcriptional and translational termination region (i.e., termination region) functional in the organism serving as a host. The transcriptional initiation region (i.e., the promoter) may be native, analogous, foreign or heterologous to the host organism and/or to the sequence of the embodiments. Additionally, the promoter may be the natural sequence or alternatively a synthetic sequence. The term "foreign" as used herein indicates that the promoter is not found in the native organism into which the promoter is introduced. Where the promoter is "foreign" or "heterologous" to the sequence of the embodiments, it is intended that the promoter is not the native or naturally occurring promoter for the operably linked sequence of the embodiments. As used herein, a chimeric gene comprises a coding sequence operably linked to a transcription initiation region that is heterologous to the coding sequence. Where the promoter is a native or natural sequence, the expression of the operably linked sequence is altered from the wild-type expression, which results in an alteration in phenotype.

The termination region may be native with the transcriptional initiation region, may be native with the operably linked DNA sequence of interest, may be native with the plant host, or may be derived from another source (i.e., foreign or heterologous to the promoter, the sequence of interest, the plant host, or any combination thereof).

Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272;

Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

Where appropriate, a nucleic acid may be optimized for increased expression in the host organism. Thus, where the host organism is a plant, the synthetic nucleic acids can be synthesized using plant-preferred codons for improved expression. See, for example, Campbell and Gowri (1990) *Plant Physiol.* 92:1-11 for a discussion of host-preferred codon usage. For example, although nucleic acid sequences of the embodiments may be expressed in both monocotyledonous and dicotyledonous plant species, sequences can be modified to account for the specific codon preferences and GC content preferences of monocotyledons or dicotyledons as these preferences have been shown to differ (Murray et al. (1989) *Nucleic Acids Res.* 17:477-498). Thus, the maize-preferred codon for a particular amino acid may be derived from known gene sequences from maize. Maize codon usage for 28 genes from maize plants is listed in Table 4 of Murray et al., supra. Methods are available in the art for synthesizing plant-preferred genes.

Additional sequence modifications are known to enhance gene expression in a cellular host. These include elimination of sequences encoding spurious polyadenylation signals, exon-intron splice site signals, transposon-like repeats, and other well-characterized sequences that may be deleterious to gene expression. The GC content of the sequence may be adjusted to levels average for a given cellular host, as calculated by reference to known genes expressed in the host cell. The term "host cell" as used herein refers to a cell which contains a vector and supports the replication and/or expression of the expression vector is intended. Host cells may be prokaryotic cells such as *E. coli*, or eukaryotic cells such as yeast, insect, amphibian, or mammalian cells, or monocotyledonous or dicotyledonous plant cells. An example of a monocotyledonous host cell is a maize host cell. When possible, the sequence is modified to avoid predicted hairpin secondary mRNA structures.

The expression cassettes may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86: 6126-6130); potyvirus leaders, for example, TEV leader (Tobacco Etch Virus) (Gallie et al. (1995) *Gene* 165(2): 233-238), MDMV leader (Maize Dwarf Mosaic Virus), human immunoglobulin heavy-chain binding protein (BiP) (Macejak et al. (1991) *Nature* 353: 90-94); untranslated leader from the coat protein mRNA of alfalfa mosaic virus (AMV RNA 4) (Jobling et al. (1987) *Nature* 325: 622-625); tobacco mosaic virus leader (TMV) (Gallie et al. (1989) in *Molecular Biology of RNA*, ed. Cech (Liss, New York), pp. 237-256); and maize chlorotic mottle virus leader (MCMV) (Lommel et al. (1991) *Virology* 81: 382-385). See also, Della-Cioppa et al. (1987) *Plant Physiol.* 84: 965-968.

In preparing the expression cassette, the various DNA fragments may be manipulated so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the practice of the embodiments. The promoters can be selected based on the desired outcome. The nucleic acids can be combined with constitutive, tissue-preferred, inducible, or other promoters for expression in the host organism. Suitable constitutive promoters for use in a plant host cell include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313: 810-812); rice actin (McElroy et al. (1990) *Plant Cell* 2: 163-171); ubiquitin (Christensen et al. (1989) *Plant Mol. Biol.* 12: 619-632 and Christensen et al. (1992) *Plant Mol. Biol.* 18: 675-689); pEMU (Last et al. (1991) *Theor. Appl. Genet.* 81: 581-588); MAS (Velten et al. (1984) *EMBO J.* 3:2723-2730); ALS promoter (U.S. Pat. No. 5,659,026), and the like. Other constitutive promoters include, for example, those discussed in U.S. Pat. Nos. 5,608,149; 5,608,144; 5,604,121; 5,569,597; 5,466,785; 5,399,680; 5,268,463; 5,608,142; and 6,177,611.

Depending on the desired outcome, it may be beneficial to express the gene from an inducible promoter. Of particular interest for regulating the expression of the nucleotide sequences of the embodiments in plants are wound-inducible promoters. Such wound-inducible promoters, may respond to damage caused by insect feeding, and include potato proteinase inhibitor (pin II) gene (Ryan (1990) *Ann. Rev. Phytopath.* 28: 425-449; Duan et al. (1996) *Nature Biotechnology* 14: 494-498); wun1 and wun2, U.S. Pat. No. 5,428,148; win1 and win2 (Stanford et al. (1989) *Mol. Gen. Genet.* 215: 200-208); systemin (McGurl et al. (1992) *Science* 225: 1570-1573); WIP1 (Rohmeier et al. (1993) *Plant Mol. Biol.* 22: 783-792; Eckelkamp et al. (1993) *FEBS Letters* 323: 73-76); MPI gene (Corderok et al. (1994) *Plant J.* 6(2): 141-150); and the like, herein incorporated by reference.

Additionally, pathogen-inducible promoters may be employed in the methods and nucleotide constructs of the embodiments. Such pathogen-inducible promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89: 245-254; Uknes et al. (1992) *Plant Cell* 4: 645-656; and Van Loon (1985) *Plant Mol. Virol.* 4: 111-116. See also WO 99/43819, herein incorporated by reference.

Of interest are promoters that are expressed locally at or near the site of pathogen infection. See, for example, Marineau et al. (1987) *Plant Mol. Biol.* 9:335-342; Matton et al. (1989) *Molecular Plant-Microbe Interactions* 2:325-331; Somsisch et al. (1986) *Proc. Natl. Acad. Sci. USA* 83:2427-2430; Somsisch et al. (1988) *Mol. Gen. Genet.* 2:93-98; and Yang (1996) *Proc. Natl. Acad. Sci. USA* 93:14972-14977. See also, Chen et al. (1996) *Plant J.* 10:955-966; Zhang et al. (1994) *Proc. Natl. Acad. Sci. USA* 91:2507-2511; Warner et al. (1993) *Plant J.* 3:191-201; Siebertz et al. (1989) *Plant Cell* 1:961-968; U.S. Pat. No. 5,750,386 (nematode-inducible); and the references cited therein. Of particular interest is the inducible promoter for the maize PRms gene, whose expression is induced by the pathogen *Fusarium moniliforme* (see, for example, Cordero et al. (1992) *Physiol. Mol. Plant Path.* 41:189-200).

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156), herein incorporated by reference.

Tissue-preferred promoters can be utilized to target enhanced pesticidal protein expression within a particular plant tissue. Tissue-preferred promoters include those discussed in Yamamoto et al. (1997) *Plant J.* 12(2)255-265; Kawamata et al. (1997) *Plant Cell Physiol.* 38(7):792-803; Hansen et al. (1997) *Mol. Gen Genet.* 254(3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol Biol.* 23(6):1129-1138; Matsuoka et al. (1993) *Proc Natl. Acad. Sci. USA* 90(20):9586-9590; and Guevara-Garcia et al. (1993) *Plant J.* 4(3):495-505. Such promoters can be modified, if necessary, for weak expression.

Leaf-preferred promoters are known in the art. See, for example, Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol. Biol.* 23(6):1129-1138; and Matsuoka et al. (1993) *Proc. Natl. Acad. Sci. USA* 90(20):9586-9590.

Root-preferred or root-specific promoters are known and can be selected from the many available from the literature or isolated de novo from various compatible species. See, for example, Hire et al. (1992) *Plant Mol. Biol.* 20(2):207-218 (soybean root-specific glutamine synthetase gene); Keller and Baumgartner (1991) *Plant Cell* 3(10):1051-1061 (root-specific control element in the GRP 1.8 gene of French bean); Sanger et al. (1990) *Plant Mol. Biol.* 14(3):433-443 (root-specific promoter of the mannopine synthase (MAS) gene of *Agrobacterium tumefaciens*); and Miao et al. (1991) *Plant Cell* 3(1):11-22 (full-length cDNA clone encoding cytosolic glutamine synthetase (GS), which is expressed in roots and root nodules of soybean). See also Bogusz et al. (1990) *Plant Cell* 2(7):633-641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi (1991) describe their analysis of the promoters of the highly expressed rolC and rolD root-inducing genes of *Agrobacterium rhizogenes* (see *Plant Science* (Limerick) 79(1):69-76). They concluded that enhancer and tissue-preferred DNA determinants are dissociated in those promoters. Teeri et al. (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see *EMBO J.* 8(2):343-350). The TR1' gene fused to nptII (neomycin phosphotransferase II) showed similar characteristics. Additional root-preferred promoters include the VfENOD-GRP3 gene promoter (Kuster et al. (1995) *Plant Mol. Biol.* 29(4):759-772); and rolB promoter (Capana et al. (1994) *Plant Mol. Biol.* 25(4):681-691. See also U.S. Pat. Nos. 5,837,876; 5,750,386; 5,633,363; 5,459,252; 5,401,836; 5,110,732; and 5,023,179.

"Seed-preferred" promoters include both "seed-specific" promoters (those promoters active during seed development such as promoters of seed storage proteins) as well as "seed-germinating" promoters (those promoters active during seed germination). See Thompson et al. (1989) *BioEssays* 10:108, herein incorporated by reference. Such seed-preferred promoters include, but are not limited to, Cim1 (cytokinin-induced message); cZ19B1 (maize 19 kDa zein); and milps (myo-inositol-1-phosphate synthase) (see U.S. Pat. No. 6,225,529, herein incorporated by reference). Gamma-zein and Glob-1 are endosperm-specific promoters. For dicots, seed-specific promoters include, but are not limited to, bean β-phaseolin, napin, β-conglycinin, soybean lectin, cruciferin, and the like. For monocots, seed-specific promoters include, but are not limited to, maize 15 kDa zein, 22 kDa zein, 27 kDa zein, g-zein, waxy, shrunken 1, shrunken 2, globulin 1, etc. See also WO 00/12733, where seed-preferred promoters from end1 and end2 genes are disclosed; herein incorporated by reference. A promoter that has "preferred" expression in a particular tissue is expressed in that tissue to a greater degree than in at least one other plant tissue. Some tissue-preferred promoters show expression almost exclusively in the particular tissue.

Where low level expression is desired, weak promoters will be used. Generally, the term "weak promoter" as used herein refers to a promoter that drives expression of a coding sequence at a low level. By low level expression at levels of about 1/1000 transcripts to about 1/100,000 transcripts to about 1/500,000 transcripts is intended. Alternatively, it is recognized that the term "weak promoters" also encompasses promoters that drive expression in only a few cells and not in others to give a total low level of expression. Where a promoter drives expression at unacceptably high levels, portions of the promoter sequence can be deleted or modified to decrease expression levels.

Such weak constitutive promoters include, for example the core promoter of the Rsyn7 promoter (WO 99/43838 and U.S. Pat. No. 6,072,050), the core 35S CaMV promoter, and the like. Other constitutive promoters include, for example, those disclosed in U.S. Pat. Nos. 5,608,149; 5,608,144; 5,604,121; 5,569,597; 5,466,785; 5,399,680; 5,268,463; 5,608,142; and 6,177,611; herein incorporated by reference.

Generally, the expression cassette will comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional examples of suitable selectable marker genes include, but are not limited to, genes encoding resistance to chloramphenicol (Herrera Estrella et al. (1983)

*EMBO J.* 2:987-992); methotrexate (Herrera Estrella et al. (1983) *Nature* 303:209-213; and Meijer et al. (1991) *Plant Mol. Biol.* 16:807-820); streptomycin (Jones et al. (1987) *Mol. Gen. Genet.* 210:86-91); spectinomycin (Bretagne-Sagnard et al. (1996) *Transgenic Res.* 5:131-137); bleomycin (Hille et al. (1990) *Plant Mol. Biol.* 7:171-176); sulfonamide (Guerineau et al. (1990) *Plant Mol. Biol.* 15:127-136); bromoxynil (Stalker et al. (1988) *Science* 242:419-423); glyphosate (Shaw et al. (1986) *Science* 233:478-481; and U.S. Pat. Nos. 7,709,702; and 7,462,481); phosphinothricin (DeBlock et al. (1987) *EMBO J.* 6:2513-2518). See generally, Yarranton (1992) *Curr. Opin. Biotech.* 3: 506-511; Christopherson et al. (1992) *Proc. Natl. Acad. Sci. USA* 89: 6314-6318; Yao et al. (1992) *Cell* 71: 63-72; Reznikoff (1992) *Mol. Microbiol.* 6: 2419-2422; Barkley et al. (1980) in *The Operon*, pp. 177-220; Hu et al. (1987) *Cell* 48: 555-566; Brown et al. (1987) *Cell* 49: 603-612; Figge et al. (1988) *Cell* 52: 713-722; Deuschle et al. (1989) *Proc. Natl. Acad. Sci. USA* 86: 5400-5404; Fuerst et al. (1989) *Proc. Natl. Acad. Sci. USA* 86: 2549-2553; Deuschle et al. (1990) *Science* 248: 480-483; Gossen (1993) Ph.D. Thesis, University of Heidelberg; Reines et al. (1993) *Proc. Natl. Acad. Sci. USA* 90: 1917-1921; Labow et al. (1990) *Mol. Cell. Biol.* 10: 3343-3356; Zambretti et al. (1992) *Proc. Natl. Acad. Sci. USA* 89: 3952-3956; Baim et al. (1991) *Proc. Natl. Acad. Sci. USA* 88: 5072-5076; Wyborski et al. (1991) *Nucleic Acids Res.* 19: 4647-4653; Hillenand-Wissman (1989) *Topics Mol. Struc. Biol.* 10: 143-162; Degenkolb et al. (1991) *Antimicrob. Agents Chemother.* 35: 1591-1595; Kleinschnidt et al. (1988) *Biochemistry* 27: 1094-1104; Bonin (1993) Ph.D. Thesis, University of Heidelberg; Gossen et al. (1992) *Proc. Natl. Acad. Sci. USA* 89: 5547-5551; Oliva et al. (1992) *Antimicrob. Agents Chemother.* 36: 913-919; Hlavka et al. (1985) *Handbook of Experimental Pharmacology*, Vol. 78 (Springer-Verlag, Berlin); and Gill et al. (1988) *Nature* 334: 721-724. Such disclosures are herein incorporated by reference.

The above list of selectable marker genes is not meant to be limiting. Any selectable marker gene can be used in the embodiments.

The methods of the embodiments involve introducing a polypeptide or polynucleotide into a plant. "Introducing" is intended to mean presenting to the plant the polynucleotide or polypeptide in such a manner that the sequence gains access to the interior of a cell of the plant. The methods of the embodiments do not depend on a particular method for introducing a polynucleotide or polypeptide into a plant, only that the polynucleotide or polypeptides gains access to the interior of at least one cell of the plant. Methods for introducing polynucleotide or polypeptides into plants are known in the art including, but not limited to, stable transformation methods, transient transformation methods, and virus-mediated methods.

"Stable transformation" is intended to mean that the nucleotide construct introduced into a plant integrates into the genome of the plant and is capable of being inherited by the progeny thereof. "Transient transformation" is intended to mean that a polynucleotide is introduced into the plant and does not integrate into the genome of the plant or a polypeptide is introduced into a plant.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4: 320-334), electroporation (Riggs et al. (1986) *Proc. Natl. Acad. Sci. USA* 83: 5602-5606), *Agrobacterium*-mediated transformation (U.S. Pat. Nos. 5,563,055 and 5,981,840), direct gene transfer (Paszkowski et al. (1984) *EMBO J.* 3: 2717-2722), and ballistic particle acceleration (see, for example, U.S. Pat. Nos. 4,945,050; 5,879,918; 5,886,244; and 5,932,782; Tomes et al. (1995) in *Plant Cell, Tissue, and Organ Culture: Fundamental Methods*, ed. Gamborg and Phillips (Springer-Verlag, Berlin); and McCabe et al. (1988) *Biotechnology* 6: 923-926); and LecI transformation (WO 00/28058). For potato transformation see Tu et al. (1998) *Plant Molecular Biology* 37: 829-838 and Chong et al. (2000) *Transgenic Research* 9: 71-78. Additional transformation procedures can be found in Weissinger et al. (1988) *Ann. Rev. Genet.* 22: 421-477; Sanford et al. (1987) *Particulate Science and Technology* 5: 27-37 (onion); Christou et al. (1988) *Plant Physiol.* 87: 671-674 (soybean); McCabe et al. (1988) *Bio/Technology* 6: 923-926 (soybean); Finer and McMullen (1991) *In Vitro Cell Dev. Biol.* 27P: 175-182 (soybean); Singh et al. (1998) *Theor. Appl. Genet.* 96: 319-324 (soybean); Datta et al. (1990) *Biotechnology* 8: 736-740 (rice); Klein et al. (1988) *Proc. Natl. Acad. Sci. USA* 85: 4305-4309 (maize); Klein et al. (1988) *Biotechnology* 6:559-563 (maize); U.S. Pat. Nos. 5,240,855; 5,322,783 and 5,324,646; Klein et al. (1988) *Plant Physiol.* 91: 440-444 (maize); Fromm et al. (1990) *Biotechnology* 8: 833-839 (maize); Hooykaas-Van Slogteren et al. (1984) *Nature* (London) 311: 763-764; U.S. Pat. No. 5,736,369 (cereals); Bytebier et al. (1987) *Proc. Natl. Acad. Sci. USA* 84: 5345-5349 (Liliaceae); De Wet et al. (1985) in *The Experimental Manipulation of Ovule Tissues, ed.* Chapman et al. (Longman, N.Y.), pp. 197-209 (pollen); Kaeppler et al. (1990) *Plant Cell Reports* 9: 415-418 and Kaeppler et al. (1992) *Theor. Appl. Genet.* 84: 560-566 (whisker-mediated transformation); D'Halluin et al. (1992) *Plant Cell* 4: 1495-1505 (electroporation); Li et al. (1993) *Plant Cell Reports* 12: 250-255 and Christou and Ford (1995) *Annals of Botany* 75: 407-413 (rice); Osjoda et al. (1996) *Nature Biotechnology* 14: 745-750 (maize via *Agrobacterium tumefaciens*); all of which are herein incorporated by reference.

In specific embodiments, the sequences of the embodiments can be provided to a plant using a variety of transient transformation methods. Such transient transformation methods include, but are not limited to, the introduction of the Cry toxin protein or variants and fragments thereof directly into the plant or the introduction of the Cry toxin transcript into the plant. Such methods include, for example, microinjection or particle bombardment. See, for example, Crossway et al. (1986) *Mol Gen. Genet.* 202: 179-185; Nomura et al. (1986) *Plant Sci.* 44: 53-58; Hepler et al. (1994) *Proc. Natl. Acad. Sci.* 91: 2176-2180 and Hush et al. (1994) *The Journal of Cell Science* 107: 775-784, all of which are herein incorporated by reference. Alternatively, the Cry toxin polynucleotide can be transiently transformed into the plant using techniques known in the art. Such techniques include viral vector system and the precipitation of the polynucleotide in a manner that precludes subsequent release of the DNA. Thus, transcription from the particle-bound DNA can occur, but the frequency with which it is released to become integrated into the genome is greatly reduced. Such methods include the use of particles coated with polyethylimine (PEI; Sigma #P3143).

Methods are known in the art for the targeted insertion of a polynucleotide at a specific location in the plant genome. In one embodiment, the insertion of the polynucleotide at a desired genomic location is achieved using a site-specific recombination system. See, for example, WO99/25821, WO99/25854, WO99/25840, WO99/25855, and WO99/25853, all of which are herein incorporated by reference. Briefly, the polynucleotide of the embodiments can be contained in transfer cassette flanked by two non-identical recombination sites. The transfer cassette is introduced into a plant have stably incorporated into its genome a target site which is flanked by two non-identical recombination sites that correspond to the sites of the transfer cassette. An appropriate recombinase is provided and the transfer cassette is integrated at the target site. The polynucleotide of interest is thereby integrated at a specific chromosomal position in the plant genome.

The cells that have been transformed may be grown into plants in accordance with conventional ways. See, for example, McCormick et al. (1986) *Plant Cell Reports* 5: 81-84. These plants may then be grown, and either pollinated with the same transformed strain or different strains, and the resulting hybrid having constitutive or inducible expression of the desired phenotypic characteristic identified. Two or more generations may be grown to ensure that expression of the desired phenotypic characteristic is stably maintained and inherited and then seeds harvested to ensure that expression of the desired phenotypic characteristic has been achieved.

The nucleotide sequences of the embodiments may be provided to the plant by contacting the plant with a virus or viral nucleic acids. Generally, such methods involve incorporating the nucleotide construct of interest within a viral DNA or RNA molecule. It is recognized that the recombinant proteins of the embodiments may be initially synthesized as part of a viral polyprotein, which later may be processed by proteolysis in vivo or in vitro to produce the desired pesticidal protein. It is also recognized that such a viral polyprotein, comprising at least a portion of the amino acid sequence of a pesticidal protein of the embodiments, may have the desired pesticidal activity. Such viral polyproteins and the nucleotide sequences that encode for them are encompassed by the embodiments. Methods for providing plants with nucleotide constructs and producing the encoded proteins in the plants, which involve viral DNA or RNA molecules are known in the art. See, for example, U.S. Pat. Nos. 5,889,191; 5,889,190; 5,866,785; 5,589,367; and 5,316,931; herein incorporated by reference.

The embodiments further relate to plant-propagating material of a transformed plant of the embodiments including, but not limited to, seeds, tubers, corms, bulbs, leaves, and cuttings of roots and shoots.

The embodiments may be used for transformation of any plant species, including, but not limited to, monocots and dicots. Examples of plants of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (Citrus spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), *papaya* (*Carica papaya*), cashew (*Anacardium occidentale*), macadamia (Macadamia *integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (Rosa spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum. Conifers that may be employed in practicing the embodiments include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Plants of the embodiments include crop plants, including, but not limited to: corn, alfalfa, sunflower, *Brassica* spp., soybean, cotton, safflower, peanut, sorghum, wheat, millet, tobacco, sugarcane, etc.

Turfgrasses include, but are not limited to: annual bluegrass (*Poa annus*); annual ryegrass (*Lolium multiflorum*); Canada bluegrass (*Poa compressa*); Chewings fescue (*Festuca rubra*); colonial bentgrass (*Agrostis tenuis*); creeping bentgrass (*Agrostis palustris*); crested wheatgrass (*Agropyron desertorum*); fairway wheatgrass (*Agropyron cristatum*); hard fescue (*Festuca longifolia*); Kentucky bluegrass (*Poa pratensis*); orchardgrass (*Dactylis glomerata*); perennial ryegrass (*Lolium perenne*); red fescue (*Festuca rubra*); redtop (*Agrostis alba*); rough bluegrass (*Poa trivialis*); sheep fescue (*Festuca ovina*); smooth bromegrass (*Bromus inermis*); tall fescue (*Festuca arundinacea*); timothy (*Phleum pratense*); velvet bentgrass (*Agrostis canina*); weeping alkaligrass (*Puccinellia distans*); western wheatgrass (*Agropyron smithii*); Bermuda grass (*Cynodon* spp.); St. Augustine grass (*Stenotaphrum secundatum*); zoysia grass (*Zoysia* spp.); Bahia grass (*Paspalum notatum*); carpet grass (*Axonopus affinis*); centipede grass (*Eremochloa ophiuroides*); kikuyu grass (*Pennisetum clandesinum*); seashore paspalum (*Paspalum vaginatum*); blue gramma (*Bouteloua gracilis*); buffalo grass (*Buchloe dactyloids*); sideoats gramma (*Bouteloua curtipendula*).

Plants of interest include grain plants that provide seeds of interest, oil-seed plants, and leguminous plants. Seeds of interest include grain seeds, such as corn, wheat, barley, rice, sorghum, rye, millet, etc. Oil-seed plants include cotton, soybean, safflower, sunflower, *Brassica*, maize, alfalfa, palm, coconut, flax, castor, olive etc. Leguminous plants include beans and peas. Beans include guar, locust bean, fenugreek, soybean, garden beans, cowpea, mung bean, lima bean, fava bean, lentils, chickpea, etc.

In certain embodiments the nucleic acid sequences of the embodiments can be stacked with any combination of polynucleotide sequences of interest in order to create plants with a desired phenotype. For example, the polynucleotides of the embodiments may be stacked with any other polynucleotides encoding polypeptides having pesticidal and/or insecticidal activity. The combinations generated can also include multiple copies of any one of the polynucleotides of interest. Genes encoding polypeptides having pesticidal and/or insecticidal activity may include a *Bacillus thuringiensis* protein, a derivative thereof or a synthetic polypeptide modeled thereon. See, for example, Geiser, et al., (1986) *Gene* 48:109, who disclose the cloning and nucleotide sequence of a Bt delta-endotoxin gene. Moreover, DNA molecules encoding delta-endotoxin genes can be purchased from American Type Culture Collection (Rockville, Md.), for example, under ATCC® Accession Numbers 40098, 67136, 31995 and 31998. Other non-limiting examples of *Bacillus thuringiensis* transgenes being genetically engineered are given in the following patents and patent applications and hereby are incorporated by reference for this purpose: U.S. Pat. Nos. 5,188,960; 5,689,052; 5,880,275; 5,986,177; 6,023,013, 6,060,594, 6,063,597, 6,077,824, 6,620,988, 6,642,030, 6,713,259, 6,893,826, 7,105,332; 7,179,965, 7,208,474; 7,227,056, 7,288,643, 7,323,556, 7,329,736, 7,449,552, 7,468,278, 7,510,878, 7,521,235, 7,544,862, 7,605,304, 7,696,412, 7,629,504, 7,705,216, 7,772,465, 7,790,846, 7,858,849 and WO 1991/14778; WO 1999/31248; WO 2001/12731; WO 1999/24581 and WO 1997/40162.

Genes encoding pesticidal proteins may also be stacked including but are not limited to: insecticidal proteins from *Pseudomonas* sp. such as PSEEN3174 (Monalysin, (2011) *PLoS Pathogens,* 7:1-13), from *Pseudomonas protegens* strain CHAO and Pf-5 (previously *fluorescens*) (Pechy-Tarr, (2008) *Environmental Microbiology* 10:2368-2386: GenBank Accession No. EU400157); from *Pseudomonas Taiwanensis* (Liu, et al., (2010) *J. Agric. Food Chem.* 58:12343-12349) and from *Pseudomonas pseudoalcligenes* (Zhang, et al., (2009) *Annals of Microbiology* 59:45-50 and Li, et al., (2007) *Plant Cell Tiss. Organ Cult.* 89:159-168); insecticidal proteins from *Photorhabdus* sp. and *Xenorhabdus* sp. (Hinchliffe, et al., (2010) *The Open Toxinology Journal* 3:101-118 and Morgan, et al., (2001) *Applied and Envir. Micro.* 67:2062-2069), U.S. Pat. Nos. 6,048,838, and 6,379,946; a PIP-1 polypeptide of U.S. Ser. No. 13/792,861; an AflP-1A and/or AflP-1B polypeptide of U.S. Ser. No. 13/800,233; a PHI-4 polypeptide of U.S. Ser. No. 13/839,702; a PIP-47 polypeptide of PCT Serial Number PCT/US14/51063; a PIP-72 polypeptide of PCT Serial Number PCT/US14/55128; a PtIP-50 polypeptide and a PtIP-65 polypeptide of PCT Publication Number WO2015/120270; a PtIP-83 polypeptide of PCT Publication Number WO2015/120276; a PtIP-96 polypeptide of PCT Serial Number PCT/US15/55502; an IPD079 polypeptide of U.S. Ser. No. 62/201,977; an IPD082 polypeptide of U.S. Ser. No. 62/269,482; and δ-endotoxins including, but not limited to, the Cry1, Cry2, Cry3, Cry4, Cry5, Cry6, Cry7, Cry8, Cry9, Cry10, Cry11, Cry12, Cry13, Cry14, Cry15, Cry16, Cry17, Cry18, Cry19, Cry20, Cry21, Cry22, Cry23, Cry24, Cry25, Cry26, Cry27, Cry 28, Cry 29, Cry 30, Cry31, Cry32, Cry33, Cry34, Cry35, Cry36, Cry37, Cry38, Cry39, Cry40, Cry41, Cry42, Cry43, Cry44, Cry45, Cry 46, Cry47, Cry49, Cry 51 and Cry55 classes of δ-endotoxin genes and the *B. thuringiensis* cytolytic Cyt1 and Cyt2 genes. Members of these classes of *B. thuringiensis* insecticidal proteins include, but are not limited to Cry1Aa1 (Accession #AAA22353); Cry1Aa2 (Accession #Accession #AAA22552); Cry1Aa3 (Accession #BAA00257); Cry1Aa4 (Accession #CAA31886); Cry1Aa5 (Accession #BAA04468); Cry1Aa6 (Accession #AAA86265); Cry1Aa7 (Accession #AAD46139); Cry1Aa8 (Accession #126149); Cry1Aa9 (Accession #BAA77213); Cry1Aa10 (Accession #AAD55382); Cry1Aa11 (Accession #CAA70856); Cry1Aa12 (Accession #AAP80146); Cry1Aa13 (Accession #AAM44305); Cry1Aa14 (Accession #AAP40639); Cry1Aa15 (Accession #AAY66993); Cry1Aa16 (Accession #HQ439776); Cry1Aa17 (Accession #HQ439788); Cry1Aa18 (Accession #HQ439790); Cry1Aa19 (Accession #HQ685121); Cry1Aa20 (Accession #JF340156); Cry1Aa21 (Accession #JN651496); Cry1Aa22 (Accession #KC158223); Cry1Ab1 (Accession #AAA22330); Cry1Ab2 (Accession #AAA22613); Cry1Ab3 (Accession #AAA22561); Cry1Ab4 (Accession #BAA00071); Cry1Ab5 (Accession #CAA28405); Cry1Ab6 (Accession #AAA22420); Cry1Ab7 (Accession #CAA31620); Cry1Ab8 (Accession #AAA22551); Cry1Ab9 (Accession #CAA38701); Cry1Ab10 (Accession #A29125); Cry1Ab11 (Accession #112419); Cry1Ab12 (Accession #AAC64003); Cry1Ab13 (Accession #AAN76494); Cry1Ab14 (Accession #AAG16877); Cry1Ab15 (Accession #AA013302); Cry1Ab16 (Accession #AAK55546); Cry1Ab17 (Accession #AAT46415); Cry1Ab18 (Accession #AAQ88259); Cry1Ab19 (Accession #AAW31761); Cry1Ab20 (Accession #ABB72460); Cry1Ab21 (Accession #ABS18384); Cry1Ab22 (Accession #ABW87320); Cry1Ab23 (Accession #HQ439777); Cry1Ab24 (Accession #HQ439778); Cry1Ab25 (Accession #HQ685122); Cry1Ab26 (Accession #HQ847729); Cry1Ab27 (Accession #JN135249); Cry1Ab28 (Accession #JN135250); Cry1Ab29 (Accession #JN135251); Cry1Ab30 (Accession #JN135252); Cry1Ab31 (Accession #JN135253); Cry1Ab32 (Accession #JN135254); Cry1Ab33 (Accession #AAS93798); Cry1Ab34 (Accession #KC156668); Cry1Ab-like (Accession #AAK14336); Cry1Ab-like (Accession #AAK14337); Cry1Ab-like (Accession #AAK14338); Cry1Ab-like (Accession #ABG88858); Cry1Ac1 (Accession #AAA22331); Cry1Ac2 (Accession #AAA22338); Cry1Ac3 (Accession #CAA38098); Cry1Ac4 (Accession #AAA73077); Cry1Ac5 (Accession #AAA22339); Cry1Ac6 (Accession #AAA86266); Cry1Ac7 (Accession #AAB46989); Cry1Ac8 (Accession #AAC44841); Cry1Ac9 (Accession #AAB49768); Cry1Ac10 (Accession #CAA05505); Cry1Ac11 (Accession #CAA10270); Cry1Ac12 (Accession #112418); Cry1Ac13 (Accession #AAD38701); Cry1Ac14 (Accession #AAQ06607); Cry1Ac15 (Accession #AAN07788); Cry1Ac16 (Accession #AAU87037); Cry1Ac17 (Accession #AAX18704); Cry1Ac18 (Accession #AAY88347); Cry1Ac19 (Accession #ABD37053); Cry1Ac20 (Accession #ABB89046); Cry1Ac21 (Accession #AAY66992); Cry1Ac22 (Accession #ABZ01836); Cry1Ac23 (Accession #CAQ30431); Cry1Ac24 (Accession #ABL01535); Cry1Ac25 (Accession #FJ513324); Cry1Ac26 (Accession #FJ617446); Cry1Ac27 (Accession #FJ617447); Cry1Ac28 (Accession #ACM90319); Cry1Ac29 (Accession #DQ438941); Cry1Ac30 (Accession #GQ227507); Cry1Ac31 (Accession #GU446674); Cry1Ac32 (Accession #HM061081); Cry1Ac33 (Accession #GQ866913); Cry1Ac34 (Accession #HQ230364); Cry1Ac35 (Accession #JF340157); Cry1Ac36 (Accession #JN387137); Cry1Ac37 (Accession #JQ317685); Cry1Ad1 (Accession #AAA22340); Cry1Ad2 (Accession #CAA01880); Cry1Ae1 (Accession #AAA22410); Cry1Af1 (Accession #AAB82749); Cry1Ag1 (Accession #AAD46137); Cry1Ah1 (Accession #AAQ14326); Cry1Ah2 (Accession #ABB76664); Cry1Ah3 (Accession #HQ439779); Cry1Ai1 (Accession #AA039719); Cry1Ai2 (Accession #HQ439780); Cry1A-like (Accession #AAK14339); Cry1Ba1 (Accession #CAA29898); Cry1Ba2 (Accession #CAA65003); Cry1Ba3 (Accession

#AAK63251); Cry1Ba4 (Accession #AAK51084); Cry1Ba5 (Accession #AB020894); Cry1Ba6 (Accession #ABL60921); Cry1Ba7 (Accession #HQ439781); Cry1Bb1 (Accession #AAA22344); Cry1Bb2 (Accession #HQ439782); Cry1Bc1 (Accession #CAA86568); Cry1Bd1 (Accession #AAD10292); Cry1Bd2 (Accession #AAM93496); Cry1Be1 (Accession #AAC32850); Cry1Be2 (Accession #AAQ52387); Cry1Be3 (Accession #ACV96720); Cry1Be4 (Accession #HM070026); Cry1Bf1 (Accession #CAC50778); Cry1Bf2 (Accession #AAQ52380); Cry1Bg1 (Accession #AA039720); Cry1Bh1 (Accession #HQ589331); Cry1Bi1 (Accession #KC156700); Cry1Ca1 (Accession #CAA30396); Cry1Ca2 (Accession #CAA31951); Cry1Ca3 (Accession #AAA22343); Cry1Ca4 (Accession #CAA01886); Cry1Ca5 (Accession #CAA65457); Cry1Ca6 [1] (Accession #AAF37224); Cry1Ca7 (Accession #AAG50438); Cry1Ca8 (Accession #AAM00264); Cry1Ca9 (Accession #AAL79362); Cry1Ca10 (Accession #AAN16462); Cry1Ca11 (Accession #AAX53094); Cry1Ca12 (Accession #HM070027); Cry1Ca13 (Accession #HQ412621); Cry1Ca14 (Accession #JN651493); Cry1Cb1 (Accession #M97880); Cry1Cb2 (Accession #AAG35409); Cry1Cb3 (Accession #ACD50894); Cry1Cb-like (Accession #AAX63901); Cry1Da1 (Accession #CAA38099); Cry1Da2 (Accession #176415); Cry1Da3 (Accession #HQ439784); Cry1Db1 (Accession #CAA80234); Cry1Db2 (Accession #AAK48937); Cry1Dc1 (Accession #ABK35074); Cry1Ea1 (Accession #CAA37933); Cry1 Ea2 (Accession #CAA39609); Cry1 Ea3 (Accession #AAA22345); Cry1Ea4 (Accession #AAD04732); Cry1Ea5 (Accession #A15535); Cry1Ea6 (Accession #AAL50330); Cry1Ea7 (Accession #AAW72936); Cry1Ea8 (Accession #ABX11258); Cry1Ea9 (Accession #HQ439785); Cry1Ea10 (Accession #ADR00398); Cry1Ea11 (Accession #JQ652456); Cry1Eb1 (Accession #AAA22346); Cry1Fa1 (Accession #AAA22348); Cry1Fa2 (Accession #AAA22347); Cry1Fa3 (Accession #HM070028); Cry1Fa4 (Accession #HM439638); Cry1 Fb1 (Accession #CAA80235); Cry1Fb2 (Accession #BAA25298); Cry1Fb3 (Accession #AAF21767); Cry1Fb4 (Accession #AAC10641); Cry1Fb5 (Accession #AA013295); Cry1Fb6 (Accession #ACD50892); Cry1Fb7 (Accession #ACD50893); Cry1Ga1 (Accession #CAA80233); Cry1Ga2 (Accession #CAA70506); Cry1Gb1 (Accession #AAD10291); Cry1Gb2 (Accession #AA013756); Cry1Gc1 (Accession #AAQ52381); Cry1Ha1 (Accession #CAA80236); Cry1Hb1 (Accession #AAA79694); Cry1Hb2 (Accession #HQ439786); Cry1H-like (Accession #AAF01213); Cry1Ia1 (Accession #CAA44633); Cry1Ia2 (Accession #AAA22354); Cry1Ia3 (Accession #AAC36999); Cry1Ia4 (Accession #AAB00958); Cry1Ia5 (Accession #CAA70124); Cry1Ia6 (Accession #AAC26910); Cry1Ia7 (Accession #AAM73516); Cry1Ia8 (Accession #AAK66742); Cry1Ia9 (Accession #AAQ08616); Cry1Ia10 (Accession #AAP86782); Cry1Ia11 (Accession #CAC85964); Cry1Ia12 (Accession #AAV53390); Cry1Ia13 (Accession #ABF83202); Cry1Ia14 (Accession #ACG63871); Cry1Ia15 (Accession #FJ617445); Cry1Ia16 (Accession #FJ617448); Cry1Ia17 (Accession #GU989199); Cry1Ia18 (Accession #ADK23801); Cry1Ia19 (Accession #HQ439787); Cry1Ia20 (Accession #JQ228426); Cry1Ia21 (Accession #JQ228424); Cry1Ia22 (Accession #JQ228427); Cry1Ia23 (Accession #JQ228428); Cry1Ia24 (Accession #JQ228429); Cry1Ia25 (Accession #JQ228430); Cry1Ia26 (Accession #JQ228431); Cry1Ia27 (Accession #JQ228432); Cry1Ia28 (Accession #JQ228433); Cry1Ia29 (Accession #JQ228434); Cry1Ia30 (Accession #JQ317686); Cry1Ia31 (Accession #JX944038); Cry1Ia32 (Accession #JX944039); Cry1Ia33 (Accession #JX944040); Cry1Ib1 (Accession #AAA82114); Cry1Ib2 (Accession #ABW88019); Cry1Ib3 (Accession #ACD75515); Cry1Ib4 (Accession #HM051227); Cry1Ib5 (Accession #HM070028); Cry1Ib6 (Accession #ADK38579); Cry1Ib7 (Accession #JN571740); Cry1Ib8 (Accession #JN675714); Cry1Ib9 (Accession #JN675715); Cry1Ib10 (Accession #JN675716); Cry1Ib11 (Accession #JQ228423); Cry1Ic1 (Accession #AAC62933); Cry1Ic2 (Accession #AAE71691); Cry1Id1 (Accession #AAD44366); Cry1Id2 (Accession #JQ228422); Cry1Ie1 (Accession #AAG43526); Cry1Ie2 (Accession #HM439636); Cry1Ie3 (Accession #KC156647); Cry1Ie4 (Accession #KC156681); Cry1If1 (Accession #AAQ52382); Cry1Ig1 (Accession #KC156701); Cry1I-like (Accession #AAC31094); Cry1I-like (Accession #ABG88859); Cry1Ja1 (Accession #AAA22341); Cry1Ja2 (Accession #HM070030); Cry1Ja3 (Accession #JQ228425); Cry1Jb1 (Accession #AAA98959); Cry1Jc1 (Accession #AAC31092); Cry1Jc2 (Accession #AAQ52372); Cry1Jd1 (Accession #CAC50779); Cry1Ka1 (Accession #AAB00376); Cry1Ka2 (Accession #HQ439783); Cry1La1 (Accession #AAS60191); Cry1La2 (Accession #HM070031); Cry1Ma1 (Accession #FJ884067); Cry1Ma2 (Accession #KC156659); Cry1Na1 (Accession #KC156648); Cry1Nb1 (Accession #KC156678); Cry1-like (Accession #AAC31091); Cry2Aa1 (Accession #AAA22335); Cry2Aa2 (Accession #AAA83516); Cry2Aa3 (Accession #D86064); Cry2Aa4 (Accession #AAC04867); Cry2Aa5 (Accession #CAA10671); Cry2Aa6 (Accession #CAA10672); Cry2Aa7 (Accession #CAA10670); Cry2Aa8 (Accession #AA013734); Cry2Aa9 (Accession #AA013750); Cry2Aa10 (Accession #AAQ04263); Cry2Aa11 (Accession #AAQ52384); Cry2Aa12 (Accession #AB183671); Cry2Aa13 (Accession #ABL01536); Cry2Aa14 (Accession #ACF04939); Cry2Aa15 (Accession #JN426947); Cry2Ab1 (Accession #AAA22342); Cry2Ab2 (Accession #CAA39075); Cry2Ab3 (Accession #AAG36762); Cry2Ab4 (Accession #AA013296); Cry2Ab5 (Accession #AAQ04609); Cry2Ab6 (Accession #AAP59457); Cry2Ab7 (Accession #AAZ66347); Cry2Ab8 (Accession #ABC95996); Cry2Ab9 (Accession #ABC74968); Cry2Ab10 (Accession #EF157306); Cry2Ab11 (Accession #CAM84575); Cry2Ab12 (Accession #ABM21764); Cry2Ab13 (Accession #ACG76120); Cry2Ab14 (Accession #ACG76121); Cry2Ab15 (Accession #HM037126); Cry2Ab16 (Accession #GQ866914); Cry2Ab17 (Accession #HQ439789); Cry2Ab18 (Accession #JN135255); Cry2Ab19 (Accession #JN135256); Cry2Ab20 (Accession #JN135257); Cry2Ab21 (Accession #JN135258); Cry2Ab22 (Accession #JN135259); Cry2Ab23 (Accession #JN135260); Cry2Ab24 (Accession #JN135261); Cry2Ab25 (Accession #JN415485); Cry2Ab26 (Accession #JN426946); Cry2Ab27 (Accession #JN415764); Cry2Ab28 (Accession #JN651494); Cry2Ac1 (Accession #CAA40536); Cry2Ac2 (Accession #AAG35410); Cry2Ac3 (Accession #AAQ52385); Cry2Ac4 (Accession #ABC95997); Cry2Ac5 (Accession #ABC74969); Cry2Ac6 (Accession #ABC74793); Cry2Ac7 (Accession #CAL18690); Cry2Ac8 (Accession #CAM09325); Cry2Ac9 (Accession #CAM09326); Cry2Ac10 (Accession #ABN15104); Cry2Ac11 (Accession #CAM83895); Cry2Ac12 (Accession #CAM83896); Cry2Ad1 (Accession #AAF09583); Cry2Ad2 (Accession #ABC86927); Cry2Ad3 (Accession

#CAK29504); Cry2Ad4 (Accession #CAM32331); Cry2Ad5 (Accession #CA078739); Cry2Ae1 (Accession #AAQ52362); Cry2Af1 (Accession #AB030519); Cry2Af2 (Accession #GQ866915); Cry2Ag1 (Accession #ACH91610); Cry2Ah1 (Accession #EU939453); Cry2Ah2 (Accession #ACL80665); Cry2Ah3 (Accession #GU073380); Cry2Ah4 (Accession #KC156702); Cry2Ai1 (Accession #FJ788388); Cry2Aj (Accession #); Cry2Ak1 (Accession #KC156660); Cry2Ba1 (Accession #KC156658); Cry3Aa1 (Accession #AAA22336); Cry3Aa2 (Accession #AAA22541); Cry3Aa3 (Accession #CAA68482); Cry3Aa4 (Accession #AAA22542); Cry3Aa5 (Accession #AAA50255); Cry3Aa6 (Accession #AAC43266); Cry3Aa7 (Accession #CAB41411); Cry3Aa8 (Accession #AAS79487); Cry3Aa9 (Accession #AAW05659); Cry3Aa10 (Accession #AAU29411); Cry3Aa11 (Accession #AAW82872); Cry3Aa12 (Accession #ABY49136); Cry3Ba1 (Accession #CAA34983); Cry3Ba2 (Accession #CAA00645); Cry3Ba3 (Accession #JQ397327); Cry3Bb1 (Accession #AAA22334); Cry3Bb2 (Accession #AAA74198); Cry3Bb3 (Accession #115475); Cry3Ca1 (Accession #CAA42469); Cry4Aa1 (Accession #CAA68485); Cry4Aa2 (Accession #BAA00179); Cry4Aa3 (Accession #CAD30148); Cry4Aa4 (Accession #AFB18317); Cry4A-like (Accession #AAY96321); Cry4Ba1 (Accession #CAA30312); Cry4Ba2 (Accession #CAA30114); Cry4Ba3 (Accession #AAA22337); Cry4Ba4 (Accession #BAA00178); Cry4Ba5 (Accession #CAD30095); Cry4Ba-like (Accession #ABC47686); Cry4Ca1 (Accession #EU646202); Cry4Cb1 (Accession #FJ403208); Cry4Cb2 (Accession #FJ597622); Cry4Cc1 (Accession #FJ403207); Cry5Aa1 (Accession #AAA67694); Cry5Ab1 (Accession #AAA67693); Cry5Ac1 (Accession #134543); Cry5Ad1 (Accession #ABQ82087); Cry5Ba1 (Accession #AAA68598); Cry5Ba2 (Accession #ABW88931); Cry5Ba3 (Accession #AFJ04417); Cry5Ca1 (Accession #HM461869); Cry5Ca2 (Accession #ZP_04123426); Cry5Da1 (Accession #HM461870); Cry5Da2 (Accession #ZP_04123980); Cry5Ea1 (Accession #HM485580); Cry5Ea2 (Accession #ZP_04124038); Cry6Aa1 (Accession #AAA22357); Cry6Aa2 (Accession #AAM46849); Cry6Aa3 (Accession #ABH03377); Cry6Ba1 (Accession #AAA22358); Cry7Aa1 (Accession #AAA22351); Cry7Ab1 (Accession #AAA21120); Cry7Ab2 (Accession #AAA21121); Cry7Ab3 (Accession #ABX24522); Cry7Ab4 (Accession #EU380678); Cry7Ab5 (Accession #ABX79555); Cry7Ab6 (Accession #ACI44005); Cry7Ab7 (Accession #ADB89216); Cry7Ab8 (Accession #GU145299); Cry7Ab9 (Accession #ADD92572); Cry7Ba1 (Accession #ABB70817); Cry7Bb1 (Accession #KC156653); Cry7Ca1 (Accession #ABR67863); Cry7Cb1 (Accession #KC156698); Cry7Da1 (Accession #ACQ99547); Cry7Da2 (Accession #HM572236); Cry7Da3 (Accession #KC156679); Cry7Ea1 (Accession #HM035086); Cry7Ea2 (Accession #HM132124); Cry7Ea3 (Accession #EEM19403); Cry7Fa1 (Accession #HM035088); Cry7Fa2 (Accession #EEM19090); Cry7Fb1 (Accession #HM572235); Cry7Fb2 (Accession #KC156682); Cry7Ga1 (Accession #HM572237); Cry7Ga2 (Accession #KC156669); Cry7Gb1 (Accession #KC156650); Cry7Gc1 (Accession #KC156654); Cry7Gd1 (Accession #KC156697); Cry7Ha1 (Accession #KC156651); Cry7Ia1 (Accession #KC156665); Cry7Ja1 (Accession #KC156671); Cry7Ka1 (Accession #KC156680); Cry7Kb1 (Accession #BAM99306); Cry7La1 (Accession #BAM99307); Cry8Aa1 (Accession #AAA21117); Cry8Ab1 (Accession #EU044830); Cry8Ac1 (Accession #KC156662); Cry8Ad1 (Accession #KC156684); Cry8Ba1 (Accession #AAA21118); Cry8Bb1 (Accession #CAD57542); Cry8Bc1 (Accession #CAD57543); Cry8Ca1 (Accession #AAA21119); Cry8Ca2 (Accession #AAR98783); Cry8Ca3 (Accession #EU625349); Cry8Ca4 (Accession #ADB54826); Cry8Da1 (Accession #BAC07226); Cry8Da2 (Accession #BD133574); Cry8Da3 (Accession #BD133575); Cry8Db1 (Accession #BAF93483); Cry8Ea1 (Accession #AAQ73470); Cry8Ea2 (Accession #EU047597); Cry8Ea3 (Accession #KC855216); Cry8Fa1 (Accession #AAT48690); Cry8Fa2 (Accession #HQ174208); Cry8Fa3 (Accession #AFH78109); Cry8Ga1 (Accession #AAT46073); Cry8Ga2 (Accession #ABC42043); Cry8Ga3 (Accession #FJ198072); Cry8Ha1 (Accession #AAW81032); Cry8Ia1 (Accession #EU381044); Cry8Ia2 (Accession #GU073381); Cry8Ia3 (Accession #HM044664); Cry8Ia4 (Accession #KC156674); Cry8Ib1 (Accession #GU325772); Cry8Ib2 (Accession #KC156677); Cry8Ja1 (Accession #EU625348); Cry8Ka1 (Accession #FJ422558); Cry8Ka2 (Accession #ACN87262); Cry8Kb1 (Accession #HM123758); Cry8Kb2 (Accession #KC156675); Cry8La1 (Accession #GU325771); Cry8Ma1 (Accession #HM044665); Cry8Ma2 (Accession #EEM86551); Cry8Ma3 (Accession #HM210574); Cry8Na1 (Accession #HM640939); Cry8Pa1 (Accession #HQ388415); Cry8Qa1 (Accession #HQ441166); Cry8Qa2 (Accession #KC152468); Cry8Ra1 (Accession #AFP87548); Cry8Sa1 (Accession #JQ740599); Cry8Ta1 (Accession #KC156673); Cry8-like (Accession #FJ770571); Cry8-like (Accession #ABS53003); Cry9Aa1 (Accession #CAA41122); Cry9Aa2 (Accession #CAA41425); Cry9Aa3 (Accession #GQ249293); Cry9Aa4 (Accession #GQ249294); Cry9Aa5 (Accession #JX174110); Cry9Aa like (Accession #AAQ52376); Cry9Ba1 (Accession #CAA52927); Cry9Ba2 (Accession #GU299522); Cry9Bb1 (Accession #AAV28716); Cry9Ca1 (Accession #CAA85764); Cry9Ca2 (Accession #AAQ52375); Cry9Da1 (Accession #BAA19948); Cry9Da2 (Accession #AAB97923); Cry9Da3 (Accession #GQ249293); Cry9Da4 (Accession #GQ249297); Cry9Db1 (Accession #AAX78439); Cry9Dc1 (Accession #KC156683); Cry9Ea1 (Accession #BAA34908); Cry9Ea2 (Accession #AA012908); Cry9Ea3 (Accession #ABM21765); Cry9Ea4 (Accession #ACE88267); Cry9Ea5 (Accession #ACF04743); Cry9Ea6 (Accession #ACG63872); Cry9Ea7 (Accession #FJ380927); Cry9Ea8 (Accession #GQ249292); Cry9Ea9 (Accession #JN651495); Cry9Eb1 (Accession #CAC50780); Cry9Eb2 (Accession #GQ249298); Cry9Eb3 (Accession #KC156646); Cry9Ec1 (Accession #AAC63366); Cry9Ed1 (Accession #AAX78440); Cry9Ee1 (Accession #GQ249296); Cry9Ee2 (Accession #KC156664); Cry9Fa1 (Accession #KC156692); Cry9Ga1 (Accession #KC156699); Cry9-like (Accession #AAC63366); Cry10Aa1 (Accession #AAA22614); Cry10Aa2 (Accession #E00614); Cry10Aa3 (Accession #CAD30098); Cry10Aa4 (Accession #AFB18318); Cry10A-like (Accession #DQ167578); Cry11Aa1 (Accession #AAA22352); Cry11Aa2 (Accession #AAA22611); Cry11Aa3 (Accession #CAD30081); Cry11Aa4 (Accession #AFB18319); Cry11Aa-like (Accession #DQ166531); Cry11Ba1 (Accession #CAA60504); Cry11Bb1 (Accession #AAC97162); Cry11Bb2 (Accession #HM068615); Cry12Aa1 (Accession #AAA22355); Cry13Aa1 (Accession #AAA22356); Cry14Aa1 (Accession #AAA21516); Cry14Ab1 (Accession #KC156652); Cry15Aa1 (Accession #AAA22333);

Cry16Aa1 (Accession #CAA63860); Cry17Aa1 (Accession #CAA67841); Cry18Aa1 (Accession #CAA67506); Cry18Ba1 (Accession #AAF89667); Cry18Ca1 (Accession #AAF89668); Cry19Aa1 (Accession #CAA68875); Cry19Ba1 (Accession #BAA32397); Cry19Ca1 (Accession #AFM37572); Cry20Aa1 (Accession #AAB93476); Cry20Ba1 (Accession #ACS93601); Cry20Ba2 (Accession #KC156694); Cry20-like (Accession #GQ144333); Cry21Aa1 (Accession #132932); Cry21Aa2 (Accession #166477); Cry21Ba1 (Accession #BAC06484); Cry21Ca1 (Accession #JF521577); Cry21Ca2 (Accession #KC156687); Cry21 Da1 (Accession #JF521578); Cry22Aa1 (Accession #134547); Cry22Aa2 (Accession #CAD43579); Cry22Aa3 (Accession #ACD93211); Cry22Ab1 (Accession #AAK50456); Cry22Ab2 (Accession #CAD43577); Cry22Ba1 (Accession #CAD43578); Cry22Bb1 (Accession #KC156672); Cry23Aa1 (Accession #AAF76375); Cry24Aa1 (Accession #AAC61891); Cry24Ba1 (Accession #BAD32657); Cry24Ca1 (Accession #CAJ43600); Cry25Aa1 (Accession #AAC61892); Cry26Aa1 (Accession #AAD25075); Cry27Aa1 (Accession #BAA82796); Cry28Aa1 (Accession #AAD24189); Cry28Aa2 (Accession #AAG00235); Cry29Aa1 (Accession #CAC80985); Cry30Aa1 (Accession #CAC80986); Cry30Ba1 (Accession #BAD00052); Cry30Ca1 (Accession #BAD67157); Cry30Ca2 (Accession #ACU24781); Cry30Da1 (Accession #EF095955); Cry30Db1 (Accession #BAE80088); Cry30Ea1 (Accession #ACC95445); Cry30Ea2 (Accession #FJ499389); Cry30Fa1 (Accession #ACI22625); Cry30Ga1 (Accession #ACG60020); Cry30Ga2 (Accession #HQ638217); Cry31Aa1 (Accession #BAB11757); Cry31Aa2 (Accession #AAL87458); Cry31Aa3 (Accession #BAE79808); Cry31Aa4 (Accession #BAF32571); Cry31Aa5 (Accession #BAF32572); Cry31Aa6 (Accession #BA144026); Cry31Ab1 (Accession #BAE79809); Cry31Ab2 (Accession #BAF32570); Cry31Ac1 (Accession #BAF34368); Cry31Ac2 (Accession #AB731600); Cry31Ad1 (Accession #BA144022); Cry32Aa1 (Accession #AAG36711); Cry32Aa2 (Accession #GU063849); Cry32Ab1 (Accession #GU063850); Cry32Ba1 (Accession #BAB78601); Cry32Ca1 (Accession #BAB78602); Cry32Cb1 (Accession #KC156708); Cry32Da1 (Accession #BAB78603); Cry32Ea1 (Accession #GU324274); Cry32Ea2 (Accession #KC156686); Cry32Eb1 (Accession #KC156663); Cry32Fa1 (Accession #KC156656); Cry32Ga1 (Accession #KC156657); Cry32Ha1 (Accession #KC156661); Cry32Hb1 (Accession #KC156666); Cry32Ia1 (Accession #KC156667); Cry32Ja1 (Accession #KC156685); Cry32Ka1 (Accession #KC156688); Cry32La1 (Accession #KC156689); Cry32Ma1 (Accession #KC156690); Cry32Mb1 (Accession #KC156704); Cry32Na1 (Accession #KC156691); Cry32Oa1 (Accession #KC156703); Cry32Pa1 (Accession #KC156705); Cry32Qa1 (Accession #KC156706); Cry32Ra1 (Accession #KC156707); Cry32Sa1 (Accession #KC156709); Cry32Ta1 (Accession #KC156710); Cry32Ua1 (Accession #KC156655); Cry33Aa1 (Accession #AAL26871); Cry34Aa1 (Accession #AAG50341); Cry34Aa2 (Accession #AAK64560); Cry34Aa3 (Accession #AAT29032); Cry34Aa4 (Accession #AAT29030); Cry34Ab1 (Accession #AAG41671); Cry34Ac1 (Accession #AAG50118); Cry34Ac2 (Accession #AAK64562); Cry34Ac3 (Accession #AAT29029); Cry34Ba1 (Accession #AAK64565); Cry34Ba2 (Accession #AAT29033); Cry34Ba3 (Accession #AAT29031); Cry35Aa1 (Accession #AAG50342); Cry35Aa2 (Accession #AAK64561); Cry35Aa3 (Accession #AAT29028); Cry35Aa4 (Accession #AAT29025); Cry35Ab1 (Accession #AAG41672); Cry35Ab2 (Accession #AAK64563); Cry35Ab3 (Accession #AY536891); Cry35Ac1 (Accession #AAG50117); Cry35Ba1 (Accession #AAK64566); Cry35Ba2 (Accession #AAT29027); Cry35Ba3 (Accession #AAT29026); Cry36Aa1 (Accession #AAK64558); Cry37Aa1 (Accession #AAF76376); Cry38Aa1 (Accession #AAK64559); Cry39Aa1 (Accession #BAB72016); Cry40Aa1 (Accession #BAB72018); Cry40Ba1 (Accession #BAC77648); Cry40Ca1 (Accession #EU381045); Cry40Da1 (Accession #ACF15199); Cry41Aa1 (Accession #BAD35157); Cry41Ab1 (Accession #BAD35163); Cry41Ba1 (Accession #HM461871); Cry41Ba2 (Accession #ZP_04099652); Cry42Aa1 (Accession #BAD35166); Cry43Aa1 (Accession #BAD15301); Cry43Aa2 (Accession #BAD95474); Cry43Ba1 (Accession #BAD15303); Cry43Ca1 (Accession #KC156676); Cry43Cb1 (Accession #KC156695); Cry43Cc1 (Accession #KC156696); Cry43-like (Accession #BAD15305); Cry44Aa (Accession #BAD08532); Cry45Aa (Accession #BAD22577); Cry46Aa (Accession #BAC79010); Cry46Aa2 (Accession #BAG68906); Cry46Ab (Accession #BAD35170); Cry47Aa (Accession #AAY24695); Cry48Aa (Accession #CAJ18351); Cry48Aa2 (Accession #CAJ86545); Cry48Aa3 (Accession #CAJ86546); Cry48Ab (Accession #CAJ86548); Cry48Ab2 (Accession #CAJ86549); Cry49Aa (Accession #CAH56541); Cry49Aa2 (Accession #CAJ86541); Cry49Aa3 (Accession #CAJ86543); Cry49Aa4 (Accession #CAJ86544); Cry49Ab1 (Accession #CAJ86542); Cry50Aa1 (Accession #BAE86999); Cry50Ba1 (Accession #GU446675); Cry50Ba2 (Accession #GU446676); Cry51Aa1 (Accession #AB114444); Cry51Aa2 (Accession #GU570697); Cry52Aa1 (Accession #EF613489); Cry52Ba1 (Accession #FJ361760); Cry53Aa1 (Accession #EF633476); Cry53Ab1 (Accession #FJ361759); Cry54Aa1 (Accession #ACA52194); Cry54Aa2 (Accession #GQ140349); Cry54Ba1 (Accession #GU446677); Cry55Aa1 (Accession #ABW88932); Cry54Ab1 (Accession #JQ916908); Cry55Aa2 (Accession #AAE33526); Cry56Aa1 (Accession #ACU57499); Cry56Aa2 (Accession #GQ483512); Cry56Aa3 (Accession #JX025567); Cry57Aa1 (Accession #ANC87261); Cry58Aa1 (Accession #ANC87260); Cry59Ba1 (Accession #JN790647); Cry59Aa1 (Accession #ACR43758); Cry60Aa1 (Accession #ACU24782); Cry60Aa2 (Accession #EA057254); Cry60Aa3 (Accession #EEM99278); Cry60Ba1 (Accession #GU810818); Cry60Ba2 (Accession #EA057253); Cry60Ba3 (Accession #EEM99279); Cry61Aa1 (Accession #HM035087); Cry61Aa2 (Accession #HM132125); Cry61Aa3 (Accession #EEM19308); Cry62Aa1 (Accession #HM054509); Cry63Aa1 (Accession #BA144028); Cry64Aa1 (Accession #BAJ05397); Cry65Aa1 (Accession #HM461868); Cry65Aa2 (Accession #ZP_04123838); Cry66Aa1 (Accession #HM485581); Cry66Aa2 (Accession #ZP_04099945); Cry67Aa1 (Accession #HM485582); Cry67Aa2 (Accession #ZP_04148882); Cry68Aa1 (Accession #HQ113114); Cry69Aa1 (Accession #HQ401006); Cry69Aa2 (Accession #JQ821388); Cry69Ab1 (Accession #JN209957); Cry70Aa1 (Accession #JN646781); Cry70Ba1 (Accession #AD051070); Cry70Bb1 (Accession #EEL67276); Cry71Aa1 (Accession #JX025568); Cry72Aa1 (Accession #JX025569).

Examples of δ-endotoxins also include but are not limited to Cry1A proteins of U.S. Pat. Nos. 5,880,275 and 7,858,849; a DIG-3 or DIG-11 toxin (N-terminal deletion of α-helix 1 and/or α-helix 2 variants of Cry proteins such as Cry1A) of U.S. Pat. Nos. 8,304,604 and 8,304,605, Cry1B of U.S. patent application Ser. No. 10/525,318; Cry1C of U.S. Pat. No. 6,033,874; Cry1F of U.S. Pat. Nos. 5,188,960, 6,218,188; Cry1A/F chimeras of U.S. Pat. Nos. 7,070,982; 6,962,705 and 6,713,063); a Cry2 protein such as Cry2Ab protein of U.S. Pat. No. 7,064,249); a Cry3A protein including but not limited to an engineered hybrid insecticidal protein (eHIP) created by fusing unique combinations of variable regions and conserved blocks of at least two different Cry proteins (US Patent Application Publication Number 2010/0017914); a Cry4 protein; a Cry5 protein; a Cry6 protein; Cry8 proteins of U.S. Pat. Nos. 7,329,736, 7,449,552, 7,803,943, 7,476,781, 7,105,332, 7,378,499 and 7,462,760; a Cry9 protein such as such as members of the Cry9A, Cry9B, Cry9C, Cry9D, Cry9E, and Cry9F families; a Cry15 protein of Naimov, et al., (2008) *Applied and Environmental Microbiology* 74:7145-7151; a Cry22, a Cry34Ab1 protein of U.S. Pat. Nos. 6,127,180, 6,624,145 and 6,340,593; a CryET33 and CryET34 protein of U.S. Pat. Nos. 6,248,535, 6,326,351, 6,399,330, 6,949,626, 7,385,107 and 7,504,229; a CryET33 and CryET34 homologs of US Patent Publication Number 2006/0191034, 2012/0278954, and PCT Publication Number WO 2012/139004; a Cry35Ab1 protein of U.S. Pat. Nos. 6,083,499, 6,548,291 and 6,340,593; a Cry46 protein, a Cry 51 protein, a Cry binary toxin; a TIC901 or related toxin; TIC807 of US 2008/0295207; ET29, ET37, TIC809, TIC810, TIC812, TIC127, TIC128 of PCT US 2006/033867; TIC3131, TIC 3400, and TIC3407 of US Patent Application Publication Number 2015/0047076; AXMI-027, AXMI-036, and AXMI-038 of U.S. Pat. No. 8,236,757; AXMI-031, AXMI-039, AXMI-040, AXMI-049 of U.S. Pat. No. 7,923,602; AXMI-018, AXMI-020, and AXMI-021 of WO 2006/083891; AXMI-010 of WO 2005/038032; AXMI-003 of WO 2005/021585; AXMI-008 of US 2004/0250311; AXMI-006 of US 2004/0216186; AXMI-007 of US 2004/0210965; AXMI-009 of US 2004/0210964; AXMI-014 of US 2004/0197917; AXMI-004 of US 2004/0197916; AXMI-028 and AXMI-029 of WO 2006/119457; AXMI-007, AXMI-008, AXMI-0080rf2, AXMI-009, AXMI-014 and AXMI-004 of WO 2004/074462; AXMI-150 of U.S. Pat. No. 8,084,416; AXMI-205 of US20110023184; AXMI-011, AXMI-012, AXMI-013, AXMI-015, AXMI-019, AXMI-044, AXMI-037, AXMI-043, AXMI-033, AXMI-034, AXMI-022, AXMI-023, AXMI-041, AXMI-063, and AXMI-064 of US 2011/0263488; AXMI-R1 and related proteins of US 2010/0197592; AXMI221Z, AXMI222z, AXMI223z, AXMI224z and AXMI225z of WO 2011/103248; AXMI218, AXMI219, AXMI220, AXMI226, AXMI227, AXMI228, AXMI229, AXMI230, and AXMI231 of WO11/103247; AXMI-115, AXMI-113, AXMI-005, AXMI-163 and AXMI-184 of U.S. Pat. No. 8,334,431; AXMI-001, AXMI-002, AXMI-030, AXMI-035, and AXMI-045 of US 2010/0298211; AXMI-066 and AXMI-076 of US20090144852; AXMI128, AXMI130, AXMI131, AXMI133, AXMI140, AXMI141, AXMI142, AXMI143, AXMI144, AXMI146, AXMI148, AXMI149, AXMI152, AXMI153, AXMI154, AXMI155, AXMI156, AXMI157, AXMI158, AXMI162, AXMI165, AXMI166, AXMI167, AXMI168, AXMI169, AXMI170, AXMI171, AXMI172, AXMI173, AXMI174, AXMI175, AXMI176, AXMI177, AXMI178, AXMI179, AXMI180, AXMI181, AXMI182, AXMI185, AXMI186, AXMI187, AXMI188, AXMI189 of U.S. Pat. No. 8,318,900; AXMI079, AXMI080, AXMI081, AXMI082, AXMI091, AXMI092, AXMI096, AXMI097, AXMI098, AXMI099, AXMI100, AXMI101, AXMI102, AXMI103, AXMI104, AXMI107, AXMI108, AXMI109, AXMI110, AXMI111, AXMI112, AXMI114, AXMI116, AXMI117, AXMI118, AXMI119, AXMI120, AXMI121, AXMI122, AXMI123, AXMI124, AXMI1257, AXMI1268, AXMI127, AXMI129, AXMI164, AXMI151, AXMI161, AXMI183, AXMI132, AXMI138, AXMI137 of US 2010/0005543; and Cry proteins such as Cry1A and Cry3A having modified proteolytic sites of U.S. Pat. No. 8,319,019; and a Cry1Ac, Cry2Aa and Cry1Ca toxin protein from *Bacillus thuringiensis* strain VBTS 2528 of US Patent Application Publication Number 2011/0064710. Other Cry proteins are well known to one skilled in the art (see, Crickmore, et al., "*Bacillus thuringiensis* toxin nomenclature" (2011), at lifesci.sussex.ac.uk/home/Neil_Crickmore/Bt/which can be accessed on the world-wide web using the "www" prefix). The insecticidal activity of Cry proteins is well known to one skilled in the art (for review, see, van Frannkenhuyzen, (2009) *J. Invert. Path.* 101:1-16). The use of Cry proteins as transgenic plant traits is well known to one skilled in the art and Cry-transgenic plants including but not limited to Cry1Ac, Cry1Ac+Cry2Ab, Cry1Ab, Cry1A.105, Cry1F, Cry1Fa2, Cry1F+Cry1Ac, Cry2Ab, Cry3A, mCry3A, Cry3Bb1, Cry34Ab1, Cry35Ab1, Vip3A, mCry3A, Cry9c and CBI-Bt have received regulatory approval (see, Sanahuja, (2011) *Plant Biotech Journal* 9:283-300 and the CERA (2010) GM Crop Database Center for Environmental Risk Assessment (CERA), ILSI Research Foundation, Washington D.C. at cera-gmc.org/index.php?action=gm_crop_database which can be accessed on the world-wide web using the "www" prefix). More than one pesticidal proteins well known to one skilled in the art can also be expressed in plants such as Vip3Ab & Cry1Fa (US2012/0317682), Cry1BE & Cry1F (US2012/0311746), Cry1CA & Cry1AB (US2012/0311745), Cry1F & CryCa (US2012/0317681), Cry1DA & Cry1BE (US2012/0331590), Cry1DA & Cry1Fa (US2012/0331589), Cry1AB & Cry1BE (US2012/0324606), and Cry1Fa & Cry2Aa, Cry1I or Cry1E (US2012/0324605)); Cry34Ab/35Ab and Cry6Aa (US20130167269); Cry34Ab/VCry35Ab & Cry3Aa (US20130167268); Cry3A and Cry1Ab or Vip3Aa (US20130116170); and Cry1F, Cry34Ab1, and Cry35Ab1 (PCT/US2010/060818). Pesticidal proteins also include insecticidal lipases including lipid acyl hydrolases of U.S. Pat. No. 7,491,869, and cholesterol oxidases such as from *Streptomyces* (Purcell et al. (1993) *Biochem Biophys Res Commun* 15:1406-1413). Pesticidal proteins also include VIP (vegetative insecticidal proteins) toxins of U.S. Pat. Nos. 5,877,012, 6,107,279, 6,137,033, 7,244,820, 7,615,686, and 8,237,020, and the like. Other VIP proteins are well known to one skilled in the art (see, lifesci.sussex.ac.uk/home/Neil_Crickmore/Bt/vip.html which can be accessed on the world-wide web using the "www" prefix). Pesticidal proteins also include toxin complex (TC) proteins, obtainable from organisms such as *Xenorhabdus, Photorhabdus* and *Paenibacillus* (see, U.S. Pat. Nos. 7,491,698 and 8,084,418). Some TC proteins have "stand alone" insecticidal activity and other TC proteins enhance the activity of the stand-alone toxins produced by the same given organism. The toxicity of a "stand-alone" TC protein (from *Photorhabdus, Xenorhabdus* or *Paenibacillus*, for example) can be enhanced by one or more TC protein "potentiators" derived from a source organism of a different genus. There are three main types of TC proteins. As referred to herein, Class A proteins ("Protein A") are stand-alone toxins. Class B proteins ("Protein B") and Class C proteins ("Protein C") enhance the toxicity of Class A proteins. Examples of Class A proteins are TcbA, TcdA, XptA1 and XptA2. Examples of Class B proteins are TcaC, TcdB, XptB1Xb and XptC1Wi. Examples of Class C proteins are TccC, XptC1Xb and XptB1Wi. Pesticidal proteins also include spider, snake and scorpion venom proteins. Examples of spider venom peptides include but are not limited to lycotoxin-1 peptides and mutants thereof (U.S. Pat. No. 8,334,366).

The polynucleotides of the embodiments can also be stacked with any other gene or combination of genes to produce plants with a variety of desired trait combinations including but not limited to traits desirable for animal feed such as high oil genes (e.g., U.S. Pat. No. 6,232,529); balanced amino acids (e.g. hordothionins (U.S. Pat. Nos. 5,990,389; 5,885,801; 5,885,802; and 5,703,049); barley high lysine (Williamson et al. (1987) *Eur. J. Biochem.* 165: 99-106; and WO 98/20122) and high methionine proteins (Pedersen et al. (1986) *J. Biol. Chem.* 261: 6279; Kirihara et al. (1988) *Gene* 71: 359; and Musumura et al. (1989) *Plant Mol. Biol.* 12: 123)); increased digestibility (e.g., modified storage proteins (U.S. Pat. No. 6,858,778); and thioredoxins (U.S. Pat. No. 7,009,087), the disclosures of which are herein incorporated by reference.

The polynucleotides of the embodiments can also be stacked with traits desirable for disease or herbicide resistance (e.g., fumonisin detoxification genes (U.S. Pat. No. 5,792,931); avirulence and disease resistance genes (Jones et al. (1994) *Science* 266:789; Martin et al. (1993) *Science* 262: 1432; and Mindrinos et al. (1994) *Cell* 78:1089); acetolactate synthase (ALS) mutants that lead to herbicide resistance such as the S4 and/or Hra mutations; inhibitors of glutamine synthase such as phosphinothricin or basta (e.g., bar gene); and glyphosate resistance (EPSPS gene and GAT gene as disclosed in U.S. Pat. Nos. 7,709,702; and 7,462,481; and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE) and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al. (1988) *J. Bacteriol.* 170: 5837-5847) facilitate expression of polyhydroxyalkanoates (PHAs)), the disclosures of which are herein incorporated by reference. One could also combine the polynucleotides of the embodiments with polynucleotides providing agronomic traits such as male sterility (e.g., see U.S. Pat. No. 5,583,210), stalk strength, flowering time, or transformation technology traits such as cell cycle regulation or gene targeting (e.g. WO 99/61619; WO 00/17364; WO 99/25821), the disclosures of which are herein incorporated by reference.

In some embodiment the stacked trait may be a trait or event that has received regulatory approval which are well known to one skilled in the art and can be found at the Center for Environmental Risk Assessment (cera-gmc.org/?action=gm_crop_database, which can be accessed using the www prefix) and at the International Service for the Acquisition of Agri-Biotech Applications isaaa.org/gmapprovaldatabase/default.asp, which can be accessed using the www prefix).

Transgenic plants may comprise a stack of one or more insecticidal polynucleotides disclosed herein with one or more additional polynucleotides resulting in the production or suppression of multiple polypeptide sequences. Transgenic plants comprising stacks of polynucleotide sequences can be obtained by either or both of traditional breeding methods or through genetic engineering methods. These methods include, but are not limited to, breeding individual lines each comprising a polynucleotide of interest, transforming a transgenic plant comprising a gene disclosed herein with a subsequent gene and co-transformation of genes into a single plant cell. As used herein, the term "stacked" includes having the multiple traits present in the same plant (i.e., both traits are incorporated into the nuclear genome, one trait is incorporated into the nuclear genome and one trait is incorporated into the genome of a plastid or both traits are incorporated into the genome of a plastid). In one non-limiting example, "stacked traits" comprise a molecular stack where the sequences are physically adjacent to each other. A trait, as used herein, refers to the phenotype derived from a particular sequence or groups of sequences. Co-transformation of genes can be carried out using single transformation vectors comprising multiple genes or genes carried separately on multiple vectors. If the sequences are stacked by genetically transforming the plants, the polynucleotide sequences of interest can be combined at any time and in any order. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO 1999/25821, WO 1999/25854, WO 1999/25840, WO 1999/25855 and WO 1999/25853. Transgenic plants may comprise a stack of one or more insecticidal polynucleotides disclosed herein with one or more additional polynucleotides resulting in the production of multiple polypeptide sequences. Transgenic plants comprising stacks of polynucleotide sequences can be obtained by either or both of traditional breeding methods or through genetic engineering methods. These methods include, but are not limited to, breeding individual lines each comprising a polynucleotide of interest, transforming a transgenic plant comprising a gene disclosed herein with a subsequent gene and co-transformation of genes into a single plant cell. As used herein, the term "stacked" includes having the multiple traits present in the same plant (i.e., both traits are incorporated into the nuclear genome, one trait is incorporated into the nuclear genome and one trait is incorporated into the genome of a plastid or both traits are incorporated into the genome of a plastid). In one non-limiting example, "stacked traits" comprise a molecular stack where the sequences are physically adjacent to each other. A trait, as used herein, refers to the phenotype derived from a particular sequence or groups of sequences. Co-transformation of genes can be carried out using single transformation vectors comprising multiple genes or genes carried separately on multiple vectors. If the sequences are stacked by genetically transforming the plants, the polynucleotide sequences of interest can be combined at any time and in any order. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO 1999/25821, WO 1999/25854, WO 1999/25840, WO 1999/25855 and WO 1999/25853.

In some embodiments one or more polynucleotide encoding a variant Cry1B polypeptide or fragments or variants thereof disclosed herein may be stacked with one or more polynucleotides encoding PtIP-50 and PtIP-65 polypeptides or fragments or variants thereof disclosed in International Publication No. WO2015/120270, which is herein incorporated by reference in its entirety. In another embodiment, one or more polynucleotides encoding a variant Cry1B polypeptide or fragments or variants thereof disclosed herein may be stacked with one or more polynucleotides encoding PtIP-50 polypeptides or fragments or variants thereof disclosed in International Publication No. WO2015/120270. In another embodiment, one or more polynucleotides encoding a variant Cry1B polypeptide or fragments or variants thereof disclosed herein may be stacked with one or more polynucleotides encoding PtIP-50 polypeptides or fragments or variants thereof disclosed in SEQ ID NOs: 88-115. In another embodiment, one or more polynucleotides encoding a variant Cry1B polypeptide or fragments or variants thereof disclosed herein may be stacked with one or more polynucleotides encoding PtIP-65 polypeptides or fragments or variants thereof disclosed in International Publication No. WO2015/120270. In another embodiment, one or more polynucleotides encoding a variant Cry1B polypeptide or fragments or variants thereof disclosed herein may be stacked with one or more polynucleotides encoding PtIP-65 polypeptides or fragments or variants thereof disclosed in SEQ ID NOs: 67-87. In some embodiments, one or more polynucleotides encoding a variant Cry1B polypeptide or fragments or variants thereof disclosed herein may be stacked with one or more polynucleotides encoding PtIP-83 polypeptides or fragments or variants thereof disclosed in International Publication No. WO2015/120276, which is herein incorporated by reference. In some embodiments, one or more polynucleotides encoding a variant Cry1B polypeptide or fragments or variants thereof disclosed herein may be stacked with one or more polynucleotides encoding PtIP-83 polypeptides or fragments or variants thereof disclosed in SEQ ID NOs: 62, 64, or 66. In another embodiment, one or more polynucleotides encoding a variant Cry1B polypeptide or fragments or variants thereof disclosed herein may be stacked with one or more polynucleotides encoding PtIP-83 polypeptides or fragments or variants thereof disclosed in International Publication No. WO2015/120276 and one or more polynucleotides encoding PtIP-50 and PtIP-65 polypeptides or fragments or variants thereof disclosed in International Publication No. WO2015/120270. In another embodiment, one or more polynucleotides encoding a variant Cry1B polypeptide or fragments or variants thereof disclosed herein may be stacked with one or more polynucleotides encoding PtIP-83 polypeptides or fragments or variants thereof disclosed in International Publication No. WO2015/120276 and one or more polynucleotides encoding PtIP-50 polypeptides or fragments or variants thereof disclosed in International Publication No. WO2015/120270. In another embodiment, one or more polynucleotides encoding a variant Cry1B polypeptide or fragments or variants thereof disclosed herein may be stacked with one or more polynucleotides encoding PtIP-83 polypeptides or fragments or variants thereof disclosed in International Publication No. WO2015/120276 and one or more polynucleotides encoding PtIP-65 polypeptides or fragments or variants thereof disclosed in International Publication No. WO2015/120270. In another embodiment, one or more polynucleotides encoding a variant Cry1B polypeptide or fragments or variants thereof disclosed herein may be stacked with at least one of one or more polynucleotides encoding PtIP-83 polypeptides or fragments or variants thereof disclosed in SEQ ID NOs: 62, 64, or 66, or one or more polynucleotides encoding PtIP-65 polypeptides or fragments or variants thereof disclosed in SEQ ID NOs: 67-87 and/or one or more polynucleotides encoding PtIP-50 polypeptides or fragments or variants thereof disclosed in SEQ ID NOs: 88-115.

Compositions of the embodiments find use in protecting plants, seeds, and plant products in a variety of ways. For example, the compositions can be used in a method that involves placing an effective amount of the pesticidal composition in the environment of the pest by a procedure selected from the group consisting of spraying, dusting, broadcasting, or seed coating.

Before plant propagation material (fruit, tuber, bulb, corm, grains, seed), but especially seed, is sold as a commercial product, it is customarily treated with a protectant coating comprising herbicides, insecticides, fungicides, bactericides, nematicides, molluscicides, or mixtures of several of these preparations, if desired together with further carriers, surfactants, or application-promoting adjuvants customarily employed in the art of formulation to provide protection against damage caused by bacterial, fungal, or animal pests. In order to treat the seed, the protectant coating may be applied to the seeds either by impregnating the tubers or grains with a liquid formulation or by coating them with a combined wet or dry formulation. In addition, in special cases, other methods of application to plants are possible, e.g., treatment directed at the buds or the fruit.

The plant seed of the embodiments comprising a nucleotide sequence encoding a pesticidal protein of the embodiments may be treated with a seed protectant coating comprising a seed treatment compound, such as, for example, captan, carboxin, thiram, methalaxyl, pirimiphos-methyl, and others that are commonly used in seed treatment. In one embodiment, a seed protectant coating comprising a pesticidal composition of the embodiments is used alone or in combination with one of the seed protectant coatings customarily used in seed treatment.

It is recognized that the genes encoding the pesticidal proteins can be used to transform insect pathogenic organisms. Such organisms include baculovirus, fungi, protozoa, bacteria, and nematodes.

A gene encoding a pesticidal protein of the embodiments may be introduced via a suitable vector into a microbial host, and said host applied to the environment, or to plants or animals. The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid, or mitochondrial DNA), converted into an autonomous replicon, or transiently expressed (e.g., transfected mRNA).

Microorganism hosts that are known to occupy the "phytosphere" (phylloplane, phyllosphere, rhizosphere, and/or rhizoplana) of one or more crops of interest may be selected.

These microorganisms are selected so as to be capable of successfully competing in the particular environment with the wild-type microorganisms, provide for stable maintenance and expression of the gene expressing the pesticidal protein, and desirably, provide for improved protection of the pesticide from environmental degradation and inactivation.

Such microorganisms include bacteria, algae, and fungi. Of particular interest are microorganisms such as bacteria, e.g., *Pseudomonas, Erwinia, Serratia, Klebsiella, Xanthomonas, Streptomyces, Rhizobium, Rhodopseudomonas, Methylius, Agrobacterium, Acetobacter, Lactobacillus, Arthrobacter, Azotobacter, Leuconostoc*, and *Alcaligenes*, fungi, particularly yeast, e.g., *Saccharomyces, Cryptococcus, Kluyveromyces, Sporobolomyces, Rhodotorula*, and *Aureobasidium*. Of particular interest are such phytosphere bacterial species as *Pseudomonas syringae, Pseudomonas fluorescens, Serratia marcescens, Acetobacter xylinum*, Agrobacteria, *Rhodopseudomonas spheroides, Xanthomonas campestris, Rhizobium melioti, Alcaligenes entrophus, Clavibacter xyli* and *Azotobacter vinelandii* and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae*, and *Aureobasidium pollulans*. Of particular interest are the pigmented microorganisms.

A number of ways are available for introducing a gene expressing the pesticidal protein into the microorganism host under conditions that allow for stable maintenance and expression of the gene. For example, expression cassettes can be constructed which include the nucleotide constructs of interest operably linked with the transcriptional and translational regulatory signals for expression of the nucleotide constructs, and a nucleotide sequence homologous with a sequence in the host organism, whereby integration will occur, and/or a replication system that is functional in the host, whereby integration or stable maintenance will occur.

Transcriptional and translational regulatory signals include, but are not limited to, promoters, transcriptional initiation start sites, operators, activators, enhancers, other regulatory elements, ribosomal binding sites, an initiation codon, termination signals, and the like. See, for example, U.S. Pat. Nos. 5,039,523 and 4,853,331; EPO 0480762A2; Sambrook; Maniatis et al. (Cold Spring Harbor Laboratory Press, Cold Spring Harbor, N.Y.); Davis et al., eds. (1980) *Advanced Bacterial Genetics* (Cold Spring Harbor Laboratory Press, Cold Spring Harbor, N.Y.) and the references cited therein.

Suitable host cells, where the pesticidal protein-containing cells will be treated to prolong the activity of the pesticidal proteins in the cell when the treated cell is applied to the environment of the target pest(s), may include either prokaryotes or eukaryotes, normally being limited to those cells that do not produce substances toxic to higher organisms, such as mammals. However, organisms that produce substances toxic to higher organisms could be used, where the toxin is unstable or the level of application sufficiently low as to avoid any possibility of toxicity to a mammalian host. As hosts, of particular interest will be the prokaryotes and the lower eukaryotes, such as fungi. Illustrative prokaryotes, both Gram-negative and gram-positive, include Enterobacteriaceae, such as *Escherichia, Erwinia, Shigella, Salmonella*, and *Proteus*; Bacillaceae; Rhizobiaceae, such as *Rhizobium*; Spirillaceae, such as photobacterium, *Zymomonas, Serratia, Aeromonas, Vibrio, Desulfovibrio, Spirillum*; Lactobacillaceae; Pseudomonadaceae, such as *Pseudomonas* and *Acetobacter* Azotobacteraceae and Nitrobacteraceae. Among eukaryotes are fungi, such as Phycomycetes and Ascomycetes, which includes yeast, such as *Saccharomyces* and *Schizosaccharomyces*; and Basidiomycetes yeast, such as *Rhodotorula, Aureobasidium, Sporobolomyces*, and the like.

Characteristics of particular interest in selecting a host cell for purposes of pesticidal protein production include ease of introducing the pesticidal protein gene into the host, availability of expression systems, efficiency of expression, stability of the protein in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; leaf affinity; lack of mammalian toxicity; attractiveness to pests for ingestion; ease of killing and fixing without damage to the toxin; and the like. Other considerations include ease of formulation and handling, economics, storage stability, and the like.

Host organisms of particular interest include yeast, such as *Rhodotorula* spp., *Aureobasidium* spp., *Saccharomyces* spp. (such as *S. cerevisiae*), Sporobolomyces spp., phylloplane organisms such as *Pseudomonas* spp. (such as *P. aeruginosa, P. fluorescens*), *Erwinia* spp., and *Flavobacterium* spp., and other such organisms, including Bt, *E. coli, Bacillus subtilis*, and the like.

Genes encoding the pesticidal proteins of the embodiments can be introduced into microorganisms that multiply on plants (epiphytes) to deliver pesticidal proteins to potential target pests. Epiphytes, for example, can be gram-positive or gram-negative bacteria.

Root-colonizing bacteria, for example, can be isolated from the plant of interest by methods known in the art. Specifically, a *Bacillus cereus* strain that colonizes roots can be isolated from roots of a plant (see, for example, Handelsman et al. (1991) *Appl. Environ. Microbiol.* 56:713-718). Genes encoding the pesticidal proteins of the embodiments can be introduced into a root-colonizing *Bacillus cereus* by standard methods known in the art.

Genes encoding pesticidal proteins can be introduced, for example, into the root-colonizing *Bacillus* by means of electro transformation. Specifically, genes encoding the pesticidal proteins can be cloned into a shuttle vector, for example, pHT3101 (Lerecius et al. (1989) *FEMS Microbiol. Letts.* 60: 211-218. The shuttle vector pHT3101 containing the coding sequence for the particular pesticidal protein gene can, for example, be transformed into the root-colonizing *Bacillus* by means of electroporation (Lerecius et al. (1989) *FEMS Microbiol. Letts.* 60: 211-218).

Expression systems can be designed so that pesticidal proteins are secreted outside the cytoplasm of gram-negative bacteria, such as *E. coli*, for example. Advantages of having pesticidal proteins secreted are: (1) avoidance of potential cytotoxic effects of the pesticidal protein expressed; and (2) improvement in the efficiency of purification of the pesticidal protein, including, but not limited to, increased efficiency in the recovery and purification of the protein per volume cell broth and decreased time and/or costs of recovery and purification per unit protein.

Pesticidal proteins can be made to be secreted in *E. coli*, for example, by fusing an appropriate *E. coli* signal peptide to the amino-terminal end of the pesticidal protein. Signal peptides recognized by *E. coli* can be found in proteins already known to be secreted in *E. coli*, for example the OmpA protein (Ghrayeb et al. (1984) *EMBO J*, 3:2437-2442). OmpA is a major protein of the *E. coli* outer membrane, and thus its signal peptide is thought to be efficient in the translocation process. Also, the OmpA signal peptide does not need to be modified before processing as may be the case for other signal peptides, for example lipoprotein signal peptide (Duffaud et al. (1987) *Meth. Enzymol.* 153: 492).

Pesticidal proteins of the embodiments can be fermented in a bacterial host and the resulting bacteria processed and used as a microbial spray in the same manner that Bt strains have been used as insecticidal sprays. In the case of a pesticidal protein(s) that is secreted from *Bacillus*, the secretion signal is removed or mutated using procedures known in the art. Such mutations and/or deletions prevent secretion of the pesticidal protein(s) into the growth medium during the fermentation process. The pesticidal proteins are retained within the cell, and the cells are then processed to yield the encapsulated pesticidal proteins. Any suitable microorganism can be used for this purpose. *Pseudomonas* has been used to express Bt toxins as encapsulated proteins and the resulting cells processed and sprayed as an insecticide (Gaertner et al. (1993), in: *Advanced Engineered Pesticides*, ed. Kim).

Alternatively, the pesticidal proteins are produced by introducing a heterologous gene into a cellular host. Expression of the heterologous gene results, directly or indirectly, in the intracellular production and maintenance of the pesticide. These cells are then treated under conditions that prolong the activity of the toxin produced in the cell when the cell is applied to the environment of target pest(s). The resulting product retains the toxicity of the toxin. These naturally encapsulated pesticidal proteins may then be formulated in accordance with conventional techniques for application to the environment hosting a target pest, e.g., soil, water, and foliage of plants. See, for example EP0192319, and the references cited therein.

In the embodiments, a transformed microorganism (which includes whole organisms, cells, spore(s), pesticidal protein(s), pesticidal component(s), pest-impacting component(s), mutant(s), living or dead cells and cell components, including mixtures of living and dead cells and cell components, and including broken cells and cell components) or an isolated pesticidal protein can be formulated with an acceptable carrier into a pesticidal composition(s) that is, for example, a suspension, a solution, an emulsion, a dusting powder, a dispersible granule or pellet, a wettable powder, and an emulsifiable concentrate, an aerosol or spray, an impregnated granule, an adjuvant, a coatable paste, a colloid, and also encapsulations in, for example, polymer substances. Such formulated compositions may be prepared by such conventional means as desiccation, lyophilization, homogenization, extraction, filtration, centrifugation, sedimentation, or concentration of a culture of cells comprising the polypeptide.

Such compositions disclosed above may be obtained by the addition of a surface-active agent, an inert carrier, a preservative, a humectant, a feeding stimulant, an attractant, an encapsulating agent, a binder, an emulsifier, a dye, a UV protectant, a buffer, a flow agent or fertilizers, micronutrient donors, or other preparations that influence plant growth. One or more agrochemicals including, but not limited to, herbicides, insecticides, fungicides, bactericides, nematicides, molluscicides, acaricides, plant growth regulators, harvest aids, and fertilizers, can be combined with carriers, surfactants or adjuvants customarily employed in the art of formulation or other components to facilitate product handling and application for particular target pests. Suitable carriers and adjuvants can be solid or liquid and correspond to the substances ordinarily employed in formulation technology, e.g., natural or regenerated mineral substances, solvents, dispersants, wetting agents, tackifiers, binders, or fertilizers. The active ingredients of the embodiments are normally applied in the form of compositions and can be applied to the crop area, plant, or seed to be treated. For example, the compositions of the embodiments may be applied to grain in preparation for or during storage in a grain bin or silo, etc. The compositions of the embodiments may be applied simultaneously or in succession with other compounds. Methods of applying an active ingredient of the embodiments or an agrochemical composition of the embodiments that contains at least one of the pesticidal proteins produced by the bacterial strains of the embodiments include, but are not limited to, foliar application, seed coating, and soil application. The number of applications and the rate of application depend on the intensity of infestation by the corresponding pest.

Suitable surface-active agents include, but are not limited to, anionic compounds such as a carboxylate of, for example, a metal; a carboxylate of a long chain fatty acid; an N-acylsarcosinate; mono or di-esters of phosphoric acid with fatty alcohol ethoxylates or salts of such esters; fatty alcohol sulfates such as sodium dodecyl sulfate, sodium octadecyl sulfate or sodium cetyl sulfate; ethoxylated fatty alcohol sulfates; ethoxylated alkylphenol sulfates; lignin sulfonates; petroleum sulfonates; alkyl aryl sulfonates such as alkyl-benzene sulfonates or lower alkylnaphtalene sulfonates, e.g., butyl-naphthalene sulfonate; salts of sulfonated naphthalene-formaldehyde condensates; salts of sulfonated phenol-formaldehyde condensates; more complex sulfonates such as the amide sulfonates, e.g., the sulfonated condensation product of oleic acid and N-methyl taurine; or the dialkyl sulfosuccinates, e.g., the sodium sulfonate of dioctyl succinate. Non-ionic agents include condensation products of fatty acid esters, fatty alcohols, fatty acid amides or fatty-alkyl- or alkenyl-substituted phenols with ethylene oxide, fatty esters of polyhydric alcohol ethers, e.g., sorbitan fatty acid esters, condensation products of such esters with ethylene oxide, e.g., polyoxyethylene sorbitar fatty acid esters, block copolymers of ethylene oxide and propylene oxide, acetylenic glycols such as 2,4,7,9-tetraethyl-5-decyn-4,7-diol, or ethoxylated acetylenic glycols. Examples of a cationic surface-active agent include, for instance, an aliphatic mono-, di-, or polyamine such as an acetate, naphthenate or oleate; or oxygen-containing amine such as an amine oxide of polyoxyethylene alkylamine; an amide-linked amine prepared by the condensation of a carboxylic acid with a di- or polyamine; or a quaternary ammonium salt.

Examples of inert materials include but are not limited to inorganic minerals such as kaolin, phyllosilicates, carbonates, sulfates, phosphates, or botanical materials such as cork, powdered corncobs, peanut hulls, rice hulls, and walnut shells.

The compositions of the embodiments can be in a suitable form for direct application or as a concentrate of primary composition that requires dilution with a suitable quantity of water or other diluent before application. The pesticidal concentration will vary depending upon the nature of the particular formulation, specifically, whether it is a concentrate or to be used directly. The composition contains 1 to 98% of a solid or liquid inert carrier, and 0 to 50% or 0.1 to 50% of a surfactant. These compositions will be administered at the labeled rate for the commercial product, for example, about 0.01 lb-5.0 lb. per acre when in dry form and at about 0.01 pts.-10 pts. per acre when in liquid form.

In a further embodiment, the compositions, as well as the transformed microorganisms and pesticidal proteins of the embodiments, can be treated prior to formulation to prolong the pesticidal activity when applied to the environment of a target pest as long as the pretreatment is not deleterious to the pesticidal activity. Such treatment can be by chemical and/or physical means as long as the treatment does not deleteriously affect the properties of the composition(s). Examples of chemical reagents include but are not limited to halogenating agents; aldehydes such as formaldehyde and glutaraldehyde; anti-infectives, such as zephiran chloride; alcohols, such as isopropanol and ethanol; and histological fixatives, such as Bouin's fixative and Helly's fixative (see, for example, Humason (1967) *Animal Tissue Techniques* (W.H. Freeman and Co.).

In other embodiments, it may be advantageous to treat the Cry toxin polypeptides with a protease, for example trypsin, to activate the protein prior to application of a pesticidal protein composition of the embodiments to the environment of the target pest. Methods for the activation of protoxin by a serine protease are well known in the art. See, for example, Cooksey (1968) *Biochem. J.* 6:445-454 and Carroll and Ellar (1989) *Biochem. J.* 261:99-105, the teachings of which are herein incorporated by reference. For example, a suitable activation protocol includes, but is not limited to, combining a polypeptide to be activated, for example a purified novel Cry polypeptide (e.g., having the amino acid sequence set forth in SEQ ID NO: 4 or SEQ ID NO: 8, and trypsin at a 1/100 weight ratio of protein/trypsin in 20 nM $NaHCO_3$, pH 8 and digesting the sample at 36° C. for 3 hours.

The compositions (including the transformed microorganisms and pesticidal proteins of the embodiments) can be applied to the environment of an insect pest by, for example, spraying, atomizing, dusting, scattering, coating or pouring, introducing into or on the soil, introducing into irrigation water, by seed treatment or general application or dusting at the time when the pest has begun to appear or before the appearance of pests as a protective measure. For example, the pesticidal protein and/or transformed microorganisms of the embodiments may be mixed with grain to protect the grain during storage. It is generally important to obtain good control of pests in the early stages of plant growth, as this is the time when the plant can be most severely damaged. The compositions of the embodiments can conveniently contain another insecticide if this is thought necessary. In one embodiment, the composition is applied directly to the soil, at a time of planting, in granular form of a composition of a carrier and dead cells of a *Bacillus* strain or transformed microorganism of the embodiments. Another embodiment is a granular form of a composition comprising an agrochemical such as, for example, an herbicide, an insecticide, a fertilizer, an inert carrier, and dead cells of a *Bacillus* strain or transformed microorganism of the embodiments.

Those skilled in the art will recognize that not all compounds are equally effective against all pests. Compounds of the embodiments display activity against insect pests, which may include economically important agronomic, forest, greenhouse, nursery, ornamentals, food and fiber, public and animal health, domestic and commercial structure, household, and stored product pests. Insect pests include insects selected from the orders Coleoptera, Diptera, Hymenoptera, Lepidoptera, Mallophaga, Homoptera, Hemiptera, Orthoptera, Thysanoptera, Dermaptera, Isoptera, Anoplura, Siphonaptera, Trichoptera, etc., particularly Coleoptera and Lepidoptera.

Insects of the order Lepidoptera include, but are not limited to, armyworms, cutworms, loopers, and heliothines in the family Noctuidae: *Agrotis ipsilon* Hufnagel (black cutworm); *A. orthogonia* Morrison (western cutworm); *A. segetum* Denis & Schiffermüller (turnip moth); *A. subterranea* Fabricius (granulate cutworm); *Alabama argillacea* Hübner (cotton leaf worm); *Anticarsia gemmatalis* Hübner (velvetbean caterpillar); *Athetis mindara* Barnes and McDunnough (rough skinned cutworm); *Earias insulana* Boisduval (spiny bollworm); *E. vittella* Fabricius (spotted bollworm); *Egira* (*Xylomyges*) *curialis* Grote (citrus cutworm); *Euxoa messoria* Harris (darksided cutworm); *Helicoverpa armigera* Hübner (American bollworm); *H. zea* Boddie (corn earworm or cotton bollworm); *Heliothis virescens* Fabricius (tobacco budworm); *Hypena scabra* Fabricius (green cloverworm); *Mamestra configurata* Walker (bertha armyworm); *M. brassicae* Linnaeus (cabbage moth); *Melanchra picta* Harris (zebra caterpillar); *Pseudaletia unipuncta* Haworth (armyworm); *Pseudoplusia includens* Walker (soybean looper); Richia albicosta Smith (Western bean cutworm); *Spodoptera frugiperda* JE Smith (fall armyworm); *S. exigua* Hübner (beet armyworm); *S. litura* Fabricius (tobacco cutworm, cluster caterpillar); *Trichoplusia ni* Hübner (cabbage looper); borers, casebearers, webworms, coneworms, and skeletonizers from the families Pyralidae and Crambidae such as *Achroia grisella* Fabricius (lesser wax moth); *Amyelois transitella* Walker (naval orangeworm); *Anagasta kuehniella* Zeller (Mediterranean flour moth); *Cadra cautella* Walker (almond moth); *Chilo partellus* Swinhoe (spotted stalk borer); *C. suppressalis* Walker (striped stem/rice borer); *C. terrenellus* Pagenstecher (sugarcane stemp borer); *Corcyra cephalonica* Stainton (rice moth); *Crambus caliginosellus* Clemens (corn root webworm); *C. teterrellus* Zincken (bluegrass webworm); *Cnaphalocrocis medinalis* Guenee (rice leaf roller); *Desmia funeralis* Hübner (grape leaffolder); *Diaphania hyalinata* Linnaeus (melon worm); *D. nitidalis* Stoll (pickleworm); *Diatraea grandiosella* Dyar (southwestern corn borer), *D. saccharalis* Fabricius (surgarcane borer); *Elasmopalpus lignosellus* Zeller (lesser cornstalk borer); *Eoreuma loftini* Dyar (Mexican rice borer); *Ephestia elutella* Hübner (tobacco (cacao) moth); *Galleria mellonella* Linnaeus (greater wax moth); *Hedylepta accepta* Butler (sugarcane leafroller); *Herpetogramma licarsisalis* Walker (sod webworm); *Homoeosoma electellum* Hulst (sunflower moth); *Loxostege sticticalis* Linnaeus (beet webworm); *Maruca testulalis* Geyer (bean pod borer); *Orthaga thyrisalis* Walker (tea tree web moth); *Ostrinia nubilalis* Hübner (European corn borer); *Plodia interpunctella* Hübner (Indian meal moth); *Scirpophaga incertulas* Walker (yellow stem borer); *Udea rubigalis* Guenee (celery leaftier); and leafrollers, budworms, seed worms, and fruit worms in the family Tortricidae *Acleris gloverana* Walsingham (Western blackheaded budworm); *A. variana* Fernald (Eastern blackheaded budworm); *Adoxophyes orana* Fischer von Rösslerstamm (summer fruit tortrix moth); *Archips* spp. including *A. argyrospila* Walker (fruit tree leaf roller) and *A. rosana* Linnaeus (European leaf roller); *Argyrotaenia* spp.; *Bonagota salubricola* Meyrick (Brazilian apple leafroller); *Choristoneura* spp.; *Cochylis hospes* Walsingham (banded sunflower moth); *Cydia latiferreana* Walsingham (filbertworm); *C. pomonella* Linnaeus (codling moth); *Endopiza viteana* Clemens (grape berry moth); *Eupoecilia ambiguella* Hübner (vine moth); *Grapholita molesta* Busck (oriental fruit moth); *Lobesia botrana* Denis & Schiffermuller (European grape vine moth); *Platynota flavedana* Clemens (variegated leafroller); *P. stultana* Walsingham (omnivorous leafroller); *Spilonota ocellana* Denis & Schiffermuller (eyespotted bud moth); and *Suleima helianthana* Riley (sunflower bud moth).

Selected other agronomic pests in the order Lepidoptera include, but are not limited to, *Alsophila pometaria* Harris (fall cankerworm); *Anarsia lineatella* Zeller (peach twig borer); *Anisota senatoria* J. E. Smith (orange striped oakworm); *Antheraea pernyi* Guérin-Méneville (Chinese Oak Silkmoth); *Bombyx mori* Linnaeus (Silkworm); *Bucculatrix thurberiella* Busck (cotton leaf perforator); *Collas eurytheme* Boisduval (alfalfa caterpillar); *Datana integerrima* Grote & Robinson (walnut caterpillar); *Dendrolimus sibiricus* Tschetwerikov (Siberian silk moth), *Ennomos subsignaria* Hübner (elm spanworm); *Erannis tiliaria* Harris (linden looper); *Erechthias flavistriata* Walsingham (sugarcane bud moth); *Euproctis chrysorrhoea* Linnaeus (browntail moth); *Harrisina americana* Guérin-Meneville (grapeleaf skeletonizer); *Heliothis subflexa* Guenee; *Hemileuca oliviae* Cockrell (range caterpillar); *Hyphantria cunea* Drury (fall webworm); *Keiferia lycopersicella* Walsingham (tomato pinworm); *Lambdina fiscellaria fiscellaria* Hulst (Eastern hemlock looper); *L. fiscellaria lugubrosa* Hulst (Western hemlock looper); *Leucoma salicis* Linnaeus (satin moth); *Lymantria dispar* Linnaeus (gypsy moth); *Malacosoma* spp.; *Manduca quinquemaculata* Haworth (five spotted hawk moth, tomato hornworm); *M. sexta* Haworth (tomato hornworm, tobacco hornworm); *Operophtera brumata* Linnaeus (winter moth); *Orgyia* spp.; *Paleacrita vernata* Peck (spring cankerworm); *Papilio cresphontes* Cramer (giant swallowtail, orange dog); *Phryganidia califomica* Packard (California oakworm); *Phyllocnistis citrella* Stainton (citrus leafminer); *Phyllonotycter blancardella* Fabricius (spotted tentiform leafminer); *Pieris brassicae* Linnaeus (large white butterfly); *P. rapae* Linnaeus (small white butterfly); *P. napi* Linnaeus (green veined white butterfly); *Platyptilia carduidactyla* Riley (artichoke plume moth); *Plutella xylostella* Linnaeus (diamondback moth); *Pectinophora gossypiella* Saunders (pink bollworm); *Pontia protodice* Boisduval & Leconte (Southern cabbageworm); *Sabulodes aegrotata* Guenee (omnivorous looper); *Schizura concinna* J. E. Smith (red humped caterpillar); *Sitotroga* cerealella Olivier (Angoumois grain moth); *Thaumetopoea pityocampa* Schiffermuller (pine processionary caterpillar); *Tineola bisselliella* Hummel (webbing clothesmoth); *Tuta absoluta* Meyrick (tomato leafminer) and *Yponomeuta padella* Linnaeus (ermine moth).

Of interest are larvae and adults of the order Coleoptera including weevils from the families Anthribidae, Bruchidae, and Curculionidae including, but not limited to: *Anthonomus grandis* Boheman (boll weevil); *Cylindrocopturus adspersus* LeConte (sunflower stem weevil); *Diaprepes abbreviatus* Linnaeus (*Diaprepes* root weevil); *Hypera punctata* Fabricius (clover leaf weevil); *Lissorhoptrus oryzophilus* Kuschel (rice water weevil); *Metamasius hemipterus hemipterus* Linnaeus (West Indian cane weevil); *M. hemipterus sericeus* Olivier (silky cane weevil); *Sitophilus granarius* Linnaeus (granary weevil); *S. oryzae* Linnaeus (rice weevil); *Smicronyx fulvus* LeConte (red sunflower seed weevil); *S. sordidus* LeConte (gray sunflower seed weevil); *Sphenophorus maidis* Chittenden (maize billbug); *Rhabdoscelus obscurus* Boisduval (New Guinea sugarcane weevil); flea beetles, cucumber beetles, rootworms, leaf beetles, potato beetles, and leafminers in the family Chrysomelidae including, but not limited to: *Chaetocnema ectypa* Horn (desert corn flea beetle); *C. pulicaria* Melsheimer (corn flea beetle); *Colaspis brunnea* Fabricius (grape *colaspis*); *Diabrotica barberi* Smith & Lawrence (northern corn rootworm); *D. undecimpunctata howardi* Barber (southern corn rootworm); *D. virgifera virgifera* LeConte (western corn rootworm); *Leptinotarsa decemlineata* Say (Colorado potato beetle); *Oulema melanopus* Linnaeus (cereal leaf beetle); *Phyllotreta cruciferae* Goeze (corn flea beetle); *Zygogramma exciamationis* Fabricius (sunflower beetle); beetles from the family Coccinellidae including, but not limited to: *Epilachna varivestis* Mulsant (Mexican bean beetle); chafers and other beetles from the family Scarabaeidae including, but not limited to: *Antitrogus parvulus* Britton (Childers cane grub); *Cyclocephala borealis* Arrow (northern masked chafer, white grub); *C. immaculata* Olivier (southern masked chafer, white grub); *Dermolepida albohirtum* Waterhouse (Greyback cane beetle); *Euetheola humilis rugiceps* LeConte (sugarcane beetle); *Lepidiota frenchi* Blackburn (French's cane grub); *Tomarus gibbosus* De Geer (carrot beetle); *T. subtropicus* Blatchley (sugarcane grub); *Phyllophaga crinita* Burmeister (white grub); *P. latifrons* LeConte (June beetle); *Popillia japonica* Newman (Japanese beetle); *Rhizotrogus majalis* Razoumowsky (European chafer); carpet beetles from the family Dermestidae; wireworms from the family Elateridae, *Eleodes* spp., *Melanotus* spp. including *M. communis* Gyllenhal (wireworm); *Conoderus* spp.; *Limonius* spp.; *Agriotes* spp.; *Ctenicera* spp.; *Aeolus* spp.; bark beetles from the family Scolytidae; beetles from the family Tenebrionidae; beetles from the family Cerambycidae such as, but not limited to, *Migdolus fryanus* Westwood (longhorn beetle); and beetles from the Buprestidae family including, but not limited to, *Aphanisticus cochinchinae seminulum* Obenberger (leaf-mining buprestid beetle).

Adults and immatures of the order Diptera are of interest, including leafminers *Agromyza parvicomis* Loew (corn blotch leafminer); midges including, but not limited to: *Contarinia sorghicola* Coquillett (sorghum midge); *Mayetiola destructor* Say (Hessian fly); *Neolasioptera murtfeldtiana* Felt, (sunflower seed midge); *Sitodiplosis mosellana* Géhin (wheat midge); fruit flies (Tephritidae), *Oscinella frit* Linnaeus (frit flies); maggots including, but not limited to: *Delia* spp. including *Delia platura* Meigen (seedcorn maggot); *D. coarctata* Fallen (wheat bulb fly); *Fannia canicularis* Linnaeus, *F. femoralis* Stein (lesser house flies); *Meromyza americana* Fitch (wheat stem maggot); *Musca domestica* Linnaeus (house flies); *Stomoxys calcitrans* Linnaeus (stable flies)); face flies, horn flies, blow flies, *Chrysomya* spp.; *Phormia* spp.; and other muscoid fly pests, horse flies *Tabanus* spp.; bot flies *Gastrophilus* spp.; *Oestrus* spp.; cattle grubs *Hypoderma* spp.; deer flies *Chrysops* spp.; *Melophagus ovinus* Linnaeus (keds); and other Brachycera, mosquitoes *Aedes* spp.; *Anopheles* spp.; *Culex* spp.; black flies *Prosimulium* spp.; *Simulium* spp.; biting midges, sand flies, sciarids, and other *Nematocera.*

Included as insects of interest are those of the order Hemiptera such as, but not limited to, the following families: Adelgidae, Aleyrodidae, Aphididae, Asterolecaniidae, Cercopidae, Cicadellidae, Cicadidae, Cixiidae, Coccidae, Coreidae, Dactylopiidae, Delphacidae, Diaspididae, Eriococcidae, Flatidae, Fulgoridae, Issidae, Lygaeidae, Margarodidae, Membracidae, Miridae, Ortheziidae, Pentatomidae, Phoenicococcidae, Phylloxeridae, Pseudococcidae, Psyllidae, Pyrrhocoridae and Tingidae.

Agronomically important members from the order Hemiptera include, but are not limited to: *Acrosternum hilare* Say (green stink bug); *Acyrthisiphon pisum* Harris (pea aphid); *Adelges* spp. (adelgids); *Adelphocoris rapidus* Say (rapid plant bug); *Anasa tristis* De Geer (squash bug); *Aphis craccivora* Koch (cowpea aphid); *A. fabae* Scopoli (black bean aphid); *A. gossypii* Glover (cotton aphid, melon aphid); *A. maidiradicis* Forbes (corn root aphid); *A. pomi* De Geer (apple aphid); *A. spiraecola* Patch (spirea aphid);

*Aulacaspis tegalensis* Zehntner (sugarcane scale); *Aulacorthum solani* Kaltenbach (foxglove aphid); *Bemisia tabaci* Gennadius (tobacco whitefly, sweetpotato whitefly); *B. argentifolii* Bellows & Perring (silverleaf whitefly); *Blissus leucopterus leucopterus* Say (chinch bug); *Blostomatidae* spp.; *Brevicoryne brassicae* Linnaeus (cabbage aphid); *Cacopsylla pyricola* Foerster (pear psylla); *Calocoris norvegicus* Gmelin (potato capsid bug); *Chaetosiphon fragaefolii* Cockerell (strawberry aphid); Cimicidae spp.; Coreidae spp.; *Corythuca gossypii* Fabricius (cotton lace bug); *Cyrtopeltis modesta* Distant (tomato bug); *C. notatus* Distant (suckfly); *Deois flavopicta* Stål (spittlebug); *Dialeurodes citri* Ashmead (citrus whitefly); *Diaphnocoris chlorionis* Say (honeylocust plant bug); *Diuraphis noxia* Kurdjumov/Mordvilko (Russian wheat aphid); *Duplachionaspis divergens* Green (armored scale); *Dysaphis plantaginea* Paaserini (rosy apple aphid); *Dysdercus suturellus* Herrich-Schaffer (cotton stainer); *Dysmicoccus boninsis* Kuwana (gray sugarcane mealybug); *Empoasca fabae* Harris (potato leafhopper); *Eriosoma lanigerum* Hausmann (woolly apple aphid); *Erythroneoura* spp. (grape leafhoppers); *Eumetopina flavipes* Muir (Island sugarcane planthopper); *Eurygaster* spp.; *Euschistus servus* Say (brown stink bug); *E. variolarius* Palisot de Beauvois (one-spotted stink bug); *Graptostethus* spp. (complex of seed bugs); and *Hyalopterus pruni* Geoffroy (mealy plum aphid); *Icerya purchasi* Maskell (cottony cushion scale); *Labopidicola allii* Knight (onion plant bug); *Laodelphax striatellus* Fallen (smaller brown planthopper); *Leptoglossus corculus* Say (leaf-footed pine seed bug); *Leptodictya tabida* Herrich-Schaeffer (sugarcane lace bug); *Lipaphis erysimi* Kaltenbach (turnip aphid); *Lygocoris pabulinus* Linnaeus (common green capsid); *Lygus lineolaris* Palisot de Beauvois (tarnished plant bug); *L. Hesperus* Knight (Western tarnished plant bug); *L. pratensis* Linnaeus (common meadow bug); *L. rugulipennis* Poppius (European tarnished plant bug); *Macrosiphum euphorbiae* Thomas (potato aphid); *Macrosteles quadrilineatus* Forbes (aster leafhopper); *Magicicada septendecim* Linnaeus (periodical cicada); *Mahanarva fimbriolata* Stål (sugarcane spittlebug); *Melanaphis sacchari* Zehntner (sugarcane aphid); *Melanaspis glomerata* Green (black scale); *Metopolophium dirhodum* Walker (rose grain aphid); *Myzus persicae* Sulzer (peach-potato aphid, green peach aphid); *Nasonovia ribisnigri* Mosley (lettuce aphid); *Nephotettix cinticeps* Uhler (green leafhopper); *N. nigropictus* Stål (rice leafhopper); *Nezara viridula* Linnaeus (southern green stink bug); *Nilaparvata lugens* Stål (brown planthopper); *Nysius ericae* Schilling (false chinch bug); *Nysius raphanus* Howard (false chinch bug); *Oebalus pugnax* Fabricius (rice stink bug); *Oncopeltus fasciatus* Dallas (large milkweed bug); *Orthops campestris* Linnaeus; *Pemphigus* spp. (root aphids and gall aphids); *Peregrinus maidis* Ashmead (corn planthopper); *Perkinsiella saccharicida* Kirkaldy (sugarcane delphacid); *Phylloxera devastatrix* Pergande (pecan phylloxera); *Planococcus citri* Risso (citrus mealybug); *Plesiocoris rugicollis* Fallen (apple capsid); *Poecilocapsus lineatus* Fabricius (four-lined plant bug); *Pseudatomoscelis seriatus* Reuter (cotton fleahopper); *Pseudococcus* spp. (other mealybug complex); *Pulvinaria elongata* Newstead (cottony grass scale); *Pyrilla perpusilla* Walker (sugarcane leafhopper); *Pyrrhocoridae* spp.; *Quadraspidiotus perniciosus* Comstock (San Jose scale); *Reduviidae* spp.; *Rhopalosiphum maidis* Fitch (corn leaf aphid); *R. padi* Linnaeus (bird cherry-oat aphid); *Saccharicoccus sacchari* Cockerell (pink sugarcane mealybug); *Schizaphis graminum* Rondani (greenbug); *Sipha flava* Forbes (yellow sugarcane aphid); *Sitobion avenae* Fabricius (English grain aphid); *Sogatella furcifera* Horvath (white-backed planthopper); *Sogatodes oryzicola* Muir (rice delphacid); *Spanagonicus albofasciatus* Reuter (whitemarked fleahopper); *Therioaphis maculata* Buckton (spotted alfalfa aphid); *Tinidae* spp.; *Toxoptera aurantii* Boyer de Fonscolombe (black citrus aphid); and *T. citricida* Kirkaldy (brown citrus aphid); *Trialeurodes abutiloneus* (bandedwinged whitefly) and *T. vaporariorum* Westwood (greenhouse whitefly); *Trioza diospyri* Ashmead (persimmon psylla); and *Typhlocyba pomaria* McAtee (white apple leafhopper).

Also included are adults and larvae of the order Acari (mites) such as *Aceria tosichella* Keifer (wheat curl mite); *Panonychus ulmi* Koch (European red mite); *Petrobia latens* Müller (brown wheat mite); *Steneotarsonemus bancrofti* Michael (sugarcane stalk mite); spider mites and red mites in the family Tetranychidae, *Oligonychus grypus* Baker & Pritchard, *O. indicus* Hirst (sugarcane leaf mite), *O. pratensis* Banks (Banks grass mite), *O. stickneyi* McGregor (sugarcane spider mite); *Tetranychus urticae* Koch (two spotted spider mite); *T. mcdanieli* McGregor (McDaniel mite); *T. cinnabarinus* Boisduval (carmine spider mite); *T. turkestani* Ugarov & Nikolski (strawberry spider mite), flat mites in the family Tenuipalpidae, *Brevipalpus lewisi* McGregor (citrus flat mite); rust and bud mites in the family Eriophyidae and other foliar feeding mites and mites important in human and animal health, i.e. dust mites in the family Epidermoptidae, follicle mites in the family Demodicidae, grain mites in the family Glycyphagidae, ticks in the order Ixodidae. *Ixodes scapularis* Say (deer tick); *I. holocyclus* Neumann (Australian paralysis tick); *Dermacentor variabilis* Say (American dog tick); *Amblyomma americanum* Linnaeus (lone star tick); and scab and itch mites in the families Psoroptidae, Pyemotidae, and Sarcoptidae.

Insect pests of the order Thysanura are of interest, such as *Lepisma saccharina* Linnaeus (silverfish); *Thermobia domestica* Packard (firebrat).

Additional arthropod pests covered include: spiders in the order Araneae such as *Loxosceles reclusa* Gertsch & Mulaik (brown recluse spider); and the *Latrodectus mactans* Fabricius (black widow spider); and centipedes in the order Scutigeromorpha such as *Scutigera coleoptrata* Linnaeus (house centipede). In addition, insect pests of the order Isoptera are of interest, including those of the termitidae family, such as, but not limited to, *Cylindrotermes nordenskioeldi* Holmgren and *Pseudacanthotermes militaris* Hagen (sugarcane termite). Insects of the order Thysanoptera are also of interest, including but not limited to thrips, such as *Stenchaetothrips minutus* van Deventer (sugarcane thrips).

Insect pests may be tested for pesticidal activity of compositions of the embodiments in early developmental stages, e.g., as larvae or other immature forms. The insects may be reared in total darkness at from about 20° C. to about 30° C. and from about 30% to about 70% relative humidity. Bioassays may be performed as described in Czapla and Lang (1990) *J. Econ. Entomol.* 83(6): 2480-2485. Methods of rearing insect larvae and performing bioassays are well known to one of ordinary skill in the art.

A wide variety of bioassay techniques are known to one skilled in the art. General procedures include addition of the experimental compound or organism to the diet source in an enclosed container. Pesticidal activity can be measured by, but is not limited to, changes in mortality, weight loss, attraction, repellency and other behavioral and physical changes after feeding and exposure for an appropriate length of time. Bioassays described herein can be used with any feeding insect pest in the larval or adult stage.

The following examples are presented by way of illustration, not by way of limitation.

EXPERIMENTALS

Example 1—Generation of Cry1B Variants with Improved Spectrum of Insecticidal Activity The Cry1Bd insecticidal protein having an amino acid of SEQ ID NO: 1 (U.S. Pat. No. 8,692,065) has high insecticidal activity (ILC50=1 ppm) against European corn borer (*Ostrinia nubilalis*) larvae but low insecticidal activity (ILC50>1000 ppm and ~400 ppm respectively) against corn earworm (*Helicoverpa zea*) and fall armyworm (*Spodoptera frugiperda*). The Cry1B insecticidal protein, referred to as MP258 (Serial No. PCT/US14/49923) having an amino acid of SEQ ID NO: 47 has high insecticidal activity (ILC50=4 ppm) against European corn borer (*Ostrinia nubilalis*) larvae but lower insecticidal activity (ILC50 24 ppm and 62 ppm respectively) against corn earworm (*Helicoverpa zea*) and fall armyworm (*Spodoptera frugiperda*). A series of variant Cry1B polypeptides derived from Cry1Bd (SEQ ID NO: 1) and MP258 were designed to improve the insecticidal activity against corn earworm (CEVV) and/or fall armyworm (FAVV) compared to Cry1Bd (SEQ ID NO: 1) and/or MP258 (SEQ ID NO: 47) while maintaining the ECB insecticidal activity. Variant Cry1B polypeptides having improved insecticidal activity that were generated include those indicated in Table 1. The insecticidal activity of the Cry1B variants was determined as described in Example 4 and the insecticidal activity results are shown in Table 3. An amino acid sequence alignment of the variant Cry1B polypeptides is shown in FIG. 1.

TABLE 1

| Clone ID | Polypeptide | Polynucleotide |
|---|---|---|
| Cry1Bd | SEQ ID NO: 1 | SEQ ID NO: 2 |
| IP1B-B1 | SEQ ID NO: 3 | SEQ ID NO: 4 |
| IP1B-B21 | SEQ ID NO: 5 | SEQ ID NO: 6 |
| IP1B-B22 | SEQ ID NO: 7 | SEQ ID NO: 8 |
| IP1B-B23 | SEQ ID NO: 9 | SEQ ID NO: 10 |
| IP1B-B24 | SEQ ID NO: 11 | SEQ ID NO: 12 |
| IP1B-B25 | SEQ ID NO: 13 | SEQ ID NO: 14 |
| IP1B-B26 | SEQ ID NO: 15 | SEQ ID NO: 16 |
| IP1B-B27 | SEQ ID NO: 17 | SEQ ID NO: 18 |
| IP1B-B28 | SEQ ID NO: 19 | SEQ ID NO: 20 |
| IP1B-B29 | SEQ ID NO: 21 | SEQ ID NO: 22 |
| IP1B-B31 | SEQ ID NO: 23 | SEQ ID NO: 24 |
| IP1B-B32 | SEQ ID NO: 25 | SEQ ID NO: 26 |
| IP1B-B33 | SEQ ID NO: 27 | SEQ ID NO: 28 |
| IP1B-B34 | SEQ ID NO: 29 | SEQ ID NO: 30 |
| IP1B-B40 | SEQ ID NO: 31 | SEQ ID NO: 32 |
| IP1B-B41 | SEQ ID NO: 33 | SEQ ID NO: 34 |
| IP1B-B42 | SEQ ID NO: 35 | SEQ ID NO: 36 |
| IP1B-B43 | SEQ ID NO: 37 | SEQ ID NO: 38 |
| IP1B-B44 | SEQ ID NO: 39 | SEQ ID NO: 40 |
| IP1B-B45 | SEQ ID NO: 41 | SEQ ID NO: 42 |
| IP1B-B46 | SEQ ID NO: 43 | SEQ ID NO: 44 |
| IP1B-B47 | SEQ ID NO: 45 | SEQ ID NO: 46 |
| MP258 | SEQ ID NO: 47 | SEQ ID NO: 48 |
| GS060 | SEQ ID NO: 49 | SEQ ID NO: 50 |

The percent amino acid sequence identity of the Cry1B variant polypeptides calculated using the Needleman-Wunsch algorithm, as implemented in the Needle program (EMBOSS tool suite), are shown as a matrix table in Table 2a-2b. The void part of the matrix table is not shown.

TABLE 2a

| . | GS060 | IP1B-B1 | IP1B-B21 | IP1B-B22 | IP1B-B23 | IP1B-B24 | IP1B-B25 | IP1B-B26 | IP1B-B27 | IP1B-B28 | IP1B-B29 |
|---|---|---|---|---|---|---|---|---|---|---|---|
| Cry1Bd | 65.6 | 95.4 | 84.3 | 82.6 | 82.5 | 84.3 | 84.3 | 84.2 | 83.7 | 83.7 | 83.7 |
| GS060 | — | 67.0 | 60.1 | 60.2 | 60.1 | 60.1 | 60.2 | 60.1 | 60.0 | 59.9 | 60.1 |
| IP1B-B1 | — | — | 83.4 | 82.6 | 84.5 | 83.4 | 83.4 | 83.2 | 82.9 | 82.9 | 82.9 |
| IP1B-B21 | — | — | — | 95.4 | 96.9 | 99.7 | 99.7 | 99.5 | 99.1 | 99.1 | 99.1 |
| IP1B-B22 | — | — | — | — | 95.4 | 95.1 | 95.1 | 95.0 | 94.5 | 94.8 | 94.8 |
| IP1B-B23 | — | — | — | — | — | 96.6 | 96.6 | 96.5 | 96.0 | 96.0 | 96.0 |
| IP1B-B24 | — | — | — | — | — | — | 99.4 | 99.2 | 98.8 | 98.8 | 98.8 |
| IP1B-B25 | — | — | — | — | — | — | — | 99.8 | 99.4 | 99.4 | 99.4 |
| IP1B-B26 | — | — | — | — | — | — | — | — | 99.5 | 99.2 | 99.2 |
| IP1B-B27 | — | — | — | — | — | — | — | — | — | 99.4 | 99.4 |
| IP1B-B28 | — | — | — | — | — | — | — | — | — | — | 99.8 |

TABLE 2b

| . | IP1B-B31 | IP1B-B32 | IP1B-B33 | IP1B-B34 | IP1B-B40 | IP1B-B41 | IP1B-B42 | IP1B-B43 | IP1B-B44 | IP1B-B45 | IP1B-B46 | IP1B-B47 | MP258 |
|---|---|---|---|---|---|---|---|---|---|---|---|---|---|
| Cry1Bd | 80.4 | 80.4 | 81.0 | 82.0 | 83.7 | 83.9 | 83.9 | 83.9 | 83.9 | 83.9 | 83.9 | 83.9 | 82.3 |
| GS060 | 66.6 | 66.9 | 66.3 | 65.5 | 59.8 | 59.9 | 60.1 | 60.1 | 60.1 | 60.1 | 59.9 | 59.9 | 59.9 |
| IP1B-B1 | 83.6 | 83.0 | 82.7 | 81.6 | 82.8 | 82.9 | 83.1 | 83.1 | 83.1 | 83.1 | 83.1 | 83.1 | 80.9 |
| IP1B-B21 | 71.6 | 71.5 | 71.8 | 71.8 | 99.1 | 99.1 | 99.2 | 99.2 | 99.2 | 99.2 | 99.2 | 99.2 | 96.9 |
| IP1B-B22 | 70.7 | 70.4 | 70.7 | 71.0 | 94.7 | 94.7 | 94.7 | 94.7 | 94.7 | 94.7 | 94.8 | 94.8 | 97.6 |
| IP1B-B23 | 72.5 | 72.3 | 72.6 | 72.3 | 96.0 | 96.0 | 96.2 | 96.2 | 96.2 | 96.2 | 96.2 | 96.2 | 96.0 |
| IP1B-B24 | 71.6 | 71.5 | 71.8 | 71.8 | 98.8 | 98.9 | 98.9 | 98.9 | 98.9 | 98.9 | 98.9 | 98.9 | 96.6 |
| IP1B-B25 | 71.8 | 71.6 | 71.9 | 71.9 | 99.4 | 99.4 | 99.5 | 99.5 | 99.5 | 99.5 | 99.5 | 99.5 | 96.6 |
| IP1B-B26 | 71.6 | 71.5 | 71.8 | 71.8 | 99.5 | 99.2 | 99.4 | 99.4 | 99.4 | 99.4 | 99.4 | 99.4 | 96.5 |
| IP1B-B27 | 71.3 | 71.2 | 71.5 | 71.3 | 99.2 | 98.9 | 99.7 | 99.5 | 99.5 | 99.5 | 99.2 | 99.2 | 96.0 |
| IP1B-B28 | 71.3 | 71.2 | 71.5 | 71.3 | 99.1 | 99.1 | 99.4 | 99.2 | 99.2 | 99.2 | 99.5 | 99.5 | 96.3 |
| IP1B-B29 | 71.3 | 71.2 | 71.5 | 71.3 | 99.1 | 99.1 | 99.4 | 99.2 | 99.2 | 99.2 | 99.4 | 99.4 | 96.3 |
| IP1B-B31 | — | 99.4 | 99.1 | 98.0 | 71.3 | 71.6 | 71.5 | 71.5 | 71.5 | 71.5 | 71.5 | 71.5 | 69.2 |
| IP1B-B32 | — | — | 99.2 | 98.0 | 71.2 | 71.5 | 71.3 | 71.3 | 71.3 | 71.3 | 71.3 | 71.3 | 69.1 |
| IP1B-B33 | — | — | — | 98.0 | 71.5 | 71.8 | 71.6 | 71.6 | 71.6 | 71.6 | 71.6 | 71.6 | 69.4 |

TABLE 2b-continued

| . | IP1B-B31 | IP1B-B32 | IP1B-B33 | IP1B-B34 | IP1B-B40 | IP1B-B41 | IP1B-B42 | IP1B-B43 | IP1B-B44 | IP1B-B45 | IP1B-B46 | IP1B-B47 | MP258 |
|---|---|---|---|---|---|---|---|---|---|---|---|---|---|
| IP1B-B34 | — | — | — | — | 71.5 | 71.8 | 71.5 | 71.5 | 71.5 | 71.5 | 71.5 | 71.5 | 69.7 |
| IP1B-B40 | — | — | — | — | — | 99.7 | 99.1 | 99.1 | 99.1 | 99.2 | 99.2 | 99.4 | 96.2 |
| IP1B-B41 | — | — | — | — | — | — | 99.1 | 99.1 | 99.1 | 99.2 | 99.2 | 99.4 | 96.2 |
| IP1B-B42 | — | — | — | — | — | — | — | 99.8 | 99.8 | 99.7 | 99.5 | 99.4 | 96.2 |
| IP1B-B43 | — | — | — | — | — | — | — | — | 99.8 | 99.8 | 99.5 | 99.5 | 96.2 |
| IP1B-B44 | — | — | — | — | — | — | — | — | — | 99.7 | 99.7 | 99.4 | 96.2 |
| IP1B-B45 | — | — | — | — | — | — | — | — | — | — | 99.4 | 99.7 | 96.2 |
| IP1B-B46 | — | — | — | — | — | — | — | — | — | — | — | 99.7 | 96.3 |
| IP1B-B47 | — | — | — | — | — | — | — | — | — | — | — | — | 96.3 |

Example 2—Saturation Mutagenesis at Selected Positions of MP258 and IP-1B Variant Cry1B Polypeptides The polynucleotides of SEQ ID NO: 48, SEQ ID NO: 6, SEQ ID NO: 14, and SEQ ID NO: 42 encoding MP258, IP1B-B21, IP1B-B25 and IP1B-B45 (SEQ ID NO: 47, SEQ ID NO: 5, SEQ ID NO: 13, and SEQ ID NO: 41 respectively) were used as the templates for saturation mutagenesis at selected amino acid positions. A reverse mutagenesis primer and a complementary forward mutagenesis primer were designed to create the desired amino acid substitution(s) at the site(s) of interest. Typically the mutagenesis primer was between 30 to 45 bases in length with two or more bases, usually 10 to 15, on both sides of the site of interest. In order to make saturation mutagenesis, degenerated primers that cover all possible amino acid residues were used. The mutagenic reactions were carried out using Agilent's QuikChange™ Lightening Site-Directed Mutagenesis kit. Materials provided in the kit are QuikChange™ Lightening Enzyme, 10× QuikChange™ Lightning Buffer, dNTP mix, QuikSolution™ reagent and Don restriction enzyme according to the manufactures directions.

PCR amplifications were typically carried out with Expand™ High Fidelity PCR system (Roche, Switzerland) in 50 ul containing 50-100 ng templates, 0.4-2 μM primer pair, 200 μM dNTPs and 2 Units of DNA polymerase. The mutagenesis reaction was initiated by pre-heating the reaction mixture to 94° C. for 3 min, followed by 16 cycles of the following cycling program: 94° C. for 1 min, 52° C. for 1 min and 68° C. for 8, 12, 16 or 24 min according to the length of template. The mutagenesis reaction was completed by incubation at 68° C. for 1 h. The PCR-amplification products were evaluated by agarose gel electrophoresis. The PCR products were purified by QIAquick™ PCR purification kit (Qiagen, Germany) and further treated with the restriction enzyme DpnI. An aliquot of 1 μl of the PCR product was typically transformed into BL21(DE3) cells and inoculated on Luria-Bertani (LB) plate containing 100 μg/ml ampicillin. About 48 or more colonies for saturation mutagenesis were selected and plasmid DNA was isolated for sequencing. Two step sequencing was used, first for specific mutation site(s) with one sequencing primer followed by full length sequence confirmation with multiple sequencing primers. After all 19 amino acid mutations were confirmed by sequencing, those mutant genes were advanced for expression and protein purification.

In the case of mutations made to cover the entire IP1B-B25 Domain III spanning from T495 to E655, 48 mutant clones were picked from each site and screened for the CEW activity, as described in Example 4. In order to sequence those mutant clones to determine mutated amino acids, among 151 amino acid residues subjected to mutagenesis, 103 sites were sequenced based on the number of up-mutations and down-mutations. Those sites containing mutants showing no significant activity changes were not sequenced.

Example 3—Purification of Variant Cry1B Insecticidal Proteins

Variant cry1B insecticidal protein genes were expressed in a modified pMAL vector (Cat #E8000S from New England Biolabs) as a fusion with MBP (maltose binding protein). The pMAL vector was modified to attach a 6× His tag to the N-terminal end of MBP after methionine at position 1. The plasmid containing the insecticidal protein gene was cloned in *E. coli* BL21 (DE3). The BL21 cells were grown in MagicMedia™ (Life Technologies) in either 96 deep well plates or flasks in a shaker running at 250 rpm at 37° C. for 8 hrs followed by 16° C. for 64 hrs. During the 16° C. incubation, the MBP-toxin fusion protein was accumulated in the BL21 cell as a soluble protein.

In order to purify the fusion protein, the *E. coli* cells were harvested by centrifugation and treated in a lysozyme solution consisting of 2 mg/ml lysozyme in 50 ml sodium phosphate buffer at pH8 containing 300 mM NaCl, 2 U/ml endonuclease (Epicentre) and 5 mM MaCl2 for 3 hrs at 37° C. with gentle shaking. The lysozyme treated *E. coli* cells were then disrupted with 1% Triton X100 and clear lysate containing the IP-1B proteins were prepared by centrifugation at 4000 rpm, 30 min (96 well plates) or 9000 rpm (flask produced samples). His tagged MBP-toxin proteins were purified from the clear lysate by affinity chromatography using NiNTA agarose from Qiagen™ following the manufacturer's standard procedure. For those clear lysate samples made in 96 well plates, Pall Corporation™ (25 Harbor Park Drive Port Washington, N.Y. 11050) 96 deep well filter plates were used as affinity chromatography columns. The purified toxin proteins eluted from NiNTA agarose was passed through Sephadex G25 to change the phosphate buffer to 25 mM HEPES-NaOH, pH8 and used in insect bioassay for determining the insecticidal. MBP was digested with 1/100 (w/w) Factor Xa (New England Biolabs) at 25° C. for overnight and removed from the IP-1B proteins by Superdex 200 column chromatography utilizing the size difference and a weak affinity of MBP to Superdex.

Protein concentrations were determined by capillary electrophoresis with the LabChip™ GXII device (Caliper LifeSciences). The protein analysis was repeated at least 3 times until the final concentrations were considered to be reliable within the predetermined deviation, less than 10%.

Example 4—Determination of the Insecticidal Activity of Variant IP-1B Proteins The activity of Cry1B polypeptide variants against major corn pests, European Corn Borer (ECB, *Ostrinia nubilalis*), Corn Earworm (ECW, *Helicoverpa zea*) and Fall Armyworm (FAW, *Spodoptera frugiperda*), was determined by feeding assay as described by Cong, R., et al. Proceedings of the 4th Pacific Rim Conferences on Biotechnology of *Bacillus thuringiensis* and its environmental impact, pp. 118-123, ed. by R. J. Akhurst, C. E. Beard and P. Hughes, published in 2002, Canberra, Australia. Briefly, the assays were conducted on an artificial diet containing the insecticidal proteins. The insecticidal proteins were prepared as described in Example 1, and 10 μL of protein samples were mixed with 40 μL of molten (40-50° C.) artificial insect diet prepared based on Southland Premix formulated for Lepidopteran insects (Southland Products, Lake Village, Ark.) with low temperature melting agarose. The diet-insecticidal protein mixture was placed in each well of a 96 well micro-titer plate. One or more neonate insect larvae were placed in each well to feed for 4 days for CEW and FAW and 5 days for ECB at 28° C.

Alternatively, insect eggs or larvae were sorted by Large Particle Flow Cytometry using COPAS™ (Complex Object Parametric Analyzer and Sorter) obtained from Union Biometrica (Holliston, Mass.) to place one egg or larva per well in a 96-well micro-titer plate that contains solidified artificial insect diet. When eggs were used to place in the assay plates, only those wells containing hatched larvae after 16 hours were used for assay data collection. Usually 90 to 95% hatch rates were obtained due to efficient COPAS sorting. After certain feeding periods, the response of insects towards the proteins was scored using a 0-3 numerical scoring system based on the size and mortality of the larvae in each well. If no response (or normal growth) was seen, a score of 0 was given. When the growth was slightly retarded, a score of 1 was given. A score of 2 meant that the larvae were severely retarded in growth (close to neonate size). A score of 3 meant death to all the larvae in the well. The percent response (Response) for each treatment was calculated by dividing the total score, a sum of scores from replicating wells for each treatment by the total highest possible scores. For example, if one treatment (one sample, one dose) had 6 replicating wells, the total highest possible score would be 3×6=18.

In order to identify variant Cry1B polypeptides that have increased levels of the activity toward those corn pests, significantly higher than the activity reference such as the wild type, non-mutated reference protein (e.g. MP258 SEQ ID NO: 47). Variant polypeptides at certain concentrations were assayed along with 4 doses of the reference protein within one 96-well assay plate. The concentrations of the insecticidal proteins were within the 4 doses of the reference protein concentrations, preferably around the middle point of the 4 dose concentrations. Each sample plate contained the reference protein in a significant number of wells such as 16 wells in 4 separate doses. Also in each plate, up to 80 mutants proteins for activity comparison with the reference protein were included. From a sample plate, 10 ul of samples from each well were picked by multi-channel pipette and dispensed in one assay plate containing 40 ul molten diet in each well and mixed on a shaker. This process of producing the assay plate was repeated as many as 6 times or more to produce a desired number of assay plates. After the diet was solidified and cooled to 4 C, neonate insect larvae were placed in each well, sealed with perforated Mylar film and incubated in a constant temperature incubator at 28° C. After certain feeding period, the insect responses were scored under a magnifying glass. The sigmoid dose-response values (Responses) were converted to liner probit dose-response values using SAS-JMP®, Generalized Linear Model, Binomial Response, Probit). The response for each protein in replicates was summed and compared with the probit dose-response line of the activity reference protein, creating a new number called the FAE guide number (Fast Activity Evaluation). For example, if a mutant protein showed a certain probit value at 40 ppm and the actual dose with the same probit value for the reference protein was 100 ppm; then the FAE value is 2.5 (100/40). This means the mutant protein is 2.5 times more potent than the reference protein. This assay was done with 2 different doses of mutant proteins at a time and repeated 3 times generating 6 FAE guide number data points for each mutant. The mean FAE guide number was called the FAE Index. For each protein, a two sided t-test was done comparing the 6 FAE guide numbers. The Bonferroni correction was used to evaluate p-values (number of novel proteins/alpha) to determine if the FAE Index was statistically significant.

The other screening method used in this patent application is High Dose Assay (HDA). In this method, test proteins at high concentrations (above EC50) were placed on the insect assay plates as described above, along with a similar concentration of one or more reference proteins with a known activity level. This HDA was often used in a tiered screening to eliminate low or no activity proteins quickly.

Yet another screening method used was High throughput Functional Assay (HFA). This assay was similar to FAE but used only one dose instead of 2 doses. Otherwise HFA, especially the way it calculates the index was identical to FAE. Therefor the HFA index has the same significance as the FAE index.

The predicted point with 50% response in the scoring scheme is called ILC50 as it is a combination of growth or feeding Inhibition and Lethal responses. In order to determine ILC50 values, each treatment (one dose) was repeated 6 or more, usually 24, times. The insecticidal activity of the Cry1B variants is shown in Table 3.

Table 4 shows the insecticidal activity against corn earworm for the amino acid substitutions having increased activity (FAE score 1.2) compared to the reference polypeptide MP258 (SEQ ID NO: 47), IP1B-B21 (SEQ ID NO: 5), IP1B-B25 (SEQ ID NO: 13), or IP1B-B45 (SEQ ID NO: 41). Table 4 indicates the position number and amino acid corresponding to positions 50-651 of MP258 (SEQ ID NO: 47); the predicted secondary structure and assignment; solvent exposure score; an alignment of the amino acid sequence of MP258 (SEQ ID NO: 47); IP1B-B21 (SEQ ID NO: 5), IP1B-B25 (SEQ ID NO: 13), IP1B-B45 (SEQ ID NO: 41), IP1B-B21 (SEQ ID NO: 5), Cry1Bd (SEQ ID NO: 1), Cry1Bh (SEQ ID NO: 52), and Cry1Bi (SEQ ID NO: 54); the polypeptide backbone the variant was made in; the amino acid substitution variant (e.g. L50R); and the FAE insecticidal score against corn earworm compared to the corresponding polypeptide backbone (MP258—SEQ ID NO: 47, IP1B-B21—SEQ ID NO: 5, IP1B-B25—SEQ ID NO: 13, or IP1B-B45—SEQ ID NO: 41).

TABLE 3

| Clone ID | Polypeptide SEQ ID NO | ECB | CEW | FAW |
|---|---|---|---|---|
| Cry1Bd | SEQ ID NO: 1 | ILC50 = 1 ppm | ILC50 = >1000 ppm | ILC50 = ~400 ppm |
| IP1B-B1 | SEQ ID NO: 3 | ILC50 = 1.3 ppm | ILC50 = 21 ppm | ILC50 = 34.3 ppm |
| IP1B-B21 | SEQ ID NO: 5 | | ILC50 = 22.4 ppm | |
| IP1B-B22 | SEQ ID NO: 7 | | ILC50 = 27.1 ppm | |
| IP1B-B23 | SEQ ID NO: 9 | | ILC50 = 29.2 ppm | |
| IP1B-B24 | SEQ ID NO: 11 | | ILC50 = 12.6 ppm | |
| IP1B-B25 | SEQ ID NO: 13 | | ILC50 = 11.91 ppm | |
| IP1B-B26 | SEQ ID NO: 15 | | ILC50 = 8.36 ppm | |
| IP1B-B27 | SEQ ID NO: 17 | | ILC50 = 7.99 ppm | |
| IP1B-B28 | SEQ ID NO: 19 | | ILC50 = 7.74 ppm | |
| IP1B-B29 | SEQ ID NO: 21 | | ILC50 = 8.45 ppm | |
| IP1B-B31 | SEQ ID NO: 23 | | | ILC50 = 2.8 ppm |
| IP1B-B32 | SEQ ID NO: 25 | | | ILC50 = 2.9 ppm |
| IP1B-B33 | SEQ ID NO: 27 | | | ILC50 = 3.0 ppm |
| IP1B-B34 | SEQ ID NO: 29 | | | ILC50 = 2.9 ppm |
| IP1B-B40 | SEQ ID NO: 31 | | ILC50 = 5.78 ppm | |
| IP1B-B41 | SEQ ID NO: 33 | | ILC50 = 4.54 ppm | |
| IP1B-B42 | SEQ ID NO: 35 | | ILC50 = 6.2 ppm | |
| IP1B-B43 | SEQ ID NO: 37 | | ILC50 = 6.7 ppm | |
| IP1B-B44 | SEQ ID NO: 39 | | ILC50 = 6.9 ppm | |
| IP1B-B45 | SEQ ID NO: 41 | | ILC50 = 5.7 ppm | |
| IP1B-B46 | SEQ ID NO: 43 | | ILC50 = 8 ppm | |
| IP1B-B47 | SEQ ID NO: 45 | | ILC50 = 6.1 ppm | |
| MP258 | SEQ ID NO: 47 | ILC50 = 4 ppm | ILC50 = 24 ppm | ILC50 = 62 ppm |

Table 5 shows the insecticidal activity against corn earworm for the amino acid substitutions having a FAE score 1.2 compared to the polypeptide backbone MP258 (SEQ ID NO: 47), IP1B-B21 (SEQ ID NO: 5), IP1B-B25 (SEQ ID NO: 13), or IP1B-B45 (SEQ ID NO: 41). Table 5 indicates the position number and amino acid corresponding to positions 50-651 of MP258 (SEQ ID NO: 47); the polypeptide backbone the variant was made in; the amino acid substitution variant (e.g. L50R); and the FAE insecticidal score against corn earworm compared to the corresponding polypeptide backbone (MP258—SEQ ID NO: 47, IP1B-B21—SEQ ID NO: 5, IP1B-B25—SEQ ID NO: 13, or IP1B-B45—SEQ ID NO: 41.

TABLE 4

| MP258 position | a.a. | 2D Struc | 2D Assign | Sol. Exp. | MP258 | B21 | B25 | B45 | Bd | Bh | Bi | backbone |
|---|---|---|---|---|---|---|---|---|---|---|---|---|
| 50 | L | Coil | | 90 | L | L | L | L | L | F | F | B45 |
| 51 | V | Helix | a1 | 37 | V | V | V | V | V | V | V | |
| 52 | S | Helix | | 20 | S | S | S | S | S | S | S | |
| 53 | A | Helix | | 67 | A | A | A | A | A | A | A | B45 |
| 54 | S | Helix | | 47 | S | S | S | S | S | S | S | B45 |
| 55 | T | Helix | | 0 | T | T | T | T | T | T | T | |
| 56 | V | Helix | | 5 | V | V | V | V | V | V | V | |
| 57 | Q | Helix | | 75 | Q | Q | Q | Q | Q | Q | Q | B45 |
| 58 | T | Helix | | 33 | T | T | T | T | T | T | T | |
| 59 | G | Helix | | 4 | G | G | G | G | G | G | G | |
| 60 | I | Helix | | 3 | I | I | I | I | I | I | I | |
| 61 | N | Helix | | 27 | N | N | N | N | N | N | S | |
| 62 | I | Helix | | 3 | I | I | I | I | I | I | I | |
| 63 | A | Helix | | 19 | A | A | A | A | A | A | A | |
| 64 | G | Helix | | 4 | G | G | G | G | G | G | G | |
| 65 | R | Helix | | 42 | R | R | R | R | R | R | R | B45 |
| 66 | I | Helix | | 4 | I | I | I | I | I | I | I | |
| 67 | L | Helix | | 27 | L | L | L | L | L | L | L | B45 |
| 68 | G | Helix | | 113 | G | G | G | G | G | G | G | B45 |
| 69 | V | Helix | | 6 | V | V | V | V | V | V | V | |
| 70 | L | Turn | | 1 | L | L | L | L | L | L | L | B45 |
| 71 | G | Turn | | 8 | G | G | G | G | G | G | G | B45 |
| 72 | V | Coil | | 22 | V | V | V | V | V | V | V | B45 |
| 73 | P | Coil | | 46 | P | P | P | P | P | P | P | B45 |
| 74 | F | Coil | | 94 | F | F | F | F | F | F | F | B45 |
| 75 | A | Helix | a2 | 33 | A | A | A | A | A | A | A | B45 |
| 76 | G | Helix | | 115 | G | G | G | G | G | G | G | B45 |
| 77 | Q | Helix | | 53 | Q | Q | Q | Q | Q | Q | Q | B45 |
| 78 | L | Helix | | 8 | L | L | L | L | L | L | L | |
| 79 | A | Helix | | 36 | A | A | A | A | A | A | A | B45 |
| 80 | S | Helix | | 61 | S | S | S | S | S | S | S | B45 |
| 81 | F | Helix | | 4 | F | F | F | F | F | F | F | |
| 82 | Y | Helix | | 4 | Y | Y | Y | Y | Y | Y | Y | B45 |
| 83 | S | Helix | | 85 | S | S | S | S | S | S | S | B45 |
| 84 | F | Helix | | 54 | F | F | F | F | F | F | F | |
| 85 | I | Helix | | 5 | I | I | I | I | L | L | I | |

TABLE 4-continued

| | | | | | | | | | | | |
|---|---|---|---|---|---|---|---|---|---|---|---|
| 86 | V | Helix | | 22 | V | V | V | V | V | V | V | |
| 87 | G | Helix | | 101 | G | G | G | G | G | G | G | B45 |
| 88 | E | Helix | | 19 | E | E | E | E | E | E | E | |
| 89 | L | Helix | | 2 | L | L | L | L | L | L | L | |
| 90 | W | Coil | | 11 | W | W | W | W | W | W | W | |
| 91 | P | Coil | | 44 | P | P | P | P | P | P | P | B45 |
| 92 | S | Coil | | 93 | S | S | S | S | S | S | K | B45 |
| 93 | G | Coil | | 140 | G | G | G | G | G | G | G | B45 |
| 94 | R | Coil | | 97 | R | R | R | R | R | R | R | B45 |
| 95 | D | Coil | | 35 | D | D | D | D | D | D | D | B45 |
| 96 | P | Helix | a2 | 18 | P | P | P | P | P | P | Q | |
| 97 | W | Helix | | 2 | W | W | W | W | W | W | W | |
| 98 | E | Helix | | 35 | E | E | E | E | E | E | E | |
| 99 | I | Helix | | 29 | I | I | I | I | I | I | I | |
| 100 | F | Helix | | 1 | F | F | F | F | F | F | F | |
| 101 | L | Helix | | 4 | L | M | M | M | L | L | M | |
| 102 | E | Helix | | 40 | E | E | E | E | E | E | E | |
| 103 | H | Helix | | 0 | H | H | H | H | H | H | H | |
| 104 | V | Helix | | 0 | V | V | V | V | V | V | V | |
| 105 | E | Helix | | 16 | E | E | E | E | E | E | E | |
| 106 | Q | Helix | | 75 | Q | Q | Q | Q | Q | Q | Q | B45 |
| 107 | L | Helix | | 0 | L | L | L | L | L | L | L | |
| 108 | V | Helix | | 5 | V | V | V | V | I | I | V | B45 |
| 109 | R | Turn | | 94 | R | R | R | R | R | R | R | 258 |
| 110 | Q | Coil | | 54 | Q | Q | Q | Q | Q | Q | Q | 258 |
| 111 | Q | Coil | | 87 | Q | Q | Q | H | Q | Q | Q | 258 |
| 112 | I | Coil | | 0 | I | I | I | I | V | V | I | B45 |
| 113 | T | Coil | | 80 | T | T | T | T | T | T | T | B45 |
| 114 | E | Helix | a3 | 73 | E | E | E | M | E | E | A | 258 |
| 115 | N | Helix | | 116 | N | N | N | N | N | N | N | B45 |
| 116 | A | Helix | | 11 | A | A | A | A | T | T | A | |
| 117 | R | Helix | | 18 | R | R | R | R | R | R | R | |
| 118 | N | Helix | | 79 | N | N | N | N | N | N | N | B45 |
| 119 | T | Helix | | 55 | T | T | T | T | T | T | T | B45 |
| 120 | A | Helix | | 5 | A | A | A | A | A | A | A | |
| 121 | L | Helix | | 20 | L | L | L | L | I | I | L | |
| 122 | A | Helix | | 87 | A | A | A | A | A | A | A | B45 |
| 123 | R | Helix | | 55 | R | R | R | R | R | R | R | B45 |
| 124 | L | Helix | | 6 | L | L | L | L | L | L | L | |
| 125 | Q | Helix | | 58 | Q | Q | Q | Q | E | E | Q | B45 |
| 126 | G | Helix | | 103 | G | G | G | G | G | G | G | |
| 127 | L | Helix | | 9 | L | L | L | L | L | L | L | |
| 128 | G | Helix | | 0 | G | G | G | G | G | G | G | |
| 129 | A | Helix | | 96 | A | A | A | A | R | R | D | B45 |
| 130 | S | Helix | | 37 | S | S | S | S | G | G | S | |
| 131 | F | Helix | | 2 | F | F | F | F | Y | Y | F | |
| 132 | R | Helix | | 95 | R | R | R | R | R | R | R | |
| 133 | A | Helix | | 49 | A | A | A | A | S | S | A | |
| 134 | Y | Helix | | 1 | Y | Y | Y | Y | Y | Y | Y | |
| 135 | Q | Helix | | 24 | Q | Q | Q | Q | Q | Q | Q | |
| 136 | Q | Helix | | 77 | Q | Q | Q | Q | Q | Q | Q | B45 |
| 137 | S | Helix | | 5 | S | S | S | S | A | A | S | |
| 138 | L | Helix | | 10 | L | L | L | L | L | L | L | |
| 139 | E | Helix | | 55 | E | E | E | E | E | E | E | |
| 140 | D | Helix | | 77 | D | D | D | D | T | T | D | B45 |
| 141 | W | Helix | | 6 | W | W | W | W | W | W | W | |
| 142 | L | Helix | | 67 | L | L | L | L | L | L | L | |
| 143 | E | Helix | | 76 | E | E | E | E | D | D | E | B45 |
| 144 | N | Coil | | 62 | N | N | N | N | N | N | N | B45 |
| 145 | R | Coil | | 67 | R | R | R | R | R | R | R | B45 |
| 146 | D | Coil | | 85 | D | D | D | D | N | N | N | B45 |
| 147 | D | Coil | | 31 | D | N | N | N | D | D | D | B45 |
| 148 | A | Helix | a4 | 64 | A | A | A | A | A | A | A | B45 |
| 149 | R | Helix | | 80 | R | R | R | R | R | R | R | B45 |
| 150 | T | Helix | | 22 | T | T | T | T | S | S | T | |
| 151 | R | Helix | | 57 | R | R | R | R | R | R | R | |
| 152 | S | Helix | | 93 | S | S | S | S | S | S | S | |
| 153 | V | Helix | | 65 | V | V | V | V | I | I | V | |
| 154 | L | Helix | | 0 | L | L | L | L | I | I | L | |
| 155 | Y | Helix | | 42 | Y | Y | Y | Y | L | L | Y | |
| 156 | T | Helix | | 77 | T | T | T | T | E | E | T | |
| 157 | Q | Helix | | 31 | Q | Q | Q | Q | R | R | Q | |
| 158 | Y | Helix | | 3 | Y | Y | Y | Y | Y | Y | Y | B45 |
| 159 | I | Helix | | 31 | I | I | I | I | V | V | I | B45 |
| 160 | A | Helix | | 72 | A | A | A | A | A | A | A | B45 |
| 161 | L | Helix | | 0 | L | L | L | L | L | L | L | |
| 162 | E | Helix | | 13 | E | E | E | E | E | E | E | |
| 163 | L | Helix | | 87 | L | L | L | L | L | L | L | |
| 164 | D | Helix | | 29 | D | D | D | D | D | D | D | |
| 165 | F | Helix | | 2 | F | F | F | F | I | I | F | |

TABLE 4-continued

| | | | | | | | | | | | | |
|---|---|---|---|---|---|---|---|---|---|---|---|---|
| 166 | L | Helix | | 89 | L | L | L | L | T | T | L | B45 |
| 167 | N | Helix | | 56 | N | N | N | N | T | T | N | B45 |
| 168 | A | Helix | | 16 | A | A | A | A | A | A | A | |
| 169 | M | Helix | | 10 | M | M | M | M | I | I | M | |
| 170 | P | Helix | | 70 | P | P | P | P | P | P | P | |
| 171 | L | Helix | | 30 | L | L | L | L | L | L | L | |
| 172 | F | Turn | | 4 | F | F | F | F | F | F | F | |
| 173 | A | Coil | | 48 | A | A | A | A | R | R | A | B45 |
| 174 | I | Coil | | 45 | I | I | I | I | I | I | I | |
| 175 | N | Turn | | 118 | N | N | N | N | R | R | R | |
| 176 | N | Turn | | 112 | N | N | N | N | N | N | E | |
| 177 | Q | Coil | | 12 | Q | Q | Q | Q | E | Q | Q | B45 |
| 178 | Q | Turn | | 16 | Q | Q | Q | Q | E | E | E | B45 |
| 179 | V | Turn | | 21 | V | V | V | V | V | V | V | B45 |
| 180 | P | Turn | | 2 | P | P | P | P | P | P | P | B45 |
| 181 | L | Turn | | 3 | L | L | L | L | L | L | L | |
| 182 | L | Helix | a5 | 0 | L | L | L | L | L | L | L | |
| 183 | M | Helix | | 1 | M | M | M | M | M | M | M | |
| 184 | V | Helix | | 1 | V | V | V | V | V | V | V | |
| 185 | Y | Helix | | 6 | Y | Y | Y | Y | Y | Y | Y | |
| 186 | A | Helix | | 0 | A | A | A | A | A | A | A | |
| 187 | Q | Helix | | 2 | Q | Q | Q | Q | Q | Q | Q | |
| 188 | A | Helix | | 1 | A | A | A | A | A | A | A | |
| 189 | A | Helix | | 0 | A | A | A | A | A | A | A | |
| 190 | N | Helix | | 1 | N | N | N | N | N | N | N | |
| 191 | L | Helix | | 5 | L | L | L | L | L | L | L | |
| 192 | H | Helix | | 0 | H | H | H | H | H | H | H | |
| 193 | L | Helix | | 1 | L | L | L | L | L | L | L | |
| 194 | L | Helix | | 5 | L | L | L | L | L | L | L | |
| 195 | L | Helix | | 0 | L | L | L | L | L | L | L | |
| 196 | L | Helix | | 0 | L | L | L | L | L | L | L | |
| 197 | R | Helix | | 7 | R | R | R | R | R | R | R | |
| 198 | D | Helix | | 0 | D | D | D | D | D | D | D | |
| 199 | A | Helix | | 2 | A | A | A | A | A | A | A | |
| 200 | S | Helix | | 10 | S | S | S | S | S | S | S | |
| 201 | L | Helix | | 16 | L | L | L | L | L | L | L | B45 |
| 202 | F | Helix | | 9 | F | F | F | F | F | F | Y | |
| 203 | G | Turn | | 0 | G | G | G | G | G | G | G | |
| 204 | S | Turn | | 101 | S | S | S | S | S | S | R | |
| 205 | E | Turn | | 66 | E | E | E | E | E | E | E | |
| 206 | F | Turn | | 3 | F | F | F | F | W | W | F | B45 |
| 207 | G | Turn | | 88 | G | G | G | G | G | G | G | |
| 208 | L | Coil | | 12 | L | L | L | L | M | T | L | |
| 209 | T | Coil | | 87 | T | T | T | T | A | A | T | B45 |
| 210 | S | Helix | a6 | 126 | S | S | S | S | S | S | S | B45 |
| 211 | Q | Helix | | 95 | Q | Q | Q | Q | S | S | Q | B45 |
| 212 | E | Helix | | 40 | E | E | E | E | D | D | E | |
| 213 | I | Helix | | 35 | I | I | I | I | V | V | I | B45 |
| 214 | Q | Helix | | 58 | Q | Q | Q | Q | N | N | Q | B21 |
| 215 | R | Helix | | 82 | R | R | R | R | Q | Q | R | |
| 216 | Y | Helix | | 1 | Y | Y | Y | Y | Y | Y | Y | |
| 217 | Y | Helix | | 17 | Y | Y | Y | Y | Y | Y | Y | |
| 218 | E | Helix | | 86 | E | E | E | E | Q | Q | E | B45 |
| 219 | R | Helix | | 28 | R | R | R | R | E | E | R | B21 |
| 220 | Q | Helix | | 6 | Q | Q | Q | Q | Q | Q | Q | |
| 221 | A | Helix | | 66 | A | A | A | A | I | I | V | B45 |
| 222 | E | Helix | | 70 | E | E | E | E | R | R | E | B45 |
| 223 | K | Helix | | 16 | K | K | K | K | Y | Y | R | |
| 224 | T | Helix | | 33 | T | T | T | T | T | T | T | |
| 225 | R | Helix | | 67 | R | R | R | R | E | E | R | B45 |
| 226 | E | Helix | | 66 | E | E | E | E | E | E | D | B45 |
| 227 | Y | Helix | | 3 | Y | Y | Y | Y | Y | Y | Y | |
| 228 | S | Helix | | 11 | S | S | S | S | S | S | S | |
| 229 | D | Helix | | 31 | D | D | D | D | N | N | D | |
| 230 | Y | Helix | | 17 | Y | Y | Y | Y | H | H | H | B45 |
| 231 | C | Helix | | 1 | C | C | C | C | C | C | C | |
| 232 | A | Helix | | 27 | A | A | A | A | V | V | V | |
| 233 | R | Helix | | 87 | R | R | R | R | Q | Q | Q | B45 |
| 234 | W | Helix | | 31 | W | W | W | W | W | W | W | B45 |
| 235 | Y | Helix | | 12 | Y | Y | Y | Y | Y | Y | Y | |
| 236 | N | Helix | | 71 | N | N | N | N | N | N | N | B45 |
| 237 | T | Helix | | 50 | T | T | T | T | T | T | T | |
| 238 | G | Helix | | 8 | G | G | G | G | G | G | G | |
| 239 | L | Helix | | 19 | L | L | L | L | L | L | L | |
| 240 | N | Helix | | 100 | N | N | N | N | N | N | N | B45 |
| 241 | N | Helix | | 92 | N | N | N | N | N | N | N | B45 |
| 242 | L | Helix | | 13 | L | L | L | L | L | L | L | B45 |
| 243 | R | Coil | | 76 | R | R | R | R | R | R | R | B45 |
| 244 | G | Coil | | 46 | G | G | G | G | G | G | G | |
| 245 | T | Coil | | 107 | T | T | T | T | T | T | T | B45 |

TABLE 4-continued

| | | | | | | | | | | | | |
|---|---|---|---|---|---|---|---|---|---|---|---|---|
| 246 | N | Coil | | 57 | N | N | N | N | N | N | N | B45 |
| 247 | A | Helix | a7 | 0 | A | A | A | A | A | A | A | B45 |
| 248 | E | Helix | | 60 | E | E | E | E | E | E | E | B45 |
| 249 | S | Helix | | 58 | S | S | S | S | S | S | S | |
| 250 | W | Helix | | 1 | W | W | W | W | W | W | W | |
| 251 | L | Helix | | 31 | L | L | L | L | L | V | V | |
| 252 | R | Helix | | 67 | R | R | R | R | R | R | R | B45 |
| 253 | Y | Helix | | 20 | Y | Y | Y | Y | Y | Y | Y | |
| 254 | N | Helix | | 0 | N | N | N | N | N | N | N | |
| 255 | Q | Helix | | 37 | Q | Q | Q | Q | Q | Q | Q | |
| 256 | F | Helix | | 0 | F | F | F | F | F | F | F | |
| 257 | R | Helix | | 23 | R | R | R | R | R | R | R | |
| 258 | R | Helix | | 2 | R | R | R | R | R | R | R | |
| 259 | D | Helix | | 7 | D | D | D | D | D | D | D | |
| 260 | L | Helix | | 0 | L | L | L | L | L | L | L | |
| 261 | T | Helix | | 20 | T | T | T | T | T | T | T | |
| 262 | L | Helix | | 2 | L | L | L | L | L | L | L | |
| 263 | G | Helix | | 13 | G | G | G | G | G | G | G | |
| 264 | V | Turn | | 0 | V | V | V | V | V | V | V | |
| 265 | L | Helix | | 15 | L | L | L | L | L | L | L | |
| 266 | D | Helix | | 6 | D | D | D | D | D | D | D | |
| 267 | L | Helix | | 6 | L | L | L | L | L | L | L | |
| 268 | V | Helix | | 3 | V | V | V | V | V | V | V | |
| 269 | A | Helix | | 7 | A | A | A | A | A | A | A | |
| 270 | L | Turn | | 9 | L | L | L | L | L | L | L | |
| 271 | F | Turn | | 0 | F | F | F | F | F | F | F | |
| 272 | P | Helix | | 29 | P | P | P | P | P | P | P | |
| 273 | S | Helix | | 2 | S | S | S | S | S | S | S | |
| 274 | Y | Helix | | 0 | Y | Y | Y | Y | Y | Y | Y | |
| 275 | D | Coil | | 22 | D | D | D | D | D | D | D | |
| 276 | T | Turn | | 30 | T | T | T | T | T | T | T | |
| 277 | R | Turn | | 58 | R | R | R | R | R | R | R | B45 |
| 278 | I | Turn | | 44 | I | I | I | I | T | T | T | |
| 279 | Y | Coil | | 4 | Y | Y | Y | Y | Y | Y | Y | |
| 280 | P | Coil | | 30 | P | P | P | P | P | P | P | B45 |
| 281 | I | Coil | | 39 | I | I | I | I | I | I | I | B45 |
| 282 | N | Coil | | 42 | N | N | N | N | N | N | N | |
| 283 | T | Sheet | | 0 | T | T | T | T | T | T | T | |
| 284 | S | Sheet | | 72 | S | S | S | S | S | S | S | |
| 285 | A | Coil | | 8 | A | A | A | A | A | A | A | |
| 286 | Q | Coil | | 6 | Q | Q | Q | Q | Q | Q | Q | |
| 287 | L | Coil | | 9 | L | L | L | L | L | L | L | |
| 288 | T | Coil | | 2 | T | T | T | T | T | T | T | |
| 289 | R | Coil | | 8 | R | R | R | R | R | R | R | |
| 290 | E | Sheet | b1 | 11 | E | E | E | E | E | E | E | |
| 291 | I | Sheet | | 1 | I | I | I | I | I | V | V | |
| 292 | Y | Sheet | | 7 | Y | Y | Y | Y | Y | Y | Y | |
| 293 | T | Coil | | 8 | T | T | T | T | T | T | T | |
| 294 | D | Coil | | 24 | D | D | D | D | D | D | D | |
| 295 | P | Coil | | 4 | P | P | P | P | P | A | A | |
| 296 | I | Coil | | 3 | I | I | I | I | I | I | I | |
| 297 | G | Coil | | 15 | G | G | G | G | G | G | G | |
| 298 | R | Coil | | 16 | R | R | R | R | R | T | A | |
| 299 | T | Coil | | 48 | T | T | T | T | T | V | T | |
| 300 | N | Coil | | 59 | N | N | N | N | N | H | G | |
| 301 | A | Coil | | 109 | A | A | A | A | A | P | V | |
| 302 | P | Coil | | 63 | P | P | P | P | P | S | N | |
| 303 | S | Coil | | 0 | S | S | S | S | S | Q | — | 258 |
| 304 | G | Coil | | 67 | G | G | G | G | G | A | — | |
| 305 | F | Coil | | 78 | F | F | F | F | F | F | M | |
| 306 | A | Coil | | 31 | A | A | A | A | A | A | A | 258 |
| 307 | S | Coil | | 11 | S | S | S | S | S | S | S | |
| 308 | T | Coil | | 29 | T | T | T | T | T | T | M | |
| 309 | N | Coil | | 20 | N | N | N | N | N | T | N | |
| 310 | W | Helix | | 5 | W | W | W | W | W | W | W | |
| 311 | F | Helix | | 8 | F | F | F | F | F | F | Y | |
| 312 | N | Helix | | 48 | N | N | N | N | N | N | N | |
| 313 | N | Coil | | 60 | N | N | N | N | N | N | N | |
| 314 | N | Coil | | 96 | N | N | N | N | N | N | N | |
| 315 | A | Coil | | 0 | A | A | A | A | A | A | A | |
| 316 | P | Coil | | 33 | P | P | P | P | P | P | P | |
| 317 | S | Coil | | 65 | S | S | S | S | S | S | S | |
| 318 | F | Helix | a8 | 6 | F | F | F | F | F | F | F | |
| 319 | S | Helix | | 96 | S | S | S | S | S | S | S | |
| 320 | A | Helix | | 58 | A | A | A | A | A | A | A | |
| 321 | I | Helix | | 4 | I | I | I | I | I | I | I | |
| 322 | E | Helix | | 39 | E | E | E | E | E | E | E | |
| 323 | A | Helix | | 98 | A | A | A | A | A | A | T | |
| 324 | A | Helix | | 52 | A | A | A | A | A | A | A | |
| 325 | V | Helix | | 18 | V | I | I | I | I | V | V | |

TABLE 4-continued

| | | | | | | | | | | | | |
|---|---|---|---|---|---|---|---|---|---|---|---|---|
| 326 | I | Coil | | 24 | I | F | F | F | F | I | I | |
| 327 | R | Coil | | 11 | R | R | R | R | R | R | R | |
| 328 | P | Coil | | 77 | P | P | P | P | P | P | S | |
| 329 | P | Coil | | 53 | P | P | P | P | P | P | P | |
| 330 | H | Coil | | 21 | H | H | H | H | H | H | H | |
| 331 | L | Coil | | 17 | L | L | L | L | L | L | L | |
| 332 | L | Coil | | 3 | L | L | L | L | L | L | L | |
| 333 | D | Sheet | | 21 | D | D | D | D | D | D | D | |
| 334 | F | Sheet | | 6 | F | F | F | F | F | F | F | |
| 335 | P | Sheet | | 13 | P | P | P | P | P | P | L | |
| 336 | E | Coil | | 19 | E | E | E | E | E | E | E | |
| 337 | Q | Sheet | b2 | 48 | Q | Q | Q | Q | Q | Q | Q | |
| 338 | L | Sheet | | 11 | L | L | L | L | L | L | L | |
| 339 | T | Sheet | | 13 | T | T | T | T | T | T | K | |
| 340 | I | Sheet | | 0 | I | I | I | I | I | I | I | |
| 341 | F | Sheet | | 30 | F | Y | Y | Y | Y | Y | F | |
| 342 | S | Sheet | | 5 | S | S | S | S | S | S | S | |
| 343 | V | Sheet | | 29 | V | A | A | A | A | T | A | |
| 344 | L | Sheet | | 88 | L | S | S | S | S | L | S | |
| 345 | S | Sheet | | 39 | S | S | S | S | S | S | S | |
| 346 | R | Sheet | | 67 | R | R | R | R | R | R | R | |
| 347 | W | Sheet | | 41 | W | W | W | W | W | W | W | |
| 348 | S | Turn | L1 | 51 | S | S | S | S | S | S | S | |
| 349 | N | Turn | | 113 | N | S | S | S | S | N | N | |
| 350 | T | Turn | | 78 | T | T | T | T | T | T | T | |
| 351 | Q | Sheet | b3 | 36 | Q | Q | Q | Q | Q | Q | R | |
| 352 | Y | Sheet | | 45 | Y | H | H | H | H | F | H | |
| 353 | M | Sheet | | 0 | M | M | M | M | M | M | M | |
| 354 | N | Sheet | | 19 | N | N | N | N | N | N | T | |
| 355 | Y | Sheet | | 4 | Y | Y | Y | Y | Y | I | Y | |
| 356 | W | Sheet | | 1 | W | W | W | W | W | W | W | |
| 357 | V | Coil | | 9 | V | V | V | V | V | A | R | |
| 358 | G | Sheet | | 0 | G | G | G | G | G | G | G | |
| 359 | H | Sheet | | 0 | H | H | H | H | H | H | H | |
| 360 | R | Sheet | | 61 | R | R | R | R | R | R | T | B21 |
| 361 | L | Sheet | | 13 | L | L | L | L | L | L | I | |
| 362 | E | Sheet | | 20 | E | N | N | N | N | E | Q | B21 |
| 363 | S | Sheet | | 8 | S | F | F | F | F | S | S | |
| 364 | R | Sheet | | 40 | R | R | R | R | R | R | R | |
| 365 | T | Sheet | | 10 | T | P | P | P | P | P | P | |
| 366 | I | Turn | | 1 | I | I | I | I | I | I | I | |
| 367 | R | Turn | | 70 | R | G | G | G | G | A | R | B21 |
| 368 | G | Coil | | 21 | G | G | G | G | G | G | G | |
| 369 | S | Coil | | 116 | S | T | T | T | T | S | A | |
| 370 | L | Sheet | b4 | 37 | L | L | L | L | L | L | L | |
| 371 | S | Sheet | | 117 | S | N | N | N | N | N | I | |
| 372 | T | Sheet | | 29 | T | T | T | T | T | T | T | |
| 373 | S | Sheet | | 45 | S | S | S | S | S | S | S | |
| 374 | T | Sheet | | 63 | T | T | T | T | T | T | T | |
| 375 | H | Sheet | | 29 | H | H | H | H | Q | Q | H | |
| 376 | G | Sheet | | 23 | G | G | G | G | G | G | G | |
| 377 | N | Coil | | 80 | N | A | A | A | L | S | N | |
| 378 | T | Coil | | 24 | T | T | T | T | T | T | T | |
| 379 | N | Coil | | 106 | N | N | N | N | N | N | N | |
| — | — | | | | — | — | — | — | N | — | — | |
| 380 | T | Coil | | 74 | T | T | T | T | T | T | T | |
| 381 | S | Coil | | 124 | S | S | S | S | S | S | S | |
| 382 | I | Coil | | 20 | I | I | I | I | I | I | I | |
| 383 | N | Sheet | b5 | 76 | N | N | N | N | N | N | N | |
| 384 | P | Sheet | | 66 | P | P | P | P | P | P | P | |
| 385 | V | Sheet | | 42 | V | V | V | V | V | V | V | |
| 386 | T | Sheet | | 99 | T | T | T | T | T | T | T | |
| 387 | L | Sheet | | 5 | L | L | L | L | L | L | F | |
| 388 | Q | Sheet | | 109 | Q | Q | Q | Q | Q | Q | Q | |
| 389 | F | Coil | | 3 | F | F | F | F | F | F | F | |
| 390 | T | Turn | | 66 | T | T | T | T | T | T | P | |
| 391 | S | Turn | | 56 | S | S | S | S | S | S | S | |
| 392 | R | Coil | | 28 | R | R | R | R | R | R | R | |
| 393 | D | Sheet | | 3 | D | D | D | D | D | D | D | |
| 394 | V | Sheet | | 1 | V | V | V | V | V | I | V | |
| 395 | Y | Coil | | 8 | Y | Y | Y | Y | Y | Y | Y | |
| 396 | R | Sheet | b6 | 31 | R | R | R | R | R | R | R | |
| 397 | T | Sheet | | 6 | T | T | T | T | T | T | T | |
| 398 | E | Sheet | | 35 | E | E | E | E | E | E | E | |
| 399 | S | Sheet | | 3 | S | S | S | S | S | S | S | |
| 400 | Y | Sheet | | 35 | Y | Y | Y | Y | N | L | Y | |
| 401 | A | Sheet | | 1 | A | A | A | A | A | A | A | |
| 402 | G | Sheet | | 0 | G | G | G | G | G | G | G | |
| 403 | I | Sheet | | 0 | I | I | I | I | T | L | V | |
| 404 | N | Sheet | | 0 | N | N | N | N | N | N | L | |

TABLE 4-continued

| | | | | | | | | | | | | |
|---|---|---|---|---|---|---|---|---|---|---|---|---|
| 405 | I | Sheet | | 53 | I | I | I | I | I | I | L | |
| 406 | L | Coil | L2 | 38 | L | L | L | L | L | F | W | 258 |
| — | — | | | | — | — | — | — | — | — | G | |
| — | — | | | | — | — | — | — | — | — | I | |
| 407 | L | Coil | | 114 | L | L | L | L | F | I | Y | 258 |
| 408 | T | Coil | | 107 | T | T | T | T | T | T | L | |
| 409 | T | Coil | | 50 | T | T | T | T | T | Q | E | |
| 410 | P | Sheet | | 1 | P | P | P | P | P | P | P | |
| 411 | V | Sheet | | 12 | V | V | V | V | V | V | I | |
| 412 | N | Sheet | | 3 | N | N | N | N | N | N | H | |
| 413 | G | Sheet | | 0 | G | G | G | G | G | G | G | |
| 414 | V | Coil | | 0 | V | V | V | V | V | V | V | |
| 415 | P | Coil | | 6 | P | P | P | P | P | P | P | |
| 416 | W | Sheet | b7 | 21 | W | W | W | W | W | W | T | |
| 417 | A | Sheet | | 1 | A | A | A | A | A | V | V | |
| 418 | R | Sheet | | 42 | R | R | R | R | R | R | R | B21 |
| 419 | F | Sheet | | 2 | F | F | F | F | F | F | F | |
| 420 | N | Sheet | | 17 | N | N | N | N | N | N | N | |
| 421 | W | Sheet | | 4 | W | W | W | W | F | W | F | |
| 422 | R | Sheet | | 17 | R | R | R | R | I | R | R | |
| 423 | N | Sheet | | 18 | N | N | N | N | N | N | N | |
| 424 | P | Turn | | 23 | P | P | P | P | P | P | P | |
| 425 | L | Turn | | 96 | L | L | L | L | Q | L | Q | B21 |
| 426 | N | Turn | | 50 | N | N | N | N | N | N | N | |
| 427 | S | Turn | | 71 | S | S | S | S | I | S | T | B21 |
| 428 | L | Sheet | b8 | 104 | L | L | L | L | Y | L | F | |
| 429 | R | Sheet | | 57 | R | R | R | R | E | R | E | B21 |
| — | — | | | | — | — | — | — | R | — | R | |
| 430 | G | Sheet | | 71 | G | G | G | G | G | G | G | |
| 431 | S | Sheet | | 56 | S | S | S | S | A | S | T | B21 |
| 432 | L | Sheet | | 42 | L | L | L | L | T | L | A | |
| 433 | L | Sheet | | 39 | L | L | L | L | T | L | N | |
| 434 | Y | Sheet | | 4 | Y | Y | Y | Y | Y | Y | Y | |
| 435 | T | Sheet | | 54 | T | T | T | T | S | T | S | B21 |
| 436 | I | Coil | | 21 | I | I | I | I | Q | I | Q | |
| 437 | G | Coil | | 75 | G | G | G | G | P | G | P | B21 |
| 438 | Y | Coil | | 5 | Y | Y | Y | Y | Y | Y | Y | |
| 439 | T | Coil | | 60 | T | T | T | T | Q | T | E | B21 |
| 440 | G | Coil | | 77 | G | G | G | G | G | G | S | |
| 441 | V | Coil | | 13 | V | V | V | V | V | V | P | |
| 442 | G | Sheet | b9 | 67 | G | G | G | G | G | G | G | |
| 443 | T | Sheet | | 37 | T | T | T | T | I | T | L | |
| 444 | Q | Sheet | | 39 | Q | Q | Q | Q | Q | Q | Q | |
| 445 | L | Sheet | | 87 | L | L | L | L | L | L | L | |
| 446 | F | Sheet | | 31 | F | F | F | F | F | Q | K | |
| 447 | D | Sheet | | 41 | D | D | D | D | D | D | D | B21 |
| 448 | S | Helix | | 2 | S | S | S | S | S | S | S | |
| 449 | E | Helix | | 31 | E | E | E | E | E | E | E | |
| 450 | T | Helix | | 76 | T | T | T | T | T | T | T | |
| 451 | E | Helix | | 15 | E | E | E | E | E | E | E | |
| 452 | L | Coil | | 2 | L | L | L | L | L | L | L | |
| 453 | P | Coil | | 14 | P | P | P | P | P | P | P | |
| 454 | P | Coil | | 21 | P | P | P | P | P | P | P | |
| 455 | E | Coil | | 38 | E | E | E | E | E | E | E | |
| 456 | T | Coil | | 45 | T | T | T | T | T | T | T | |
| 457 | T | Coil | | 119 | T | T | T | T | T | T | T | |
| 458 | E | Coil | | 95 | E | E | E | E | E | E | E | |
| 459 | R | Coil | | 75 | R | R | R | R | R | R | R | |
| 460 | P | Coil | | 32 | P | P | P | P | P | P | P | |
| 461 | N | Helix | | 34 | N | N | N | N | N | N | N | |
| 462 | Y | Helix | | 41 | Y | Y | Y | Y | Y | Y | Y | |
| 463 | E | Helix | | 57 | E | E | E | E | E | E | E | |
| 464 | S | Helix | | 2 | S | S | S | S | S | S | S | |
| 465 | Y | Coil | | 3 | Y | Y | Y | Y | Y | Y | Y | |
| 466 | S | Coil | | 0 | S | S | S | S | S | S | S | |
| 467 | H | Sheet | b10 | 1 | H | H | H | H | H | H | H | |
| 468 | R | Sheet | | 3 | R | R | R | R | R | R | R | |
| 469 | L | Sheet | | 13 | L | L | L | L | L | L | L | |
| 470 | S | Coil | | 1 | S | S | S | S | S | S | S | |
| 471 | N | Sheet | | 2 | N | N | N | N | H | H | H | |
| 472 | I | Sheet | | 7 | I | I | I | I | I | I | I | |
| 473 | R | Sheet | | 15 | R | R | R | R | G | G | G | B21 |
| 474 | L | Sheet | | 1 | L | L | L | L | L | L | I | |
| 475 | I | Sheet | | 20 | I | I | I | I | I | I | I | |
| 476 | S | Coil | L3 | 2 | S | I | I | I | I | S | L | B21 |
| 477 | G | Turn | | 126 | G | G | G | G | G | S | Q | B21 |
| 478 | N | Turn | | 105 | N | N | N | G | N | S | T | B21 |
| 479 | T | Coil | | 31 | T | T | T | T | T | H | R | B21 |
| 480 | L | Coil | | 16 | L | L | L | L | L | V | L | |
| 481 | R | Coil | | 22 | R | R | R | R | R | R | N | |

TABLE 4-continued

| | | | | | | | | | | | | |
|---|---|---|---|---|---|---|---|---|---|---|---|---|
| 482 | A | Sheet | b11 | 4 | A | A | A | A | A | A | V | |
| 483 | P | Sheet | | 0 | P | P | P | P | P | L | P | |
| 484 | V | Sheet | | 3 | V | V | V | V | V | V | V | |
| 485 | Y | Sheet | | 1 | Y | Y | Y | Y | Y | Y | Y | |
| 486 | S | Sheet | | 0 | S | S | S | S | S | S | S | |
| 487 | W | Sheet | | 1 | W | W | W | W | W | W | W | |
| 488 | T | Sheet | | 1 | T | T | T | T | T | T | T | |
| 489 | H | Sheet | | 8 | H | H | H | H | H | H | H | |
| 490 | R | Turn | | 39 | R | R | R | R | R | R | R | 258 |
| 491 | S | Turn | | 2 | S | S | S | S | S | S | S | |
| 492 | A | Coil | | 0 | A | A | A | A | A | A | A | |
| 493 | D | Coil | | 30 | D | D | D | D | D | D | D | |
| 494 | R | Coil | | 20 | R | R | R | R | R | R | R | |
| 495 | T | Coil | | 49 | T | T | T | T | T | T | T | B25 |
| 496 | N | Coil | | 5 | N | N | N | N | N | N | N | |
| 497 | T | Sheet | | 60 | T | T | T | T | T | T | T | |
| 498 | I | Sheet | | 9 | I | I | I | I | I | I | I | |
| 499 | A | Coil | | 68 | A | A | A | A | G | G | G | B25 |
| 500 | T | Coil | | 41 | T | T | T | T | P | P | P | |
| 501 | N | Coil | | 103 | N | N | N | N | N | N | N | |
| 502 | I | Coil | | 16 | I | I | I | I | R | R | R | B25 |
| 503 | I | Sheet | b13 | 0 | I | I | I | I | I | I | I | |
| 504 | T | Sheet | | 5 | T | T | T | T | T | T | T | |
| 505 | Q | Sheet | | 8 | Q | Q | Q | Q | Q | Q | Q | |
| 506 | I | Sheet | | 12 | I | I | I | I | I | I | I | |
| 507 | P | Sheet | | 3 | P | P | P | P | P | P | P | |
| 508 | A | Helix | | 0 | A | A | A | A | A | A | A | |
| 509 | V | Helix | | 8 | V | V | V | V | V | V | V | B25 |
| 510 | K | Helix | | 0 | K | K | K | K | K | K | K | |
| 511 | G | Coil | | 0 | G | G | G | G | G | G | G | |
| 512 | N | Coil | | 13 | N | N | N | N | R | R | N | 258 |
| 513 | F | Sheet | b14 | 47 | F | F | F | F | F | F | L | B25 |
| 514 | L | Sheet | | 23 | L | L | L | L | L | L | L | |
| 515 | F | Coil | | 29 | F | F | F | F | F | F | F | B25 |
| 516 | N | Coil | | 125 | N | N | N | N | N | N | N | |
| 517 | G | Coil | | 13 | G | G | G | G | G | G | G | B25 |
| 518 | S | Coil | | 37 | S | S | S | S | S | S | S | B25 |
| 519 | V | Sheet | | 7 | V | V | V | V | V | V | V | |
| 520 | I | Sheet | | 34 | I | I | I | I | I | I | I | B25 |
| 521 | S | Coil | | 110 | S | S | S | S | S | S | S | B25 |
| 522 | G | Coil | | 2 | G | G | G | G | G | G | G | |
| 523 | P | Coil | | 4 | P | P | P | P | P | P | P | |
| 524 | G | Coil | | 46 | G | G | G | G | G | G | G | |
| 525 | F | Coil | | 11 | F | F | F | F | F | F | F | |
| 526 | T | Coil | | 0 | T | T | T | T | T | T | T | B25 |
| 527 | G | Coil | | 13 | G | G | G | G | G | G | G | |
| 528 | G | Coil | | 2 | G | G | G | G | G | G | G | |
| 529 | D | Coil | | 47 | D | D | D | D | D | D | D | |
| 530 | L | Sheet | b15 | 8 | L | L | L | L | V | V | L | |
| 531 | V | Sheet | | 2 | V | V | V | V | V | V | V | |
| 532 | R | Sheet | | 50 | R | R | R | R | R | R | R | B25 |
| 533 | L | Sheet | | 6 | L | L | L | L | L | L | L | |
| 534 | N | Coil | | 52 | N | N | N | N | N | N | N | B25 |
| 535 | N | Coil | | 62 | N | N | N | N | R | R | N | B25 |
| 536 | S | Coil | | 50 | S | S | S | S | N | N | S | |
| 537 | G | Sheet | | 92 | G | G | G | G | N | N | G | 258 |
| 538 | N | Sheet | | 72 | N | N | N | N | G | G | N | 258 |
| 539 | N | Coil | | 4 | N | N | N | N | N | N | N | |
| 540 | I | Sheet | b16 | 2 | I | I | I | I | I | I | I | |
| 541 | Q | Sheet | | 50 | Q | Q | Q | Q | Q | Q | Q | 258 |
| 542 | N | Sheet | | 23 | N | N | N | N | N | N | N | |
| 543 | R | Sheet | | 35 | R | R | R | R | R | R | R | |
| 544 | G | Sheet | | 38 | G | G | G | G | G | G | G | |
| 545 | Y | Sheet | | 37 | Y | Y | Y | Y | Y | Y | Y | 258 |
| 546 | L | Sheet | | 8 | L | I | I | I | I | I | L | |
| 547 | E | Coil | | 101 | E | E | E | E | E | E | E | 258 |
| 548 | V | Coil | | 4 | V | V | V | V | V | V | V | |
| 549 | P | Coil | | 50 | P | P | P | P | P | P | P | |
| 550 | I | Coil | | 7 | I | I | I | I | I | I | I | |
| 551 | Q | Coil | | 90 | Q | Q | Q | Q | Q | Q | Q | B25 |
| 552 | F | Coil | | 103 | F | F | F | F | F | F | F | B25 |
| 553 | I | Coil | | 75 | I | I | I | I | T | T | T | B25 |
| 554 | S | Coil | | 120 | S | S | S | S | S | S | S | B25 |
| 555 | T | Coil | | 79 | T | T | T | T | T | T | T | B25 |
| 556 | S | Coil | | 24 | S | S | S | S | S | S | S | B25 |
| 557 | T | Coil | | 21 | T | T | T | T | T | T | T | B25 |
| 558 | R | Sheet | b17 | 65 | R | R | R | R | R | R | R | B25 |
| 559 | Y | Sheet | | 1 | Y | Y | Y | Y | Y | Y | Y | B25 |
| 560 | R | Sheet | | 38 | R | R | R | R | R | R | R | |
| 561 | V | Sheet | | 7 | V | V | V | V | V | V | V | |

TABLE 4-continued

| | | | | | | | | | | | |
|---|---|---|---|---|---|---|---|---|---|---|---|
| 562 | R | Sheet | | 21 | R | R | R | R | R | R | R | |
| 563 | V | Sheet | | 5 | V | V | V | V | V | V | V | B25 |
| 564 | R | Sheet | | 7 | R | R | R | R | R | R | R | B25 |
| 565 | Y | Sheet | | 5 | Y | Y | Y | Y | Y | Y | Y | B25 |
| 566 | A | Sheet | | 55 | A | A | A | A | A | A | A | |
| 567 | S | Sheet | | 2 | S | S | S | S | S | S | S | |
| 568 | V | Coil | | 29 | V | V | V | V | V | V | V | B25 |
| 569 | T | Coil | | 33 | T | T | T | T | T | T | T | B25 |
| 570 | P | Coil | | 69 | P | P | P | P | S | S | P | 258 |
| 571 | I | Sheet | b18 | 4 | I | I | I | I | I | I | I | B25 |
| 572 | Q | Sheet | | 32 | Q | Q | R | R | E | E | H | 258 |
| 573 | L | Sheet | | 7 | L | L | L | L | L | L | L | B25 |
| 574 | S | Sheet | | 21 | S | S | S | S | N | N | S | 258 |
| 575 | V | Sheet | | 11 | V | V | V | V | V | V | V | |
| 576 | N | Sheet | | 26 | N | N | N | N | N | N | N | |
| 577 | W | Sheet | | 6 | W | W | W | W | L | W | W | 258 |
| 578 | G | Turn | | 109 | G | G | G | G | G | G | G | |
| 579 | N | Turn | | 120 | N | N | N | N | N | N | N | |
| 580 | S | Coil | | 66 | S | S | S | S | S | S | S | |
| 581 | N | Coil | | 85 | N | N | N | N | S | S | N | 258 |
| 582 | I | Coil | | 14 | I | I | I | I | I | I | I | B25 |
| 583 | F | Sheet | b19 | 3 | F | F | F | F | F | F | F | B25 |
| 584 | S | Sheet | | 71 | S | S | S | S | T | T | S | B21 |
| 585 | S | Sheet | | 33 | S | S | S | S | N | N | S | 258 |
| 586 | I | Sheet | | 73 | I | I | I | I | T | T | T | 258 |
| 587 | V | Sheet | | 17 | V | V | V | V | L | L | V | 258 |
| 588 | P | Coil | | 77 | P | P | P | P | P | P | P | |
| 589 | A | Coil | | 38 | A | A | A | A | A | A | A | |
| 590 | T | Coil | | 6 | T | T | T | T | T | T | T | B25 |
| 591 | A | Coil | | 42 | A | A | A | A | A | A | A | 258 |
| 592 | T | Coil | | 87 | T | T | T | T | A | A | A | 258 |
| 593 | S | Turn | | 102 | S | S | S | S | S | S | S | B21 |
| 594 | L | Turn | | 130 | L | L | L | L | L | L | L | |
| 595 | D | Coil | | 63 | D | D | D | D | D | D | D | B21 |
| 596 | N | Coil | | 100 | N | N | N | N | N | N | N | B21 |
| 597 | L | Coil | | 64 | L | L | L | L | L | L | L | |
| 598 | Q | Coil | | 57 | Q | Q | Q | Q | Q | Q | Q | B21 |
| 599 | S | Coil | | 35 | S | S | S | S | S | S | S | B25 |
| 600 | R | Coil | | 58 | R | R | R | R | G | G | R | |
| 601 | D | Sheet | b20 | 20 | D | N | N | N | D | D | D | B21 |
| 602 | F | Sheet | | 55 | F | F | F | F | F | F | F | B25 |
| 603 | G | Sheet | | 27 | G | G | G | G | G | G | G | B25 |
| 604 | Y | Coil | | 4 | Y | Y | Y | Y | Y | Y | Y | |
| 605 | F | Coil | | 108 | F | F | F | F | V | V | F | 258 |
| 606 | E | Coil | | 86 | E | E | E | E | E | E | E | B21 |
| 607 | S | Coil | | 9 | S | S | S | S | I | I | S | 258 |
| 608 | T | Sheet | | 14 | T | T | R | R | N | N | T | 258 |
| 609 | N | Sheet | | 40 | N | N | N | N | N | N | N | B25 |
| 610 | A | Coil | | 0 | A | A | A | A | A | A | A | B25 |
| 611 | F | Coil | | 90 | F | F | F | F | F | F | F | B25 |
| 612 | T | Coil | | 73 | T | T | T | T | T | T | T | B25 |
| 613 | S | Coil | | 89 | S | S | S | S | S | S | S | B25 |
| 614 | A | Sheet | b22 | 51 | A | A | A | A | A | A | V | B25 |
| 615 | T | Sheet | | 14 | T | T | T | T | T | T | T | |
| 616 | G | Sheet | | 50 | G | G | G | G | G | G | G | |
| 617 | N | Sheet | | 31 | N | N | N | N | N | N | N | B25 |
| 618 | V | Sheet | | 17 | V | V | V | V | I | I | V | 258 |
| 619 | V | Sheet | | 10 | V | V | V | V | V | V | V | |
| 620 | G | Sheet | | 2 | G | G | G | G | G | G | G | |
| 621 | V | Sheet | | 4 | V | V | V | V | A | V | V | |
| 622 | R | Sheet | | 61 | R | R | R | R | R | R | R | |
| 623 | N | Coil | | 89 | N | N | N | N | N | N | N | |
| 624 | F | Coil | | 0 | F | F | F | F | F | F | F | B25 |
| 625 | S | Coil | | 123 | S | S | S | S | S | S | S | |
| 626 | E | Coil | | 83 | E | E | E | E | A | A | E | 258 |
| 627 | N | Coil | | 98 | N | N | N | N | N | N | N | |
| 628 | A | Coil | | 19 | A | A | A | A | A | A | A | B25 |
| 629 | G | Coil | | 42 | G | G | G | G | E | E | R | 258 |
| 630 | V | Sheet | b23 | 2 | V | V | V | V | V | V | V | B25 |
| 631 | I | Sheet | | 12 | I | I | I | I | I | I | I | |
| 632 | I | Sheet | | 8 | I | I | I | I | I | I | I | |
| 633 | D | Coil | | 4 | D | D | D | D | D | D | D | |
| 634 | R | Sheet | | 7 | R | R | R | R | R | R | R | |
| 635 | F | Sheet | | 23 | F | F | F | F | F | F | F | |
| 636 | E | Sheet | | 0 | E | E | E | E | E | E | E | |
| 637 | F | Sheet | | 15 | F | F | F | F | F | F | F | |
| 638 | I | Sheet | | 12 | I | I | I | I | I | I | I | |
| 639 | P | Sheet | | 6 | P | P | P | P | P | P | P | |
| 640 | V | Turn | | 33 | V | V | V | V | V | V | V | |
| 641 | T | Turn | | 113 | T | T | T | T | T | T | T | B25 |

TABLE 4-continued

| | | | | | | | | | | | |
|---|---|---|---|---|---|---|---|---|---|---|---|
| 642 | A | Coil | 3 | A | A | A | A | A | A | A | |
| 643 | T | Coil | 117 | T | T | T | T | T | T | T | B25 |
| 644 | F | | | F | F | F | F | F | F | F | |
| 645 | E | | | E | E | E | E | E | E | E | B25 |
| 646 | A | | | A | A | A | A | A | A | A | B25 |
| 647 | E | | | E | E | E | E | E | K | E | |
| 648 | Y | | | Y | Y | Y | Y | Y | Y | Y | |
| 649 | D | | | D | D | D | D | D | D | D | |
| 650 | L | | | L | L | L | L | L | L | L | |
| 651 | E | | | E | E | E | E | E | E | E | |

| MP258 position | Variant | FAE | Variant | FAE | Variant | FAE | Variant | FAE | Variant | FAE |
|---|---|---|---|---|---|---|---|---|---|---|
| 50 | L50R | 1.72 | L50I | 1.52 | L50D | 1.5 | L50A | 1.43 | L50H | 1.42 |
| | L50Y | 1.42 | L50S | 1.38 | L50F | 1.38 | L50V | 1.37 | L50K | 1.34 |
| | L50N | 1.26 | | | | | | | | |
| 51 | | | | | | | | | | |
| 52 | | | | | | | | | | |
| 53 | A53R | 1.79 | A53Y | 1.72 | A53K | 1.7 | A53H | 1.45 | A53P | 1.42 |
| | A53V | 1.35 | A53Q | 1.31 | A53D | 1.25 | A53E | 1.23 | A53G | 1.22 |
| | A53T | 1.21 | | | | | | | | |
| 54 | S54P | 1.6 | S54K | 1.4 | S54G | 1.39 | S54A | 1.36 | S54I | 1.25 |
| | S54R | 1.21 | | | | | | | | |
| 55 | | | | | | | | | | |
| 56 | | | | | | | | | | |
| 57 | Q57V | 1.76 | Q57R | 1.71 | Q57L | 1.54 | Q57N | 1.53 | Q57G | 1.38 |
| | Q57D | 1.3 | | | | | | | | |
| 58 | | | | | | | | | | |
| 59 | | | | | | | | | | |
| 60 | | | | | | | | | | |
| 61 | | | | | | | | | | |
| 62 | | | | | | | | | | |
| 63 | | | | | | | | | | |
| 64 | | | | | | | | | | |
| 65 | R65Q | 1.54 | R65A | 1.53 | R65S | 1.48 | R65G | 1.36 | | |
| 66 | | | | | | | | | | |
| 67 | L67M | 2.03 | L67F | 1.41 | L67I | 1.27 | | | | |
| 68 | G68A | 1.83 | G68R | 1.3 | G68F | 1.27 | | | | |
| 69 | | | | | | | | | | |
| 70 | L70E | 1.51 | L70W | 1.3 | L70H | 1.23 | | | | |
| 71 | G71S | 1.33 | | | | | | | | |
| 72 | V72G | 1.87 | | | | | | | | |
| 73 | P73S | 1.27 | P73G | 1.35 | | | | | | |
| 74 | F74I | 1.92 | F74E | 1.91 | F74S | 1.64 | F74R | 1.33 | F74V | 1.25 |
| | F74D | 1.24 | | | | | | | | |
| 75 | A75S | 2.23 | A75P | 1.67 | A75E | 1.28 | | | | |
| 76 | G76T | 2.01 | G76S | 1.76 | G76Y | 1.6 | G76V | 1.6 | G76D | 1.41 |
| | G76R | 1.4 | | | | | | | | |
| 77 | Q77N | 1.86 | Q77D | 1.82 | Q77G | 1.78 | Q77L | 1.76 | Q77I | 1.69 |
| | Q77H | 1.64 | Q77P | 1.63 | Q77A | 1.59 | Q77T | 1.58 | Q77M | 1.39 |
| | Q77C | 1.38 | Q77S | 1.22 | | | | | | |
| 78 | | | | | | | | | | |
| 79 | A79S | 1.83 | A79V | 1.78 | A79T | 1.71 | A79L | 1.69 | A79R | 1.65 |
| | A79I | 1.55 | A79P | 1.5 | A79N | 1.32 | A79Q | 1.31 | A79K | 1.23 |
| 80 | S80Q | 2.06 | S80K | 1.97 | S80G | 1.93 | S80E | 1.86 | S80R | 1.84 |
| | S80M | 1.77 | S80N | 1.66 | S80C | 1.56 | S80W | 1.45 | S80Y | 1.44 |
| | S80D | 1.29 | | | | | | | | |
| 81 | | | | | | | | | | |
| 82 | Y82F | 1.41 | | | | | | | | |
| 83 | S83E | 1.97 | S83D | 1.91 | S83G | 1.89 | S83A | 1.87 | S83K | 1.8 |
| | S83H | 1.7 | S83R | 1.51 | S83Y | 1.39 | S83L | 1.32 | | |
| 84 | | | | | | | | | | |
| 85 | | | | | | | | | | |
| 86 | | | | | | | | | | |
| 87 | G87D | 1.95 | G87K | 1.65 | G87N | 1.44 | G87C | 1.42 | G87W | 1.28 |
| | G87H | 1.24 | | | | | | | | |
| 88 | | | | | | | | | | |
| 89 | | | | | | | | | | |
| 90 | | | | | | | | | | |
| 91 | P91S | 1.64 | P91Y | 1.49 | P91T | 1.46 | P91D | 1.28 | | |
| 92 | S92E | 2.54 | S92G | 1.88 | S92F | 1.72 | S92V | 1.72 | S92L | 1.71 |
| | S92T | 1.47 | | | | | | | | |
| 93 | G93H | 1.68 | G93D | 1.53 | G93I | 1.28 | | | | |
| 94 | R94L | 2.27 | R94H | 2.19 | R94T | 1.7 | R94S | 1.35 | | |
| 95 | D95G | 1.86 | D95Q | 1.67 | D95V | 1.55 | D95F | 1.2 | | |
| 96 | | | | | | | | | | |
| 97 | | | | | | | | | | |
| 98 | | | | | | | | | | |
| 99 | | | | | | | | | | |

TABLE 4-continued

| | | | | | | | | | | |
|---|---|---|---|---|---|---|---|---|---|---|
| 100 | | | | | | | | | | |
| 101 | | | | | | | | | | |
| 102 | | | | | | | | | | |
| 103 | | | | | | | | | | |
| 104 | | | | | | | | | | |
| 105 | | | | | | | | | | |
| 106 | Q106I | 2.16 | Q106A | 1.77 | Q106F | 1.74 | Q106G | 1.71 | | |
| | Q106H | 1.67 | Q106C | 1.52 | Q106K | 1.43 | Q106V | 1.32 | Q106R | 1.29 |
| | Q106S | 1.25 | | | | | | | | |
| 107 | | | | | | | | | | |
| 108 | V108L | 1.92 | V108M | 1.55 | V108T | 1.29 | | | | |
| 109 | R109S | 1.35 | R109V | 1.28 | R109N | 1.23 | | | | |
| 110 | Q110T | 1.93 | Q110R | 1.51 | Q110V | 1.32 | Q110F | 1.26 | Q110H | 1.24 |
| 111 | Q111H | 4.5 | Q111L | 2.97 | O111S | 2.37 | Q111M | 2.16 | Q111R | 2.14 |
| | Q111A | 1.99 | Q111K | 1.8 | Q111E | 1.54 | | | | |
| 112 | I112L | 2.03 | | | | | | | | |
| 113 | T113L | 1.44 | T113V | 1.4 | T113S | 1.34 | T113N | 1.29 | T113K | 1.25 |
| 114 | E114L | 2.67 | E114T | 2.29 | E114M | 2.11 | E114H | 2.03 | E114Y | 1.94 |
| | E114A | 1.73 | E114S | 1.67 | E114V | 1.54 | E114F | 1.39 | | |
| 115 | N115P | 1.39 | | | | | | | | |
| 116 | | | | | | | | | | |
| 117 | | | | | | | | | | |
| 118 | N118V | 2.16 | N118T | 1.84 | N118E | 1.72 | N118D | 1.4 | N118F | 1.37 |
| | N118G | 1.22 | | | | | | | | |
| 119 | T119A | 2.3 | T119M | 2.08 | T119S | 1.89 | T119K | 1.76 | T119H | 1.69 |
| | T119E | 1.66 | T119R | 1.65 | T119V | 1.44 | | | | |
| 120 | | | | | | | | | | |
| 121 | | | | | | | | | | |
| 122 | A122R | 1.38 | A122I | 1.32 | A122F | 1.27 | A122N | 1.26 | A122G | 1.23 |
| | A122T | 1.23 | | | | | | | | |
| 123 | R123K | 1.81 | | | | | | | | |
| 124 | | | | | | | | | | |
| 125 | Q125N | 1.83 | Q125R | 1.58 | Q125E | 1.48 | | | | |
| 126 | | | | | | | | | | |
| 127 | | | | | | | | | | |
| 128 | | | | | | | | | | |
| 129 | A129K | 1.69 | A129W | 1.56 | A129L | 1.38 | A129P | 1.32 | A129V | 1.23 |
| 130 | | | | | | | | | | |
| 131 | | | | | | | | | | |
| 132 | | | | | | | | | | |
| 133 | | | | | | | | | | |
| 134 | | | | | | | | | | |
| 135 | | | | | | | | | | |
| 136 | Q136I | 1.52 | Q136F | 1.34 | Q1361 | 1.31 | | | | |
| 137 | | | | | | | | | | |
| 138 | | | | | | | | | | |
| 139 | | | | | | | | | | |
| 140 | D140E | 1.65 | | | | | | | | |
| 141 | | | | | | | | | | |
| 142 | | | | | | | | | | |
| 143 | E143S | 2.18 | E143R | 1.78 | E143G | 1.64 | E143Y | 1.62 | E143M | 1.62 |
| | E143Q | 1.58 | E143L | 1.55 | E143W | 1.55 | E143T | 1.5 | E143A | 1.48 |
| | E143N | 1.37 | E143P | 1.34 | | | | | | |
| 144 | N144M | 1.81 | N144A | 1.56 | N144T | 1.21 | | | | |
| 145 | R145N | 1.81 | R145P | 1.55 | R145A | 1.45 | R145L | 1.44 | R145S | 1.23 |
| 146 | D146W | 1.53 | D146T | 1.3 | D146H | 1.22 | D146V | 1.21 | | |
| 147 | N147V | 1.77 | N147R | 1.65 | N147D | 1.42 | N147S | 1.37 | | |
| 148 | A148F | 2.22 | A148W | 1.83 | A148P | 1.75 | A148N | 1.74 | A148L | 1.73 |
| 149 | R149V | 2.2 | R149A | 1.89 | R149S | 1.88 | R149L | 1.49 | | |
| 150 | | | | | | | | | | |
| 151 | | | | | | | | | | |
| 152 | | | | | | | | | | |
| 153 | | | | | | | | | | |
| 154 | | | | | | | | | | |
| 155 | | | | | | | | | | |
| 156 | | | | | | | | | | |
| 157 | | | | | | | | | | |
| 158 | Y158F | 1.7 | | | | | | | | |
| 159 | I159V | 1.37 | | | | | | | | |
| 160 | A160V | 1.65 | | | | | | | | |
| 161 | | | | | | | | | | |
| 162 | | | | | | | | | | |
| 163 | | | | | | | | | | |
| 164 | | | | | | | | | | |
| 165 | | | | | | | | | | |
| 166 | L166V | 1.67 | L166E | 1.62 | L166C | 1.34 | L166I | 1.28 | L166T | 1.25 |
| 167 | N167T | 1.43 | N167M | 1.37 | N167Q | 1.3 | N167L | 1.29 | N167A | 1.22 |
| 168 | | | | | | | | | | |
| 169 | | | | | | | | | | |
| 170 | | | | | | | | | | |

TABLE 4-continued

| | | | | | | | | | | |
|---|---|---|---|---|---|---|---|---|---|---|
| 171 | | | | | | | | | | |
| 172 | | | | | | | | | | |
| 173 | A173F | 1.56 | A173T | 1.56 | | | | | | |
| 174 | | | | | | | | | | |
| 175 | | | | | | | | | | |
| 176 | | | | | | | | | | |
| 177 | Q177C | 1.78 | Q177S | 1.48 | Q177T | 1.3 | Q177P | 1.21 | | |
| 178 | Q178K | 1.69 | | | | | | | | |
| 179 | V179I | 2.06 | V179L | 1.67 | | | | | | |
| 180 | P180A | 1.7 | P180S | 1.51 | P180L | 1.51 | P180M | 1.38 | | |
| 181 | | | | | | | | | | |
| 182 | | | | | | | | | | |
| 183 | | | | | | | | | | |
| 184 | | | | | | | | | | |
| 185 | | | | | | | | | | |
| 186 | | | | | | | | | | |
| 187 | | | | | | | | | | |
| 188 | | | | | | | | | | |
| 189 | | | | | | | | | | |
| 190 | | | | | | | | | | |
| 191 | | | | | | | | | | |
| 192 | | | | | | | | | | |
| 193 | | | | | | | | | | |
| 194 | | | | | | | | | | |
| 195 | | | | | | | | | | |
| 196 | | | | | | | | | | |
| 197 | | | | | | | | | | |
| 198 | | | | | | | | | | |
| 199 | | | | | | | | | | |
| 200 | | | | | | | | | | |
| 201 | L201V | 1.27 | | | | | | | | |
| 202 | | | | | | | | | | |
| 203 | | | | | | | | | | |
| 204 | | | | | | | | | | |
| 205 | | | | | | | | | | |
| 206 | F206L | 2.37 | F206I | 1.47 | F206T | 1.46 | F206W | 1.45 | | |
| 207 | | | | | | | | | | |
| 208 | | | | | | | | | | |
| 209 | T209E | 1.86 | T209R | 1.7 | T209D | 1.66 | T209L | 1.59 | T209V | 1.3 |
| | T209C | 1.22 | | | | | | | | |
| 210 | S210P | 2.15 | S210T | 1.78 | S210I | 1.46 | S210R | 1.25 | | |
| 211 | Q211I | 1.9 | Q211R | 1.74 | Q211G | 1.55 | Q211T | 1.44 | Q211P | 1.33 |
| | Q211L | 1.22 | | | | | | | | |
| 212 | | | | | | | | | | |
| 213 | I213V | 1.71 | I213T | 1.66 | I213L | 1.64 | I213M | 1.53 | 1213Q | 1.5 |
| | I213N | 1.28 | I213G | 1.21 | | | | | | |
| 214 | Q214W | 3.46 | | | | | | | | |
| 215 | | | | | | | | | | |
| 216 | | | | | | | | | | |
| 217 | | | | | | | | | | |
| 218 | E218T | 1.76 | E218A | 1.65 | E218H | 1.62 | E218S | 1.55 | E218I | 1.51 |
| | E218V | 1.33 | E218Y | 1.29 | E218W | 1.21 | E218D | 1.21 | | |
| 219 | R219N | 1.63 | | | | | | | | |
| 220 | | | | | | | | | | |
| 221 | A221L | 2.21 | A221Y | 1.86 | A221V | 1.84 | A221K | 1.81 | A221I | 1.62 |
| | A221D | 1.48 | A221G | 1.43 | A221H | 1.42 | A221W | 1.3 | A221R | 1.28 |
| | A221T | 1.25 | | | | | | | | |
| 222 | E222G | 1.89 | E222M | 1.75 | E222K | 1.72 | E222T | 1.67 | E222D | 1.39 |
| | E222I | 1.36 | | | | | | | | |
| 223 | | | | | | | | | | |
| 224 | | | | | | | | | | |
| 225 | R225V | 4.65 | R225Q | 2.37 | R225M | 2.32 | R225F | 2.07 | R225L | 2.04 |
| | R225G | 1.58 | R225I | 1.58 | R225Y | 1.55 | R225C | 1.54 | R225N | 1.46 |
| 226 | E226D | 2.17 | E226S | 2.13 | E226V | 1.68 | E226C | 1.52 | E226Y | 1.46 |
| | E226R | 1.33 | E226A | 1.24 | | | | | | |
| 227 | | | | | | | | | | |
| 228 | | | | | | | | | | |
| 229 | | | | | | | | | | |
| 230 | Y230A | 2.65 | Y230L | 1.83 | Y230S | 1.22 | | | | |
| 231 | | | | | | | | | | |
| 232 | | | | | | | | | | |
| 233 | R233K | 2.13 | R233D | 1.96 | R233Q | 1.91 | R233G | 1.56 | R233I | 1.41 |
| | R233A | 1.26 | R233Y | 1.2 | | | | | | |
| 234 | W234V | 2.15 | W234M | 2.15 | W234L | 2.06 | W234I | 1.87 | W234A | 1.55 |
| | W234R | 1.55 | W234F | 1.52 | W234Y | 1.48 | W234S | 1.22 | | |
| 235 | | | | | | | | | | |
| 236 | N236E | 2.2 | N236K | 1.87 | N236S | 1.43 | N236T | 1.41 | N236L | 1.41 |
| 237 | | | | | | | | | | |
| 238 | | | | | | | | | | |
| 239 | | | | | | | | | | |

TABLE 4-continued

| | | | | | | | | | | |
|---|---|---|---|---|---|---|---|---|---|---|
| 240 | N240Y | 1.77 | N240A | 1.56 | N240M | 1.53 | N240S | 1.5 | N240T | 1.49 |
| | N240G | 1.46 | N240K | 1.46 | N240F | 1.36 | N240L | 1.28 | N240R | 1.26 |
| | N240W | 1.22 | N240C | 1.22 | | | | | | |
| 241 | N241S | 1.7 | N241I | 1.68 | N241W | 1.62 | N241M | 1.57 | N241K | 1.48 |
| | N241Y | 1.47 | N241V | 1.33 | N241L | 1.27 | N241C | 1.21 | | |
| 242 | L242P | 2.07 | L242V | 1.44 | | | | | | |
| 243 | R243M | 2.3 | R243V | 2 | R243T | 1.84 | R243C | 1.75 | R243K | 1.72 |
| | R243I | 1.68 | R243S | 1.59 | R243Q | 1.54 | | | | |
| 244 | | | | | | | | | | |
| 245 | T245Q | 2.71 | T245Y | 2.46 | T245K | 2.4 | T245G | 2.13 | T245A | 2.03 |
| | T245I | 1.96 | T245W | 1.95 | T245H | 1.91 | T245S | 1.89 | T245M | 1.82 |
| | T245D | 1.82 | T245N | 1.77 | T245V | 1.66 | T245R | 1.64 | T245F | 1.34 |
| 246 | N246T | 1.73 | N246S | 1.69 | N246G | 1.66 | N246Q | 1.63 | | |
| 247 | A247E | 1.73 | A247S | 1.73 | A247G | 1.57 | A247P | 1.53 | | |
| 248 | E248S | 2.17 | E248N | 1.55 | E248T | 1.53 | E248L | 1.49 | E248Y | 1.49 |
| | E248V | 1.42 | E248R | 1.42 | E248F | 1.24 | | | | |
| 249 | | | | | | | | | | |
| 250 | | | | | | | | | | |
| 251 | | | | | | | | | | |
| 252 | R252N | 1.47 | R252A | 1.4 | R252F | 1.24 | | | | |
| 253 | | | | | | | | | | |
| 254 | | | | | | | | | | |
| 255 | | | | | | | | | | |
| 256 | | | | | | | | | | |
| 257 | | | | | | | | | | |
| 258 | | | | | | | | | | |
| 259 | | | | | | | | | | |
| 260 | | | | | | | | | | |
| 261 | | | | | | | | | | |
| 262 | | | | | | | | | | |
| 263 | | | | | | | | | | |
| 264 | | | | | | | | | | |
| 265 | | | | | | | | | | |
| 266 | | | | | | | | | | |
| 267 | | | | | | | | | | |
| 268 | | | | | | | | | | |
| 269 | | | | | | | | | | |
| 270 | | | | | | | | | | |
| 271 | | | | | | | | | | |
| 272 | | | | | | | | | | |
| 273 | | | | | | | | | | |
| 274 | | | | | | | | | | |
| 275 | | | | | | | | | | |
| 276 | | | | | | | | | | |
| 277 | R277Q | 1.35 | R277G | 1.27 | R277V | 1.23 | | | | |
| 278 | | | | | | | | | | |
| 279 | | | | | | | | | | |
| 280 | P280H | 1.54 | P280C | 1.32 | P280T | 1.29 | | | | |
| 281 | I281Q | 2.16 | I281M | 1.93 | I281R | 1.46 | I281K | 1.35 | I281S | 1.31 |
| | I281H | 1.29 | I281A | 1.23 | | | | | | |
| 282 | | | | | | | | | | |
| 283 | | | | | | | | | | |
| 284 | | | | | | | | | | |
| 285 | | | | | | | | | | |
| 286 | | | | | | | | | | |
| 287 | | | | | | | | | | |
| 288 | | | | | | | | | | |
| 289 | | | | | | | | | | |
| 290 | | | | | | | | | | |
| 291 | | | | | | | | | | |
| 292 | | | | | | | | | | |
| 293 | | | | | | | | | | |
| 294 | | | | | | | | | | |
| 295 | | | | | | | | | | |
| 296 | | | | | | | | | | |
| 297 | | | | | | | | | | |
| 298 | | | | | | | | | | |
| 299 | | | | | | | | | | |
| 300 | | | | | | | | | | |
| 301 | | | | | | | | | | |
| 302 | | | | | | | | | | |
| 303 | S303N | 1.28 | S303P | 1.24 | | | | | | |
| 304 | | | | | | | | | | |
| 305 | | | | | | | | | | |
| 306 | A306G | 1.47 | | | | | | | | |
| 307 | | | | | | | | | | |
| 308 | | | | | | | | | | |
| 309 | | | | | | | | | | |
| 310 | | | | | | | | | | |
| 311 | | | | | | | | | | |

TABLE 4-continued

| | | | | | | | | | | |
|---|---|---|---|---|---|---|---|---|---|---|
| 312 | | | | | | | | | | |
| 313 | | | | | | | | | | |
| 314 | | | | | | | | | | |
| 315 | | | | | | | | | | |
| 316 | | | | | | | | | | |
| 317 | | | | | | | | | | |
| 318 | | | | | | | | | | |
| 319 | | | | | | | | | | |
| 320 | | | | | | | | | | |
| 321 | | | | | | | | | | |
| 322 | | | | | | | | | | |
| 323 | | | | | | | | | | |
| 324 | | | | | | | | | | |
| 325 | | | | | | | | | | |
| 326 | | | | | | | | | | |
| 327 | | | | | | | | | | |
| 328 | | | | | | | | | | |
| 329 | | | | | | | | | | |
| 330 | | | | | | | | | | |
| 331 | | | | | | | | | | |
| 332 | | | | | | | | | | |
| 333 | | | | | | | | | | |
| 334 | | | | | | | | | | |
| 335 | | | | | | | | | | |
| 336 | | | | | | | | | | |
| 337 | | | | | | | | | | |
| 338 | | | | | | | | | | |
| 339 | | | | | | | | | | |
| 340 | | | | | | | | | | |
| 341 | | | | | | | | | | |
| 342 | | | | | | | | | | |
| 343 | | | | | | | | | | |
| 344 | | | | | | | | | | |
| 345 | | | | | | | | | | |
| 346 | | | | | | | | | | |
| 347 | | | | | | | | | | |
| 348 | | | | | | | | | | |
| 349 | | | | | | | | | | |
| 350 | | | | | | | | | | |
| 351 | | | | | | | | | | |
| 352 | | | | | | | | | | |
| 353 | | | | | | | | | | |
| 354 | | | | | | | | | | |
| 355 | | | | | | | | | | |
| 356 | | | | | | | | | | |
| 357 | | | | | | | | | | |
| 358 | | | | | | | | | | |
| 359 | | | | | | | | | | |
| 360 | R360S | 1.68 | R360N | 1.57 | R360T | 1.38 | R360Y | 1.29 | R360M | 1.23 |
| 361 | | | | | | | | | | |
| 362 | N362Y | 2.25 | N362H | 1.79 | N362W | 1.64 | N362K | 1.57 | N362I | 1.57 |
| | N362D | 1.45 | N362V | 1.45 | N362A | 1.32 | N362L | 1.3 | N362G | 1.26 |
| | N362E | 1.26 | | | | | | | | |
| 363 | | | | | | | | | | |
| 364 | | | | | | | | | | |
| 365 | | | | | | | | | | |
| 366 | | | | | | | | | | |
| 367 | G367H | 3.17 | G367Q | 2.72 | G367N | 1.97 | G367W | 1.84 | G367T | 1.62 |
| | G367L | 1.58 | G367Y | 1.45 | G367I | 1.37 | G367A | 1.36 | | |
| 368 | | | | | | | | | | |
| 369 | | | | | | | | | | |
| 370 | | | | | | | | | | |
| 371 | | | | | | | | | | |
| 372 | | | | | | | | | | |
| 373 | | | | | | | | | | |
| 374 | | | | | | | | | | |
| 375 | | | | | | | | | | |
| 376 | | | | | | | | | | |
| 377 | | | | | | | | | | |
| 378 | | | | | | | | | | |
| 379 | | | | | | | | | | |
| — | | | | | | | | | | |
| 380 | | | | | | | | | | |
| 381 | | | | | | | | | | |
| 382 | | | | | | | | | | |
| 383 | | | | | | | | | | |
| 384 | | | | | | | | | | |
| 385 | | | | | | | | | | |
| 386 | | | | | | | | | | |
| 387 | | | | | | | | | | |

TABLE 4-continued

| | | | | | | | | | | |
|---|---|---|---|---|---|---|---|---|---|---|
| 388 | | | | | | | | | | |
| 389 | | | | | | | | | | |
| 390 | | | | | | | | | | |
| 391 | | | | | | | | | | |
| 392 | | | | | | | | | | |
| 393 | | | | | | | | | | |
| 394 | | | | | | | | | | |
| 395 | | | | | | | | | | |
| 396 | | | | | | | | | | |
| 397 | | | | | | | | | | |
| 398 | | | | | | | | | | |
| 399 | | | | | | | | | | |
| 400 | | | | | | | | | | |
| 401 | | | | | | | | | | |
| 402 | | | | | | | | | | |
| 403 | | | | | | | | | | |
| 404 | | | | | | | | | | |
| 405 | | | | | | | | | | |
| 406 | L406M | 1.65 | | | | | | | | |
| — | | | | | | | | | | |
| — | | | | | | | | | | |
| 407 | L407W | 1.99 | | | | | | | | |
| 408 | | | | | | | | | | |
| 409 | | | | | | | | | | |
| 410 | | | | | | | | | | |
| 411 | | | | | | | | | | |
| 412 | | | | | | | | | | |
| 413 | | | | | | | | | | |
| 414 | | | | | | | | | | |
| 415 | | | | | | | | | | |
| 416 | | | | | | | | | | |
| 417 | | | | | | | | | | |
| 418 | R418K | 1.26 | R418T | 1.24 | | | | | | |
| 419 | | | | | | | | | | |
| 420 | | | | | | | | | | |
| 421 | | | | | | | | | | |
| 422 | | | | | | | | | | |
| 423 | | | | | | | | | | |
| 424 | | | | | | | | | | |
| 425 | L425P | 1.94 | L425G | 1.31 | | | | | | |
| 426 | | | | | | | | | | |
| 427 | S427Y | 1.44 | | | | | | | | |
| 428 | | | | | | | | | | |
| 429 | R429I | 1.36 | | | | | | | | |
| — | | | | | | | | | | |
| 430 | | | | | | | | | | |
| 431 | S431L | 1.63 | S431H | 1.63 | S431G | 1.42 | S431A | 1.3 | | |
| 432 | | | | | | | | | | |
| 433 | | | | | | | | | | |
| 434 | | | | | | | | | | |
| 435 | T435Y | 2.14 | T435H | 1.43 | T435L | 1.21 | | | | |
| 436 | | | | | | | | | | |
| 437 | G437S | 1.57 | G437N | 1.57 | G437A | 1.43 | G437K | 1.34 | G437R | 1.34 |
| 438 | G437Q | 1.33 | | | | | | | | |
| 439 | T439M | 1.22 | T439Q | 1.21 | | | | | | |
| 440 | | | | | | | | | | |
| 441 | | | | | | | | | | |
| 442 | | | | | | | | | | |
| 443 | | | | | | | | | | |
| 444 | | | | | | | | | | |
| 445 | | | | | | | | | | |
| 446 | | | | | | | | | | |
| 447 | D447N | 1.55 | D447V | 1.52 | D447I | 1.47 | D447S | 1.34 | D447L | 1.33 |
| | D447A | 1.31 | D447E | 1.3 | D447M | 1.21 | | | | |
| 448 | | | | | | | | | | |
| 449 | | | | | | | | | | |
| 450 | | | | | | | | | | |
| 451 | | | | | | | | | | |
| 452 | | | | | | | | | | |
| 453 | | | | | | | | | | |
| 454 | | | | | | | | | | |
| 455 | | | | | | | | | | |
| 456 | | | | | | | | | | |
| 457 | | | | | | | | | | |
| 458 | | | | | | | | | | |
| 459 | | | | | | | | | | |
| 460 | | | | | | | | | | |
| 461 | | | | | | | | | | |
| 462 | | | | | | | | | | |
| 463 | | | | | | | | | | |

TABLE 4-continued

| | | | | | | | | | | |
|---|---|---|---|---|---|---|---|---|---|---|
| 464 | | | | | | | | | | |
| 465 | | | | | | | | | | |
| 466 | | | | | | | | | | |
| 467 | | | | | | | | | | |
| 468 | | | | | | | | | | |
| 469 | | | | | | | | | | |
| 470 | | | | | | | | | | |
| 471 | | | | | | | | | | |
| 472 | | | | | | | | | | |
| 473 | R473T | 12.6 | R473G | 5.48 | R473A | 4.94 | R473S | 3.04 | R473M | 1.94 |
| | R473N | 1.43 | R473K | 1.42 | R473D | 1.39 | R473Y | 1.22 | R473N | 1.43 |
| 474 | | | | | | | | | | |
| 475 | | | | | | | | | | |
| 476 | I476Y | 1.71 | I476H | 1.55 | I476G | 1.48 | I476L | 1.32 | I476S | 1.28 |
| | I476F | 1.25 | I476M | 1.23 | | | | | | |
| 477 | G477S | 2.35 | G477A | 1.29 | | | | | | |
| 478 | N478G | 2.96 | N478K | 1.23 | | | | | | |
| 479 | T479V | 2.16 | | | | | | | | |
| 480 | | | | | | | | | | |
| 481 | | | | | | | | | | |
| 482 | | | | | | | | | | |
| 483 | | | | | | | | | | |
| 484 | | | | | | | | | | |
| 485 | | | | | | | | | | |
| 486 | | | | | | | | | | |
| 487 | | | | | | | | | | |
| 488 | | | | | | | | | | |
| 489 | | | | | | | | | | |
| 490 | R490Q | 3.53 | | | | | | | | |
| 491 | | | | | | | | | | |
| 492 | | | | | | | | | | |
| 493 | | | | | | | | | | |
| 494 | | | | | | | | | | |
| 495 | T495N | 1.54 | | | | | | | | |
| 496 | | | | | | | | | | |
| 497 | | | | | | | | | | |
| 498 | | | | | | | | | | |
| 499 | A499R | 1.69 | A499S | 1.56 | A499G | 1.52 | A499M | 1.5 | A499C | 1.49 |
| | A499V | 1.42 | A499P | 1.28 | A499W | 1.26 | | | | |
| 500 | | | | | | | | | | |
| 501 | | | | | | | | | | |
| 502 | I502K | 2.45 | I502V | 2.26 | I502A | 1.97 | I502T | 1.96 | I502N | 1.83 |
| | I502E | 1.83 | I502L | 1.71 | I502Q | 1.61 | I502P | 1.58 | I502H | 1.57 |
| | I502R | 1.54 | I502F | 1.48 | I502S | 1.42 | I502Y | 1.37 | | |
| 503 | | | | | | | | | | |
| 504 | | | | | | | | | | |
| 505 | | | | | | | | | | |
| 506 | | | | | | | | | | |
| 507 | | | | | | | | | | |
| 508 | | | | | | | | | | |
| 509 | V509T | 1.26 | | | | | | | | |
| 510 | | | | | | | | | | |
| 511 | | | | | | | | | | |
| 512 | N512Y | 1.75 | N512P | 1.71 | N512M | 1.42 | N512R | 1.41 | N512K | 1.34 |
| | N512G | 1.31 | N512Q | 1.26 | N512I | 1.21 | N512W | 1.21 | | |
| 513 | F513G | 1.84 | F513V | 1.71 | F513P | 1.67 | F513L | 1.56 | F513H | 1.44 |
| 514 | | | | | | | | | | |
| 515 | F515H | 2.24 | | | | | | | | |
| 516 | | | | | | | | | | |
| 517 | G517A | 2.22 | G517H | 1.58 | G517S | 1.44 | | | | |
| 518 | S518D | 3.21 | S518A | 2.55 | S518Y | 2.53 | S518K | 2.39 | S518V | 2.37 |
| | S518L | 2.36 | S518G | 2.26 | S518H | 2.25 | S518E | 2.24 | S518R | 2.18 |
| | S518T | 2.08 | S518C | 1.76 | | | | | | |
| 519 | | | | | | | | | | |
| 520 | I520V | 3.39 | I520R | 2.18 | I520Y | 2.08 | I520C | 2.05 | I520K | 1.93 |
| | I520M | 1.74 | I520E | 1.67 | I520L | 1.49 | I520F | 1.34 | I520S | 1.31 |
| | I520A | 1.25 | | | | | | | | |
| 521 | S521G | 2.71 | S521L | 2.52 | S521V | 2.47 | S521A | 2.34 | S521D | 2.09 |
| | S521I | 1.73 | S521Q | 1.56 | S521F | 1.54 | S521P | 1.52 | S521N | 1.44 |
| | S521M | 1.4 | | | | | | | | |
| 522 | | | | | | | | | | |
| 523 | | | | | | | | | | |
| 524 | | | | | | | | | | |
| 525 | | | | | | | | | | |
| 526 | T526L | 1.23 | | | | | | | | |
| 527 | | | | | | | | | | |
| 528 | | | | | | | | | | |
| 529 | | | | | | | | | | |
| 530 | | | | | | | | | | |
| 531 | | | | | | | | | | |

TABLE 4-continued

| | | | | | | | | | | |
|---|---|---|---|---|---|---|---|---|---|---|
| 532 | R532K | 2.58 | R532C | 1.98 | R532W | 1.63 | R532S | 1.59 | R532L | 1.53 |
| | R532V | 1.49 | R532H | 1.37 | R532G | 1.24 | | | | |
| 533 | | | | | | | | | | |
| 534 | N534S | 2.2 | N534Y | 1.95 | N534Q | 1.9 | N534W | 1.78 | N534E | 1.58 |
| | N534H | 1.51 | N534D | 1.49 | N534L | 1.48 | | | | |
| 535 | N535M | 2.96 | N535Q | 2.26 | N535E | 1.88 | N535F | 1.68 | N535K | 1.68 |
| | N535L | 1.48 | N535R | 1.48 | N535A | 1.43 | N535S | 1.29 | N535I | 1.23 |
| | N535D | 1.21 | | | | | | | | |
| 536 | | | | | | | | | | |
| 537 | G537W | 2.23 | G537E | 2.02 | G537F | 1.9 | G537A | 1.77 | G537K | 1.69 |
| | G537S | 1.48 | G537Q | 1.48 | G537Y | 1.43 | G537R | 1.4 | G537D | 1.33 |
| | G537V | 1.33 | G537N | 1.3 | G537H | 1.3 | G537T | 1.25 | | |
| 538 | N538G | 2.22 | N538T | 2 | N538S | 1.95 | N538V | 1.57 | N538W | 1.5 |
| | N538L | 1.47 | N538H | 1.43 | N538Q | 1.42 | N538I | 1.41 | N538D | 1.32 |
| | N538V | 1.57 | N538W | 1.5 | N538L | 1.47 | N538Q | 1.42 | N538I | 1.4 |
| | N538E | 1.3 | N538P | 1.25 | N538A | 1.23 | N538M | 1.2 | | |
| 539 | | | | | | | | | | |
| 540 | | | | | | | | | | |
| 541 | Q541Y | 2.48 | Q541W | 1.35 | Q541F | 1.27 | | | | |
| 542 | | | | | | | | | | |
| 543 | | | | | | | | | | |
| 544 | | | | | | | | | | |
| 545 | Y545F | 1.3 | | | | | | | | |
| 546 | | | | | | | | | | |
| 547 | E547A | 1.88 | E547S | 1.82 | E547G | 1.72 | E547I | 1.25 | E547M | 1.24 |
| | E547Q | 1.21 | | | | | | | | |
| 548 | | | | | | | | | | |
| 549 | | | | | | | | | | |
| 550 | | | | | | | | | | |
| 551 | Q551C | 2.51 | Q551R | 2.17 | Q551A | 1.98 | Q551S | 1.76 | Q551D | 1.54 |
| | Q551Y | 1.34 | | | | | | | | |
| 552 | F552T | 1.72 | F552V | 1.69 | F552W | 1.57 | | | | |
| 553 | I553Q | 2.41 | I553D | 2.15 | I553R | 1.96 | I553E | 1.83 | I553A | 1.78 |
| | I553F | 1.71 | I553L | 1.69 | I553P | 1.65 | I553G | 1.5 | I553W | 1.49 |
| | I553S | 1.49 | I553T | 1.47 | | | | | | |
| 554 | S554K | 1.87 | S554R | 1.56 | S554D | 1.45 | S554H | 1.43 | S554N | 1.25 |
| | S554G | 1.22 | | | | | | | | |
| 555 | T555V | 2.13 | T555M | 1.64 | T555I | 1.32 | T555W | 1.3 | | |
| 556 | S556A | 2.65 | S556W | 2.25 | S556G | 2.05 | S556D | 1.6 | S556C | 1.41 |
| | S556P | 1.27 | | | | | | | | |
| 557 | T557I | 1.75 | T557R | 1.61 | T557G | 1.55 | T557S | 1.39 | T557Q | 1.38 |
| | T557M | 1.31 | T557V | 1.28 | T557A | 1.27 | T557C | 1.26 | | |
| 558 | R558Y | 2.16 | R558K | 2.01 | R558T | 1.95 | R558L | 1.83 | R558N | 1.79 |
| | R558G | 1.75 | R558S | 1.59 | R558E | 1.53 | R558I | 1.43 | R558D | 1.4 |
| | R558F | 1.37 | R558P | 1.27 | R558V | 1.26 | R558M | 1.23 | R558H | 1.22 |
| 559 | Y559W | 1.26 | | | | | | | | |
| 560 | | | | | | | | | | |
| 561 | | | | | | | | | | |
| 562 | | | | | | | | | | |
| 563 | V563N | 4.65 | V563L | 2.56 | V563I | 2.1 | V563A | 1.39 | | |
| 564 | R564H | 4.11 | R564V | 3.28 | R564W | 3.03 | R564I | 3.02 | R564K | 2.71 |
| | R564C | 1.79 | R564S | 1.42 | R564A | 1.36 | | | | |
| 565 | Y565F | 3.4 | | | | | | | | |
| 566 | | | | | | | | | | |
| 567 | | | | | | | | | | |
| 568 | V568C | 2.44 | V568A | 2.31 | V568E | 1.81 | V568F | 1.8 | V568R | 1.65 |
| | V568G | 1.54 | V568L | 1.52 | V568S | 1.5 | V568W | 1.39 | V568N | 1.31 |
| 569 | T569I | 1.75 | T569M | 1.67 | T569G | 1.29 | T569S | 1.2 | | |
| 570 | P570M | 2.08 | P570F | 1.6 | P570W | 1.45 | P570T | 1.38 | | |
| 571 | I571G | 4.18 | I571V | 3.13 | I571T | 3.07 | I571C | 2.72 | I571L | 2.2 |
| 572 | Q572H | 2.51 | Q572P | 2.29 | Q572R | 2.03 | Q5721 | 1.96 | Q572K | 1.69 |
| | Q572F | 1.65 | Q572S | 1.54 | Q572A | 1.38 | Q572V | 1.35 | Q572W | 1.3 |
| | Q572M | 1.28 | | | | | | | | |
| 573 | L573A | 3.14 | L573T | 3.09 | L573G | 2.12 | | | | |
| 574 | S574R | 1.22 | | | | | | | | |
| 575 | | | | | | | | | | |
| 576 | | | | | | | | | | |
| 577 | W577R | 3.24 | W577F | 2.01 | W577K | 1.74 | W577M | 1.72 | W577V | 1.63 |
| | W577A | 1.56 | W577T | 1.47 | W577H | 1.33 | W577G | 1.28 | W577I | 1.24 |
| 578 | | | | | | | | | | |
| 579 | | | | | | | | | | |
| 580 | | | | | | | | | | |
| 581 | N581S | 1.83 | N581K | 1.57 | | | | | | |
| 582 | I582V | 1.69 | | | | | | | | |
| 583 | F583S | 2.8 | | | | | | | | |
| 584 | S584R | 1.21 | | | | | | | | |
| 585 | S585R | 3.33 | S585T | 2.53 | S585K | 2.17 | S585H | 2.14 | S5850 | 2.04 |
| | S585L | 1.86 | S585W | 1.69 | S585N | 1.59 | S585M | 1.3 | S585F | 1.3 |
| | S585I | 1.27 | | | | | | | | |

TABLE 4-continued

| | | | | | | | | | | |
|---|---|---|---|---|---|---|---|---|---|---|
| 586 | I586M | 4.11 | I586Y | 2.77 | I586P | 2.19 | I586A | 1.97 | I586S | 1.84 |
| | I586K | 1.83 | I586R | 1.77 | I586F | 1.73 | I586G | 1.65 | I586V | 1.6 |
| | I586Q | 1.48 | I586N | 1.41 | I586L | 1.35 | I586W | 1.32 | I586T | 1.26 |
| 587 | V587H | 2.82 | V587C | 2.28 | V587N | 1.97 | V587S | 1.85 | V587D | 1.76 |
| | V587R | 1.7 | V587A | 1.7 | V587T | 1.65 | V587K | 1.57 | V587E | 1.43 |
| | V587W | 1.4 | V587L | 1.4 | V587Y | 1.4 | V587F | 1.37 | | |
| 588 | | | | | | | | | | |
| 589 | | | | | | | | | | |
| 590 | T590A | 1.8 | T590D | 1.56 | T590F | 1.54 | T590S | 1.3 | T590G | 1.26 |
| 591 | A591H | 2.82 | A591V | 2.28 | A591N | 1.97 | A591T | 1.85 | A591D | 1.76 |
| | A591R | 1.7 | A591S | 1.7 | A591K | 1.65 | A591C | 1.65 | A591E | 1.43 |
| | A591W | 1.4 | A591L | 1.4 | A591Y | 1.4 | A591F | 1.37 | A591P | 1.26 |
| | A591Q | 1.2 | | | | | | | | |
| 592 | T592Q | 2.9 | T592M | 2.39 | T592A | 2.02 | T592Y | 1.82 | T592N | 1.8 |
| | T592K | 1.78 | T592P | 1.7 | T592S | 1.63 | T592D | 1.57 | T592I | 1.41 |
| | T592G | 1.33 | T592F | 1.23 | T592V | 1.21 | T592W | 1.21 | | |
| 593 | S593Y | 1.66 | S593G | 1.44 | S593R | 1.24 | S593V | 1.24 | | |
| 594 | | | | | | | | | | |
| 595 | D595R | 1.83 | D595S | 1.77 | D595G | 1.74 | D595H | 1.72 | D595N | 1.57 |
| | D595V | 1.55 | D595F | 1.54 | D595K | 1.52 | D595T | 1.5 | D595Y | 1.4 |
| | D595I | 1.36 | D595M | 1.3 | D595A | 1.25 | D595P | 1.21 | | |
| 596 | N596V | 2.7 | N596T | 2.45 | N596I | 2.15 | N596S | 2.14 | N596G | 1.97 |
| | N596L | 1.7 | N596W | 1.54 | N596Y | 1.33 | N596H | 1.3 | N596P | 1.3 |
| | N596D | 1.29 | | | | | | | | |
| 597 | | | | | | | | | | |
| 598 | Q598V | 1.5 | Q598G | 1.27 | Q598D | 1.22 | Q598I | 1.21 | | |
| 599 | S599C | 1.72 | S599Q | 1.72 | S599L | 1.6 | S599Y | 1.48 | S599T | 1.47 |
| | S599V | 1.44 | S599A | 1.27 | S599P | 1.24 | | | | |
| 600 | | | | | | | | | | |
| 601 | N601Y | 1.47 | N601F | 1.33 | N601V | 1.33 | N601G | 1.25 | N601M | 1.24 |
| | N601E | 1.22 | | | | | | | | |
| 602 | F602M | 2.53 | | | | | | | | |
| 603 | G603M | 2.12 | G603A | 2.04 | G603Y | 2.04 | G603R | 1.88 | G603S | 1.75 |
| | G603L | 1.57 | G603W | 1.46 | G603D | 1.3 | G603T | 1.23 | | |
| 604 | | | | | | | | | | |
| 605 | F605S | 2.2 | F605W | 1.91 | F605R | 1.89 | F605M | 1.85 | F605A | 1.63 |
| | F605I | 1.56 | F605C | 1.52 | F605V | 1.49 | F605K | 1.45 | F605I | 1.56 |
| | F605D | 1.39 | F605Y | 1.38 | F605N | 1.38 | F605Q | 1.35 | F605G | 1.34 |
| | F605E | 1.27 | F605P | 1.25 | | | | | | |
| 606 | E606R | 3.03 | E606H | 2.38 | E606K | 2.27 | E606F | 2.19 | E606Q | 2.12 |
| | E606W | 1.83 | E606G | 1.78 | E606Y | 1.76 | E606M | 1.74 | E606T | 1.64 |
| | E606A | 1.51 | E606I | 1.37 | E606L | 1.34 | E606N | 1.28 | | |
| 607 | S607R | 2.59 | S607C | 1.58 | S607T | 1.58 | S607I | 1.55 | S607Q | 1.48 |
| | S607G | 1.34 | S607D | 1.31 | S607E | 1.27 | S607V | 1.26 | | |
| 608 | T608R | 2.35 | T608S | 2.24 | T608V | 2.2 | T608L | 1.88 | T608F | 1.7 |
| | T608G | 1.5 | T608Y | 1.47 | T608A | 1.33 | T608K | 1.32 | T608W | 1.23 |
| | T608Q | 1.22 | | | | | | | | |
| 609 | N609G | 2.52 | N609P | 2.4 | N609L | 2.23 | N609R | 2.2 | N609S | 1.93 |
| | N609V | 1.91 | N609F | 1.46 | N609I | 1.31 | | | | |
| 610 | A610G | 2.13 | A610F | 1.45 | A610P | 1.29 | A610L | 1.28 | | |
| 611 | F611L | 2.19 | F611K | 1.58 | F611G | 1.48 | F611W | 1.44 | F611V | 1.38 |
| 612 | T612F | 2.32 | T612H | 2.07 | T612G | 1.36 | T612E | 1.35 | T612N | 1.31 |
| | T612D | 1.23 | T612P | 1.21 | | | | | | |
| 613 | S613M | 2.85 | S613T | 1.98 | S613W | 1.58 | S613V | 1.54 | S613N | 1.5 |
| | S613R | 1.47 | S613Y | 1.33 | S613G | 1.25 | | | | |
| 614 | A614M | 2.07 | A614S | 2.01 | A614L | 1.73 | A614H | 1.66 | A614V | 1.66 |
| | A614R | 1.64 | A614G | 1.55 | A614Y | 1.35 | A614D | 1.2 | A614R | 1.64 |
| 615 | | | | | | | | | | |
| 616 | | | | | | | | | | |
| 617 | N617V | 2.25 | N617Q | 1.96 | N617G | 1.96 | N617K | 1.76 | N617M | 1.57 |
| | N617R | 1.56 | N617C | 1.25 | N617L | 1.23 | | | | |
| 618 | V618N | 1.82 | V618H | 1.51 | V618W | 1.44 | V618R | 1.4 | V618G | 1.31 |
| | V618L | 1.3 | V618D | 1.29 | V618T | 1.24 | | | | |
| 619 | | | | | | | | | | |
| 620 | | | | | | | | | | |
| 621 | | | | | | | | | | |
| 622 | | | | | | | | | | |
| 623 | | | | | | | | | | |
| 624 | F624A | 1.27 | F624M | | | | | | | |
| 625 | | | | | | | | | | |
| 626 | E626K | 3.16 | E626G | 2.62 | E626R | 2.01 | E626T | 1.84 | E626H | 1.81 |
| | E626A | 1.71 | E626N | 1.45 | E626I | 1.44 | E626Y | 1.43 | E626Q | 1.37 |
| | E626P | 1.31 | E626S | 1.29 | | | | | | |
| 627 | | | | | | | | | | |
| 628 | A628V | 2.38 | A628F | 2.05 | A628K | 1.86 | A628Q | 1.81 | A628W | 1.62 |
| | A628S | 1.59 | A628R | 1.49 | A628G | 1.49 | A628L | 1.42 | A628I | 1.21 |
| | A628D | 1.21 | | | | | | | | |
| 629 | G629M | 1.57 | G629Q | 1.42 | G629R | 1.4 | G629P | 1.36 | G629A | 1.32 |
| | G629S | 1.28 | G629T | 1.28 | G629E | 1.23 | | | | |

TABLE 4-continued

| | | | | | | | | | | |
|---|---|---|---|---|---|---|---|---|---|---|
| 630 | V630A | 1.9 | V630C | 1.62 | | | | | | |
| 631 | | | | | | | | | | |
| 632 | | | | | | | | | | |
| 633 | | | | | | | | | | |
| 634 | | | | | | | | | | |
| 635 | | | | | | | | | | |
| 636 | | | | | | | | | | |
| 637 | | | | | | | | | | |
| 638 | | | | | | | | | | |
| 639 | | | | | | | | | | |
| 640 | | | | | | | | | | |
| 641 | T641P | 3.01 | T641H | 2.65 | T641A | 2.45 | T641L | 2.43 | T641Q | 2.31 |
| | T641Y | 2.21 | T641E | 2.1 | T641I | 1.96 | T641S | 1.91 | T641V | 1.82 |
| | T641D | 1.57 | T641G | 1.21 | | | | | | |
| 642 | | | | | | | | | | |
| 643 | T643L | 2.72 | T643A | 2.09 | T643Q | 2.04 | T643H | 1.94 | T643S | 1.58 |
| | T643D | 1.53 | T643M | 1.51 | T643C | 1.38 | T643R | 1.26 | | |
| 644 | | | | | | | | | | |
| 645 | E645T | 2.28 | E645M | 2.26 | E645L | 1.8 | E645Y | 1.77 | E645A | 1.73 |
| | E645N | 1.71 | E645V | 1.67 | E645P | 1.65 | E645I | 1.61 | E645W | 1.48 |
| | E645C | 1.28 | E645S | 1.21 | | | | | | |
| 646 | A646S | 1.96 | A646Y | 1.95 | A646D | 1.78 | A646E | 1.65 | A646M | 1.57 |
| | A646F | 1.51 | A646H | 1.46 | A646V | 1.41 | A646W | 1.37 | A646I | 1.37 |
| | A646C | 1.27 | A646C | 1.27 | | | | | | |
| 647 | | | | | | | | | | |
| 648 | | | | | | | | | | |
| 649 | | | | | | | | | | |
| 650 | | | | | | | | | | |
| 651 | | | | | | | | | | |

TABLE 5

| MP258 position | MP258 a.a. | Backbone | Variant | FAE | Variant | FAE | Variant | FAE | Variant | FAE |
|---|---|---|---|---|---|---|---|---|---|---|
| 50 | L | B45 | L50W | 1.06 | L50M | 1.05 | L50E | 0.98 | L50T | 0.89 |
| 53 | A | B45 | A53N | 1.19 | A53I | 1.15 | A53W | 1.13 | A53L | 1.08 |
| 54 | S | B45 | S54M | 1.16 | S54Y | 1.13 | S54H | 1.11 | S54L | 1.08 |
| | | | S54D | 0.87 | S54W | 0.57 | | | | |
| 57 | Q | B45 | Q57C | 1.19 | Q57E | 1.14 | Q57S | 1.13 | Q57W | 1.13 |
| 65 | R | B45 | R65M | 1.19 | R65T | 1.15 | R65K | 1.04 | R65L | 0.99 |
| | | | R65W | 0.50 | | | | | | |
| 67 | L | B45 | L67P | 1.12 | L67Q | 1.11 | L67W | 0.54 | L67A | 0.52 |
| | | | L67S | 0.49 | L67C | 0.48 | L67D | 0.48 | L67V | 0.46 |
| 68 | G | B45 | G68D | 1.16 | G68K | 1.08 | G68M | 0.75 | G68L | 0.62 |
| | | | G68P | 0.48 | G68W | 0.37 | | | | |
| 70 | L | B45 | L70S | 1.16 | L70T | 1.11 | L70Q | 1.10 | L70A | 0.98 |
| | | | L70Y | 0.92 | L70V | 0.92 | L70P | 0.90 | L70R | 0.87 |
| 71 | G | B45 | G71D | 1.12 | G71E | 1.11 | G71F | 1.10 | G71N | 1.00 |
| | | | G71Q | 0.79 | G71C | 0.75 | G71V | 0.72 | G71L | 0.61 |
| 72 | V | B45 | V72S | 0.85 | V72R | 0.84 | V72L | 0.81 | V72F | 0.79 |
| | | | V72A | 0.66 | V72W | 0.64 | V72C | 0.64 | V72K | 0.55 |
| 73 | P | B45 | P73F | 1.14 | P73R | 1.11 | P73V | 0.80 | P73A | 0.33 |
| 74 | F | B45 | F74N | 1.19 | F74T | 1.15 | F74W | 1.04 | F74L | 1.00 |
| | | | F74C | 0.78 | F74M | 0.37 | | | | |
| 75 | A | B45 | A75D | 1.03 | A75F | 0.94 | A75R | 0.90 | A75V | 0.83 |
| 76 | G | B45 | G76K | 1.15 | G76W | 0.94 | G76Q | 0.91 | G76H | 0.54 |
| 77 | Q | B45 | Q77V | 1.15 | Q77F | 1.13 | Q77Y | 1.08 | Q77R | 0.96 |
| 79 | A | B45 | A79E | 0.98 | A79G | 0.71 | A79F | 0.57 | | |
| 80 | S | B45 | S80I | 1.20 | S80T | 0.54 | | | | |
| 83 | S | B45 | S83T | 1.19 | S83V | 0.60 | S83I | 0.60 | S83P | 0.58 |
| 87 | G | B45 | G87Y | 1.10 | G87S | 1.05 | G87F | 1.01 | G87L | 0.97 |
| 91 | P | B45 | P91I | 1.17 | P91Q | 1.14 | P91W | 1.13 | P91G | 1.05 |
| | | | P91K | 0.54 | P91C | 0.53 | P91H | 0.53 | P91A | 0.50 |
| 92 | S | B45 | S92K | 1.03 | S92W | 0.85 | S92R | 0.76 | S92M | 0.70 |
| 93 | G | B45 | G93E | 0.93 | G93N | 0.90 | G93V | 0.86 | G93L | 0.86 |
| | | | G93W | 0.74 | G93C | 0.72 | G93R | 0.69 | G93Y | 0.53 |
| 94 | R | B45 | R94E | 0.99 | R94K | 0.95 | R94V | 0.95 | R94G | 0.92 |
| | | | R94M | 0.70 | | | | | | |
| 95 | D | B45 | D95W | 1.10 | D95T | 0.94 | D95L | 0.87 | D95R | 0.83 |
| 106 | Q | B45 | Q106P | 1.08 | Q106L | 1.08 | Q106N | 0.98 | Q106Y | 0.96 |
| 108 | V | B45 | V108G | 1.14 | V108K | 1.14 | V108S | 1.06 | V108C | 1.04 |
| 109 | R | 258 | R109K | 1.07 | R109A | 1.05 | R109Q | 1.02 | R109W | 0.97 |
| | | | R109T | 0.85 | R109I | 0.84 | R109D | 0.83 | R109F | 0.79 |
| 110 | Q | 258 | Q110K | 1.19 | Q110D | 1.18 | Q110I | 1.18 | Q110M | 1.14 |
| | | | Q110C | 0.84 | Q110A | 0.77 | Q110W | 0.73 | Q110G | 0.70 |

TABLE 5-continued

| | | | | | | | | | | |
|---|---|---|---|---|---|---|---|---|---|---|
| 111 | Q | 258 | Q111V | 1.14 | Q111W | 1.08 | Q111N | 1.01 | Q111F | 1.01 |
| | | | Q111D | 0.25 | | | | | | |
| 112 | I | B45 | I112K | 0.93 | I112G | 0.84 | I112M | 0.64 | I112C | 0.57 |
| | | | I112S | 0.27 | I112F | 0.27 | I112D | 0.26 | I112R | 0.24 |
| 113 | T | B45 | T113W | 0.98 | T113F | 0.82 | T113C | 0.75 | T113P | 0.73 |
| 114 | E | 258 | E114Q | 1.15 | E114W | 1.13 | E114C | 0.79 | E114R | 0.41 |
| 115 | N | B45 | N115I | 0.96 | N115Y | 0.93 | N115M | 0.91 | N115S | 0.88 |
| | | | N115W | 0.57 | N115K | 0.51 | N115R | 0.35 | N115H | 0.24 |
| 118 | N | B45 | N118W | 1.05 | N118K | 0.99 | N118Y | 0.92 | N118R | 0.84 |
| 119 | T | B45 | T119Y | 1.00 | T119F | 0.95 | T119P | 0.94 | T119W | 0.84 |
| 122 | A | B45 | A122E | 1.11 | A122L | 1.06 | A122S | 1.06 | A122W | 1.04 |
| 123 | R | B45 | R123H | 0.73 | R123A | 0.73 | R123Y | 0.72 | R123P | 0.63 |
| | | | R123G | 0.55 | R123N | 0.49 | R123S | 0.49 | R123M | 0.46 |
| | | | R123I | 0.24 | | | | | | |
| 125 | Q | B45 | Q125V | 1.14 | Q125I | 0.96 | Q125K | 0.63 | | |
| 129 | A | B45 | A129E | 1.08 | A129Y | 1.08 | A129R | 1.07 | A129Q | 1.06 |
| | | | A129F | 0.83 | A129I | 0.83 | | | | |
| 132 | R | B45 | R132Y | 0.98 | R132A | 0.96 | R132V | 0.96 | R132M | 0.89 |
| | | | R132F | 0.68 | R132D | 0.66 | R132G | 0.65 | R132N | 0.59 |
| 133 | A | B45 | A133D | 0.87 | A133V | 0.85 | A133S | 0.63 | A133T | 0.54 |
| | | | A133Q | 0.32 | A133F | 0.32 | A133E | 0.29 | A133L | 0.26 |
| 136 | Q | B45 | Q136G | 1.06 | Q136W | 1.03 | Q136D | 0.96 | Q136S | 0.92 |
| 140 | D | B45 | D140G | 0.92 | D140Y | 0.73 | D140S | 0.46 | D140T | 0.40 |
| | | | D140R | 0.24 | D140A | 0.22 | D140L | 0.22 | | |
| 142 | L | B45 | L142H | 1.03 | L142Q | 0.86 | L142S | 0.78 | L142R | 0.73 |
| | | | L142W | 0.58 | L142D | 0.52 | L142C | 0.47 | L142E | 0.43 |
| 143 | E | B45 | E143K | 0.98 | E143D | 0.98 | E143V | 0.95 | | |
| 144 | N | B45 | N144F | 1.13 | N144P | 1.09 | N144S | 1.07 | N144Y | 0.94 |
| 145 | R | B45 | R145F | 1.16 | R145Q | 1.02 | R145V | 0.99 | R145T | 0.94 |
| 146 | D | B45 | D146E | 1.16 | D146A | 1.15 | D146P | 1.14 | D146S | 1.11 |
| | | | D146F | 0.95 | D146G | 0.83 | D146M | 0.80 | | |
| 147 | D | B45 | N147T | 1.02 | N147L | 1.01 | N147Y | 0.63 | N147K | 0.62 |
| | | | N147Q | 0.49 | N147G | 0.45 | | | | |
| 148 | A | B45 | A148G | 1.18 | A148Q | 1.00 | A148M | 0.95 | A148R | 0.90 |
| | | | A148E | 0.76 | | | | | | |
| 149 | R | B45 | R149F | 1.00 | R149Q | 0.99 | R149H | 0.94 | R149W | 0.94 |
| 151 | R | B45 | R151S | 1.06 | R151V | 0.90 | R151K | 0.72 | R151M | 0.69 |
| | | | B151A | 0.50 | B151I | 0.42 | B151N | 0.42 | B151Y | 0.39 |
| | | | B151F | 0.27 | | | | | | |
| 152 | S | B45 | S152K | 1.07 | S152M | 0.98 | S152C | 0.95 | S152Q | 0.89 |
| | | | S152P | 0.47 | S152Y | 0.44 | S152F | 0.41 | S152W | 0.37 |
| 159 | I | B45 | I159G | 0.92 | I159D | 0.78 | I159S | 0.59 | I159T | 0.32 |
| | | | I159P | 0.27 | I159F | 0.26 | I159W | 0.26 | I159E | 0.26 |
| 160 | A | B45 | A160F | 1.12 | A160E | 0.92 | A160P | 0.89 | A160G | 0.85 |
| 163 | L | B45 | L163F | 0.80 | L163Q | 0.72 | L163V | 0.60 | L163M | 0.56 |
| | | | L163E | 0.24 | L163G | 0.24 | L163S | 0.24 | L163B | 0.24 |
| 164 | D | B45 | D164A | 0.90 | D164S | 0.88 | D164G | 0.81 | D164M | 0.81 |
| | | | D164V | 0.54 | D164F | 0.51 | D164T | 0.49 | D164C | 0.49 |
| 166 | L | B45 | L166Q | 1.07 | L166D | 1.01 | L166M | 0.98 | L166P | 0.98 |
| | | | L166S | 0.95 | L166N | 0.92 | L166Y | 0.73 | L166F | 0.62 |
| 167 | N | B45 | N167B | 1.15 | N167G | 1.13 | N167S | 1.04 | N167C | 0.98 |
| | | | N167I | 0.67 | | | | | | |
| 173 | A | B45 | A173N | 1.12 | A173P | 0.97 | A173G | 0.92 | A173V | 0.88 |
| 174 | I | B45 | I174V | 0.91 | I174Q | 0.89 | I174H | 0.77 | I174K | 0.73 |
| | | | I174S | 0.56 | I174B | 0.33 | I174D | 0.32 | | |
| 177 | Q | B45 | Q177F | 1.10 | Q177N | 1.06 | Q177H | 1.05 | Q177Y | 1.01 |
| | | | Q177L | 0.89 | Q177D | 0.78 | Q177G | 0.74 | Q177K | 0.40 |
| 178 | Q | B45 | Q178E | 0.98 | Q178H | 0.92 | Q178W | 0.83 | Q178G | 0.78 |
| | | | Q178F | 0.53 | Q178Y | 0.50 | Q178L | 0.37 | Q178D | 0.31 |
| 179 | V | B45 | V179C | 1.01 | V179A | 0.86 | V179N | 0.80 | V179M | 0.80 |
| | | | V179B | 0.61 | V179F | 0.44 | V179W | 0.41 | V179D | 0.37 |
| 180 | P | B45 | P180C | 1.05 | P180K | 1.00 | P180T | 0.94 | P180V | 0.88 |
| | | | P180Y | 0.53 | P180W | 0.38 | P180D | 0.28 | | |
| 201 | L | B45 | L201C | 0.79 | L201N | 0.67 | L201A | 0.64 | L201P | 0.64 |
| | | | L201H | 0.55 | L201B | 0.54 | L201D | 0.52 | | |
| 206 | F | B45 | F206V | 1.00 | F206C | 0.86 | F206E | 0.76 | F206A | 0.75 |
| | | | F206S | 0.53 | F206D | 0.51 | F206K | 0.49 | F206N | 0.47 |
| 208 | L | B45 | L208F | 0.91 | L208I | 0.79 | L208Y | 0.71 | L208S | 0.71 |
| | | | L208Q | 0.44 | L208W | 0.44 | L208C | 0.39 | L208G | 0.37 |
| | | | L208D | 0.29 | | | | | | |
| 209 | T | B45 | T209S | 0.94 | T209Q | 0.88 | T209I | 0.75 | T209G | 0.68 |
| 210 | S | B45 | S210G | 1.13 | | | | | | |
| 211 | Q | B45 | Q211V | 1.17 | Q211K | 1.15 | Q211H | 1.10 | Q211E | 1.08 |
| | | | Q211S | 0.94 | Q211D | 0.54 | | | | |
| 212 | E | B45 | E212F | 1.05 | E212A | 0.86 | E212V | 0.79 | E212N | 0.78 |
| | | | E212L | 0.64 | E212Q | 0.63 | E212K | 0.61 | E212S | 0.59 |
| 213 | I | B45 | I213C | 1.11 | I213S | 0.98 | I213B | 0.94 | I213E | 0.91 |
| | | | I213P | 0.59 | I213H | 0.58 | I213A | 0.49 | | |
| 214 | Q | B21 | Q214S | 1.12 | Q214F | 1.05 | Q214Y | 1.01 | Q214D | 0.76 |
| | | | Q214T | 0.53 | Q214H | 0.52 | Q214L | 0.43 | Q214G | 0.40 |

TABLE 5-continued

| | | | | | | | | | | |
|---|---|---|---|---|---|---|---|---|---|---|
| 215 | R | B45 | R215V | 0.95 | R215A | 0.94 | R215I | 0.85 | R215N | 0.83 |
| | | | R215S | 0.67 | R215G | 0.66 | R215T | 0.66 | R215P | 0.59 |
| 218 | E | B45 | E218G | 1.18 | E218L | 1.10 | E218C | 1.10 | E218K | 1.08 |
| 219 | R | B21 | R219Y | 1.15 | R219E | 1.13 | R219W | 1.08 | R219Q | 0.71 |
| | | | R219T | 0.05 | R219M | 0.03 | R219L | 0.01 | R219A | 0.01 |
| 221 | A | B45 | A221S | 1.16 | A221C | 1.03 | A221E | 0.91 | A221M | 0.83 |
| 222 | E | B45 | E222C | 1.13 | E222S | 1.11 | E222L | 1.10 | E222F | 1.10 |
| | | | E222R | 0.84 | E222P | 0.59 | | | | |
| 225 | R | B45 | R225W | 1.19 | R225S | 1.17 | R225E | 1.14 | R225A | 1.02 |
| 226 | E | B45 | E226T | 1.18 | E226F | 1.17 | E226G | 1.15 | E226W | 1.13 |
| | | | E226H | 0.96 | E226Q | 0.96 | | | | |
| 230 | Y | B45 | Y230F | 1.19 | Y230M | 1.15 | Y230R | 1.01 | Y230C | 0.93 |
| | | | Y230I | 0.63 | Y230V | 0.57 | Y230P | 0.53 | | |
| 233 | R | B45 | R233E | 1.19 | R233V | 1.10 | R233F | 1.09 | R233N | 1.05 |
| | | | R233H | 0.50 | | | | | | |
| 234 | W | B45 | W234G | 1.06 | W234K | 0.93 | W234T | 0.63 | W234E | 0.60 |
| 236 | N | B45 | N236Q | 1.18 | N236D | 1.16 | N236R | 1.08 | N236A | 1.04 |
| | | | N236M | 0.54 | N236C | 0.53 | N236W | 0.42 | | |
| 240 | N | B45 | N240I | 1.18 | N240D | 1.17 | N240V | 1.16 | N240E | 0.57 |
| 241 | N | B45 | N241G | 1.17 | N241F | 1.16 | N241Q | 1.15 | N241E | 1.13 |
| | | | N241R | 0.49 | | | | | | |
| 242 | L | B45 | L242M | 0.95 | L242I | 0.93 | L242C | 0.83 | L242R | 0.75 |
| | | | L242F | 0.49 | L242H | 0.46 | L242W | 0.40 | L242G | 0.39 |
| 243 | R | B45 | R243L | 0.98 | R243A | 0.86 | R243Y | 0.82 | R243F | 0.76 |
| | | | R243P | 0.46 | | | | | | |
| 244 | G | B45 | G244C | 0.94 | G244L | 0.72 | G244A | 0.71 | G244Q | 0.60 |
| | | | G244Y | 0.53 | G244E | 0.53 | G244H | 0.47 | G244M | 0.47 |
| | | | G244I | 0.26 | | | | | | |
| 245 | T | B45 | T245P | 0.96 | T245L | 0.82 | T245C | 0.71 | | |
| 246 | N | B45 | N246A | 0.85 | N246K | 0.84 | N246P | 0.79 | N246E | 0.78 |
| | | | N246Y | 0.60 | N246V | 0.60 | N246I | 0.58 | | |
| 247 | A | B45 | A247C | 0.52 | A247N | 0.52 | A247L | 0.41 | A247D | 0.41 |
| | | | A247Y | 0.30 | A247M | 0.28 | A247K | 0.28 | A247H | 0.25 |
| 248 | E | B45 | E248I | 1.11 | E248W | 1.06 | E248H | 1.01 | E248C | 0.82 |
| 252 | R | B45 | R252L | 1.09 | R252Y | 1.06 | R252K | 1.06 | R252G | 1.05 |
| | | | R252V | 0.92 | R252D | 0.90 | R252E | 0.79 | R252L | 0.76 |
| 277 | R | B45 | R277H | 1.13 | R277N | 1.07 | R277C | 0.95 | R277E | 0.88 |
| | | | R277Y | 0.82 | R277D | 0.70 | R277A | 0.69 | R277I | 0.55 |
| 280 | P | B45 | P280Q | 1.18 | P280Y | 1.08 | P280V | 0.98 | P280R | 0.90 |
| | | | P280G | 0.62 | P280A | 0.58 | P280S | 0.54 | P280D | 0.50 |
| 281 | I | B45 | I281T | 1.15 | I281N | 1.14 | I281Y | 1.14 | I281C | 1.07 |
| 303 | S | 258 | S303A | 1.09 | S303M | 0.95 | S303L | 0.70 | S303Y | 0.66 |
| | | | S303F | 0.56 | S303C | 0.43 | S303Q | 0.39 | S303V | 0.37 |
| | | | S303R | 0.03 | | | | | | |
| 304 | G | 258 | G304N | 0.22 | G304C | 0.02 | G304S | 0.01 | G304A | 0.01 |
| | | | G304E | 0.01 | G304Q | 0.01 | G304K | 0.01 | G304P | 0.01 |
| | | | G304D | 0.01 | G304M | 0.00 | G304Y | 0.00 | | |
| 305 | F | 258 | F305A | 0.07 | F305Q | 0.03 | F305N | 0.03 | F305M | 0.02 |
| | | | F305V | 0.01 | F305K | 0.01 | F305E | 0.00 | F305D | 0.00 |
| | | | F305H | 0.00 | F305P | 0.00 | F305Y | 0.00 | | |
| 306 | A | 258 | A306Q | 1.14 | A306K | 0.96 | A306N | 0.93 | A306S | 0.87 |
| | | | A306W | 0.44 | A306L | 0.33 | A306F | 0.30 | A306I | 0.30 |
| | | | A306E | 0.02 | A306Y | 0.00 | | | | |
| 308 | T | 258 | T308S | 0.63 | T308A | 0.03 | T308G | 0.02 | T308K | 0.02 |
| | | | T308N | 0.01 | T308E | 0.01 | T308R | 0.01 | T308D | 0.01 |
| | | | T308Y | 0.01 | T308W | 0.01 | T308H | 0.00 | | |
| 360 | R | B21 | R360K | 0.97 | R360A | 0.94 | R360G | 0.66 | R360H | 0.63 |
| 362 | E | B21 | N362Q | 1.20 | N362M | 1.16 | N362C | 0.95 | N362T | 0.88 |
| 364 | R | B21 | R364G | 1.02 | R364S | 0.89 | R364A | 0.39 | R364K | 0.38 |
| 367 | R | B21 | G367S | 1.09 | G367M | 0.97 | G367C | 0.53 | G367F | 0.38 |
| 406 | L | 258 | L406I | 0.76 | L406W | 0.53 | L406A | 0.39 | L406F | 0.31 |
| | | | L406N | 0.23 | L406K | 0.13 | L406T | 0.05 | L406S | 0.03 |
| | | | L406E | 0.01 | | | | | | |
| 407 | L | 258 | L407E | 1.13 | L407D | 1.00 | L407V | 0.66 | L407C | 0.56 |
| | | | L407N | 0.20 | L407M | 0.17 | L407H | 0.11 | L407S | 0.10 |
| 408 | T | 258 | T408A | 0.96 | T408Y | 0.54 | T408S | 0.48 | T408V | 0.47 |
| | | | T408R | 0.26 | T408H | 0.25 | T408K | 0.25 | T408F | 0.24 |
| | | | T408G | 0.08 | T408E | 0.02 | | | | |
| 409 | T | 258 | T409Q | 0.53 | T409M | 0.30 | T409A | 0.26 | T409I | 0.21 |
| | | | T409H | 0.11 | T409W | 0.11 | T409E | 0.10 | T409R | 0.10 |
| | | | T409D | 0.01 | T409P | 0.01 | T409G | 0.01 | | |
| 411 | V | 258 | V411I | 0.82 | V411M | 0.52 | V411L | 0.51 | V411C | 0.32 |
| | | | V411H | 0.12 | V411W | 0.11 | V411A | 0.10 | V411F | 0.09 |
| | | | V411Y | 0.02 | V411D | 0.01 | V411P | 0.01 | | |
| 418 | R | B21 | R418S | 1.13 | R418A | 1.11 | R418L | 1.09 | R418H | 0.91 |
| | | | R418Y | 0.76 | R418M | 0.69 | R418E | 0.63 | R418G | 0.58 |
| | | | R418P | 0.14 | | | | | | |
| 420 | N | B21 | N420D | 1.11 | N420Y | 1.10 | N420E | 1.04 | N420P | 1.00 |
| | | | N420V | 0.81 | N420M | 0.74 | N420K | 0.71 | N420T | 0.68 |
| | | | N420I | 0.60 | N420C | 0.50 | N420A | 0.47 | | |

TABLE 5-continued

| | | | | | | | | | | |
|---|---|---|---|---|---|---|---|---|---|---|
| 422 | R | B21 | R422Q | 1.13 | R422S | 1.13 | R422Y | 1.06 | R422A | 1.01 |
| | | | R422N | 0.79 | R422D | 0.77 | R422W | 0.74 | R422M | 0.72 |
| | | | R422F | 0.59 | R422I | 0.51 | R422P | 0.03 | | |
| 425 | L | B21 | L425V | 1.19 | L425A | 1.16 | L425Y | 1.15 | L425M | 1.15 |
| | | | L425Q | 0.93 | L425I | 0.93 | L425W | 0.93 | L425N | 0.92 |
| | | | L425D | 0.54 | | | | | | |
| 426 | N | B21 | N426M | 1.17 | N426S | 1.09 | N426D | 1.05 | N426Y | 1.01 |
| | | | N426Q | 0.83 | N426R | 0.80 | N426T | 0.77 | N426G | 0.68 |
| | | | N426C | 0.34 | N426W | 0.31 | N426P | 0.29 | | |
| 427 | S | B21 | S427H | 1.20 | S427P | 1.14 | S427Q | 1.13 | S427N | 1.12 |
| | | | S427F | 0.87 | S427I | 0.84 | S427E | 0.83 | S427M | 0.78 |
| | | | S427V | 0.53 | S427R | 0.48 | | | | |
| 428 | L | B21 | L428N | 1.15 | L428Q | 1.08 | L428G | 1.07 | L428P | 0.96 |
| | | | L428S | 0.82 | L428W | 0.76 | L428A | 0.74 | L428V | 0.73 |
| | | | L428K | 0.52 | L428F | 0.42 | L428C | 0.28 | | |
| 429 | R | B21 | R429L | 1.13 | R429H | 1.09 | R429W | 1.09 | R429N | 1.08 |
| | | | R429Y | 0.88 | R429Q | 0.86 | R429T | 0.83 | R429G | 0.79 |
| | | | R429S | 0.54 | R429C | 0.36 | | | | |
| 431 | S | B21 | S431K | 1.15 | S431M | 1.00 | S431V | 0.90 | S431T | 0.87 |
| | | | S431R | 0.81 | S431N | 0.81 | S431I | 0.73 | S431W | 0.71 |
| 435 | T | B21 | T435M | 1.13 | T435W | 1.01 | T435F | 1.00 | T435I | 0.90 |
| | | | T435N | 0.57 | T435D | 0.55 | T435E | 0.52 | T435A | 0.52 |
| 437 | G | B21 | G437M | 1.15 | G437T | 1.13 | G437Y | 1.00 | G437F | 0.95 |
| | | | G437I | 0.75 | G437E | 0.67 | G437D | 0.62 | G437P | 0.36 |
| 439 | T | B21 | T439S | 1.20 | T439F | 1.16 | T439V | 1.16 | T439A | 1.15 |
| | | | T439K | 0.83 | T439R | 0.80 | T439L | 0.79 | T439G | 0.67 |
| | | | T439P | 0.02 | | | | | | |
| 444 | Q | B21 | Q444E | 0.91 | Q444M | 0.89 | Q444A | 0.62 | Q444H | 0.58 |
| | | | Q444F | 0.34 | Q444D | 0.31 | Q444N | 0.28 | Q444K | 0.28 |
| | | | Q444C | 0.10 | Q444R | 0.05 | Q444P | 0.01 | | |
| 447 | D | B21 | D447Q | 1.17 | D447Y | 1.16 | D447K | 1.01 | D447G | 0.94 |
| | | | D447R | 0.63 | D447P | 0.52 | D447C | 0.52 | | |
| 473 | R | B21 | R473H | 1.07 | R473C | 1.07 | R473L | 1.02 | R473Q | 1.02 |
| 476 | S | B21 | I476K | 1.13 | I476T | 1.12 | I476N | 1.07 | I476C | 0.84 |
| 477 | G | B21 | G477R | 1.04 | G477T | 1.01 | G477Q | 0.90 | G477K | 0.53 |
| | | | G477Y | 0.24 | G477C | 0.13 | G477W | 0.04 | | |
| 478 | N | B21 | N478Q | 1.14 | N478R | 1.12 | N478H | 1.06 | N478T | 1.04 |
| | | | N478D | 0.31 | N478F | 0.26 | N478C | 0.13 | | |
| 479 | T | B21 | T479G | 1.00 | T479I | 0.93 | T479L | 0.81 | T479S | 0.75 |
| | | | T479P | 0.40 | T479R | 0.30 | T479M | 0.23 | T479F | 0.19 |
| 481 | R | B21 | R481K | 0.65 | R481L | 0.48 | R481W | 0.30 | R481Y | 0.23 |
| | | | R481A | 0.13 | R481S | 0.13 | R481G | 0.07 | R481E | 0.04 |
| 492 | A | B25 | A492S | 0.93 | A492C | 0.70 | A492V | 0.69 | A492G | 0.38 |
| 498 | I | B25 | I498V | 1.02 | I498E | 0.93 | I498L | 0.90 | I498C | 0.65 |
| | | | I498R | 0.27 | | | | | | |
| 499 | A | B25 | A499D | 1.09 | | | | | | |
| 503 | I | B25 | I503C | 0.63 | I503L | 0.59 | I503V | 0.44 | | |
| 504 | T | B25 | T504S | 0.78 | T504G | 0.66 | T504A | 0.63 | T504C | 0.60 |
| 505 | Q | B25 | Q505C | 0.34 | Q505L | 0.28 | Q505E | 0.26 | Q505S | 0.20 |
| 506 | I | B25 | I506L | 0.96 | I506V | 0.94 | I506W | 0.19 | I506A | 0.11 |
| 507 | P | B25 | P507A | 0.44 | P507G | 0.34 | P507S | 0.29 | | |
| 508 | A | B25 | A508V | 0.91 | A508M | 0.64 | A508S | 0.48 | A508I | 0.23 |
| 509 | V | B25 | V509I | 0.95 | V509C | 0.86 | V509N | 0.86 | V509G | 0.83 |
| | | | V509D | 0.31 | V509E | 0.24 | | | | |
| 511 | G | B25 | G511A | 0.88 | G511S | 0.62 | | | | |
| 512 | N | 258 | N512S | 1.13 | N512C | 1.10 | N512H | 1.08 | N512L | 1.05 |
| 513 | F | B25 | F513R | 1.18 | F513A | 1.02 | F513Y | 0.91 | F513M | 0.75 |
| 514 | L | | | | | | | | | |
| 515 | F | B25 | F515W | 1.04 | F515G | 0.60 | F515R | 0.56 | F515V | 0.53 |
| | | | F515S | 0.43 | F515E | 0.22 | F515D | 0.19 | | |
| 517 | G | B25 | G517V | 0.39 | | | | | | |
| 520 | I | B25 | I520G | 1.02 | I520N | 0.93 | | | | |
| 525 | F | B25 | F525T | 0.82 | F525S | 0.79 | F525V | 0.77 | F525W | 0.72 |
| 526 | T | B25 | T526A | 0.79 | T526S | 0.70 | T526V | 0.69 | T526G | 0.24 |
| 527 | G | B25 | G527T | 0.45 | G527S | 0.23 | | | | |
| 530 | L | B25 | L530I | 0.86 | L530V | 0.80 | L530C | 0.56 | L530Y | 0.52 |
| | | | L530K | 0.22 | | | | | | |
| 531 | V | B25 | V531I | 0.96 | V531C | 0.75 | V531A | 0.21 | | |
| 533 | L | B25 | L533I | 0.86 | L533N | 0.62 | L533V | 0.54 | V531A | 0.21 |
| 534 | N | B25 | N534R | 1.17 | N534V | 1.12 | N534M | 1.04 | N534A | 0.86 |
| 535 | N | B25 | N535G | 1.10 | N535C | 0.92 | N535V | 0.91 | | |
| 536 | S | 258 | S536Y | 1.03 | S536T | 1.02 | S536A | 0.85 | S536N | 0.83 |
| | | | S536F | 0.55 | S536G | 0.49 | S536W | 0.47 | S536D | 0.35 |
| | | | S536R | 0.18 | S536L | 0.11 | S536I | 0.09 | | |
| 537 | G | 258 | G537L | 1.18 | G537M | 1.17 | G537I | 1.06 | G537C | 0.95 |
| 538 | N | 258 | N538K | 1.17 | N538Y | 0.98 | N538R | 0.80 | | |
| 539 | N | B25 | N539D | 0.95 | N539A | 0.92 | N539S | 0.88 | N539H | 0.79 |
| | | | N539T | 0.57 | N539V | 0.56 | N539G | 0.51 | N539C | 0.49 |
| 540 | I | B25 | I540V | 0.90 | I540H | 0.86 | I540S | 0.84 | I540P | 0.84 |

TABLE 5-continued

| | | | | | | | | | | |
|---|---|---|---|---|---|---|---|---|---|---|
| 541 | Q | 258 | Q541H | 0.92 | Q541G | 0.71 | Q541A | 0.62 | Q541S | 0.54 |
| | | | Q541K | 0.20 | Q541R | 0.12 | | | | |
| 542 | N | B25 | N542R | 0.87 | N542M | 0.86 | N542A | 0.65 | N542L | 0.64 |
| | | | N542S | 0.50 | N542G | 0.41 | N542V | 0.31 | N542I | 0.24 |
| 543 | R | 258 | R543Y | 0.1104 | R543H | 0.0972 | R543G | 0.068 | R543W | 0.06 |
| | | | R543A | 0.0329 | R543V | 0.0262 | R543C | 0.0171 | R543Q | 0.0079 |
| 545 | Y | 258 | Y545A | 0.39 | Y545L | 0.34 | Y545C | 0.28 | Y545V | 0.26 |
| | | | Y545K | 0.19 | Y545R | 0.11 | Y545D | 0.10 | Y545G | 0.08 |
| 546 | L | B25 | I546V | 1.04 | I546L | 1.02 | I546M | 1.01 | I546F | 0.80 |
| 547 | E | 258 | E547K | 1.11 | E547V | 1.04 | E547R | 1.01 | E547Y | 0.94 |
| | | | E547C | 0.53 | E547W | 0.28 | E547D | 0.28 | E547F | 0.27 |
| 548 | V | B25 | V548L | 1.02 | V548S | 0.58 | V548A | 0.57 | V548G | 0.45 |
| 549 | P | B25 | P549Y | 0.52 | P549V | 0.38 | P549T | 0.50 | P549S | 0.75 |
| | | | P549D | 0.78 | P549C | 0.89 | | | | |
| 550 | I | B25 | I550V | 0.96 | I550L | 0.95 | I550A | 0.61 | I550F | 0.45 |
| 551 | Q | B25 | Q551V | 1.12 | Q551F | 1.09 | Q551M | 1.05 | Q551G | 1.01 |
| 552 | F | B25 | F552C | 1.10 | F552D | 1.06 | F552G | 1.00 | F552A | 0.98 |
| 553 | I | B25 | I553N | 1.12 | | | | | | |
| 554 | S | B25 | S554M | 0.93 | | | | | | |
| 555 | T | B25 | T555R | 1.13 | T555C | 1.13 | T555S | 0.85 | T555G | 0.78 |
| 557 | T | B25 | T557L | 1.16 | T557W | 1.05 | | | | |
| 558 | R | B25 | R558A | 1.11 | | | | | | |
| 559 | Y | B25 | Y559L | 0.67 | Y559M | 0.63 | Y559V | 0.61 | Y559A | 0.47 |
| | | | Y559R | 0.10 | Y559P | 0.07 | Y559G | 0.05 | | |
| 563 | V | B25 | V563G | 1.05 | V563S | 0.69 | V563C | 0.68 | V563T | 0.54 |
| 564 | R | B25 | R564M | 1.04 | R564G | 0.78 | R564L | 0.24 | R564P | 0.20 |
| 568 | V | B25 | V568P | 1.17 | | | | | | |
| 569 | T | B25 | T569V | 1.19 | T569E | 1.15 | T569L | 1.12 | T569R | 1.10 |
| 570 | P | 258 | P570A | 1.15 | P570K | 1.07 | P570G | 1.07 | P570Y | 1.07 |
| | | | P570S | 0.89 | P570Q | 0.79 | P570N | 0.79 | P570C | 0.70 |
| 571 | I | B25 | I571E | 1.09 | I571A | 0.90 | | | | |
| 572 | Q | 258 | Q572G | 1.16 | Q572T | 1.07 | Q572Y | 1.07 | Q572N | 0.87 |
| 574 | S | 258 | S574V | 0.82 | S574I | 0.76 | S574M | 0.69 | S574W | 0.64 |
| | | | S574N | 0.48 | S574L | 0.38 | S574E | 0.32 | S574P | 0.29 |
| 577 | W | 258 | W577L | 1.18 | W577N | 1.16 | W577C | 1.08 | W577S | 1.04 |
| 581 | N | 258 | N581I | 1.02 | N581G | 1.02 | N581F | 1.00 | N581T | 0.90 |
| | | | N581P | 0.63 | N581W | 0.58 | N581E | 0.57 | N581Q | 0.46 |
| | | | N581R | 0.00 | | | | | | |
| 584 | S | B21 | S584K | 1.14 | S584G | 1.11 | S584A | 1.00 | S584Q | 0.90 |
| | | | S584L | 0.66 | S584H | 0.65 | S584T | 0.64 | S584F | 0.59 |
| | | | S584E | 0.21 | S584P | 0.12 | | | | |
| 585 | S | 258 | S585E | 1.11 | S585Y | 1.09 | S585G | 0.93 | S585P | 0.79 |
| 590 | T | B25 | T590K | 1.00 | T590V | 0.98 | T590M | 0.73 | T590W | 0.72 |
| 591 | A | 258 | A591I | 1.17 | A591G | 1.17 | A591M | 0.94 | | |
| 592 | T | 258 | T592E | 1.04 | T592C | 0.66 | | | | |
| 593 | S | B21 | S593A | 1.10 | S593F | 1.07 | S593L | 1.06 | S593Q | 1.06 |
| | | | S593I | 0.87 | S593W | 0.84 | S593E | 0.80 | S593K | 0.79 |
| 595 | D | B21 | D595L | 1.19 | D595W | 1.18 | D595Q | 1.13 | D595C | 0.91 |
| 596 | N | B21 | N596F | 1.14 | N596C | 1.10 | N596Q | 1.06 | N596M | 0.98 |
| 598 | Q | B21 | Q598H | 1.03 | Q598F | 1.03 | Q598Y | 1.02 | Q598R | 0.95 |
| | | | Q598P | 0.82 | Q598M | 0.80 | Q598A | 0.76 | Q598T | 0.60 |
| 599 | S | B25 | S599G | 1.09 | S599D | 1.07 | S599I | 0.85 | S599W | 0.81 |
| 600 | R | B21 | R600G | 0.88 | R600S | 0.85 | R600M | 0.77 | R600A | 0.74 |
| | | | R600V | 0.65 | R600Q | 0.60 | R600I | 0.57 | R600H | 0.56 |
| | | | R600Y | 0.36 | R600D | 0.34 | R600W | 0.31 | | |
| 601 | D | B21 | N601Q | 1.14 | N601W | 1.07 | N601T | 1.00 | N601A | 0.96 |
| | | | N601R | 0.73 | N601C | 0.73 | N601I | 0.64 | N601D | 0.58 |
| 602 | F | B25 | F602L | 1.15 | F602V | 0.75 | F602Y | 0.70 | F602K | 0.59 |
| 605 | F | 258 | F605H | 1.12 | F605T | 0.96 | F605L | 0.83 | | |
| 606 | E | B21 | E606C | 1.15 | E606V | 1.03 | E606S | 0.97 | E606D | 0.85 |
| 607 | S | 258 | S607N | 1.14 | S607H | 1.08 | S607K | 1.01 | S607M | 1.01 |
| | | | S607L | 0.75 | | | | | | |
| 608 | T | 258 | T608M | 1.19 | T608H | 1.16 | T608E | 1.05 | T608D | 0.98 |
| 609 | N | B25 | N609D | 0.74 | | | | | | |
| 612 | T | B25 | T612A | 1.17 | T612L | 1.09 | T612K | 0.97 | T612Y | 0.86 |
| 613 | S | B25 | S613E | 1.01 | S613L | 0.98 | S613A | 0.97 | | |
| 614 | A | B25 | A614W | 1.15 | A614P | 1.14 | A614Q | 0.98 | | |
| 617 | N | B25 | N617E | 1.19 | N617S | 1.14 | N617F | 0.96 | | |
| 618 | V | 258 | V618F | 1.17 | V618Y | 1.11 | V618M | 1.10 | V618A | 1.10 |
| | | | V618S | 0.70 | V618C | 0.69 | V618Q | 0.67 | | |
| 620 | G | B25 | G620S | 0.38 | G620A | 0.35 | G620E | 0.27 | G620L | 0.25 |
| | | | G620W | 0.21 | G620R | 0.20 | G620M | 0.15 | | |
| 622 | R | B25 | R622H | 0.28 | R622W | 0.20 | R622C | 0.19 | R622E | 0.09 |
| 623 | N | B25 | N623S | 1.19 | N623A | 1.14 | N623D | 0.88 | N623H | 0.85 |
| | | | N623I | 0.57 | | | | | | |
| 624 | F | B25 | F624M | 1.14 | F624E | 0.86 | F624V | 0.76 | F624S | 0.73 |
| | | | F624T | 0.33 | | | | | | |
| 626 | E | 258 | E626D | 1.18 | E626L | 1.10 | E626F | 1.09 | E626C | 0.66 |
| 628 | A | B25 | A628E | 1.15 | A628T | 1.14 | | | | |

TABLE 5-continued

| | | | | | | | | | | |
|---|---|---|---|---|---|---|---|---|---|---|
| 629 | G | 258 | G629C | 1.18 | G629L | 1.15 | G629H | 1.08 | G629I | 1.07 |
| | | | G629F | 0.85 | G629Y | 0.81 | | | | |
| 630 | V | B25 | V630I | 1.12 | V630T | 1.08 | V630L | 0.82 | V630G | 0.76 |
| 641 | T | B25 | T641M | 1.18 | T641C | 0.98 | T641K | 0.97 | | |
| 643 | T | B25 | T643V | 1.14 | T643P | 0.98 | T643E | 0.93 | T643F | 0.70 |
| 645 | E | B25 | E645R | 1.16 | E645F | 1.13 | E645D | 0.75 | | |
| 646 | A | B25 | A646N | 1.08 | A646Q | 1.06 | | | | |

| MP258 position | Variant | FAE | Variant | FAE | Variant | FAE | Variant | FAE |
|---|---|---|---|---|---|---|---|---|
| 50 | L50G | 0.73 | | | | | | |
| 53 | A53M | 1.06 | A53S | 0.55 | | | | |
| 54 | S54V | 1.03 | S54N | 0.99 | S54E | 0.95 | S54T | 0.89 |
| 57 | Q57F | 0.91 | | | | | | |
| 65 | R65V | 0.94 | R65F | 0.87 | R65E | 0.74 | R65P | 0.53 |
| 67 | L67E | 0.52 | L67Y | 0.51 | L67T | 0.51 | L67R | 0.50 |
| 68 | G68V | 0.60 | G68S | 0.54 | G68I | 0.50 | G68N | 0.50 |
| 70 | L70F | 0.97 | L70C | 0.97 | L70N | 0.96 | L70G | 0.92 |
| | L70D | 0.85 | | | | | | |
| 71 | G71R | 1.00 | G71K | 0.96 | G71A | 0.88 | G71I | 0.87 |
| | G71Y | 0.26 | G71W | 0.25 | G71T | 0.22 | | |
| 72 | V72Y | 0.75 | V72I | 0.74 | V72N | 0.72 | V72H | 0.66 |
| | V72E | 0.35 | V72P | 0.28 | | | | |
| 73 | | | | | | | | |
| 74 | F74H | 0.91 | F74K | 0.88 | F74A | 0.82 | F74Y | 0.80 |
| 75 | A75L | 0.59 | A75T | 0.59 | A75G | 0.57 | A75I | 0.29 |
| 76 | G76C | 0.52 | G76N | 0.51 | G76L | 0.50 | G76F | 0.48 |
| 77 | | | | | | | | |
| 79 | | | | | | | | |
| 80 | | | | | | | | |
| 83 | S83W | 0.53 | | | | | | |
| 87 | G87V | 0.92 | G87T | 0.69 | G87Q | 0.50 | G87I | 0.46 |
| 91 | P91F | 1.01 | P91M | 0.67 | P91L | 0.55 | P91V | 0.55 |
| 92 | S92A | 0.39 | S92P | 0.32 | | | | |
| 93 | G93A | 0.83 | G93T | 0.82 | G93S | 0.80 | G93K | 0.75 |
| 94 | R94A | 0.88 | R94W | 0.88 | R94N | 0.77 | R94I | 0.71 |
| 95 | D95K | 0.80 | D95S | 0.64 | D95E | 0.50 | D95A | 0.28 |
| 106 | Q106T | 0.52 | | | | | | |
| 108 | V108E | 0.95 | V108W | 0.83 | | | | |
| 109 | R109H | 0.92 | R109L | 0.91 | R109E | 0.91 | R109G | 0.86 |
| | R109M | 0.74 | R109C | 0.73 | R109Y | 0.49 | R109P | 0.07 |
| 110 | Q110N | 1.13 | Q110E | 1.09 | Q110S | 1.09 | Q110L | 0.89 |
| | Q110P | 0.15 | | | | | | |
| 111 | Q111P | 0.85 | Q111T | 0.79 | Q111C | 0.77 | Q111Y | 0.50 |
| 112 | I112T | 0.57 | I112E | 0.39 | I112Y | 0.28 | I112N | 0.28 |
| | I112W | 0.24 | | | | | | |
| 113 | T113I | 0.61 | | | | | | |
| 114 | E114P | 0.09 | | | | | | |
| 115 | N115V | 0.87 | N115D | 0.82 | N115L | 0.69 | N115C | 0.61 |
| 118 | N118M | 0.60 | | | | | | |
| 119 | T119L | 0.78 | T119C | 0.62 | T119G | 0.50 | T119N | 0.42 |
| 122 | A122D | 1.01 | A122V | 1.00 | A122K | 0.96 | A122C | 0.96 |
| 123 | R123T | 0.61 | R123V | 0.61 | R123L | 0.61 | R123F | 0.57 |
| | R123C | 0.43 | R123W | 0.42 | R123D | 0.32 | R123E | 0.28 |
| 125 | | | | | | | | |
| 129 | A129C | 1.05 | A129M | 0.91 | A129G | 0.90 | A129N | 0.87 |
| 132 | R132L | 0.86 | R132Q | 0.80 | R132S | 0.72 | R132E | 0.70 |
| | R132C | 0.59 | R132P | 0.36 | | | | |
| 133 | A133G | 0.47 | A133P | 0.36 | A133H | 0.33 | A133M | 0.32 |
| | A133R | 0.23 | A133Q | | | | | |
| 136 | Q136V | 0.59 | | | | | | |
| 140 | D140Q | 0.40 | D140M | 0.36 | D140C | 0.36 | D140K | 0.30 |
| 142 | L142A | 0.67 | L142G | 0.67 | L142Y | 0.66 | L142M | 0.62 |
| 143 | | | | | | | | |
| 144 | N144E | 0.86 | N144G | 0.84 | N144D | 0.52 | | |
| 145 | R145C | 0.69 | | | | | | |
| 146 | D146R | 1.05 | D146N | 1.05 | D146L | 1.01 | D146Q | 0.95 |
| 147 | N147F | 0.61 | N147I | 0.59 | N147P | 0.57 | N147M | 0.55 |
| 148 | A148Y | 0.87 | A148T | 0.85 | A148S | 0.84 | A148D | 0.83 |
| 149 | R149Y | 0.87 | R149P | 0.84 | R149G | 0.82 | R149C | 0.24 |
| 151 | R151L | 0.68 | R151G | 0.63 | R151T | 0.56 | R151Q | 0.52 |
| | B151W | 0.39 | B151E | 0.38 | B151P | 0.32 | R151D | 0.32 |
| 152 | S152L | 0.83 | S152I | 0.76 | S152B | 0.61 | S152G | 0.60 |
| | S152D | 0.32 | S152V | 0.25 | | | | |
| 159 | I159B | 0.32 | I159Y | 0.29 | I159N | 0.28 | I159M | 0.28 |
| | I159Q | 0.25 | I159L | 0.25 | | | | |
| 160 | A160K | 0.82 | A160T | 0.81 | A160I | 0.75 | | |
| 163 | L163C | 0.28 | L163A | 0.28 | L163K | 0.27 | L163P | 0.26 |
| | L163D | 0.23 | L163N | 0.23 | | | | |

TABLE 5-continued

| | | | | | | | | |
|---|---|---|---|---|---|---|---|---|
| 164 | D164B | 0.72 | D164N | 0.71 | D164L | 0.63 | D164Y | 0.56 |
| | D164I | 0.42 | D164E | 0.30 | D164P | 0.25 | | |
| 166 | L166H | 0.98 | L166G | 0.97 | L166B | 0.96 | L166K | 0.96 |
| | L166S | 0.95 | | | | | | |
| 167 | N167F | 0.92 | N167E | 0.90 | N167D | 0.87 | N167P | 0.83 |
| 173 | A173S | 0.77 | A173E | 0.56 | | | | |
| 174 | I174G | 0.72 | I174M | 0.72 | I174E | 0.63 | I174N | 0.59 |
| 177 | Q177I | 1.00 | Q177B | 0.96 | Q177M | 0.95 | Q177V | 0.93 |
| 178 | Q178S | 0.75 | Q178V | 0.74 | Q178P | 0.67 | Q178I | 0.54 |
| 179 | V179E | 0.77 | V179S | 0.75 | V179P | 0.67 | V179G | 0.61 |
| 180 | P180G | 0.83 | P180F | 0.62 | P180B | 0.60 | P180N | 0.56 |
| 201 | L201Q | 0.62 | L201G | 0.61 | L201W | 0.60 | L201Y | 0.60 |
| 206 | F206Y | 0.74 | F206Q | 0.69 | F206G | 0.58 | F206R | 0.53 |
| | F206P | 0.37 | | | | | | |
| 208 | L208E | 0.67 | L208V | 0.66 | L208M | 0.56 | L208H | 0.50 |
| | L208T | 0.35 | L208A | 0.35 | L208P | 0.34 | L208R | 0.30 |
| 209 | T209W | 0.67 | T209F | 0.64 | T209Y | 0.62 | T209P | 0.28 |
| 210 | | | | | | | | |
| 211 | Q211W | 1.03 | Q211F | 1.01 | Q211Y | 1.01 | Q211C | 1.00 |
| 212 | E212P | 0.77 | E212C | 0.72 | E212T | 0.68 | E212G | 0.64 |
| | E212B | 0.56 | | | | | | |
| 213 | I213W | 0.74 | I213D | 0.67 | I213Y | 0.63 | I213F | 0.62 |
| 214 | Q214V | 0.68 | Q214C | 0.67 | Q214E | 0.58 | Q214I | 0.53 |
| | Q214K | 0.28 | Q214R | 0.27 | | | | |
| 215 | R215Y | 0.77 | R215F | 0.75 | R215Q | 0.73 | R215K | 0.72 |
| | R215D | 0.56 | R215E | 0.54 | | | | |
| 218 | E218R | 0.93 | E218F | 0.92 | E218P | 0.55 | | |
| 219 | R219K | 0.63 | R219D | 0.53 | R219P | 0.23 | R219H | 0.07 |
| | R219V | 0.01 | R219I | 0.01 | R219C | 0.00 | | |
| 221 | A221P | 0.62 | A221Q | 0.50 | | | | |
| 222 | E222A | 0.98 | E222N | 0.98 | E222V | 0.94 | E222W | 0.90 |
| 225 | R225P | 0.87 | R225K | 0.85 | R225T | 0.77 | | |
| 226 | E226N | 1.11 | E226M | 1.05 | E226I | 1.00 | E226L | 0.98 |
| 230 | Y230T | 0.93 | Y230D | 0.88 | Y230N | 0.85 | Y230G | 0.81 |
| 233 | R233L | 1.03 | R233M | 1.01 | R233S | 0.87 | R233C | 0.78 |
| 234 | W234D | 0.59 | W234P | 0.46 | W234Q | 0.45 | | |
| 236 | N236I | 0.93 | N236Y | 0.89 | N236V | 0.89 | N236G | 0.58 |
| 240 | N240P | 0.44 | | | | | | |
| 241 | N241T | 1.12 | N241D | 1.07 | N241H | 0.90 | N241P | 0.50 |
| 242 | L242S | 0.70 | L242Q | 0.68 | L242A | 0.66 | L242N | 0.58 |
| | L242Y | 0.33 | L242K | 0.32 | | | | |
| 243 | R243H | 0.73 | R243W | 0.71 | R243G | 0.67 | R243D | 0.57 |
| 244 | G244S | 0.58 | G244D | 0.56 | G244K | 0.54 | G244R | 0.54 |
| | G244N | 0.46 | G244T | 0.37 | G244V | 0.28 | G244P | 0.28 |
| 245 | | | | | | | | |
| 246 | N246M | 0.77 | N246R | 0.76 | N246F | 0.66 | N246L | 0.61 |
| 247 | A247V | 0.39 | A247W | 0.39 | A247R | 0.31 | A247F | 0.30 |
| 248 | E248G | 0.76 | E248M | 0.74 | E248K | 0.50 | | |
| 252 | R252M | 1.05 | R252S | 0.99 | R252Q | 0.98 | R252H | 0.96 |
| | R252P | 0.66 | R252T | 0.48 | | | | |
| 277 | R277W | 0.87 | R277S | 0.87 | R277F | 0.86 | R277T | 0.85 |
| | R277P | 0.47 | | | | | | |
| 280 | P280F | 0.90 | P280W | 0.87 | P280E | 0.86 | P280K | 0.64 |
| | P280I | 0.47 | P280L | 0.46 | | | | |
| 281 | I281G | 1.00 | I281F | 0.94 | I281W | 0.82 | I281D | 0.72 |
| 303 | S303G | 0.64 | S303I | 0.61 | S303T | 0.57 | S303H | 0.57 |
| | S303W | 0.29 | S303D | 0.15 | S303K | 0.13 | S303E | 0.07 |
| 304 | G304I | 0.01 | G304L | 0.01 | G304T | 0.01 | G304F | 0.01 |
| | G304R | 0.01 | G304H | 0.01 | G304W | 0.01 | G304V | 0.01 |
| 305 | F305I | 0.01 | F305L | 0.01 | F305R | 0.01 | F305G | 0.01 |
| | F305C | 0.00 | F305W | 0.00 | F305T | 0.00 | F305S | 0.00 |
| 306 | A306M | 0.78 | A306T | 0.52 | A306H | 0.50 | A306R | 0.48 |
| | A306V | 0.26 | A306P | 0.22 | A306D | 0.09 | A306C | 0.07 |
| 308 | T308F | 0.02 | T308Q | 0.01 | T308V | 0.01 | T308C | 0.01 |
| | T308L | 0.01 | T308I | 0.01 | T308P | 0.01 | T308M | 0.01 |
| 360 | R360Q | 0.44 | R360E | 0.41 | R360L | 0.28 | | |
| 362 | | | | | | | | |
| 364 | R364M | 0.25 | | | | | | |
| 367 | | | | | | | | |
| 406 | L406C | 0.29 | L406V | 0.27 | L406Q | 0.27 | L406H | 0.24 |
| | L406Y | 0.03 | L406G | 0.02 | L406D | 0.01 | L406P | 0.01 |
| 407 | L407F | 0.46 | L407A | 0.41 | L407R | 0.34 | L407T | 0.34 |
| | L407G | 0.06 | L407K | 0.04 | L407Q | 0.02 | L407P | 0.01 |
| 408 | T408L | 0.36 | T408M | 0.32 | T408Q | 0.30 | T408N | 0.27 |
| | T408P | 0.22 | T408W | 0.20 | T408I | 0.17 | T408C | 0.11 |
| 409 | T409V | 0.20 | T409L | 0.17 | T409S | 0.16 | T409K | 0.13 |
| | T409Y | 0.08 | T409N | 0.08 | T409F | 0.05 | T409C | 0.02 |
| 411 | V411R | 0.27 | V411N | 0.21 | V411Q | 0.19 | V411T | 0.14 |
| | V411S | 0.08 | V411G | 0.06 | V411K | 0.03 | V411E | 0.02 |

TABLE 5-continued

| | | | | | | | | |
|---|---|---|---|---|---|---|---|---|
| 418 | R418D | 0.89 | R418I | 0.83 | R418V | 0.78 | R418N | 0.76 |
| | R418Q | 0.58 | R418W | 0.54 | R418F | 0.43 | R418C | 0.36 |
| 420 | N420G | 0.98 | N420L | 0.91 | N420F | 0.90 | N420W | 0.89 |
| | N420H | 0.68 | N420R | 0.68 | N420Q | 0.65 | N420S | 0.63 |
| 422 | R422T | 0.92 | R422K | 0.91 | R422L | 0.87 | R422V | 0.84 |
| | R422G | 0.67 | R422H | 0.66 | R422C | 0.63 | R422E | 0.60 |
| 425 | L425F | 1.08 | L425R | 1.04 | L425S | 1.00 | L425K | 0.96 |
| | L425H | 0.89 | L425T | 0.84 | L425E | 0.83 | L425C | 0.67 |
| 426 | N426A | 0.99 | N426V | 0.91 | N426E | 0.83 | N426L | 0.83 |
| | N426F | 0.59 | N426K | 0.59 | N426I | 0.53 | N426H | 0.51 |
| 427 | S427W | 1.10 | S427T | 1.10 | S427G | 1.03 | S427L | 0.97 |
| | S427K | 0.74 | S427A | 0.73 | S427C | 0.68 | S427D | 0.55 |
| 428 | L428T | 0.92 | L428M | 0.85 | L428H | 0.83 | L428R | 0.82 |
| | L428E | 0.72 | L428D | 0.65 | L428Y | 0.63 | L428I | 0.60 |
| 429 | R429K | 1.00 | R429M | 0.99 | R429F | 0.91 | R429A | 0.89 |
| | R429V | 0.73 | R429P | 0.72 | R429E | 0.65 | R429D | 0.63 |
| 431 | S431E | 0.87 | S431Y | 0.86 | S431Q | 0.86 | S431F | 0.82 |
| | S431P | 0.61 | S431D | 0.60 | S431C | 0.32 | | |
| 435 | T435K | 0.88 | T435Q | 0.82 | T435V | 0.79 | T435S | 0.58 |
| | T435R | 0.47 | T435C | 0.24 | T435G | 0.20 | T435P | 0.04 |
| 437 | G437H | 0.94 | G437V | 0.88 | G437W | 0.88 | G437L | 0.84 |
| | G437C | 0.26 | | | | | | |
| 439 | T439H | 1.08 | T439N | 0.99 | T439Y | 0.92 | T439I | 0.89 |
| | T439D | 0.64 | T439E | 0.58 | T439W | 0.54 | T439C | 0.17 |
| 444 | Q444T | 0.53 | Q444L | 0.48 | Q444S | 0.48 | Q444V | 0.47 |
| | Q444Y | 0.26 | Q444W | 0.24 | Q444I | 0.18 | Q444G | 0.12 |
| 447 | D447F | 0.94 | D447H | 0.94 | D447T | 0.88 | D447W | 0.78 |
| 473 | | | | | | | | |
| 476 | I476R | 0.59 | I476D | 0.40 | I476A | 0.29 | | |
| 477 | G477H | 0.42 | G477M | 0.41 | G477E | 0.33 | G477F | 0.25 |
| 478 | N478L | 0.88 | N478V | 0.82 | N478M | 0.68 | N478I | 0.59 |
| 479 | T479A | 0.66 | T479N | 0.50 | T479Q | 0.44 | T479Y | 0.40 |
| | T479W | 0.18 | | | | | | |
| 481 | R481N | 0.18 | R481T | 0.18 | R481D | 0.15 | R481F | 0.14 |
| 492 | | | | | | | | |
| 498 | I498W | 0.47 | I498M | 0.43 | I498Y | 0.37 | I498A | 0.28 |
| 499 | | | | | | | | |
| 503 | | | | | | | | |
| 504 | T504Q | 0.52 | | | | | | |
| 505 | | | | | | | | |
| 506 | | | | | | | | |
| 507 | | | | | | | | |
| 508 | | | | | | | | |
| 509 | V509S | 0.72 | V509A | 0.67 | V509W | 0.57 | V509M | 0.55 |
| 511 | | | | | | | | |
| 512 | N512T | 1.04 | N512F | 0.96 | N512A | 0.82 | | |
| 513 | | | | | | | | |
| 514 | | | | | | | | |
| 515 | F515Q | 0.51 | F515K | 0.50 | F515T | 0.45 | F515A | 0.44 |
| 517 | | | | | | | | |
| 520 | | | | | | | | |
| 525 | F525C | 0.60 | F525A | 0.40 | F525G | 0.39 | | |
| 526 | | | | | | | | |
| 527 | | | | | | | | |
| 530 | S536N | 0.41 | L530G | 0.31 | L530S | 0.27 | L530E | 0.22 |
| 531 | | | | | | | | |
| 533 | | | | | | | | |
| 534 | N534T | 0.81 | | | | | | |
| 535 | | | | | | | | |
| 536 | S536Q | 0.66 | S536C | 0.62 | S536M | 0.60 | S536H | 0.56 |
| | S536E | 0.30 | S536P | 0.27 | S536K | 0.21 | S536V | 0.20 |
| 537 | G537P | 0.57 | | | | | | |
| 538 | | | | | | | | |
| 539 | N539E | 0.77 | N539L | 0.72 | N539A | 0.60 | N539F | 0.57 |
| | N539W | 0.43 | N539Y | 0.39 | N539R | 0.18 | N539K | 0.17 |
| 540 | I540L | 0.82 | I540G | 0.51 | I540C | 0.50 | I540R | 0.17 |
| 541 | Q541E | 0.39 | Q541C | 0.37 | Q541T | 0.30 | Q541L | 0.30 |
| 542 | N542Y | 0.63 | N542H | 0.61 | N542T | 0.53 | N542C | 0.52 |
| | N542P | 0.05 | | | | | | |
| 543 | R543M | 0.0587 | R543L | 0.0419 | R543K | 0.0394 | R543S | 0.033 |
| | R543P | 0.0079 | R543D | 0.002 | R543T | 0.0011 | R543E | 0.0002 |
| 545 | Y545H | 0.26 | Y545N | 0.25 | Y545W | 0.24 | Y545T | 0.21 |
| | Y545I | 0.07 | Y545Q | 0.07 | Y545E | 0.06 | Y545P | 0.04 |
| 546 | I546S | 0.32 | I546G | 0.23 | | | | |
| 547 | E547T | 0.85 | E547H | 0.78 | E547P | 0.75 | E547L | 0.58 |
| 548 | V548W | 0.26 | | | | | | |
| 549 | P549R | 1.03 | P549M | 0.55 | P549L | 0.86 | P549G | 1.73 |
| 550 | | | | | | | | |
| 551 | Q551E | 0.93 | Q551N | 0.87 | Q551L | 0.85 | | |
| 552 | F552Q | 0.80 | F552R | 0.51 | | | | |

TABLE 5-continued

| | | | | | | | | |
|---|---|---|---|---|---|---|---|---|
| 553 | | | | | | | | |
| 554 | | | | | | | | |
| 555 | T555L | 0.27 | | | | | | |
| 557 | | | | | | | | |
| 558 | | | | | | | | |
| 559 | Y559E | 0.43 | Y559T | 0.27 | Y559S | 0.17 | Y559D | 0.10 |
| 563 | V563E | 0.05 | | | | | | |
| 564 | | | | | | | | |
| 568 | | | | | | | | |
| 569 | T569W | 1.02 | T569K | 0.82 | T569A | 0.58 | T569Y | 0.35 |
| 570 | P570V | 1.06 | P570H | 1.05 | P570R | 1.03 | P570I | 1.03 |
| | P570D | 0.52 | P570L | 0.47 | | | | |
| 571 | | | | | | | | |
| 572 | Q572E | 0.75 | Q572D | 0.75 | Q572C | 0.57 | | |
| 574 | S574Q | 0.64 | S574F | 0.56 | S574Y | 0.56 | S574A | 0.53 |
| | S574C | 0.29 | S574D | 0.26 | | | | |
| 577 | W577P | 0.97 | W577D | 0.92 | W577E | 0.81 | | |
| 581 | N581V | 0.86 | N581H | 0.70 | N581Y | 0.64 | N581M | 0.63 |
| | N581A | 0.42 | N581L | 0.32 | N581D | 0.29 | N581C | 0.13 |
| 584 | S584V | 0.81 | S584C | 0.78 | S584N | 0.67 | S584Y | 0.66 |
| | S584I | 0.54 | S584M | 0.41 | S584W | 0.38 | S584D | 0.31 |
| 585 | S585A | 0.74 | S585D | 0.67 | S585C | 0.60 | S585V | 0.47 |
| 590 | T590L | 0.54 | T590R | 0.53 | T590E | 0.52 | T590P | 0.15 |
| 591 | | | | | | | | |
| 592 | | | | | | | | |
| 593 | S593T | 1.00 | S593M | 0.96 | S593H | 0.92 | S593D | 0.89 |
| | S593N | 0.75 | S593P | 0.75 | S593C | 0.59 | | |
| 595 | D595E | 0.09 | | | | | | |
| 596 | N596E | 0.93 | N596R | 0.92 | N596K | 0.92 | | |
| 598 | Q598L | 0.92 | Q598E | 0.89 | Q598W | 0.88 | Q598N | 0.83 |
| | Q598K | 0.58 | Q598S | 0.58 | Q598C | 0.55 | | |
| 599 | S599E | 0.61 | | | | | | |
| 600 | R600E | 0.70 | R600T | 0.69 | R600K | 0.69 | R600F | 0.66 |
| | R600C | 0.54 | R600L | 0.54 | R600P | 0.47 | R600N | 0.45 |
| 601 | N601S | 0.81 | N601H | 0.79 | N601L | 0.78 | N601K | 0.76 |
| 602 | | | | | | | | |
| 605 | | | | | | | | |
| 606 | E606P | 0.39 | | | | | | |
| 607 | S607W | 1.01 | S607Y | 0.90 | S607P | 0.86 | S607F | 0.83 |
| 608 | T608P | 0.68 | T608I | 0.53 | T608C | 0.53 | T608N | 0.50 |
| 609 | | | | | | | | |
| 612 | T612W | 0.84 | T612I | 0.53 | | | | |
| 613 | | | | | | | | |
| 614 | | | | | | | | |
| 617 | | | | | | | | |
| 618 | V618P | 1.07 | V618E | 1.05 | V618K | 1.03 | V618I | 0.94 |
| 620 | G620F | 0.23 | G620K | 0.23 | G620V | 0.23 | G620Q | 0.22 |
| 622 | | | | | | | | |
| 623 | N623C | 0.70 | N623V | 0.68 | N623T | 0.65 | N623Q | 0.61 |
| 624 | F624D | 0.68 | F624C | 0.59 | F624H | 0.56 | F624R | 0.44 |
| 626 | E626M | 0.08 | | | | | | |
| 628 | | | | | | | | |
| 629 | G629V | 1.05 | G629K | 1.03 | G629D | 0.87 | G629W | 0.86 |
| 630 | V630R | 0.66 | V630D | 0.64 | V630S | 0.55 | | |
| 641 | | | | | | | | |
| 643 | | | | | | | | |
| 645 | | | | | | | | |
| 646 | | | | | | | | |

Example 5—Transient Expression in Maize Leaves and Insect Bioassay

Polynucleotides encoding the variant Cry1B polypeptides were cloned into transient expression vectors under control of the maize ubiquitin promoter (Christensen and Quail, (1996) Transgenic Research 5:213-218) and a duplicated version of the promoter from the mirabilis mosaic virus (DMMV PRO; Dey and Maiti, (1999) Plant Mol. Biol., 40:771-82). The agro-infiltration method of introducing an *Agrobacterium* cell suspension to plant cells of intact tissues so that reproducible infection and subsequent plant derived transgene expression may be measured or studied is well known in the art (Kapila, et. al., (1997) Plant Science 122:101-108). Briefly, young plantlets of maize were agro-infiltrated with normalized bacterial cell cultures of test and control strains. Leaf discs were generated from each plantlet and infested with WCRW (Diabrotica virgifera) along with appropriate controls. The degree of consumption of green leaf tissues was scored after 2 days of infestation.

Example 6—Transient Expression in Bush Bean Leaves and Insect Bioassay

For soybean expression optimized coding sequences can be designed. The agro-infiltration method of introducing an *Agrobacterium* cell suspension to plant cells of intact tissues so that reproducible infection and subsequent plant derived transgene expression may be measured or studied is well known in the art (Kapila, et. al., (1997) *Plant Science* 122:101-108). Briefly, excised leaf disks of bush bean, are agro-infiltrated with normalized bacterial cell cultures of test and control strains. After 4 days leaf disks are infested with 2 neonates of Soybean Looper (SBL) (*Chrysodeixis includens*), Corn Earworm, (CEVV) (*Helicoverpa zea*), Velvetbean Caterpillar (VBC) (*Anticarsia gemmatalis*), or Fall Armyworm (*Spodoptera frugiperda*) alone. Control leaf discs are generated with *Agrobacterium* containing only a DsRed2 fluorescence marker (Clontech™, 1290 Terra Bella Ave. Mountain View, Calif. 94043) expression vector. Leaf discs from non-infiltrated plants are included as a second control. The consumption of green leaf tissue is scored three days after infestation and given scores of 0 to 9.

Example 7—*Agrobacterium*-Mediated Transformation of Maize and Regeneration of Transgenic Plants For *Agrobacterium*-mediated transformation of maize with a polynucleotide sequence of the disclosure, the method of Zhao can be used (U.S. Pat. No. 5,981,840 and PCT patent publication WO98/32326; the contents of which are hereby incorporated by reference). Briefly, immature embryos are isolated from maize and the embryos contacted with a suspension of *Agrobacterium* under conditions whereby the bacteria are capable of transferring the toxin nucleotide sequence to at least one cell of at least one of the immature embryos (step 1: the infection step). In this step the immature embryos can be immersed in an *Agrobacterium* suspension for the initiation of inoculation. The embryos are co-cultured for a time with the *Agrobacterium* (step 2: the co-cultivation step). The immature embryos can be cultured on solid medium following the infection step. Following this co-cultivation period an optional "resting" step is contemplated. In this resting step, the embryos are incubated in the presence of at least one antibiotic known to inhibit the growth of *Agrobacterium* without the addition of a selective agent for plant transformants (step 3: resting step). The immature embryos can be cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step). The immature embryos are cultured on solid medium with a selective agent resulting in the selective growth of transformed cells. The callus is then regenerated into plants (step 5: the regeneration step), and calli grown on selective medium can be cultured on solid medium to regenerate the plants.

Example 8—Transformation of Soybean Embryos

Soybean embryos are bombarded with a plasmid containing the toxin nucleotide sequence operably linked to a suitable promoter as follows. To induce somatic embryos, cotyledons, 3-5 mm in length dissected from surface-sterilized, immature seeds of an appropriate soybean cultivar are cultured in the light or dark at 26° C. on an appropriate agar medium for six to ten weeks. Somatic embryos producing secondary embryos are then excised and placed into a suitable liquid medium. After repeated selection for clusters of somatic embryos that multiplied as early, globular-staged embryos, the suspensions are maintained as described below.

Soybean embryogenic suspension cultures can be maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein, et al., (1987) Nature (London) 327:70-73, U.S. Pat. No. 4,945,050). A Du Pont Biolistic PDS1000/HE instrument (helium retrofit) can be used for these transformations.

A selectable marker gene that can be used to facilitate soybean transformation includes, but is not limited to: the 35S promoter from Cauliflower Mosaic Virus (Odell, et al., (1985) Nature 313:810-812), the hygromycin phosphotransferase gene from plasmid pJR225 (from *E. coli*; Gritz, et al., (1983) Gene 25:179-188), and the 3' region of the nopaline synthase gene from the T DNA of the Ti plasmid of *Agrobacterium tumefaciens*. The expression cassette comprising a toxin nucleotide sequence (e.g., SEQ ID NO: 1, SEQ ID NO: 3 or a maize optimized sequence) operably linked to a suitable promoter can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μL spermidine (0.1M), and 50 μL $CaCl_2$) (2.5M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five microliters of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi, and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment the liquid media may be exchanged with fresh media, and eleven to twelve days post-bombardment with fresh media containing 50 mg/mL hygromycin. This selective media can be refreshed weekly. Seven to eight weeks post-bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

All publications, patents and patent applications mentioned in the specification are indicative of the level of those skilled in the art to which this disclosure pertains. All publications, patents and patent applications are herein incorporated by reference to the same extent as if each individual publication, patent or patent application was specifically and individually indicated to be incorporated by reference.

Although the foregoing disclosure has been described in some detail by way of illustration and example for purposes of clarity of understanding, it will be obvious that certain changes and modifications may be practiced within the scope of the embodiments.

That which is claimed:

1. A DNA construct comprising a nucleic acid molecule encoding a variant Cry1B polypeptide having at least 95% sequence identity to SEQ ID NO: 29 and having insecticidal activity; and a nucleic acid molecule encoding a PtIP-83 polypeptide having at least 95% sequence identity to SEQ ID NO: 62, 64, or 66 and having insecticidal activity.

2. The DNA construct of claim 1, wherein the nucleic acid molecules encoding the variant Cry1B polypeptide and the PtIP-83 polypeptide are each operably linked to a heterologous regulatory element.

3. A transgenic plant comprising a molecular stack of a nucleic acid molecule encoding a variant Cry1B polypeptide having at least 95% sequence identity to SEQ ID NO: 29 and having insecticidal activity; and a nucleic acid molecule encoding a PtIP-83 polypeptide having at least 95% sequence identity to SEQ ID NO: 62, 64, or 66 and having insecticidal activity.

4. The transgenic plant of claim 3, wherein the nucleic acid molecules encoding the variant Cry1B polypeptide and the PtIP-83 polypeptide are each operably linked to a heterologous regulatory element.

5. A transgenic plant comprising a breeding stack of a nucleic acid molecule encoding a variant Cry1B polypeptide having at least 95% sequence identity to SEQ ID NO: 29 and having insecticidal activity; and a nucleic acid molecule encoding a PtIP-83 polypeptide having at least 95% sequence identity to SEQ ID NO: 62, 64, or 66 and having insecticidal activity.

6. The transgenic plant of claim 5, wherein the nucleic acid molecule encoding the variant Cry1B polypeptide and the PtIP-83 polypeptide are each operably linked to a heterologous regulatory element.

7. A transgenic plant or progeny thereof comprising the DNA construct of claim 1, wherein said transgenic plant is corn or soy.

8. The transgenic plant or progeny thereof comprising the molecular stack of claim 3, wherein said transgenic plant is corn or soy.

9. The transgenic plant or progeny thereof comprising the breeding stack of claim 5, wherein said transgenic plant is corn or soy.

10. A composition comprising a nucleic acid molecule encoding a variant Cry1B polypeptide having at least 95% sequence identity to SEQ ID NO: 29 and having insecticidal activity and a nucleic acid molecule encoding a PtIP-83 polypeptide having at least 95% sequence identity to SEQ ID NO: 62, 64, or 66 and having insecticidal activity.

* * * * *

SEQUENCE LISTING

<160> NUMBER OF SEQ ID NOS: 115

<210> SEQ ID NO 1
<211> LENGTH: 657
<212> TYPE: PRT
<213> ORGANISM: Bacillus thuringiensis

<400> SEQUENCE: 1

```
Met Thr Ser Asn Arg Lys Asn Glu Asn Glu Ile Ile Asn Ala Leu Ser
1               5                   10                  15

Ile Pro Ala Val Ser Asn His Ser Ala Gln Met Asp Leu Ser Leu Asp
            20                  25                  30

Ala Arg Ile Glu Asp Ser Leu Cys Ile Ala Glu Gly Asn Asn Ile Asn
        35                  40                  45

Pro Leu Val Ser Ala Ser Thr Val Gln Thr Gly Ile Asn Ile Ala Gly
    50                  55                  60

Arg Ile Leu Gly Val Leu Gly Val Pro Phe Ala Gly Gln Leu Ala Ser
65                  70                  75                  80

Phe Tyr Ser Phe Leu Val Gly Glu Leu Trp Pro Ser Gly Arg Asp Pro
                85                  90                  95

Trp Glu Ile Phe Leu Glu His Val Glu Gln Leu Ile Arg Gln Gln Val
            100                 105                 110

Thr Glu Asn Thr Arg Asn Thr Ala Ile Ala Arg Leu Glu Gly Leu Gly
        115                 120                 125

Arg Gly Tyr Arg Ser Tyr Gln Gln Ala Leu Glu Thr Trp Leu Asp Asn
    130                 135                 140

Arg Asn Asp Ala Arg Ser Arg Ser Ile Ile Leu Glu Arg Tyr Val Ala
145                 150                 155                 160

Leu Glu Leu Asp Ile Thr Thr Ala Ile Pro Leu Phe Arg Ile Arg Asn
                165                 170                 175

Glu Glu Val Pro Leu Leu Met Val Tyr Ala Gln Ala Ala Asn Leu His
            180                 185                 190

Leu Leu Leu Leu Arg Asp Ala Ser Leu Phe Gly Ser Glu Trp Gly Met
        195                 200                 205

Ala Ser Ser Asp Val Asn Gln Tyr Tyr Gln Glu Gln Ile Arg Tyr Thr
    210                 215                 220

Glu Glu Tyr Ser Asn His Cys Val Gln Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Thr Tyr Pro Ile Asn Thr Ser Ala Gln Leu Thr
        275                 280                 285

Arg Glu Ile Tyr Thr Asp Pro Ile Gly Arg Thr Asn Ala Pro Ser Gly
    290                 295                 300

Phe Ala Ser Thr Asn Trp Phe Asn Asn Asn Ala Pro Ser Phe Ser Ala
305                 310                 315                 320

Ile Glu Ala Ala Ile Phe Arg Pro Pro His Leu Leu Asp Phe Pro Glu
                325                 330                 335

Gln Leu Thr Ile Tyr Ser Ala Ser Ser Arg Trp Ser Ser Thr Gln His
            340                 345                 350

Met Asn Tyr Trp Val Gly His Arg Leu Asn Phe Arg Pro Ile Gly Gly
        355                 360                 365
```

-continued

```
Thr Leu Asn Thr Ser Thr Gln Gly Leu Thr Asn Asn Thr Ser Ile Asn
    370                 375                 380

Pro Val Thr Leu Gln Phe Thr Ser Arg Asp Val Tyr Arg Thr Glu Ser
385                 390                 395                 400

Asn Ala Gly Thr Asn Ile Leu Phe Thr Thr Pro Val Asn Gly Val Pro
                405                 410                 415

Trp Ala Arg Phe Asn Phe Ile Asn Pro Gln Asn Ile Tyr Glu Arg Gly
            420                 425                 430

Ala Thr Thr Tyr Ser Gln Pro Tyr Gln Gly Val Gly Ile Gln Leu Phe
        435                 440                 445

Asp Ser Glu Thr Glu Leu Pro Pro Glu Thr Thr Glu Arg Pro Asn Tyr
    450                 455                 460

Glu Ser Tyr Ser His Arg Leu Ser His Ile Gly Leu Ile Ile Gly Asn
465                 470                 475                 480

Thr Leu Arg Ala Pro Val Tyr Ser Trp Thr His Arg Ser Ala Asp Arg
                485                 490                 495

Thr Asn Thr Ile Gly Pro Asn Arg Ile Thr Gln Ile Pro Ala Val Lys
            500                 505                 510

Gly Arg Phe Leu Phe Asn Gly Ser Val Ile Ser Gly Pro Gly Phe Thr
        515                 520                 525

Gly Gly Asp Val Val Arg Leu Asn Arg Asn Asn Gly Asn Ile Gln Asn
    530                 535                 540

Arg Gly Tyr Ile Glu Val Pro Ile Gln Phe Thr Ser Thr Ser Thr Arg
545                 550                 555                 560

Tyr Arg Val Arg Val Arg Tyr Ala Ser Val Thr Ser Ile Glu Leu Asn
                565                 570                 575

Val Asn Leu Gly Asn Ser Ser Ile Phe Thr Asn Thr Leu Pro Ala Thr
            580                 585                 590

Ala Ala Ser Leu Asp Asn Leu Gln Ser Gly Asp Phe Gly Tyr Val Glu
        595                 600                 605

Ile Asn Asn Ala Phe Thr Ser Ala Thr Gly Asn Ile Val Gly Ala Arg
    610                 615                 620

Asn Phe Ser Ala Asn Ala Glu Val Ile Ile Asp Arg Phe Glu Phe Ile
625                 630                 635                 640

Pro Val Thr Ala Thr Phe Glu Ala Glu Tyr Asp Leu Glu Arg Ala Gln
                645                 650                 655

Lys
```

<210> SEQ ID NO 2
<211> LENGTH: 1971
<212> TYPE: DNA
<213> ORGANISM: Bacillus thuringiensis

<400> SEQUENCE: 2

```
atgccttcaa ataggaaaaa tgagaatgaa attataaatg ccttatcgat tccagctgta     60

tcgaatcatt ccgcacaaat ggatctatcg ctagatgctc gtattgagga ttctttgtgt    120

atagccgagg ggaataatat caatccactt gttagcgcat caacagtcca aacgggtata    180

aacatagctg gtagaatatt gggcgtatta ggtgtgccgt ttgctggaca actagctagt    240

ttttatagtt ttcttgttgg ggaattatgg cctagtggca gagatccatg ggaaattttc    300

ctggaacatg tagaacaact tataagacaa caagtaacag aaaatactag gaatacggct    360

attgctcgat tagaaggtct aggaagaggc tatagatctt accagcaggc tcttgaaact    420

tggttagata accgaaatga tgcaagatca agaagcatta ttcttgagcg ctatgttgct    480
```

```
ttagaacttg acattactac tgctataccg cttttcagaa tacgaaatga agaagttcca    540

ttattaatgg tatatgctca agctgcaaat ttacacctat tattattgag agacgcatcc    600

ctttttggta gtgaatgggg gatggcatct tccgatgtta accaatatta ccaagaacaa    660

atcagatata cagaggaata ttctaaccat tgcgtacaat ggtataatac agggctaaat    720

aacttaagag ggacaaatgc tgaaagttgg ttgcggtata atcaattccg tagagaccta    780

acgttagggg tattagattt agtagcccta ttcccaagct atgatactcg cacttatcca    840

atcaatacga gtgctcagtt aacaagagaa atttatacag atccaattgg gagaacaaat    900

gcaccttcag gatttgcaag tacgaattgg tttaataata atgcaccatc gttttctgcc    960

atagaggctg ccattttcag gcctccgcat ctacttgatt ttccagaaca acttacaatt   1020

tacagtgcat caagccgttg gagtagcact caacatatga attattgggt gggacatagg   1080

cttaacttcc gcccaatagg agggacatta aatacctcaa cacaaggact tactaataat   1140

acttcaatta atcctgtaac attacagttt acgtctcgtg acgtttatag aacagaatca   1200

aatgcaggga caaatatact atttactact cctgtgaatg gagtaccttg ggctagattt   1260

aattttataa accctcagaa tatttatgaa agaggcgcca ctacctacag tcaaccgtat   1320

cagggagttg ggattcaatt atttgattca gaaactgaat taccaccaga aacaacagaa   1380

cgaccaaatt atgaatcata tagtcataga ttatctcata taggactaat cataggaaac   1440

actttgagag caccagtcta ttcttggacg catcgtagtg cagatcgtac gaatacgatt   1500

ggaccaaata gaattactca aattcctgca gtgaagggaa gatttctttt taatggttct   1560

gtaatttcag gaccaggatt tactggtgga gacgtagtta gattgaatag gaataatggt   1620

aatattcaaa atagagggta tattgaagtt ccaattcaat tcacgtcgac atctaccaga   1680

tatcgagttc gagtacgtta tgcttctgta acctcgattg agctcaatgt taatttgggc   1740

aattcatcaa tttttacgaa cacattacca gcaacagctg catcattaga taatctacaa   1800

tcaggggatt ttggttatgt tgaaatcaac aatgctttta catccgcaac aggtaatata   1860

gtaggtgcta gaaattttag tgcaaatgca gaagtaataa tagacagatt tgaatttatc   1920

ccagttactg caaccttcga ggcagaatat gatttagaaa gagcacaaaa g            1971
```

<210> SEQ ID NO 3
<211> LENGTH: 651
<212> TYPE: PRT
<213> ORGANISM: Artificial Sequence
<220> FEATURE:
<223> OTHER INFORMATION: Cry1B variant

<400> SEQUENCE: 3

```
Met Pro Ser Asn Arg Lys Asn Glu Asn Glu Ile Ile Asn Ala Val Ser
1               5                   10                  15

Asn His Ser Ala Gln Met Asp Leu Ser Leu Asp Ala Arg Ile Glu Asp
            20                  25                  30

Ser Leu Cys Val Ala Glu Val Asn Asn Ile Asp Pro Phe Val Ser Ala
        35                  40                  45

Ser Thr Val Gln Thr Gly Ile Ser Ile Ala Gly Arg Ile Leu Gly Val
    50                  55                  60

Leu Gly Val Pro Phe Ala Gly Gln Leu Ala Ser Phe Tyr Ser Phe Leu
65                  70                  75                  80

Val Gly Glu Leu Trp Pro Ser Gly Arg Asp Pro Trp Glu Ile Phe Met
                85                  90                  95
```

-continued

```
Glu His Val Glu Gln Ile Val Arg Gln Gln Ile Thr Asp Ser Val Arg
            100                 105                 110

Asp Thr Ala Ile Ala Arg Leu Glu Gly Leu Gly Arg Gly Tyr Arg Ser
        115                 120                 125

Tyr Gln Gln Ala Leu Glu Thr Trp Leu Asp Asn Arg Asn Asp Ala Arg
    130                 135                 140

Ser Arg Ser Ile Ile Arg Glu Arg Tyr Ile Ala Leu Glu Leu Asp Ile
145                 150                 155                 160

Thr Thr Ala Ile Pro Leu Phe Ser Ile Arg Asn Gln Glu Val Pro Leu
                165                 170                 175

Leu Met Val Tyr Ala Gln Ala Ala Asn Leu His Leu Leu Leu Leu Arg
            180                 185                 190

Asp Ala Ser Leu Phe Gly Ser Glu Trp Gly Met Ser Ser Ser Asp Val
        195                 200                 205

Asn Gln Tyr Tyr Gln Glu Gln Ile Arg Tyr Thr Glu Glu Tyr Ser Asn
    210                 215                 220

His Cys Val Gln Trp Tyr Asn Thr Gly Leu Asn Asn Leu Arg Gly Thr
225                 230                 235                 240

Asn Ala Glu Ser Trp Leu Arg Tyr Asn Gln Phe Arg Arg Asp Leu Thr
                245                 250                 255

Leu Gly Val Leu Asp Leu Val Ala Leu Phe Pro Ser Tyr Asp Thr Arg
            260                 265                 270

Val Tyr Pro Met Asn Thr Ser Ala Gln Leu Thr Arg Glu Ile Tyr Thr
        275                 280                 285

Asp Pro Ile Gly Arg Thr Asn Ala Pro Ser Gly Phe Ala Ser Thr Asn
    290                 295                 300

Trp Phe Asn Asn Asn Ala Pro Ser Phe Ser Ala Ile Glu Ala Ala Ile
305                 310                 315                 320

Phe Arg Pro Pro His Leu Leu Asp Phe Pro Glu Gln Leu Thr Ile Tyr
                325                 330                 335

Ser Ala Ser Ser Arg Trp Ser Ser Thr Gln His Met Asn Tyr Trp Val
            340                 345                 350

Gly His Arg Leu Asn Phe Arg Pro Ile Gly Gly Thr Leu Asn Thr Ser
        355                 360                 365

Thr His Gly Ala Thr Asn Thr Ser Ile Asn Pro Val Thr Leu Gln Phe
    370                 375                 380

Thr Ser Arg Asp Val Tyr Arg Thr Glu Ser Phe Ala Gly Thr Asn Ile
385                 390                 395                 400

Leu Phe Thr Thr Pro Val Asn Gly Val Pro Trp Ala Arg Phe Asn Phe
                405                 410                 415

Ile Asn Pro Gln Asn Ile Tyr Glu Arg Gly Ala Thr Thr Tyr Ser Gln
            420                 425                 430

Pro Tyr Gln Gly Val Gly Ile Gln Leu Phe Asp Ser Glu Thr Glu Leu
        435                 440                 445

Pro Pro Glu Thr Thr Glu Arg Pro Asn Tyr Glu Ser Tyr Ser His Arg
    450                 455                 460

Leu Ser His Ile Gly Leu Ile Ile Gly Asn Thr Leu Arg Ala Pro Val
465                 470                 475                 480

Tyr Ser Trp Thr His Arg Ser Ala Asp Arg Thr Asn Thr Ile Gly Pro
                485                 490                 495

Asn Arg Ile Thr Gln Ile Pro Ala Val Lys Gly Arg Phe Leu Phe Asn
            500                 505                 510

Gly Ser Val Ile Ser Gly Pro Gly Phe Thr Gly Gly Asp Val Val Arg
```

-continued

```
        515                 520                 525

Leu Asn Arg Asn Asn Gly Asn Ile Gln Asn Arg Gly Tyr Ile Glu Val
    530                 535                 540

Pro Ile Gln Phe Thr Ser Thr Ser Thr Arg Tyr Arg Val Arg Val Arg
545                 550                 555                 560

Tyr Ala Ser Val Thr Ser Ile Glu Leu Asn Val Asn Leu Gly Asn Ser
                565                 570                 575

Ser Ile Phe Thr Asn Thr Leu Pro Ala Thr Ala Ala Ser Leu Asp Asn
            580                 585                 590

Leu Gln Ser Gly Asp Phe Gly Tyr Val Glu Ile Asn Asn Ala Phe Thr
        595                 600                 605

Ser Ala Thr Gly Asn Ile Val Gly Ala Arg Asn Phe Ser Ala Asn Ala
    610                 615                 620

Glu Val Ile Ile Asp Arg Phe Glu Phe Ile Pro Val Thr Ala Thr Phe
625                 630                 635                 640

Glu Ala Glu Tyr Asp Leu Glu Arg Ala Gln Lys
                645                 650


<210> SEQ ID NO 4
<211> LENGTH: 1953
<212> TYPE: DNA
<213> ORGANISM: Artificial Sequence
<220> FEATURE:
<223> OTHER INFORMATION: coding sequence of Cry1B variant

<400> SEQUENCE: 4

atgccttcaa ataggaaaaa tgagaatgaa attataaatg ctgtatcgaa tcattccgca     60

caaatggatc tatcgctaga tgctcgtatt gaagatagct tgtgtgtagc cgaggtgaac    120

aatattgatc catttgttag cgcatcaaca gtccaaacag gtattagtat agctggtaga    180

atattgggcg tattaggtgt gccgtttgct ggacaactag ctagttttta tagttttctt    240

gttggggaat tatggcctag cggcagagat ccatgggaaa tttttatgga acatgtcgag    300

caaattgtaa gacaacaaat aacggacagt gttagggata ccgctattgc tcgtttagaa    360

ggtctaggaa gagggtatag atcttaccag caggctcttg aaacttggtt agataaccga    420

aatgatgcaa gatcaagaag cattattcgt gagagatata ttgctttaga acttgacatt    480

actactgcta taccgctttt cagcatacga aatcaagagg ttccattatt aatggtatat    540

gctcaagctg caaatttaca cctattatta ttgagagacg catccctttt tggtagtgaa    600

tgggggatgt catcttccga tgttaaccaa tattaccaag aacaaatcag atatacagag    660

gaatattcta accattgcgt acaatggtat aatacagggc taaataactt aagagggaca    720

aatgctgaaa gttggttgcg gtataatcaa ttccgtagag atctaacgtt aggagtatta    780

gatctagtgg cactattccc aagctatgac acgcgtgttt atccaatgaa taccagtgct    840

caattaacaa gagaaattta tacagatcca attgggagaa caaatgcacc ttcaggattt    900

gcaagtacga attggtttaa taataatgca ccatcgtttt ctgccataga ggctgccatt    960

ttcaggcctc cgcatctact tgattttcca gaacaactta caatttacag tgcatcaagc   1020

cgttggagta gcactcaaca tatgaattat tgggtgggac ataggcttaa cttccgccca   1080

ataggaggga cattaaatac ctcaacgcat ggggctacca atacttctat taatcctgta   1140

acattacagt tcacatctcg agacgtttat aggactgaat catttgcagg gacaaatata   1200

ctatttacta ctcctgtgaa tggagtacct tgggctagat ttaattttat aaaccctcag   1260

aatatttatg aaagaggcgc cactacctac agtcaaccgt atcagggagt tgggattcaa   1320
```

```
ttatttgatt cagaaactga attaccacca gaaacaacag aacgaccaaa ttatgaatca   1380

tatagtcata gattatctca tataggacta atcataggaa acactttgag agcaccagtc   1440

tattcttgga cgcaccgtag tgcagatcgt acgaatacga ttggaccaaa tagaattact   1500

caaattcctg cagtgaaggg aagatttctt tttaatggtt ctgtaatttc aggaccagga   1560

tttactggtg gagacgtagt tagattgaat aggaataatg gtaatattca aaatagaggg   1620

tatattgaag ttccaattca attcacgtcg acatctacca gatatcgagt tcgagtacgt   1680

tatgcttctg taacctcgat tgagctcaat gttaatttgg gcaattcatc aatttttacg   1740

aacacattac cagcaacagc tgcatcatta gataatctac aatcagggga ttttggttat   1800

gttgaaatca acaatgcttt tacatccgca acaggtaata tagtaggtgc tagaaatttt   1860

agtgcaaatg cagaagtaat aatagacaga tttgaattta tcccagttac tgcaaccttc   1920

gaggcagaat atgatttaga aagagcacaa aag                                1953

<210> SEQ ID NO 5
<211> LENGTH: 655
<212> TYPE: PRT
<213> ORGANISM: Artificial Sequence
<220> FEATURE:
<223> OTHER INFORMATION: Cry1B variant

<400> SEQUENCE: 5

Met Pro Ser Asn Arg Lys Asn Glu Asn Glu Ile Ile Asn Ala Leu Ser
1               5                   10                  15

Ile Pro Ala Val Ser Asn His Ser Ala Gln Met Asp Leu Ser Leu Asp
            20                  25                  30

Ala Arg Ile Glu Asp Ser Leu Cys Ile Ala Glu Gly Asn Asn Ile Asn
        35                  40                  45

Pro Leu Val Ser Ala Ser Thr Val Gln Thr Gly Ile Asn Ile Ala Gly
    50                  55                  60

Arg Ile Leu Gly Val Leu Gly Val Pro Phe Ala Gly Gln Leu Ala Ser
65                  70                  75                  80

Phe Tyr Ser Phe Ile Val Gly Glu Leu Trp Pro Ser Gly Arg Asp Pro
                85                  90                  95

Trp Glu Ile Phe Met Glu His Val Glu Gln Leu Val Arg Gln Gln Ile
            100                 105                 110

Thr Glu Asn Ala Arg Asn Thr Ala Leu Ala Arg Leu Gln Gly Leu Gly
        115                 120                 125

Ala Ser Phe Arg Ala Tyr Gln Gln Ser Leu Glu Asp Trp Leu Glu Asn
    130                 135                 140

Arg Asp Asn Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Asn Asn
                165                 170                 175

Gln Gln Val Pro Leu Leu Met Val Tyr Ala Gln Ala Ala Asn Leu His
            180                 185                 190

Leu Leu Leu Leu Arg Asp Ala Ser Leu Phe Gly Ser Glu Phe Gly Leu
        195                 200                 205

Thr Ser Gln Glu Ile Gln Arg Tyr Tyr Glu Arg Gln Ala Glu Lys Thr
    210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
```

```
                245                 250                 255

Arg Arg Asp Leu Thr Leu Gly Val Leu Asp Leu Val Ala Leu Phe Pro
            260                 265                 270

Ser Tyr Asp Thr Arg Ile Tyr Pro Ile Asn Thr Ser Ala Gln Leu Thr
        275                 280                 285

Arg Glu Ile Tyr Thr Asp Pro Ile Gly Arg Thr Asn Ala Pro Ser Gly
    290                 295                 300

Phe Ala Ser Thr Asn Trp Phe Asn Asn Asn Ala Pro Ser Phe Ser Ala
305                 310                 315                 320

Ile Glu Ala Ala Ile Phe Arg Pro Pro His Leu Leu Asp Phe Pro Glu
                325                 330                 335

Gln Leu Thr Ile Tyr Ser Ala Ser Ser Arg Trp Ser Ser Thr Gln His
            340                 345                 350

Met Asn Tyr Trp Val Gly His Arg Leu Asn Phe Arg Pro Ile Gly Gly
        355                 360                 365

Thr Leu Asn Thr Ser Thr His Gly Ala Thr Asn Thr Ser Ile Asn Pro
    370                 375                 380

Val Thr Leu Gln Phe Thr Ser Arg Asp Val Tyr Arg Thr Glu Ser Tyr
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
            420                 425                 430

Leu Tyr Thr Ile Gly Tyr Thr Gly Val Gly Thr Gln Leu Phe Asp Ser
        435                 440                 445

Glu Thr Glu Leu Pro Pro Glu Thr Thr Glu Arg Pro Asn Tyr Glu Ser
    450                 455                 460

Tyr Ser His Arg Leu Ser Asn Ile Arg Leu Ile Ile Gly Asn Thr Leu
465                 470                 475                 480

Arg Ala Pro Val Tyr Ser Trp Thr His Arg Ser Ala Asp Arg Thr Asn
                485                 490                 495

Thr Ile Ala Thr Asn Ile Ile Thr Gln Ile Pro Ala Val Lys Gly Asn
            500                 505                 510

Phe Leu Phe Asn Gly Ser Val Ile Ser Gly Pro Gly Phe Thr Gly Gly
        515                 520                 525

Asp Leu Val Arg Leu Asn Asn Ser Gly Asn Asn Ile Gln Asn Arg Gly
    530                 535                 540

Tyr Ile Glu Val Pro Ile Gln Phe Ile Ser Thr Ser Thr Arg Tyr Arg
545                 550                 555                 560

Val Arg Val Arg Tyr Ala Ser Val Thr Pro Ile Gln Leu Ser Val Asn
                565                 570                 575

Trp Gly Asn Ser Asn Ile Phe Ser Ser Ile Val Pro Ala Thr Ala Thr
            580                 585                 590

Ser Leu Asp Asn Leu Gln Ser Arg Asn Phe Gly Tyr Phe Glu Ser Thr
        595                 600                 605

Asn Ala Phe Thr Ser Ala Thr Gly Asn Val Val Gly Val Arg Asn Phe
    610                 615                 620

Ser Glu Asn Ala Gly Val Ile Ile Asp Arg Phe Glu Phe Ile Pro Val
625                 630                 635                 640

Thr Ala Thr Phe Glu Ala Glu Tyr Asp Leu Glu Arg Ala Gln Glu
                645                 650                 655
```

<210> SEQ ID NO 6

<211> LENGTH: 1965
<212> TYPE: DNA
<213> ORGANISM: Artificial Sequence
<220> FEATURE:
<223> OTHER INFORMATION: coding sequence of Cry1B variant

<400> SEQUENCE: 6

```
atgccgagca atcgtaagaa tgaaaatgaa atcattaacg cactgtccat ccctgcagtg     60
agcaatcaca gcgcgcagat ggatttgagc ctggatgcgc gtatcgagga cagcctgtgt    120
attgccgagg gcaacaacat caatccgttg gtcagcgcga gcaccgtgca aaccggcatt    180
aacattgccg gtcgtatcct gggtgtcctg ggcgttccgt ttgcgggtca gctggcgagc    240
ttttacagct ttatcgttgg tgagttgtgg ccgtcgggtc gtgacccttg ggagattttc    300
atggagcacg tcgagcaact ggtgcgccaa cagattacgg agaatgcgcg caacaccgct    360
ctggcgcgtc tgcaaggtct gggtgcaagc ttccgcgctt accagcagtc cctggaagat    420
tggttggaaa accgtgataa tgcgcgcact cgctccgtcc tgtacacgca gtacatcgcg    480
ctggagctgg acttcttgaa cgcgatgccg ctgtttgcaa tcaacaacca gcaagtgccg    540
ctgctgatgg tctacgccca agccgcgaat ctgcacttgc tgctgctgcg cgacgcatct    600
ctgttcggta gcgaatttgg cctgaccagc caggagatcc agcgctacta tgagcgtcag    660
gccgagaaaa cgcgtgaata ctccgactac tgcgctcgtt ggtacaacac gggtctgaac    720
aatctgcgtg gcaccaacgc ggagtcctgg ctgcgttaca accagtttcg tcgcgatctg    780
accctgggtg ttttggattt ggttgcgctg tttccgagct atgacacccg catctatccg    840
atcaacacca gcgcgcaact gactcgtgaa atctatacgg acccgattgg ccgcactaat    900
gcaccgtccg gtttcgcaag caccaactgg ttcaataaca atgcaccgag cttcagcgcg    960
atcgaggccg cgatctttcg tccgccgcac ctgttggact tcccggagca gctgaccatc   1020
tactctgcat ctagccgttg gagcagcacg cagcacatga attactgggt tggccatcgt   1080
ctgaacttcc gcccgattgg tggtacgctg aacactagca cgcacggtgc cactaacacg   1140
agcatcaacc cggtgacgct gcaattcacc agccgtgatg tttaccgtac cgagtcctac   1200
gccggcatca acattctgct gaccaccccg gttaacggcg tcccttgggc tcgtttcaat   1260
tggcgtaacc cactgaatag cctgcgtggt tctttgctgt acaccattgg ttataccggc   1320
gtcggtacgc aactgtttga ctcggaaact gagctgccac cggaaactac cgagcgtccg   1380
aactacgaat cttatagcca ccgtctgtcc aatatccgtc tgatcatcgg caacaccctg   1440
cgtgcgccgg tgtacagctg gacccatcgt agcgccgatc gcacgaacac gattgccacc   1500
aacattatca cccagatccc ggcagtgaaa ggcaactttc tgtttaacgg cagcgtgatc   1560
agcggtccag gttttaccgg cggtgacctg gtgcgcctga acaacagcgg caacaatatc   1620
caaaaccgtg gttatatcga agtcccgatt caattcatca gcacgagcac ccgttaccgc   1680
gtccgtgttc gctacgcatc cgttacgccg atccaactga gcgttaactg gggcaattcc   1740
aacattttca gcagcattgt ccctgctacg gcgacctctc tggacaattt gcagagccgt   1800
aacttcggct atttcgaaag caccaacgct ttcaccagcg ctacgggcaa tgtggttggt   1860
gttcgcaatt tcagcgagaa tgcgggcgtc atcattgacc gttttgagtt tatcccggtg   1920
accgcgacct tcgaagcgga gtacgatctg gagcgtgcgc aggaa                   1965
```

<210> SEQ ID NO 7
<211> LENGTH: 655
<212> TYPE: PRT
<213> ORGANISM: Artificial Sequence
<220> FEATURE:
<223> OTHER INFORMATION: Cry1B variant

<400> SEQUENCE: 7

```
Met Pro Ser Asn Arg Lys Asn Glu Asn Gly Ile Ile Asn Ala Leu Ser
1               5                   10                  15

Ile Pro Ala Val Ser Asn His Ser Ala Gln Met Asp Leu Ser Pro Asp
            20                  25                  30

Ala Arg Ile Glu Asp Ser Leu Cys Val Ala Glu Val Asn Asn Ile Asp
        35                  40                  45

Pro Phe Val Ser Ala Ser Thr Val Gln Thr Gly Ile Asn Ile Ala Gly
    50                  55                  60

Arg Ile Leu Gly Val Leu Gly Val Pro Phe Ala Gly Gln Leu Ala Ser
65                  70                  75                  80

Phe Tyr Ser Phe Ile Val Gly Glu Leu Trp Pro Ser Gly Arg Asp Pro
                85                  90                  95

Trp Glu Ile Phe Leu Glu His Val Glu Gln Leu Val Arg Gln Gln Ile
            100                 105                 110

Thr Glu Asn Ala Arg Asn Thr Ala Leu Ala Arg Leu Gln Gly Leu Gly
        115                 120                 125

Ala Ser Phe Arg Ala Tyr Gln Gln Ser Leu Glu Asp Trp Leu Glu Asn
    130                 135                 140

Arg Asp Asp Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Asn Asn
                165                 170                 175

Gln Arg Val Pro Leu Leu Met Val Tyr Ala Gln Ala Ala Asn Leu His
            180                 185                 190

Leu Leu Leu Leu Arg Asp Ala Ser Leu Phe Gly Ser Glu Phe Gly Leu
        195                 200                 205

Thr Ser Gln Glu Ile Gln Arg Tyr Tyr Glu Arg Gln Ala Glu Lys Thr
    210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Val Tyr Pro Ile Asn Thr Ser Ala Gln Leu Thr
        275                 280                 285

Arg Glu Ile Tyr Thr Asp Pro Ile Gly Arg Thr Asn Ala Pro Ser Gly
    290                 295                 300

Phe Ala Ser Thr Asn Trp Phe Asn Asn Asn Ala Pro Ser Phe Ser Ala
305                 310                 315                 320

Ile Glu Ala Ala Val Ile Arg Pro Pro His Leu Leu Asp Phe Pro Glu
                325                 330                 335

Gln Leu Thr Ile Phe Ser Val Leu Ser Arg Trp Ser Ser Thr Gln His
            340                 345                 350

Met Asn Tyr Trp Val Gly His Arg Leu Glu Ser Arg Thr Ile Arg Gly
        355                 360                 365

Ser Leu Ser Thr Ser Thr His Gly Asn Thr Asn Thr Ser Ile Asn Pro
    370                 375                 380

Val Thr Leu Gln Phe Thr Ser Arg Asp Val Tyr Arg Thr Glu Ser Tyr
385                 390                 395                 400
```

-continued

```
Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
            420                 425                 430

Leu Tyr Thr Ile Gly Tyr Thr Gly Val Gly Thr Gln Leu Phe Asp Ser
        435                 440                 445

Glu Thr Glu Leu Pro Pro Glu Thr Thr Glu Arg Pro Asn Tyr Glu Ser
    450                 455                 460

Tyr Ser His Arg Leu Ser His Ile Gly Leu Ile Ile Gly Asn Thr Leu
465                 470                 475                 480

Arg Ala Pro Val Tyr Ser Trp Thr His Arg Ser Ala Asp Arg Thr Asn
                485                 490                 495

Thr Thr Gly Pro Asn Arg Ile Thr Gln Ile Pro Ala Val Lys Gly Asn
            500                 505                 510

Phe Leu Phe Asn Gly Ser Val Ile Ser Gly Pro Gly Phe Thr Gly Gly
        515                 520                 525

Asp Leu Val Arg Leu Asn Asn Ser Gly Asn Asn Ile Gln Asn Arg Gly
    530                 535                 540

Tyr Leu Glu Val Pro Ile Gln Phe Ile Ser Thr Ser Thr Arg Tyr Arg
545                 550                 555                 560

Val Arg Val Arg Tyr Ala Ser Val Thr Pro Ile Gln Leu Ser Val Asn
                565                 570                 575

Trp Gly Asn Ser Asn Ile Phe Ser Ser Ile Val Pro Ala Thr Ala Thr
            580                 585                 590

Ser Leu Asp Asn Leu Gln Ser Arg Asp Phe Gly Tyr Phe Glu Ser Thr
        595                 600                 605

Asn Ala Phe Thr Ser Ala Thr Gly Asn Val Val Gly Val Arg Asn Phe
    610                 615                 620

Ser Glu Asn Ala Gly Val Ile Ile Asp Arg Phe Glu Phe Ile Pro Val
625                 630                 635                 640

Thr Ala Thr Phe Glu Ala Glu Tyr Asp Leu Glu Arg Ala Gln Glu
                645                 650                 655
```

```
<210> SEQ ID NO 8
<211> LENGTH: 1965
<212> TYPE: DNA
<213> ORGANISM: Artificial Sequence
<220> FEATURE:
<223> OTHER INFORMATION: coding sequence of Cry1B variant

<400> SEQUENCE: 8

atgccgagca atcgtaagaa tgaaaatgga atcattaacg cgctgtccat ccctgcagtg      60

agcaatcaca gcgcgcagat ggatttgagc ccggatgcgc gtatcgagga cagcctgtgt     120

gtcgccgagg taaacaatat tgatccgttc gtcagcgcga gcaccgtgca aaccggcatt     180

aacattgccg gtcgtatcct gggtgtcctg ggcgttccgt ttgcgggtca gctggcgagc     240

ttttacagct ttatcgttgg tgagttgtgg ccgtcgggtc gtgacccttg ggagattttc     300

ttggagcacg tcgagcaact ggtgcgccaa cagattacgg agaatgcgcg caacaccgct     360

ctggcgcgtc tgcaaggtct gggtgcaagc ttccgcgctt accagcagtc cctggaagat     420

tggttggaaa accgtgatga tgcgcgcact cgctccgtcc tgtacacgca gtacatcgcg     480

ctggagctgg acttcttgaa cgcgatgccg ctgtttgcaa tcaacaacca gcgagtgccg     540

ctgctgatgg tctacgccca agccgcgaat ctgcacttgc tgctgctgcg cgacgcatct     600
```

-continued

```
ctgttcggta gcgaatttgg cctgaccagc caggagatcc agcgctacta tgagcgtcag    660

gccgagaaaa cgcgtgaata ctccgactac tgcgctcgtt ggtacaacac gggtctgaac    720

aatctgcgtg gcaccaacgc ggagtcctgg ctgcgttata accagtttcg tcgcgatctg    780

accctgggtg tattggattt ggttgcgctg tttccgagct atgacacccg cgtgtatccg    840

atcaacacca gcgcgcaact gactcgtgaa atctatacgg acccgattgg ccgcactaat    900

gcaccgtccg gtttcgcaag caccaactgg ttcaataaca atgcaccgag cttcagcgcg    960

atcgaggcgg ctgtcatccg tccgccgcac ctgttggact tcccggagca gctgaccatc   1020

ttttctgtgt tgtctcgttg gagcagcacg cagcacatga attactgggt tggccatcgt   1080

ctggaaagcc gcaccattcg cggtagcctg agcactagca cgcacggtaa tactaacacg   1140

agcatcaacc cggtgacgct gcaattcacc agccgtgatg tttaccgtac cgagtcctac   1200

gccggcatca acattctgct gaccaccccg gttaacggcg tcccttgggc tcgtttcaat   1260

tggcgtaacc cactgaatag cctgcgtggt tctttgctgt acaccattgg ttataccggc   1320

gtcggtacgc aactgtttga ctcggaaact gagctgccac cggaaactac cgagcgtccg   1380

aactacgaat cttatagcca ccgtctgtcc catattggtc tgatcatcgg caacaccctg   1440

cgtgcaccgg tgtacagctg gacccatcgt agcgccgatc gcacgaacac gactggtccg   1500

aaccgtatca cccagatccc ggcagtgaaa ggcaactttc tgtttaacgg cagcgtgatc   1560

agcggtccag gttttaccgg cggtgacctg gtgcgcctga acaacagcgg caacaatatc   1620

caaaaccgtg gttatctgga agtcccgatt caattcatca gcacgagcac ccgttaccgc   1680

gtccgtgttc gctacgcatc cgttacgccg atccaactga gcgttaactg gggcaattcc   1740

aacattttca gcagcattgt ccctgctacg gcgacctctc tggacaattt gcagagccgt   1800

gacttcggct atttcgaaag caccaacgct ttcaccagcg ctacgggcaa tgtggttggt   1860

gttcgcaatt tcagcgagaa tgcgggcgtc atcattgacc gttttgagtt tatcccggtg   1920

accgcgacct tcgaagcgga gtacgatctg gagcgtgcgc aggaa                   1965
```

<210> SEQ ID NO 9
<211> LENGTH: 650
<212> TYPE: PRT
<213> ORGANISM: Artificial Sequence
<220> FEATURE:
<223> OTHER INFORMATION: Cry1B variant

<400> SEQUENCE: 9

```
Met Pro Ser Asn Arg Lys Asn Glu Asn Glu Ile Ile Asn Ala Val Ser
1               5                   10                  15

Asn His Ser Ala Gln Met Asp Leu Ser Pro Asp Ala Arg Ile Glu Asp
            20                  25                  30

Ser Leu Cys Val Ala Glu Val Asn Asn Ile Asp Pro Phe Val Ser Ala
        35                  40                  45

Ser Thr Val Gln Thr Gly Ile Asn Ile Ala Gly Arg Ile Leu Gly Val
    50                  55                  60

Leu Gly Val Pro Phe Ala Gly Gln Leu Ala Ser Phe Tyr Ser Phe Leu
65                  70                  75                  80

Val Gly Glu Leu Trp Pro Ser Gly Arg Asp Pro Trp Glu Ile Phe Met
                85                  90                  95

Glu His Val Glu Gln Ile Val Arg Gln Gln Ile Thr Glu Asn Ala Arg
            100                 105                 110

Asn Thr Ala Leu Ala Arg Leu Gln Gly Leu Gly Ala Ser Phe Arg Ala
        115                 120                 125
```

-continued

```
Tyr Gln Gln Ser Leu Glu Asp Trp Leu Glu Asn Arg Asp Asp Ala Arg
    130                 135                 140

Thr Arg Ser Val Leu Tyr Thr Gln Tyr Ile Ala Leu Glu Leu Asp Phe
145                 150                 155                 160

Leu Asn Ala Met Pro Leu Phe Ala Ile Asn Asn Gln Gln Val Pro Leu
                165                 170                 175

Leu Met Val Tyr Ala Gln Ala Ala Asn Leu His Leu Leu Leu Leu Arg
            180                 185                 190

Asp Ala Ser Leu Phe Gly Ser Glu Phe Gly Leu Thr Ser Gln Glu Ile
        195                 200                 205

Gln Arg Tyr Tyr Glu Arg Gln Ala Glu Lys Thr Arg Glu Tyr Ser Asp
    210                 215                 220

Tyr Cys Ala Arg Trp Tyr Asn Thr Gly Leu Asn Asn Leu Arg Gly Thr
225                 230                 235                 240

Asn Ala Glu Ser Trp Leu Arg Tyr Asn Gln Phe Arg Arg Asp Leu Thr
                245                 250                 255

Leu Gly Val Leu Asp Leu Val Ala Leu Phe Pro Ser Tyr Asp Thr Arg
            260                 265                 270

Ile Tyr Pro Ile Asn Thr Ser Ala Gln Leu Thr Arg Glu Ile Tyr Thr
        275                 280                 285

Asp Pro Ile Gly Arg Thr Asn Ala Pro Ser Gly Phe Ala Ser Thr Asn
    290                 295                 300

Trp Phe Asn Asn Asn Ala Pro Ser Phe Ser Ala Ile Glu Ala Ala Val
305                 310                 315                 320

Ile Arg Pro Pro His Leu Leu Asp Phe Pro Glu Gln Leu Thr Ile Tyr
                325                 330                 335

Ser Ala Ser Ser Arg Trp Ser Ser Thr Gln His Met Asn Tyr Trp Val
            340                 345                 350

Gly His Arg Leu Asn Phe Arg Pro Ile Gly Gly Thr Leu Asn Thr Ser
        355                 360                 365

Thr His Gly Ala Thr Asn Thr Ser Ile Asn Pro Val Thr Leu Gln Phe
    370                 375                 380

Thr Ser Arg Asp Val Tyr Arg Thr Glu Ser Tyr Ala Gly Ile Asn Ile
385                 390                 395                 400

Leu Leu Thr Thr Pro Val Asn Gly Val Pro Trp Ala Arg Phe Asn Trp
                405                 410                 415

Arg Asn Pro Leu Asn Ser Leu Arg Gly Ser Leu Leu Tyr Thr Ile Gly
            420                 425                 430

Tyr Thr Gly Val Gly Ile Gln Leu Phe Asp Ser Glu Thr Glu Leu Pro
        435                 440                 445

Pro Glu Thr Thr Glu Arg Pro Asn Tyr Glu Ser Tyr Ser His Arg Leu
    450                 455                 460

Ser Asn Ile Arg Leu Ile Ser Gly Asn Thr Leu Arg Ala Pro Val Tyr
465                 470                 475                 480

Ser Trp Thr His Arg Ser Ala Asp Arg Thr Asn Thr Ile Ala Thr Asn
                485                 490                 495

Ile Ile Thr Gln Ile Pro Ala Val Lys Gly Asn Phe Leu Phe Asn Gly
            500                 505                 510

Ser Val Thr Ser Gly Pro Gly Phe Thr Gly Gly Asp Leu Val Arg Leu
        515                 520                 525

Asn Asn Ser Gly Asn Asn Ile Gln Asn Arg Gly Tyr Leu Glu Val Pro
    530                 535                 540
```

-continued

```
Ile Gln Phe Ile Ser Thr Ser Thr Arg Tyr Arg Val Arg Val Arg Tyr
545                 550                 555                 560

Ala Ser Val Thr Pro Ile Gln Leu Ser Val Asn Trp Gly Asn Ser Asn
                565                 570                 575

Ile Phe Ser Ser Ile Val Pro Ala Thr Ala Thr Ser Leu Asp Asn Leu
            580                 585                 590

Gln Ser Arg Asp Phe Gly Tyr Phe Glu Ser Thr Asn Ala Phe Thr Ser
        595                 600                 605

Ala Thr Gly Asn Val Val Gly Val Arg Asn Phe Ser Glu Asn Ala Gly
    610                 615                 620

Val Ile Ile Asp Arg Phe Glu Phe Ile Pro Val Thr Ala Thr Phe Glu
625                 630                 635                 640

Ala Glu Tyr Asp Leu Glu Arg Ala Gln Glu
                645                 650

<210> SEQ ID NO 10
<211> LENGTH: 1950
<212> TYPE: DNA
<213> ORGANISM: Artificial Sequence
<220> FEATURE:
<223> OTHER INFORMATION: coding sequence of Cry1B variant

<400> SEQUENCE: 10
atgccgagca atcgtaagaa tgaaaatgaa atcattaacg cagtgagcaa tcacagcgcg     60
cagatggatt tgagcccgga tgcgcgtatc gaggacagcc tgtgtgtcgc cgaggtaaac    120
aatattgatc cgttcgtcag cgcgagcacc gtgcaaaccg gcattaacat tgccggtcgt    180
atcctgggtg tcctgggcgt tccgtttgcg ggtcagctgg cgagctttta cagctttttg    240
gttggtgagt tgtggccgtc gggtcgtgac ccttgggaga ttttcatgga gcacgtcgag    300
caaattgtgc gccaacagat tacggagaat gcgcgcaaca ccgctctggc gcgtctgcaa    360
ggtctgggtg caagcttccg cgcttaccag cagtccctgg aagattggtt ggaaaaccgt    420
gatgatgcgc gcactcgctc cgtcctgtac acgcagtaca tcgcgctgga gctggacttc    480
ttgaacgcga tgccgctgtt tgcaatcaac aaccagcaag tgccgctgct gatggtctac    540
gcccaagccg cgaatctgca cttgctgctg ctgcgcgacg catctctgtt cggtagcgaa    600
tttggcctga ccagccagga gatccagcgc tactatgagc gtcaggccga gaaaacgcgt    660
gaatactccg actactgcgc tcgttggtac aacacgggtc tgaacaatct gcgtggcacc    720
aacgcggagt cctggctgcg ttacaaccag tttcgtcgcg atctgaccct gggtgttttg    780
gatttggttg cgctgtttcc gagctatgac acccgcatct atccgatcaa caccagcgcg    840
caactgactc gtgaaatcta tacggacccg attggccgca ctaatgcacc gtccggtttc    900
gcaagcacca actggttcaa taacaatgca ccgagcttca gcgcgatcga ggcggctgtc    960
atccgtccgc cgcacctgtt ggacttcccg gagcagctga ccatctactc tgcatctagc   1020
cgttggagca gcacgcagca catgaattac tgggttggcc atcgtctgaa cttccgcccg   1080
attggtggta cgctgaacac tagcacgcac ggtgccacta acacgagcat caacccggtg   1140
acgctgcaat tcaccagccg tgatgtttac cgtaccgagt cctacgccgg gatcaacatt   1200
ctgctgacca ccccggttaa cggcgtccct tgggctcgtt tcaattggcg taacccactg   1260
aatagcctgc gtggttcttt gctgtacacc attggttata ccggcgtcgg tattcaactg   1320
tttgactcgg aaactgagct gccaccggaa actaccgagc gtccgaacta cgaatcttat   1380
agccaccgtc tgtccaatat ccgtctgatc agcggcaaca ccctgcgtgc gccggtgtac   1440
```

-continued

```
agctggaccc accgtagcgc cgatcgcacg aacacgattg ccaccaacat tatcacccag   1500

atcccggcag tgaaaggcaa ctttctgttt aacggcagcg tgaccagcgg tccaggtttt   1560

accggcggtg acctggtgcg cctgaacaac agcggcaaca atatccaaaa ccgtggttat   1620

ctggaagtcc cgattcaatt catcagcacg agcacccgtt accgcgtccg tgttcgctac   1680

gcatccgtta cgccgatcca actgagcgtt aactggggca attccaacat tttcagcagc   1740

attgtccctg ctacggcgac ctctctggac aatttgcaga gccgtgactt cggctatttc   1800

gaaagcacca acgctttcac cagcgctacg ggcaatgtgg ttggtgttcg caatttcagc   1860

gagaatgcgg gcgtcatcat tgaccgtttt gagtttatcc cggtgaccgc gaccttcgaa   1920

gcggagtacg atctggagcg tgcgcaggaa                                     1950


<210> SEQ ID NO 11
<211> LENGTH: 655
<212> TYPE: PRT
<213> ORGANISM: Artificial Sequence
<220> FEATURE:
<223> OTHER INFORMATION: Cry1B variant

<400> SEQUENCE: 11

Met Pro Ser Asn Arg Lys Asn Glu Asn Glu Ile Ile Asn Ala Leu Ser
1               5                   10                  15

Ile Pro Ala Val Ser Asn His Ser Ala Gln Met Asp Leu Ser Leu Asp
            20                  25                  30

Ala Arg Ile Glu Asp Ser Leu Cys Ile Ala Glu Gly Asn Asn Ile Asn
        35                  40                  45

Pro Leu Val Ser Ala Ser Thr Val Gln Thr Gly Ile Asn Ile Ala Gly
    50                  55                  60

Arg Ile Leu Gly Val Leu Gly Val Pro Phe Ala Gly Gln Leu Ala Ser
65                  70                  75                  80

Phe Tyr Ser Phe Ile Val Gly Glu Leu Trp Pro Ser Gly Arg Asp Pro
                85                  90                  95

Trp Glu Ile Phe Met Glu His Val Glu Gln Leu Val Arg Gln Gln Ile
            100                 105                 110

Thr Glu Asn Ala Arg Asn Thr Ala Leu Ala Arg Leu Gln Gly Leu Gly
        115                 120                 125

Ala Ser Phe Arg Ala Tyr Gln Gln Ser Leu Glu Asp Trp Leu Glu Asn
    130                 135                 140

Arg Asp Asn Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Asn Asn
                165                 170                 175

Gln Gln Val Pro Leu Leu Met Val Tyr Ala Gln Ala Ala Asn Leu His
            180                 185                 190

Leu Leu Leu Leu Arg Asp Ala Ser Leu Phe Gly Ser Glu Phe Gly Leu
        195                 200                 205

Thr Ser Gln Glu Ile Gln Arg Tyr Tyr Glu Arg Gln Ala Glu Lys Thr
    210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
            260                 265                 270
```

```
Ser Tyr Asp Thr Arg Ile Tyr Pro Ile Asn Thr Ser Ala Gln Leu Thr
        275                 280                 285

Arg Glu Ile Tyr Thr Asp Pro Ile Gly Arg Thr Asn Ala Pro Ser Gly
    290                 295                 300

Phe Ala Ser Thr Asn Trp Phe Asn Asn Asn Ala Pro Ser Phe Ser Ala
305                 310                 315                 320

Ile Glu Ala Ala Ile Phe Arg Pro Pro His Leu Leu Asp Phe Pro Glu
                325                 330                 335

Gln Leu Thr Ile Tyr Ser Ala Ser Ser Arg Trp Ser Ser Thr Gln His
            340                 345                 350

Met Asn Tyr Trp Val Gly His Arg Leu Asn Phe Arg Pro Ile Gly Gly
        355                 360                 365

Thr Leu Asn Thr Ser Thr His Gly Ala Thr Asn Thr Ser Ile Asn Pro
    370                 375                 380

Val Thr Leu Gln Phe Thr Ser Arg Asp Val Tyr Arg Thr Glu Ser Tyr
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
            420                 425                 430

Leu Tyr Thr Ile Gly Tyr Thr Gly Val Gly Thr Gln Leu Phe Asp Ser
        435                 440                 445

Glu Thr Glu Leu Pro Pro Glu Thr Thr Glu Arg Pro Asn Tyr Glu Ser
    450                 455                 460

Tyr Ser His Arg Leu Ser Asn Ile Arg Leu Ile Ile Gly Asn Thr Leu
465                 470                 475                 480

Arg Ala Pro Val Tyr Ser Trp Thr His Arg Ser Ala Asp Arg Thr Asn
                485                 490                 495

Thr Ile Ala Thr Asn Ile Ile Thr Gln Ile Pro Ala Val Lys Gly Asn
            500                 505                 510

Phe Leu Phe Asn Gly Ser Val Ile Ser Gly Pro Gly Phe Thr Gly Gly
        515                 520                 525

Asp Leu Val Arg Leu Asn Asn Ser Gly Asn Asn Ile Gln Asn Arg Gly
    530                 535                 540

Tyr Ile Glu Val Pro Ile Gln Phe Ile Ser Thr Ser Thr Arg Tyr Arg
545                 550                 555                 560

Val Arg Val Arg Tyr Ala Ser Val Thr Pro Ile Gln Leu Ser Val Asn
                565                 570                 575

Trp Gly Asn Ser Asn Ile Phe Ser Arg Ile Val Pro Ala Thr Ala Tyr
            580                 585                 590

Ser Leu Asp Asn Leu Gln Ser Arg Asn Phe Gly Tyr Phe Glu Ser Thr
        595                 600                 605

Asn Ala Phe Thr Ser Ala Thr Gly Asn Val Val Gly Val Arg Asn Phe
    610                 615                 620

Ser Glu Asn Ala Gly Val Ile Ile Asp Arg Phe Glu Phe Ile Pro Val
625                 630                 635                 640

Thr Ala Thr Phe Glu Ala Glu Tyr Asp Leu Glu Arg Ala Gln Glu
                645                 650                 655
```

<210> SEQ ID NO 12
<211> LENGTH: 1965
<212> TYPE: DNA
<213> ORGANISM: Artificial Sequence
<220> FEATURE:
<223> OTHER INFORMATION: coding sequence of Cry1B variant

<400> SEQUENCE: 12

```
atgccgagca atcgtaagaa tgaaaatgaa atcattaacg cactgtccat ccctgcagtg      60
agcaatcaca gcgcgcagat ggatttgagc ctggatgcgc gtatcgagga cagcctgtgt     120
attgccgagg gcaacaacat caatccgttg gtcagcgcga gcaccgtgca aaccggcatt     180
aacattgccg gtcgtatcct gggtgtcctg ggcgttccgt ttgcgggtca gctggcgagc     240
ttttacagct ttatcgttgg tgagttgtgg ccgtcgggtc gtgacccttg ggagattttc     300
atggagcacg tcgagcaact ggtgcgccaa cagattacgg agaatgcgcg caacaccgct     360
ctggcgcgtc tgcaaggtct gggtgcaagc ttccgcgctt accagcagtc cctggaagat     420
tggttggaaa accgtgataa tgcgcgcact cgctccgtcc tgtacacgca gtacatcgcg     480
ctggagctgg acttcttgaa cgcgatgccg ctgtttgcaa tcaacaacca gcaagtgccg     540
ctgctgatgg tctacgccca agccgcgaat ctgcacttgc tgctgctgcg cgacgcatct     600
ctgttcggta gcgaatttgg cctgaccagc caggagatcc agcgctacta tgagcgtcag     660
gccgagaaaa cgcgtgaata ctccgactac tgcgctcgtt ggtacaacac gggtctgaac     720
aatctgcgtg gcaccaacgc ggagtcctgg ctgcgttaca accagtttcg tcgcgatctg     780
accctgggtg ttttggattt ggttgcgctg tttccgagct atgacacccg catctatccg     840
atcaacacca gcgcgcaact gactcgtgaa atctatacgg acccgattgg ccgcactaat     900
gcaccgtccg gtttcgcaag caccaactgg ttcaataaca atgcaccgag cttcagcgcg     960
atcgaggccg cgatctttcg tccgccgcac ctgttggact tcccggagca gctgaccatc    1020
tactctgcat ctagccgttg gagcagcacg cagcacatga attactgggt tggccatcgt    1080
ctgaacttcc gcccgattgg tggtacgctg aacactagca cgcacggtgc cactaacacg    1140
agcatcaacc cggtgacgct gcaattcacc agccgtgatg tttaccgtac cgagtcctac    1200
gccggcatca acattctgct gaccaccccg gttaacggcg tcccttgggc tcgtttcaat    1260
tggcgtaacc cactgaatag cctgcgtggt tctttgctgt acaccattgg ttataccggc    1320
gtcggtacgc aactgtttga ctcggaaact gagctgccac cggaaactac cgagcgtccg    1380
aactacgaat cttatagcca ccgtctgtcc aatatccgtc tgatcatcgg caacaccctg    1440
cgtgcgccgg tgtacagctg gacccatcgt agcgccgatc gcacgaacac gattgccacc    1500
aacattatca cccagatccc ggcagtgaaa ggcaactttc tgtttaacgg cagcgtgatc    1560
agcggtccag gttttaccgg cggtgacctg gtgcgcctga acaacagcgg caacaatatc    1620
caaaaccgtg gttatatcga agtcccgatt caattcatca gcacgagcac ccgttaccgc    1680
gtccgtgttc gctacgcatc cgttacgccg atccaactga gcgttaactg ggcaattcc    1740
aacattttca gccgcattgt ccctgctacg gcgtactctc tggacaattt gcagagccgt    1800
aacttcggct atttcgaaag caccaacgct ttcaccagcg ctacgggcaa tgtggttggt    1860
gttcgcaatt tcagcgagaa tgcgggcgtc atcattgacc gttttgagtt tatcccggtg    1920
accgcgacct tcgaagcgga gtacgatctg gagcgtgcgc aggaa                    1965
```

<210> SEQ ID NO 13
<211> LENGTH: 655
<212> TYPE: PRT
<213> ORGANISM: Artificial Sequence
<220> FEATURE:
<223> OTHER INFORMATION: Cry1B variant

<400> SEQUENCE: 13

-continued

```
Met Pro Ser Asn Arg Lys Asn Glu Asn Glu Ile Ile Asn Ala Leu Ser
1               5                   10                  15

Ile Pro Ala Val Ser Asn His Ser Ala Gln Met Asp Leu Ser Leu Asp
            20                  25                  30

Ala Arg Ile Glu Asp Ser Leu Cys Ile Ala Glu Gly Asn Asn Ile Asn
        35                  40                  45

Pro Leu Val Ser Ala Ser Thr Val Gln Thr Gly Ile Asn Ile Ala Gly
    50                  55                  60

Arg Ile Leu Gly Val Leu Gly Val Pro Phe Ala Gly Gln Leu Ala Ser
65                  70                  75                  80

Phe Tyr Ser Phe Ile Val Gly Glu Leu Trp Pro Ser Gly Arg Asp Pro
                85                  90                  95

Trp Glu Ile Phe Met Glu His Val Glu Gln Leu Val Arg Gln Gln Ile
            100                 105                 110

Thr Glu Asn Ala Arg Asn Thr Ala Leu Ala Arg Leu Gln Gly Leu Gly
        115                 120                 125

Ala Ser Phe Arg Ala Tyr Gln Gln Ser Leu Glu Asp Trp Leu Glu Asn
    130                 135                 140

Arg Asp Asn Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Asn Asn
                165                 170                 175

Gln Gln Val Pro Leu Leu Met Val Tyr Ala Gln Ala Ala Asn Leu His
            180                 185                 190

Leu Leu Leu Leu Arg Asp Ala Ser Leu Phe Gly Ser Glu Phe Gly Leu
        195                 200                 205

Thr Ser Gln Glu Ile Gln Arg Tyr Tyr Glu Arg Gln Ala Glu Lys Thr
    210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Ile Tyr Pro Ile Asn Thr Ser Ala Gln Leu Thr
        275                 280                 285

Arg Glu Ile Tyr Thr Asp Pro Ile Gly Arg Thr Asn Ala Pro Ser Gly
    290                 295                 300

Phe Ala Ser Thr Asn Trp Phe Asn Asn Asn Ala Pro Ser Phe Ser Ala
305                 310                 315                 320

Ile Glu Ala Ala Ile Phe Arg Pro Pro His Leu Leu Asp Phe Pro Glu
                325                 330                 335

Gln Leu Thr Ile Tyr Ser Ala Ser Ser Arg Trp Ser Ser Thr Gln His
            340                 345                 350

Met Asn Tyr Trp Val Gly His Arg Leu Asn Phe Arg Pro Ile Gly Gly
        355                 360                 365

Thr Leu Asn Thr Ser Thr His Gly Ala Thr Asn Thr Ser Ile Asn Pro
    370                 375                 380

Val Thr Leu Gln Phe Thr Ser Arg Asp Val Tyr Arg Thr Glu Ser Tyr
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
```

```
            420                 425                 430

Leu Tyr Thr Ile Gly Tyr Thr Gly Val Gly Thr Gln Leu Phe Asp Ser
        435                 440                 445

Glu Thr Glu Leu Pro Pro Glu Thr Thr Glu Arg Pro Asn Tyr Glu Ser
    450                 455                 460

Tyr Ser His Arg Leu Ser Asn Ile Arg Leu Ile Ile Gly Asn Thr Leu
465                 470                 475                 480

Arg Ala Pro Val Tyr Ser Trp Thr His Arg Ser Ala Asp Arg Thr Asn
                485                 490                 495

Thr Ile Ala Thr Asn Ile Ile Thr Gln Ile Pro Ala Val Lys Gly Asn
            500                 505                 510

Phe Leu Phe Asn Gly Ser Val Ile Ser Gly Pro Gly Phe Thr Gly Gly
        515                 520                 525

Asp Leu Val Arg Leu Asn Asn Ser Gly Asn Asn Ile Gln Asn Arg Gly
    530                 535                 540

Tyr Ile Glu Val Pro Ile Gln Phe Ile Ser Thr Ser Thr Arg Tyr Arg
545                 550                 555                 560

Val Arg Val Arg Tyr Ala Ser Val Thr Pro Ile Arg Leu Ser Val Asn
                565                 570                 575

Trp Gly Asn Ser Asn Ile Phe Ser Ser Ile Val Pro Ala Thr Ala Thr
            580                 585                 590

Ser Leu Asp Asn Leu Gln Ser Arg Asn Phe Gly Tyr Phe Glu Ser Arg
        595                 600                 605

Asn Ala Phe Thr Ser Ala Thr Gly Asn Val Val Gly Val Arg Asn Phe
    610                 615                 620

Ser Glu Asn Ala Gly Val Ile Ile Asp Arg Phe Glu Phe Ile Pro Val
625                 630                 635                 640

Thr Ala Thr Phe Glu Ala Glu Tyr Asp Leu Glu Arg Ala Gln Glu
                645                 650                 655
```

<210> SEQ ID NO 14
<211> LENGTH: 1965
<212> TYPE: DNA
<213> ORGANISM: Artificial Sequence
<220> FEATURE:
<223> OTHER INFORMATION: coding sequence of Cry1B variant

<400> SEQUENCE: 14

```
atgccgagca atcgtaagaa tgaaaatgaa atcattaacg cactgtccat ccctgcagtg     60

agcaatcaca gcgcgcagat ggatttgagc ctggatgcgc gtatcgagga cagcctgtgt    120

attgccgagg gcaacaacat caatccgttg gtcagcgcga gcaccgtgca aaccggcatt    180

aacattgccg gtcgtatcct gggtgtcctg ggcgttccgt ttgcgggtca gctggcgagc    240

ttttacagct ttatcgttgg tgagttgtgg ccgtcgggtc gtgacccttg ggagattttc    300

atggagcacg tcgagcaact ggtgcgccaa cagattacgg agaatgcgcg caacaccgct    360

ctggcgcgtc tgcaaggtct gggtgcaagc ttccgcgctt accagcagtc cctggaagat    420

tggttggaaa accgtgataa tgcgcgcact cgctccgtcc tgtacacgca gtacatcgcg    480

ctggagctgg acttcttgaa cgcgatgccg ctgtttgcaa tcaacaacca gcaagtgccg    540

ctgctgatgg tctacgccca agccgcgaat ctgcacttgc tgctgctgcg cgacgcatct    600

ctgttcggta gcgaatttgg cctgaccagc caggagatcc agcgctacta tgagcgtcag    660

gccgagaaaa cgcgtgaata ctccgactac tgcgctcgtt ggtacaacac gggtctgaac    720

aatctgcgtg gcaccaacgc ggagtcctgg ctgcgttaca accagtttcg tcgcgatctg    780
```

```
accctgggtg ttttggattt ggttgcgctg tttccgagct atgacacccg catctatccg    840

atcaacacca gcgcgcaact gactcgtgaa atctatacgg acccgattgg ccgcactaat    900

gcaccgtccg gtttcgcaag caccaactgg ttcaataaca atgcaccgag cttcagcgcg    960

atcgaggccg cgatctttcg tccgccgcac ctgttggact tcccggagca gctgaccatc   1020

tactctgcat ctagccgttg gagcagcacg cagcacatga attactgggt tggccatcgt   1080

ctgaacttcc gcccgattgg tggtacgctg aacactagca cgcacggtgc cactaacacg   1140

agcatcaacc cggtgacgct gcaattcacc agccgtgatg tttaccgtac cgagtcctac   1200

gccggcatca acattctgct gaccaccccg gttaacggcg tcccttgggc tcgtttcaat   1260

tggcgtaacc cactgaatag cctgcgtggt tctttgctgt acaccattgg ttataccggc   1320

gtcggtacgc aactgtttga ctcggaaact gagctgccac cggaaactac cgagcgtccg   1380

aactacgaat cttatagcca ccgtctgtcc aatatccgtc tgatcatcgg caacaccctg   1440

cgtgcgccgg tgtacagctg gacccatcgt agcgccgatc gcacgaacac gattgccacc   1500

aacattatca cccagatccc ggcagtgaaa ggcaactttc tgtttaacgg cagcgtgatc   1560

agcggtccag gttttaccgg cggtgacctg gtgcgcctga acaacagcgg caacaatatc   1620

caaaaccgtg gttatatcga agtcccgatt caattcatca gcacgagcac ccgttaccgc   1680

gtccgtgttc gctacgcatc cgttacgccg atccgcctga gcgttaactg gggcaattcc   1740

aacattttca gcagcattgt ccctgctacg gcgacctctc tggacaattt gcagagccgt   1800

aacttcggct atttcgaaag ccgcaacgct ttcaccagcg ctacgggcaa tgtggttggt   1860

gttcgcaatt tcagcgagaa tgcgggcgtc atcattgacc gttttgagtt tatcccggtg   1920

accgcgacct tcgaagcgga gtacgatctg gagcgtgcgc aggaa                    1965
```

<210> SEQ ID NO 15
<211> LENGTH: 655
<212> TYPE: PRT
<213> ORGANISM: Artificial Sequence
<220> FEATURE:
<223> OTHER INFORMATION: Cry1B variant

<400> SEQUENCE: 15

```
Met Pro Ser Asn Arg Lys Asn Glu Asn Glu Ile Ile Asn Ala Leu Ser
1               5                   10                  15

Ile Pro Ala Val Ser Asn His Ser Ala Gln Met Asp Leu Ser Leu Asp
            20                  25                  30

Ala Arg Ile Glu Asp Ser Leu Cys Ile Ala Glu Gly Asn Asn Ile Asn
        35                  40                  45

Pro Leu Val Ser Ala Ser Thr Val Gln Thr Gly Ile Asn Ile Ala Gly
    50                  55                  60

Arg Ile Leu Gly Val Leu Gly Val Pro Phe Ala Gly Gln Leu Ala Ser
65                  70                  75                  80

Phe Tyr Ser Phe Ile Val Gly Glu Leu Trp Pro Ser Gly Arg Asp Pro
                85                  90                  95

Trp Glu Ile Phe Met Glu His Val Glu Gln Leu Val Arg Gln Gln Ile
            100                 105                 110

Thr Glu Asn Ala Arg Asn Thr Ala Leu Ala Arg Leu Gln Gly Leu Gly
        115                 120                 125

Ala Ser Phe Arg Ala Tyr Gln Gln Ser Leu Glu Asp Trp Leu Glu Asn
    130                 135                 140

Arg Asp Asn Ala Arg Thr Arg Ser Val Leu Tyr Thr Gln Tyr Ile Ala
```

```
145                 150                 155                 160

Leu Glu Leu Asp Phe Leu Asn Ala Met Pro Leu Phe Ala Ile Asn Asn
                165                 170                 175

Gln Gln Val Pro Leu Leu Met Val Tyr Ala Gln Ala Ala Asn Leu His
            180                 185                 190

Leu Leu Leu Leu Arg Asp Ala Ser Leu Phe Gly Ser Glu Phe Gly Leu
        195                 200                 205

Thr Ser Gln Glu Ile Gln Arg Tyr Tyr Glu Arg Gln Ala Glu Lys Thr
    210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Ile Tyr Pro Ile Asn Thr Ser Ala Gln Leu Thr
        275                 280                 285

Arg Glu Ile Tyr Thr Asp Pro Ile Gly Arg Thr Asn Ala Pro Ser Gly
    290                 295                 300

Phe Ala Ser Thr Asn Trp Phe Asn Asn Asn Ala Pro Ser Phe Ser Ala
305                 310                 315                 320

Ile Glu Ala Ala Ile Phe Arg Pro Pro His Leu Leu Asp Phe Pro Glu
                325                 330                 335

Gln Leu Thr Ile Tyr Ser Ala Ser Ser Arg Trp Ser Ser Thr Gln His
            340                 345                 350

Met Asn Tyr Trp Val Gly His Arg Leu Asn Phe Arg Pro Ile Gly Gly
        355                 360                 365

Thr Leu Asn Thr Ser Thr His Gly Ala Thr Asn Thr Ser Ile Asn Pro
    370                 375                 380

Val Thr Leu Gln Phe Thr Ser Arg Asp Val Tyr Arg Thr Glu Ser Tyr
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
            420                 425                 430

Leu Tyr Thr Ile Gly Tyr Thr Gly Val Gly Thr Gln Leu Phe Asp Ser
        435                 440                 445

Glu Thr Glu Leu Pro Pro Glu Thr Thr Glu Arg Pro Asn Tyr Glu Ser
    450                 455                 460

Tyr Ser His Arg Leu Ser Asn Ile Arg Leu Ile Ile Ser Asn Thr Leu
465                 470                 475                 480

Arg Ala Pro Val Tyr Ser Trp Thr His Arg Ser Ala Asp Arg Thr Asn
                485                 490                 495

Thr Ile Ala Thr Asn Ile Ile Thr Gln Ile Pro Ala Val Lys Gly Asn
            500                 505                 510

Phe Leu Phe Asn Gly Ser Val Ile Ser Gly Pro Gly Phe Thr Gly Gly
        515                 520                 525

Asp Leu Val Arg Leu Asn Asn Ser Gly Asn Asn Ile Gln Asn Arg Gly
    530                 535                 540

Tyr Ile Glu Val Pro Ile Gln Phe Ile Ser Thr Ser Thr Arg Tyr Arg
545                 550                 555                 560

Val Arg Val Arg Tyr Ala Ser Val Thr Pro Ile Arg Leu Ser Val Asn
                565                 570                 575
```

```
Trp Gly Asn Ser Asn Ile Phe Ser Ser Ile Val Pro Ala Thr Ala Thr
            580                 585                 590

Ser Leu Asp Asn Leu Gln Ser Arg Asn Phe Gly Tyr Phe Glu Ser Arg
        595                 600                 605

Asn Ala Phe Thr Ser Ala Thr Gly Asn Val Val Gly Val Arg Asn Phe
    610                 615                 620

Ser Glu Asn Ala Gly Val Ile Ile Asp Arg Phe Glu Phe Ile Pro Val
625                 630                 635                 640

Thr Ala Thr Phe Glu Ala Glu Tyr Asp Leu Glu Arg Ala Gln Glu
                645                 650                 655


<210> SEQ ID NO 16
<211> LENGTH: 1965
<212> TYPE: DNA
<213> ORGANISM: Artificial Sequence
<220> FEATURE:
<223> OTHER INFORMATION: coding sequence of Cry1B variant

<400> SEQUENCE: 16

atgccgagca atcgtaagaa tgaaaatgaa atcattaacg cactgtccat ccctgcagtg     60

agcaatcaca gcgcgcagat ggatttgagc ctggatgcgc gtatcgagga cagcctgtgt    120

attgccgagg gcaacaacat caatccgttg gtcagcgcga gcaccgtgca aaccggcatt    180

aacattgccg gtcgtatcct gggtgtcctg ggcgttccgt ttgcgggtca gctggcgagc    240

ttttacagct ttatcgttgg tgagttgtgg ccgtcgggtc gtgacccttg ggagattttc    300

atggagcacg tcgagcaact ggtgcgccaa cagattacgg agaatgcgcg caacaccgct    360

ctggcgcgtc tgcaaggtct gggtgcaagc ttccgcgctt accagcagtc cctggaagat    420

tggttggaaa accgtgataa tgcgcgcact cgctccgtcc tgtacacgca gtacatcgcg    480

ctggagctgg acttcttgaa cgcgatgccg ctgtttgcaa tcaacaacca gcaagtgccg    540

ctgctgatgg tctacgccca agccgcgaat ctgcacttgc tgctgctgcg cgacgcatct    600

ctgttcggta gcgaatttgg cctgaccagc caggagatcc agcgctacta tgagcgtcag    660

gccgagaaaa cgcgtgaata ctccgactac tgcgctcgtt ggtacaacac gggtctgaac    720

aatctgcgtg gcaccaacgc ggagtcctgg ctgcgttaca accagtttcg tcgcgatctg    780

accctgggtg ttttggattt ggttgcgctg tttccgagct atgacacccg catctatccg    840

atcaacacca gcgcgcaact gactcgtgaa atctatacgg acccgattgg ccgcactaat    900

gcaccgtccg gtttcgcaag caccaactgg ttcaataaca atgcaccgag cttcagcgcg    960

atcgaggccg cgatctttcg tccgccgcac ctgttggact tcccggagca gctgaccatc   1020

tactctgcat ctagccgttg gagcagcacg cagcacatga attactgggt tggccatcgt   1080

ctgaacttcc gcccgattgg tggtacgctg aacactagca cgcacggtgc cactaacacg   1140

agcatcaacc cggtgacgct gcaattcacc agccgtgatg tttaccgtac cgagtcctac   1200

gccggcatca acattctgct gaccaccccg gttaacggcg tcccttgggc tcgtttcaat   1260

tggcgtaacc cactgaatag cctgcgtggt tctttgctgt acaccattgg ttataccggc   1320

gtcggtacgc aactgtttga ctcggaaact gagctgccac cggaaactac cgagcgtccg   1380

aactacgaat cttatagcca ccgtctgtcc aatatccgtc tgatcatcag caacaccctg   1440

cgtgcgccgg tgtacagctg gacccatcgt agcgccgatc gcacgaacac gattgccacc   1500

aacattatca cccagatccc ggcagtgaaa ggcaactttc tgtttaacgg cagcgtgatc   1560

agcggtccag gttttaccgg cggtgacctg gtgcgcctga acaacagcgg caacaatatc   1620
```

```
caaaaccgtg gttatatcga agtcccgatt caattcatca gcacgagcac ccgttaccgc   1680

gtccgtgttc gctacgcatc cgttacgccg atccgcctga gcgttaactg gggcaattcc   1740

aacattttca gcagcattgt ccctgctacg gcgacctctc tggacaattt gcagagccgt   1800

aacttcggct atttcgaaag ccgcaacgct ttcaccagcg ctacgggcaa tgtggttggt   1860

gttcgcaatt tcagcgagaa tgcgggcgtc atcattgacc gttttgagtt tatcccggtg   1920

accgcgacct tcgaagcgga gtacgatctg gagcgtgcgc aggaa                   1965
```

<210> SEQ ID NO 17
<211> LENGTH: 655
<212> TYPE: PRT
<213> ORGANISM: Artificial Sequence
<220> FEATURE:
<223> OTHER INFORMATION: Cry1B variant

<400> SEQUENCE: 17

```
Met Pro Ser Asn Arg Lys Asn Glu Asn Glu Ile Ile Asn Ala Leu Ser
1               5                   10                  15

Ile Pro Ala Val Ser Asn His Ser Ala Gln Met Asp Leu Ser Leu Asp
            20                  25                  30

Ala Arg Ile Glu Asp Ser Leu Cys Ile Ala Glu Gly Asn Asn Ile Asn
        35                  40                  45

Pro Leu Val Ser Ala Ser Thr Val Gln Thr Gly Ile Asn Ile Ala Gly
    50                  55                  60

Arg Ile Leu Gly Val Leu Gly Val Pro Phe Ala Gly Gln Leu Ala Ser
65                  70                  75                  80

Phe Tyr Ser Phe Ile Val Gly Glu Leu Trp Pro Ser Gly Arg Asp Pro
                85                  90                  95

Trp Glu Ile Phe Met Glu His Val Glu Gln Leu Val Arg Gln Ala Ile
            100                 105                 110

Thr Leu Asn Ala Arg Asn Thr Ala Leu Ala Arg Leu Gln Gly Leu Gly
        115                 120                 125

Ala Ser Phe Arg Ala Tyr Gln Gln Ser Leu Glu Asp Trp Leu Glu Asn
    130                 135                 140

Arg Asp Asn Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Asn Asn
                165                 170                 175

Gln Gln Val Pro Leu Leu Met Val Tyr Ala Gln Ala Ala Asn Leu His
            180                 185                 190

Leu Leu Leu Leu Arg Asp Ala Ser Leu Phe Gly Ser Glu Phe Gly Leu
        195                 200                 205

Thr Ser Gln Glu Ile Gln Arg Tyr Tyr Glu Arg Gln Ala Glu Lys Thr
    210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Ile Tyr Pro Ile Asn Thr Ser Ala Gln Leu Thr
        275                 280                 285

Arg Glu Ile Tyr Thr Asp Pro Ile Gly Arg Thr Asn Ala Pro Ser Gly
    290                 295                 300
```

```
Phe Ala Ser Thr Asn Trp Phe Asn Asn Asn Ala Pro Ser Phe Ser Ala
305                 310                 315                 320

Ile Glu Ala Ala Ile Phe Arg Pro Pro His Leu Leu Asp Phe Pro Glu
                325                 330                 335

Gln Leu Thr Ile Tyr Ser Ala Ser Ser Arg Trp Ser Ser Thr Gln His
            340                 345                 350

Met Asn Tyr Trp Val Gly His Arg Leu Asn Phe Arg Pro Ile Gly Gly
        355                 360                 365

Thr Leu Asn Thr Ser Thr His Gly Ala Thr Asn Thr Ser Ile Asn Pro
    370                 375                 380

Val Thr Leu Gln Phe Thr Ser Arg Asp Val Tyr Arg Thr Glu Ser Tyr
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
            420                 425                 430

Leu Tyr Thr Ile Gly Tyr Thr Gly Val Gly Thr Gln Leu Phe Asp Ser
        435                 440                 445

Glu Thr Glu Leu Pro Pro Glu Thr Thr Glu Arg Pro Asn Tyr Glu Ser
    450                 455                 460

Tyr Ser His Arg Leu Ser Asn Ile Arg Leu Ile Ile Ser Gly Thr Leu
465                 470                 475                 480

Arg Ala Pro Val Tyr Ser Trp Thr His Arg Ser Ala Asp Arg Thr Asn
                485                 490                 495

Thr Ile Ala Thr Asn Ile Ile Thr Gln Ile Pro Ala Val Lys Gly Asn
            500                 505                 510

Phe Leu Phe Asn Gly Ser Val Ile Ser Gly Pro Gly Phe Thr Gly Gly
        515                 520                 525

Asp Leu Val Arg Leu Asn Asn Ser Gly Asn Asn Ile Gln Asn Arg Gly
    530                 535                 540

Tyr Ile Glu Val Pro Ile Gln Phe Ile Ser Thr Ser Thr Arg Tyr Arg
545                 550                 555                 560

Val Arg Val Arg Tyr Ala Ser Val Thr Pro Ile Arg Leu Ser Val Asn
                565                 570                 575

Trp Gly Asn Ser Asn Ile Phe Ser Ser Ile Val Pro Ala Thr Ala Thr
            580                 585                 590

Ser Leu Asp Asn Leu Gln Ser Arg Asn Phe Gly Tyr Phe Glu Ser Arg
        595                 600                 605

Asn Ala Phe Thr Ser Ala Thr Gly Asn Val Val Gly Val Arg Asn Phe
    610                 615                 620

Ser Glu Asn Ala Gly Val Ile Ile Asp Arg Phe Glu Phe Ile Pro Val
625                 630                 635                 640

Thr Ala Thr Phe Glu Ala Glu Tyr Asp Leu Glu Arg Ala Gln Glu
                645                 650                 655
```

<210> SEQ ID NO 18
<211> LENGTH: 1965
<212> TYPE: DNA
<213> ORGANISM: Artificial Sequence
<220> FEATURE:
<223> OTHER INFORMATION: coding sequence of Cry1B variant

<400> SEQUENCE: 18
atgccgagca atcgtaagaa tgaaaatgaa atcattaacg cactgtccat ccctgcagtg 60

-continued

```
agcaatcaca gcgcgcagat ggatttgagc ctggatgcgc gtatcgagga cagcctgtgt    120

attgccgagg gcaacaacat caatccgttg gtcagcgcga gcaccgtgca aaccggcatt    180

aacattgccg gtcgtatcct gggtgtcctg ggcgttccgt ttgcgggtca gctggcgagc    240

ttttacagct ttatcgttgg tgagttgtgg ccgtcgggtc gtgacccttg ggagattttc    300

atggagcacg tcgagcaact ggtgcgccaa gcgattacgc tgaatgcgcg caacaccgct    360

ctggcgcgtc tgcaaggtct gggtgcaagc ttccgcgctt accagcagtc cctggaagat    420

tggttggaaa accgtgataa tgcgcgcact cgctccgtcc tgtacacgca gtacatcgcg    480

ctggagctgg acttcttgaa cgcgatgccg ctgtttgcaa tcaacaacca gcaagtgccg    540

ctgctgatgg tctacgccca agccgcgaat ctgcacttgc tgctgctgcg cgacgcatct    600

ctgttcggta gcgaatttgg cctgaccagc caggagatcc agcgctacta tgagcgtcag    660

gccgagaaaa cgcgtgaata ctccgactac tgcgctcgtt ggtacaacac gggtctgaac    720

aatctgcgtg gcaccaacgc ggagtcctgg ctgcgttaca accagtttcg tcgcgatctg    780

accctgggtg ttttggattt ggttgcgctg tttccgagct atgacacccg catctatccg    840

atcaacacca gcgcgcaact gactcgtgaa atctatacgg acccgattgg ccgcactaat    900

gcaccgtccg gtttcgcaag caccaactgg ttcaataaca atgcaccgag cttcagcgcg    960

atcgaggccg cgatctttcg tccgccgcac ctgttggact tcccggagca gctgaccatc   1020

tactctgcat ctagccgttg gagcagcacg cagcacatga attactgggt tggccatcgt   1080

ctgaacttcc gcccgattgg tggtacgctg aacactagca cgcacggtgc cactaacacg   1140

agcatcaacc cggtgacgct gcaattcacc agccgtgatg tttaccgtac cgagtcctac   1200

gccggcatca acattctgct gaccaccccg gttaacggcg tcccttgggc tcgtttcaat   1260

tggcgtaacc cactgaatag cctgcgtggt tctttgctgt acaccattgg ttataccggc   1320

gtcggtacgc aactgtttga ctcggaaact gagctgccac cggaaactac cgagcgtccg   1380

aactacgaat cttatagcca ccgtctgtcc aatatccgtc tgatcatcag cggcaccctg   1440

cgtgcgccgg tgtacagctg gacccatcgt agcgccgatc gcacgaacac gattgccacc   1500

aacattatca cccagatccc ggcagtgaaa ggcaactttc tgtttaacgg cagcgtgatc   1560

agcggtccag gttttaccgg cggtgacctg gtgcgcctga acaacagcgg caacaatatc   1620

caaaaccgtg gttatatcga agtcccgatt caattcatca gcacgagcac ccgttaccgc   1680

gtccgtgttc gctacgcatc cgttacgccg atccgcctga gcgttaactg ggcaattcc   1740

aacattttca gcagcattgt ccctgctacg gcgacctctc tggacaattt gcagagccgt   1800

aacttcggct atttcgaaag ccgcaacgct ttcaccagcg ctacgggcaa tgtggttggt   1860

gttcgcaatt tcagcgagaa tgcgggcgtc atcattgacc gttttgagtt tatcccggtg   1920

accgcgacct tcgaagcgga gtacgatctg gagcgtgcgc aggaa                   1965
```

<210> SEQ ID NO 19
<211> LENGTH: 655
<212> TYPE: PRT
<213> ORGANISM: Artificial Sequence
<220> FEATURE:
<223> OTHER INFORMATION: Cry1B variant

<400> SEQUENCE: 19

```
Met Pro Ser Asn Arg Lys Asn Glu Asn Glu Ile Ile Asn Ala Leu Ser
1               5                   10                  15

Ile Pro Ala Val Ser Asn His Ser Ala Gln Met Asp Leu Ser Leu Asp
            20                  25                  30
```

-continued

```
Ala Arg Ile Glu Asp Ser Leu Cys Ile Ala Glu Gly Asn Asn Ile Asn
        35                  40                  45

Pro Leu Val Ser Ala Ser Thr Val Gln Thr Gly Ile Asn Ile Ala Gly
    50                  55                  60

Arg Ile Leu Gly Val Leu Gly Val Pro Phe Ala Gly Gln Leu Ala Ser
65                  70                  75                  80

Phe Tyr Ser Phe Ile Val Gly Glu Leu Trp Pro Ser Gly Arg Asp Pro
                85                  90                  95

Trp Glu Ile Phe Met Glu His Val Glu Gln Leu Val Arg Gln Ala Ile
            100                 105                 110

Thr Leu Asn Ala Arg Asn Thr Ala Leu Ala Arg Leu Gln Gly Leu Gly
        115                 120                 125

Ala Ser Phe Arg Ala Tyr Gln Gln Ser Leu Glu Asp Trp Leu Glu Asn
    130                 135                 140

Arg Asp Asn Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Asn Asn
                165                 170                 175

Gln Gln Val Pro Leu Leu Met Val Tyr Ala Gln Ala Ala Asn Leu His
            180                 185                 190

Leu Leu Leu Leu Arg Asp Ala Ser Leu Phe Gly Ser Glu Phe Gly Leu
        195                 200                 205

Thr Ser Gln Glu Ile Gln Arg Tyr Tyr Glu Arg Gln Ala Glu Lys Thr
    210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Ile Tyr Pro Ile Asn Thr Ser Ala Gln Leu Thr
        275                 280                 285

Arg Glu Ile Tyr Thr Asp Pro Ile Gly Arg Thr Asn Ala Pro Ser Gly
    290                 295                 300

Phe Ala Ser Thr Asn Trp Phe Asn Asn Asn Ala Pro Ser Phe Ser Ala
305                 310                 315                 320

Ile Glu Ala Ala Ile Phe Arg Pro Pro His Leu Leu Asp Phe Pro Glu
                325                 330                 335

Gln Leu Thr Ile Tyr Ser Ala Ser Ser Arg Trp Ser Ser Thr Gln His
            340                 345                 350

Met Asn Tyr Trp Val Gly His Arg Leu Tyr Phe Arg Pro Ile Asn Gly
        355                 360                 365

Thr Leu Asn Thr Ser Thr His Gly Ala Thr Asn Thr Ser Ile Asn Pro
    370                 375                 380

Val Thr Leu Gln Phe Thr Ser Arg Asp Val Tyr Arg Thr Glu Ser Tyr
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
            420                 425                 430

Leu Tyr Thr Ile Gly Tyr Thr Gly Val Gly Thr Gln Leu Phe Asp Ser
        435                 440                 445
```

-continued

```
Glu Thr Glu Leu Pro Pro Glu Thr Thr Glu Arg Pro Asn Tyr Glu Ser
    450                 455                 460

Tyr Ser His Arg Leu Ser Asn Ile Arg Leu Ile Ile Gly Asn Thr Leu
465                 470                 475                 480

Arg Ala Pro Val Tyr Ser Trp Thr His Arg Ser Ala Asp Arg Thr Asn
                485                 490                 495

Thr Ile Ala Thr Asn Ile Ile Thr Gln Ile Pro Ala Val Lys Gly Asn
            500                 505                 510

Phe Leu Phe Asn Gly Ser Val Ile Ser Gly Pro Gly Phe Thr Gly Gly
        515                 520                 525

Asp Leu Val Arg Leu Asn Asn Ser Gly Asn Asn Ile Gln Asn Arg Gly
    530                 535                 540

Tyr Ile Glu Val Pro Ile Gln Phe Ile Ser Thr Ser Thr Arg Tyr Arg
545                 550                 555                 560

Val Arg Val Arg Tyr Ala Ser Val Thr Pro Ile Arg Leu Ser Val Asn
                565                 570                 575

Trp Gly Asn Ser Asn Ile Phe Ser Ser Ile Val Pro Ala Thr Ala Thr
            580                 585                 590

Ser Leu Asp Asn Leu Gln Ser Arg Asn Phe Gly Tyr Phe Glu Ser Arg
        595                 600                 605

Asn Ala Phe Thr Ser Ala Thr Gly Asn Val Val Gly Val Arg Asn Phe
    610                 615                 620

Ser Glu Asn Ala Gly Val Ile Ile Asp Arg Phe Glu Phe Ile Pro Val
625                 630                 635                 640

Thr Ala Thr Phe Glu Ala Glu Tyr Asp Leu Glu Arg Ala Gln Glu
                645                 650                 655


<210> SEQ ID NO 20
<211> LENGTH: 1965
<212> TYPE: DNA
<213> ORGANISM: Artificial Sequence
<220> FEATURE:
<223> OTHER INFORMATION: coding sequence of Cry1B variant

<400> SEQUENCE: 20

atgccgagca atcgtaagaa tgaaaatgaa atcattaacg cactgtccat ccctgcagtg      60

agcaatcaca gcgcgcagat ggatttgagc ctggatgcgc gtatcgagga cagcctgtgt     120

attgccgagg gcaacaacat caatccgttg gtcagcgcga gcaccgtgca aaccggcatt     180

aacattgccg gtcgtatcct gggtgtcctg ggcgttccgt ttgcgggtca gctggcgagc     240

ttttacagct ttatcgttgg tgagttgtgg ccgtcgggtc gtgacccttg ggagattttc     300

atggagcacg tcgagcaact ggtgcgccaa gcgattacgc tgaatgcgcg caacaccgct     360

ctggcgcgtc tgcaaggtct gggtgcaagc ttccgcgctt accagcagtc cctggaagat     420

tggttggaaa accgtgataa tgcgcgcact cgctccgtcc tgtacacgca gtacatcgcg     480

ctggagctgg acttcttgaa cgcgatgccg ctgtttgcaa tcaacaacca gcaagtgccg     540

ctgctgatgg tctacgccca agccgcgaat ctgcacttgc tgctgctgcg cgacgcatct     600

ctgttcggta gcgaatttgg cctgaccagc caggagatcc agcgctacta tgagcgtcag     660

gccgagaaaa cgcgtgaata ctccgactac tgcgctcgtt ggtacaacac gggtctgaac     720

aatctgcgtg gcaccaacgc ggagtcctgg ctgcgttaca accagtttcg tcgcgatctg     780

accctgggtg ttttggattt ggttgcgctg tttccgagct atgacacccg catctatccg     840

atcaacacca gcgcgcaact gactcgtgaa atctatacgg acccgattgg ccgcactaat     900
```

```
gcaccgtccg gtttcgcaag caccaactgg ttcaataaca atgcaccgag cttcagcgcg    960

atcgaggccg cgatctttcg tccgccgcac ctgttggact tcccggagca gctgaccatc   1020

tactctgcat ctagccgttg gagcagcacg cagcacatga attactgggt tggccatcgt   1080

ctgtatttcc gcccgattaa cggtacgctg aacactagca cgcacggtgc cactaacacg   1140

agcatcaacc cggtgacgct gcaattcacc agccgtgatg tttaccgtac cgagtcctac   1200

gccggcatca acattctgct gaccaccccg gttaacggcg tcccttgggc tcgtttcaat   1260

tggcgtaacc cactgaatag cctgcgtggt tctttgctgt acaccattgg ttataccggc   1320

gtcggtacgc aactgtttga ctcggaaact gagctgccac cggaaactac cgagcgtccg   1380

aactacgaat cttatagcca ccgtctgtcc aatatccgtc tgatcatcgg caacaccctg   1440

cgtgcgccgg tgtacagctg gacccatcgt agcgccgatc gcacgaacac gattgccacc   1500

aacattatca cccagatccc ggcagtgaaa ggcaactttc tgtttaacgg cagcgtgatc   1560

agcggtccag gttttaccgg cggtgacctg gtgcgcctga acaacagcgg caacaatatc   1620

caaaaccgtg gttatatcga agtcccgatt caattcatca gcacgagcac ccgttaccgc   1680

gtccgtgttc gctacgcatc cgttacgccg atccgcctga gcgttaactg ggcaattcc    1740

aacattttca gcagcattgt ccctgctacg gcgacctctc tggacaattt gcagagccgt   1800

aacttcggct atttcgaaag ccgcaacgct ttcaccagcg ctacgggcaa tgtggttggt   1860

gttcgcaatt tcagcgagaa tgcgggcgtc atcattgacc gttttgagtt tatcccggtg   1920

accgcgacct tcgaagcgga gtacgatctg gagcgtgcgc aggaa                   1965


<210> SEQ ID NO 21
<211> LENGTH: 655
<212> TYPE: PRT
<213> ORGANISM: Artificial Sequence
<220> FEATURE:
<223> OTHER INFORMATION: Cry1B variant

<400> SEQUENCE: 21

Met Pro Ser Asn Arg Lys Asn Glu Asn Glu Ile Ile Asn Ala Leu Ser
1               5                   10                  15

Ile Pro Ala Val Ser Asn His Ser Ala Gln Met Asp Leu Ser Leu Asp
            20                  25                  30

Ala Arg Ile Glu Asp Ser Leu Cys Ile Ala Glu Gly Asn Asn Ile Asn
        35                  40                  45

Pro Leu Val Ser Ala Ser Thr Val Gln Thr Gly Ile Asn Ile Ala Gly
    50                  55                  60

Arg Ile Leu Gly Val Leu Gly Val Pro Phe Ala Gly Gln Leu Ala Ser
65                  70                  75                  80

Phe Tyr Ser Phe Ile Val Gly Glu Leu Trp Pro Ser Gly Arg Asp Pro
                85                  90                  95

Trp Glu Ile Phe Met Glu His Val Glu Gln Leu Val Arg Gln Ala Ile
            100                 105                 110

Thr Leu Asn Ala Arg Asn Thr Ala Leu Ala Arg Leu Gln Gly Leu Gly
        115                 120                 125

Ala Ser Phe Arg Ala Tyr Gln Gln Ser Leu Glu Asp Trp Leu Glu Asn
    130                 135                 140

Arg Asp Asn Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Asn Asn
                165                 170                 175
```

```
Gln Gln Val Pro Leu Leu Met Val Tyr Ala Gln Ala Ala Asn Leu His
            180                 185                 190

Leu Leu Leu Leu Arg Asp Ala Ser Leu Phe Gly Ser Glu Phe Gly Leu
        195                 200                 205

Thr Ser Gln Glu Ile Gln Arg Tyr Tyr Glu Arg Gln Ala Glu Lys Thr
    210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Ile Tyr Pro Ile Asn Thr Ser Ala Gln Leu Thr
        275                 280                 285

Arg Glu Ile Tyr Thr Asp Pro Ile Gly Arg Thr Asn Ala Pro Ser Gly
    290                 295                 300

Phe Ala Ser Thr Asn Trp Phe Asn Asn Asn Ala Pro Ser Phe Ser Ala
305                 310                 315                 320

Ile Glu Ala Ala Ile Phe Arg Pro Pro His Leu Leu Asp Phe Pro Glu
                325                 330                 335

Gln Leu Thr Ile Tyr Ser Ala Ser Ser Arg Trp Ser Ser Thr Gln His
            340                 345                 350

Met Asn Tyr Trp Val Gly His Arg Leu Tyr Phe Arg Pro Ile Gln Gly
        355                 360                 365

Thr Leu Asn Thr Ser Thr His Gly Ala Thr Asn Thr Ser Ile Asn Pro
    370                 375                 380

Val Thr Leu Gln Phe Thr Ser Arg Asp Val Tyr Arg Thr Glu Ser Tyr
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
            420                 425                 430

Leu Tyr Thr Ile Gly Tyr Thr Gly Val Gly Thr Gln Leu Phe Asp Ser
        435                 440                 445

Glu Thr Glu Leu Pro Pro Glu Thr Thr Glu Arg Pro Asn Tyr Glu Ser
    450                 455                 460

Tyr Ser His Arg Leu Ser Asn Ile Arg Leu Ile Ile Gly Asn Thr Leu
465                 470                 475                 480

Arg Ala Pro Val Tyr Ser Trp Thr His Arg Ser Ala Asp Arg Thr Asn
                485                 490                 495

Thr Ile Ala Thr Asn Ile Ile Thr Gln Ile Pro Ala Val Lys Gly Asn
            500                 505                 510

Phe Leu Phe Asn Gly Ser Val Ile Ser Gly Pro Gly Phe Thr Gly Gly
        515                 520                 525

Asp Leu Val Arg Leu Asn Asn Ser Gly Asn Asn Ile Gln Asn Arg Gly
    530                 535                 540

Tyr Ile Glu Val Pro Ile Gln Phe Ile Ser Thr Ser Thr Arg Tyr Arg
545                 550                 555                 560

Val Arg Val Arg Tyr Ala Ser Val Thr Pro Ile Arg Leu Ser Val Asn
                565                 570                 575

Trp Gly Asn Ser Asn Ile Phe Ser Ser Ile Val Pro Ala Thr Ala Thr
            580                 585                 590

Ser Leu Asp Asn Leu Gln Ser Arg Asn Phe Gly Tyr Phe Glu Ser Arg
```

```
        595                 600                 605

Asn Ala Phe Thr Ser Ala Thr Gly Asn Val Val Gly Val Arg Asn Phe
    610                 615                 620

Ser Glu Asn Ala Gly Val Ile Ile Asp Arg Phe Glu Phe Ile Pro Val
625                 630                 635                 640

Thr Ala Thr Phe Glu Ala Glu Tyr Asp Leu Glu Arg Ala Gln Glu
                645                 650                 655


<210> SEQ ID NO 22
<211> LENGTH: 1965
<212> TYPE: DNA
<213> ORGANISM: Artificial Sequence
<220> FEATURE:
<223> OTHER INFORMATION: coding sequence of Cry1B variant

<400> SEQUENCE: 22

atgccgagca atcgtaagaa tgaaaatgaa atcattaacg cactgtccat ccctgcagtg     60

agcaatcaca gcgcgcagat ggatttgagc ctggatgcgc gtatcgagga cagcctgtgt    120

attgccgagg gcaacaacat caatccgttg gtcagcgcga gcaccgtgca aaccggcatt    180

aacattgccg gtcgtatcct gggtgtcctg ggcgttccgt ttgcgggtca gctggcgagc    240

ttttacagct ttatcgttgg tgagttgtgg ccgtcgggtc gtgacccttg ggagattttc    300

atggagcacg tcgagcaact ggtgcgccaa gcgattacgc tgaatgcgcg caacaccgct    360

ctggcgcgtc tgcaaggtct gggtgcaagc ttccgcgctt accagcagtc cctggaagat    420

tggttggaaa accgtgataa tgcgcgcact cgctccgtcc tgtacacgca gtacatcgcg    480

ctggagctgg acttcttgaa cgcgatgccg ctgtttgcaa tcaacaacca gcaagtgccg    540

ctgctgatgg tctacgccca agccgcgaat ctgcacttgc tgctgctgcg cgacgcatct    600

ctgttcggta gcgaatttgg cctgaccagc caggagatcc agcgctacta tgagcgtcag    660

gccgagaaaa cgcgtgaata ctccgactac tgcgctcgtt ggtacaacac gggtctgaac    720

aatctgcgtg gcaccaacgc ggagtcctgg ctgcgttaca accagtttcg tcgcgatctg    780

accctgggtg ttttggattt ggttgcgctg tttccgagct atgacacccg catctatccg    840

atcaacacca gcgcgcaact gactcgtgaa atctatacgg acccgattgg ccgcactaat    900

gcaccgtccg gtttcgcaag caccaactgg ttcaataaca atgcaccgag cttcagcgcg    960

atcgaggccg cgatctttcg tccgccgcac ctgttggact tcccggagca gctgaccatc   1020

tactctgcat ctagccgttg gagcagcacg cagcacatga attactgggt tggccatcgt   1080

ctgtatttcc gcccgattca gggtacgctg aacactagca cgcacggtgc cactaacacg   1140

agcatcaacc cggtgacgct gcaattcacc agccgtgatg tttaccgtac cgagtcctac   1200

gccggcatca acattctgct gaccaccccg gttaacggcg tcccttgggc tcgtttcaat   1260

tggcgtaacc cactgaatag cctgcgtggt tctttgctgt acaccattgg ttataccggc   1320

gtcggtacgc aactgtttga ctcggaaact gagctgccac cggaaactac cgagcgtccg   1380

aactacgaat cttatagcca ccgtctgtcc aatatccgtc tgatcatcgg caacaccctg   1440

cgtgcgccgg tgtacagctg gacccatcgt agcgccgatc gcacgaacac gattgccacc   1500

aacattatca cccagatccc ggcagtgaaa ggcaactttc tgtttaacgg cagcgtgatc   1560

agcggtccag gttttaccgg cggtgacctg gtgcgcctga acaacagcgg caacaatatc   1620

caaaaccgtg gttatatcga agtcccgatt caattcatca gcacgagcac ccgttaccgc   1680

gtccgtgttc gctacgcatc cgttacgccg atccgcctga gcgttaactg ggcaattcc    1740
```

```
aacattttca gcagcattgt ccctgctacg gcgacctctc tggacaattt gcagagccgt   1800

aacttcggct atttcgaaag ccgcaacgct ttcaccagcg ctacgggcaa tgtggttggt   1860

gttcgcaatt tcagcgagaa tgcgggcgtc atcattgacc gttttgagtt tatcccggtg   1920

accgcgacct tcgaagcgga gtacgatctg gagcgtgcgc aggaa                   1965


<210> SEQ ID NO 23
<211> LENGTH: 663
<212> TYPE: PRT
<213> ORGANISM: Artificial Sequence
<220> FEATURE:
<223> OTHER INFORMATION: Cry1B variant

<400> SEQUENCE: 23

Met Pro Ser Asn Arg Lys Asn Glu Asn Glu Ile Ile Asn Ala Val Ser
1               5                   10                  15

Asn His Ser Ala Gln Met Asp Leu Ser Leu Asp Ala Arg Ile Glu Asp
            20                  25                  30

Ser Leu Cys Val Ala Glu Val Asn Asn Ile Asp Pro Phe Val Ser Ala
        35                  40                  45

Ser Thr Val Gln Thr Gly Ile Ser Ile Ala Gly Arg Ile Leu Gly Val
    50                  55                  60

Leu Gly Val Pro Phe Ala Gly Gln Leu Ala Ser Phe Tyr Ser Phe Leu
65                  70                  75                  80

Val Gly Glu Leu Trp Pro Ser Gly Arg Asp Pro Trp Glu Ile Phe Met
                85                  90                  95

Glu His Val Glu Gln Ile Val Arg Gln Gln Ile Thr Asp Ser Val Arg
            100                 105                 110

Asp Thr Ala Ile Ala Arg Leu Glu Gly Leu Gly Arg Gly Tyr Arg Ser
        115                 120                 125

Tyr Gln Gln Ala Leu Glu Thr Trp Leu Asp Asn Arg Asn Asp Ala Arg
    130                 135                 140

Ser Arg Ser Ile Ile Arg Glu Arg Tyr Ile Ala Leu Glu Leu Asp Ile
145                 150                 155                 160

Thr Thr Ala Ile Pro Leu Phe Ser Ile Arg Asn Gln Glu Val Pro Leu
                165                 170                 175

Leu Met Val Tyr Ala Gln Ala Ala Asn Leu His Leu Leu Leu Leu Arg
            180                 185                 190

Asp Ala Ser Leu Phe Gly Ser Glu Trp Gly Met Ser Ser Ser Asp Val
        195                 200                 205

Asn Gln Tyr Tyr Gln Glu Gln Ile Arg Tyr Thr Glu Glu Tyr Ser Asn
    210                 215                 220

His Cys Val Gln Trp Tyr Asn Thr Gly Leu Asn Asn Leu Arg Gly Thr
225                 230                 235                 240

Asn Ala Glu Ser Trp Leu Arg Tyr Asn Gln Phe Arg Arg Asp Leu Thr
                245                 250                 255

Leu Gly Val Leu Asp Leu Val Ala Leu Phe Pro Ser Tyr Asp Thr Arg
            260                 265                 270

Val Tyr Pro Met Asn Thr Ser Ala Gln Leu Thr Arg Glu Ile Tyr Thr
        275                 280                 285

Asp Pro Ile Gly Arg Thr Asn Ala Pro Ser Gly Phe Ala Ser Thr Asn
    290                 295                 300

Trp Phe Asn Asn Asn Ala Pro Ser Phe Ser Ala Ile Glu Ala Ala Ile
305                 310                 315                 320

Phe Arg Pro Pro His Leu Leu Asp Phe Pro Glu Gln Leu Thr Ile Tyr
```

```
                325                 330                 335

Ser Ala Ser Ser Arg Trp Ser Ser Thr Gln His Met Asn Tyr Trp Val
            340                 345                 350

Gly His Arg Leu Asn Phe Arg Pro Ile Gly Gly Thr Leu Asn Thr Ser
        355                 360                 365

Thr Gln Gly Leu Thr Asn Asn Thr Ser Ile Asn Pro Val Thr Leu Gln
    370                 375                 380

Phe Thr Ser Arg Asp Val Tyr Arg Thr Glu Ser Asn Ala Gly Thr Asn
385                 390                 395                 400

Ile Leu Phe Thr Thr Pro Val Asn Gly Val Pro Trp Ala Arg Phe Asn
                405                 410                 415

Phe Ile Asn Pro Gln Asn Ile Tyr Glu Arg Gly Ala Thr Thr Tyr Ser
            420                 425                 430

Gln Pro Tyr Gln Gly Val Gly Ile Gln Leu Phe Asp Ser Glu Thr Glu
        435                 440                 445

Leu Pro Pro Glu Thr Thr Glu Arg Pro Asn Tyr Glu Ser Tyr Ser His
    450                 455                 460

Arg Leu Ser His Ile Gly Leu Ile Ile Gly Asn Thr Leu Arg Ala Pro
465                 470                 475                 480

Val Tyr Ser Trp Thr His Arg Ser Ala Thr Leu Thr Asn Thr Ile Asp
                485                 490                 495

Pro Glu Arg Ile Asn Gln Ile Pro Leu Val Lys Gly Phe Arg Val Trp
            500                 505                 510

Gly Gly Thr Ser Val Ile Thr Gly Pro Gly Phe Thr Gly Gly Asp Ile
        515                 520                 525

Leu Arg Arg Asn Thr Phe Gly Asp Phe Val Ser Leu Gln Val Asn Ile
    530                 535                 540

Asn Ser Pro Ile Thr Gln Arg Tyr Arg Leu Arg Phe Arg Tyr Ala Ser
545                 550                 555                 560

Ser Arg Asp Ala Arg Val Ile Val Leu Thr Gly Ala Ala Ser Thr Gly
                565                 570                 575

Val Gly Gly Gln Val Ser Val Asn Met Pro Leu Gln Lys Thr Met Glu
            580                 585                 590

Ile Gly Glu Asn Leu Thr Ser Arg Thr Phe Arg Tyr Thr Asp Phe Ser
        595                 600                 605

Asn Pro Phe Ser Phe Arg Ala Asn Pro Asp Ile Ile Gly Ile Ser Glu
    610                 615                 620

Gln Pro Leu Phe Gly Ala Gly Ser Ile Ser Ser Gly Glu Leu Tyr Ile
625                 630                 635                 640

Asp Lys Ile Glu Ile Ile Leu Ala Asp Ala Thr Phe Glu Ala Glu Ser
                645                 650                 655

Asp Leu Glu Arg Ala Gln Lys
            660


<210> SEQ ID NO 24
<211> LENGTH: 1989
<212> TYPE: DNA
<213> ORGANISM: Artificial Sequence
<220> FEATURE:
<223> OTHER INFORMATION: coding sequence of Cry1B variant

<400> SEQUENCE: 24

atgccttcaa ataggaaaaa tgagaatgaa attataaatg ctgtatcgaa tcattccgca      60

caaatggatc tatcgctaga tgctcgtatt gaagatagct tgtgtgtagc cgaggtgaac     120
```

```
aatattgatc catttgttag cgcatcaaca gtccaaacag gtattagtat agctggtaga    180

atattgggcg tattaggtgt gccgtttgct ggacaactag ctagttttta tagttttctt    240

gttggggaat tatggcctag cggcagagat ccatgggaaa tttttatgga acatgtcgag    300

caaattgtaa gacaacaaat aacggacagt gttagggata ccgctattgc tcgtttagaa    360

ggtctaggaa gagggtatag atcttaccag caggctcttg aaacttggtt agataaccga    420

aatgatgcaa gatcaagaag cattattcgt gagagatata ttgctttaga acttgacatt    480

actactgcta taccgctttt cagcatacga aatcaagagg ttccattatt aatggtatat    540

gctcaagctg caaatttaca cctattatta ttgagagacg catccctttt tggtagtgaa    600

tgggggatgt catcttccga tgttaaccaa tattaccaag aacaaatcag atatacagag    660

gaatattcta accattgcgt acaatggtat aatacagggc taaataactt aagagggaca    720

aatgctgaaa gttggttgcg gtataatcaa ttccgtagag atctaacgtt aggagtatta    780

gatctagtgg cactattccc aagctatgac acgcgtgttt atccaatgaa tacgagtgct    840

cagttaacaa gagaaattta tacagatcca attgggagaa caaatgcacc ttcaggattt    900

gcaagtacga attggtttaa taataatgca ccatcgtttt ctgccataga ggctgccatt    960

ttcaggcctc cgcatctact tgatttttcca gaacaactta caatttacag tgcatcaagc  1020

cgttggagta gcactcaaca tatgaattat tgggtgggac ataggcttaa cttccgccca   1080

ataggaggga cattaaatac ctcaacacaa ggacttacta ataatacttc aattaatcct   1140

gtaacattac agtttacgtc tcgtgacgtt tatagaacag aatcaaatgc agggacaaat   1200

atactattta ctactcctgt gaatggagta ccttgggcta gatttaattt tataaaccct   1260

cagaatattt atgaaagagg cgccactacc tacagtcaac cgtatcaggg agttgggatt   1320

caattatttg attcagaaac tgaattacca ccagaaacaa cagaacgacc aaattatgaa   1380

tcatatagtc atagattatc tcatatagga ctaatcatag gaaacacttt gagagcacca   1440

gtctattctt ggacgcatcg tagtgcaact cttacaaata caattgatcc agagagaatt   1500

aatcaaatac ctttagtgaa aggatttaga gtttgggggg gcacctctgt cattacagga   1560

ccaggattta caggagggga tatccttcga agaaatacct ttggtgattt tgtatctcta   1620

caagtcaata ttaattcacc aattacccaa agataccgtt taagatttcg ttacgcttcc   1680

agtagggatg cacgagttat agtattaaca ggagcggcat ccacaggagt gggaggccaa   1740

gttagtgtaa atatgcctct tcagaaaact atggaaatag gggagaactt aacatctaga   1800

acatttagat ataccgattt tagtaatcct ttttcattta gagctaatcc agatataatt   1860

gggataagtg aacaacctct atttggtgca ggttctatta gtagcggtga actttatata   1920

gataaaattg aaattattct agcagatgca acatttgaag cagaatctga tttagaaaga   1980

gcacaaaag                                                           1989
```

<210> SEQ ID NO 25
<211> LENGTH: 663
<212> TYPE: PRT
<213> ORGANISM: Artificial Sequence
<220> FEATURE:
<223> OTHER INFORMATION: Cry1B variant

<400> SEQUENCE: 25

```
Met Pro Ser Asn Arg Lys Asn Glu Asn Glu Ile Ile Asn Ala Val Ser
1               5                   10                  15

Asn His Ser Ala Gln Met Asp Leu Ser Leu Asp Ala Arg Ile Glu Asp
            20                  25                  30
```

```
Ser Leu Cys Val Ala Glu Val Asn Asn Ile Asp Pro Phe Val Ser Ala
        35                  40                  45

Ser Thr Val Gln Thr Gly Ile Ser Ile Ala Gly Arg Ile Leu Gly Val
    50                  55                  60

Leu Gly Val Pro Phe Ala Gly Gln Leu Ala Ser Phe Tyr Ser Phe Leu
65                  70                  75                  80

Val Gly Glu Leu Trp Pro Ser Gly Arg Asp Pro Trp Glu Ile Phe Met
                85                  90                  95

Glu His Val Glu Gln Ile Val Arg Gln Gln Ile Thr Asp Ser Val Arg
            100                 105                 110

Asp Thr Ala Ile Ala Arg Leu Glu Gly Leu Gly Arg Gly Tyr Arg Ser
        115                 120                 125

Tyr Gln Gln Ala Leu Glu Thr Trp Leu Asp Asn Arg Asn Asp Ala Arg
    130                 135                 140

Ser Arg Ser Ile Ile Arg Glu Arg Tyr Ile Ala Leu Glu Leu Asp Ile
145                 150                 155                 160

Thr Thr Ala Ile Pro Leu Phe Ser Ile Arg Asn Gln Glu Val Pro Leu
                165                 170                 175

Leu Met Val Tyr Ala Gln Ala Ala Asn Leu His Leu Leu Leu Leu Arg
            180                 185                 190

Asp Ala Ser Leu Phe Gly Ser Glu Trp Gly Met Ser Ser Ser Asp Val
        195                 200                 205

Asn Gln Tyr Tyr Gln Glu Gln Ile Arg Tyr Thr Glu Glu Tyr Ser Asn
    210                 215                 220

His Cys Val Gln Trp Tyr Asn Thr Gly Leu Asn Asn Leu Arg Gly Thr
225                 230                 235                 240

Asn Ala Glu Ser Trp Leu Arg Tyr Asn Gln Phe Arg Arg Asp Leu Thr
                245                 250                 255

Leu Gly Val Leu Asp Leu Val Ala Leu Phe Pro Ser Tyr Asp Thr Arg
            260                 265                 270

Thr Tyr Pro Ile Asn Thr Ser Ala Gln Leu Thr Arg Glu Ile Tyr Thr
        275                 280                 285

Asp Pro Ile Gly Arg Thr Asn Ala Pro Ser Gly Phe Ala Ser Thr Asn
    290                 295                 300

Trp Phe Asn Asn Asn Ala Pro Ser Phe Ser Ala Ile Glu Ala Ala Ile
305                 310                 315                 320

Phe Arg Pro Pro His Leu Leu Asp Phe Pro Glu Gln Leu Thr Ile Tyr
                325                 330                 335

Ser Ala Ser Ser Arg Trp Ser Ser Thr Gln His Met Asn Tyr Trp Val
            340                 345                 350

Gly His Arg Leu Asn Phe Arg Pro Ile Gly Gly Thr Leu Asn Thr Ser
        355                 360                 365

Thr Gln Gly Leu Thr Asn Asn Thr Ser Ile Asn Pro Val Thr Leu Gln
    370                 375                 380

Phe Thr Ser Arg Asp Val Tyr Arg Thr Glu Ser Asn Ala Gly Thr Asn
385                 390                 395                 400

Ile Leu Phe Thr Thr Pro Val Asn Gly Val Pro Trp Ala Arg Phe Asn
                405                 410                 415

Phe Ile Asn Pro Gln Asn Ile Tyr Glu Arg Gly Ala Thr Thr Tyr Ser
            420                 425                 430

Gln Pro Tyr Gln Gly Val Gly Ile Gln Leu Phe Asp Ser Glu Thr Glu
        435                 440                 445
```

Leu Pro Pro Glu Thr Thr Glu Arg Pro Asn Tyr Glu Ser Tyr Ser His
    450                 455                 460

Arg Leu Ser His Ile Gly Leu Ile Ile Gly Asn Thr Leu Arg Ala Pro
465                 470                 475                 480

Val Tyr Ser Trp Thr His Arg Ser Ala Thr Leu Thr Asn Thr Ile Asp
                485                 490                 495

Pro Glu Arg Ile Asn Gln Ile Pro Leu Val Lys Gly Phe Arg Val Trp
            500                 505                 510

Gly Gly Thr Ser Val Ile Thr Gly Pro Gly Phe Thr Gly Gly Asp Ile
        515                 520                 525

Leu Arg Arg Asn Thr Phe Gly Asp Phe Val Ser Leu Gln Val Asn Ile
    530                 535                 540

Asn Ser Pro Ile Thr Gln Arg Tyr Arg Leu Arg Phe Arg Tyr Ala Ser
545                 550                 555                 560

Ser Arg Asp Ala Arg Val Ile Val Leu Thr Gly Ala Ala Ser Thr Gly
                565                 570                 575

Val Gly Gly Gln Val Ser Val Asn Met Pro Leu Gln Lys Thr Met Glu
            580                 585                 590

Ile Gly Glu Asn Leu Thr Ser Arg Thr Phe Arg Tyr Thr Asp Phe Ser
        595                 600                 605

Asn Pro Phe Ser Phe Arg Ala Asn Pro Asp Ile Ile Gly Ile Ser Glu
    610                 615                 620

Gln Pro Leu Phe Gly Ala Gly Ser Ile Ser Ser Gly Glu Leu Tyr Ile
625                 630                 635                 640

Asp Lys Ile Glu Ile Ile Leu Ala Asp Ala Thr Phe Glu Ala Glu Ser
                645                 650                 655

Asp Leu Glu Gly Ala Arg Lys
            660

<210> SEQ ID NO 26
<211> LENGTH: 1989
<212> TYPE: DNA
<213> ORGANISM: Artificial Sequence
<220> FEATURE:
<223> OTHER INFORMATION: coding sequence of Cry1B variant

<400> SEQUENCE: 26
atgccttcaa ataggaaaaa tgagaatgaa attataaatg ctgtatcgaa tcattccgca 60
caaatggatc tatcgctaga tgctcgtatt gaagatagct tgtgtgtagc cgaggtgaac 120
aatattgatc catttgttag cgcatcaaca gtccaaacag gtattagtat agctggtaga 180
atattgggcg tattaggtgt gccgtttgct ggacaactag ctagttttta tagttttctt 240
gttggggaat tatggcctag cggcagagat ccatgggaaa tttttatgga acatgtcgag 300
caaattgtaa gacaacaaat aacggacagt gttagggata ccgctattgc tcgtttagaa 360
ggtctaggaa gagggtatag atcttaccag caggctcttg aaacttggtt agataaccga 420
aatgatgcaa gatcaagaag cattattcgt gagagatata ttgctttaga acttgacatt 480
actactgcta taccgctttt cagcatacga aatcaagagg ttccattatt aatggtatat 540
gctcaagctg caaatttaca cctattatta ttgagagacg catccctttt tggtagtgaa 600
tgggggatgt catcttccga tgttaaccaa tattaccaag aacaaatcag atatacagag 660
gaatattcta accattgcgt acaatggtat aatacagggc taaataactt aagagggaca 720
aatgctgaaa gttggttgcg gtataatcaa ttccgtagag atctaacgtt aggagtatta 780
gatctagtgg cactattccc aagctatgac actcgcactt atccaatcaa tacgagtgct 840

```
cagttaacaa gagaaattta tacagatcca attgggagaa caaatgcacc ttcaggattt    900

gcaagtacga attggtttaa taataatgca ccatcgtttt ctgccataga ggctgccatt    960

ttcaggcctc cgcatctact tgattttcca gaacaactta caatttacag tgcatcaagc   1020

cgttggagta gcactcaaca tatgaattat tgggtgggac ataggcttaa cttccgccca   1080

ataggaggga cattaaatac ctcaacacaa ggacttacta ataatacttc aattaatcct   1140

gtaacattac agtttacgtc tcgtgacgtt tatagaacag aatcaaatgc agggacaaat   1200

atactattta ctactcctgt gaatggagta ccttgggcta gatttaattt tataaaccct   1260

cagaatattt atgaaagagg cgccactacc tacagtcaac cgtatcaggg agttgggatt   1320

caattatttg attcagaaac tgaattacca ccagaaacaa cagaacgacc aaattatgaa   1380

tcatatagtc atagattatc tcatatagga ctaatcatag gaaacacttt gagagcacca   1440

gtctattctt ggacgcatcg tagtgcaact cttacaaata caattgatcc agagagaatt   1500

aatcaaatac ctttagtgaa aggatttaga gtttgggggg gcacctctgt cattacagga   1560

ccaggattta caggaggggga tatccttcga agaaatacct ttggtgattt tgtatctcta   1620

caagtcaata ttaattcacc aattacccaa agataccgtt taagatttcg ttacgcttcc   1680

agtagggatg cacgagttat agtattaaca ggagcggcat ccacaggagt gggaggccaa   1740

gttagtgtaa atatgcctct tcagaaaact atggaaatag gggagaactt aacatctaga   1800

acatttagat ataccgattt tagtaatcct tttcatttta gagctaatcc agatataatt   1860

gggataagtg aacaacctct atttggtgca ggttctatta gtagcggtga actttatata   1920

gataaaattg aaattattct agcagatgca acatttgaag cagaatctga tttagaaggg   1980

gcgcggaag                                                           1989
```

<210> SEQ ID NO 27
<211> LENGTH: 663
<212> TYPE: PRT
<213> ORGANISM: Artificial Sequence
<220> FEATURE:
<223> OTHER INFORMATION: Cry1B variant

<400> SEQUENCE: 27

```
Met Pro Ser Asn Arg Lys Asn Glu Asn Glu Ile Ile Asn Ala Val Ser
1               5                   10                  15

Asn His Ser Ala Gln Met Asp Leu Ser Leu Asp Ala Arg Ile Glu Asp
            20                  25                  30

Ser Leu Cys Val Ala Glu Val Asn Asn Ile Asp Pro Phe Val Ser Ala
        35                  40                  45

Ser Thr Val Gln Thr Gly Ile Asn Ile Ala Gly Arg Ile Leu Gly Val
    50                  55                  60

Leu Gly Val Pro Phe Ala Gly Gln Leu Ala Ser Phe Tyr Ser Phe Leu
65                  70                  75                  80

Val Gly Glu Leu Trp Pro Ser Gly Arg Asp Pro Trp Glu Ile Phe Met
                85                  90                  95

Glu His Val Glu Gln Ile Val Arg Gln Gln Ile Thr Asp Ser Val Arg
            100                 105                 110

Asp Thr Ala Ile Ala Arg Leu Glu Gly Leu Gly Arg Gly Tyr Arg Ser
        115                 120                 125

Tyr Gln Gln Ala Leu Glu Thr Trp Leu Asp Asn Arg Asn Asp Ala Arg
    130                 135                 140

Ser Arg Ser Ile Ile Leu Glu Arg Tyr Ile Ala Leu Glu Leu Asp Ile
```

```
145                 150                 155                 160

Thr Thr Ala Ile Pro Leu Phe Ser Ile Arg Asn Gln Glu Val Pro Leu
                165                 170                 175

Leu Met Val Tyr Ala Gln Ala Ala Asn Leu His Leu Leu Leu Leu Arg
            180                 185                 190

Asp Ala Ser Leu Phe Gly Ser Glu Trp Gly Met Ala Ser Ser Asp Val
        195                 200                 205

Asn Gln Tyr Tyr Gln Glu Gln Ile Arg Tyr Thr Glu Glu Tyr Ser Asn
    210                 215                 220

His Cys Val Gln Trp Tyr Asn Thr Gly Leu Asn Asn Leu Arg Gly Thr
225                 230                 235                 240

Asn Ala Glu Ser Trp Leu Arg Tyr Asn Gln Phe Arg Arg Asp Leu Thr
                245                 250                 255

Leu Gly Val Leu Asp Leu Val Ala Leu Phe Pro Ser Tyr Asp Thr Arg
            260                 265                 270

Thr Tyr Pro Ile Asn Thr Ser Ala Gln Leu Thr Arg Glu Ile Tyr Thr
        275                 280                 285

Asp Pro Ile Gly Arg Thr Asn Ala Pro Ser Gly Phe Ala Ser Thr Asn
    290                 295                 300

Trp Phe Asn Asn Asn Ala Pro Ser Phe Ser Ala Ile Glu Ala Ala Ile
305                 310                 315                 320

Phe Arg Pro Pro His Leu Leu Asp Phe Pro Glu Gln Leu Thr Ile Tyr
                325                 330                 335

Ser Ala Ser Ser Arg Trp Ser Ser Thr Gln His Met Asn Tyr Trp Val
            340                 345                 350

Gly His Arg Leu Asn Phe Arg Pro Ile Gly Gly Thr Leu Asn Thr Ser
        355                 360                 365

Thr Gln Gly Leu Thr Asn Asn Thr Ser Ile Asn Pro Val Thr Leu Gln
    370                 375                 380

Phe Thr Ser Arg Asp Val Tyr Arg Thr Glu Ser Asn Ala Gly Thr Asn
385                 390                 395                 400

Ile Leu Phe Thr Thr Pro Val Asn Gly Val Pro Trp Ala Arg Phe Asn
                405                 410                 415

Phe Ile Asn Pro Gln Asn Ile Tyr Glu Arg Gly Ala Thr Thr Tyr Ser
            420                 425                 430

Gln Pro Tyr Gln Gly Val Gly Ile Gln Leu Phe Asp Ser Glu Thr Glu
        435                 440                 445

Leu Pro Pro Glu Thr Thr Glu Arg Pro Asn Tyr Glu Ser Tyr Ser His
    450                 455                 460

Arg Leu Ser His Ile Gly Leu Ile Ile Gly Asn Thr Leu Arg Ala Pro
465                 470                 475                 480

Val Tyr Ser Trp Thr His Arg Ser Ala Thr Leu Thr Asn Thr Ile Asp
                485                 490                 495

Pro Glu Arg Ile Asn Gln Ile Pro Leu Val Lys Gly Phe Arg Val Trp
            500                 505                 510

Gly Gly Thr Ser Val Ile Thr Gly Pro Gly Phe Thr Gly Gly Asp Ile
        515                 520                 525

Leu Arg Arg Asn Thr Phe Gly Asp Phe Val Ser Leu Gln Val Asn Ile
    530                 535                 540

Asn Ser Pro Ile Thr Gln Arg Tyr Arg Leu Arg Phe Arg Tyr Ala Ser
545                 550                 555                 560

Ser Arg Asp Ala Arg Val Ile Val Leu Thr Gly Ala Ala Ser Thr Gly
                565                 570                 575
```

```
Val Gly Gly Gln Val Ser Val Asn Met Pro Leu Gln Lys Thr Met Glu
            580                 585                 590

Ile Gly Glu Asn Leu Thr Ser Arg Thr Phe Arg Tyr Thr Asp Phe Ser
        595                 600                 605

Asn Pro Phe Ser Phe Arg Ala Asn Pro Asp Ile Ile Gly Ile Ser Glu
    610                 615                 620

Gln Pro Leu Phe Gly Ala Gly Ser Ile Ser Ser Gly Glu Leu Tyr Ile
625                 630                 635                 640

Asp Lys Ile Glu Ile Ile Leu Ala Asp Ala Thr Phe Glu Ala Glu Ser
                645                 650                 655

Asp Leu Glu Lys Ala Gln Lys
            660

<210> SEQ ID NO 28
<211> LENGTH: 1989
<212> TYPE: DNA
<213> ORGANISM: Artificial Sequence
<220> FEATURE:
<223> OTHER INFORMATION: coding sequence of Cry1B variant

<400> SEQUENCE: 28
atgccttcaa ataggaaaaa tgagaatgaa attataaatg ctgtatcgaa tcattccgca      60
caaatggatc tatcgctaga tgctcgtatt gaagatagct tgtgtgtagc cgaggtgaac     120
aatattgatc catttgttag cgcatcaaca gtccaaacgg gtattaacat agctggtaga     180
atactaggcg tattaggggt gccgtttgct ggacaactag ctagttttta tagttttctt     240
gttggggaat tatggcctag cggcagagat ccatgggaaa tttttatgga acatgtcgag     300
caaattgtaa gacaacaaat aacggacagt gttagggata ccgctattgc tcgtttagaa     360
ggtctaggaa gagggtatag atcttaccag caggctcttg aaacttggtt agataaccga     420
aatgatgcaa gatcaagaag cattattctt gagcgctata ttgctttaga acttgacatt     480
actactgcta taccgctttt cagcatacga aatcaagagg ttccattatt gatggtatat     540
gctcaagctg caaatttaca cctattatta ttgagagacg catccctttt tggtagtgaa     600
tgggggatgg catcttccga tgttaaccaa tattaccaag aacaaatcag atatacagag     660
gaatattcta accattgcgt acaatggtat aatacagggc taaataactt aagagggaca     720
aatgctgaaa gttggttgcg gtataatcaa ttccgtagag acctaacgtt aggggtatta     780
gatttagtag ccctattccc aagctatgat actcgcactt atccaatcaa tacgagtgct     840
cagttaacaa gagaaattta tacagatcca attgggagaa caaatgcacc ttcaggattt     900
gcaagtacga attggtttaa taataatgca ccatcgtttt ctgccataga ggctgccatt     960
ttcaggcctc cgcatctact tgattttcca gaacaactta caatttacag tgcatcaagc    1020
cgttggagta gcactcaaca tatgaattat tgggtgggac ataggcttaa cttccgccca    1080
ataggaggga cattaaatac ctcaacacaa ggacttacta ataatacttc aattaatcct    1140
gtaacattac agtttacgtc tcgtgacgtt tatagaacag aatcaaatgc agggacaaat    1200
atactattta ctactcctgt gaatggagta ccttgggcta gatttaattt tataaaccct    1260
cagaatattt atgaaagagg cgccactacc tacagtcaac cgtatcaggg agttgggatt    1320
caattatttg attcagaaac tgaattacca ccagaaacaa cagaacgacc aaattatgaa    1380
tcatatagtc atagattatc tcatatagga ctaatcatag gaaacacttt gagagcacca    1440
gtctattctt ggacgcatcg tagtgcaact cttacaaata caattgatcc agagagaatt    1500
```

-continued

```
aatcaaatac ctttagtgaa aggatttaga gtttgggggg gcacctctgt cattacagga   1560

ccaggattta caggaggga tatccttcga agaaatacct ttggtgattt tgtatctcta   1620

caagtcaata ttaattcacc aattacccaa agataccgtt taagatttcg ttacgcttcc   1680

agtagggatg cacgagttat agtattaaca ggagcggcat ccacaggagt gggaggccaa   1740

gttagtgtaa atatgcctct tcagaaaact atggaaatag gggagaactt aacatctaga   1800

acatttagat ataccgattt tagtaatcct ttttcattta gagctaatcc agatataatt   1860

gggataagtg aacaacctct atttggtgca ggttctatta gtagcggtga actttatata   1920

gataaaattg aaattattct agcagatgca acatttgaag cagaatctga tttagagaaa   1980

gctcagaaa                                                           1989
```

<210> SEQ ID NO 29
<211> LENGTH: 663
<212> TYPE: PRT
<213> ORGANISM: Artificial Sequence
<220> FEATURE:
<223> OTHER INFORMATION: Cry1B variant

<400> SEQUENCE: 29

```
Met Pro Ser Asn Arg Lys Asn Glu Asn Glu Ile Ile Asn Ala Val Ser
1               5                   10                  15

Asn His Ser Ala Gln Met Asp Leu Ser Leu Asp Ala Arg Ile Glu Asp
            20                  25                  30

Ser Leu Cys Val Ala Glu Val Asn Asn Ile Asp Pro Phe Val Ser Ala
        35                  40                  45

Ser Thr Val Gln Thr Gly Ile Ser Ile Ala Gly Arg Ile Leu Gly Val
    50                  55                  60

Leu Gly Val Pro Phe Ala Gly Gln Leu Ala Ser Phe Tyr Ser Phe Leu
65                  70                  75                  80

Val Gly Glu Leu Trp Pro Ser Gly Arg Asp Pro Trp Glu Ile Phe Leu
                85                  90                  95

Glu His Val Glu Gln Leu Ile Arg Gln Gln Val Thr Glu Asn Thr Arg
            100                 105                 110

Asn Thr Ala Ile Ala Arg Leu Glu Gly Leu Gly Arg Gly Tyr Arg Ser
        115                 120                 125

Tyr Gln Gln Ala Leu Glu Thr Trp Leu Asp Asn Arg Asn Asp Ala Arg
    130                 135                 140

Ser Arg Ser Ile Ile Leu Glu Arg Tyr Val Ala Leu Glu Leu Asp Ile
145                 150                 155                 160

Thr Thr Ala Ile Pro Leu Phe Ser Ile Arg Asn Gln Glu Val Pro Leu
                165                 170                 175

Leu Met Val Tyr Ala Gln Ala Ala Asn Leu His Leu Leu Leu Leu Arg
            180                 185                 190

Asp Ala Ser Leu Phe Gly Ser Glu Trp Gly Met Ser Ser Ala Asp Val
        195                 200                 205

Asn Gln Tyr Tyr Gln Glu Gln Ile Arg Tyr Thr Glu Glu Tyr Ser Asn
    210                 215                 220

His Cys Val Gln Trp Tyr Asn Thr Gly Leu Asn Asn Leu Arg Gly Thr
225                 230                 235                 240

Asn Ala Glu Ser Trp Leu Arg Tyr Asn Gln Phe Arg Arg Asp Leu Thr
                245                 250                 255

Leu Gly Val Leu Asp Leu Val Ala Leu Phe Pro Ser Tyr Asp Thr Arg
            260                 265                 270
```

```
Thr Tyr Pro Ile Asn Thr Ser Ala Gln Leu Thr Arg Glu Ile Tyr Thr
        275                 280                 285

Asp Pro Ile Gly Arg Thr Asn Ala Pro Ser Gly Phe Ala Ser Thr Asn
    290                 295                 300

Trp Phe Asn Asn Asn Ala Pro Ser Phe Ser Ala Ile Glu Ala Ala Ile
305                 310                 315                 320

Phe Arg Pro Pro His Leu Leu Asp Phe Pro Glu Gln Leu Thr Ile Tyr
                325                 330                 335

Ser Ala Ser Ser Arg Trp Ser Ser Thr Gln His Met Asn Tyr Trp Val
            340                 345                 350

Gly His Arg Leu Asn Phe Arg Pro Ile Gly Gly Thr Leu Asn Thr Ser
        355                 360                 365

Thr Gln Gly Leu Thr Asn Asn Thr Ser Ile Asn Pro Val Thr Leu Gln
    370                 375                 380

Phe Thr Ser Arg Asp Val Tyr Arg Thr Glu Ser Asn Ala Gly Thr Asn
385                 390                 395                 400

Ile Leu Phe Thr Thr Pro Val Asn Gly Val Pro Trp Ala Arg Phe Asn
                405                 410                 415

Phe Ile Asn Pro Gln Asn Ile Tyr Glu Arg Gly Ala Thr Thr Tyr Ser
            420                 425                 430

Gln Pro Tyr Gln Gly Val Gly Ile Gln Leu Phe Asp Ser Glu Thr Glu
        435                 440                 445

Leu Pro Pro Glu Thr Thr Glu Arg Pro Asn Tyr Glu Ser Tyr Ser His
    450                 455                 460

Arg Leu Ser His Ile Gly Leu Ile Ile Gly Asn Thr Leu Arg Ala Pro
465                 470                 475                 480

Val Tyr Ser Trp Thr His Arg Ser Ala Thr Leu Thr Asn Thr Ile Asp
                485                 490                 495

Pro Glu Arg Ile Asn Gln Ile Pro Leu Val Lys Gly Phe Arg Val Trp
            500                 505                 510

Gly Gly Thr Ser Val Ile Thr Gly Pro Gly Phe Thr Gly Gly Asp Ile
        515                 520                 525

Leu Arg Arg Asn Thr Phe Gly Asp Phe Val Ser Leu Gln Val Asn Ile
    530                 535                 540

Asn Ser Pro Ile Thr Gln Arg Tyr Arg Leu Arg Phe Arg Tyr Ala Ser
545                 550                 555                 560

Ser Arg Asp Ala Arg Val Ile Val Leu Thr Gly Ala Ala Ser Thr Gly
                565                 570                 575

Val Gly Gly Gln Val Ser Val Asn Met Pro Leu Gln Lys Thr Met Glu
            580                 585                 590

Ile Gly Glu Asn Leu Thr Ser Arg Thr Phe Arg Tyr Thr Asp Phe Ser
        595                 600                 605

Asn Pro Phe Ser Phe Arg Ala Asn Pro Asp Ile Ile Gly Ile Ser Glu
    610                 615                 620

Gln Pro Leu Phe Gly Ala Gly Ser Ile Ser Ser Gly Glu Leu Tyr Ile
625                 630                 635                 640

Asp Lys Ile Glu Ile Ile Leu Ala Asp Ala Thr Phe Glu Ala Glu Ser
                645                 650                 655

Asp Leu Glu Arg Ala Gln Lys
            660
```

<210> SEQ ID NO 30
<211> LENGTH: 1989
<212> TYPE: DNA

<213> ORGANISM: Artificial Sequence
<220> FEATURE:
<223> OTHER INFORMATION: coding sequence of Cry1B variant

<400> SEQUENCE: 30
atgccttcaa ataggaaaaa tgagaatgaa attataaatg ctgtatcgaa tcattccgca 60
caaatggatc tatcgctaga tgctcgtatt gaagatagct tgtgtgtagc cgaggtgaac 120
aatattgatc catttgttag cgcatcaaca gtccaaacag gtattagtat agctggtaga 180
atattgggcg tattaggtgt gccgtttgct ggacaactag ctagttttta tagttttctt 240
gttggggaat tatggcctag cggcagagat ccatgggaaa ttttcctgga acatgtcgaa 300
caacttataa gacaacaagt aacagaaaat actaggaata cggctattgc tcgattagaa 360
ggtctaggaa gaggctatag atcttaccag caggctcttg aaacttggtt agataaccga 420
aatgatgcaa gatcaagaag cattattctt gagcgctatg ttgctttaga acttgacatt 480
actactgcta taccgctttt cagcatacga aatcaagagg ttccattatt aatggtatat 540
gctcaagctg caaatttaca cctattatta ttgagagacg catccctttt tggtagtgaa 600
tgggggatgt catctgccga tgttaaccaa tattaccaag aacaaatcag atatacagag 660
gaatattcta accattgcgt acaatggtat aatacagggc taaataactt aagagggaca 720
aatgctgaaa gttggttgcg gtataatcaa ttccgtagag acctaacgtt aggggtatta 780
gatttagtag ccctattccc aagctatgac actcgcactt atccaatcaa tacgagtgct 840
cagttaacaa gagaaattta tacagatcca attgggagaa caaatgcacc ttcaggattt 900
gcaagtacga attggtttaa taataatgca ccatcgtttt ctgccataga ggctgccatt 960
ttcaggcctc cgcatctact tgattttcca gaacaactta caatttacag tgcatcaagc 1020
cgttggagta gcactcaaca tatgaattat tgggtgggac ataggcttaa cttccgccca 1080
ataggaggga cattaaatac ctcaacacaa ggacttacta ataatacttc aattaatcct 1140
gtaacattac agtttacgtc tcgtgacgtt tatagaacag aatcaaatgc agggacaaat 1200
atactattta ctactcctgt gaatggagta ccttgggcta gatttaattt tataaaccct 1260
cagaatattt atgaaagagg cgccactacc tacagtcaac cgtatcaggg agttgggatt 1320
caattatttg attcagaaac tgaattacca ccagaaacaa cagaacgacc aaattatgaa 1380
tcatatagtc atagattatc tcatatagga ctaatcatag gaaacacttt gagagcacca 1440
gtctattctt ggacgcatcg tagtgcaact cttacaaata caattgatcc agagagaatt 1500
aatcaaatac ctttagtgaa aggatttaga gtttgggggg gcacctctgt cattacagga 1560
ccaggattta caggaggga tatccttcga agaaatacct ttggtgattt tgtatctcta 1620
caagtcaata ttaattcacc aattacccaa agataccgtt taagatttcg ttacgcttcc 1680
agtagggatg cacgagttat agtattaaca ggagcggcat ccacaggagt gggaggccaa 1740
gttagtgtaa atatgcctct tcagaaaact atggaaatag gggagaactt aacatctaga 1800
acatttagat ataccgattt tagtaatcct ttttcattta gagctaatcc agatataatt 1860
gggataagtg aacaacctct atttggtgca ggttctatta gtagcggtga actttatata 1920
gataaaattg aaattattct agcagatgca acatttgaag cagaatctga tttagaaaga 1980
gcacaaaag 1989

<210> SEQ ID NO 31
<211> LENGTH: 655
<212> TYPE: PRT
<213> ORGANISM: Artificial Sequence
<220> FEATURE:
<223> OTHER INFORMATION: Cry1B variant

<400> SEQUENCE: 31

Met Pro Ser Asn Arg Lys Asn Glu Asn Glu Ile Ile Asn Ala Leu Ser
1 5 10 15

Ile Pro Ala Val Ser Asn His Ser Ala Gln Met Asp Leu Ser Leu Asp
20 25 30

Ala Arg Ile Glu Asp Ser Leu Cys Ile Ala Glu Gly Asn Asn Ile Asn
35 40 45

Pro Leu Val Ser Ala Ser Thr Val Gln Thr Gly Ile Asn Ile Ala Gly
50 55 60

Arg Ile Leu Gly Val Leu Gly Val Pro Phe Ala Gly Gln Leu Ala Ser
65 70 75 80

Phe Tyr Ser Phe Ile Val Gly Glu Leu Trp Pro Ser Gly Arg Asp Pro
85 90 95

Trp Glu Ile Phe Met Glu His Val Glu Gln Leu Val Arg Gln His Ile
100 105 110

Thr Glu Asn Ala Arg Asn Thr Ala Leu Ala Arg Leu Gln Gly Leu Gly
115 120 125

Ala Ser Phe Arg Ala Tyr Gln Gln Ser Leu Glu Asp Trp Leu Glu Asn
130 135 140

Arg Asp Asn Ala Arg Thr Arg Ser Val Leu Tyr Thr Gln Tyr Ile Ala
145 150 155 160

Leu Glu Leu Asp Phe Leu Asn Ala Met Pro Leu Phe Ala Ile Asn Asn
165 170 175

Gln Gln Val Pro Leu Leu Met Val Tyr Ala Gln Ala Ala Asn Leu His
180 185 190

Leu Leu Leu Leu Arg Asp Ala Ser Leu Phe Gly Ser Glu Phe Gly Leu
195 200 205

Thr Ser Gln Glu Ile Gln Arg Tyr Tyr Glu Arg Gln Ala Glu Lys Thr
210 215 220

Arg Glu Tyr Ser Asp Tyr Cys Ala Arg Trp Tyr Asn Thr Gly Leu Asn
225 230 235 240

Asn Leu Arg Gly Thr Asn Ala Glu Ser Trp Leu Arg Tyr Asn Gln Phe
245 250 255

Arg Arg Asp Leu Thr Leu Gly Val Leu Asp Leu Val Ala Leu Phe Pro
260 265 270

Ser Tyr Asp Thr Arg Ile Tyr Pro Ile Asn Thr Ser Ala Gln Leu Thr
275 280 285

Arg Glu Ile Tyr Thr Asp Pro Ile Gly Arg Thr Asn Ala Pro Ser Gly
290 295 300

Phe Ala Ser Thr Asn Trp Phe Asn Asn Asn Ala Pro Ser Phe Ser Ala
305 310 315 320

Ile Glu Ala Ala Ile Phe Arg Pro Pro His Leu Leu Asp Phe Pro Glu
325 330 335

Gln Leu Thr Ile Tyr Ser Ala Ser Ser Arg Trp Ser Ser Thr Gln His
340 345 350

Met Asn Tyr Trp Val Gly His Arg Leu Asn Phe Arg Pro Ile His Gly
355 360 365

Thr Leu Asn Thr Ser Thr His Gly Ala Thr Asn Thr Ser Ile Asn Pro
370 375 380

Val Thr Leu Gln Phe Thr Ser Arg Asp Val Tyr Arg Thr Glu Ser Tyr
385 390 395 400

```
Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
            420                 425                 430

Leu Tyr Thr Ile Gly Tyr Thr Gly Val Gly Thr Gln Leu Phe Asp Ser
        435                 440                 445

Glu Thr Glu Leu Pro Pro Glu Thr Thr Glu Arg Pro Asn Tyr Glu Ser
    450                 455                 460

Tyr Ser His Arg Leu Ser Asn Ile Arg Leu Ile Ile Ser Asn Thr Leu
465                 470                 475                 480

Arg Ala Pro Val Tyr Ser Trp Thr His Arg Ser Ala Asp Arg Thr Asn
                485                 490                 495

Thr Ile Ala Thr Asn Ile Ile Thr Gln Ile Pro Ala Val Lys Gly Asn
            500                 505                 510

Phe Leu Phe Asn Gly Ser Val Ile Ser Gly Pro Gly Phe Thr Gly Gly
        515                 520                 525

Asp Leu Val Arg Leu Asn Asn Ser Gly Asn Asn Ile Tyr Asn Arg Gly
    530                 535                 540

Tyr Ile Glu Val Pro Ile Gln Phe Ile Ser Thr Ser Thr Arg Tyr Arg
545                 550                 555                 560

Val Arg Val Arg Tyr Ala Ser Val Thr Pro Ile Arg Leu Ser Val Asn
                565                 570                 575

Trp Gly Asn Ser Asn Ile Phe Ser Ser Ile Val Pro Ala Thr Ala Thr
            580                 585                 590

Ser Leu Asp Asn Leu Gln Ser Arg Asn Phe Gly Tyr Phe Glu Ser Arg
        595                 600                 605

Asn Ala Phe Thr Ser Ala Thr Gly Asn Val Val Gly Val Arg Asn Phe
    610                 615                 620

Ser Glu Asn Ala Gly Val Ile Ile Asp Arg Phe Glu Phe Ile Pro Val
625                 630                 635                 640

Thr Ala Thr Phe Glu Ala Glu Tyr Asp Leu Glu Arg Ala Gln Glu
                645                 650                 655
```

```
<210> SEQ ID NO 32
<211> LENGTH: 1968
<212> TYPE: DNA
<213> ORGANISM: Artificial Sequence
<220> FEATURE:
<223> OTHER INFORMATION: coding sequence of Cry1B variant

<400> SEQUENCE: 32

atgccctcca accgcaagaa cgagaacgag ataatcaacg ccctgtcgat cccagccgtc      60

tccaaccact ccgcgcagat ggacctctca ctggacgctc gcatcgagga ctcactctgc     120

atcgccgagg gcaacaacat caacccgctc gtcagcgcct cgaccgtgca gactggcatc     180

aacatcgccg gtcgcatact cggcgtcctc ggagtcccat tcgcaggtca gctggcgagc     240

ttctacagct tcatcgtcgg cgagctctgg ccatcaggtc gcgatccctg ggagatcttc     300

atggagcacg tcgagcagct ggtcaggcag cacatcacgg agaacgctcg caacacggct     360

ctcgccagac tccaaggcct cggagccagc ttcagagcct accagcagtc cctcgaggac     420

tggctcgaga accgcgacaa cgcgaggacc cggagcgtcc tctacaccca gtacatcgcg     480

ctggagctcg acttcctgaa cgcgatgcca ctcttcgcca tcaacaacca gcaggtgccg     540

ctcctcatgg tctacgccca agctgccaac ctccacctcc tgctcctcag agacgctagc     600
```

ctgttcggca gcgagttcgg actcacgtcg caggagatcc agcgctacta cgagcgccag 660
gcggagaaga cccgggagta cagcgactac tgcgcacgct ggtacaacac cggcctgaac 720
aacctgcgcg gcacgaacgc tgagagctgg ctccgctaca accagttccg cagggacctc 780
acactcggag tcctcgacct cgtcgcgctg ttcccgagct acgacacgcg gatctacccg 840
atcaacacga gcgcgcagct cactcgcgag atctacacgg accccatcgg tcgcacgaac 900
gctccatccg gcttcgcctc caccaactgg ttcaacaaca acgcgccgtc gttcagcgcc 960
atcgaagctg caatcttccg cccacctcac ctgctggact tcccagagca gctcaccatc 1020
tacagcgcct ccagccgctg gtccagcacg cagcacatga actactgggt cggccaccgc 1080
ctcaacttca ggcctatcca cggtaccctc aacacctcga cccacggcgc cacgaacacg 1140
tccatcaacc cggtgacgct ccagttcacg agccgggacg tctaccgcac tgagagctac 1200
gctggcatca acatcctgct cacgacgcca gtgaacggcg tcccgtgggc acgcttcaac 1260
tggaggaacc ctctcaactc cctgcgcgga tcgctcctct acaccatcgg ctacaccgga 1320
gtcggtaccc agctcttcga cagcgagacc gagctcccac ctgagaccac cgagaggccc 1380
aactacgaga gctactccca ccgcctgtcg aacatccgcc tcatcatctc caacacgctc 1440
agagctcccg tctactcctg gacgcacagg tcagctgacc ggacgaacac catcgcgacg 1500
aacatcatca cccagatccc ggccgtcaag ggcaacttcc tcttcaacgg ctccgtcatc 1560
tccggaccag gcttcaccgg aggagacctc gtccgcctca acaactccgg caacaacatc 1620
tacaaccggg gctacatcga ggtgccgatc cagttcatct ccacgagcac tcggtaccgc 1680
gtcagagtgc gctacgcgag cgtcactccg atccgcctct ccgtcaactg gggcaactcg 1740
aacatcttca gctccatcgt cccagccacc gcgactagcc tcgacaacct gcagtcccgc 1800
aacttcggct acttcgagag ccgcaacgcc ttcacgagcg cgactggcaa cgtcgtcggc 1860
gtccgcaact tctccgagaa cgccggagtg atcatcgacc gcttcgagtt catccccgtg 1920
accgcgacct tcgaggccga gtacgacctt gagagagctc aggaggcc 1968

<210> SEQ ID NO 33
<211> LENGTH: 655
<212> TYPE: PRT
<213> ORGANISM: Artificial Sequence
<220> FEATURE:
<223> OTHER INFORMATION: Cry1B variant

<400> SEQUENCE: 33

Met Pro Ser Asn Arg Lys Asn Glu Asn Glu Ile Ile Asn Ala Leu Ser
1 5 10 15

Ile Pro Ala Val Ser Asn His Ser Ala Gln Met Asp Leu Ser Leu Asp
20 25 30

Ala Arg Ile Glu Asp Ser Leu Cys Ile Ala Glu Gly Asn Asn Ile Asn
35 40 45

Pro Leu Val Ser Ala Ser Thr Val Gln Thr Gly Ile Asn Ile Ala Gly
50 55 60

Arg Ile Leu Gly Val Leu Gly Val Pro Phe Ala Gly Gln Leu Ala Ser
65 70 75 80

Phe Tyr Ser Phe Ile Val Gly Glu Leu Trp Pro Ser Gly Arg Asp Pro
85 90 95

Trp Glu Ile Phe Met Glu His Val Glu Gln Leu Val Arg Gln His Ile
100 105 110

Thr Glu Asn Ala Arg Asn Thr Ala Leu Ala Arg Leu Gln Gly Leu Gly
115 120 125

-continued

```
Ala Ser Phe Arg Ala Tyr Gln Gln Ser Leu Glu Asp Trp Leu Glu Asn
    130                 135                 140

Arg Asp Asn Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Asn Asn
                165                 170                 175

Gln Gln Val Pro Leu Leu Met Val Tyr Ala Gln Ala Ala Asn Leu His
            180                 185                 190

Leu Leu Leu Leu Arg Asp Ala Ser Leu Phe Gly Ser Glu Phe Gly Leu
        195                 200                 205

Thr Ser Gln Glu Ile Gln Arg Tyr Tyr Glu Arg Gln Ala Glu Lys Thr
    210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Ile Tyr Pro Ile Asn Thr Ser Ala Gln Leu Thr
        275                 280                 285

Arg Glu Ile Tyr Thr Asp Pro Ile Gly Arg Thr Asn Ala Pro Ser Gly
    290                 295                 300

Phe Ala Ser Thr Asn Trp Phe Asn Asn Asn Ala Pro Ser Phe Ser Ala
305                 310                 315                 320

Ile Glu Ala Ala Ile Phe Arg Pro Pro His Leu Leu Asp Phe Pro Glu
                325                 330                 335

Gln Leu Thr Ile Tyr Ser Ala Ser Ser Arg Trp Ser Ser Thr Gln His
            340                 345                 350

Met Asn Tyr Trp Val Gly His Arg Leu Asn Phe Arg Pro Ile His Gly
        355                 360                 365

Thr Leu Asn Thr Ser Thr His Gly Ala Thr Asn Thr Ser Ile Asn Pro
    370                 375                 380

Val Thr Leu Gln Phe Thr Ser Arg Asp Val Tyr Arg Thr Glu Ser Tyr
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
            420                 425                 430

Leu Tyr Thr Ile Gly Tyr Thr Gly Val Gly Thr Gln Leu Phe Asp Ser
        435                 440                 445

Glu Thr Glu Leu Pro Pro Glu Thr Thr Glu Arg Pro Asn Tyr Glu Ser
    450                 455                 460

Tyr Ser His Arg Leu Ser Asn Ile Arg Leu Ile Ile Gly Asn Thr Leu
465                 470                 475                 480

Arg Ala Pro Val Tyr Ser Trp Thr His Arg Ser Ala Asp Arg Thr Asn
                485                 490                 495

Thr Ile Ala Thr Asn Ile Ile Thr Gln Ile Pro Ala Val Lys Gly Asn
            500                 505                 510

Phe Leu Phe Asn Gly Ser Val Ile Ser Gly Pro Gly Phe Thr Gly Gly
        515                 520                 525

Asp Leu Val Arg Leu Asn Asn Ser Gly Asn Asn Ile Tyr Asn Arg Gly
    530                 535                 540
```

```
Tyr Ile Glu Val Pro Ile Gln Phe Ile Ser Thr Ser Thr Arg Tyr Arg
545                 550                 555                 560

Val Arg Val Arg Tyr Ala Ser Val Thr Pro Ile Arg Leu Ser Val Asn
                565                 570                 575

Trp Gly Asn Ser Asn Ile Phe Ser Thr Ile Val Pro Ala Thr Ala Thr
            580                 585                 590

Ser Leu Asp Asn Leu Gln Ser Arg Asn Phe Gly Tyr Phe Glu Ser Arg
        595                 600                 605

Asn Ala Phe Thr Ser Ala Thr Gly Asn Val Val Gly Val Arg Asn Phe
    610                 615                 620

Ser Glu Asn Ala Gly Val Ile Ile Asp Arg Phe Glu Phe Ile Pro Val
625                 630                 635                 640

Thr Ala Thr Phe Glu Ala Glu Tyr Asp Leu Glu Arg Ala Gln Glu
                645                 650                 655


<210> SEQ ID NO 34
<211> LENGTH: 1968
<212> TYPE: DNA
<213> ORGANISM: Artificial Sequence
<220> FEATURE:
<223> OTHER INFORMATION: coding sequence of Cry1B variant

<400> SEQUENCE: 34

atgccctcca accgcaagaa cgagaacgag ataatcaacg ccctgtcgat cccagccgtc     60

tccaaccact ccgcgcagat ggacctctca ctggacgctc gcatcgagga ctcactctgc    120

atcgccgagg gcaacaacat caacccgctc gtcagcgcct cgaccgtgca gactggcatc    180

aacatcgccg gtcgcatact cggcgtcctc ggagtcccat tcgcaggtca gctggcgagc    240

ttctacagct tcatcgtcgg cgagctctgg ccatcaggtc gcgatccctg ggagatcttc    300

atggagcacg tcgagcagct ggtcaggcag cacatcacgg agaacgctcg caacacggct    360

ctcgccagac tccaaggcct cggagccagc ttcagagcct accagcagtc cctcgaggac    420

tggctcgaga accgcgacaa cgcgaggacc cggagcgtcc tctacaccca gtacatcgcg    480

ctggagctcg acttcctgaa cgcgatgcca ctcttcgcca tcaacaacca gcaggtgccg    540

ctcctcatgg tctacgccca agctgccaac ctccacctcc tgctcctcag agacgctagc    600

ctgttcggca gcgagttcgg actcacgtcg caggagatcc agcgctacta cgagcgccag    660

gcggagaaga cccgggagta cagcgactac tgcgcacgct ggtacaacac cggcctgaac    720

aacctgcgcg gcacgaacgc tgagagctgg ctccgctaca accagttccg cagggacctc    780

acactcggag tcctcgacct cgtcgcgctg ttcccgagct acgacacgcg gatctacccg    840

atcaacacga gcgcgcagct cactcgcgag atctacacgg accccatcgg tcgcacgaac    900

gctccatccg gcttcgcctc caccaactgg ttcaacaaca acgcgccgtc gttcagcgcc    960

atcgaagctg caatcttccg cccacctcac ctgctggact tcccagagca gctcaccatc   1020

tacagcgcct ccagccgctg gtccagcacg cagcacatga actactgggt cggccaccgc   1080

ctcaacttca ggcctatcca cggtaccctc aacacctcga cccacggcgc cacgaacacg   1140

tccatcaacc cggtgacgct ccagttcacg agccgggacg tctaccgcac tgagagctac   1200

gctggcatca acatcctgct cacgacgcca gtgaacggcg tcccgtgggc acgcttcaac   1260

tggaggaacc ctctcaactc cctgcgcgga tcgctcctct acaccatcgg ctacaccgga   1320

gtcggtaccc agctcttcga cagcgagacc gagctcccac ctgagaccac cgagaggccc   1380

aactacgaga gctactccca ccgcctgtcg aacatccgcc tcatcatcgg caacacgctc   1440
```

-continued

```
agagctcccg tctactcctg gacgcacagg tcagctgacc ggacgaacac catcgcgacg   1500

aacatcatca cccagatccc ggccgtcaag ggcaacttcc tcttcaacgg ctccgtcatc   1560

tccggaccag gcttcaccgg aggagacctc gtccgcctca acaactccgg caacaacatc   1620

tacaaccggg gctacatcga ggtgccgatc cagttcatct ccacgagcac tcggtaccgc   1680

gtcagagtgc gctacgcgag cgtcactccg atccgcctct ccgtcaactg gggcaactcg   1740

aacatcttca gcaccatcgt cccagccacc gcgactagcc tcgacaacct gcagtcccgc   1800

aacttcggct acttcgagag ccgcaacgcc ttcacgagcg cgactggcaa cgtcgtcggc   1860

gtccgcaact tctccgagaa cgccggagtg atcatcgacc gcttcgagtt catccccgtg   1920

accgcgacct tcgaggccga gtacgacctt gagagagctc aggaggcc                1968
```

<210> SEQ ID NO 35
<211> LENGTH: 655
<212> TYPE: PRT
<213> ORGANISM: Artificial Sequence
<220> FEATURE:
<223> OTHER INFORMATION: Cry1B variant

<400> SEQUENCE: 35

```
Met Pro Ser Asn Arg Lys Asn Glu Asn Glu Ile Ile Asn Ala Leu Ser
1               5                   10                  15

Ile Pro Ala Val Ser Asn His Ser Ala Gln Met Asp Leu Ser Leu Asp
            20                  25                  30

Ala Arg Ile Glu Asp Ser Leu Cys Ile Ala Glu Gly Asn Asn Ile Asn
        35                  40                  45

Pro Leu Val Ser Ala Ser Thr Val Gln Thr Gly Ile Asn Ile Ala Gly
    50                  55                  60

Arg Ile Leu Gly Val Leu Gly Val Pro Phe Ala Gly Gln Leu Ala Ser
65                  70                  75                  80

Phe Tyr Ser Phe Ile Val Gly Glu Leu Trp Pro Ser Gly Arg Asp Pro
                85                  90                  95

Trp Glu Ile Phe Met Glu His Val Glu Gln Leu Val Arg Gln Met Ile
            100                 105                 110

Thr Leu Asn Ala Arg Asn Thr Ala Leu Ala Arg Leu Gln Gly Leu Gly
        115                 120                 125

Ala Ser Phe Arg Ala Tyr Gln Gln Ser Leu Glu Asp Trp Leu Glu Asn
    130                 135                 140

Arg Asp Asn Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Asn Asn
                165                 170                 175

Gln Gln Val Pro Leu Leu Met Val Tyr Ala Gln Ala Ala Asn Leu His
            180                 185                 190

Leu Leu Leu Leu Arg Asp Ala Ser Leu Phe Gly Ser Glu Phe Gly Leu
        195                 200                 205

Thr Ser Gln Glu Ile Gln Arg Tyr Tyr Glu Arg Gln Ala Glu Lys Thr
    210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
            260                 265                 270
```

```
Ser Tyr Asp Thr Arg Ile Tyr Pro Ile Asn Thr Ser Ala Gln Leu Thr
        275                 280                 285

Arg Glu Ile Tyr Thr Asp Pro Ile Gly Arg Thr Asn Ala Pro Ser Gly
    290                 295                 300

Phe Ala Ser Thr Asn Trp Phe Asn Asn Asn Ala Pro Ser Phe Ser Ala
305                 310                 315                 320

Ile Glu Ala Ala Ile Phe Arg Pro Pro His Leu Leu Asp Phe Pro Glu
                325                 330                 335

Gln Leu Thr Ile Tyr Ser Ala Ser Ser Arg Trp Ser Ser Thr Gln His
            340                 345                 350

Met Asn Tyr Trp Val Gly His Arg Leu Asn Phe Arg Pro Ile Gly Gly
        355                 360                 365

Thr Leu Asn Thr Ser Thr His Gly Ala Thr Asn Thr Ser Ile Asn Pro
    370                 375                 380

Val Thr Leu Gln Phe Thr Ser Arg Asp Val Tyr Arg Thr Glu Ser Tyr
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
            420                 425                 430

Leu Tyr Thr Ile Gly Tyr Thr Gly Val Gly Thr Gln Leu Phe Asp Ser
        435                 440                 445

Glu Thr Glu Leu Pro Pro Glu Thr Thr Glu Arg Pro Asn Tyr Glu Ser
    450                 455                 460

Tyr Ser His Arg Leu Ser Asn Ile Arg Leu Ile Ile Gly Gly Thr Leu
465                 470                 475                 480

Arg Ala Pro Val Tyr Ser Trp Thr His Arg Ser Ala Asp Arg Thr Asn
                485                 490                 495

Thr Ile Ala Thr Asn Ile Ile Thr Gln Ile Pro Ala Val Lys Gly Asn
            500                 505                 510

Phe Leu Phe Asn Gly Ser Val Ile Ser Gly Pro Gly Phe Thr Gly Gly
        515                 520                 525

Asp Leu Val Arg Leu Asn Asn Ser Gly Asn Asn Ile Gln Asn Arg Gly
    530                 535                 540

Tyr Ile Glu Val Pro Ile Gln Phe Ile Ser Thr Ser Thr Arg Tyr Arg
545                 550                 555                 560

Val Arg Val Arg Tyr Ala Ser Val Thr Pro Ile Arg Leu Ser Val Asn
                565                 570                 575

Trp Gly Asn Ser Asn Ile Phe Ser Ser Ile Val Pro Ala Thr Ala Thr
            580                 585                 590

Ser Leu Asp Asn Leu Gln Ser Arg Asn Phe Gly Tyr Phe Glu Ser Arg
        595                 600                 605

Asn Ala Phe Thr Ser Ala Thr Gly Asn Val Val Gly Val Arg Asn Phe
    610                 615                 620

Ser Glu Asn Ala Gly Val Ile Ile Asp Arg Phe Glu Phe Ile Pro Val
625                 630                 635                 640

Thr Ala Thr Phe Glu Ala Glu Tyr Asp Leu Glu Arg Ala Gln Glu
                645                 650                 655
```

<210> SEQ ID NO 36
<211> LENGTH: 1968
<212> TYPE: DNA
<213> ORGANISM: Artificial Sequence
<220> FEATURE:
<223> OTHER INFORMATION: coding sequence of Cry1B variant

<400> SEQUENCE: 36
atgccctcca accgcaagaa cgagaacgag ataatcaacg ccctgtcgat cccagccgtc 60
tccaaccact ccgcgcagat ggacctctca ctggacgctc gcatcgagga ctcactctgc 120
atcgccgagg gcaacaacat caacccgctc gtcagcgcct cgaccgtgca gactggcatc 180
aacatcgccg gtcgcatact cggcgtcctc ggagtcccat tcgcaggtca gctggcgagc 240
ttctacagct tcatcgtcgg cgagctctgg ccatcaggtc gcgatccctg ggagatcttc 300
atggagcacg tcgagcagct ggtcaggcag atgatcacgc tcaacgctcg caacacggct 360
ctcgccagac tccaaggcct cggagccagc ttcagagcct accagcagtc cctcgaggac 420
tggctcgaga accgcgacaa cgcgaggacc cggagcgtcc tctacaccca gtacatcgcg 480
ctggagctcg acttcctgaa cgcgatgcca ctcttcgcca tcaacaacca gcaggtgccg 540
ctcctcatgg tctacgccca agctgccaac ctccacctcc tgctcctcag agacgctagc 600
ctgttcggca gcgagttcgg actcacgtcg caggagatcc agcgctacta cgagcgccag 660
gcggagaaga cccgggagta cagcgactac tgcgcacgct ggtacaacac cggcctgaac 720
aacctgcgcg gcacgaacgc tgagagctgg ctccgctaca accagttccg cagggacctc 780
acactcggag tcctcgacct cgtcgcgctg ttcccgagct acgacacgcg gatctacccg 840
atcaacacga gcgcgcagct cactcgcgag atctacacgg accccatcgg tcgcacgaac 900
gctccatccg gcttcgcctc caccaactgg ttcaacaaca acgcgccgtc gttcagcgcc 960
atcgaagctg caatcttccg cccacctcac ctgctggact tcccagagca gctcaccatc 1020
tacagcgcct ccagccgctg gtccagcacg cagcacatga actactgggt cggccaccgc 1080
ctcaacttca ggcctatcgg cggtaccctc aacacctcga cccacggcgc cacgaacacg 1140
tccatcaacc cggtgacgct ccagttcacg agccgggacg tctaccgcac tgagagctac 1200
gctggcatca acatcctgct cacgacgcca gtgaacggcg tcccgtgggc acgcttcaac 1260
tggaggaacc ctctcaactc cctgcgcgga tcgctcctct acaccatcgg ctacaccgga 1320
gtcggtaccc agctcttcga cagcgagacc gagctcccac ctgagaccac cgagaggccc 1380
aactacgaga gctactccca ccgcctgtcg aacatccgcc tcatcatcgg cggcacgctc 1440
agagctcccg tctactcctg gacgcacagg tcagctgacc ggacgaacac catcgcgacg 1500
aacatcatca cccagatccc ggccgtcaag ggcaacttcc tcttcaacgg ctccgtcatc 1560
tccggaccag gcttcaccgg aggagacctc gtccgcctca acaactccgg caacaacatc 1620
cagaaccggg gctacatcga ggtgccgatc cagttcatct ccacgagcac tcggtaccgc 1680
gtcagagtgc gctacgcgag cgtcactccg atccgcctct ccgtcaactg gggcaactcg 1740
aacatcttca gctccatcgt cccagccacc gcgactagcc tcgacaacct gcagtcccgc 1800
aacttcggct acttcgagag ccgcaacgcc ttcacgagcg cgactggcaa cgtcgtcggc 1860
gtccgcaact tctccgagaa cgccggagtg atcatcgacc gcttcgagtt catccccgtg 1920
accgcgacct tcgaggccga gtacgacctt gagagagctc aggaggcc 1968

<210> SEQ ID NO 37
<211> LENGTH: 655
<212> TYPE: PRT
<213> ORGANISM: Artificial Sequence
<220> FEATURE:
<223> OTHER INFORMATION: Cry1B variant

<400> SEQUENCE: 37

```
Met Pro Ser Asn Arg Lys Asn Glu Asn Glu Ile Ile Asn Ala Leu Ser
1               5                   10                  15

Ile Pro Ala Val Ser Asn His Ser Ala Gln Met Asp Leu Ser Leu Asp
            20                  25                  30

Ala Arg Ile Glu Asp Ser Leu Cys Ile Ala Glu Gly Asn Asn Ile Asn
        35                  40                  45

Pro Leu Val Ser Ala Ser Thr Val Gln Thr Gly Ile Asn Ile Ala Gly
    50                  55                  60

Arg Ile Leu Gly Val Leu Gly Val Pro Phe Ala Gly Gln Leu Ala Ser
65                  70                  75                  80

Phe Tyr Ser Phe Ile Val Gly Glu Leu Trp Pro Ser Gly Arg Asp Pro
                85                  90                  95

Trp Glu Ile Phe Met Glu His Val Glu Gln Leu Val Arg Gln Met Ile
            100                 105                 110

Thr Met Asn Ala Arg Asn Thr Ala Leu Ala Arg Leu Gln Gly Leu Gly
        115                 120                 125

Ala Ser Phe Arg Ala Tyr Gln Gln Ser Leu Glu Asp Trp Leu Glu Asn
    130                 135                 140

Arg Asp Asn Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Asn Asn
                165                 170                 175

Gln Gln Val Pro Leu Leu Met Val Tyr Ala Gln Ala Ala Asn Leu His
            180                 185                 190

Leu Leu Leu Leu Arg Asp Ala Ser Leu Phe Gly Ser Glu Phe Gly Leu
        195                 200                 205

Thr Ser Gln Glu Ile Gln Arg Tyr Tyr Glu Arg Gln Ala Glu Lys Thr
    210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Ile Tyr Pro Ile Asn Thr Ser Ala Gln Leu Thr
        275                 280                 285

Arg Glu Ile Tyr Thr Asp Pro Ile Gly Arg Thr Asn Ala Pro Ser Gly
    290                 295                 300

Phe Ala Ser Thr Asn Trp Phe Asn Asn Asn Ala Pro Ser Phe Ser Ala
305                 310                 315                 320

Ile Glu Ala Ala Ile Phe Arg Pro Pro His Leu Leu Asp Phe Pro Glu
                325                 330                 335

Gln Leu Thr Ile Tyr Ser Ala Ser Ser Arg Trp Ser Ser Thr Gln His
            340                 345                 350

Met Asn Tyr Trp Val Gly His Arg Leu Asn Phe Arg Pro Ile Gly Gly
        355                 360                 365

Thr Leu Asn Thr Ser Thr His Gly Ala Thr Asn Thr Ser Ile Asn Pro
    370                 375                 380

Val Thr Leu Gln Phe Thr Ser Arg Asp Val Tyr Arg Thr Glu Ser Tyr
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
```

```
            420                 425                 430

Leu Tyr Thr Ile Gly Tyr Thr Gly Val Gly Thr Gln Leu Phe Asp Ser
        435                 440                 445

Glu Thr Glu Leu Pro Pro Glu Thr Thr Glu Arg Pro Asn Tyr Glu Ser
    450                 455                 460

Tyr Ser His Arg Leu Ser Asn Ile Arg Leu Ile Ile Gly Gly Thr Leu
465                 470                 475                 480

Arg Ala Pro Val Tyr Ser Trp Thr His Arg Ser Ala Asp Arg Thr Asn
                485                 490                 495

Thr Ile Ala Thr Asn Ile Ile Thr Gln Ile Pro Ala Val Lys Gly Asn
            500                 505                 510

Phe Leu Phe Asn Gly Ser Val Ile Ser Gly Pro Gly Phe Thr Gly Gly
        515                 520                 525

Asp Leu Val Arg Leu Asn Asn Ser Gly Asn Asn Ile Gln Asn Arg Gly
    530                 535                 540

Tyr Ile Glu Val Pro Ile Gln Phe Ile Ser Thr Ser Thr Arg Tyr Arg
545                 550                 555                 560

Val Arg Val Arg Tyr Ala Ser Val Thr Pro Ile Arg Leu Ser Val Asn
                565                 570                 575

Trp Gly Asn Ser Asn Ile Phe Ser Ser Ile Val Pro Ala Thr Ala Thr
            580                 585                 590

Ser Leu Asp Asn Leu Gln Ser Arg Asn Phe Gly Tyr Phe Glu Ser Arg
        595                 600                 605

Asn Ala Phe Thr Ser Ala Thr Gly Asn Val Val Gly Val Arg Asn Phe
    610                 615                 620

Ser Glu Asn Ala Gly Val Ile Ile Asp Arg Phe Glu Phe Ile Pro Val
625                 630                 635                 640

Thr Ala Thr Phe Glu Ala Glu Tyr Asp Leu Glu Arg Ala Gln Glu
                645                 650                 655
```

<210> SEQ ID NO 38
<211> LENGTH: 1968
<212> TYPE: DNA
<213> ORGANISM: Artificial Sequence
<220> FEATURE:
<223> OTHER INFORMATION: coding sequence of Cry1B variant

<400> SEQUENCE: 38

```
atgccctcca accgcaagaa cgagaacgag ataatcaacg ccctgtcgat cccagccgtc     60

tccaaccact ccgcgcagat ggacctctca ctggacgctc gcatcgagga ctcactctgc    120

atcgccgagg gcaacaacat caacccgctc gtcagcgcct cgaccgtgca gactggcatc    180

aacatcgccg gtcgcatact cggcgtcctc ggagtcccat tcgcaggtca gctggcgagc    240

ttctacagct tcatcgtcgg cgagctctgg ccatcaggtc gcgatccctg ggagatcttc    300

atggagcacg tcgagcagct ggtcaggcag atgatcacga tgaacgctcg caacacggct    360

ctcgccagac tccaaggcct cggagccagc ttcagagcct accagcagtc cctcgaggac    420

tggctcgaga accgcgacaa cgcgaggacc cggagcgtcc tctacaccca gtacatcgcg    480

ctggagctcg acttcctgaa cgcgatgcca ctcttcgcca tcaacaacca gcaggtgccg    540

ctcctcatgg tctacgccca agctgccaac ctccacctcc tgctcctcag agacgctagc    600

ctgttcggca gcgagttcgg actcacgtcg caggagatcc agcgctacta cgagcgccag    660

gcggagaaga cccgggagta cagcgactac tgcgcacgct ggtacaacac cggcctgaac    720

aacctgcgcg gcacgaacgc tgagagctgg ctccgctaca accagttccg cagggacctc    780
```

```
acactcggag tcctcgacct cgtcgcgctg ttcccgagct acgacacgcg gatctacccg    840

atcaacacga gcgcgcagct cactcgcgag atctacacgg accccatcgg tcgcacgaac    900

gctccatccg gcttcgcctc caccaactgg ttcaacaaca acgcgccgtc gttcagcgcc    960

atcgaagctg caatcttccg cccacctcac ctgctggact tcccagagca gctcaccatc   1020

tacagcgcct ccagccgctg gtccagcacg cagcacatga actactgggt cggccaccgc   1080

ctcaacttca ggcctatcgg cggtaccctc aacacctcga cccacggcgc cacgaacacg   1140

tccatcaacc cggtgacgct ccagttcacg agccgggacg tctaccgcac tgagagctac   1200

gctggcatca acatcctgct cacgacgcca gtgaacggcg tcccgtgggc acgcttcaac   1260

tggaggaacc ctctcaactc cctgcgcgga tcgctcctct acaccatcgg ctacaccgga   1320

gtcggtaccc agctcttcga cagcgagacc gagctcccac ctgagaccac cgagaggccc   1380

aactacgaga gctactccca ccgcctgtcg aacatccgcc tcatcatcgg cggcacgctc   1440

agagctcccg tctactcctg gacgcacagg tcagctgacc ggacgaacac catcgcgacg   1500

aacatcatca cccagatccc ggccgtcaag ggcaacttcc tcttcaacgg ctccgtcatc   1560

tccggaccag gcttcaccgg aggagacctc gtccgcctca acaactccgg caacaacatc   1620

cagaaccggg gctacatcga ggtgccgatc cagttcatct ccacgagcac tcggtaccgc   1680

gtcagagtgc gctacgcgag cgtcactccg atccgcctct ccgtcaactg gggcaactcg   1740

aacatcttca gctccatcgt cccagccacc gcgactagcc tcgacaacct gcagtcccgc   1800

aacttcggct acttcgagag ccgcaacgcc ttcacgagcg cgactggcaa cgtcgtcggc   1860

gtccgcaact tctccgagaa cgccggagtg atcatcgacc gcttcgagtt catccccgtg   1920

accgcgacct tcgaggccga gtacgacctt gagagagctc aggaggcc                1968
```

<210> SEQ ID NO 39
<211> LENGTH: 655
<212> TYPE: PRT
<213> ORGANISM: Artificial Sequence
<220> FEATURE:
<223> OTHER INFORMATION: Cry1B variant

<400> SEQUENCE: 39

```
Met Pro Ser Asn Arg Lys Asn Glu Asn Glu Ile Ile Asn Ala Leu Ser
1               5                   10                  15

Ile Pro Ala Val Ser Asn His Ser Ala Gln Met Asp Leu Ser Leu Asp
            20                  25                  30

Ala Arg Ile Glu Asp Ser Leu Cys Ile Ala Glu Gly Asn Asn Ile Asn
        35                  40                  45

Pro Leu Val Ser Ala Ser Thr Val Gln Thr Gly Ile Asn Ile Ala Gly
    50                  55                  60

Arg Ile Leu Gly Val Leu Gly Val Pro Phe Ala Gly Gln Leu Ala Ser
65                  70                  75                  80

Phe Tyr Ser Phe Ile Val Gly Glu Leu Trp Pro Ser Gly Arg Asp Pro
                85                  90                  95

Trp Glu Ile Phe Met Glu His Val Glu Gln Leu Val Arg Gln Met Ile
            100                 105                 110

Thr His Asn Ala Arg Asn Thr Ala Leu Ala Arg Leu Gln Gly Leu Gly
        115                 120                 125

Ala Ser Phe Arg Ala Tyr Gln Gln Ser Leu Glu Asp Trp Leu Glu Asn
    130                 135                 140

Arg Asp Asn Ala Arg Thr Arg Ser Val Leu Tyr Thr Gln Tyr Ile Ala
```

```
145                 150                 155                 160

Leu Glu Leu Asp Phe Leu Asn Ala Met Pro Leu Phe Ala Ile Asn Asn
                165                 170                 175

Gln Gln Val Pro Leu Leu Met Val Tyr Ala Gln Ala Ala Asn Leu His
            180                 185                 190

Leu Leu Leu Leu Arg Asp Ala Ser Leu Phe Gly Ser Glu Phe Gly Leu
        195                 200                 205

Thr Ser Gln Glu Ile Gln Arg Tyr Tyr Glu Arg Gln Ala Glu Lys Thr
    210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Ile Tyr Pro Ile Asn Thr Ser Ala Gln Leu Thr
        275                 280                 285

Arg Glu Ile Tyr Thr Asp Pro Ile Gly Arg Thr Asn Ala Pro Ser Gly
    290                 295                 300

Phe Ala Ser Thr Asn Trp Phe Asn Asn Asn Ala Pro Ser Phe Ser Ala
305                 310                 315                 320

Ile Glu Ala Ala Ile Phe Arg Pro Pro His Leu Leu Asp Phe Pro Glu
                325                 330                 335

Gln Leu Thr Ile Tyr Ser Ala Ser Ser Arg Trp Ser Ser Thr Gln His
            340                 345                 350

Met Asn Tyr Trp Val Gly His Arg Leu Asn Phe Arg Pro Ile Gly Gly
        355                 360                 365

Thr Leu Asn Thr Ser Thr His Gly Ala Thr Asn Thr Ser Ile Asn Pro
    370                 375                 380

Val Thr Leu Gln Phe Thr Ser Arg Asp Val Tyr Arg Thr Glu Ser Tyr
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
            420                 425                 430

Leu Tyr Thr Ile Gly Tyr Thr Gly Val Gly Thr Gln Leu Phe Asp Ser
        435                 440                 445

Glu Thr Glu Leu Pro Pro Glu Thr Thr Glu Arg Pro Asn Tyr Glu Ser
    450                 455                 460

Tyr Ser His Arg Leu Ser Asn Ile Arg Leu Ile Ile Gly Gly Thr Leu
465                 470                 475                 480

Arg Ala Pro Val Tyr Ser Trp Thr His Arg Ser Ala Asp Arg Thr Asn
                485                 490                 495

Thr Ile Ala Thr Asn Ile Ile Thr Gln Ile Pro Ala Val Lys Gly Asn
            500                 505                 510

Phe Leu Phe Asn Gly Ser Val Ile Ser Gly Pro Gly Phe Thr Gly Gly
        515                 520                 525

Asp Leu Val Arg Leu Asn Asn Ser Gly Asn Asn Ile Gln Asn Arg Gly
    530                 535                 540

Tyr Ile Glu Val Pro Ile Gln Phe Ile Ser Thr Ser Thr Arg Tyr Arg
545                 550                 555                 560

Val Arg Val Arg Tyr Ala Ser Val Thr Pro Ile Arg Leu Ser Val Asn
                565                 570                 575
```

```
Trp Gly Asn Ser Asn Ile Phe Ser Ser Ile Val Pro Ala Thr Ala Thr
            580                 585                 590

Ser Leu Asp Asn Leu Gln Ser Arg Asn Phe Gly Tyr Phe Glu Ser Arg
        595                 600                 605

Asn Ala Phe Thr Ser Ala Thr Gly Asn Val Val Gly Val Arg Asn Phe
    610                 615                 620

Ser Glu Asn Ala Gly Val Ile Ile Asp Arg Phe Glu Phe Ile Pro Val
625                 630                 635                 640

Thr Ala Thr Phe Glu Ala Glu Tyr Asp Leu Glu Arg Ala Gln Glu
                645                 650                 655


<210> SEQ ID NO 40
<211> LENGTH: 1968
<212> TYPE: DNA
<213> ORGANISM: Artificial Sequence
<220> FEATURE:
<223> OTHER INFORMATION: coding sequence of Cry1B variant

<400> SEQUENCE: 40

atgccctcca accgcaagaa cgagaacgag ataatcaacg ccctgtcgat cccagccgtc      60

tccaaccact ccgcgcagat ggacctctca ctggacgctc gcatcgagga ctcactctgc     120

atcgccgagg gcaacaacat caacccgctc gtcagcgcct cgaccgtgca gactggcatc     180

aacatcgccg gtcgcatact cggcgtcctc ggagtcccat tcgcaggtca gctggcgagc     240

ttctacagct tcatcgtcgg cgagctctgg ccatcaggtc gcgatccctg ggagatcttc     300

atggagcacg tcgagcagct ggtcaggcag atgatcacgc acaacgctcg caacacggct     360

ctcgccagac tccaaggcct cggagccagc ttcagagcct accagcagtc cctcgaggac     420

tggctcgaga accgcgacaa cgcgaggacc cggagcgtcc tctacaccca gtacatcgcg     480

ctggagctcg acttcctgaa cgcgatgcca ctcttcgcca tcaacaacca gcaggtgccg     540

ctcctcatgg tctacgccca agctgccaac ctccacctcc tgctcctcag agacgctagc     600

ctgttcggca gcgagttcgg actcacgtcg caggagatcc agcgctacta cgagcgccag     660

gcggagaaga cccgggagta cagcgactac tgcgcacgct ggtacaacac cggcctgaac     720

aacctgcgcg gcacgaacgc tgagagctgg ctccgctaca accagttccg cagggacctc     780

acactcggag tcctcgacct cgtcgcgctg ttcccgagct acgacacgcg gatctacccg     840

atcaacacga gcgcgcagct cactcgcgag atctacacgg accccatcgg tcgcacgaac     900

gctccatccg gcttcgcctc caccaactgg ttcaacaaca acgcgccgtc gttcagcgcc     960

atcgaagctg caatcttccg cccacctcac ctgctggact tcccagagca gctcaccatc    1020

tacagcgcct ccagccgctg gtccagcacg cagcacatga actactgggt cggccaccgc    1080

ctcaacttca ggcctatcgg cggtaccctc aacacctcga cccacggcgc cacgaacacg    1140

tccatcaacc cggtgacgct ccagttcacg agccgggacg tctaccgcac tgagagctac    1200

gctggcatca acatcctgct cacgacgcca gtgaacggcg tcccgtgggc acgcttcaac    1260

tggaggaacc ctctcaactc cctgcgcgga tcgctcctct acaccatcgg ctacaccgga    1320

gtcggtaccc agctcttcga cagcgagacc gagctcccac ctgagaccac cgagaggccc    1380

aactacgaga gctactccca ccgcctgtcg aacatccgcc tcatcatcgg cggcacgctc    1440

agagctcccg tctactcctg gacgcacagg tcagctgacc ggacgaacac catcgcgacg    1500

aacatcatca cccagatccc ggccgtcaag ggcaacttcc tcttcaacgg ctccgtcatc    1560

tccggaccag gcttcaccgg aggagacctc gtccgcctca acaactccgg caacaacatc    1620
```

```
cagaaccggg gctacatcga ggtgccgatc cagttcatct ccacgagcac tcggtaccgc   1680

gtcagagtgc gctacgcgag cgtcactccg atccgcctct ccgtcaactg ggcaactcg    1740

aacatcttca gctccatcgt cccagccacc gcgactagcc tcgacaacct gcagtcccgc   1800

aacttcggct acttcgagag ccgcaacgcc ttcacgagcg cgactggcaa cgtcgtcggc   1860

gtccgcaact tctccgagaa cgccggagtg atcatcgacc gcttcgagtt catccccgtg   1920

accgcgacct tcgaggccga gtacgacctt gagagagctc aggaggcc                1968
```

<210> SEQ ID NO 41
<211> LENGTH: 655
<212> TYPE: PRT
<213> ORGANISM: Artificial Sequence
<220> FEATURE:
<223> OTHER INFORMATION: Cry1B variant

<400> SEQUENCE: 41

```
Met Pro Ser Asn Arg Lys Asn Glu Asn Glu Ile Ile Asn Ala Leu Ser
1               5                   10                  15

Ile Pro Ala Val Ser Asn His Ser Ala Gln Met Asp Leu Ser Leu Asp
            20                  25                  30

Ala Arg Ile Glu Asp Ser Leu Cys Ile Ala Glu Gly Asn Asn Ile Asn
        35                  40                  45

Pro Leu Val Ser Ala Ser Thr Val Gln Thr Gly Ile Asn Ile Ala Gly
    50                  55                  60

Arg Ile Leu Gly Val Leu Gly Val Pro Phe Ala Gly Gln Leu Ala Ser
65                  70                  75                  80

Phe Tyr Ser Phe Ile Val Gly Glu Leu Trp Pro Ser Gly Arg Asp Pro
                85                  90                  95

Trp Glu Ile Phe Met Glu His Val Glu Gln Leu Val Arg Gln His Ile
            100                 105                 110

Thr Met Asn Ala Arg Asn Thr Ala Leu Ala Arg Leu Gln Gly Leu Gly
        115                 120                 125

Ala Ser Phe Arg Ala Tyr Gln Gln Ser Leu Glu Asp Trp Leu Glu Asn
    130                 135                 140

Arg Asp Asn Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Asn Asn
                165                 170                 175

Gln Gln Val Pro Leu Leu Met Val Tyr Ala Gln Ala Ala Asn Leu His
            180                 185                 190

Leu Leu Leu Leu Arg Asp Ala Ser Leu Phe Gly Ser Glu Phe Gly Leu
        195                 200                 205

Thr Ser Gln Glu Ile Gln Arg Tyr Tyr Glu Arg Gln Ala Glu Lys Thr
    210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Ile Tyr Pro Ile Asn Thr Ser Ala Gln Leu Thr
        275                 280                 285

Arg Glu Ile Tyr Thr Asp Pro Ile Gly Arg Thr Asn Ala Pro Ser Gly
    290                 295                 300
```

```
Phe Ala Ser Thr Asn Trp Phe Asn Asn Asn Ala Pro Ser Phe Ser Ala
305                 310                 315                 320

Ile Glu Ala Ala Ile Phe Arg Pro Pro His Leu Leu Asp Phe Pro Glu
                325                 330                 335

Gln Leu Thr Ile Tyr Ser Ala Ser Ser Arg Trp Ser Ser Thr Gln His
            340                 345                 350

Met Asn Tyr Trp Val Gly His Arg Leu Asn Phe Arg Pro Ile Gly Gly
        355                 360                 365

Thr Leu Asn Thr Ser Thr His Gly Ala Thr Asn Thr Ser Ile Asn Pro
    370                 375                 380

Val Thr Leu Gln Phe Thr Ser Arg Asp Val Tyr Arg Thr Glu Ser Tyr
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
            420                 425                 430

Leu Tyr Thr Ile Gly Tyr Thr Gly Val Gly Thr Gln Leu Phe Asp Ser
        435                 440                 445

Glu Thr Glu Leu Pro Pro Glu Thr Thr Glu Arg Pro Asn Tyr Glu Ser
    450                 455                 460

Tyr Ser His Arg Leu Ser Asn Ile Arg Leu Ile Ile Gly Gly Thr Leu
465                 470                 475                 480

Arg Ala Pro Val Tyr Ser Trp Thr His Arg Ser Ala Asp Arg Thr Asn
                485                 490                 495

Thr Ile Ala Thr Asn Ile Ile Thr Gln Ile Pro Ala Val Lys Gly Asn
            500                 505                 510

Phe Leu Phe Asn Gly Ser Val Ile Ser Gly Pro Gly Phe Thr Gly Gly
        515                 520                 525

Asp Leu Val Arg Leu Asn Asn Ser Gly Asn Asn Ile Gln Asn Arg Gly
    530                 535                 540

Tyr Ile Glu Val Pro Ile Gln Phe Ile Ser Thr Ser Thr Arg Tyr Arg
545                 550                 555                 560

Val Arg Val Arg Tyr Ala Ser Val Thr Pro Ile Arg Leu Ser Val Asn
                565                 570                 575

Trp Gly Asn Ser Asn Ile Phe Ser Ser Ile Val Pro Ala Thr Ala Thr
            580                 585                 590

Ser Leu Asp Asn Leu Gln Ser Arg Asn Phe Gly Tyr Phe Glu Ser Arg
        595                 600                 605

Asn Ala Phe Thr Ser Ala Thr Gly Asn Val Val Gly Val Arg Asn Phe
    610                 615                 620

Ser Glu Asn Ala Gly Val Ile Ile Asp Arg Phe Glu Phe Ile Pro Val
625                 630                 635                 640

Thr Ala Thr Phe Glu Ala Glu Tyr Asp Leu Glu Arg Ala Gln Glu
                645                 650                 655
```

<210> SEQ ID NO 42
<211> LENGTH: 1968
<212> TYPE: DNA
<213> ORGANISM: Artificial Sequence
<220> FEATURE:
<223> OTHER INFORMATION: coding sequence of Cry1B variant

<400> SEQUENCE: 42

```
atgccctcca accgcaagaa cgagaacgag ataatcaacg ccctgtcgat cccagccgtc      60
```

```
tccaaccact ccgcgcagat ggacctctca ctggacgctc gcatcgagga ctcactctgc    120

atcgccgagg gcaacaacat caacccgctc gtcagcgcct cgaccgtgca gactggcatc    180

aacatcgccg gtcgcatact cggcgtcctc ggagtcccat tcgcaggtca gctggcgagc    240

ttctacagct tcatcgtcgg cgagctctgg ccatcaggtc gcgatccctg ggagatcttc    300

atggagcacg tcgagcagct ggtcaggcag cacatcacga tgaacgctcg caacacggct    360

ctcgccagac tccaaggcct cggagccagc ttcagagcct accagcagtc cctcgaggac    420

tggctcgaga accgcgacaa cgcgaggacc cggagcgtcc tctacaccca gtacatcgcg    480

ctggagctcg acttcctgaa cgcgatgcca ctcttcgcca tcaacaacca gcaggtgccg    540

ctcctcatgg tctacgccca agctgccaac ctccacctcc tgctcctcag agacgctagc    600

ctgttcggca gcgagttcgg actcacgtcg caggagatcc agcgctacta cgagcgccag    660

gcggagaaga cccgggagta cagcgactac tgcgcacgct ggtacaacac cggcctgaac    720

aacctgcgcg gcacgaacgc tgagagctgg ctccgctaca accagttccg cagggacctc    780

acactcggag tcctcgacct cgtcgcgctg ttcccgagct acgacacgcg gatctacccg    840

atcaacacga gcgcgcagct cactcgcgag atctacacgg accccatcgg tcgcacgaac    900

gctccatccg gcttcgcctc caccaactgg ttcaacaaca acgcgccgtc gttcagcgcc    960

atcgaagctg caatcttccg cccacctcac ctgctggact tcccagagca gctcaccatc   1020

tacagcgcct ccagccgctg gtccagcacg cagcacatga actactgggt cggccaccgc   1080

ctcaacttca ggcctatcgg cggtaccctc aacacctcga cccacggcgc cacgaacacg   1140

tccatcaacc cggtgacgct ccagttcacg agccgggacg tctaccgcac tgagagctac   1200

gctggcatca acatcctgct cacgacgcca gtgaacggcg tcccgtgggc acgcttcaac   1260

tggaggaacc ctctcaactc cctgcgcgga tcgctcctct acaccatcgg ctacaccgga   1320

gtcggtaccc agctcttcga cagcgagacc gagctcccac ctgagaccac cgagaggccc   1380

aactacgaga gctactccca ccgcctgtcg aacatccgcc tcatcatcgg cggcacgctc   1440

agagctcccg tctactcctg gacgcacagg tcagctgacc ggacgaacac catcgcgacg   1500

aacatcatca cccagatccc ggccgtcaag ggcaacttcc tcttcaacgg ctccgtcatc   1560

tccggaccag gcttcaccgg aggagacctc gtccgcctca acaactccgg caacaacatc   1620

cagaaccggg gctacatcga ggtgccgatc cagttcatct ccacgagcac tcggtaccgc   1680

gtcagagtgc gctacgcgag cgtcactccg atccgcctct ccgtcaactg gggcaactcg   1740

aacatcttca gctccatcgt cccagccacc gcgactagcc tcgacaacct gcagtcccgc   1800

aacttcggct acttcgagag ccgcaacgcc ttcacgagcg cgactggcaa cgtcgtcggc   1860

gtccgcaact tctccgagaa cgccggagtg atcatcgacc gcttcgagtt catccccgtg   1920

accgcgacct tcgaggccga gtacgacctt gagagagctc aggaggcc                1968
```

<210> SEQ ID NO 43
<211> LENGTH: 655
<212> TYPE: PRT
<213> ORGANISM: Artificial Sequence
<220> FEATURE:
<223> OTHER INFORMATION: Cry1B variant

<400> SEQUENCE: 43

```
Met Pro Ser Asn Arg Lys Asn Glu Asn Glu Ile Ile Asn Ala Leu Ser
1               5                   10                  15

Ile Pro Ala Val Ser Asn His Ser Ala Gln Met Asp Leu Ser Leu Asp
            20                  25                  30
```

```
Ala Arg Ile Glu Asp Ser Leu Cys Ile Ala Glu Gly Asn Asn Ile Asn
        35                  40                  45

Pro Leu Val Ser Ala Ser Thr Val Gln Thr Gly Ile Asn Ile Ala Gly
    50                  55                  60

Arg Ile Leu Gly Val Leu Gly Val Pro Phe Ala Gly Gln Leu Ala Ser
65                  70                  75                  80

Phe Tyr Ser Phe Ile Val Gly Glu Leu Trp Pro Ser Gly Arg Asp Pro
                85                  90                  95

Trp Glu Ile Phe Met Glu His Val Glu Gln Leu Val Arg Gln Met Ile
            100                 105                 110

Thr His Asn Ala Arg Asn Thr Ala Leu Ala Arg Leu Gln Gly Leu Gly
        115                 120                 125

Ala Ser Phe Arg Ala Tyr Gln Gln Ser Leu Glu Asp Trp Leu Glu Asn
    130                 135                 140

Arg Asp Asn Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Asn Asn
                165                 170                 175

Gln Gln Val Pro Leu Leu Met Val Tyr Ala Gln Ala Ala Asn Leu His
            180                 185                 190

Leu Leu Leu Leu Arg Asp Ala Ser Leu Phe Gly Ser Glu Phe Gly Leu
        195                 200                 205

Thr Ser Gln Glu Ile Gln Arg Tyr Tyr Glu Arg Gln Ala Glu Lys Thr
    210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Ile Tyr Pro Ile Asn Thr Ser Ala Gln Leu Thr
        275                 280                 285

Arg Glu Ile Tyr Thr Asp Pro Ile Gly Arg Thr Asn Ala Pro Ser Gly
    290                 295                 300

Phe Ala Ser Thr Asn Trp Phe Asn Asn Asn Ala Pro Ser Phe Ser Ala
305                 310                 315                 320

Ile Glu Ala Ala Ile Phe Arg Pro Pro His Leu Leu Asp Phe Pro Glu
                325                 330                 335

Gln Leu Thr Ile Tyr Ser Ala Ser Ser Arg Trp Ser Ser Thr Gln His
            340                 345                 350

Met Asn Tyr Trp Val Gly His Arg Leu Asn Phe Arg Pro Ile Asn Gly
        355                 360                 365

Thr Leu Asn Thr Ser Thr His Gly Ala Thr Asn Thr Ser Ile Asn Pro
    370                 375                 380

Val Thr Leu Gln Phe Thr Ser Arg Asp Val Tyr Arg Thr Glu Ser Tyr
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
            420                 425                 430

Leu Tyr Thr Ile Gly Tyr Thr Gly Val Gly Thr Gln Leu Phe Asp Ser
        435                 440                 445
```

```
Glu Thr Glu Leu Pro Pro Glu Thr Thr Glu Arg Pro Asn Tyr Glu Ser
    450                 455                 460

Tyr Ser His Arg Leu Ser Asn Ile Arg Leu Ile Ile Gly Asn Thr Leu
465                 470                 475                 480

Arg Ala Pro Val Tyr Ser Trp Thr His Arg Ser Ala Asp Arg Thr Asn
                485                 490                 495

Thr Ile Ala Thr Asn Ile Ile Thr Gln Ile Pro Ala Val Lys Gly Asn
            500                 505                 510

Phe Leu Phe Asn Gly Ser Val Ile Ser Gly Pro Gly Phe Thr Gly Gly
        515                 520                 525

Asp Leu Val Arg Leu Asn Asn Ser Gly Asn Asn Ile Gln Asn Arg Gly
    530                 535                 540

Tyr Ile Glu Val Pro Ile Gln Phe Ile Ser Thr Ser Thr Arg Tyr Arg
545                 550                 555                 560

Val Arg Val Arg Tyr Ala Ser Val Thr Pro Ile Arg Leu Ser Val Asn
                565                 570                 575

Trp Gly Asn Ser Asn Ile Phe Ser Ser Ile Val Pro Ala Thr Ala Thr
            580                 585                 590

Ser Leu Asp Asn Leu Gln Ser Arg Asn Phe Gly Tyr Phe Glu Ser Arg
        595                 600                 605

Asn Ala Phe Thr Ser Ala Thr Gly Asn Val Val Gly Val Arg Asn Phe
    610                 615                 620

Ser Glu Asn Ala Gly Val Ile Ile Asp Arg Phe Glu Phe Ile Pro Val
625                 630                 635                 640

Thr Ala Thr Phe Glu Ala Glu Tyr Asp Leu Glu Arg Ala Gln Glu
                645                 650                 655
```

<210> SEQ ID NO 44
<211> LENGTH: 1968
<212> TYPE: DNA
<213> ORGANISM: Artificial Sequence
<220> FEATURE:
<223> OTHER INFORMATION: coding sequence of Cry1B variant

<400> SEQUENCE: 44

```
atgccctcca accgcaagaa cgagaacgag ataatcaacg ccctgtcgat cccagccgtc      60

tccaaccact ccgcgcagat ggacctctca ctggacgctc gcatcgagga ctcactctgc     120

atcgccgagg gcaacaacat caacccgctc gtcagcgcct cgaccgtgca gactggcatc     180

aacatcgccg gtcgcatact cggcgtcctc ggagtcccat tcgcaggtca gctggcgagc     240

ttctacagct tcatcgtcgg cgagctctgg ccatcaggtc gcgatccctg ggagatcttc     300

atggagcacg tcgagcagct ggtcaggcag atgatcacgc acaacgctcg caacacggct     360

ctcgccagac tccaaggcct cggagccagc ttcagagcct accagcagtc cctcgaggac     420

tggctcgaga accgcgacaa cgcgaggacc cggagcgtcc tctacaccca gtacatcgcg     480

ctggagctcg acttcctgaa cgcgatgcca ctcttcgcca tcaacaacca gcaggtgccg     540

ctcctcatgg tctacgccca agctgccaac ctccacctcc tgctcctcag agacgctagc     600

ctgttcggca gcgagttcgg actcacgtcg caggagatcc agcgctacta cgagcgccag     660

gcggagaaga cccgggagta cagcgactac tgcgcacgct ggtacaacac cggcctgaac     720

aacctgcgcg gcacgaacgc tgagagctgg ctccgctaca accagttccg cagggacctc     780

acactcggag tcctcgacct cgtcgcgctg ttcccgagct acgacacgcg gatctacccg     840

atcaacacga gcgcgcagct cactcgcgag atctacacgg accccatcgg tcgcacgaac     900
```

```
gctccatccg gcttcgcctc caccaactgg ttcaacaaca acgcgccgtc gttcagcgcc    960

atcgaagctg caatcttccg cccacctcac ctgctggact tcccagagca gctcaccatc   1020

tacagcgcct ccagccgctg gtccagcacg cagcacatga actactgggt cggccaccgc   1080

ctcaacttca ggcctatcaa cggtaccctc aacacctcga cccacggcgc cacgaacacg   1140

tccatcaacc cggtgacgct ccagttcacg agccgggacg tctaccgcac tgagagctac   1200

gctggcatca acatcctgct cacgacgcca gtgaacggcg tcccgtgggc acgcttcaac   1260

tggaggaacc ctctcaactc cctgcgcgga tcgctcctct acaccatcgg ctacaccgga   1320

gtcggtaccc agctcttcga cagcgagacc gagctcccac ctgagaccac cgagaggccc   1380

aactacgaga gctactccca ccgcctgtcg aacatccgcc tcatcatcgg caacacgctc   1440

agagctcccg tctactcctg gacgcacagg tcagctgacc ggacgaacac catcgcgacg   1500

aacatcatca cccagatccc ggccgtcaag ggcaacttcc tcttcaacgg ctccgtcatc   1560

tccggaccag gcttcaccgg aggagacctc gtccgcctca acaactccgg caacaacatc   1620

cagaaccggg gctacatcga ggtgccgatc cagttcatct ccacgagcac tcggtaccgc   1680

gtcagagtgc gctacgcgag cgtcactccg atccgcctct ccgtcaactg gggcaactcg   1740

aacatcttca gctccatcgt cccagccacc gcgactagcc tcgacaacct gcagtcccgc   1800

aacttcggct acttcgagag ccgcaacgcc ttcacgagcg cgactggcaa cgtcgtcggc   1860

gtccgcaact tctccgagaa cgccggagtg atcatcgacc gcttcgagtt catccccgtg   1920

accgcgacct tcgaggccga gtacgacctt gagagagctc aggaggcc                1968
```

```
<210> SEQ ID NO 45
<211> LENGTH: 655
<212> TYPE: PRT
<213> ORGANISM: Artificial Sequence
<220> FEATURE:
<223> OTHER INFORMATION: Cry1B variant

<400> SEQUENCE: 45

Met Pro Ser Asn Arg Lys Asn Glu Asn Glu Ile Ile Asn Ala Leu Ser
1               5                   10                  15

Ile Pro Ala Val Ser Asn His Ser Ala Gln Met Asp Leu Ser Leu Asp
            20                  25                  30

Ala Arg Ile Glu Asp Ser Leu Cys Ile Ala Glu Gly Asn Asn Ile Asn
        35                  40                  45

Pro Leu Val Ser Ala Ser Thr Val Gln Thr Gly Ile Asn Ile Ala Gly
    50                  55                  60

Arg Ile Leu Gly Val Leu Gly Val Pro Phe Ala Gly Gln Leu Ala Ser
65                  70                  75                  80

Phe Tyr Ser Phe Ile Val Gly Glu Leu Trp Pro Ser Gly Arg Asp Pro
                85                  90                  95

Trp Glu Ile Phe Met Glu His Val Glu Gln Leu Val Arg Gln His Ile
            100                 105                 110

Thr Met Asn Ala Arg Asn Thr Ala Leu Ala Arg Leu Gln Gly Leu Gly
        115                 120                 125

Ala Ser Phe Arg Ala Tyr Gln Gln Ser Leu Glu Asp Trp Leu Glu Asn
    130                 135                 140

Arg Asp Asn Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Asn Asn
                165                 170                 175
```

```
Gln Gln Val Pro Leu Leu Met Val Tyr Ala Gln Ala Ala Asn Leu His
            180                 185                 190

Leu Leu Leu Leu Arg Asp Ala Ser Leu Phe Gly Ser Glu Phe Gly Leu
        195                 200                 205

Thr Ser Gln Glu Ile Gln Arg Tyr Tyr Glu Arg Gln Ala Glu Lys Thr
    210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Ile Tyr Pro Ile Asn Thr Ser Ala Gln Leu Thr
        275                 280                 285

Arg Glu Ile Tyr Thr Asp Pro Ile Gly Arg Thr Asn Ala Pro Ser Gly
    290                 295                 300

Phe Ala Ser Thr Asn Trp Phe Asn Asn Asn Ala Pro Ser Phe Ser Ala
305                 310                 315                 320

Ile Glu Ala Ala Ile Phe Arg Pro Pro His Leu Leu Asp Phe Pro Glu
                325                 330                 335

Gln Leu Thr Ile Tyr Ser Ala Ser Ser Arg Trp Ser Ser Thr Gln His
            340                 345                 350

Met Asn Tyr Trp Val Gly His Arg Leu Asn Phe Arg Pro Ile Asn Gly
        355                 360                 365

Thr Leu Asn Thr Ser Thr His Gly Ala Thr Asn Thr Ser Ile Asn Pro
    370                 375                 380

Val Thr Leu Gln Phe Thr Ser Arg Asp Val Tyr Arg Thr Glu Ser Tyr
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
            420                 425                 430

Leu Tyr Thr Ile Gly Tyr Thr Gly Val Gly Thr Gln Leu Phe Asp Ser
        435                 440                 445

Glu Thr Glu Leu Pro Pro Glu Thr Thr Glu Arg Pro Asn Tyr Glu Ser
    450                 455                 460

Tyr Ser His Arg Leu Ser Asn Ile Arg Leu Ile Ile Gly Asn Thr Leu
465                 470                 475                 480

Arg Ala Pro Val Tyr Ser Trp Thr His Arg Ser Ala Asp Arg Thr Asn
                485                 490                 495

Thr Ile Ala Thr Asn Ile Ile Thr Gln Ile Pro Ala Val Lys Gly Asn
            500                 505                 510

Phe Leu Phe Asn Gly Ser Val Ile Ser Gly Pro Gly Phe Thr Gly Gly
        515                 520                 525

Asp Leu Val Arg Leu Asn Asn Ser Gly Asn Asn Ile Gln Asn Arg Gly
    530                 535                 540

Tyr Ile Glu Val Pro Ile Gln Phe Ile Ser Thr Ser Thr Arg Tyr Arg
545                 550                 555                 560

Val Arg Val Arg Tyr Ala Ser Val Thr Pro Ile Arg Leu Ser Val Asn
                565                 570                 575

Trp Gly Asn Ser Asn Ile Phe Ser Ser Ile Val Pro Ala Thr Ala Thr
            580                 585                 590

Ser Leu Asp Asn Leu Gln Ser Arg Asn Phe Gly Tyr Phe Glu Ser Arg
```

```
        595                 600                 605

Asn Ala Phe Thr Ser Ala Thr Gly Asn Val Val Gly Val Arg Asn Phe
    610                 615                 620

Ser Glu Asn Ala Gly Val Ile Ile Asp Arg Phe Glu Phe Ile Pro Val
625                 630                 635                 640

Thr Ala Thr Phe Glu Ala Glu Tyr Asp Leu Glu Arg Ala Gln Glu
                645                 650                 655


<210> SEQ ID NO 46
<211> LENGTH: 1968
<212> TYPE: DNA
<213> ORGANISM: Artificial Sequence
<220> FEATURE:
<223> OTHER INFORMATION: coding sequence of Cry1B variant

<400> SEQUENCE: 46

atgccctcca accgcaagaa cgagaacgag ataatcaacg ccctgtcgat cccagccgtc     60

tccaaccact ccgcgcagat ggacctctca ctggacgctc gcatcgagga ctcactctgc    120

atcgccgagg gcaacaacat caacccgctc gtcagcgcct cgaccgtgca gactggcatc    180

aacatcgccg gtcgcatact cggcgtcctc ggagtcccat tcgcaggtca gctggcgagc    240

ttctacagct tcatcgtcgg cgagctctgg ccatcaggtc gcgatccctg ggagatcttc    300

atggagcacg tcgagcagct ggtcaggcag cacatcacga tgaacgctcg caacacggct    360

ctcgccagac tccaaggcct cggagccagc ttcagagcct accagcagtc cctcgaggac    420

tggctcgaga accgcgacaa cgcgaggacc cggagcgtcc tctacaccca gtacatcgcg    480

ctggagctcg acttcctgaa cgcgatgcca ctcttcgcca tcaacaacca gcaggtgccg    540

ctcctcatgg tctacgccca agctgccaac ctccacctcc tgctcctcag agacgctagc    600

ctgttcggca gcgagttcgg actcacgtcg caggagatcc agcgctacta cgagcgccag    660

gcggagaaga cccgggagta cagcgactac tgcgcacgct ggtacaacac cggcctgaac    720

aacctgcgcg gcacgaacgc tgagagctgg ctccgctaca accagttccg cagggacctc    780

acactcggag tcctcgacct cgtcgcgctg ttcccgagct acgacacgcg gatctacccg    840

atcaacacga gcgcgcagct cactcgcgag atctacacgg accccatcgg tcgcacgaac    900

gctccatccg gcttcgcctc caccaactgg ttcaacaaca acgcgccgtc gttcagcgcc    960

atcgaagctg caatcttccg cccacctcac ctgctggact tcccagagca gctcaccatc   1020

tacagcgcct ccagccgctg gtccagcacg cagcacatga actactgggt cggccaccgc   1080

ctcaacttca ggcctatcaa cggtaccctc aacacctcga cccacggcgc cacgaacacg   1140

tccatcaacc cggtgacgct ccagttcacg agccgggacg tctaccgcac tgagagctac   1200

gctggcatca acatcctgct cacgacgcca gtgaacggcg tcccgtgggc acgcttcaac   1260

tggaggaacc ctctcaactc cctgcgcgga tcgctcctct acaccatcgg ctacaccgga   1320

gtcggtaccc agctcttcga cagcgagacc gagctcccac ctgagaccac cgagaggccc   1380

aactacgaga gctactccca ccgcctgtcg aacatccgcc tcatcatcgg caacacgctc   1440

agagctcccg tctactcctg gacgcacagg tcagctgacc ggacgaacac catcgcgacg   1500

aacatcatca cccagatccc ggccgtcaag ggcaacttcc tcttcaacgg ctccgtcatc   1560

tccggaccag gcttcaccgg aggagacctc gtccgcctca acaactccgg caacaacatc   1620

cagaaccggg gctacatcga ggtgccgatc cagttcatct ccacgagcac tcggtaccgc   1680

gtcagagtgc gctacgcgag cgtcactccg atccgcctct ccgtcaactg ggcaactcg    1740
```

```
aacatcttca gctccatcgt cccagccacc gcgactagcc tcgacaacct gcagtcccgc   1800

aacttcggct acttcgagag ccgcaacgcc ttcacgagcg cgactggcaa cgtcgtcggc   1860

gtccgcaact tctccgagaa cgccggagtg atcatcgacc gcttcgagtt catccccgtg   1920

accgcgacct tcgaggccga gtacgacctt gagagagctc aggaggcc                1968


<210> SEQ ID NO 47
<211> LENGTH: 655
<212> TYPE: PRT
<213> ORGANISM: Bacillus thuringiensis

<400> SEQUENCE: 47

Met Thr Ser Asn Arg Lys Asn Glu Asn Glu Ile Ile Asn Ala Leu Ser
1               5                   10                  15

Ile Pro Ala Val Ser Asn His Ser Ala Gln Met Asp Leu Ser Pro Asp
            20                  25                  30

Ala Arg Ile Glu Asp Ser Leu Cys Ile Ala Glu Gly Asn Asn Ile Asn
        35                  40                  45

Pro Leu Val Ser Ala Ser Thr Val Gln Thr Gly Ile Asn Ile Ala Gly
    50                  55                  60

Arg Ile Leu Gly Val Leu Gly Val Pro Phe Ala Gly Gln Leu Ala Ser
65                  70                  75                  80

Phe Tyr Ser Phe Ile Val Gly Glu Leu Trp Pro Ser Gly Arg Asp Pro
                85                  90                  95

Trp Glu Ile Phe Leu Glu His Val Glu Gln Leu Val Arg Gln Gln Ile
            100                 105                 110

Thr Glu Asn Ala Arg Asn Thr Ala Leu Ala Arg Leu Gln Gly Leu Gly
        115                 120                 125

Ala Ser Phe Arg Ala Tyr Gln Gln Ser Leu Glu Asp Trp Leu Glu Asn
    130                 135                 140

Arg Asp Asp Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Asn Asn
                165                 170                 175

Gln Gln Val Pro Leu Leu Met Val Tyr Ala Gln Ala Ala Asn Leu His
            180                 185                 190

Leu Leu Leu Leu Arg Asp Ala Ser Leu Phe Gly Ser Glu Phe Gly Leu
        195                 200                 205

Thr Ser Gln Glu Ile Gln Arg Tyr Tyr Glu Arg Gln Ala Glu Lys Thr
    210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Ile Tyr Pro Ile Asn Thr Ser Ala Gln Leu Thr
        275                 280                 285

Arg Glu Ile Tyr Thr Asp Pro Ile Gly Arg Thr Asn Ala Pro Ser Gly
    290                 295                 300

Phe Ala Ser Thr Asn Trp Phe Asn Asn Asn Ala Pro Ser Phe Ser Ala
305                 310                 315                 320

Ile Glu Ala Ala Val Ile Arg Pro Pro His Leu Leu Asp Phe Pro Glu
                325                 330                 335
```

```
Gln Leu Thr Ile Phe Ser Val Leu Ser Arg Trp Ser Asn Thr Gln Tyr
            340                 345                 350

Met Asn Tyr Trp Val Gly His Arg Leu Glu Ser Arg Thr Ile Arg Gly
        355                 360                 365

Ser Leu Ser Thr Ser Thr His Gly Asn Thr Asn Thr Ser Ile Asn Pro
    370                 375                 380

Val Thr Leu Gln Phe Thr Ser Arg Asp Val Tyr Arg Thr Glu Ser Tyr
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
            420                 425                 430

Leu Tyr Thr Ile Gly Tyr Thr Gly Val Gly Thr Gln Leu Phe Asp Ser
        435                 440                 445

Glu Thr Glu Leu Pro Pro Glu Thr Thr Glu Arg Pro Asn Tyr Glu Ser
    450                 455                 460

Tyr Ser His Arg Leu Ser Asn Ile Arg Leu Ile Ser Gly Asn Thr Leu
465                 470                 475                 480

Arg Ala Pro Val Tyr Ser Trp Thr His Arg Ser Ala Asp Arg Thr Asn
                485                 490                 495

Thr Ile Ala Thr Asn Ile Ile Thr Gln Ile Pro Ala Val Lys Gly Asn
            500                 505                 510

Phe Leu Phe Asn Gly Ser Val Ile Ser Gly Pro Gly Phe Thr Gly Gly
        515                 520                 525

Asp Leu Val Arg Leu Asn Asn Ser Gly Asn Asn Ile Gln Asn Arg Gly
    530                 535                 540

Tyr Leu Glu Val Pro Ile Gln Phe Ile Ser Thr Ser Thr Arg Tyr Arg
545                 550                 555                 560

Val Arg Val Arg Tyr Ala Ser Val Thr Pro Ile Gln Leu Ser Val Asn
                565                 570                 575

Trp Gly Asn Ser Asn Ile Phe Ser Ser Ile Val Pro Ala Thr Ala Thr
            580                 585                 590

Ser Leu Asp Asn Leu Gln Ser Arg Asp Phe Gly Tyr Phe Glu Ser Thr
        595                 600                 605

Asn Ala Phe Thr Ser Ala Thr Gly Asn Val Val Gly Val Arg Asn Phe
    610                 615                 620

Ser Glu Asn Ala Gly Val Ile Ile Asp Arg Phe Glu Phe Ile Pro Val
625                 630                 635                 640

Thr Ala Thr Phe Glu Ala Glu Tyr Asp Leu Glu Arg Ala Gln Glu
                645                 650                 655
```

<210> SEQ ID NO 48
<211> LENGTH: 1965
<212> TYPE: DNA
<213> ORGANISM: Bacillus thuringiensis

<400> SEQUENCE: 48

```
atgacttcaa ataggaaaaa tgagaatgaa attataaatg ctttatcgat tccagctgta      60

tcgaatcatt ccgcacaaat ggatctatca ccagatgctc gtattgagga ttctttgtgt     120

atagccgagg ggaataatat caatccactt gttagcgcat caacagtcca aacgggtatt     180

aacattgctg gtagaatact aggcgtatta ggcgtaccgt ttgctggaca actagctagt     240

ttttatagtt ttattgtcgg tgaattatgg cctagcggca gagatccgtg ggaaatcttt     300

ctagaacatg ttgaacaact tgtaagacaa caaataacag aaaatgctag gaatacggca     360
```

cttgctcgat tacaaggttt aggagcttcc tttagagcct atcaacaatc acttgaagac 420
tggctagaaa accgtgatga tgcaagaacg agaagtgttc tttataccca atatatagcc 480
ttagagcttg attttcttaa tgcgatgccg cttttcgcaa taaacaatca acaggttcca 540
ttattgatgg tatatgctca agctgcaaat ttacatctat tattattgag agatgcctct 600
ctttttggta gtgaatttgg gcttacatcg caggaaattc aacgttatta tgagcgccaa 660
gcggaaaaaa cgagagaata ttctgattat tgcgcaagat ggtataatac gggtttaaat 720
aatttgagag ggacaaatgc tgaaagttgg ttgcgatata atcaattccg tagagactta 780
acgctaggag tattagatct agtggcacta ttcccaagct atgacacgcg tatttatcca 840
ataaatacca gtgctcaatt aacaagagaa atttatacag atccaattgg gagaacaaat 900
gcaccttcag gatttgcaag tacgaattgg tttaataata atgcaccatc gttttctgcc 960
atagaggctg ccgttattag gcctccgcat ctacttgatt ttccagaaca gcttacaatt 1020
ttcagcgtat taagtcgatg gagtaatact caatatatga attactgggt gggacataga 1080
cttgaatcgc gaacaataag ggggtcatta agtacctcga cacacggaaa taccaatact 1140
tctattaatc ctgtaacatt acagttcaca tctcgtgacg tttatagaac agaatcatat 1200
gcagggataa atatacttct aactactcct gtgaatggag taccttgggc tagatttaat 1260
tggagaaatc ccctgaattc tcttagaggt agccttctct atactatagg gtatactgga 1320
gtggggacac aactatttga ttcagaaact gaattaccac cagaaacaac agaacgacca 1380
aattatgaat cttacagtca tagattatct aatataagac taatatcagg aaacactttg 1440
agagcaccag tatattcttg gacgcaccgt agtgcagatc gtacgaatac gattgctaca 1500
aatattatta ctcaaattcc tgcagtgaag ggaaactttc tttttaatgg ttctgtaatt 1560
tcaggaccag gatttactgg tggggactta gttagattaa ataatagtgg aaataatatt 1620
caaaatagag gctaccttga ggttccgatt caattcatct ccacatctac cagatatcga 1680
gttcgtgtac gttatgcttc tgtaaccccg attcaactca gtgttaattg gggtaattca 1740
aacatttttt ccagcatagt accagctaca gctacgtcat tagataatct acaatcaagg 1800
gattttggtt attttgaaag taccaatgca tttacatctg caacaggtaa tgtagtaggt 1860
gttagaaatt ttagtgagaa tgcaggagtg ataatagaca gatttgaatt tatcccagtt 1920
actgcaacct tcgaagcaga atatgattta gaaagagcgc aagag 1965

<210> SEQ ID NO 49
<211> LENGTH: 650
<212> TYPE: PRT
<213> ORGANISM: Bacillus thuringiensis

<400> SEQUENCE: 49

Met Pro Ser Asn Arg Lys Asn Glu Asn Glu Ile Ile Asn Ala Leu Ser
1 5 10 15

Ile Pro Ala Val Ser Asn His Ser Ala Gln Met Asp Leu Ser Pro Asp
20 25 30

Ala Arg Ile Glu Asp Ser Leu Cys Val Ala Glu Gly Asn Asn Ile Asp
35 40 45

Pro Phe Val Ser Ala Ser Thr Val Gln Thr Gly Ile Ser Ile Ala Gly
50 55 60

Arg Ile Leu Gly Val Leu Gly Val Pro Phe Ala Gly Gln Leu Ala Ser
65 70 75 80

Phe Tyr Ser Phe Leu Val Gly Glu Leu Trp Pro Ser Gly Arg Asp Pro

-continued

```
                85                  90                  95

Trp Glu Ile Phe Met Glu His Val Glu Gln Ile Val Arg Gln Gln Ile
            100                 105                 110

Thr Asp Ser Val Arg Asp Thr Ala Ile Ala Arg Leu Glu Gly Leu Gly
        115                 120                 125

Arg Gly Tyr Arg Ser Tyr Gln Gln Ala Leu Glu Thr Trp Leu Asp Asn
    130                 135                 140

Arg Asn Asp Ala Arg Ser Arg Ser Ile Ile Arg Glu Arg Tyr Ile Ala
145                 150                 155                 160

Leu Glu Leu Asp Ile Thr Thr Ala Ile Pro Leu Phe Ser Ile Arg Asn
                165                 170                 175

Gln Glu Val Pro Leu Leu Met Val Tyr Ala Gln Ala Ala Asn Leu His
            180                 185                 190

Leu Leu Leu Leu Arg Asp Ala Ser Leu Phe Gly Ser Glu Trp Gly Met
        195                 200                 205

Ser Ser Ala Asp Val Asn Gln Tyr Tyr Gln Glu Gln Ile Arg Tyr Thr
    210                 215                 220

Glu Glu Tyr Ser Asn His Cys Val Gln Trp Tyr Asn Thr Gly Leu Asn
225                 230                 235                 240

Arg Leu Arg Gly Thr Thr Ala Glu Ser Trp Val Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Thr Tyr Pro Ile Pro Thr Thr Ala Gln Leu Thr
        275                 280                 285

Arg Glu Val Tyr Thr Asp Pro Asn Gly Val Val Ala Gly Pro Asn Asn
    290                 295                 300

Ser Trp Phe Arg Asn Gly Ala Ser Phe Ser Ala Ile Glu Asn Ala Ile
305                 310                 315                 320

Ile Arg Gln Pro His Leu Tyr Asp Phe Leu Thr Asn Leu Thr Ile Tyr
                325                 330                 335

Thr Arg Arg Ser Gln Val Gly Thr Thr Ile Met Asn Leu Trp Ala Gly
            340                 345                 350

His Arg Ile Thr Phe Asn Arg Ile Gln Gly Gly Ser Thr Ser Glu Met
        355                 360                 365

Val Tyr Gly Ala Ile Thr Asn Pro Val Ser Val Ser Asp Ile Pro Phe
    370                 375                 380

Val Asn Arg Asp Val Tyr Arg Thr Val Ser Leu Ala Gly Gly Leu Gly
385                 390                 395                 400

Ser Leu Ser Gly Ile Arg Tyr Gly Leu Thr Arg Val Asp Phe Asp Met
                405                 410                 415

Ile Phe Arg Asn His Pro Asp Ile Val Thr Gly Leu Phe Tyr His Pro
            420                 425                 430

Gly His Ala Gly Ile Ala Thr Gln Val Lys Asp Ser Glu Thr Glu Leu
        435                 440                 445

Pro Pro Glu Thr Thr Glu Gln Pro Asn Tyr Arg Ala Phe Ser His Leu
    450                 455                 460

Leu Ser His Ile Ser Met Gly Pro Thr Thr Gln Asp Val Pro Pro Val
465                 470                 475                 480

Tyr Ser Trp Thr His Gln Ser Ala Asp Arg Thr Asn Thr Ile Asn Ser
                485                 490                 495

Asp Arg Ile Thr Gln Ile Pro Leu Val Lys Ala His Thr Leu Gln Ser
            500                 505                 510
```

```
Gly Thr Thr Val Val Lys Gly Pro Gly Phe Thr Gly Gly Asp Ile Leu
        515                 520                 525

Arg Arg Thr Ser Gly Gly Pro Phe Ala Phe Ser Asn Val Asn Leu Asp
    530                 535                 540

Phe Asn Leu Ser Gln Arg Tyr Arg Ala Arg Ile Arg Tyr Ala Ser Thr
545                 550                 555                 560

Thr Asn Leu Arg Ile Tyr Val Thr Val Ala Gly Glu Arg Ile Phe Ala
                565                 570                 575

Gly Gln Phe Asp Lys Thr Met Asp Ala Gly Ala Pro Leu Thr Phe Gln
            580                 585                 590

Ser Phe Ser Tyr Ala Thr Ile Asn Thr Ala Phe Thr Phe Pro Glu Arg
        595                 600                 605

Ser Ser Ser Leu Thr Val Gly Ala Asp Thr Phe Ser Ser Gly Asn Glu
    610                 615                 620

Val Tyr Val Asp Arg Phe Glu Leu Ile Pro Val Thr Ala Thr Phe Glu
625                 630                 635                 640

Ala Glu Ser Asp Leu Glu Arg Ala Arg Lys
                645                 650


<210> SEQ ID NO 50
<211> LENGTH: 1950
<212> TYPE: DNA
<213> ORGANISM: Bacillus thuringiensis

<400> SEQUENCE: 50

atgccttcaa ataggaaaaa tgagaatgaa attataaatg ctttatcgat tccagctgta      60

tcgaatcatt ccgcacaaat ggatctatca ccagatgctc gcattgagga tagcttgtgt     120

gtagccgagg ggaacaatat tgatccattt gttagcgcat caacagtcca aacaggtatt     180

agtatagctg gtagaatatt aggcgtatta ggggtgccgt ttgccggaca actagctagt     240

ttttatagtt ttcttgttgg ggaattatgg cctagcggca gagatccatg ggaaattttt     300

atggaacatg tcgaacaaat tgtaagacaa caaataacgg acagtgttag ggataccgct     360

attgctcgtt tagaaggtct aggaagaggg tatagatctt accagcaggc tcttgaaact     420

tggttagata accgaaatga tgcaagatca agaagcatta ttcgtgagag atatattgct     480

ttagaacttg acattactac tgctataccg cttttcagca tacgaaatca agaggttcca     540

ttattaatgg tatatgctca agctgcaaat ttacacctat tattattgag agacgcatcc     600

ctttttggta gtgaatgggg gatgtcatct gccgatgtta accaatatta ccaagaacaa     660

atcagatata cagaggaata ttctaaccat tgcgtacaat ggtataatac agggctaaat     720

agattaagag ggacaactgc cgaaagttgg gtacggtata atcaattccg tagagaccta     780

acattaggtg tattagattt agtggcacta ttcccaagct atgacactcg gacttatccc     840

attccaacta ccgcccaact tacaagagaa gtgtatacag atccaaacgg tgttgtagca     900

ggacccaata atagttggtt tagaaatgga gcttcgtttt ccgctataga aaacgcaatt     960

attcgacaac ctcacctata tgattttcta acgaacctta caatttacac gagaagaagt    1020

caagtaggca ctacaattat gaatttgtgg gcagggcata gaatcacgtt taatagaata    1080

caaggtggtt ctactagtga aatggtgtat ggggctatta ctaacccagt tagtgttagt    1140

gacataccat ttgtcaatcg ggatgtttac cgaactgtat cattagctgg tgggcttggc    1200

tctctgagtg gaatacgtta tggtttaact agagttgatt ttgatatgat atttcgtaac    1260

catcctgata tagtaactgg attattttat catccgggac acgcgggcat tgcaacccaa    1320
```

gtaaaagatt cagaaacaga attaccacct gaaacgacag aacagccaaa ttatagagca 1380
tttagtcatc tactaagtca tatttcaatg ggtccaacga ctcaagacgt acctccagta 1440
tattcttgga cacaccagag tgcagatcgt acgaatacaa tcaattcgga taggataaca 1500
caaataccat tggtaaaggc gcataccctc caatcgggta ccactgtagt aaaagggcca 1560
gggtttacag gaggggatat cctccgtcga acaagtggag gaccatttgc ttttagtaat 1620
gttaatctag attttaactt gtcacaaagg tatcgtgcta gaattcgtta tgcctctact 1680
actaacctaa gaatttacgt aacggttgca ggtgaacgaa tttttgctgg tcaatttgac 1740
aaaactatgg atgctggtgc cccattaaca ttccaatctt ttagttacgc aactattaat 1800
acagctttta cattcccaga aagatcgagc agcttgactg taggtgccga tacgtttagt 1860
tcaggtaatg aagtttatgt agatagattt gaattaatcc cagttactgc aaccttcgag 1920
gcagaatctg atttagaaag agcgcggaag 1950

<210> SEQ ID NO 51
<211> LENGTH: 3771
<212> TYPE: DNA
<213> ORGANISM: Bacillus thuringiensis

<400> SEQUENCE: 51
ttgacttcaa ataggaaaaa tgagaatgaa attataaatg ctttatcgat tccaacggta 60
tcgaatcctt ccacgcaaat gaatctatca ccagatgctc gtattgaaga tagcttgtgt 120
gtagccgagg tgaacaatat tgatccattt gttagcgcat caacagtcca aacgggtata 180
aacatagctg gtagaatatt gggcgtatta ggtgtgccgt ttgctggaca actagctagt 240
ttttatagtt ttcttgttgg tgaattatgg cctagtggca gagatccatg ggaaattttc 300
ctggaacatg tagaacaact tataagacaa caagtaacag aaaatactag gaatacggct 360
attgctcgat tagaaggtct aggaagaggc tatagatctt accagcaggc tcttgaaact 420
tggttagata accgaaatga tgcaagatca agaagcatta ttcttgagcg ctatgttgct 480
ttagaacttg acattactac tgctataccg cttttcagaa tacgaaatca agaggttcca 540
ttattaatgg tatatgctca agctgcaaat ttacacctat tattattgag ggacgcatcc 600
ctttttggta gtgaatgggg gacggcatct tccgatgtta accaatatta ccaagaacaa 660
atcagatata cagaggaata ttctaaccat tgcgtacaat ggtataatac ggggctaaat 720
aacttaagag ggacaaatgc tgaaagttgg gtacggtata atcaattccg cagagaccta 780
acattagggg tattagatct agtggcccta ttcccaagtt atgacactcg cacttatcca 840
atcaatacga gtgctcagtt aacaagagaa gtttatacag acgcaattgg gaccgtacat 900
ccgagtcaag cttttgcaag tacgacttgg tttaataata atgcaccatc gttttctgcc 960
atagaagctg ccgttatcag gcctccgcat ctacttgatt ttccagaaca acttacaatt 1020
tacagcacat taagtcgatg gagtaacact cagtttatga atatatgggc aggtcataga 1080
cttgaatccc gcccaatagc agggtcatta aatacctcta cacaaggatc taccaatact 1140
tctattaatc ctgtaacatt acagtttacg tctcgagaca tttataggac tgaatcattg 1200
gcagggctaa atatatttat aactcaacct gttaatgggg ttccttgggt tagatttaat 1260
tggagaaatc ccctgaattc tcttagaggt agccttctct atacgatagg gtatactgga 1320
gttgggacgc aattacaaga ttcagaaact gaattacccc cagaaacaac agaacgacca 1380
aattatgaat catatagtca tagattatct catataggac tcatttcatc atctcatgtg 1440
agagcattgg tatattcttg gacgcaccgt agtgcagatc gtacgaatac gattggacca 1500
aatagaatta ctcaaattcc tgcagtgaag ggaagatttc tttttaatgg ctctgtaatt 1560
tcaggaccag gatttactgg tggagacgta gttagattga ataggaataa tggtaatatt 1620
caaaatagag ggtatattga agttccaatt caattcacgt cgacatctac cagatatcga 1680
gttcgagtac gttatgcttc tgtaacctcg attgagctca atgttaattg gggcaattca 1740
tcaattttta cgaacacatt accagcaaca gctgcatcat tagataatct acaatcaggg 1800
gattttggtt atgttgaaat caacaatgct tttacatccg caacaggtaa tatagtaggt 1860
gttagaaatt ttagtgcaaa tgcagaggta ataatagaca gatttgaatt tatcccagtt 1920
actgcaacct tcgaggcaaa atatgattta gaaagagcac aaaaggcggt gaatgctctg 1980
tttacttcta caaatccaag aagattgaag acagatgtga cagattatca tattgaccaa 2040
gtgtccaatc tggtggtatg tttatcagat gaattttgct tggatgagaa gcgagaatta 2100
tttgagaaag tgaaatatgc gaagcgactc agtgatgaaa gaaacttact ccaagatcca 2160
aacttcacat tcatcaatgg gcaaccaagt tttgcatcca tcgatggaca atcaaacttc 2220
acctctatta atgagctatc taatcatgga tggtggggca gtgcgaatgt taccattcag 2280
gaagggaatg acgtatttaa agagaattac gtcacactac cgggtacttt taatgagtgt 2340
tatccaaatt atttatatca aaaaatagga gagtcagaat taaaggctta tacgcgctat 2400
caattaagag ggtatattga agatagtcaa gatctagaga tttatttaat tcgttacaat 2460
gcaaagcatg aaacattaaa tgttccaggt accgagtccc tatggccgct ttcagttgaa 2520
agcccaatcg gaaggtgcgg agaaccaaat cgatgcgcac cacattttgg atggaatcct 2580
gatctagatt gttcctgcag agatagagaa aaatgtgcgc atcattccca tcatttcact 2640
ttggatattg atgttggatg cacagacttg caagaggatc taggcgtgtg ggttgtattc 2700
aagattaaga cgcaggaagg ttatgcaaga ttaggaaatc tggaatttat cgaagagaaa 2760
ccattaattg gagaagcact gtctcgtgtg aagagagcgg aaaaaaaatg gagagacaaa 2820
agggaaaaac tacaagtgga aacaaaacga gtatatatag acgcaaaaga agctgtggat 2880
gctttattcg tagattctca atatgataga ttacaagcag atacaaacat cggtatgatt 2940
catgcggcag atagacttgt tcatcggatc cacgaggctt atcttccaga actacctttc 3000
attccaggaa taaatgtggt gatttttgaa gaattagaaa accgtatttc tactgcattt 3060
tccttatatg atgcgagaaa tgtcattaaa aatggcgatt tcaataatgg attgacatgc 3120
tggaacgtga aagggcatgt agaggtacag cagctgaaca atcatcgttc ggtccttgtc 3180
atcccggaat gggaagcaga agtttcacaa aaggtgcgcg tctgtccagg tcgtggctat 3240
attcttcgtg tcacagcgta caaagaggga tatggggaag gctgcgtaac tattcatgaa 3300
gtcgataata atacagacca attgaagttt agcaactgtg agaaaggaca agtatatcca 3360
ggtaatacga tagcatgtaa tgattataat aagaatcatg gtgcgaatgc atgtagttct 3420
cgtaatcgtg gatatgacga attctatgga aacaccccag ctgattattc tgcaaatcaa 3480
aaagaatacg gggtgcgtta cacttcccac aatcatgcat atggcgaatc ttatgaaagt 3540
aattcgtcca taccagctga ttatgcgccg gtttatgaag aagaagcgta tacacatgga 3600
cgaagaggta attcttgtga atataacaga gggtatacac cattaccagc tggttatgtg 3660
acagcagagt tagaatactt cccagaaacg gatacagtat gggttgagat tggagaaacg 3720
gaaggaacat ttatcgtgga caatgtggaa ttactcctta tggaggaata g 3771

<210> SEQ ID NO 52
<211> LENGTH: 1256
<212> TYPE: PRT
<213> ORGANISM: Bacillus thuringiensis

<400> SEQUENCE: 52

Met Thr Ser Asn Arg Lys Asn Glu Asn Glu Ile Ile Asn Ala Leu Ser
1 5 10 15

Ile Pro Thr Val Ser Asn Pro Ser Thr Gln Met Asn Leu Ser Pro Asp
20 25 30

Ala Arg Ile Glu Asp Ser Leu Cys Val Ala Glu Val Asn Asn Ile Asp
35 40 45

Pro Phe Val Ser Ala Ser Thr Val Gln Thr Gly Ile Asn Ile Ala Gly
50 55 60

Arg Ile Leu Gly Val Leu Gly Val Pro Phe Ala Gly Gln Leu Ala Ser
65 70 75 80

Phe Tyr Ser Phe Leu Val Gly Glu Leu Trp Pro Ser Gly Arg Asp Pro
85 90 95

Trp Glu Ile Phe Leu Glu His Val Glu Gln Leu Ile Arg Gln Gln Val
100 105 110

Thr Glu Asn Thr Arg Asn Thr Ala Ile Ala Arg Leu Glu Gly Leu Gly
115 120 125

Arg Gly Tyr Arg Ser Tyr Gln Gln Ala Leu Glu Thr Trp Leu Asp Asn
130 135 140

Arg Asn Asp Ala Arg Ser Arg Ser Ile Ile Leu Glu Arg Tyr Val Ala
145 150 155 160

Leu Glu Leu Asp Ile Thr Thr Ala Ile Pro Leu Phe Arg Ile Arg Asn
165 170 175

Gln Glu Val Pro Leu Leu Met Val Tyr Ala Gln Ala Ala Asn Leu His
180 185 190

Leu Leu Leu Leu Arg Asp Ala Ser Leu Phe Gly Ser Glu Trp Gly Thr
195 200 205

Ala Ser Ser Asp Val Asn Gln Tyr Tyr Gln Glu Gln Ile Arg Tyr Thr
210 215 220

Glu Glu Tyr Ser Asn His Cys Val Gln Trp Tyr Asn Thr Gly Leu Asn
225 230 235 240

Asn Leu Arg Gly Thr Asn Ala Glu Ser Trp Val Arg Tyr Asn Gln Phe
245 250 255

Arg Arg Asp Leu Thr Leu Gly Val Leu Asp Leu Val Ala Leu Phe Pro
260 265 270

Ser Tyr Asp Thr Arg Thr Tyr Pro Ile Asn Thr Ser Ala Gln Leu Thr
275 280 285

Arg Glu Val Tyr Thr Asp Ala Ile Gly Thr Val His Pro Ser Gln Ala
290 295 300

Phe Ala Ser Thr Thr Trp Phe Asn Asn Asn Ala Pro Ser Phe Ser Ala
305 310 315 320

Ile Glu Ala Ala Val Ile Arg Pro Pro His Leu Leu Asp Phe Pro Glu
325 330 335

Gln Leu Thr Ile Tyr Ser Thr Leu Ser Arg Trp Ser Asn Thr Gln Phe
340 345 350

Met Asn Ile Trp Ala Gly His Arg Leu Glu Ser Arg Pro Ile Ala Gly
355 360 365

Ser Leu Asn Thr Ser Thr Gln Gly Ser Thr Asn Thr Ser Ile Asn Pro
370 375 380

```
Val Thr Leu Gln Phe Thr Ser Arg Asp Ile Tyr Arg Thr Glu Ser Leu
385                 390                 395                 400

Ala Gly Leu Asn Ile Phe Ile Thr Gln Pro Val Asn Gly Val Pro Trp
                405                 410                 415

Val Arg Phe Asn Trp Arg Asn Pro Leu Asn Ser Leu Arg Gly Ser Leu
            420                 425                 430

Leu Tyr Thr Ile Gly Tyr Thr Gly Val Gly Thr Gln Leu Gln Asp Ser
        435                 440                 445

Glu Thr Glu Leu Pro Pro Glu Thr Thr Glu Arg Pro Asn Tyr Glu Ser
    450                 455                 460

Tyr Ser His Arg Leu Ser His Ile Gly Leu Ile Ser Ser Ser His Val
465                 470                 475                 480

Arg Ala Leu Val Tyr Ser Trp Thr His Arg Ser Ala Asp Arg Thr Asn
                485                 490                 495

Thr Ile Gly Pro Asn Arg Ile Thr Gln Ile Pro Ala Val Lys Gly Arg
            500                 505                 510

Phe Leu Phe Asn Gly Ser Val Ile Ser Gly Pro Gly Phe Thr Gly Gly
        515                 520                 525

Asp Val Val Arg Leu Asn Arg Asn Asn Gly Asn Ile Gln Asn Arg Gly
    530                 535                 540

Tyr Ile Glu Val Pro Ile Gln Phe Thr Ser Thr Ser Thr Arg Tyr Arg
545                 550                 555                 560

Val Arg Val Arg Tyr Ala Ser Val Thr Ser Ile Glu Leu Asn Val Asn
                565                 570                 575

Trp Gly Asn Ser Ser Ile Phe Thr Asn Thr Leu Pro Ala Thr Ala Ala
            580                 585                 590

Ser Leu Asp Asn Leu Gln Ser Gly Asp Phe Gly Tyr Val Glu Ile Asn
        595                 600                 605

Asn Ala Phe Thr Ser Ala Thr Gly Asn Ile Val Gly Val Arg Asn Phe
    610                 615                 620

Ser Ala Asn Ala Glu Val Ile Ile Asp Arg Phe Glu Phe Ile Pro Val
625                 630                 635                 640

Thr Ala Thr Phe Glu Ala Lys Tyr Asp Leu Glu Arg Ala Gln Lys Ala
                645                 650                 655

Val Asn Ala Leu Phe Thr Ser Thr Asn Pro Arg Arg Leu Lys Thr Asp
            660                 665                 670

Val Thr Asp Tyr His Ile Asp Gln Val Ser Asn Leu Val Val Cys Leu
        675                 680                 685

Ser Asp Glu Phe Cys Leu Asp Glu Lys Arg Glu Leu Phe Glu Lys Val
    690                 695                 700

Lys Tyr Ala Lys Arg Leu Ser Asp Glu Arg Asn Leu Leu Gln Asp Pro
705                 710                 715                 720

Asn Phe Thr Phe Ile Asn Gly Gln Pro Ser Phe Ala Ser Ile Asp Gly
                725                 730                 735

Gln Ser Asn Phe Thr Ser Ile Asn Glu Leu Ser Asn His Gly Trp Trp
            740                 745                 750

Gly Ser Ala Asn Val Thr Ile Gln Glu Gly Asn Asp Val Phe Lys Glu
        755                 760                 765

Asn Tyr Val Thr Leu Pro Gly Thr Phe Asn Glu Cys Tyr Pro Asn Tyr
    770                 775                 780

Leu Tyr Gln Lys Ile Gly Glu Ser Glu Leu Lys Ala Tyr Thr Arg Tyr
785                 790                 795                 800

Gln Leu Arg Gly Tyr Ile Glu Asp Ser Gln Asp Leu Glu Ile Tyr Leu
```

```
                805                 810                 815

Ile Arg Tyr Asn Ala Lys His Glu Thr Leu Asn Val Pro Gly Thr Glu
            820                 825                 830

Ser Leu Trp Pro Leu Ser Val Glu Ser Pro Ile Gly Arg Cys Gly Glu
        835                 840                 845

Pro Asn Arg Cys Ala Pro His Phe Gly Trp Asn Pro Asp Leu Asp Cys
    850                 855                 860

Ser Cys Arg Asp Arg Glu Lys Cys Ala His His Ser His His Phe Thr
865                 870                 875                 880

Leu Asp Ile Asp Val Gly Cys Thr Asp Leu Gln Glu Asp Leu Gly Val
                885                 890                 895

Trp Val Val Phe Lys Ile Lys Thr Gln Glu Gly Tyr Ala Arg Leu Gly
            900                 905                 910

Asn Leu Glu Phe Ile Glu Glu Lys Pro Leu Ile Gly Glu Ala Leu Ser
        915                 920                 925

Arg Val Lys Arg Ala Glu Lys Lys Trp Arg Asp Lys Arg Glu Lys Leu
    930                 935                 940

Gln Val Glu Thr Lys Arg Val Tyr Ile Asp Ala Lys Glu Ala Val Asp
945                 950                 955                 960

Ala Leu Phe Val Asp Ser Gln Tyr Asp Arg Leu Gln Ala Asp Thr Asn
                965                 970                 975

Ile Gly Met Ile His Ala Ala Asp Arg Leu Val His Arg Ile His Glu
            980                 985                 990

Ala Tyr Leu Pro Glu Leu Pro Phe  Ile Pro Gly Ile Asn  Val Val Ile
        995                 1000                1005

Phe Glu  Glu Leu Glu Asn Arg  Ile Ser Thr Ala Phe  Ser Leu Tyr
    1010                 1015                1020

Asp Ala  Arg Asn Val Ile Lys  Asn Gly Asp Phe Asn  Asn Gly Leu
    1025                 1030                1035

Thr Cys  Trp Asn Val Lys Gly  His Val Glu Val Gln  Gln Leu Asn
    1040                 1045                1050

Asn His  Arg Ser Val Leu Val  Ile Pro Glu Trp Glu  Ala Glu Val
    1055                 1060                1065

Ser Gln  Lys Val Arg Val Cys  Pro Gly Arg Gly Tyr  Ile Leu Arg
    1070                 1075                1080

Val Thr  Ala Tyr Lys Glu Gly  Tyr Gly Glu Gly Cys  Val Thr Ile
    1085                 1090                1095

His Glu  Val Asp Asn Asn Thr  Asp Gln Leu Lys Phe  Ser Asn Cys
    1100                 1105                1110

Glu Lys  Gly Gln Val Tyr Pro  Gly Asn Thr Ile Ala  Cys Asn Asp
    1115                 1120                1125

Tyr Asn  Lys Asn His Gly Ala  Asn Ala Cys Ser Ser  Arg Asn Arg
    1130                 1135                1140

Gly Tyr  Asp Glu Phe Tyr Gly  Asn Thr Pro Ala Asp  Tyr Ser Ala
    1145                 1150                1155

Asn Gln  Lys Glu Tyr Gly Gly  Ala Tyr Thr Ser His  Asn His Ala
    1160                 1165                1170

Tyr Gly  Glu Ser Tyr Glu Ser  Asn Ser Ser Ile Pro  Ala Asp Tyr
    1175                 1180                1185

Ala Pro  Val Tyr Glu Glu Glu  Ala Tyr Thr His Gly  Arg Arg Gly
    1190                 1195                1200

Asn Ser  Cys Glu Tyr Asn Arg  Gly Tyr Thr Pro Leu  Pro Ala Gly
    1205                 1210                1215
```

Tyr Val Thr Ala Glu Leu Glu Tyr Phe Pro Glu Thr Asp Thr Val
1220 1225 1230

Trp Val Glu Ile Gly Glu Thr Glu Gly Thr Phe Ile Val Asp Asn
1235 1240 1245

Val Glu Leu Leu Leu Met Glu Glu
1250 1255

<210> SEQ ID NO 53
<211> LENGTH: 3714
<212> TYPE: DNA
<213> ORGANISM: Bacillus thuringiensis

<400> SEQUENCE: 53
ttgaattcaa ataggaaaaa tgagaacgaa attatagatg cttcatttat tcccgcagta 60
tccaatgagt ctgttacaat ctctaaagaa tatgcacaaa caaatcaatt acaaaacaat 120
agcattgagg atggtttgtg tatagccgaa ggggaatata ttgatccatt tgttagcgca 180
tcaacagtcc aaacggggat tagtatcgct ggtagaatat tgggtgtatt aggtgtgccg 240
tttgccggac aattagctag tttttatagt tttattgttg gtgaattatg gcctaaaggc 300
agagaccaat gggaaatttt tatggaacat gtagaacaac ttgtaagaca acaaataaca 360
gcaaatgcta ggaatacggc ccttgctcga ttacaaggtt taggagattc ctttagagcc 420
tatcaacagt cacttgaaga ttggctagag aaccgtaatg atgcaagaac gagaagtgtt 480
ctttatactc aatatatagc cttagagctt gattttctaa atgcgatgcc gcttttcgca 540
ataagagagc aagaggttcc cttattaatg gtatacgctc aagctgcaaa cttgcaccta 600
ttattattga gagacgcctc cctttatggt cgtgaatttg ggcttacctc ccaagaaatt 660
caacgttatt atgaacgcca agtagaaaga acgagggact attctgacca ttgcgtgcaa 720
tggtataata cgggtctaaa taacttaaga gggacaaatg ctgaaagttg ggtgcggtat 780
aatcaattcc gtagagacct aacattaggg gtattagatc tagtggcact attcccaagc 840
tatgacactc gcacttatcc aataaatacg agtgctcagt taacaaggga agtttataca 900
gacgcaattg gagcaacagg ggtaaatatg gcaagtatga attggtataa taataatgca 960
ccttcgtttt ccgctataga gactgcggtt atccgaagcc cgcatctact tgattttcta 1020
gaacaactta aatttttag cgcttcatca cgatggagta atactaggca tatgacttat 1080
tggcgggggc acacgattca atctcggcca ataagagggg cattaattac ctcgacacac 1140
ggaaatacca atacttctat taaccctgta acattccagt tcccgtcccg agacgtttat 1200
aggactgaat catatgcagg agtgcttcta tggggaattt accttgaacc tattcatggt 1260
gttcctactg ttagatttaa ttttaggaac cctcagaata cttttgaaag aggtactgct 1320
aactatagtc aaccctatga gtcacctggg cttcaattaa aagattcaga aactgaatta 1380
ccaccagaaa caacagaacg accaaattat gaatcatata gtcatagatt atctcacata 1440
gggatcattt tacaaactag gttgaatgta ccggtatatt cttggacgca tcgtagtgca 1500
gatcgtacaa atacaattgg accaaataga attactcaaa ttcctgcagt gaagggaaac 1560 cttctttta atggttctgt aatttcagga ccaggattta ctggtgggga cttagttaga 1620
ttaaataata gtggaaataa tattcaaaat agaggctatc ttgaggttcc aattcaattc 1680
acatcgacat ctaccagata tcgagttcgt gtacgttatg cttctgtaac cccgattcac 1740
ctcagtgtta attggggtaa ttcaaacatt ttttccagca cagttccagc tacagctgcg 1800
tcattagata atctacaatc aagggatttt ggttattttg aaagtaccaa tgcatttaca 1860

```
tctgtaacag gtaatgtagt aggtgtaaga aattttagtg aaaatgccag agtgataata   1920
gacagatttg aatttattcc agttactgca accttcgaag cagaatacga tttagaaagg   1980
gcgcaagagg cggtgaatgc tctgtttact aatacgaatc caagaagatt gaaaacagat   2040
gtgacagatt atcatattga tcaagtatcc aatttagtgg cgtgtttatc ggatgaattc   2100
tgcttagatg aaaagagaga attacttgag aaagtgaaat atgcgaaacg actcagtgat   2160
gaaagaaact tactccaaga tccaaacttc acatccatca ataagcaacc agacttcata   2220
tctactaatg agcaatcgaa tttcacatct atccatgaac aatctgaaca tggatggtgg   2280
ggaagtgaga acattacaat ccaggaagga aatgacgtat ttaaagagaa ttacgtcaca   2340
ctaccaggta cttataatga gtgttatccg acgtatttat atcaaaaaat aggagagtcg   2400
gaattaaaag cttatactcg ctaccaatta agaggttata ttgaagatag tcaagattta   2460
gagatatatt tgattcgtta taatgcgaaa catgaaacat tggatgttcc aggtaccgag   2520
tccgtatggc cgctttcagt tgaaagccca atcagaaggt gcggagaacc gaatcgatgc   2580
gcaccacatt ttgaatggaa tcctgatcta gattgttcct gcagagatgg agaaaaatgt   2640
gcgcatcatt cccatcattt ctctttggat attgatgttg gatgcataga cttgcatgag   2700
aacctaggcg tgtgggtggt attcaagatt aagacgcagg aaggtcatgc aagactaggg   2760
aacctggaat ttattgaaga gaaaccatta ttaggagaag cactgtctcg tgtgaagaga   2820
gcagagaaaa aatggagaga caaacgtgaa aaactacaat tggaaacaaa acgagtatat   2880
acagaggcaa aagaagctgt ggatgcttta tttgtagatt ctcaatatga tagattacaa   2940
gcggatacaa acattggcat gattcatgcg gcagataaac ttgttcatcg aattcgagag   3000
gcgtatcttt cagaattatc tgttatccca ggtgtaaatg cggaaatttt tgaagaatta   3060
gaaggtcgca ttatcactgc aatctcccta tacgatgcga gaaatgtcgt taaaaatggt   3120
gattttaata atggattagc atgctggaat gtaaaagggc atgtagatgt acaacagagc   3180
catcaccgtt ctgtccttgt tatcccagaa tgggaagcag aagtgtcaca agcagttcgc   3240
gtctgtccgg ggcgtggcta tatcctccgt gtcacagcgt acaaagaggg atatggagag   3300
ggttgtgtaa cgatccatga aatcgagaac aatacagacg aactaaaatt taaaaactgt   3360
gaagaagagg aagtgtatcc aacggataca ggaacgtgta atgattatac tgcacaccaa   3420
ggtacagcag catgtaattc ccgtaatgct ggatatgagg atgcatatga agttgatact   3480
acagcatctg ttaattacaa accgacttat gaagaagaaa cgtatacaga tgtacgaaga   3540
gataatcatt gtgaatatga cagagggtat gtgaattatc caccagtacc agctggttat   3600
atgacaaaag aattagaata cttcccagaa accgataagg tatggattga gattggagaa   3660
acggaaggga agtttattgt agacagcgtg gaattactcc ttatggagga atag         3714
```

<210> SEQ ID NO 54
<211> LENGTH: 1237
<212> TYPE: PRT
<213> ORGANISM: Bacillus thuringiensis

<400> SEQUENCE: 54

```
Met Asn Ser Asn Arg Lys Asn Glu Asn Glu Ile Ile Asp Ala Ser Phe
1               5                   10                  15

Ile Pro Ala Val Ser Asn Glu Ser Val Thr Ile Ser Lys Glu Tyr Ala
            20                  25                  30

Gln Thr Asn Gln Leu Gln Asn Asn Ser Ile Glu Asp Gly Leu Cys Ile
        35                  40                  45
```

```
Ala Glu Gly Glu Tyr Ile Asp Pro Phe Val Ser Ala Ser Thr Val Gln
    50                  55                  60

Thr Gly Ile Ser Ile Ala Gly Arg Ile Leu Gly Val Leu Gly Val Pro
65                  70                  75                  80

Phe Ala Gly Gln Leu Ala Ser Phe Tyr Ser Phe Ile Val Gly Glu Leu
                85                  90                  95

Trp Pro Lys Gly Arg Asp Gln Trp Glu Ile Phe Met Glu His Val Glu
            100                 105                 110

Gln Leu Val Arg Gln Gln Ile Thr Ala Asn Ala Arg Asn Thr Ala Leu
        115                 120                 125

Ala Arg Leu Gln Gly Leu Gly Asp Ser Phe Arg Ala Tyr Gln Gln Ser
    130                 135                 140

Leu Glu Asp Trp Leu Glu Asn Arg Asn Asp Ala Arg Thr Arg Ser Val
145                 150                 155                 160

Leu Tyr Thr Gln Tyr Ile Ala Leu Glu Leu Asp Phe Leu Asn Ala Met
                165                 170                 175

Pro Leu Phe Ala Ile Arg Glu Gln Glu Val Pro Leu Leu Met Val Tyr
            180                 185                 190

Ala Gln Ala Ala Asn Leu His Leu Leu Leu Leu Arg Asp Ala Ser Leu
        195                 200                 205

Tyr Gly Arg Glu Phe Gly Leu Thr Ser Gln Glu Ile Gln Arg Tyr Tyr
    210                 215                 220

Glu Arg Gln Val Glu Arg Thr Arg Asp Tyr Ser Asp His Cys Val Gln
225                 230                 235                 240

Trp Tyr Asn Thr Gly Leu Asn Asn Leu Arg Gly Thr Asn Ala Glu Ser
                245                 250                 255

Trp Val Arg Tyr Asn Gln Phe Arg Arg Asp Leu Thr Leu Gly Val Leu
            260                 265                 270

Asp Leu Val Ala Leu Phe Pro Ser Tyr Asp Thr Arg Thr Tyr Pro Ile
        275                 280                 285

Asn Thr Ser Ala Gln Leu Thr Arg Glu Val Tyr Thr Asp Ala Ile Gly
    290                 295                 300

Ala Thr Gly Val Asn Met Ala Ser Met Asn Trp Tyr Asn Asn Asn Ala
305                 310                 315                 320

Pro Ser Phe Ser Ala Ile Glu Thr Ala Val Ile Arg Ser Pro His Leu
                325                 330                 335

Leu Asp Phe Leu Glu Gln Leu Lys Ile Phe Ser Ala Ser Ser Arg Trp
            340                 345                 350

Ser Asn Thr Arg His Met Thr Tyr Trp Arg Gly His Thr Ile Gln Ser
        355                 360                 365

Arg Pro Ile Arg Gly Ala Leu Ile Thr Ser Thr His Gly Asn Thr Asn
    370                 375                 380

Thr Ser Ile Asn Pro Val Thr Phe Gln Phe Pro Ser Arg Asp Val Tyr
385                 390                 395                 400

Arg Thr Glu Ser Tyr Ala Gly Val Leu Leu Trp Gly Ile Tyr Leu Glu
                405                 410                 415

Pro Ile His Gly Val Pro Thr Val Arg Phe Asn Phe Arg Asn Pro Gln
            420                 425                 430

Asn Thr Phe Glu Arg Gly Thr Ala Asn Tyr Ser Gln Pro Tyr Glu Ser
        435                 440                 445

Pro Gly Leu Gln Leu Lys Asp Ser Glu Thr Glu Leu Pro Pro Glu Thr
    450                 455                 460
```

-continued

```
Thr Glu Arg Pro Asn Tyr Glu Ser Tyr Ser His Arg Leu Ser His Ile
465                 470                 475                 480

Gly Ile Ile Leu Gln Thr Arg Leu Asn Val Pro Val Tyr Ser Trp Thr
                485                 490                 495

His Arg Ser Ala Asp Arg Thr Asn Thr Ile Gly Pro Asn Arg Ile Thr
            500                 505                 510

Gln Ile Pro Ala Val Lys Gly Asn Leu Leu Phe Asn Gly Ser Val Ile
        515                 520                 525

Ser Gly Pro Gly Phe Thr Gly Gly Asp Leu Val Arg Leu Asn Asn Ser
    530                 535                 540

Gly Asn Asn Ile Gln Asn Arg Gly Tyr Leu Glu Val Pro Ile Gln Phe
545                 550                 555                 560

Thr Ser Thr Ser Thr Arg Tyr Arg Val Arg Val Arg Tyr Ala Ser Val
                565                 570                 575

Thr Pro Ile His Leu Ser Val Asn Trp Gly Asn Ser Asn Ile Phe Ser
            580                 585                 590

Ser Thr Val Pro Ala Thr Ala Ala Ser Leu Asp Asn Leu Gln Ser Arg
        595                 600                 605

Asp Phe Gly Tyr Phe Glu Ser Thr Asn Ala Phe Thr Ser Val Thr Gly
    610                 615                 620

Asn Val Val Gly Val Arg Asn Phe Ser Glu Asn Ala Arg Val Ile Ile
625                 630                 635                 640

Asp Arg Phe Glu Phe Ile Pro Val Thr Ala Thr Phe Glu Ala Glu Tyr
                645                 650                 655

Asp Leu Glu Arg Ala Gln Glu Ala Val Asn Ala Leu Phe Thr Asn Thr
            660                 665                 670

Asn Pro Arg Arg Leu Lys Thr Asp Val Thr Asp Tyr His Ile Asp Gln
        675                 680                 685

Val Ser Asn Leu Val Ala Cys Leu Ser Asp Glu Phe Cys Leu Asp Glu
    690                 695                 700

Lys Arg Glu Leu Leu Glu Lys Val Lys Tyr Ala Lys Arg Leu Ser Asp
705                 710                 715                 720

Glu Arg Asn Leu Leu Gln Asp Pro Asn Phe Thr Ser Ile Asn Lys Gln
                725                 730                 735

Pro Asp Phe Ile Ser Thr Asn Glu Gln Ser Asn Phe Thr Ser Ile His
            740                 745                 750

Glu Gln Ser Glu His Gly Trp Trp Gly Ser Glu Asn Ile Thr Ile Gln
        755                 760                 765

Glu Gly Asn Asp Val Phe Lys Glu Asn Tyr Val Thr Leu Pro Gly Thr
    770                 775                 780

Tyr Asn Glu Cys Tyr Pro Thr Tyr Leu Tyr Gln Lys Ile Gly Glu Ser
785                 790                 795                 800

Glu Leu Lys Ala Tyr Thr Arg Tyr Gln Leu Arg Gly Tyr Ile Glu Asp
                805                 810                 815

Ser Gln Asp Leu Glu Ile Tyr Leu Ile Arg Tyr Asn Ala Lys His Glu
            820                 825                 830

Thr Leu Asp Val Pro Gly Thr Glu Ser Val Trp Pro Leu Ser Val Glu
        835                 840                 845

Ser Pro Ile Arg Arg Cys Gly Glu Pro Asn Arg Cys Ala Pro His Phe
    850                 855                 860

Glu Trp Asn Pro Asp Leu Asp Cys Ser Cys Arg Asp Gly Glu Lys Cys
865                 870                 875                 880

Ala His His Ser His His Phe Ser Leu Asp Ile Asp Val Gly Cys Ile
```

-continued

```
                885                 890                 895

Asp Leu His Glu Asn Leu Gly Val Trp Val Val Phe Lys Ile Lys Thr
            900                 905                 910

Gln Glu Gly His Ala Arg Leu Gly Asn Leu Glu Phe Ile Glu Glu Lys
        915                 920                 925

Pro Leu Leu Gly Glu Ala Leu Ser Arg Val Lys Arg Ala Glu Lys Lys
    930                 935                 940

Trp Arg Asp Lys Arg Glu Lys Leu Gln Leu Glu Thr Lys Arg Val Tyr
945                 950                 955                 960

Thr Glu Ala Lys Glu Ala Val Asp Ala Leu Phe Val Asp Ser Gln Tyr
                965                 970                 975

Asp Arg Leu Gln Ala Asp Thr Asn Ile Gly Met Ile His Ala Ala Asp
            980                 985                 990

Lys Leu Val His Arg Ile Arg Glu  Ala Tyr Leu Ser Glu  Leu Ser Val
        995                 1000                1005

Ile Pro  Gly Val Asn Ala Glu  Ile Phe Glu Glu Leu  Glu Gly Arg
    1010                1015                1020

Ile Ile  Thr Ala Ile Ser Leu  Tyr Asp Ala Arg Asn  Val Val Lys
    1025                1030                1035

Asn Gly  Asp Phe Asn Asn Gly  Leu Ala Cys Trp Asn  Val Lys Gly
    1040                1045                1050

His Val  Asp Val Gln Gln Ser  His His Arg Ser Val  Leu Val Ile
    1055                1060                1065

Pro Glu  Trp Glu Ala Glu Val  Ser Gln Ala Val Arg  Val Cys Pro
    1070                1075                1080

Gly Arg  Gly Tyr Ile Leu Arg  Val Thr Ala Tyr Lys  Glu Gly Tyr
    1085                1090                1095

Gly Glu  Gly Cys Val Thr Ile  His Glu Ile Glu Asn  Asn Thr Asp
    1100                1105                1110

Glu Leu  Lys Phe Lys Asn Cys  Glu Glu Glu Glu Val  Tyr Pro Thr
    1115                1120                1125

Asp Thr  Gly Thr Cys Asn Asp  Tyr Thr Ala His Gln  Gly Thr Ala
    1130                1135                1140

Ala Cys  Asn Ser Arg Asn Ala  Gly Tyr Glu Asp Ala  Tyr Glu Val
    1145                1150                1155

Asp Thr  Thr Ala Ser Val Asn  Tyr Lys Pro Thr Tyr  Glu Glu Glu
    1160                1165                1170

Thr Tyr  Thr Asp Val Arg Arg  Asp Asn His Cys Glu  Tyr Asp Arg
    1175                1180                1185

Gly Tyr  Val Asn Tyr Pro Pro  Val Pro Ala Gly Tyr  Met Thr Lys
    1190                1195                1200

Glu Leu  Glu Tyr Phe Pro Glu  Thr Asp Lys Val Trp  Ile Glu Ile
    1205                1210                1215

Gly Glu  Thr Glu Gly Lys Phe  Ile Val Asp Ser Val  Glu Leu Leu
    1220                1225                1230

Leu Met  Glu Glu
    1235
```

<210> SEQ ID NO 55
<211> LENGTH: 650
<212> TYPE: PRT
<213> ORGANISM: Bacillus thuringiensis

<400> SEQUENCE: 55

-continued

```
Met Thr Ser Asn Arg Lys Asn Glu Asn Glu Ile Ile Asn Ala Val Ser
1               5                   10                  15

Asn His Ser Ala Gln Met Asp Leu Leu Pro Asp Ala Arg Ile Glu Asp
            20                  25                  30

Ser Leu Cys Ile Ala Glu Gly Asn Asn Ile Asp Pro Phe Val Ser Ala
        35                  40                  45

Ser Thr Val Gln Thr Gly Ile Asn Ile Ala Gly Arg Ile Leu Gly Val
    50                  55                  60

Leu Gly Val Pro Phe Ala Gly Gln Leu Ala Ser Phe Tyr Ser Phe Leu
65                  70                  75                  80

Val Gly Glu Leu Trp Pro Arg Gly Arg Asp Gln Trp Glu Ile Phe Leu
                85                  90                  95

Glu His Val Glu Gln Leu Ile Asn Gln Gln Ile Thr Glu Asn Ala Arg
            100                 105                 110

Asn Thr Ala Leu Ala Arg Leu Gln Gly Leu Gly Asp Ser Phe Arg Ala
        115                 120                 125

Tyr Gln Gln Ser Leu Glu Asp Trp Leu Glu Asn Arg Asp Asp Ala Arg
    130                 135                 140

Thr Arg Ser Val Leu Tyr Thr Gln Tyr Ile Ala Leu Glu Leu Asp Phe
145                 150                 155                 160

Leu Asn Ala Met Pro Leu Phe Ala Ile Arg Asn Gln Glu Val Pro Leu
                165                 170                 175

Leu Met Val Tyr Ala Gln Ala Ala Asn Leu His Leu Leu Leu Leu Arg
            180                 185                 190

Asp Ala Ser Leu Phe Gly Ser Glu Phe Gly Leu Thr Ser Gln Glu Ile
        195                 200                 205

Gln Arg Tyr Tyr Glu Arg Gln Val Glu Arg Thr Arg Asp Tyr Ser Asp
    210                 215                 220

Tyr Cys Val Glu Trp Tyr Asn Thr Gly Leu Asn Ser Leu Arg Gly Thr
225                 230                 235                 240

Asn Ala Ala Ser Trp Val Arg Tyr Asn Gln Phe Arg Arg Asp Leu Thr
                245                 250                 255

Leu Gly Val Leu Asp Leu Val Ala Leu Phe Pro Ser Tyr Asp Thr Arg
            260                 265                 270

Thr Tyr Pro Ile Asn Thr Ser Ala Gln Leu Thr Arg Glu Val Tyr Thr
        275                 280                 285

Asp Ala Ile Gly Ala Thr Gly Val Asn Met Ala Ser Met Asn Trp Tyr
    290                 295                 300

Asn Asn Asn Ala Pro Ser Phe Ser Ala Ile Glu Ala Ala Ala Ile Arg
305                 310                 315                 320

Ser Pro His Leu Leu Asp Phe Leu Glu Gln Leu Thr Ile Phe Ser Ala
                325                 330                 335

Ser Ser Arg Trp Ser Asn Thr Arg His Met Thr Tyr Trp Arg Gly His
            340                 345                 350

Thr Ile Gln Ser Arg Pro Ile Gly Gly Gly Leu Asn Thr Ser Thr His
        355                 360                 365

Gly Ala Thr Asn Thr Ser Ile Asn Pro Val Thr Leu Arg Phe Ala Ser
    370                 375                 380

Arg Asp Val Tyr Arg Thr Glu Ser Tyr Ala Gly Val Leu Leu Trp Gly
385                 390                 395                 400

Ile Tyr Leu Glu Pro Ile His Gly Val Pro Thr Val Arg Phe Asn Phe
                405                 410                 415

Thr Asn Pro Gln Asn Ile Ser Asp Arg Gly Thr Ala Asn Tyr Ser Gln
```

```
            420                 425                 430

Pro Tyr Glu Ser Pro Gly Leu Gln Leu Lys Asp Ser Glu Thr Glu Leu
        435                 440                 445

Pro Pro Glu Thr Thr Glu Arg Pro Asn Tyr Glu Ser Tyr Ser His Arg
    450                 455                 460

Leu Ser His Ile Gly Ile Ile Leu Gln Ser Arg Val Asn Val Pro Val
465                 470                 475                 480

Tyr Ser Trp Thr His Arg Ser Ala Asp Arg Thr Asn Thr Ile Gly Pro
                485                 490                 495

Asn Arg Ile Thr Gln Ile Pro Met Val Lys Ala Ser Glu Leu Pro Gln
            500                 505                 510

Gly Thr Thr Val Val Arg Gly Pro Gly Phe Thr Gly Gly Asp Ile Leu
        515                 520                 525

Arg Arg Thr Asn Thr Gly Gly Phe Gly Pro Ile Arg Val Thr Val Asn
    530                 535                 540

Gly Pro Leu Thr Gln Arg Tyr Arg Ile Gly Phe Arg Tyr Ala Ser Thr
545                 550                 555                 560

Val Asp Phe Asp Phe Phe Val Ser Arg Gly Gly Thr Thr Val Asn Asn
                565                 570                 575

Phe Arg Phe Leu Arg Thr Met Asn Ser Gly Asp Glu Leu Lys Tyr Gly
            580                 585                 590

Asn Phe Val Arg Arg Ala Phe Thr Thr Pro Phe Thr Phe Thr Gln Ile
        595                 600                 605

Gln Asp Ile Ile Arg Thr Ser Ile Gln Gly Leu Ser Gly Asn Gly Glu
    610                 615                 620

Val Tyr Ile Asp Lys Ile Glu Ile Ile Pro Val Thr Ala Thr Phe Glu
625                 630                 635                 640

Ala Glu Tyr Asp Leu Glu Arg Ala Gln Glu
                645                 650


<210> SEQ ID NO 56
<211> LENGTH: 655
<212> TYPE: PRT
<213> ORGANISM: Bacillus thuringiensis

<400> SEQUENCE: 56

Met Thr Ser Asn Arg Lys Asn Glu Asn Glu Ile Ile Asn Ala Leu Ser
1               5                   10                  15

Ile Pro Thr Val Ser Asn Pro Ser Thr Gln Met Asn Leu Ser Pro Asp
            20                  25                  30

Ala Arg Ile Glu Asp Ser Leu Cys Val Ala Glu Val Asn Asn Ile Asp
        35                  40                  45

Pro Phe Val Ser Ala Ser Thr Val Gln Thr Gly Ile Asn Ile Ala Gly
    50                  55                  60

Arg Ile Leu Gly Val Leu Gly Val Pro Phe Ala Gly Gln Leu Ala Ser
65                  70                  75                  80

Phe Tyr Ser Phe Leu Val Gly Glu Leu Trp Pro Ser Gly Arg Asp Pro
                85                  90                  95

Trp Glu Ile Phe Leu Glu His Val Glu Gln Leu Ile Arg Gln Gln Val
            100                 105                 110

Thr Glu Asn Thr Arg Asn Thr Ala Ile Ala Arg Leu Glu Gly Leu Gly
        115                 120                 125

Arg Gly Tyr Arg Ser Tyr Gln Gln Ala Leu Glu Thr Trp Leu Asp Asn
    130                 135                 140
```

-continued

```
Arg Asn Asp Ala Arg Ser Arg Ser Ile Ile Leu Glu Arg Tyr Val Ala
145                 150                 155                 160

Leu Glu Leu Asp Ile Thr Thr Ala Ile Pro Leu Phe Arg Ile Arg Asn
                165                 170                 175

Glu Glu Val Pro Leu Leu Met Val Tyr Ala Gln Ala Ala Asn Leu His
            180                 185                 190

Leu Leu Leu Leu Arg Asp Ala Ser Leu Phe Gly Ser Glu Trp Gly Met
        195                 200                 205

Ala Ser Ser Asp Val Asn Gln Tyr Tyr Gln Glu Gln Ile Arg Tyr Thr
    210                 215                 220

Glu Glu Tyr Ser Asn His Cys Val Gln Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Thr Tyr Pro Ile Asn Thr Ser Ala Gln Leu Thr
        275                 280                 285

Arg Glu Ile Tyr Thr Asp Pro Ile Gly Arg Thr Asn Ala Pro Ser Gly
    290                 295                 300

Phe Ala Ser Thr Asn Trp Phe Asn Asn Asn Ala Pro Ser Phe Ser Ala
305                 310                 315                 320

Ile Glu Ala Ala Ile Phe Arg Pro Pro His Leu Leu Asp Phe Pro Glu
                325                 330                 335

Gln Leu Thr Ile Tyr Ser Ala Ser Ser Arg Trp Ser Ser Thr Gln His
            340                 345                 350

Met Asn Tyr Trp Val Gly His Arg Leu Asn Phe Arg Pro Ile Gly Gly
        355                 360                 365

Thr Leu Asn Thr Ser Thr Gln Gly Leu Thr Asn Asn Thr Ser Ile Asn
    370                 375                 380

Pro Val Thr Leu Gln Phe Thr Ser Arg Asp Val Tyr Arg Thr Glu Ser
385                 390                 395                 400

Asn Ala Gly Thr Asn Ile Leu Phe Thr Thr Pro Val Asn Gly Val Pro
                405                 410                 415

Trp Ala Arg Phe Asn Phe Ile Asn Pro Gln Asn Ile Tyr Glu Arg Gly
            420                 425                 430

Ala Thr Thr Tyr Ser Gln Pro Tyr Gln Gly Val Gly Ile Gln Leu Phe
        435                 440                 445

Asp Ser Glu Thr Glu Leu Pro Pro Glu Thr Thr Glu Arg Pro Asn Tyr
    450                 455                 460

Glu Ser Tyr Ser His Arg Leu Ser His Ile Gly Leu Ile Ile Gly Asn
465                 470                 475                 480

Thr Leu Arg Ala Pro Val Tyr Ser Trp Thr His Arg Ser Ala Asp Arg
                485                 490                 495

Thr Asn Thr Ile Gly Pro Asn Arg Ile Thr Gln Ile Pro Leu Val Lys
            500                 505                 510

Ala Leu Asn Leu His Ser Gly Val Thr Val Val Gly Gly Pro Gly Phe
        515                 520                 525

Thr Gly Gly Asp Ile Leu Arg Arg Thr Asn Thr Gly Thr Phe Gly Asp
    530                 535                 540

Ile Arg Leu Asn Ile Asn Val Pro Leu Ser Gln Arg Tyr Arg Val Arg
545                 550                 555                 560

Ile Arg Tyr Ala Ser Thr Thr Asp Leu Gln Phe Phe Thr Arg Ile Asn
```

```
                565                 570                 575

Gly Thr Thr Val Asn Ile Gly Asn Phe Ser Arg Thr Met Asn Arg Gly
            580                 585                 590

Asp Asn Leu Glu Tyr Arg Ser Phe Arg Thr Ala Gly Phe Ser Thr Pro
        595                 600                 605

Phe Asn Phe Leu Asn Ala Gln Ser Thr Phe Thr Leu Gly Ala Gln Ser
    610                 615                 620

Phe Ser Asn Gln Glu Val Tyr Ile Asp Arg Val Glu Phe Val Pro Ala
625                 630                 635                 640

Glu Val Thr Phe Glu Ala Glu Tyr Asp Leu Glu Arg Ala Gln Lys
                645                 650                 655


<210> SEQ ID NO 57
<211> LENGTH: 655
<212> TYPE: PRT
<213> ORGANISM: Bacillus thuringiensis

<400> SEQUENCE: 57

Met Thr Ser Asn Arg Lys Asn Glu Asn Glu Ile Ile Asn Ala Leu Ser
1               5                   10                  15

Ile Pro Thr Val Ser Asn Pro Ser Thr Gln Met Asn Leu Ser Pro Asp
            20                  25                  30

Ala Arg Ile Glu Asp Ser Leu Cys Val Ala Glu Val Asn Asn Ile Asp
        35                  40                  45

Pro Phe Val Ser Ala Ser Thr Val Gln Thr Gly Ile Asn Ile Ala Gly
    50                  55                  60

Arg Ile Leu Gly Val Leu Gly Val Pro Phe Ala Gly Gln Leu Ala Ser
65                  70                  75                  80

Phe Tyr Ser Phe Leu Val Gly Glu Leu Trp Pro Ser Gly Arg Asp Pro
                85                  90                  95

Trp Glu Ile Phe Leu Glu His Val Glu Gln Leu Ile Arg Gln Gln Val
            100                 105                 110

Thr Glu Asn Thr Arg Asn Thr Ala Ile Ala Arg Leu Glu Gly Leu Gly
        115                 120                 125

Arg Gly Tyr Arg Ser Tyr Gln Gln Ala Leu Glu Thr Trp Leu Asp Asn
    130                 135                 140

Arg Asn Asp Ala Arg Ser Arg Ser Ile Ile Leu Glu Arg Tyr Val Ala
145                 150                 155                 160

Leu Glu Leu Asp Ile Thr Thr Ala Ile Pro Leu Phe Arg Ile Arg Asn
                165                 170                 175

Glu Glu Val Pro Leu Leu Met Val Tyr Ala Gln Ala Ala Asn Leu His
            180                 185                 190

Leu Leu Leu Leu Arg Asp Ala Ser Leu Phe Gly Ser Glu Trp Gly Met
        195                 200                 205

Ala Ser Ser Asp Val Asn Gln Tyr Tyr Gln Glu Gln Ile Arg Tyr Thr
    210                 215                 220

Glu Glu Tyr Ser Asn His Cys Val Gln Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Thr Tyr Pro Ile Asn Thr Ser Ala Gln Leu Thr
        275                 280                 285
```

```
Arg Glu Ile Tyr Thr Asp Pro Ile Gly Arg Thr Asn Ala Pro Ser Gly
    290                 295                 300

Phe Ala Ser Thr Asn Trp Phe Asn Asn Asn Ala Pro Ser Phe Ser Ala
305                 310                 315                 320

Ile Glu Ala Ala Ile Phe Arg Pro Pro His Leu Leu Asp Phe Pro Glu
                325                 330                 335

Gln Leu Thr Ile Tyr Ser Ala Ser Ser Arg Trp Ser Ser Thr Gln His
            340                 345                 350

Met Asn Tyr Trp Val Gly His Arg Leu Asn Phe Arg Pro Ile Gly Gly
        355                 360                 365

Thr Leu Asn Thr Ser Thr Gln Gly Leu Thr Asn Asn Thr Ser Ile Asn
    370                 375                 380

Pro Val Thr Leu Gln Phe Thr Ser Arg Asp Val Tyr Arg Thr Glu Ser
385                 390                 395                 400

Asn Ala Gly Thr Asn Ile Leu Phe Thr Thr Pro Val Asn Gly Val Pro
                405                 410                 415

Trp Ala Arg Phe Asn Phe Ile Asn Pro Gln Asn Ile Tyr Glu Arg Gly
            420                 425                 430

Ala Thr Thr Tyr Ser Gln Pro Tyr Gln Gly Val Gly Ile Gln Leu Phe
        435                 440                 445

Asp Ser Glu Thr Glu Leu Pro Pro Glu Thr Thr Glu Arg Pro Asn Tyr
    450                 455                 460

Glu Ser Tyr Ser His Arg Leu Ser His Ile Gly Leu Ile Ile Gly Asn
465                 470                 475                 480

Thr Leu Arg Ala Pro Val Tyr Ser Trp Thr His Arg Ser Ala Asp Arg
                485                 490                 495

Thr Asn Thr Ile Gly Pro Asn Arg Ile Thr Gln Ile Pro Leu Val Lys
            500                 505                 510

Ala Leu Asn Leu His Ser Gly Val Thr Val Val Gly Gly Pro Gly Phe
        515                 520                 525

Thr Gly Gly Asp Ile Leu Arg Arg Thr Asn Thr Gly Thr Phe Gly Asp
    530                 535                 540

Ile Arg Leu Asn Ile Asn Val Pro Leu Ser Gln Arg Tyr Arg Val Arg
545                 550                 555                 560

Ile Arg Tyr Ala Ser Thr Thr Asp Leu Gln Phe Phe Thr Arg Ile Asn
                565                 570                 575

Gly Thr Thr Val Asn Ile Gly Asn Phe Ser Arg Thr Met Asn Arg Gly
            580                 585                 590

Asp Asn Leu Glu Tyr Arg Ser Phe Arg Thr Ala Gly Phe Ser Thr Pro
        595                 600                 605

Phe Asn Phe Leu Asn Ala Gln Ser Thr Phe Thr Leu Gly Ala Gln Ser
    610                 615                 620

Phe Ser Asn Gln Glu Val Tyr Ile Asp Arg Val Glu Phe Val Pro Ala
625                 630                 635                 640

Glu Val Thr Phe Glu Ala Glu Tyr Asp Leu Glu Arg Ala Gln Lys
                645                 650                 655
```

<210> SEQ ID NO 58
<211> LENGTH: 653
<212> TYPE: PRT
<213> ORGANISM: Bacillus thuringiensis

<400> SEQUENCE: 58

```
Met Thr Ser Asn Arg Lys Asn Glu Asn Glu Ile Ile Asn Ala Leu Ser
1               5                   10                  15
```

-continued

```
Ile Pro Ala Val Ser Asn His Ser Ala Gln Met Asn Leu Ser Thr Asp
            20                  25                  30

Ala Arg Ile Glu Asp Ser Leu Cys Ile Ala Glu Gly Asn Asn Ile Asp
        35                  40                  45

Pro Phe Val Ser Ala Ser Thr Val Gln Thr Gly Ile Asn Ile Ala Gly
    50                  55                  60

Arg Ile Leu Gly Val Leu Gly Val Pro Phe Ala Gly Gln Ile Ala Ser
65                  70                  75                  80

Phe Tyr Ser Phe Leu Val Gly Glu Leu Trp Pro Arg Gly Arg Asp Pro
                85                  90                  95

Trp Glu Ile Phe Leu Glu His Val Glu Gln Leu Ile Arg Gln Gln Val
            100                 105                 110

Thr Glu Asn Thr Arg Asp Thr Ala Leu Ala Arg Leu Gln Gly Leu Gly
        115                 120                 125

Asn Ser Phe Arg Ala Tyr Gln Gln Ser Leu Glu Asp Trp Leu Glu Asn
    130                 135                 140

Arg Asp Asp Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Arg Asn
                165                 170                 175

Gln Glu Val Pro Leu Leu Met Val Tyr Ala Gln Ala Ala Asn Leu His
            180                 185                 190

Leu Leu Leu Leu Arg Asp Ala Ser Leu Phe Gly Ser Glu Phe Gly Leu
        195                 200                 205

Thr Ser Gln Glu Ile Gln Arg Tyr Tyr Glu Arg Gln Val Glu Lys Thr
    210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Val Tyr Pro Met Asn Thr Ser Ala Gln Leu Thr
        275                 280                 285

Arg Glu Ile Tyr Thr Asp Pro Ile Gly Arg Thr Asn Ala Pro Ser Gly
    290                 295                 300

Phe Ala Ser Thr Asn Trp Phe Asn Asn Asn Ala Pro Ser Phe Ser Ala
305                 310                 315                 320

Ile Glu Ala Ala Val Ile Arg Pro Pro His Leu Leu Asp Phe Pro Glu
                325                 330                 335

Gln Leu Thr Ile Phe Ser Val Leu Ser Arg Trp Ser Asn Thr Gln Tyr
            340                 345                 350

Met Asn Tyr Trp Val Gly His Arg Leu Glu Ser Arg Thr Ile Arg Gly
        355                 360                 365

Ser Leu Ser Thr Ser Thr His Gly Asn Thr Asn Thr Ser Ile Asn Pro
    370                 375                 380

Val Thr Leu Gln Phe Thr Ser Arg Asp Val Tyr Arg Thr Glu Ser Phe
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
            420                 425                 430
```

```
Leu Tyr Thr Ile Gly Tyr Thr Gly Val Gly Thr Gln Leu Phe Asp Ser
        435                 440                 445

Glu Thr Glu Leu Pro Pro Glu Thr Thr Glu Arg Pro Asn Tyr Glu Ser
    450                 455                 460

Tyr Ser His Arg Leu Ser Asn Ile Arg Leu Ile Ser Gly Asn Thr Leu
465                 470                 475                 480

Arg Ala Pro Val Tyr Ser Trp Thr His Arg Ser Ala Asp Arg Thr Asn
                485                 490                 495

Thr Ile Ser Ser Asp Ser Ile Thr Gln Ile Pro Leu Val Lys Ser Phe
            500                 505                 510

Asn Leu Asn Ser Gly Thr Ser Val Val Ser Gly Pro Gly Phe Thr Gly
        515                 520                 525

Gly Asp Ile Ile Arg Thr Asn Val Asn Gly Ser Val Leu Ser Met Gly
    530                 535                 540

Leu Asn Phe Asn Asn Thr Ser Leu Gln Arg Tyr Arg Val Arg Val Arg
545                 550                 555                 560

Tyr Ala Ala Ser Gln Thr Met Val Leu Arg Val Thr Val Gly Gly Ser
                565                 570                 575

Thr Thr Phe Asp Gln Gly Phe Pro Ser Thr Met Ser Ala Asn Glu Ser
            580                 585                 590

Leu Thr Ser Gln Ser Phe Arg Phe Ala Glu Phe Pro Val Gly Ile Ser
        595                 600                 605

Ala Ser Gly Ser Gln Thr Ala Gly Ile Ser Ile Ser Asn Asn Ala Gly
    610                 615                 620

Arg Gln Thr Phe His Phe Asp Lys Ile Glu Phe Ile Pro Ile Thr Ala
625                 630                 635                 640

Thr Phe Glu Ala Glu Tyr Asp Leu Glu Arg Ala Gln Glu
                645                 650
```

<210> SEQ ID NO 59
<211> LENGTH: 654
<212> TYPE: PRT
<213> ORGANISM: Bacillus thuringiensis

<400> SEQUENCE: 59

```
Met Thr Ser Asn Arg Lys Asn Glu Asn Glu Ile Ile Asn Ala Leu Ser
1               5                   10                  15

Ile Pro Ala Val Ser Asn His Ser Thr Gln Met Asp Leu Ser Pro Asp
            20                  25                  30

Ala Arg Ile Glu Asp Ser Leu Cys Ile Ala Glu Gly Asn Asn Ile Asn
        35                  40                  45

Pro Leu Val Ser Ala Ser Thr Val Gln Thr Gly Ile Asn Ile Ala Gly
    50                  55                  60

Arg Ile Leu Gly Val Leu Gly Val Pro Phe Ala Gly Gln Ile Ala Ser
65                  70                  75                  80

Phe Tyr Ser Phe Leu Val Gly Glu Leu Trp Pro Arg Gly Arg Asp Gln
                85                  90                  95

Trp Glu Ile Phe Leu Glu His Val Glu Gln Leu Ile Asn Gln Gln Ile
            100                 105                 110

Thr Glu Asn Ala Arg Asn Thr Ala Leu Ala Arg Leu Gln Gly Leu Gly
        115                 120                 125

Asp Ser Phe Arg Ala Tyr Gln Gln Ser Leu Glu Asp Trp Leu Glu Asn
    130                 135                 140

Arg Asp Asp Ala Arg Thr Arg Ser Val Leu Tyr Thr Gln Tyr Ile Ala
145                 150                 155                 160
```

```
Leu Glu Leu Asp Phe Leu Asn Ala Met Pro Leu Phe Ala Ile Arg Asn
                165                 170                 175

Gln Glu Val Pro Leu Leu Met Val Tyr Ala Gln Ala Ala Asn Leu His
            180                 185                 190

Leu Leu Leu Leu Arg Asp Ala Ser Leu Phe Gly Ser Glu Phe Gly Leu
        195                 200                 205

Thr Ser Gln Glu Ile Gln Arg Tyr Tyr Glu Arg Gln Val Glu Gln Thr
    210                 215                 220

Arg Asp Tyr Ser Asp Tyr Cys Val Glu Trp Tyr Asn Thr Gly Leu Asn
225                 230                 235                 240

Ser Leu Arg Gly Thr Asn Ala Ala Ser Trp Val Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Thr Tyr Pro Ile Asn Thr Ser Ala Gln Leu Thr
        275                 280                 285

Arg Glu Val Tyr Thr Asp Ala Ile Gly Ala Thr Gly Val Asn Met Ala
    290                 295                 300

Ser Met Asn Trp Tyr Asn Asn Asn Ala Pro Ser Phe Ser Ala Ile Glu
305                 310                 315                 320

Thr Ala Val Ile Arg Ser Pro His Leu Leu Asp Phe Leu Glu Gln Leu
                325                 330                 335

Thr Ile Phe Ser Thr Ser Ser Arg Trp Ser Ala Thr Arg His Met Thr
            340                 345                 350

Tyr Trp Arg Gly His Thr Ile Gln Ser Arg Pro Ile Gly Gly Gly Leu
        355                 360                 365

Asn Thr Ser Thr His Gly Ser Thr Asn Thr Ser Ile Asn Pro Val Arg
    370                 375                 380

Leu Ser Phe Phe Ser Arg Asp Val Tyr Trp Thr Glu Ser Tyr Ala Gly
385                 390                 395                 400

Val Leu Leu Trp Gly Ile Tyr Leu Glu Pro Ile His Gly Val Pro Thr
                405                 410                 415

Val Arg Phe Asn Phe Arg Asn Pro Gln Asn Thr Phe Glu Arg Gly Thr
            420                 425                 430

Ala Asn Tyr Ser Gln Pro Tyr Glu Ser Pro Gly Leu Gln Leu Lys Asp
        435                 440                 445

Ser Glu Thr Glu Leu Pro Pro Glu Thr Thr Glu Arg Pro Asn Tyr Glu
    450                 455                 460

Ser Tyr Ser His Arg Leu Ser His Ile Gly Leu Ile Ser Gln Ser Arg
465                 470                 475                 480

Val His Val Pro Val Tyr Ser Trp Thr His Arg Ser Ala Asp Arg Thr
                485                 490                 495

Asn Thr Ile Ser Ser Asp Ser Ile Thr Gln Ile Pro Leu Val Lys Ser
            500                 505                 510

Phe Asn Leu Asn Ser Gly Thr Ser Val Val Ser Gly Pro Gly Phe Thr
        515                 520                 525

Gly Gly Asp Ile Ile Arg Thr Asn Val Asn Gly Ser Val Leu Ser Met
    530                 535                 540

Gly Leu Asn Phe Asn Asn Thr Ser Leu Gln Arg Tyr Arg Val Arg Val
545                 550                 555                 560

Arg Tyr Ala Ala Ser Gln Thr Met Val Leu Arg Val Thr Val Gly Gly
                565                 570                 575
```

```
Ser Thr Thr Phe Asp Gln Gly Phe Pro Ser Thr Met Ser Ala Asn Glu
            580                 585                 590

Ser Leu Thr Ser Gln Ser Phe Arg Phe Ala Glu Phe Pro Val Gly Ile
        595                 600                 605

Ser Ala Ser Gly Ser Gln Thr Ala Gly Ile Ser Ile Ser Asn Asn Ala
    610                 615                 620

Gly Arg Gln Thr Phe His Phe Asp Lys Ile Glu Phe Ile Pro Ile Thr
625                 630                 635                 640

Ala Thr Phe Glu Ala Glu Tyr Asp Leu Glu Arg Ala Gln Glu
                645                 650


<210> SEQ ID NO 60
<211> LENGTH: 661
<212> TYPE: PRT
<213> ORGANISM: Bacillus thuringiensis

<400> SEQUENCE: 60

Met Asn Ser Asn Arg Lys Asn Glu Asn Glu Ile Ile Asp Ala Ser Phe
1               5                   10                  15

Ile Pro Ala Val Ser Asn Glu Ser Val Thr Ile Ser Lys Glu Tyr Ala
            20                  25                  30

Gln Thr Asn Gln Leu Gln Asn Asn Ser Ile Glu Asp Gly Leu Cys Ile
        35                  40                  45

Ala Glu Gly Glu Tyr Ile Asp Pro Phe Val Ser Ala Ser Thr Val Gln
    50                  55                  60

Thr Gly Ile Ser Ile Ala Gly Arg Ile Leu Gly Val Leu Gly Val Pro
65                  70                  75                  80

Phe Ala Gly Gln Leu Ala Ser Phe Tyr Ser Phe Ile Val Gly Glu Leu
                85                  90                  95

Trp Pro Lys Gly Arg Asp Gln Trp Glu Ile Phe Met Glu His Val Glu
            100                 105                 110

Gln Leu Val Arg Gln Gln Ile Thr Ala Asn Ala Arg Asn Thr Ala Leu
        115                 120                 125

Ala Arg Leu Gln Gly Leu Gly Asp Ser Phe Arg Ala Tyr Gln Gln Ser
    130                 135                 140

Leu Glu Asp Trp Leu Glu Asn Arg Asn Asp Ala Arg Thr Arg Ser Val
145                 150                 155                 160

Leu Tyr Thr Gln Tyr Ile Ala Leu Glu Leu Asp Phe Leu Asn Ala Met
                165                 170                 175

Pro Leu Phe Ala Ile Arg Glu Gln Glu Val Pro Leu Leu Met Val Tyr
            180                 185                 190

Ala Gln Ala Ala Asn Leu His Leu Leu Leu Leu Arg Asp Ala Ser Leu
        195                 200                 205

Tyr Gly Arg Glu Phe Gly Leu Thr Ser Gln Glu Ile Gln Arg Tyr Tyr
    210                 215                 220

Glu Arg Gln Val Glu Arg Thr Arg Asp Tyr Ser Asp His Cys Val Gln
225                 230                 235                 240

Trp Tyr Asn Thr Gly Leu Asn Asn Leu Arg Gly Thr Asn Ala Glu Ser
                245                 250                 255

Trp Val Arg Tyr Asn Gln Phe Arg Arg Asp Leu Thr Leu Gly Val Leu
            260                 265                 270

Asp Leu Val Ala Leu Phe Pro Ser Tyr Asp Thr Arg Thr Tyr Pro Ile
        275                 280                 285

Asn Thr Ser Ala Gln Leu Thr Arg Glu Val Tyr Thr Asp Ala Ile Gly
    290                 295                 300
```

```
Ala Thr Gly Val Asn Met Ala Ser Met Asn Trp Tyr Asn Asn Asn Ala
305                 310                 315                 320

Pro Ser Phe Ser Ala Ile Glu Thr Ala Val Ile Arg Ser Pro His Leu
                325                 330                 335

Leu Asp Phe Leu Glu Gln Leu Lys Ile Phe Ser Ala Ser Ser Arg Trp
            340                 345                 350

Ser Asn Thr Arg His Met Thr Tyr Trp Arg Gly His Thr Ile Gln Ser
        355                 360                 365

Arg Pro Ile Arg Gly Ala Leu Ile Thr Ser Thr His Gly Asn Thr Asn
    370                 375                 380

Thr Ser Ile Asn Pro Val Thr Phe Gln Phe Pro Ser Arg Asp Val Tyr
385                 390                 395                 400

Arg Thr Glu Ser Tyr Ala Gly Val Leu Leu Trp Gly Ile Tyr Leu Glu
                405                 410                 415

Pro Ile His Gly Val Pro Thr Val Arg Phe Asn Phe Arg Asn Pro Gln
            420                 425                 430

Asn Thr Phe Glu Arg Gly Thr Ala Asn Tyr Ser Gln Pro Tyr Glu Ser
        435                 440                 445

Pro Gly Leu Gln Leu Lys Asp Ser Glu Thr Glu Leu Pro Pro Glu Thr
    450                 455                 460

Thr Glu Arg Pro Asn Tyr Glu Ser Tyr Ser His Arg Leu Ser His Ile
465                 470                 475                 480

Gly Ile Ile Leu Gln Thr Arg Leu Asn Val Pro Val Tyr Ser Trp Thr
                485                 490                 495

His Arg Ser Ala Asp Arg Thr Asn Thr Ile Ser Ser Asp Ser Ile Thr
            500                 505                 510

Gln Ile Pro Leu Val Lys Ser Phe Asn Leu Asn Ser Gly Thr Ser Val
        515                 520                 525

Val Ser Gly Pro Gly Phe Thr Gly Gly Asp Ile Ile Arg Thr Asn Val
    530                 535                 540

Asn Gly Ser Val Leu Ser Met Gly Leu Asn Phe Asn Asn Thr Ser Leu
545                 550                 555                 560

Gln Arg Tyr Arg Val Arg Val Arg Tyr Ala Ala Ser Gln Thr Met Val
                565                 570                 575

Leu Arg Val Thr Val Gly Gly Ser Thr Thr Phe Asp Gln Gly Phe Pro
            580                 585                 590

Ser Thr Met Ser Ala Asn Glu Ser Leu Thr Ser Gln Ser Phe Arg Phe
        595                 600                 605

Ala Glu Phe Pro Val Gly Ile Ser Ala Ser Gly Ser Gln Thr Ala Gly
    610                 615                 620

Ile Ser Ile Ser Asn Asn Ala Gly Arg Gln Thr Phe His Phe Asp Lys
625                 630                 635                 640

Ile Glu Phe Ile Pro Ile Thr Ala Thr Phe Glu Ala Glu Tyr Asp Leu
                645                 650                 655

Glu Arg Ala Gln Glu
            660


<210> SEQ ID NO 61
<211> LENGTH: 643
<212> TYPE: PRT
<213> ORGANISM: Bacillus thuringiensis

<400> SEQUENCE: 61

Met Lys Asn Ser Ile Lys Leu Ser Glu Leu Trp Tyr Phe Asn Glu Arg
```

-continued

```
1               5                   10                  15

Lys Trp Arg Tyr Phe Met Glu Ile Val Asn Asn Gln Asn Gln Cys Val
            20                  25                  30

Pro Tyr Asn Cys Leu Asn Asn Pro Glu Ile Glu Ile Leu Glu Gly Gly
        35                  40                  45

Arg Ile Ser Val Gly Asn Thr Pro Ile Asp Ile Ser Leu Ser Leu Thr
    50                  55                  60

Gln Phe Leu Leu Ser Glu Phe Val Pro Gly Ala Gly Phe Val Leu Gly
65                  70                  75                  80

Leu Ile Asp Leu Ile Trp Gly Phe Val Gly Pro Ser Gln Trp Asp Ala
                85                  90                  95

Phe Leu Ala Gln Val Glu Gln Leu Ile Asn Gln Arg Ile Ala Glu Ala
            100                 105                 110

Val Arg Asn Thr Ala Ile Gln Glu Leu Glu Gly Met Ala Arg Val Tyr
        115                 120                 125

Arg Thr Tyr Ala Thr Ala Phe Ala Glu Trp Glu Lys Ala Pro Asp Asp
    130                 135                 140

Pro Glu Leu Arg Glu Ala Leu Arg Thr Gln Phe Thr Ala Thr Glu Thr
145                 150                 155                 160

Tyr Ile Ser Gly Arg Ile Ser Val Leu Lys Ile Gln Thr Phe Glu Val
                165                 170                 175

Gln Leu Leu Ser Val Phe Ala Gln Ala Ala Asn Leu His Leu Ser Leu
            180                 185                 190

Leu Arg Asp Val Val Phe Phe Gly Gln Arg Trp Gly Phe Ser Thr Thr
        195                 200                 205

Thr Val Asn Asn Tyr Tyr Asn Asp Leu Thr Glu Gly Ile Ser Thr Tyr
    210                 215                 220

Thr Asp Tyr Ala Val Arg Trp Tyr Asn Thr Gly Leu Glu Arg Val Trp
225                 230                 235                 240

Gly Pro Asp Ser Arg Asp Trp Val Arg Tyr Asn Gln Phe Arg Arg Glu
                245                 250                 255

Leu Thr Leu Thr Val Leu Asp Ile Val Ala Leu Phe Pro Asn Tyr Asp
            260                 265                 270

Ser Arg Arg Tyr Pro Ile Arg Thr Val Ser Gln Leu Thr Arg Glu Ile
        275                 280                 285

Tyr Thr Asn Pro Val Leu Glu Asn Phe Asp Gly Ser Phe Arg Gly Ser
    290                 295                 300

Ala Gln Gly Ile Glu Arg Ser Ile Arg Ser Pro His Leu Met Asp Ile
305                 310                 315                 320

Leu Asn Ser Ile Thr Ile Tyr Thr Asp Ala His Arg Gly Tyr Tyr Tyr
                325                 330                 335

Trp Ser Gly His Gln Ile Met Ala Ser Pro Val Gly Phe Ser Gly Pro
            340                 345                 350

Glu Phe Thr Phe Pro Leu Tyr Gly Thr Met Gly Asn Ala Ala Pro Gln
        355                 360                 365

Gln Arg Ile Val Ala Gln Leu Gly Gln Gly Val Tyr Arg Thr Leu Ser
    370                 375                 380

Ser Thr Phe Tyr Arg Arg Pro Phe Asn Ile Gly Ile Asn Asn Gln Gln
385                 390                 395                 400

Leu Ser Val Leu Asp Gly Thr Glu Phe Ala Tyr Gly Thr Ser Ser Asn
                405                 410                 415

Leu Pro Ser Ala Val Tyr Arg Lys Ser Gly Thr Val Asp Ser Leu Asp
            420                 425                 430
```

Glu Ile Pro Pro Gln Asn Asn Asn Val Pro Pro Arg Gln Gly Phe Ser
435 440 445

His Arg Leu Ser His Val Ser Met Phe Arg Ser Gly Ser Ser Ser Ser
450 455 460

Val Ser Ile Ile Arg Ala Pro Met Phe Ser Trp Ile His Arg Ser Ala
465 470 475 480

Glu Phe Asn Asn Ile Ile Ala Ser Asp Ser Ile Thr Gln Ile Pro Ala
485 490 495

Val Lys Gly Asn Phe Leu Phe Asn Gly Ser Val Ile Ser Gly Pro Gly
500 505 510

Phe Thr Gly Gly Asp Leu Val Arg Leu Asn Ser Ser Gly Asn Asn Ile
515 520 525

Gln Asn Arg Gly Tyr Ile Glu Val Pro Ile His Phe Pro Ser Thr Ser
530 535 540

Thr Arg Tyr Arg Val Arg Val Arg Tyr Ala Ser Val Thr Pro Ile His
545 550 555 560

Leu Asn Val Asn Trp Gly Asn Ser Ser Ile Phe Ser Asn Thr Val Pro
565 570 575

Ala Thr Ala Thr Ser Leu Asp Asn Leu Gln Ser Ser Asp Phe Gly Tyr
580 585 590

Phe Glu Ser Ala Asn Ala Phe Thr Ser Ser Leu Gly Asn Ile Val Gly
595 600 605

Val Arg Asn Phe Ser Gly Thr Ala Gly Val Ile Ile Asp Arg Phe Glu
610 615 620

Phe Ile Pro Val Thr Ala Thr Leu Glu Ala Glu Tyr Asn Leu Glu Arg
625 630 635 640

Ala Gln Lys

<210> SEQ ID NO 62
<211> LENGTH: 867
<212> TYPE: PRT
<213> ORGANISM: Adiantum pedatum

<400> SEQUENCE: 62

Met Ala Leu Val Asp Tyr Gly Lys Leu Phe Glu Asp Leu Asn Gln Ile
1 5 10 15

Ser Met Gly Val Leu Asp Arg Val Glu Phe Ser Glu Val Met Val Ile
20 25 30

His Arg Met Tyr Val Arg Leu Ala Asp Leu Asn Val Gly Gln Leu Glu
35 40 45

Gly Ala Glu Lys Val Lys Arg Leu Tyr Val Phe Ala Asp Val Val Glu
50 55 60

Leu Pro Val Val Glu Trp Arg Trp Pro Pro Gln Ile Pro Gly Ser Val
65 70 75 80

Thr Val Ile Ile Leu Cys Arg Leu Leu Gln Trp Pro Thr Asp Gly Arg
85 90 95

Gln Ser Asp Thr Glu Leu His Leu Thr Phe Met Lys Leu His Ala Ile
100 105 110

Gln Arg Glu Glu Asn Arg Trp Glu Ile Thr Ala Ala Asp Gly Met Asn
115 120 125

Trp Gly Val Tyr Ile His Ala Glu Glu Val Gln Val Gly Val Leu Thr
130 135 140

Met Ser Trp Ser Ser Val Leu Arg Val Ser Ala Leu Arg Ser Val Ile
145 150 155 160

-continued

```
Thr Ser Gly Phe Arg Ala Val Ser Val Phe Glu Val Pro Gly Ser Val
                165                 170                 175

Arg Ser Thr Leu Gly Ala Thr Leu Arg Pro Asp His Ala Leu Tyr Ser
            180                 185                 190

Thr Thr Met Gln Ala Thr Pro Asn Ala Ser His Ile Ser Ala Phe Asn
        195                 200                 205

Leu Arg Ile Val Ser Pro Ser Ala Tyr Arg Val Cys Pro Leu Gln Asn
    210                 215                 220

Asp Thr Asp Thr Tyr Leu Gly Ile Pro Ala Asp Val Ala Ala Val Leu
225                 230                 235                 240

Pro Val Asp Val Val Thr Asp Pro Asn Ile Leu Leu Gly Met Gln Thr
                245                 250                 255

Thr Val His Ile Ala Glu Leu Val Lys Ala Cys His Pro Ser Pro Asp
            260                 265                 270

Val Val Ser Ala Val Gly Glu His Leu Asn Trp Leu Asn Lys Leu Leu
        275                 280                 285

Leu Pro Leu Lys Glu Ser Thr Gln Leu Gln Gly Ser Glu Ser Tyr Lys
    290                 295                 300

Glu Cys Leu Ala Leu Leu Gly Arg Val His Ala Ala Met Lys Met Val
305                 310                 315                 320

Arg Ile Gly Leu Val Val Pro Gln Leu Gln Tyr Arg Met Tyr Gly Ser
                325                 330                 335

Leu Ile Asn Gln Met Ala Gln Val Ala Gln Asn Tyr Asp Arg Glu Phe
            340                 345                 350

Lys Gln Phe Lys Leu Phe Ile Ile Gln Asn Gln Ile Leu Gly Ser Tyr
        355                 360                 365

Leu Leu Gln Gln Asn Arg Ala Phe Ala Glu Arg Glu Leu Gln Met Glu
    370                 375                 380

Ser Phe His Ala Ala Val Ile Ser Gln Arg Arg Glu Glu Leu Asp Asn
385                 390                 395                 400

Thr Phe Ala Lys Met Asp Arg Leu Ser Gly Gln Met Glu Ala Glu Ser
                405                 410                 415

Ser Ala Met Glu Gln Ala Lys Lys Glu Met Asp Glu Gly Leu Arg Gln
            420                 425                 430

Phe Gln Asn Arg Gln Val Ala Asn Ala Leu Phe Ala Val Leu Ser Ala
        435                 440                 445

Val Ala Gln Ile Gly Leu Ala Phe Leu Thr Ala Gly Ala Thr Ala Pro
    450                 455                 460

Gly Ala Val Ala Ser Ala Gly Gln Ala Val Ser Ile Ala Gly Gln Ala
465                 470                 475                 480

Ala Gln Gly Leu Arg Arg Val Val Glu Ile Leu Glu Gln Leu Glu Ala
                485                 490                 495

Val Met Glu Val Val Ala Ala Val Lys Asp Leu Val Asp Ser Leu Glu
            500                 505                 510

Gln Val Gly Gln Ile Val Asp Ala Pro Val Met Pro Glu Leu Pro Ser
        515                 520                 525

Glu Ala Asp Trp Ser Ile Phe Val Asn Glu Val Glu Ala Val Ala Glu
    530                 535                 540

Gly Met Pro Thr Glu Val Ser Glu Val Pro Val Trp Arg Ala Lys Cys
545                 550                 555                 560

Lys Asn Val Ala Ala Leu Gly Arg Glu Met Ser Ile Thr Ala Val Gln
                565                 570                 575
```

-continued

```
Met Ser Glu Leu Gln Tyr Asp Ile Trp Val Gln Gly Met Met Arg Asp
            580                 585                 590

Met Ala Arg Ser Gln Ala Asp Arg Leu Ala Ala Ile Gln Pro Ala Asp
        595                 600                 605

Leu Thr Asn Tyr Leu Glu Met Ala Thr Gln Met Asp Met Arg Thr Thr
    610                 615                 620

Arg Met Leu Leu Gly Leu Leu Asn Ile Leu Arg Ile Gln Asn Ala Ala
625                 630                 635                 640

Leu Arg Tyr Glu Tyr Leu Leu Met Pro Thr Glu Leu Thr Thr Trp Pro
                645                 650                 655

Leu Gly Met Asp Thr Val Gly Asp Leu Leu Ile Ala Gln Glu Asn Ala
            660                 665                 670

Ala Leu Ile Gly Leu Met Gln Leu Gly Pro Ser Ser Asp Phe Thr Ser
        675                 680                 685

Arg His Val Val Lys Asp Ile Pro Val Asn Leu Leu Leu Asp Gly Glu
    690                 695                 700

Asp Trp Glu Phe Glu Ile Pro Val Gln Ala Gly Met Ser Ser Phe Pro
705                 710                 715                 720

Ser Ser Trp Ser Arg Val Arg Ile Arg His Leu Glu Met His Phe Val
                725                 730                 735

Lys Glu Ala Ser Gly Ile Gly Gly Glu Ile Ile His Gln Pro Thr Thr
            740                 745                 750

Gln Thr Gly Thr Val Tyr Ile Leu Leu Gln Gly Ser Thr Ile Phe His
        755                 760                 765

Asp Arg Arg Arg Asp Gln Val Leu Pro Phe Gln Ala Ala Ala Pro Leu
    770                 775                 780

Asn Tyr His Tyr Ala Tyr Arg Leu Asp Thr Gly Asp Ser Thr Leu Thr
785                 790                 795                 800

Asn Glu Pro Ser Glu Gln Phe Ala Asn Lys Phe Met Gln Met Thr Pro
                805                 810                 815

Phe Thr Arg Trp Arg Leu Arg Leu Ser Ala Ser Ala Lys Glu Asn Ala
            820                 825                 830

Gly Leu Ala Phe Pro Thr Ala Thr Ala Leu Asp Ser Thr Thr Gln Ile
        835                 840                 845

Val Ile Thr Phe His Val Thr Ala Ile Arg Gln Ile Asp Trp Arg His
    850                 855                 860

Asp Glu Glu
865
```

<210> SEQ ID NO 63
<211> LENGTH: 2601
<212> TYPE: DNA
<213> ORGANISM: Adiantum pedatum

<400> SEQUENCE: 63

```
atggctctcg tggattacgg caagcttttc gaggatctga accagataag catgggtgta      60

ctggatcggg tagagttttc agaggtgatg gtgatccaca ggatgtatgt gaggctagct     120

gatctgaatg tggggcagct cgagggagcc gagaaagtga agcggttgta tgtgtttgcg     180

gacgtggtgg agctaccagt cgtggaatgg cggtggccgc cgcaaatacc aggatcggtg     240

acggtgatca tattgtgtcg tcttcttcaa tggccaactg atgggaggca gtcggacacc     300

gagctccacc tgacattcat gaagttgcat gccatacaac gagaggaaaa tcggtgggag     360

ataaccgcag cagatggcat gaactgggga gtttacatac acgcagagga agtacaggtt     420
```

-continued

```
ggcgtgctga caatgtcatg gtcttcggta cttagagttt cggcacttcg ctctgttata    480
acctccggct ttcgcgccgt tagtgtgttt gaggtaccgg gaagtgtaag gtccacccttt    540
ggagctactt taaggcccga tcacgcctta tatagtacaa ctatgcaagc cacacccaac    600
gcatcgcata ttagtgcttt taaccttcgc atagtttccc cgtcggcata tcgtgtttgt    660
cctctccaaa atgacacaga tacctactta ggtattccag cagacgtggc ggcagttctt    720
ccagtagacg tggtgactga tcctaacatc ttgctgggca tgcagacaac ggtacacatt    780
gcggagctag tcaaggcatg tcatccgtca cccgatgttg tgagcgctgt aggggagcac    840
ctgaactggc tcaacaaact cttactccca cttaaggaat cgactcagtt gcaaggaagc    900
gagtcgtaca aggagtgcct tgcactcttg ggtcgtgttc acgctgcgat gaagatggtg    960
agaattggct tagtagtgcc ccagctgcaa tacagaatgt acggtagcct catcaaccaa   1020
atggcccaag tagcacaaaa ctacgaccga gaattcaagc aattcaaatt attcatcatc   1080
caaaatcaaa tccttggcag ctatttgctg cagcagaaca gggcatttgc tgagagggag   1140
ctgcagatgg agagctttca tgctgctgtc atttctcaaa gaagggagga gttggacaat   1200
acattcgcaa agatggaccg attgagcggg caaatggagg cagagagtag tgcaatggag   1260
caagccaaaa aggaaatgga cgaaggattg aggcagttcc agaataggca agttgcgaac   1320
gccctctttg ccgttcttag cgctgtagct cagattgggc ttgcattcct tacggctggt   1380
gcaacggctc ctggagctgt ggcgtcggcg gggcaagctg tgagcatagc aggtcaggcg   1440
gcgcaaggtc tgcgaagggt ggtggaaatt ctagagcagc tggaggctgt gatggaggtt   1500
gtggctgctg tgaaggacct cgtggattca ttggaacagg taggtcagat tgtggacgca   1560
ccggtgatgc cggaattgcc ctcagaggcg gactggtcca tttttgtgaa cgaggtggag   1620
gccgtggcag agggcatgcc aacggaagtc tcggaggttc cggtgtggag ggccaagtgc   1680
aagaatgtgg ctgcactggg tcgggagatg agcatcacgg cagtacagat gtcggagctg   1740
cagtatgaca tctgggtgca aggcatgatg cgggatatgg ctcgaagcca ggcagacagg   1800
ctggccgcaa ttcaacccgc ggaccttacc aactatttgg agatggctac ccagatggat   1860
atgcggacta cgaggatgct gctggggctc ctcaacatat tgcgcatcca gaatgcggcg   1920
ctcaggtacg agtatcttct aatgcccacg gagctcacaa catggccact gggtatggat   1980
accgtgggtg acttgctcat cgcgcaggag aatgctgcac tgataggatt aatgcagcta   2040
gggccctcat ctgatttcac gagcaggcat gtggtgaaag acatacctgt gaacttgctg   2100
ctcgatggcg aggattggga gtttgagatt cctgtgcaag ctggcatgtc cagcttccct   2160
tccagctggt ctcgcgtccg tattcggcac ctggagatgc actttgtgaa ggaggccagc   2220
ggtattggtg gtgagattat ccaccagcct accacccaga ctgggaccgt ttacatcctt   2280
ctgcagggtt ccactatctt ccatgaccgc agaagagacc aggtgttgcc ttttcaggcc   2340
gctgctccgc tcaactacca ttacgcgtac cgcctcgaca ccggcgactc cactctcaca   2400
aacgaaccct ctgaacagtt tgccaacaag ttcatgcaga tgacaccctt cacccgttgg   2460
aggcttcgtc tgtctgcgtc cgcaaaagag aatgcaggat tagcctttcc cacggctaca   2520
gcacttgact ccactaccca gattgtcatc actttccatg ttacggccat cagacaaatt   2580
gactggcggc acgacgaaga g                                             2601
```

<210> SEQ ID NO 64
<211> LENGTH: 852
<212> TYPE: PRT
<213> ORGANISM: Adiantum trapeziforme

<400> SEQUENCE: 64

Met Asp Tyr Ser Thr Leu Tyr Arg Asp Leu Asn Gln Ile Ser Met Pro
1 5 10 15

Leu Asp Arg Val Glu Phe Ser Glu Val Met Val Ile His Arg Met Tyr
20 25 30

Leu Arg Leu Ser Asp Leu Asn Val Gly Glu Leu Pro Gly Ala Glu Arg
35 40 45

Val Lys Arg Leu Tyr Val Leu Ala Asp Val Val Glu Leu Ala Thr Phe
50 55 60

Ala His Pro Gln Leu Leu Asn Thr Arg Met Pro Gly Ser Val Thr Val
65 70 75 80

Ile Ile Leu Cys Arg Leu Leu Gln Phe Pro Thr Asp Gly Ser Phe Ala
85 90 95

Ala Trp Leu Glu Leu Pro Phe Met Glu Leu His Thr Leu Ile Glu Gln
100 105 110

Tyr Arg Ser Glu Ile Lys Ala Ala Asp Asp Ala Lys Trp Gly Thr Tyr
115 120 125

Val His Ala Glu Glu Val Gln Leu Ser Pro Leu Phe Asn Gly Trp Pro
130 135 140

Tyr Leu Val Val Glu Ala Gln Arg Cys Ile Ile Thr Ala Ala Met His
145 150 155 160

Asn Thr Phe Asn Arg Pro Gly Trp Val Arg Ser Ile Thr Gln Phe Thr
165 170 175

Thr Asp Gln Ser Gly Arg Val Asp Thr Thr Leu Leu Ala Arg Thr Glu
180 185 190

Phe Gly His Ile Asp Leu Pro Leu Glu Thr Asp Ser Pro Thr Ala Phe
195 200 205

Ser Val Ser His Arg Gln Ser Thr Asn Leu Pro Val Glu Tyr Thr Gly
210 215 220

Ile Pro Val Glu Val Val Thr Asp Pro Asn Ile Leu Met Gly Met Gln
225 230 235 240

Thr Ser Val His Ile Ala Glu Leu Val Lys Ala Cys Tyr Pro Ser Pro
245 250 255

Glu Leu Val Ser Ala Val Gly Val His Val Asn Trp Leu Asn Glu Val
260 265 270

Leu Leu Arg Val Val Gln Lys Glu Ser Gln Leu Gln Gly Thr Glu Ala
275 280 285

Tyr Asn Glu Cys Leu Ala Leu Leu Gly Arg Ile Gln Cys Val Met Lys
290 295 300

Met Gly Pro Phe Val Ser Val Val Pro Gln Leu Gln Tyr Arg Met Tyr
305 310 315 320

Gly Ser Leu Ile Arg Gln Met Ala Gln Val Ala Gln Asn Tyr Asp Gln
325 330 335

Asp Phe Arg Gln Leu Lys Leu Phe Ile Ala Gln Asn Gln Ile Leu Gly
340 345 350

Ser Tyr Leu Leu Gln Gln Asn Lys Ala Phe Ala Asp Arg Glu Val Gln
355 360 365

Met Glu Ser Phe His Ser Ala Val Ile Ser Gln Arg Arg Gln Glu Leu
370 375 380

Asp Asp Ala Ile Ala Lys Met Asp Arg Leu Ser Leu Gln Met Glu Glu
385 390 395 400

Glu Asp Arg Ala Met Glu Gln Ala Arg Lys Glu Met Glu Glu Gly Leu

```
                405                 410                 415

Lys Gln Phe Gln Asn Glu Gln Val Ala Arg Ala Val Phe Ala Val Leu
            420                 425                 430

Lys Ser Val Ala Met Ile Ala Leu Ala Phe Val Thr Ala Gly Ala Thr
        435                 440                 445

Ala Pro Gly Ala Ala Ala Ser Ala Ala Gln Ala Val Asn Ile Ala Gly
    450                 455                 460

Gln Ala Ala Gln Ala Leu Arg Arg Val Val Glu Ile Leu Glu Gly Leu
465                 470                 475                 480

Glu Ala Val Met Glu Val Val Ala Ala Ile Lys His Leu Val Asp Ala
                485                 490                 495

Leu Asp Gln Val Ser Gln Ile Val Asp Ala Pro Pro Met Pro Asp Met
            500                 505                 510

Pro Ser Glu Ala Asp Trp Ser Ile Phe Val Asn Glu Ile Glu Ala Val
        515                 520                 525

Ala Glu Gly Met Pro Thr Glu Val Ser Glu Val Pro Ala Trp Lys Ala
    530                 535                 540

Lys Cys Lys Asn Val Ala Ala Leu Gly Arg Glu Met Cys Ile Thr Ala
545                 550                 555                 560

Glu Gln Ile Ser Gln Leu Gln Tyr Asp Ile Trp Val Gln Gly Leu Leu
                565                 570                 575

Arg Asp Ile Ala Gln Ser His Ala Asp Arg Leu Ala Ala Ile Gln Pro
            580                 585                 590

Ala Asn Leu Thr Asn Tyr Leu Glu Met Ala Ile Gln Met Asp Met Arg
        595                 600                 605

Thr Thr Arg Ile Leu Ile Gly Leu Leu Asn Ile Met Arg Ile Gln Asn
    610                 615                 620

Ala Ala Leu Met Tyr Glu Tyr Leu Leu Thr Pro Thr Gln Leu Thr Ala
625                 630                 635                 640

Trp Pro Leu Arg Met Asp Thr Val Ala Asn Leu Leu Ile Thr His Glu
                645                 650                 655

Ser Ala Ala Leu Ser Gly Leu Ala Gln Leu Gly Pro Pro Ser Asp Phe
            660                 665                 670

Thr Ser Arg His Val Val Lys Gly Ile Pro Val Ser Leu Leu Leu Asp
        675                 680                 685

Gly Gly Asp Trp Glu Phe Glu Ile Pro Val Gln Gly Gly Met Ser Ser
    690                 695                 700

Phe Pro Ser Ser Trp Thr Arg Val Arg Ile Arg His Leu Glu Met His
705                 710                 715                 720

Phe Val Gln Glu Ala Ser Gly Gly Gly Glu Ile Ile His Gln Pro Ala
                725                 730                 735

Thr Gln Thr Gly Thr Ile Tyr Ile Leu Leu Gln Gly Ser Thr Val Phe
            740                 745                 750

His Asp Arg Arg Arg Glu Glu Val Met Thr Phe Gln Ala Ala Val Pro
        755                 760                 765

Leu Asn Tyr His Tyr Ala Tyr Arg Leu Asp Thr Gly Glu Ala Thr Leu
    770                 775                 780

Thr Asn Glu Pro Ser Glu Gln Phe Ala Asn Thr Phe Met Gln Met Thr
785                 790                 795                 800

Pro Phe Thr His Trp Arg Leu Arg Leu Ser Ala Ser Ala Ala Glu Asn
                805                 810                 815

Lys Gly Leu Ala Phe Pro Thr Ala Thr Ala Pro Asp Ser Thr Thr Glu
            820                 825                 830
```

Ile Ala Ile Thr Phe His Val Thr Ala Ile Arg Gln Ile Asp Trp Arg
        835                 840                 845

Gln Glu Glu Glu
    850

<210> SEQ ID NO 65
<211> LENGTH: 2556
<212> TYPE: DNA
<213> ORGANISM: Adiantum trapeziforme

<400> SEQUENCE: 65
atggattaca gcacgcttta cagggatctg aaccagataa gcatgcccct ggatcgggta 60
gagttctcag aggtgatggt aatccacagg atgtacttga ggttatctga tctgaatgtg 120
ggggagctcc ccggagccga gagggtgaag cggttgtatg tgttggcaga cgtggtggag 180
ctcgcaacat ttgcgcatcc acagttgctt aatacgcgga tgccaggatc ggtgacggtg 240
atcattctgt gtcgtcttct tcagtttcca actgatgggt cgttcgctgc ttggctcgag 300
ctgccgttca tggagttgca cacactcata gaacaataca ggtcagagat aaaagcagca 360
gatgacgcga aatggggaac gtatgtacac gcggaggaag tacagctcag cccgctgttt 420
aatgggtggc cttatctggt tgttgaggca cagcgctgta ttataaccgc ggccatgcac 480
aatacattta accgccctgg gtgggttcgc tccattactc aatttacaac tgatcagtcc 540
ggtcgggtag ataccacact gctcgcacga acagaattcg gccatattga tctaccactc 600
gaaacagatt ccccaacggc attcagtgtt tcacaccgcc aaagtacgaa tttgcccgta 660
gagtacaccg gtattccagt ggaggtggtg accgatccta acatcttgat gggcatgcaa 720
accagcgtgc acattgcgga gctagtgaag gcatgttacc cgtcaccaga attagtgagc 780
gctgtagggg tgcacgtgaa ttggctcaac gaagtcttgc tccgagttgt ccagaaggaa 840
tctcagttgc aagggaccga ggcctacaac gagtgccttg cgcttttagg tcgcattcaa 900
tgtgtcatga agatggggcc gtttgtctcg gtagtgccgc agctgcaata cagaatgtat 960
ggtagcctca tcagacaaat ggcccaggta gcacagaact acgaccaaga tttcaggcag 1020
ctcaagttat tcattgccca aaaccaaatc cttggcagct atttgctgca gcagaacaag 1080
gcctttgctg acagagaggt gcagatggag agctttcatt cagcggtcat ttctcaaaga 1140
aggcaggagt tggacgacgc catcgctaag atggaccgac tgagcttgca gatggaggaa 1200
gaggacagag caatggagca agcccgaaaa gaaatggaag aaggattgaa gcagttccag 1260
aatgagcaag ttgcaagggc tgtgttcgct gttcttaaat ctgtagctat gattgcgctc 1320
gcattcgtca cggctggtgc aacggctcct ggggctgcag catctgcagc gcaagctgtg 1380
aacatagccg gtcaagcggc acaagctctg cgaagggtgg tggaaattct agaggggctc 1440
gaggctgtga tggaggttgt ggctgctata aagcaccttg tggatgctct ggaccaggta 1500
agtcagattg tggatgcacc acctatgcca gacatgccct cggaggcgga ctggagtatt 1560
tttgtgaatg agattgaagc cgtggcagag gggatgccga cggaagtctc ggaggttccg 1620
gcgtggaagg ccaagtgcaa gaatgtggct gcactgggta gggagatgtg catcacggca 1680
gaacagattt cccagctcca gtatgacatc tgggtgcaag gcttgttgcg ggatatagct 1740
caaagccacg cagaccggct ggcagcgatt caacctgcta atcttaccaa ctatttggag 1800
atggcaatac agatggatat gcggactacg aggatactga tagggctcct caacataatg 1860
cgcatccaga atgcggcact tatgtatgag taccttctaa cgcccacgca gctcactgca 1920

```
tggccgctga gaatggatac tgtggccaac ttgctcatca cgcacgagag tgctgcactg   1980

tcaggattag ctcagttagg gcccccatcg gacttcacga gcaggcatgt agtgaaaggc   2040

atacctgtga gcttgcttct agacggtggg gattgggaat ttgagattcc tgtgcaaggt   2100

ggcatgtcca gtttcccttc cagctggact cgagtgcgga ttcggcacct ggagatgcac   2160

tttgtgcagg aggcgagcgg tggcggcgag attatccacc agcctgccac ccagacgggg   2220

accatttaca tcctcctgca gggctccact gtcttccatg atcgcagaag ggaggaggtg   2280

atgacctttc aggcagcggt tccgctcaac taccattacg cgtaccgcct cgacactgga   2340

gaagccactc ttacgaacga gccctcggaa cagtttgcca acacattcat gcagatgaca   2400

ccgttcactc actggaggct acgtctgtct gcgtccgcag cggagaataa aggattagcc   2460

tttcccacag ctacagctcc cgactccacc actgagattg ccatcacttt ccatgttacg   2520

gccattagac aaattgactg gcggcaagag gaggag                             2556


<210> SEQ ID NO 66
<211> LENGTH: 877
<212> TYPE: PRT
<213> ORGANISM: Adiantum raddianum

<400> SEQUENCE: 66

Met Asp Val Asp Tyr Ala Ala Asp Ala Met Asp Val Asp Tyr Ala Glu
1               5                   10                  15

Ile Tyr Lys Glu Val Asn Gln Val Thr Arg Pro Val Pro Thr Arg Val
            20                  25                  30

Cys Ser Glu Val Met Ser Ile Gln Arg Met Tyr Phe Gln Leu Asp Asp
        35                  40                  45

Leu Asp Ala Lys Leu Leu Arg Asn Thr Glu Val Val Lys Arg Leu Tyr
    50                  55                  60

Val Phe Ala Asp Val Val Glu Met Val Gly Gln Ser Val Glu Leu Ala
65                  70                  75                  80

Ala Ser Val Glu Val Val Ile Leu Cys Arg Ile Phe Lys Thr Thr Arg
                85                  90                  95

Ser Asp Ala Val Leu Arg Phe Leu Ser Leu Thr Ser Arg Leu Glu Cys
            100                 105                 110

Asp Ala Thr Pro Val Tyr Ala Ser Ala Asn Val Val Ser His Phe Phe
        115                 120                 125

Val Arg Pro Arg Pro Gly Ala Ala Asp Pro Arg Leu Leu Ile Thr Ile
    130                 135                 140

His Ala Thr Gln Leu Val Ala Pro Ala Arg Thr Gln Leu Arg Val Gln
145                 150                 155                 160

Arg Pro Asn Val Val Leu His Arg Ala Gln Phe Trp Ala Leu Glu Glu
                165                 170                 175

Ile Phe Met Pro Gly Gly Val Ser Thr Gly Ala Thr Gln Pro Val Leu
            180                 185                 190

Arg Pro Ala Val Thr Gln Asp Gly Ala Met Glu Trp Arg Ile Ser Pro
        195                 200                 205

Tyr Val Ala Gly Gly Ala Leu Ala Ala Arg Ser Phe His Phe Thr His
    210                 215                 220

Pro His Val Tyr Arg Thr Ser Gln Asp Tyr Leu Gly Phe Thr Gly Ile
225                 230                 235                 240

Phe Ile Pro Glu Pro Ile Pro Tyr Asp Leu Leu Thr Asn Ser Asn Ile
                245                 250                 255

Trp Leu Gly Met Glu Cys Thr Thr Leu Ile Cys Glu Leu Ile Asp Lys
```

```
            260                 265                 270

Tyr Gln Arg Gln Ala Thr Gln Thr Val Glu Ala Ala His His His Val
        275                 280                 285

Ala Trp Leu Asp Lys Gln Leu Leu Ser Met Gly Asn Arg Ile Thr Ser
    290                 295                 300

Ser Asn Ile Pro Lys Lys Asn Val Gln Gln Ile Glu Thr Leu His Phe
305                 310                 315                 320

Arg Val Gln Ser Leu Leu Lys Ile Tyr Arg Arg Thr Ala Asn Gly Val
                325                 330                 335

Asp Ala Pro Leu Ile Val Pro Ser Leu Gln Tyr Asp Val Tyr Asp Arg
            340                 345                 350

Ile Ile Asn Leu Met Thr Arg Ala Ala Glu Ser Tyr Asp Asn Asp Phe
        355                 360                 365

Lys Gln Leu Asn Leu Phe Ile Gln Gln Asn Glu Ile Leu Gly Ser Phe
    370                 375                 380

Leu Leu Asp Gln Asn Arg Ala Phe Ala Gln Lys Glu Arg Asp Met Glu
385                 390                 395                 400

Asn His His Leu Gln Leu Val Thr Leu Gln Gly His Glu Leu Gln Ala
                405                 410                 415

Thr Gly Asp Lys Leu Gln Ala Leu Asn Arg Gln Leu Ala Glu Gln Ser
            420                 425                 430

Glu Ala Met Asp Gln Ala Lys Ala Asp Met Asp Ala Gly Ile Lys Glu
        435                 440                 445

Tyr Arg Asp Ala Met Ile Ala Asn Ala Ile Phe Ser Val Phe Lys Ala
    450                 455                 460

Ile Ala Ala Leu Cys Leu Ala Ala Ala Thr Gly Gly Ala Ala Ala Gly
465                 470                 475                 480

Ala Ala Ala Gly Ala Ala Val Asp Thr Ala Ala Gln Leu Ser Glu Leu
                485                 490                 495

Ala Arg Val Leu Gln Ser Val Val Lys Leu Leu Lys Arg Ile Glu Asn
            500                 505                 510

Val Val Lys Thr Ile Asn Ala Ile Thr Ala Phe Leu Thr Glu Leu Glu
        515                 520                 525

Ser Leu Asn Gln Leu Ile Glu Leu Pro Glu Met Pro Glu Met Pro Thr
    530                 535                 540

Asp Ala Asp Trp Ser Ile Phe Glu Asn Glu Ile Glu Ala Val Ala Glu
545                 550                 555                 560

Gly Met Pro Thr Glu Ile Ser Glu Val Pro Ala Trp Lys Ala Lys Cys
                565                 570                 575

Lys Asn Val Ala Ala Val Gly Arg Glu Ile Ile Thr Thr Val Ala His
            580                 585                 590

Val Glu Lys Leu Gln Tyr Glu Ile Ser Val Ser Lys Met Leu Gln Asp
        595                 600                 605

Ile Ala Gln Gln Gln Ala Glu Arg Leu Glu Gly Leu Arg Ile Glu Asp
    610                 615                 620

Leu Asp Asn Tyr Leu Glu Met Ala Thr Glu Leu Asp Met Arg Thr Asn
625                 630                 635                 640

Arg Ile Leu Met Gly Leu Leu Asp Met Leu Ser Leu Gln Thr Gly Ala
                645                 650                 655

Leu Ser Tyr His Tyr Leu Leu Arg Pro Arg Pro Phe Thr Gly Trp Val
            660                 665                 670

Arg Met Glu Thr Val Trp Arg Thr Leu Leu Gln Asn Glu Ser Asp Lys
        675                 680                 685
```

```
Leu Val Ala Ile Ala Ala Leu Gly Ala Pro Gln Glu Phe Ser Arg Ser
    690                 695                 700

Tyr Val Val Glu Asn Ile Pro Val Ser Leu Leu Lys Glu Gly Ala Asp
705                 710                 715                 720

Trp Ile Phe Asp Ile Pro Val His Asp Pro Val Phe Pro Ser Leu Trp
                725                 730                 735

Ser Ser Val Arg Ile Asp Tyr Val Glu Met Lys Phe Pro Pro Asp Thr
            740                 745                 750

Thr His Leu Pro Thr Thr Lys Gly Gly Lys Val Tyr Phe Leu Leu Gln
        755                 760                 765

Ala Ala Arg Phe Phe His Asp Arg Leu Gln Glu Asp Glu Val Leu His
    770                 775                 780

Tyr Gln Ala Ala Val Pro Leu Val Tyr Gln Tyr Ala Tyr His Val Glu
785                 790                 795                 800

Ser Gly Glu Thr Thr Leu Ser Asn Arg Pro Pro Gln Ala Ser Ser Ala
                805                 810                 815

Leu Tyr Met Arg Met Thr Pro Phe Thr Arg Trp Arg Leu Arg Leu Ser
            820                 825                 830

Ala Ser Ala Pro Glu Asn Glu Gly Leu Glu Phe Pro Thr Ala Thr Thr
        835                 840                 845

Glu Asp Ala Thr Thr Glu Ile Ala Ile Thr Phe Phe Val Thr Ala Arg
    850                 855                 860

Arg Arg Ile Ser Thr Arg Val Asp Ser Ser Ser Thr Thr
865                 870                 875


<210> SEQ ID NO 67
<211> LENGTH: 339
<212> TYPE: PRT
<213> ORGANISM: Asplenium australasicum

<400> SEQUENCE: 67

Met Ala Leu Val Ile Gly Gly Leu Ile Gly Gly Gln Gly Gly Tyr Ala
1               5                   10                  15

Phe Asn Tyr Tyr Gly Gly Thr Asp Gly Arg Val Met Gln Arg Ile Lys
            20                  25                  30

Val Trp Ala Ala Thr Ser Arg Ile Lys Ala Ile Ser Val Trp Leu Ser
        35                  40                  45

Asp Gly Val Glu Arg Thr Phe Gly Asp Pro Ser Arg Pro Ala Gly Glu
    50                  55                  60

Gly Asp Leu Arg Thr Ser Glu Phe Arg Phe Asn Ser Gly Glu Thr Val
65                  70                  75                  80

Thr Ser Leu Ser Leu Trp Gly Asn Gly Ala Gly Thr Arg Ser Gly Trp
                85                  90                  95

Ile Tyr Phe Arg Thr Ser Gln Asn Arg Thr Phe Asp Phe Gly Met Tyr
            100                 105                 110

Ser Trp Gly Lys Lys Thr Glu Tyr Pro Gln Ser Val Ala Ser Gly Ile
        115                 120                 125

Trp Val Gly Ile Arg Gly Arg Ala Ser Ser Asp Ile Asp Ala Leu Gly
    130                 135                 140

Val Val Phe Leu Gln Arg Ile Gln Ser Cys Arg Leu Thr Ser Val Gln
145                 150                 155                 160

Tyr Pro Thr Leu Gln Phe Ser Gly Ser Ser Gly Gly Thr Thr Ser Ile
                165                 170                 175

Val Arg Thr Thr Pro Thr Lys Ser Phe Asn Leu Gly Asn Thr Ala Asp
```

180 185 190

Gln Asp Asp Pro Ser Ser Thr Glu Gln Leu Ala Trp Gln Leu Ala Asp
195 200 205

Glu Pro Ser Phe Asp Asn Val Ser His Ser Trp Ser Leu Ser Asn Thr
210 215 220

Ser Thr Gly Leu Leu Gln Phe Ile Ala Thr Ser Thr Val Ser Val Gln
225 230 235 240

Ala Arg Thr Pro Ala Leu Ala Val Val Asn Asp Val Val Gly Trp Gln
245 250 255

Leu Ser Ala Ser Asp Thr Gln Ser Ser Ser Leu Ser Ser Ser Ser Ser
260 265 270

Leu Leu Leu Pro Trp Ser Arg Ser Gly Ser Leu Leu Pro Ser Lys Ser
275 280 285

Phe Ala Leu Ser Ala Leu Pro Tyr Arg Gly Asn Val Ser Gly Leu Ser
290 295 300

Phe Asn Gly Ser Ala Arg Val Thr Thr Ser Gly Gly Thr Phe Ser Phe
305 310 315 320

Ser Gly Leu Gln Gly Arg Phe Thr Gly Gln Ser Tyr Ala Ile Asp Ile
325 330 335

Thr Thr Gln

<210> SEQ ID NO 68
<211> LENGTH: 356
<212> TYPE: PRT
<213> ORGANISM: Asplenium x kenzoi Sa. Kurata

<400> SEQUENCE: 68

Met Ser Ser Leu Ile Asn Pro His Leu Glu Thr Ile Arg Tyr Gly Gly
1 5 10 15

Ser Phe Ala Gly Gly Ser Pro Phe Arg Ile Leu Gly Glu Thr Glu Gly
20 25 30

Arg Val Leu Gln Arg Ile Arg Ile Ser Arg Met Ala Asn Ala Ile Asp
35 40 45

Ala Ile Glu Phe Trp Leu Thr Gly Asp Ser Thr Pro Arg Val Tyr Gly
50 55 60

Thr Val Arg Ser Glu Asn Ser Ser Phe Asp Phe Ser Glu Gly Glu Arg
65 70 75 80

Ile Thr Gly Leu Arg Phe Arg Asn Ala Leu Phe Gly Ile Gly Gln Asn
85 90 95

Gln Trp Asn His Val Ala Arg Val Trp Phe Ser Thr Ser Arg Gly Arg
100 105 110

Thr Phe Glu Tyr Gly Ser Thr Arg Glu Pro Thr Gly Gln Trp Phe Glu
115 120 125

Val Asn Val Gly Ser Gly Val Cys Val Gly Val Ala Gly Asn Val Met
130 135 140

Leu Asn Ser Leu Asn Met Leu Gly Phe Val Phe Leu Arg Ser Ile Gln
145 150 155 160

Ser Val Gly Phe Ser Ser Val Glu Tyr Pro Met Phe Ser Thr Ser Ile
165 170 175

Thr Arg Thr Ser Ile Leu Glu Gln Leu Pro Asp Thr Phe Lys Ser Asn
180 185 190

Asp Asp Asp Glu Pro Leu Gln Met Val Leu Ala Gly Ser Arg Gln Phe
195 200 205

Lys Thr Ser Ser Thr Trp Arg Val Ser Ser Pro Thr Val Gly Leu Leu

```
    210                 215                 220

Ser His Leu Thr Gly Asn Asn Ile Leu Val Asp Val Thr Leu Gly Ile
225                 230                 235                 240

Asn Thr Pro Thr Val Val Pro Thr Gly Leu Ala Gly Ala Ser Thr Thr
                245                 250                 255

Phe Gln Trp Glu Thr Val Arg Ala Phe Pro Ser Thr Asn Ala Ile Gln
            260                 265                 270

Gly Ser Ile Ser Asn Leu Thr Val Ser Thr Asp Glu Tyr Ser Val Trp
        275                 280                 285

Cys His Ile Ser Asp Thr Val Ala Pro Ala Gln Ser Leu Pro Lys His
    290                 295                 300

Ala Ala Trp Val Gly Glu Gly Arg Ile Thr Ala Leu Pro Cys Ser Ala
305                 310                 315                 320

Asn Ile Gln Val Phe Thr Ser Gly Gly Asn Asn Phe Pro Phe Gly Thr
                325                 330                 335

Phe Ser Phe Pro Val Arg Leu Leu Tyr Asp Gly Gly Ala His Ser Asn
            340                 345                 350

Val Gln Val Leu
        355


<210> SEQ ID NO 69
<211> LENGTH: 340
<212> TYPE: PRT
<213> ORGANISM: Polypodium musifolium

<400> SEQUENCE: 69

Met Ala Leu Val Ile Ser Cys Pro Val Gly Gly Gln Gly Gly Ser Phe
1               5                   10                  15

Phe Asn Tyr Tyr Gly Gly Thr Asp Gly Arg Val Met Gln Arg Ile Lys
            20                  25                  30

Val Trp Ala Ala Ala Ser Arg Ile Lys Ala Ile Ser Val Trp Leu Ser
        35                  40                  45

Asp Gly Val Gln Lys Thr Phe Gly Asp Pro Ser Arg Pro Ala Gly Glu
    50                  55                  60

Gly Asp Leu Arg Thr Ser Glu Phe Ser Phe Asn Thr Gly Glu Thr Val
65                  70                  75                  80

Thr Gln Leu Ser Leu Trp Gly Asn Gly Ala Gly Thr Arg Ser Gly Trp
                85                  90                  95

Ile Tyr Phe Arg Thr Asn Gln Asn Arg Thr Phe Asp Phe Gly Met Tyr
            100                 105                 110

Ser Trp Gly Lys Lys Thr Glu Tyr Pro Gln Asp Val Ser Ser Gly Ile
        115                 120                 125

Trp Val Gly Ile Thr Gly Arg Ala Lys Ser Asp Val Asp Ala Leu Gly
    130                 135                 140

Val Val Phe Leu Gln Pro Ile Leu Ser Cys Arg Leu Ile Ser Val Asp
145                 150                 155                 160

Tyr Pro Thr Leu Gln Phe Ser Gly Thr Ser Gly Gly Thr Thr Ser Ile
                165                 170                 175

Asn Leu Thr Thr Ala Gly Lys Thr Phe Asn Leu Gln Asn Ala Ala His
            180                 185                 190

Gln Glu Asp Pro Ser Ser Thr Glu Lys Leu Ala Trp Glu Leu Ala Asp
        195                 200                 205

Glu Pro Ser Phe Asp Asn Val Ser His Thr Trp Ser Leu Ser Asn Ile
    210                 215                 220
```

Ser Thr Arg Leu Leu Gln Phe Ile Ser Thr Ser Thr Ile Ser Val Gln
225 230 235 240

Ala Arg Thr Pro Ala Leu Ala Val Val Asn Asn Ile Val Val Gly Trp
245 250 255

Gln Leu Ser Ala Ser Asp Thr Glu Ser Ser Ser Leu Ser Ser Ser Ser
260 265 270

Ser Leu Leu Leu Pro Trp Ser Arg Asn Gly Ser Leu Leu Pro Ser Glu
275 280 285

Ser Leu Thr Leu Ser Ala Leu Pro Phe Gly Gly Thr Val Ser Gly Leu
290 295 300

Pro Phe Asp Gly Ser Ala Arg Val Thr Thr Thr Gly Gly Thr Phe Ser
305 310 315 320

Phe Ser Gly Leu His Gly Phe Tyr Thr Gly Gln Ser His Val Ile Ala
325 330 335

Ile Thr Thr Gln
340

<210> SEQ ID NO 70
<211> LENGTH: 354
<212> TYPE: PRT
<213> ORGANISM: Polypodium musifolium

<400> SEQUENCE: 70

Met Ala Leu Tyr Gln Thr Pro Val Tyr Val Ile Gly Gly Gln Gly Gly
1 5 10 15

Ser Ser Phe Thr Tyr Asp Gln Ser Arg Asn Gly Lys Val Leu Arg Lys
20 25 30

Ile Gly Val Trp Ala Gly Glu Trp Gln Leu Arg Gly Ile Arg Val Trp
35 40 45

Met Ser Gly Ser Asp Ser Pro Ala Thr Phe Gly Ser Ala Ser Gly Ser
50 55 60

Tyr Ser Glu Tyr Thr Phe Ala Asp Gly Glu Arg Ile Thr Arg Leu Ser
65 70 75 80

Leu Trp Gly Asn Gly Ala Gly Thr Arg Ser Gly Ala Ile Arg Phe Tyr
85 90 95

Thr Thr Thr Gly Gly Ser Phe Phe Pro Lys Met Thr Ser Trp Gly Leu
100 105 110

Lys Thr Glu Tyr Pro Met Asp Val Ala Ser Gly Leu Cys Val Gly Ile
115 120 125

Leu Gly Arg Ala Asn Val Asp Val Asp Ser Leu Gly Phe Leu Phe Leu
130 135 140

Arg Thr Ile Ala Ser Ala Arg Met Ile Asn Val Ser Tyr Pro Thr Leu
145 150 155 160

Gly Leu Glu Gln Ala Gly Ile Ile Pro Ile Thr Leu Asp Ser Tyr Asn
165 170 175

Asp Ser Asn Asn Ala Gly Ala Ile Ser Lys Asn Trp Thr Phe Ser Gly
180 185 190

Ser Arg Thr Val Thr Ile Ser Ser Ser Trp Thr Leu Thr Thr Gly Ile
195 200 205

Glu Ala His Ala Ser Val Thr Val Gln Ala Gly Ile Pro Ser Val Ala
210 215 220

Glu Val Ser Gly Glu Phe Gly Trp Ser Val Ser Val Thr Gly Ser Tyr
225 230 235 240

Thr Ser Thr Gln Glu Glu Ser Arg Thr Leu Thr Trp Asn Gln Ser Gly
245 250 255

Thr Leu Glu Pro Gly Gln Trp Ile Ser Ile Gln Ala Thr Thr Arg Arg
260 265 270

Gly Thr Ile Thr Leu Pro Tyr Gln Gly Thr Met Glu Ile Thr Leu Gln
275 280 285

Ser Gly Thr Val Phe Arg Tyr Pro Ile Ser Ser Met Tyr Ser Gly Val
290 295 300

Asp Tyr Thr Ser Val Asp Ile Thr Asn Thr Gly Thr Arg Ala Leu Lys
305 310 315 320

Asn Glu Val Glu Val Glu Ala Val Asp Gln Gln Ser Gln Glu Gly Asp
325 330 335

His Asn Val Gln Pro Asn Lys Glu Val Gln Glu Ser Lys Val Leu Phe
340 345 350

Ile Glu

<210> SEQ ID NO 71
<211> LENGTH: 339
<212> TYPE: PRT
<213> ORGANISM: Polypodium punctatum ‘Serratum’

<400> SEQUENCE: 71

Met Ala Leu Val Ile Gly Trp Pro Val Gly Gly Gln Gly Gly Ser Phe
1 5 10 15

Phe Asn Tyr Tyr Gly Gly Thr Asp Gly Arg Val Met Gln Arg Ile Lys
20 25 30

Val Trp Ala Ala Thr Ser Arg Ile Lys Ala Ile Ser Val Trp Leu Ser
35 40 45

Asp Gly Val Gln Lys Thr Phe Gly Asp Pro Ser Arg Pro Ser Gly Glu
50 55 60

Gly Asp Leu Glu Thr Ser Glu Phe Ser Phe Lys Thr Gly Glu Thr Val
65 70 75 80

Thr Gln Leu Ser Leu Trp Gly Asn Gly Ala Gly Thr Arg Ser Gly Trp
85 90 95

Leu Tyr Phe Arg Thr Ser His Asn Arg Thr Phe Asp Phe Gly Met Tyr
100 105 110

Ser Trp Gly Lys Lys Thr Glu Tyr Pro Gln Asn Val Ala Ser Gly Ile
115 120 125

Trp Val Gly Ile Thr Gly Arg Ala Ser Ser Asp Leu Asp Gly Leu Gly
130 135 140

Val Val Phe Leu Arg Ser Ile Gln Ser Cys Arg Leu Ile Asn Val Gln
145 150 155 160

Tyr Pro Thr Leu Gln Phe Ser Gly Thr Ala Gly Gly Thr Thr Ser Ile
165 170 175

Thr Arg Thr Thr Ala Ala Lys Thr Phe Asn Leu Gln Asn Thr Ala Asn
180 185 190

Gln Asp Asp Pro Ser Ser Thr Glu Gln Leu Ala Trp Gln Leu Ala Asp
195 200 205

Glu Pro Ser Phe Asp Asn Val Ser His Thr Trp Ser Leu Ser Asn Thr
210 215 220

Ser Thr Gly Leu Leu Gln Phe Ile Ser Thr Ser Thr Ile Ser Val Gln
225 230 235 240

Ala Arg Thr Pro Ala Leu Thr Ile Val Asn Asp Val Val Gly Trp Leu
245 250 255

Pro Ser Asp Ser Asp Thr Gln Ser Ser Ser Leu Ser Ser Ser Ser Ser
260 265 270

Leu Leu Leu Pro Trp Ser Arg Asn Gly Ser Leu Leu Pro Ser Glu Ser
        275                 280                 285

Leu Thr Leu Ser Ala Leu Pro Tyr Asp Gly Ile Val Asn Gly Leu Pro
    290                 295                 300

Phe Thr Gly Ser Ala Arg Val Thr Thr Ser His Gly Thr Phe Ser Phe
305                 310                 315                 320

Ser Gly Leu Lys Gly Ala Phe Thr Gly Glu Ser His Val Ile Ala Val
                325                 330                 335

Thr Ala Gln

<210> SEQ ID NO 72
<211> LENGTH: 354
<212> TYPE: PRT
<213> ORGANISM: Polypodium punctatum 'Serratum'

<400> SEQUENCE: 72

Met Ala Leu Tyr Gln Thr Pro Val Tyr Val Ile Gly Gly Gln Gly Gly
1               5                   10                  15

Ser Ser Phe Thr Tyr Asp Gln Ser Arg Asn Gly Arg Val Leu Thr Lys
            20                  25                  30

Ile Gly Val Trp Ala Gly Glu Trp Gln Leu Arg Gly Ile Arg Val Trp
        35                  40                  45

Met Ser Gly Ser Asp Thr Pro Ala Thr Phe Gly Ser Ala Ser Gly Ser
    50                  55                  60

Tyr Ser Glu Tyr Thr Phe Ala Asp Gly Glu Arg Ile Thr Arg Leu Ser
65                  70                  75                  80

Leu Trp Gly Asn Gly Ala Gly Thr Arg Ser Gly Ala Ile Arg Phe Tyr
                85                  90                  95

Thr Thr Thr Gly Gly Ser Phe Phe Pro Lys Met Thr Ser Trp Gly Leu
            100                 105                 110

Gln Thr Glu Tyr Pro Ile Asp Val Ala Ser Gly Leu Cys Val Gly Ile
        115                 120                 125

Leu Gly Arg Ala Asn Val Asp Val Asp Ser Leu Gly Phe Leu Phe Leu
    130                 135                 140

Arg Thr Ile Ala Ser Ala Arg Met Ile Asn Val Ser Tyr Pro Thr Leu
145                 150                 155                 160

Gly Leu Glu Gln Ala Gly Ile Ile Pro Ile Thr Leu Asp Ser Tyr Asn
                165                 170                 175

Asp Ser Asn Asn Ala Gly Ala Ile Ser Lys Asn Trp Thr Phe Ser Gly
            180                 185                 190

Ser Arg Thr Val Thr Ile Ser Ser Ser Trp Thr Leu Thr Thr Gly Ile
        195                 200                 205

Glu Ala His Ala Ser Val Thr Val Gln Ala Gly Ile Pro Ser Val Ala
    210                 215                 220

Glu Val Ser Gly Glu Phe Gly Trp Ser Val Ser Val Thr Gly Ser Tyr
225                 230                 235                 240

Thr Ser Thr Gln Glu Glu Ser Arg Thr Leu Thr Trp Asn Gln Ser Gly
                245                 250                 255

Thr Leu Glu Pro Gly Gln Trp Ile Ser Ile Gln Ala Thr Thr Arg Arg
            260                 265                 270

Gly Thr Ile Thr Leu Pro Tyr Gln Gly Thr Met Glu Ile Thr Leu Gln
        275                 280                 285

Ser Gly Thr Val Phe Arg Tyr Pro Ile Ser Ser Met Tyr Ser Gly Val
    290                 295                 300

```
Asp Tyr Thr Ser Val Asp Ile Thr Asn Thr Gly Thr Arg Ala Leu Lys
305                 310                 315                 320

Asn Glu Val Glu Val Glu Ala Val Asp Gln Gln Ser Gln Glu Gly Asp
                325                 330                 335

His Asn Val Gln Pro Asn Lys Glu Val Gln Glu Ser Lys Leu Leu Phe
            340                 345                 350

Ile Glu


<210> SEQ ID NO 73
<211> LENGTH: 358
<212> TYPE: PRT
<213> ORGANISM: Polypodium punctatum 'Serratum'

<400> SEQUENCE: 73

Met Ser Ser Leu Ile Asn Pro His Leu Glu Ser Ile Thr Tyr Ala Gly
1               5                   10                  15

Ser Phe Ala Gly Gly Ser Pro Phe Arg Ile Leu Gly Glu Thr Gln Gly
            20                  25                  30

Arg Val Leu Gln Arg Ile Arg Val Ser Arg Ile Ala Thr Arg Ile Glu
        35                  40                  45

Ala Ile Glu Phe Trp Leu Thr Gly Asp Ser Thr Pro Arg Val Tyr Gly
    50                  55                  60

Thr Val Arg Ser Glu Asn Ser Ser Tyr Asp Phe Ala Glu Gly Glu Arg
65                  70                  75                  80

Ile Thr Arg Leu Arg Phe Arg Thr Ser Arg Phe Gly Phe Gly Val Gln
                85                  90                  95

Thr Gln Trp Asp His Val Ala Arg Val Trp Phe Ser Thr Ser Arg Gly
            100                 105                 110

Arg Thr Phe Glu Tyr Gly Ser Thr Arg Glu Pro Ser Gly Gln Trp Phe
        115                 120                 125

Glu Ala Asn Val Gly Ser Gly Val Cys Val Gly Val Ala Gly Asn Val
    130                 135                 140

Met Leu Asp Ser Leu Asn Met Leu Gly Phe Val Phe Leu Arg Ser Ile
145                 150                 155                 160

Gln Arg Val Gly Phe Thr Ser Val Glu Tyr Pro Thr Ile Ser Ser Ser
                165                 170                 175

Ile Ala Arg Thr Phe Ile Leu Ser His Leu Pro Asp Thr Phe Lys Ser
            180                 185                 190

Asn Asp Asp Asp Glu Pro Leu Gln Met Val Leu Ala Gly Ser Arg Gln
        195                 200                 205

Phe Lys Thr Thr Ser Thr Trp Arg Ala Gln Ser Pro Ala Val Gly Leu
    210                 215                 220

Leu Ser His Leu Thr Ala Asn Asn Ile Thr Leu Asp Leu Thr Leu Gly
225                 230                 235                 240

Ile Asn Thr Pro Thr Val Val Pro Thr Gly Thr Ala Gly Ala Ser Thr
                245                 250                 255

Ala Phe Gln Trp Gln Thr Val Arg Thr Phe Pro Ser Ile Asn Ala Glu
            260                 265                 270

Ile Gln Gly Thr Ile Ala Asn Leu Thr Val Ser Thr Ala Glu Tyr Ser
        275                 280                 285

Val Trp Cys His Ile Ser Asp Thr Val Ala Pro Ala Gln Ser Ile Pro
    290                 295                 300

Lys His Ser Ala Trp Val Gly Glu Gly Arg Ile Thr Ala Leu Pro Cys
305                 310                 315                 320
```

Ser Ala Asn Ile Gln Val Ile Thr Ser Gly Gly Asn Asn Leu Pro Phe
325 330 335

Ala Ser Phe Ser Phe Pro Val Arg Leu Phe Tyr Asp Gly Gly Ala His
340 345 350

Ser Thr Val Gln Val Leu
355

<210> SEQ ID NO 74
<211> LENGTH: 341
<212> TYPE: PRT
<213> ORGANISM: Adiantum pedatum

<400> SEQUENCE: 74

Met Ala Leu Val Ile Gly Gly Leu Ile Gly Gly Gly Gly Gly Ser Tyr
1 5 10 15

Phe Ser Tyr Tyr Gly Gly Thr Asp Gly Arg Val Met Gln Arg Ile Arg
20 25 30

Val Trp Ala Ala Thr Ser Arg Ile Lys Ala Ile Ser Val Trp Leu Ser
35 40 45

Asp Gly Val Gln Arg Thr Phe Gly Asp Pro Ser Arg Pro Ala Gly Glu
50 55 60

Gly Asn Leu Arg Ser Ala Glu Phe Ser Phe Asn Thr Gly Glu Arg Val
65 70 75 80

Thr Arg Leu Ser Leu Trp Gly Asn Gly Ile Gly Thr Arg Ser Gly Trp
85 90 95

Ile Tyr Phe Glu Thr Asn Gln Gly Arg Arg Phe Asp Phe Gly Met Tyr
100 105 110

Ser Trp Gly Lys Gln Thr Glu Phe Pro Gln Thr Val Ala Ser Gly Ile
115 120 125

Trp Val Gly Phe Thr Gly Arg Ala Ser Leu Asp Val Asp Ala Leu Gly
130 135 140

Val Val Phe Leu Arg Pro Ile Gln Ser Cys Gln Leu Met Asn Val Gln
145 150 155 160

Tyr Pro Thr Leu Gln Phe Ser Gly Ser Ser Gly Ala Thr Ser Ile Thr
165 170 175

Pro Thr Ala Ser Ser Thr Lys Ser Phe Thr Leu Leu Asn Thr Ala Asp
180 185 190

His Glu Asp Gln Ser Ser Thr Gln Gln Leu Ala Trp Glu Leu Ala Asp
195 200 205

Glu Pro Arg Phe Asp Asn Val Phe Leu Ser Trp Ile Leu Ser Asn Pro
210 215 220

Ser Ala Gly Leu Leu Gln Phe Ile Thr Thr Ser Ser Ile Ser Val Gln
225 230 235 240

Ala Arg Ile Pro Ala Leu Ala Val Val Asn Asn Val Val Gly Trp Gln
245 250 255

Leu Ser Ala Ser Asp Thr Gln Ser Ser Ser Leu Ser Ser Ser Ser Ser
260 265 270

Leu Ser Leu Pro Trp Ser Arg Ser Gly Ser Leu Leu Pro Ser Gln Ser
275 280 285

Leu Thr Thr Leu Ser Ala Leu Thr Tyr Arg Gly Asp Ala Arg Asn Leu
290 295 300

Phe Phe Asn Gly Ser Ala Gln Val Thr Thr Thr Thr Gly Ser Arg Phe
305 310 315 320

Ser Phe Pro Gly Leu Gln Gly Leu Phe Thr Gly Gln Ser Tyr Val Pro

```
                325                 330                 335

Ala Ile Thr Ser Gln
            340


<210> SEQ ID NO 75
<211> LENGTH: 354
<212> TYPE: PRT
<213> ORGANISM: Platycerium bifurcatum

<400> SEQUENCE: 75

Met Ser Leu Val Gln Thr Pro Val Tyr Val Ile Gly Gly Gln Gly Gly
1               5                   10                  15

Asn Ala Phe Ser Tyr Asp Gln Ser Arg Asn Gly Arg Ile Leu Arg Arg
            20                  25                  30

Ile Gly Val Trp Ala Gly Glu Trp Gln Leu Arg Gly Ile Arg Val Trp
        35                  40                  45

Met Thr Gly Thr Asp Thr Pro Ala Thr Phe Gly Thr Ala Thr Gly Ser
    50                  55                  60

Tyr Ser Glu Tyr Thr Phe Thr Asp Gly Glu Arg Ile Thr Arg Leu Ser
65                  70                  75                  80

Leu Trp Gly Asn Gly Ala Gly Thr Arg Ser Gly Gly Ile Arg Phe Tyr
                85                  90                  95

Thr Thr Thr Gly Gly Ser Phe Phe His Lys Met Thr Ser Trp Gly Leu
            100                 105                 110

Gln Thr Glu Tyr Pro Ile Asp Val Ala Ser Gly Leu Cys Val Gly Ile
        115                 120                 125

Thr Gly Arg Ala Asn Val Asp Val Asp Ser Leu Gly Val Leu Phe Leu
    130                 135                 140

Arg Thr Ile Ala Pro Ala Arg Met Ile Asn Val Ser Tyr Pro Thr Leu
145                 150                 155                 160

Gly Leu Glu Gln Ala Gly Ile Ile Pro Val Thr Leu Asp Ser Tyr Asn
                165                 170                 175

Asp Ser Asn Asn Ala Gly Thr Ile Ser Lys Asn Trp Thr Phe Ser Gly
            180                 185                 190

Ser Arg Thr Val Thr Ile Ser Ser Ser Trp Ser Leu Thr Ser Gly Ile
        195                 200                 205

Glu Thr His Ala Ser Val Ser Val Gln Ala Gly Ile Pro Met Val Ala
    210                 215                 220

Glu Val Ser Gly Glu Phe Gly Trp Ser Val Ser Val Ser Gly Thr Tyr
225                 230                 235                 240

Ala Thr Thr Gln Glu Glu Ser Arg Thr Leu Thr Trp Asn Gln Ser Gly
                245                 250                 255

Thr Leu Glu Pro Gly Gln Trp Ile Ser Leu Gln Ala Thr Thr Arg Arg
            260                 265                 270

Gly Thr Ile Thr Leu Pro Phe Gln Ala Thr Met Glu Ile Thr Leu Leu
        275                 280                 285

Ser Gly Thr Ile Phe Gln Tyr Ala Ile Ser Ser Met Tyr Ser Gly Val
    290                 295                 300

Asp Tyr Thr Ser Val Asp Ile Thr Asn Thr Gly Thr Arg Ala Ser Asp
305                 310                 315                 320

His Val Glu Val Glu Ala Thr Glu Gln Gln Val Gln Gly Val Lys Asp
                325                 330                 335

Gln Ser Val Gln Pro Asn Lys Glu Ala Lys Glu Cys Thr Leu Leu Phe
            340                 345                 350
```

-continued

Ala Glu

<210> SEQ ID NO 76
<211> LENGTH: 355
<212> TYPE: PRT
<213> ORGANISM: Platycerium bifurcatum

<400> SEQUENCE: 76

Met Ser Leu Leu Thr Pro His Leu Leu Thr Ala Ser Ala Gly Gly Phe
1 5 10 15

Ile Gly Gly Asp Ile Phe Arg His Ser Gly Glu Thr Asp Gly Arg Val
20 25 30

Leu His Arg Ile Arg Leu Ser Arg Glu Val Ala Arg Ile Ser Ala Val
35 40 45

Glu Phe Trp Leu Thr Gly Asn Ser Thr Pro Tyr Val Tyr Gly Thr Pro
50 55 60

Arg Ala Asp Asn Ser Ser Tyr Glu Phe Val Asp Gly Glu Arg Ile Thr
65 70 75 80

Arg Leu Asp Phe Arg Thr His Leu Phe Gly Val Val Thr Ile Gln Trp
85 90 95

Asp Asn Ile Ala Arg Val Arg Phe Ser Thr Ser Arg Gly Arg Ile Phe
100 105 110

Glu Phe Gly Ser Ser Arg Glu Pro Ser Gly Gln Trp Phe Thr Ala Asn
115 120 125

Val Gly Ser Gly Val Cys Val Gly Met Ser Gly Val Glu Ala Asn Gly
130 135 140

Ala Leu Thr Arg Leu Gly Phe Met Phe Leu Arg Ser Ile Gln Ser Val
145 150 155 160

Gly Phe Ser Ser Val Glu Tyr Pro Thr Leu Ser Thr Ser Thr Ile Leu
165 170 175

Thr Thr Pro Ile Leu Glu Gln Leu Pro Asp Thr Phe Lys Ser Asn Asp
180 185 190

Asp Asp Glu Pro Leu His Val Val Leu Ala Gly Ser Arg Gln Leu Glu
195 200 205

Thr Thr Ser Thr Trp Thr Ser Pro Ala Val Gly Leu Leu Ser His Leu
210 215 220

Thr Gly Asn Asp Ile Thr Val Asn Val Ser Leu Gly Ile Asn Thr Pro
225 230 235 240

Thr Val Val Pro Ser Gly Pro Glu Gly Ala Ser Thr Thr Phe His Trp
245 250 255

Gln Thr Val Arg Thr Phe Pro Ser Ser Asn Ala Met Glu Gly Ser Ile
260 265 270

Ala Asn Leu Thr Val Thr Thr Asn Glu Tyr Ser Val Trp Cys His Ile
275 280 285

Ser Asp Thr Ile Ala Pro Ala Gln Leu Leu Pro Lys His Val Ala Leu
290 295 300

Val Gly Glu Gly Arg Ile Thr Ala Leu Pro Cys Ser Ala Arg Ile Gln
305 310 315 320

Val Leu Thr Ser Ser Ala Tyr Asp Leu Pro Phe Ala Thr Phe Ser Phe
325 330 335

Pro Val Gln Ser Leu Tyr Asn Gly Arg Ala His Ser Gln Val Gln Ile
340 345 350

Ile Asp Pro
355

<210> SEQ ID NO 77
<211> LENGTH: 360
<212> TYPE: PRT
<213> ORGANISM: Nephrolepis falcate

<400> SEQUENCE: 77

```
Met Ala Asn Leu Leu Thr Pro Leu Tyr Met Gln Pro Val Gln Leu Ala
1               5                   10                  15

Gly Ser Val Asn Thr Ser Leu Gly Leu Trp Arg Val Ser Ser Glu Thr
            20                  25                  30

Glu Gly Lys Val Leu Lys Arg Ile Arg Val Tyr Arg Leu Thr Arg Ser
        35                  40                  45

Ile Pro Ala Ile Glu Val Trp Leu Thr Gly Asp Ser Asn Pro His Val
    50                  55                  60

Cys Gly Thr Pro Gly Arg Ala Glu Ser Ser Thr Phe Glu Phe Ser Glu
65                  70                  75                  80

Gly Glu Arg Ile Thr Thr Leu Val Leu Gln Asp Ala Gln Asn Ile Pro
                85                  90                  95

Thr His Val Gly Arg Ile Arg Phe Gln Thr Ser Leu Leu Arg Thr Phe
            100                 105                 110

Glu Tyr Gly Met Ser Val Gln Pro Thr Gly Lys Val Thr Thr Val Asn
        115                 120                 125

Val Gly Ser Gly Val Cys Val Gly Val Arg Ala Ser His Ser Ser Thr
    130                 135                 140

Tyr Gly Ile Ser Val Phe Gly Phe Met Phe Leu Arg Pro Ile Gln Ser
145                 150                 155                 160

Val Arg Leu His Gly Leu Val Tyr Pro Thr Ile Ser Ser Thr Ser Thr
                165                 170                 175

Ile Thr Thr Thr Ile Leu Gln Glu Leu Pro Ala Thr Ile Lys Asn Asp
            180                 185                 190

Asn Asp His Glu Pro Leu His Trp Val Leu Ala Gly Ser Arg Gln Cys
        195                 200                 205

Ile Thr Ser Ser Thr Trp Arg Thr Gln Pro Ala Asp Arg Glu Gly Leu
    210                 215                 220

Val Ser His Leu Val Gly Arg Ala Ile Ser Ile Asn Ile Asp Leu Gly
225                 230                 235                 240

Ile Asp Thr Pro Lys Ile Val Ala Thr Gly Gly Thr Ala Gly Ala Ser
                245                 250                 255

Thr Asn Phe Gly Trp Glu Thr Ala Arg Thr Phe Pro Ser Thr Asn Ala
            260                 265                 270

Val Glu Gly Ser Ile Ala Asp Leu Thr Val Arg Thr Asn Glu Tyr Ser
        275                 280                 285

Val Trp Gly His Val Ser Asp Thr Leu Ala Pro Ala Gln Ser Leu Ile
    290                 295                 300

Ser Arg Arg Ala Val Leu Ile Gly Glu Gly Ser Ile Asp Asn Leu Gln
305                 310                 315                 320

Cys Ser Ala Arg Ile Gln Val Phe Thr Asp Ala Asp Gly Gly Leu Pro
                325                 330                 335

Phe Ala Thr Phe Thr Phe Pro Val Gly Val Leu Tyr Ser Ala Arg Ala
            340                 345                 350

His Ser Asp Val Gln Val Leu Ser
        355                 360
```

<210> SEQ ID NO 78

<211> LENGTH: 356
<212> TYPE: PRT
<213> ORGANISM: Nephrolepis falcate

<400> SEQUENCE: 78

```
Met Thr Ser Leu Leu Thr Pro Pro Tyr Met Gln Pro Ile Gln Ser Ala
1               5                   10                  15

Gly Gly Leu Phe Ser Ser Phe Ile Val Ser Gly Glu Thr Glu Gly Lys
            20                  25                  30

Val Leu Gln Arg Ile Arg Val Tyr Arg Phe Ser Arg Asn Ile Ala Ala
        35                  40                  45

Ile Glu Val Trp Leu Thr Gly Asp Ser Asn Pro His Leu Cys Gly Thr
    50                  55                  60

Pro Gly Arg Ala Glu Ser Ser Thr Phe Glu Phe Ser Glu Gly Glu Arg
65                  70                  75                  80

Ile Thr Thr Leu Glu Leu Gln Glu Asp Pro Gln Leu Pro Tyr Thr Val
                85                  90                  95

Val Gly Arg Ile Arg Phe Gln Thr Ser Arg Leu Arg Thr Phe Glu Tyr
            100                 105                 110

Gly Met Ser Val Gln Pro Ser Gly Arg Val Ile Thr Val Asn Val Gly
        115                 120                 125

Ser Gly Val Cys Val Gly Val Arg Ala Gly Thr Ala Leu Ser Val Ile
    130                 135                 140

Ser Ile Leu Gly Phe Met Phe Leu Arg Pro Ile Arg Ser Val Arg Leu
145                 150                 155                 160

His Gly Leu Val Tyr Pro Thr Ile Ser Ser Ile Ser Thr Ile Thr Thr
                165                 170                 175

Thr Ile Leu Gln Glu Leu Pro Ala Thr Leu Lys Asn Asp Asp Asp His
            180                 185                 190

Glu Pro Leu His Trp Val Leu Ala Gly Ser Arg Gln Cys Phe Thr Ser
        195                 200                 205

Ser Thr Trp Arg Thr Gln Leu Ala Tyr Arg Ala Gly Leu Val Ser His
    210                 215                 220

Leu Val Gly Ser Ala Ile Ser Ile Asn Met Asp Leu Gly Ile Asp Ala
225                 230                 235                 240

Pro Lys Ile Val Ala Thr Gly Gly Thr Ala Gly Ala Ser Thr Asn Phe
                245                 250                 255

Gly Trp Glu Thr Ala Arg Thr Phe Pro Ser Thr Asn Ala Ile Gln Gly
            260                 265                 270

Ser Ile Ala Asp Leu Ile Val Ser Thr Asn Ala Tyr Ser Val Trp Gly
        275                 280                 285

His Val Ser Asp Thr Leu Ala Pro Ala Gln Ser Leu Ile Ser Arg Arg
    290                 295                 300

Ala Ala Leu Ile Gly Glu Gly Arg Ile Asp Asn Leu Gln Cys Ser Ala
305                 310                 315                 320

Arg Ile Gln Val Phe Thr Asn Asp Ser Ala Leu Ser Leu Ala Thr Phe
                325                 330                 335

Thr Phe Pro Val Gly Val Leu Tyr Ser Ala Arg Ala His Ser Asp Val
            340                 345                 350

Gln Val Leu Ser
        355
```

<210> SEQ ID NO 79
<211> LENGTH: 354
<212> TYPE: PRT

<213> ORGANISM: Ophioglossum pendulum

<400> SEQUENCE: 79

```
Met Ser Leu Val Gln Thr Pro Val Tyr Val Ile Gly Gly Gln Gly Gly
1               5                   10                  15

Asn Ala Phe Thr Tyr Asp Gln Ser Arg Asn Gly Arg Ile Leu Arg Arg
            20                  25                  30

Ile Gly Val Trp Ala Gly Glu Trp Gln Leu Arg Gly Ile Arg Val Trp
        35                  40                  45

Met Thr Gly Thr Asp Thr Pro Ala Thr Phe Gly Thr Ala Thr Gly Ser
    50                  55                  60

Tyr Ser Glu Tyr Thr Phe Ala Asp Gly Glu Arg Ile Thr Arg Leu Ser
65                  70                  75                  80

Leu Trp Gly Asn Gly Ala Gly Thr Arg Ser Gly Gly Ile Arg Phe Tyr
                85                  90                  95

Thr Thr Thr Gly Gly Ser Phe Phe His Lys Met Thr Ser Trp Gly Leu
            100                 105                 110

Gln Thr Glu Tyr Pro Ile Asp Val Ala Ser Gly Leu Cys Val Gly Ile
        115                 120                 125

Met Gly Arg Ala Asn Val Asp Val Asp Ser Leu Gly Val Leu Phe Leu
    130                 135                 140

Arg Thr Ile Ala Ser Ala Arg Met Ile Asn Val Ser Tyr Pro Thr Leu
145                 150                 155                 160

Gly Leu Glu Gln Ala Gly Ile Ile Pro Val Thr Leu Asp Ser Phe Asn
                165                 170                 175

Asp Ser Asn Asn Ala Gly Thr Ile Ser Lys Asn Trp Thr Phe Ser Gly
            180                 185                 190

Ser Arg Thr Val Thr Ile Ser Ser Ser Trp Ser Leu Thr Ser Gly Ile
        195                 200                 205

Glu Thr His Ala Ser Val Ser Val Gln Ala Gly Ile Pro Met Val Ala
    210                 215                 220

Glu Val Ser Gly Glu Phe Gly Trp Ser Val Ser Val Ser Gly Thr Tyr
225                 230                 235                 240

Ala Thr Thr Gln Glu Glu Ser Arg Thr Leu Thr Trp Asn Gln Ser Gly
                245                 250                 255

Thr Leu Glu Pro Gly Gln Trp Ile Ser Leu Gln Ala Thr Thr Arg Arg
            260                 265                 270

Gly Thr Ile Thr Leu Pro Phe Gln Ala Thr Met Glu Ile Thr Leu Leu
        275                 280                 285

Ser Gly Thr Ile Phe Gln Tyr Ala Ile Ser Ser Met Tyr Ser Gly Val
    290                 295                 300

Asp Tyr Thr Ser Val Asp Ile Thr Asn Thr Gly Thr Arg Ala Ser Asp
305                 310                 315                 320

His Val Glu Val Glu Ala Thr Glu Gln Gln Val Gln Gly Val Lys Asp
                325                 330                 335

Gln Ser Val Gln Pro Asn Lys Glu Ala Lys Glu Cys Thr Leu Leu Phe
            340                 345                 350

Ala Glu
```

<210> SEQ ID NO 80
<211> LENGTH: 353
<212> TYPE: PRT
<213> ORGANISM: Colysis wrightii ‘Monstifera’

<400> SEQUENCE: 80

```
Met Ala Leu Tyr Gln Thr Pro Val Tyr Val Ile Gly Gly Gln Gly Gly
1               5                   10                  15

Asn Ser Phe Thr Tyr Asp Gln Ser Arg Asn Gly Lys Val Leu Thr Lys
            20                  25                  30

Ile Gly Val Trp Ala Gly Glu Trp Gln Leu Arg Gly Ile Arg Val Trp
        35                  40                  45

Met Ser Gly Ser Asp Ser Pro Thr Thr Phe Gly Thr Ala Ser Gly Ser
    50                  55                  60

Tyr Ser Glu Tyr Thr Phe Ala Ala Gly Glu Arg Ile Thr Arg Leu Ser
65                  70                  75                  80

Leu Trp Gly Asn Gly Ala Gly Thr Arg Ser Gly Ala Ile Arg Phe Tyr
                85                  90                  95

Thr Thr Thr Gly Gly Ser Phe Phe Pro Lys Met Thr Ser Trp Asp Leu
            100                 105                 110

Lys Thr Glu Tyr Pro Ile Asp Val Ala Ser Gly Leu Cys Val Gly Ile
        115                 120                 125

Ile Gly Arg Ala Ser Ala Asp Ile Asp Ser Leu Gly Phe Met Phe Leu
    130                 135                 140

Arg Thr Ile Ala Ser Ser Arg Met Ile Asn Val Ser Tyr Pro Thr Leu
145                 150                 155                 160

Gly Leu Glu Gln Ala Gly Ile Ile Pro Val Thr Leu Asp Ser Tyr Asn
                165                 170                 175

Asp Ser Asn Asn Ala Gly Ser Ile Ser Lys Asn Trp Thr Phe Ser Gly
            180                 185                 190

Ser Arg Thr Val Thr Ile Ser Ser Ser Trp Thr Leu Thr Ser Gly Ile
        195                 200                 205

Glu Ala His Ala Ser Val Thr Val Gln Ala Gly Ile Pro Ser Val Ala
    210                 215                 220

Glu Val Ser Gly Glu Phe Gly Trp Ser Val Ser Val Ser Gly Ser Tyr
225                 230                 235                 240

Thr Ser Thr Gln Glu Glu Ser Arg Thr Leu Thr Trp Asn Gln Ser Gly
                245                 250                 255

Thr Leu Glu Pro Gly Gln Trp Ile Ser Ile Gln Ala Thr Thr Arg Arg
            260                 265                 270

Gly Thr Ile Thr Leu Pro Tyr Gln Gly Thr Met Glu Ile Thr Leu Gln
        275                 280                 285

Ser Gly Thr Val Phe Gln Tyr Pro Ile Ser Ser Met Tyr Ser Gly Val
    290                 295                 300

Asp Tyr Thr Ser Val Asp Ile Thr Asn Thr Gly Thr Arg Ala Leu Lys
305                 310                 315                 320

Gln Val Glu Val Gln Ala Thr Asp Gln Gln Ser Gln Glu Gly Asp His
                325                 330                 335

Asn Val Gln Pro Asp Lys Glu Val Glu Glu Arg Lys Val Leu Phe Thr
            340                 345                 350

Glu


<210> SEQ ID NO 81
<211> LENGTH: 353
<212> TYPE: PRT
<213> ORGANISM: Colysis wrightii

<400> SEQUENCE: 81

Met Ala Leu Tyr Gln Thr Pro Val Tyr Val Ile Gly Gly Gln Gly Gly
1               5                   10                  15
```

Asn Ser Phe Thr Tyr Asp Gln Ser Arg Asn Gly Lys Val Leu Thr Lys
20 25 30

Ile Gly Val Trp Ala Gly Glu Trp Gln Leu Arg Gly Ile Arg Val Trp
35 40 45

Met Ser Gly Ser Asp Ser Pro Thr Thr Phe Gly Thr Ala Ser Gly Ser
50 55 60

Tyr Ser Glu Tyr Thr Phe Ala Ala Gly Glu Arg Ile Thr Arg Leu Ser
65 70 75 80

Leu Trp Gly Asn Gly Ala Gly Thr Arg Ser Gly Ala Ile Arg Phe Tyr
85 90 95

Thr Thr Thr Gly Gly Ser Phe Phe Pro Lys Met Thr Ser Trp Asp Leu
100 105 110

Lys Thr Glu Tyr Pro Ile Asp Val Ala Ser Gly Leu Cys Val Gly Ile
115 120 125

Ile Gly Arg Ala Ser Ala Asp Ile Asp Ser Leu Gly Phe Met Phe Leu
130 135 140

Arg Thr Ile Ala Ser Ser Arg Met Ile Asn Val Ser Tyr Pro Thr Leu
145 150 155 160

Gly Leu Glu Gln Ala Gly Ile Ile Pro Val Thr Leu Asp Ser Tyr Asn
165 170 175

Asp Ser Asn Asn Ala Gly Ser Ile Ser Lys Asn Trp Thr Phe Ser Gly
180 185 190

Ser Arg Thr Val Thr Ile Ser Ser Ser Trp Thr Leu Thr Ser Gly Ile
195 200 205

Glu Ala His Ala Ser Val Thr Val Gln Ala Gly Leu Pro Ser Val Ala
210 215 220

Glu Val Ser Gly Glu Phe Gly Trp Ser Val Ser Val Ser Gly Ser Tyr
225 230 235 240

Thr Ser Thr Gln Glu Glu Ser Arg Thr Leu Thr Trp Asn Gln Ser Gly
245 250 255

Thr Leu Glu Pro Gly Gln Trp Ile Ser Ile Gln Ala Thr Thr Arg Arg
260 265 270

Gly Thr Ile Thr Leu Pro Tyr Gln Gly Thr Met Glu Ile Thr Leu Gln
275 280 285

Ser Gly Thr Val Phe Gln Tyr Pro Ile Ser Ser Met Tyr Ser Gly Val
290 295 300

Asp Tyr Thr Ser Val Asp Ile Thr Asn Thr Gly Thr Arg Ala Leu Lys
305 310 315 320

Gln Val Glu Val Gln Ala Thr Asp Gln Gln Ser Gln Glu Gly Asp His
325 330 335

Asn Val Gln Pro Asp Lys Glu Val Glu Glu Arg Lys Val Leu Phe Thr
340 345 350

Glu

<210> SEQ ID NO 82
<211> LENGTH: 321
<212> TYPE: PRT
<213> ORGANISM: Colysis wrightii

<400> SEQUENCE: 82

Met Ser Ser Gly Ser Val Ile Gly Gly Val Thr Met Val Gly Gly Pro
1 5 10 15

Tyr Gly Ser Tyr Gln Glu Val Gln Ala Trp Gln Val Gly Ser Tyr Ile
20 25 30

Ser Arg Leu Thr Val Tyr Trp Glu Ser Met Arg Val Arg Gly Ala Arg
35 40 45

Val Trp Val Lys Gly Gln Ser Ala Ser Thr Thr Phe Gly Asp Ala Thr
50 55 60

Gly Ser Ser Ala Asp Phe Glu Phe Glu Thr Gly Glu Thr Ile Thr Ala
65 70 75 80

Met Ser Leu Trp Gln Gly Glu Trp Glu Asn Pro Asp His Ile Arg Ala
85 90 95

Gly His Leu Tyr Phe Thr Thr Ser Asn Gly Arg Glu Phe Ser Ala Gly
100 105 110

Pro Ser Thr Met Trp Ser Glu Thr Val Ile Asp Val Gln Ser Gly Trp
115 120 125

Leu Val Gly Leu Gln Ala Tyr Thr Gly Asp Asp Ile Asn Lys Trp Gly
130 135 140

Phe Val Phe Leu Lys Pro Leu Leu Val Phe Ala Leu Ala Asp Val Gln
145 150 155 160

Tyr Thr Gly Leu Gln Asp Val Gly Ala Ile Val Pro Thr Thr Leu Asp
165 170 175

Ser Leu Asp Glu Thr Asn Asn Ser Ser Thr Gly Ser Asp Val Asn Trp
180 185 190

Ser Leu Glu Gly Ser Lys Ala Glu Thr Val Ser Trp Ser Phe Ser Thr
195 200 205

Thr Asp Ser Leu Thr Ala Thr Ile Gly Phe Glu Val Ser Ala Gly Ile
210 215 220

Pro Glu Val Ala Gln Val Lys Glu Ser Phe Gln Phe Gln Val Gly Thr
225 230 235 240

Ser Thr Thr Arg Ser Ser Ser Tyr Ser Glu Glu His Thr Leu Thr Trp
245 250 255

Ser Thr Gly Gly Val Leu Lys Pro Gly Gln His Val Val Ala Ser Ala
260 265 270

Val Thr Gln Val Gly Thr Leu Ser Gly Leu Pro Tyr Thr Ala Thr Val
275 280 285

Val Ile Lys Thr Lys Asp Ala Ser Ser Tyr Ser Tyr Ala Thr Ser Gly
290 295 300

Ser Tyr Ser Gly Ile Ser Cys Thr Glu Val Gln Leu Asp Val Lys Val
305 310 315 320

Thr

<210> SEQ ID NO 83
<211> LENGTH: 373
<212> TYPE: PRT
<213> ORGANISM: Selaginella kraussiana ‘Variegata’

<400> SEQUENCE: 83

Met Ala Gln Leu Gln Gln His Val Val Asn Ser Lys His Ala Tyr Gly
1 5 10 15

Lys His Ala Pro Ala Ser Lys Val Cys Glu Ile Ala Arg Ala Pro Val
20 25 30

His Ala Tyr Lys Gly Ser Asn Gln Gly Asp Val Thr Ala Pro Leu Thr
35 40 45

Phe Ile Gly Gly Asp Gly Gly Lys Gln Val Ser Lys Arg Ala Trp Glu
50 55 60

Ser Gly Lys Leu Ile Thr Arg Leu Arg Val Tyr Ser Gly Tyr Ser Cys
65 70 75 80

Ile Lys Ala Met Lys Val Trp Phe Thr Gly Asp Glu Tyr Ser Glu Gly
85 90 95

Thr Cys Leu Gly Glu Pro Asp Gly Thr Asp Tyr Lys Glu Tyr Thr Phe
100 105 110

Ser Glu Gly Glu Arg Ile Thr Arg Met Ser Leu Trp Gly Asn Gly Asn
115 120 125

Gly Thr Arg Ala Gly Trp Ile Ser Leu Ser Thr Asn Lys Gly Gly Val
130 135 140

Phe Ser Tyr Gly Met His Gly Trp Pro Leu Cys Thr Glu Tyr Pro Val
145 150 155 160

Asn Val Gly Ser Gly Ile Leu Ala Gly Ala Ile Tyr Asn Ala Gly Cys
165 170 175

Asp Ile Asp Ala His Gly Tyr Tyr Phe Leu Ser Ser Ser Val Thr Ser
180 185 190

Ser Lys Leu Glu Asn Val Lys Tyr Pro Thr Leu Lys Phe Asp Thr Ser
195 200 205

Gly Ile Thr Pro Val Ser Leu Asp Thr Tyr Lys Gln Thr Asn Thr Ser
210 215 220

Ser Ser Pro Arg Asn Trp Ser Phe Gly Gly Lys Arg Thr Val Lys Ser
225 230 235 240

Thr Thr Lys Trp Gly Leu Lys Ile Ala Asn Thr Phe Asn Val Glu Leu
245 250 255

Ser Val Glu Ala Gly Val Pro Gln Val Ser Lys Ser Gly Ala Lys Phe
260 265 270

Gly Trp Thr Ile Ser Val Ala Ser Asp His Glu Glu Ser Glu Glu Arg
275 280 285

Thr Gln Glu Leu Val Trp Ser Thr Gly Gly Thr Leu Gln Pro Gly Glu
290 295 300

Thr Val Asp Leu Val Ala Leu Thr Arg Gln Gly Asn Leu Asn Asp Leu
305 310 315 320

Arg Phe Glu Gly Thr Met Val Val Thr Leu Lys Asn Gly Ala Ser Phe
325 330 335

Arg Phe Pro Leu Ser Gly Pro Tyr Lys Gly Ile Cys Tyr Thr Gly Val
340 345 350

Glu Ile Lys Asp His Glu Glu Thr Lys Thr Met Ala Met Lys Ser Tyr
355 360 365

Ala Ser Leu Cys Leu
370

<210> SEQ ID NO 84
<211> LENGTH: 400
<212> TYPE: PRT
<213> ORGANISM: Selaginella kraussiana ‘Variegata’

<400> SEQUENCE: 84

Met Ser Ile His Gln Thr Pro Val Thr Leu Ile Gly Gly Arg Gly Gly
1 5 10 15

Ala Ala Phe Thr Tyr Asn Ala Gly Ala Ser Gly Arg Ile Leu Arg Arg
20 25 30

Ile Gly Val Trp Ala Gly Gly Ser Gln Leu Arg Gly Ile Arg Val Trp
35 40 45

Trp Thr Gly Leu Asp Ser Pro Ile Thr Tyr Gly Thr Pro Asn Val Gly
50 55 60

Ser Tyr Gln Glu Phe Thr Phe Gln Asp Gly Glu Arg Ile Thr Ser Leu

```
65                  70                  75                  80

Ser Leu Trp Gly Asn Gly Ala Gly Thr Arg Ser Gly Gly Ile Arg Phe
                85                  90                  95

Tyr Thr Thr Thr Gly Arg Arg Phe Phe His His Met Thr Ser Trp Gly
            100                 105                 110

Leu Lys Gln Glu Tyr Pro Val Asp Val Val Asp Gly Val Cys Val Gly
        115                 120                 125

Leu Thr Gly Arg Gln Gly Ala Asp Ile Asp Ala Leu Gly Phe Met Phe
    130                 135                 140

Leu Arg Thr Met Thr Ser Ala Arg Met Ile Asn Val Lys Tyr Pro Thr
145                 150                 155                 160

Leu Gly Leu Glu Thr Ala Gly Ile Val Pro Val Thr Leu Asp Phe Met
                165                 170                 175

Ser Asp Ser Asn Asn Ala Ser Ser Ile Ser Lys Thr Trp Ser Phe Gln
            180                 185                 190

Gly Ser Arg Glu Val Thr Val Ser Ser Ser Trp Ser Thr Thr Thr Gly
        195                 200                 205

Ile Glu Leu His Ala Ser Ile Thr Val Ser Ala Gly Ile Pro Leu Val
    210                 215                 220

Ala Asn Val Glu Gly Gln Tyr Gly Trp Ala Ile Ser Thr Ser Ser Thr
225                 230                 235                 240

Tyr Thr Thr Asn His Ser Glu Thr Arg Thr Leu Gln Trp Gln Asn Ser
                245                 250                 255

Gly Val Leu Glu Pro Gly Gln Trp Ile Ser Leu Gln Ala Leu Thr Arg
            260                 265                 270

Arg Gly Thr Ile Thr Leu Pro Tyr Gln Ala Thr Met Gln Ile Thr Leu
        275                 280                 285

Gln Asn Gly Thr Val Phe Thr Tyr Pro Ile Thr Ala Gln Tyr Ala Gly
    290                 295                 300

Val Asp Tyr Thr Ser Val Glu Ile Val Ser Gln Gly Thr Arg Asp Leu
305                 310                 315                 320

Gly Ser Asp His Leu Ala Ile Asn Lys Asp Val Arg Tyr Ile Ala Ala
                325                 330                 335

Ala Asn Gly Ala Ala Val Gly Thr Thr Thr Thr Asn Ala Pro Pro His
            340                 345                 350

Tyr Val His Pro Ile Arg Gly Ala Pro Ile Val Glu Pro Val Lys Phe
        355                 360                 365

Ser Val Gly Ala Thr Tyr Ile Asn Asp Thr Asp Asn Ile Thr Gln Glu
    370                 375                 380

Val Asp Thr Thr Ala Ala Thr Ser Val Glu Glu Leu Thr Leu Val Tyr
385                 390                 395                 400


<210> SEQ ID NO 85
<211> LENGTH: 395
<212> TYPE: PRT
<213> ORGANISM: Selaginella victoriae

<400> SEQUENCE: 85

Met Gln Tyr Gly Leu Ala Asn Thr Glu Ala Ser Pro Leu Ile Glu Lys
1               5                   10                  15

Phe Gln Ala Leu Met Glu Gly Gly Ile Asp Glu Ser Ile Leu Ala Thr
            20                  25                  30

Lys Leu Val Gly Ala Glu Gly Asp Ala Ser His Leu Pro Pro Pro Gly
        35                  40                  45
```

```
Glu Thr Pro Ser Glu Asp Gly Ala Gly Lys Asp Pro Pro Asn Glu Ser
    50                  55                  60

Leu Glu Thr Glu Asp Val Glu Glu His Ala Asp Asp Ser Lys Ala Arg
65                  70                  75                  80

Ser Ala Ser Val Thr Ala Pro Leu Arg Phe Ile Gly Gly Pro Gly Gly
                85                  90                  95

Ser Gln Arg Ser Val Arg Gly Trp Thr Asn Gly Arg Val Ile Thr Arg
            100                 105                 110

Met Arg Val Tyr Arg Ala Arg Gly Thr Ile Lys Ala Tyr Gln Ile Trp
        115                 120                 125

Leu Thr Asp Ser Ala Pro Gln Thr His Gly Val Pro Gly Asn Ser Asp
    130                 135                 140

Phe Ala Glu Tyr Thr Phe Arg Thr Gly Glu Arg Leu Thr Arg Leu Thr
145                 150                 155                 160

Leu Trp Gly Asn Gly Met Gly Thr Arg Ala Gly Trp Ile Glu Phe Glu
                165                 170                 175

Thr Ser Leu Gly Gly Arg Phe Ser Tyr Gly Met Ser His Trp Ser Leu
            180                 185                 190

Arg Thr Pro Tyr Pro Val Asp Val Gly Ser Gly Ile Leu Val Gly Tyr
        195                 200                 205

Ile Phe Asn Ala Gly Glu Asp Val Asp Ala His Gly Phe Trp Phe Leu
    210                 215                 220

Asn His Ile Glu Gln Ala Glu Leu Thr Asn Val Arg Tyr Pro Thr Leu
225                 230                 235                 240

Gly Phe Asp Thr Ala Gly Ile Val Pro Thr Ala Leu Asp Thr Phe Arg
                245                 250                 255

Phe Arg Asn Asn Ser Ser Thr Pro Arg Asp Trp Asp Phe Ser Arg Asn
            260                 265                 270

Met Ser Arg Ser Thr Glu Arg Thr Trp Ser Ile Thr Val Asp Leu Thr
        275                 280                 285

Val His Ala Ser Ile Thr Val Ser Ala Gly Phe Pro Gly Ile Ala Asn
    290                 295                 300

Val Ser Gly Gln Tyr Gly Trp Glu Ile Gly Val Thr Gly His Phe Glu
305                 310                 315                 320

Thr Thr Glu Thr Ser Glu His Asp Leu Ser Trp Ser Val Gly Gly Arg
                325                 330                 335

Val Gln Pro Gly Asp Val Val Asp Leu Thr Ala Leu Thr Arg Thr Gly
            340                 345                 350

Thr Leu Asn Ile Pro Tyr Glu Gly Thr Met Val Val Arg Met Arg Asn
        355                 360                 365

Gly Ala Ser Phe Ser Tyr Ala Val Arg Gly Thr Tyr Arg Gly Leu Ser
    370                 375                 380

Tyr Thr Gly Thr Lys Ile Asn Asp Asn Ser Thr
385                 390                 395
```

<210> SEQ ID NO 86
<211> LENGTH: 317
<212> TYPE: PRT
<213> ORGANISM: Lycopodium phlegmaria

<400> SEQUENCE: 86

```
Met Ala Phe Gln Thr Pro Val Thr Leu Ile Gly Ala Ser Ser Gly Gly
1               5                   10                  15

Gln Gln Phe Ser Ala Tyr Gly Gly Thr Asp Gly Lys Leu Leu Glu Lys
            20                  25                  30
```

```
Ile Gly Val Trp Ala Gly Asp Ser Arg Ile Lys Ala Ile Lys Val Trp
        35                  40                  45

Leu Thr Asp Glu Ala Ala Gln Leu Phe Gly Asp Pro His Asp Pro Pro
    50                  55                  60

Gly Glu Gly Pro Leu His Tyr Lys Glu Phe Ala Phe Gln Pro Ala Glu
65                  70                  75                  80

Leu Ile Thr Arg Leu Ser Leu Trp Gly Asn Gly Ala Gly Thr Arg Ala
                85                  90                  95

Gly Trp Ile Tyr Phe Glu Thr Asn Gln Ser Arg Ser Phe Asp Phe Gly
            100                 105                 110

Met Tyr Ser Trp Gly Lys Lys Lys Glu Tyr Pro Val Asp Val Ala Ser
        115                 120                 125

Gly Ile Cys Ala Gly Val Met Gly Thr Ala Ala Ser Asp Ile Asn Asn
    130                 135                 140

Ile Gly Phe Val Phe Leu Lys Pro Ile Gln Ser Ser Lys Leu Ile Asn
145                 150                 155                 160

Val Gln Tyr Pro Ser Leu Ser Phe Asp Thr Gln Gly Ile Ser Pro Gln
                165                 170                 175

Thr Leu Lys Glu Phe Asn His Thr Asn Thr Ser Asn Asn Pro Thr Asn
            180                 185                 190

Trp Glu Phe Lys Gly Ser Ser Ala Val Thr Val Ser Ser Ser Trp Ser
        195                 200                 205

Leu Thr Thr Gly Leu Ala Val His Ala Ser Val Thr Val Glu Ala Gly
    210                 215                 220

Ile Pro Ala Val Ala Asp Val Ser Gly Glu Phe Gly Trp Glu Val Ser
225                 230                 235                 240

Ala Ser Thr Thr Ser Gln Ser Ser Thr Thr Glu Thr Asp Thr Leu Ser
                245                 250                 255

Trp Gly Val Ser Gly Thr Leu Ser Ala Gly Glu Ser Ile His Leu Lys
            260                 265                 270

Ala Leu Thr Arg Lys Gly Leu Ile Ser Val Pro Tyr Ile Gly Ser Ile
        275                 280                 285

Gln Val Thr Leu Lys Ser Gly Asp Val Phe Gln Tyr Pro Leu Lys Gly
    290                 295                 300

Gln Tyr Ser Gly Ile Ser Tyr Ser Gly Val Thr Val Thr
305                 310                 315


<210> SEQ ID NO 87
<211> LENGTH: 317
<212> TYPE: PRT
<213> ORGANISM: Huperzia salvinioides

<400> SEQUENCE: 87

Met Ala Phe Gln Thr Pro Val Thr Leu Ile Gly Gly Ser Ser Gly Gly
1               5                   10                  15

Gln Gln Phe Ser Ala Tyr Gly Gly Thr Asp Gly Lys Leu Leu Glu Lys
            20                  25                  30

Ile Gly Val Trp Ala Gly Asp Ser Arg Ile Lys Ala Ile Lys Val Trp
        35                  40                  45

Leu Thr Asp Glu Ala Ala Gln Leu Phe Gly Asp Pro His Asp Pro Pro
    50                  55                  60

Gly Glu Gly Pro Leu Leu Tyr Lys Glu Phe Thr Phe Gln Pro Ala Glu
65                  70                  75                  80

Leu Ile Thr Arg Leu Ser Leu Trp Gly Asn Gly Ala Gly Thr Arg Ala
```

```
                85                  90                  95

Gly Trp Ile Tyr Phe Glu Thr Asn Arg Ser Arg Ser Phe Asp Phe Gly
            100                 105                 110

Met Tyr Ser Trp Gly Lys Lys Lys Glu Tyr Pro Val Asp Val Ala Ser
        115                 120                 125

Gly Ile Cys Ala Gly Val Met Gly Thr Ala Ala Ser Asp Ile Asn Asn
    130                 135                 140

Ile Gly Phe Val Phe Leu Lys Pro Ile Gln Ser Ser Lys Leu Ile Asn
145                 150                 155                 160

Val Gln Tyr Pro Ser Leu Ser Phe Asp Thr Gln Gly Ile Ser Pro Gln
                165                 170                 175

Thr Leu Lys Glu Phe Asn His Thr Asn Thr Ser Asn Asn Pro Thr Ser
            180                 185                 190

Trp Glu Phe Lys Gly Ser Ser Ala Val Thr Val Ser Ser Ser Trp Ser
        195                 200                 205

Leu Thr Thr Gly Leu Ala Val His Ala Ser Val Thr Val Glu Ala Gly
    210                 215                 220

Ile Pro Ala Val Ala Asp Val Ser Gly Glu Phe Gly Trp Glu Val Ser
225                 230                 235                 240

Ala Ser Thr Thr Ser Glu Ser Ser Thr Thr Glu Thr Asp Thr Leu Ser
                245                 250                 255

Trp Gly Val Ser Gly Thr Leu Ser Ala Gly Glu Ser Ile His Leu Lys
            260                 265                 270

Ala Leu Thr Arg Lys Gly Leu Ile Ser Val Pro Tyr Thr Gly Ser Ile
        275                 280                 285

Gln Val Thr Leu Lys Ser Gly Asp Ile Phe Gln Tyr Pro Leu Lys Gly
    290                 295                 300

Gln Phe Ser Gly Val Ser Tyr Ser Gly Val Thr Val Thr
305                 310                 315


<210> SEQ ID NO 88
<211> LENGTH: 809
<212> TYPE: PRT
<213> ORGANISM: Asplenium australasicum

<400> SEQUENCE: 88

Met Ala Ala Gly Asp Tyr Ser Val Leu Tyr Gln Asp Val Asn Gln Ile
1               5                   10                  15

Ser Ile Arg Leu Glu Lys Met Asp Phe Ser Glu Val Met Ala Val His
            20                  25                  30

Arg Met Phe Val Arg Met Asp Asp Leu Asp Val Ser Ser Gly Thr Gly
        35                  40                  45

Leu Leu Ser Gly Ala Glu Lys Val Lys Arg Leu Tyr Val Phe Ala Asp
    50                  55                  60

Val Val Glu Leu Pro Ser Lys Gln Leu Arg Leu Pro Gly Thr Asp Leu
65                  70                  75                  80

Ile Val Ile Leu Cys Arg Ile Phe Val Thr Asn Gly Arg His Ser Thr
                85                  90                  95

Glu Leu Phe Leu Pro Ser Met Asn Met Ser Met Val Ala Pro Gly Thr
            100                 105                 110

Gly Ser Ile Arg Gly Val Ile Leu Ser Pro Thr Thr Val Leu Thr Thr
        115                 120                 125

Ser Ser Asp Ala Leu Gln Phe Lys Leu Gln Ser Gly Ser Met Thr Ser
    130                 135                 140
```

-continued

```
Val Met Arg Leu Lys Asp Val Ser Val Ala Ala Thr Leu Thr Cys Asn
145                 150                 155                 160

Val Gln Ala Ala Ser Ala Ser Met Pro Leu Thr Val Lys Thr Thr Gly
                165                 170                 175

Thr Ser Pro Gly Asn Ile Cys Val Leu Gly Met Ser Thr Ala Val Val
            180                 185                 190

Val Pro Glu Ser Ala Val Ala Val Ile Thr Asp Ala Asn Ile Leu Leu
        195                 200                 205

Gly Met Gln Val Thr Val Leu Ile Ala Glu Leu Val Lys Ile Ala His
    210                 215                 220

Asn Ser Asp Val Leu Ile Ala Ala Val Thr Arg His Val Glu Trp Leu
225                 230                 235                 240

Asn His Leu Leu Val Gln Ala His Ala Ala Ala Pro Ser Glu Asp Val
                245                 250                 255

Val Ala Leu Leu Tyr Arg Thr Gln Gly Phe Ile Lys Leu Arg Asn Glu
            260                 265                 270

Gly Leu Ile Val Pro Arg Leu Gln Tyr Arg Met Tyr Lys Asp Leu Ile
        275                 280                 285

Asp Arg Met Val Gln Val Ala Gln Ser Tyr Asp Gln Asp Phe Lys Gln
    290                 295                 300

Leu Lys Leu Phe Val Glu Gln Asn Lys Ile Leu Gly Ser Tyr Leu Leu
305                 310                 315                 320

Glu Gln Asn Lys Ala Phe Ala Glu Lys Glu Lys Asp Met Asp Ala Phe
                325                 330                 335

His Ser Gln Val Ile Asp Leu Arg Thr Ser Glu Leu Glu Ser Thr Ile
            340                 345                 350

Glu Arg Met Asp Asp Leu Ser Lys Gln Met Glu Glu Gln Asn Ala Ala
        355                 360                 365

Met Glu Gln Ala Lys Ala Asp Met Asp Ala Gly Leu Ile Ala Tyr Gln
    370                 375                 380

Asn Lys Gln Val Ala Asn Ala Val Phe Ala Val Leu Gly Ala Ile Ala
385                 390                 395                 400

Ser Ile Gly Leu Ala Phe Ala Thr Gly Gly Ala Thr Ala Pro Gly Ala
                405                 410                 415

Val Ala Ser Ala Gly Ala Ala Val Thr Ala Ala Gly Lys Ala Ala Glu
            420                 425                 430

Gly Leu Lys Lys Val Val Glu Ile Leu Glu Gly Leu Gln Ala Val Met
        435                 440                 445

Glu Val Val Ala Val Ile Lys Glu Leu Val Gln Ser Leu Gln Glu Ile
    450                 455                 460

Gly Gln Leu Val Asp Ala Pro Glu Met Pro Asp Leu Pro Ser Asp Ala
465                 470                 475                 480

Glu Trp Glu Ile Phe Val Asn Glu Val Glu Ala Val Ala Glu Gln Met
                485                 490                 495

Pro Thr Glu Val Thr Glu Val Pro Ala Trp Lys Ala Lys Cys Lys Asn
            500                 505                 510

Val Ala Ala Leu Gly Arg Glu Met Ser Thr Met Ala Ala His Ile Ala
        515                 520                 525

Glu Leu Gln Phe Glu Ile Gln Val Gln Glu Met Leu Arg Glu Ile Ala
    530                 535                 540

Lys Lys Gln Ala Asp Arg Leu Ser Ser Ile Lys Pro Ala Asp Leu Thr
545                 550                 555                 560

Asn Tyr Leu Glu Met Val Ser Glu Met Asp Met Arg Thr Thr Arg Met
```

```
                565                 570                 575

Leu Leu Glu Leu Ile Arg Val Leu Tyr Ile Gln Asn Ala Ala Leu Gln
            580                 585                 590

Tyr Glu Tyr Leu Gln Thr Pro Ala Pro Leu Asn Ala Trp Pro Val Thr
        595                 600                 605

Met Gln Thr Val Trp Gly Leu Leu Val Gln Gln Glu Thr Ala Ala Ile
    610                 615                 620

Asn Gly Leu Leu Gln Met Gly Ala Pro Ser Asp Tyr Thr Gln Glu Tyr
625                 630                 635                 640

Ala Val Arg Asp Val Pro Val Arg Leu Leu Leu Gly Gly Gly Asp Trp
                645                 650                 655

Glu Phe Glu Leu Pro Val Arg Asn Ala Asp Phe Pro Leu Thr Trp Cys
            660                 665                 670

Arg Val Arg Ile Arg Tyr Val Asp Met Arg Phe Asp Ala Ala Ala Glu
        675                 680                 685

His Leu Pro Val Thr Ser Thr Gly Glu Val Tyr Met Leu Leu Gln Ser
    690                 695                 700

Ser Arg Phe Phe Glu Asp Arg Ala Lys Arg Glu Asn Glu Phe Ile Ser
705                 710                 715                 720

Tyr Glu Gly Gly Met Gly Leu Gln Tyr Gln Tyr Ala Tyr Arg Leu Ala
                725                 730                 735

Thr Gly Asp Ala Thr Val Thr Asn Val Pro Ser Glu Glu Tyr Ala Asn
            740                 745                 750

Thr Phe Met Arg Leu Ala Pro Phe Thr Arg Trp Arg Leu Arg Leu Ser
        755                 760                 765

Ala Ser Ala Pro Glu Asn Lys Gly Leu Ala Phe Pro Thr Ala Thr Leu
    770                 775                 780

Ala Asp Ala Thr Thr Arg Ile Lys Ile Thr Phe His Val Ser Ala Ile
785                 790                 795                 800

Arg Arg Ile Ser Thr Arg Val Ala Val
                805


<210> SEQ ID NO 89
<211> LENGTH: 861
<212> TYPE: PRT
<213> ORGANISM: Asplenium australasicum

<400> SEQUENCE: 89

Met Gly Gly Ala Val Pro Asp Tyr Ser His Leu Tyr Arg Glu Leu Asn
1               5                   10                  15

Gln Val Ser Glu Gly Met Lys Leu Asp Gln Met Glu Phe Ser Glu Val
            20                  25                  30

Met Val Ile His Arg Met Phe Ile Arg Leu His Asp Leu Asn Ile Ala
        35                  40                  45

His Arg Glu Gly Ala Glu Gln Val Lys Arg Leu Tyr Val Phe Ala Asp
    50                  55                  60

Val Val Glu Leu Ser Gly Thr Ser Leu Thr Thr Leu Leu Pro Gly Thr
65                  70                  75                  80

Met Met Val Val Ile Leu Cys Arg Val Leu Ser Val Arg Ser Phe Gln
                85                  90                  95

Ser Gln His Gly Leu Asp Phe Pro His Met Arg Leu His Ala Val Pro
            100                 105                 110

Gly Asp Asn Gln Met Leu Arg Ile His Arg Arg Asn Pro Asp Ser Ala
        115                 120                 125
```

```
Gln Tyr Asp Asp Tyr Pro Val Val Cys Val His Ala Asp Val Leu Glu
    130                 135                 140

Phe Pro Val Thr Gly Gly Arg Asp Ile Phe His Leu Gly Pro Leu Ala
145                 150                 155                 160

Asn Pro Cys Met Val Ile Thr Phe Pro Pro Gln Ser Leu Glu Glu Ala
                165                 170                 175

Pro Val Ser Ser Phe Thr Gly Ser Val Arg Leu Trp Thr Ala Ala Ala
            180                 185                 190

Ser Ser Pro His Arg Ile Asp Pro Asn Asn Leu Thr Phe Thr Pro Gly
        195                 200                 205

Phe Met Val Gln Gln Gly Gly Ser Phe Asn Leu Pro Phe Asn Thr Gln
    210                 215                 220

Ser Glu Asp Phe Trp Leu Leu Arg Arg Asn Leu Pro Asp Ala Leu Leu
225                 230                 235                 240

Lys Asp Ser Ser Ile Leu Leu Cys Met Gln Thr Ser Met Leu Ile Ala
                245                 250                 255

Glu Leu Val Glu Phe Ser His Pro Ser Ser Asp Val Arg Ala Ala Val
            260                 265                 270

Thr Leu His Ala Glu Trp Leu Asn Asn Leu Leu Leu Gln Ala Ser Ala
        275                 280                 285

Lys Ser Gln Gly Thr Pro His His Asp Asp Tyr Arg Ala Leu Leu Phe
    290                 295                 300

Arg Ala Gln Tyr Val Val Lys Gly Ile Gly Arg Ser Arg Gly Ala Val
305                 310                 315                 320

Val Pro Gln Leu Gln Tyr Asp Met Tyr Ser Asn Leu Ile Asn Gln Met
                325                 330                 335

Ala Arg Ala Ala Asp Ser Tyr Asp Gln Ser Leu Lys Gln Leu Lys Leu
            340                 345                 350

Phe Ile Ala Gln Asn Glu Ile Leu Gly Glu Tyr Leu Leu Glu Gln Asn
        355                 360                 365

Arg Val Phe Ala Ala Lys Glu Arg Asp Met Glu Val Phe His Ser Glu
    370                 375                 380

Leu Ile Ala Gln Lys Thr Thr Glu Leu Gln Thr Val Met Val Lys Ile
385                 390                 395                 400

Asp Asn Leu Ser Leu Gln Met Glu Ala Gln Val Glu Asp Met Glu Gln
                405                 410                 415

Ala Arg Glu Asp Met Glu Ala Gly Leu Arg Arg Phe Arg Asn Arg Gln
            420                 425                 430

Val Ala Asn Ala Met Phe Ser Val Phe Arg Ala Ile Gly Ala Val Ala
        435                 440                 445

Leu Thr Val Leu Thr Gly Gly Ala Ala Ala Pro Leu Ala Ile Ser Ala
    450                 455                 460

Ala Lys Gly Ala Val Ser Ile Ala Gly Gln Ala Ala Arg Gly Leu Glu
465                 470                 475                 480

Arg Val Leu Arg Ile Leu Asp Asp Leu Gln Ala Ala Met Glu Leu Leu
                485                 490                 495

Lys Ile Ile Lys Asp Leu Val Glu Ser Leu Gln Glu Ile Gly Gln Leu
            500                 505                 510

Val Asp Ala Pro Asp Met Pro Glu Met Pro Thr Glu Ala Asp Trp Ala
        515                 520                 525

Ile Phe Val Asn Glu Ile Glu Gly Val Ala Glu Gln Met Pro Glu Glu
    530                 535                 540

Val Ser Glu Val Ser Ala Trp Lys Thr Ser Cys Lys Asn Val Ala Ala
```

-continued

```
545                 550                 555                 560

Val Gly Arg Glu Leu Met Thr Thr Thr Ala Tyr Met Ser Gln Leu Gln
                565                 570                 575

Tyr Asp Ile Gln Val Gln Ala Met Leu Gln Gly Ile Ala Ser Lys Gln
            580                 585                 590

Ala Asp Arg Leu Ser Ser Ile Gln Ala Ala Asp Leu Ser Ser Phe Thr
        595                 600                 605

Glu Met Val Thr Glu Met Asp Met Arg Thr Thr Arg Leu Leu Val Glu
    610                 615                 620

Leu Ile Lys Val Leu His Met Gln Ser Val Ala Leu Met Tyr Gln Ser
625                 630                 635                 640

Leu Thr Leu Pro Glu Leu Met Asn Ala Trp Pro Val Thr Met Glu Thr
                645                 650                 655

Val Trp Arg Met Leu Ile Gln His Glu His Ala Ala Val Leu Gly Leu
            660                 665                 670

Ile Arg Leu Gly Pro Ser Phe Asp Phe Arg Lys Thr Leu Thr Val Lys
        675                 680                 685

Asp Ile Pro Val Asp Leu Leu Leu His Gly Glu Asp Trp Glu Phe Glu
    690                 695                 700

Ile Ser Val Asp Asp Phe Thr Val Phe Pro Arg Thr Trp Ser Arg Val
705                 710                 715                 720

Arg Ile His His Leu Glu Met Lys Phe Val Gly Ser Gly Asp Glu Ala
                725                 730                 735

Ala Pro Gly Gly Gly Met Gln Gly Ala His Gln Pro Ala Thr Lys Thr
            740                 745                 750

Gly Glu Val Tyr Ile Leu Leu Gln Ser Ser Arg Val Phe His Asp Arg
        755                 760                 765

Asn Lys Thr Lys Pro Leu His Tyr Glu Ala Gly Ile Pro Leu Asp Tyr
    770                 775                 780

His Tyr Ala Tyr Asn Leu Glu Thr Gly Glu Thr Thr Leu Ser Asn Leu
785                 790                 795                 800

Pro Ser His Asp Phe Ile Arg Ala Phe Met Arg Met Thr Pro Phe Ala
                805                 810                 815

Thr Trp Arg Leu Arg Val Ser Ala Ser Ala Gln Glu Asn Glu Gly Leu
            820                 825                 830

Ala Phe Pro Thr Ala Thr Val Gly Ala Gly Asp Thr Thr Gln Ile Ala
        835                 840                 845

Ile Thr Phe His Val Ser Ala Ile Arg Glu Ile Ala Leu
    850                 855                 860
```

<210> SEQ ID NO 90
<211> LENGTH: 905
<212> TYPE: PRT
<213> ORGANISM: Asplenium nidus

<400> SEQUENCE: 90

```
Arg Glu Arg Gly Val Leu Asn Gly Met Leu Thr Ser Asp His Pro Phe
1               5                   10                  15

Trp Gly Asp Trp Gly Val Cys Ser Glu Ala His Arg Ser Ile Cys Leu
            20                  25                  30

Val Cys Pro Asp Gln Ser Leu His Glu Ile Ala Met Gly Gly Ala Val
        35                  40                  45

Pro Asp Tyr Ser His Met Tyr Arg Glu Leu Asn Gln Val Ser Glu Arg
    50                  55                  60
```

-continued

```
Met Arg Leu Asp His Met Glu Phe Ser Glu Val Met Val Ile His Arg
65                  70                  75                  80

Met Phe Ile Arg Leu Pro Asp Leu Asp Ile Ala Leu Gln Glu Gly Ala
                85                  90                  95

Gln Gln Val Lys Arg Leu Tyr Val Phe Ala Asp Val Val Glu Leu Pro
            100                 105                 110

Glu Met Ser Thr Ser Val Thr Val Ser Glu Thr Val Thr Leu Arg Leu
        115                 120                 125

Pro Gly Thr Val Ile Val Val Ile Leu Cys Arg Val Leu Phe Tyr Gln
    130                 135                 140

Gly Phe Ala Arg Tyr Asp Leu Asp Phe Pro His Met Arg Leu His Ala
145                 150                 155                 160

Val Gln Pro Ser Gly Ala Gly Val Leu Arg Met His Arg Leu Asn Pro
                165                 170                 175

Asp Ser Val Gln Tyr Asp Asp Tyr Pro Val Val Cys Val Leu Ala Asp
            180                 185                 190

Val Val Glu Phe Thr Arg Gln Arg Pro Ser Arg Leu Phe Arg Ile Gly
        195                 200                 205

Pro Leu Ala Tyr Pro Ser Met Ile Phe Thr Asp Glu Arg Pro Pro Ala
    210                 215                 220

Ser Ser Ile Val Glu Pro Arg Pro Val Ser Ser Phe Tyr Cys Thr Ile
225                 230                 235                 240

Glu Phe Arg Trp Ser Ser Ser Asn Asn Ile Gly Pro Asn Ser Val Gly
                245                 250                 255

Ile Gly Cys Val Phe Arg Leu Ser Gly Gly Ser Thr Phe Ser Thr Gly
            260                 265                 270

Ser Pro Arg Glu Asp Phe Trp Leu Phe Arg Arg Asp Leu Pro Asp Ala
        275                 280                 285

Leu Phe Lys Asp Ser Ser Ile Leu Pro Cys Met Gln Thr Ser Met Leu
    290                 295                 300

Val Ala Glu Leu Val Glu Phe Cys His Pro Ser Pro Asp Val Arg Ala
305                 310                 315                 320

Ala Ile Arg Ser His Ala Lys Trp Leu Asn Thr Leu Leu Leu Gln Ala
                325                 330                 335

Ser Val Ala Ser Glu Gly Thr Pro His His Ser Asp Tyr Asn Ala Leu
            340                 345                 350

Leu Phe Arg Ala Gln Tyr Val Ile Lys Gly Val Gly Lys Ser Arg Gly
        355                 360                 365

Ala Val Val Pro Gln Leu Gln Tyr Asp Met Tyr Ser Asn Leu Val Asn
    370                 375                 380

Gln Val Ala Arg Ala Ala Asp Ser Tyr Asp Gln Ser Leu Lys Gln Leu
385                 390                 395                 400

Gln Leu Phe Ile Ala Gln Asn Glu Ile Leu Gly Glu Tyr Leu Leu Glu
                405                 410                 415

Gln Asn Arg Val Phe Ala Ala Lys Glu Arg Asp Met Glu Val Phe His
            420                 425                 430

Ser Glu Leu Ile Ser Gln Lys Glu Thr Glu Leu Arg Thr Val Val Ala
        435                 440                 445

Lys Ile Asp Leu Leu Ser Leu Gln Met Glu Thr Gln Val Ala Asp Met
    450                 455                 460

Glu Gln Ala Arg Glu Asp Met Glu Ala Gly Leu Arg Arg Phe Arg Asn
465                 470                 475                 480

Arg Gln Val Ala Asn Ala Ile Phe Ser Val Phe Arg Ala Ile Ala Ala
```

-continued

```
                485                 490                 495

Val Ala Leu Thr Val Val Thr Gly Gly Ala Ala Ala Pro Leu Ala Met
            500                 505                 510

Ser Thr Ala Lys Gly Ala Val Ser Ala Ala Gly Gln Ala Ala Arg Gly
        515                 520                 525

Leu Glu Arg Val Leu Gln Ile Leu Asp Asp Leu Gln Ala Ala Met Glu
    530                 535                 540

Leu Leu Lys Ile Ile Lys Asp Leu Leu Glu Ser Leu Gln Ala Val Gly
545                 550                 555                 560

Gln Leu Val Asp Ala Pro Asp Met Pro Glu Met Pro Thr Glu Ala Asp
                565                 570                 575

Trp Ala Ile Phe Val Asn Glu Ile Glu Gly Val Ala Glu Gln Met Pro
            580                 585                 590

Glu Glu Val Ser Glu Val Ser Ala Trp Lys Thr Ser Ser Lys Asn Val
        595                 600                 605

Ala Ala Val Gly Arg Glu Leu Met Thr Thr Thr Ala Tyr Met Ser Gln
    610                 615                 620

Leu Gln Tyr Asp Ile Gln Val Gln Ala Met Leu Gln Asp Ile Ala Ser
625                 630                 635                 640

Lys Gln Ala Asp Arg Leu Ser Ser Thr Gln Ala Ala Asp Leu Ser Ser
                645                 650                 655

Phe Thr Glu Met Val Thr Gln Met Asp Met Arg Thr Ile Arg Leu Gln
            660                 665                 670

Val Glu Leu Ile Lys Val Leu Asp Val Gln Asn Val Ala Leu Met Tyr
        675                 680                 685

Gln Ser Leu Val Lys Pro Glu Leu Met Asn Ala Trp Pro Val Thr Met
    690                 695                 700

Asp Met Val Trp Arg Leu Leu Ile Gln His Glu His Ala Ala Val Leu
705                 710                 715                 720

Gly Leu Met Arg Leu Gly Pro Ser Phe Asp Phe Arg Lys Thr Leu Thr
                725                 730                 735

Val Lys Asp Ile Pro Val Asp Leu Leu Leu His Gly Glu Asp Trp Glu
            740                 745                 750

Phe Glu Ile Pro Val Asp Asp Phe Arg Val Phe Pro Ala Thr Trp Ser
        755                 760                 765

Arg Val Arg Ile His His Leu Glu Met Lys Phe Ala Ala Ala Pro Ala
    770                 775                 780

Gly Thr Gln Gly Ala His Gln Pro Ala Thr Lys Ser Gly Glu Ile Tyr
785                 790                 795                 800

Ile Leu Leu Gln Ser Ser Arg Val Phe His Asp Arg Asn Lys Ala Glu
                805                 810                 815

Pro Leu His Tyr Glu Ala Gly Val Pro Leu Asp Tyr His Tyr Ala Tyr
            820                 825                 830

Asn Leu Glu Thr Gly Glu Thr Thr Leu Ser Asn Leu Pro Ser Tyr Asp
        835                 840                 845

Phe Ile Arg Ala Phe Met Arg Met Thr Pro Phe Thr Thr Trp Arg Leu
    850                 855                 860

Arg Val Ser Ala Ser Ala Gln Glu Asn Glu Gly Leu Ala Phe Pro Thr
865                 870                 875                 880

Ala Thr Val Gly Thr Gly Asp Thr Thr Gln Ile Ala Ile Thr Phe His
                885                 890                 895

Val Ser Ala Ile Arg Glu Ile Ala Leu
            900                 905
```

<210> SEQ ID NO 91
<211> LENGTH: 866
<212> TYPE: PRT
<213> ORGANISM: Asplenium x kenzoi

<400> SEQUENCE: 91

```
Met Gly Gly Ala Val Pro Asp Tyr Ser His Met Tyr Arg Glu Leu Asn
1               5                   10                  15

Gln Val Ser Glu Arg Met Arg Leu Asp His Ile Glu Phe Ser Glu Val
            20                  25                  30

Met Val Ile His Arg Met Phe Ile Arg Leu Pro Asp Leu Asp Ile Ala
        35                  40                  45

Leu Gln Glu Gly Ala Gln Gln Val Lys Arg Leu Tyr Val Phe Ala Asp
    50                  55                  60

Val Val Glu Leu Pro Glu Thr Ser Thr Ser Ala Ser Ala Glu Pro Val
65                  70                  75                  80

Thr Leu Arg Leu Pro Gly Thr Val Met Val Val Ile Leu Cys Arg Val
                85                  90                  95

Leu Leu Phe Gln Gly Ser Tyr Ser Ala Tyr Asp Leu Asp Phe Pro His
            100                 105                 110

Met Arg Leu His Ala Val Pro Gly Glu Ala Gln Ile Leu Arg Ile His
        115                 120                 125

Arg Arg Asn Pro Asp Ser Ala Gln Tyr Asp Asp Tyr Pro Val Val Cys
    130                 135                 140

Val His Ala Asp Val Leu Glu Phe Pro Val Thr Gly Gly Arg Asp Ile
145                 150                 155                 160

Phe His Leu Gly Pro Leu Ala Asn Pro Cys Met Val Val Thr His Pro
                165                 170                 175

Gln Leu Ser Leu Val Glu Ala Pro Val Ser Ser Phe Thr Gly Ser Val
            180                 185                 190

Arg Leu Trp Ser Ala Ala Thr Ser Ser Pro His Ser Ile Asp Pro Asn
        195                 200                 205

Asn Leu Thr Phe Thr Pro Ser Phe Ser Val Gln Gly Gly Gly Ser Phe
    210                 215                 220

Asn Leu Ser Phe Ala Thr Arg Ser Glu Asp Phe Trp Leu Leu Gln Arg
225                 230                 235                 240

Asn Leu Pro Asp Ala Leu Leu Lys Asp Ser Ser Ile Leu Leu Cys Met
                245                 250                 255

Gln Thr Ser Met Leu Ile Ala Glu Leu Val Glu Phe Ser His Pro Ser
            260                 265                 270

Ser Asp Val Arg Ala Ala Val Thr Leu His Ala Lys Trp Leu Asn Thr
        275                 280                 285

Leu Leu Leu Gln Ala Ser Ala Lys Ser Glu Gly Thr Pro His His Ala
    290                 295                 300

Asp Tyr Arg Ala Leu Leu Phe Arg Ala Gln Tyr Val Val Lys Gly Val
305                 310                 315                 320

Gly Lys Ser Arg Gly Ala Val Val Pro Gln Leu Gln Tyr Asp Met Tyr
                325                 330                 335

Ser Asn Leu Val Asn Gln Val Ala Arg Ala Ala Asp Ser Tyr Asp Gln
            340                 345                 350

Ser Leu Lys Gln Leu Gln Leu Phe Ile Thr Gln Asn Glu Ile Leu Gly
        355                 360                 365

Asp Tyr Leu Leu Glu Gln Asn Arg Val Phe Ala Ala Lys Glu Arg Asp
```

```
    370                 375                 380

Met Glu Val Phe His Ser Glu Leu Ile Ala Gln Lys Lys Thr Glu Leu
385                 390                 395                 400

Leu Thr Val Met Ala Lys Ile Asp Leu Leu Ser Leu Gln Met Glu Thr
                405                 410                 415

Gln Ala Ala Asp Met Glu Gln Ala Arg Glu Asp Met Glu Ala Gly Leu
            420                 425                 430

Arg Arg Phe Arg Asn Arg Gln Val Ala Asn Ala Met Phe Ala Val Phe
        435                 440                 445

Arg Ala Ile Gly Ala Val Ala Leu Thr Val Leu Thr Gly Gly Ala Ala
    450                 455                 460

Ala Pro Leu Ala Ile Ser Thr Ala Lys Gly Ala Val Ser Ile Ala Gly
465                 470                 475                 480

Gln Ala Ala Arg Gly Leu Gln Arg Val Leu Gln Ile Leu Asp Asp Leu
                485                 490                 495

Gln Ala Ala Met Glu Leu Leu Lys Ile Ile Lys Asp Leu Val Glu Ser
            500                 505                 510

Leu Gln Glu Val Gly Gln Leu Val Asp Ala Pro Asp Met Pro Glu Met
        515                 520                 525

Pro Thr Glu Ala Asp Trp Ala Ile Phe Val Asn Glu Ile Glu Gly Val
    530                 535                 540

Ala Glu Gln Met Pro Glu Glu Val Ser Glu Val Ser Ala Trp Lys Thr
545                 550                 555                 560

Ser Cys Lys Asn Val Ala Ala Val Gly Arg Glu Leu Met Thr Thr Thr
                565                 570                 575

Ala Tyr Met Ser Gln Leu Gln Tyr Asp Ile Gln Val Gln Ala Met Leu
            580                 585                 590

Gln Asp Ile Ala Ser Lys Gln Ala Asp Arg Leu Ser Ser Ile Gln Ala
        595                 600                 605

Ala Asp Leu Ser Ser Phe Thr Glu Met Val Thr Gln Met Asp Met Arg
    610                 615                 620

Thr Thr Arg Leu Leu Val Glu Leu Ile Lys Val Leu Asn Met Gln Asn
625                 630                 635                 640

Val Ala Leu Met Tyr Gln Ser Leu Thr Met Pro Glu Pro Met Asn Gly
                645                 650                 655

Trp Pro Val Thr Met Glu Thr Val Trp Arg Met Leu Ile Gln His Glu
            660                 665                 670

His Ala Ala Val Leu Gly Leu Met Arg Leu Gly Pro Ser Phe Asp Phe
        675                 680                 685

Arg Lys Thr Leu Thr Val Lys Asp Ile Pro Val Asp Leu Leu Leu His
    690                 695                 700

Gly Glu Asp Trp Glu Phe Glu Ile Ser Val Asp Asp Phe Thr Ala Phe
705                 710                 715                 720

Pro Ala Thr Trp Ser Arg Val Arg Ile His His Leu Glu Met Lys Phe
                725                 730                 735

Val Gly Ser Glu Glu Ala Ala Pro Trp Gly Met Gln Gly Pro His Gln
            740                 745                 750

Pro Ala Thr Lys Ser Gly Glu Ile Tyr Ile Leu Leu Gln Ser Ser Arg
        755                 760                 765

Val Phe His Asp Arg Asn Lys Thr Lys Pro Leu His Tyr Glu Ala Gly
    770                 775                 780

Ile Pro Leu Asp Tyr His Tyr Ala Tyr Asn Leu Gly Thr Gly Glu Thr
785                 790                 795                 800
```

Thr Leu Ser Asn Leu Pro Ser Tyr Asp Phe Val Arg Ala Phe Met Arg
805 810 815

Met Thr Pro Phe Thr Ala Trp Arg Leu Arg Val Ser Ala Ser Ala Gln
820 825 830

Glu Asn Glu Gly Leu Ala Phe Pro Thr Ala Thr Val Gly Ala Gly His
835 840 845

Thr Thr Gln Ile Ala Ile Thr Phe His Val Ser Ala Ile Arg Glu Ile
850 855 860

Ala Phe
865

<210> SEQ ID NO 92
<211> LENGTH: 903
<212> TYPE: PRT
<213> ORGANISM: Asplenium x kenzoi

<400> SEQUENCE: 92

Met Ala Ala Arg Ser Ala Gly Ala Ala Asp Gly Trp Arg Glu Val Tyr
1 5 10 15

Arg Gly Leu Asn Gln Val Ser Asp Arg Ile Arg Phe Asp Gln Leu Glu
20 25 30

Phe Ser Glu Val Met Val Ile His Arg Met His Ile Lys Met Ser Glu
35 40 45

Leu Asp Leu Gly His Leu Ala Gly Ala Glu Lys Val Glu Arg Leu His
50 55 60

Val Phe Ala Asp Val Val Glu Cys Asp Val Pro Pro His Glu Asn Ser
65 70 75 80

Ser Asp Pro Asp Leu Val Ile Arg Leu Pro Gly Ser Val Ser Val Thr
85 90 95

Phe Met Cys Arg Val Trp His Val Asn Tyr Gly Ile Val Gln Arg Thr
100 105 110

Ser Thr Val Arg Val Ala Arg Thr Val Val Val Gln Leu Pro His Met
115 120 125

Arg Leu His Phe Asn Ala Thr Thr Gly Ser Met His Arg Leu His Pro
130 135 140

Gln Thr Ser Gln Asp Gly Ser Asp Thr Cys Phe Cys Val Tyr Ala Glu
145 150 155 160

Val Val Gln Ile Ala Tyr Tyr Pro Asp Val Thr Tyr Pro Glu Ser Asn
165 170 175

Asp Ser Pro Val Gly Leu Arg Phe Leu Arg Leu Glu Phe Gly Ser Asp
180 185 190

Gln Leu Arg Val Thr Arg Gln Ser Glu Gly Pro Val Trp Ala Leu Arg
195 200 205

Gly Ser Leu Asn Tyr Ser Met Ser Pro Asp Asn Asp Gly Leu Met Asn
210 215 220

Glu Val Ser Ser Gln Pro Ala Gly Thr Ser Phe Ile Leu Asn Ile Leu
225 230 235 240

Pro Asp Asn Leu Asn Leu Gln Leu Met Ala Ser Leu Arg Arg Asn Ser
245 250 255

Asn Ser Thr Leu Thr Arg Asp Pro Asp Asn Ile Val Pro Ala Phe Ser
260 265 270

Val Tyr Arg Glu Lys Leu Ala Val Glu Leu Leu Thr Asp Pro Asn Thr
275 280 285

Leu Pro Pro Met Gln Thr Ser Met Leu Ile Gly Glu Leu Val Glu Val

```
    290                 295                 300

Gly Gln Pro Pro Glu Ala Thr Ile Glu Val Val Arg Lys His Ile Glu
305                 310                 315                 320

Trp Leu Asn Asn Leu Leu Leu Lys Val Ile Glu Ala Lys Gln Gly Glu
                325                 330                 335

Pro Val Glu Asp Tyr Ile Glu Leu Ser Phe Arg Ala Gln Tyr Val Ile
            340                 345                 350

Lys Lys Val Gly Arg Val Gln Arg Leu Val Val Pro Gln Leu Gln Tyr
        355                 360                 365

Ser Ala Tyr Ser Asn Leu Ile Asn Arg Leu Ala Gln Val Ala Glu Asn
    370                 375                 380

Tyr Asp Gln Ala Leu Arg Gln Phe Arg Leu Phe Ile Gln Gln Asn Lys
385                 390                 395                 400

Ile Leu Gly Gly Phe Leu Leu Glu Gln Asn Arg Ala Phe Ala Glu Arg
                405                 410                 415

Glu Gln Asp Met Asp Val Phe Tyr Ser Glu Leu Ile Thr Gln Arg Lys
            420                 425                 430

Ile Glu Leu Asp Asn Thr Leu Gln Thr Met Lys His Leu Gly Ala Gln
        435                 440                 445

Met Glu Thr Gln Thr Ala Gly Met Glu Gln Ala Gln Ala Asp Met Glu
    450                 455                 460

Ala Ala Gly Ile Arg Arg Phe Gln Asn Ala Gln Val Ala Arg Gly Leu
465                 470                 475                 480

Phe Ala Val Leu Gly Ala Ile Ala Ala Val Gly Leu Thr Leu Leu Thr
                485                 490                 495

Gly Gly Ala Ala Ala Pro Leu Ala Val Ser Ala Ala Arg Arg Val Val
            500                 505                 510

Thr Val Ala Gly Ala Val Ala Gln Gly Leu Gln Arg Val Ile Asp Ile
        515                 520                 525

Leu Glu Gly Leu Gln Val Val Met Glu Val Val Glu Leu Ile Asn Asp
    530                 535                 540

Leu Ile Ser Ser Leu Gln Asp Leu Gly Gln Pro Val Asp Leu Pro Glu
545                 550                 555                 560

Met Ala Glu Leu Pro Thr Gln Ala Asp Trp Leu Ile Phe Val Asn Glu
                565                 570                 575

Val Glu Gly Val Ala Glu Gln Met Pro Thr Glu Val Ser Glu Val Val
            580                 585                 590

Ala Trp Lys Thr Lys Cys Lys Asn Val Ala Val Leu Gly Arg Glu Met
        595                 600                 605

Thr Thr Leu Ala Ala Tyr Ile Ser Gln Leu Gln Tyr Asp Ile Gln Met
    610                 615                 620

Gln His Met Leu Gln Gln Ile Ala Arg Lys Gln Val Asp Arg Leu Ser
625                 630                 635                 640

Ala Ile Gln Leu Pro Asp Leu Lys Asn Tyr Ala Glu Leu Val Thr Gln
                645                 650                 655

Met Asp Met Arg Thr Thr Arg Leu Leu Val Ala Leu Ile Lys Val Val
            660                 665                 670

Asn Ile Gln Asn Ala Ala Leu Met Tyr Gln Tyr Leu Ser Glu Pro Thr
        675                 680                 685

Pro Val Tyr Ala Trp Pro Val Ser Met Asp Ser Val Trp Arg Met Leu
    690                 695                 700

Val Gln His Glu Gln Phe Ala Val Gln Gly Leu Met Arg Leu Gly Pro
705                 710                 715                 720
```

Ala Phe Asp Ile Val Arg Ala Tyr Val Val Lys Ser Ile Pro Val Ser
725 730 735

Leu Leu Leu Glu Gly Asp Asp Tyr Glu Phe Glu Leu Pro Val Glu Asp
740 745 750

His Ile Thr Phe Pro Leu Ser Leu Ser Arg Val Arg Ile His His Leu
755 760 765

Glu Met Lys Phe Val Gln Gly Ala Ala Gly Gly Ser Asp Gln Gly Thr
770 775 780

Gln Ile Val His Met Pro Ile Thr Asp Thr Gly Ser Ile Tyr Ile Leu
785 790 795 800

Leu Gln Gly Ser Arg Asn Phe His Asp Arg Asn Glu Ser Ala Ile Leu
805 810 815

His Tyr Glu Ala Ala Thr Ser Leu Asp Tyr His Phe Ala Tyr Arg Leu
820 825 830

Asp Thr Gly Ala Ser Thr Val Thr Asn Leu Pro Ser Ala Glu Phe Leu
835 840 845

Thr Thr Phe Met Arg Met Thr Pro Phe Thr Asn Trp Arg Val Arg Val
850 855 860

Ser Ala Ser Ala Glu Glu Asn Lys Gly Leu Ala Phe Pro Thr Ala Thr
865 870 875 880

Ser Ala Asp Ala Ala Thr Thr His Ile Ala Ile Thr Phe Phe Ile Ser
885 890 895

Ala Ile Arg Gln Val Ala Leu
900

<210> SEQ ID NO 93
<211> LENGTH: 892
<212> TYPE: PRT
<213> ORGANISM: Asplenium x kenzoi

<400> SEQUENCE: 93

Met His Pro Thr Gly His Asp Gly Ile Ser Ile Pro Leu Glu Gln Gly
1 5 10 15

Asp Asp Asp Tyr Ala Glu Glu Ser Arg Gln Met Ile Arg Pro Arg Phe
20 25 30

Lys Ala Asn Gly Leu Glu Leu Asp Tyr Glu Arg Ile Tyr Ala Gly Ser
35 40 45

Asn Ser Ile Ala Arg Glu Val Gly Leu Asn Lys Val Ile Cys Gly Glu
50 55 60

Val Met Ala Ile His Arg Met Phe Phe Arg Leu Asp Thr Leu Ser Gln
65 70 75 80

Glu Leu Leu Arg Gln Pro Glu Leu Val Lys Arg Leu Val Val Val Ala
85 90 95

Asp Val Val Glu Ile Glu Gly Ala Asn Ala Thr Leu Ser Leu Pro Gly
100 105 110

Ser Ser Leu Val Leu Ile Phe Cys Arg Ile Leu Ile Leu Lys Ser Arg
115 120 125

Asp Val Val Leu Asp Leu Ser Asn Trp Asp Leu Arg Val Ala Thr Thr
130 135 140

Thr Pro Leu His Arg Cys Ser Ile Arg Ala Gln Arg Val Val Val Ala
145 150 155 160

Ser Gly Ser Leu Ser Ala Ser Leu Leu Ile Gln Val Lys His Lys Phe
165 170 175

Glu Trp Ser Asp Gly Thr His Leu Asp Gln Tyr Phe Arg Arg Pro Ile

```
            180                 185                 190

Ser Phe Thr Ala Ser Arg Ile Asn Ser Ser Ala Ala Ile Thr Thr Arg
        195                 200                 205

Thr Thr Ser Ala Thr Arg Ser Ile Asn Thr Trp Pro Gly Thr Ala Pro
    210                 215                 220

Val Ser Asn Phe Ile Gln Val Asn Ser Glu Lys Phe Asn Val Leu Val
225                 230                 235                 240

Asn Ala Val Pro Trp Lys Gly Val Val Asp Cys Gln Ala Ala Leu Pro
                245                 250                 255

Ser Leu Asp Asp Leu Leu His Pro Asp Val Ile Ser Gly Ile Gln Ser
            260                 265                 270

Thr Leu Leu Ile Val Glu Thr Ile Leu Asn Phe Gln Thr Asp Asn Pro
        275                 280                 285

Asp Ile Ile Val Leu Ala Arg Gln His Ala Glu Trp Ile Val Asp Ser
    290                 295                 300

Leu Leu Gln Val Val Pro Leu Pro Asn Ser Thr Leu Gly Val Pro Glu
305                 310                 315                 320

Val Lys Thr Leu Leu Ala Arg Ala Gln Met Leu Ile Lys Leu Pro Thr
                325                 330                 335

Asp Gly Ser Gln His Leu Arg Val Pro Leu Leu Ala Tyr Gly Glu Tyr
            340                 345                 350

Gln Glu Asp Ile Glu Arg Leu Leu Arg Asn Ala Glu Ala Tyr Asp Gln
        355                 360                 365

Glu Tyr Arg Ala Leu Thr Arg Phe Val Gln Leu Val Glu Ile Ile Gly
    370                 375                 380

Ser Glu Phe Leu Gln Leu Ser Lys Thr Leu Ala Gln Arg Glu Arg Asp
385                 390                 395                 400

Ile Glu Thr Phe Glu Ser Leu Val Val Ile Arg Lys Gln Ser Glu Leu
                405                 410                 415

Asp Gln Ala Ile Arg Arg Met Asn Ser Leu Met Thr Glu Ile Glu Arg
            420                 425                 430

Arg Ser Phe Glu Met Ala Asp Ala Lys Ala Arg Met Glu Glu Gly Leu
        435                 440                 445

Gln Asp Tyr Asn Arg Arg Gln Leu Thr Arg Ala Ile Phe Gly Ile Leu
    450                 455                 460

Gly Ala Leu Leu Gln Leu Cys Ala Ser Leu Lys Phe Gly Gly Gly Ala
465                 470                 475                 480

Asp Ile Ala Gly Gly Ile Ala Thr Thr Val Pro Ala Ala Ile Asp Leu
                485                 490                 495

Ile His Ala Val Gln Asp Asp Ser Ala Ser Thr Lys Leu Leu Ala Ile
            500                 505                 510

Ser Gln Thr Leu Met Asp Leu Glu Lys Ile Val Asp Val Val Asn Ala
        515                 520                 525

Val Asn Glu Leu Val Glu Ser Ala Thr Glu Leu Glu Asp Ile Ile His
    530                 535                 540

Ala Pro Glu Leu Pro Ile Ile Leu Pro Tyr Thr Trp Asp Ile Leu Glu
545                 550                 555                 560

Asn Asp Ile Glu Glu Phe Ala Ala Leu Met Pro Ser Glu Val Ser Glu
                565                 570                 575

Val Val Thr Trp Lys Ala Lys Cys Arg Asn Leu Val Ala Val Cys Arg
            580                 585                 590

Glu Ile Cys Ile Ala Ala Ser Phe Ala Cys Glu Val Gln Tyr Glu Leu
        595                 600                 605
```

Phe Val His Ala Arg Gln Gln Glu Met Ala Arg Arg Gln Ala Glu Arg
    610                 615                 620

Leu Glu Gly Met Gln Thr Ala Ala Asp Leu Ser Ser Phe Ile Glu Leu
625                 630                 635                 640

Ala Thr Gln Ala Asp Met Arg Thr Thr Arg Leu Leu Leu Ser Leu Leu
                645                 650                 655

Asn Val Leu Ala Gly His Gln Gly Ala Leu His Tyr His Tyr Leu Met
            660                 665                 670

Glu Leu Glu Val Phe Thr Ser Ser Trp Pro Ser Val Asp Gly Val Arg
        675                 680                 685

Met His Leu Leu Gln Leu Asn Gln Arg Ala Arg Ala Arg Glu Asn Ala
    690                 695                 700

Leu Phe Gly Asp Gly Val Leu Thr Val Asp Leu Gln His Asp Tyr Val
705                 710                 715                 720

Leu Asp Ala Ile Pro Val Ser Leu Leu Leu Ser Gly Glu Asp Trp Ser
                725                 730                 735

Phe Thr Ile Asn Pro Glu Arg Asn Ala Ser Ala Phe Pro Thr Pro Trp
            740                 745                 750

Asp Tyr Val Arg Ile Arg Tyr Val Glu Met Lys Phe Thr Gly Glu His
        755                 760                 765

Leu Pro Val Thr Asp Thr Gly Glu Ile Tyr Leu Leu Leu Arg Ser Ser
    770                 775                 780

Ala Asn Phe Gln Asp Arg Leu Glu Glu Gln Val Phe Glu Tyr Glu Ala
785                 790                 795                 800

Ala Val Pro Leu Val Tyr Gln Tyr Ala Tyr Asn Leu Ser Thr Gly Glu
                805                 810                 815

Thr Thr Leu Pro Asn Leu Pro Ser Glu Ser Gly Lys Phe Phe Arg Met
            820                 825                 830

Thr Pro Phe Thr Arg Trp Arg Leu Arg Leu Ser Ala Ser Ala Tyr Gln
        835                 840                 845

Asn Glu Gly Val Ser Phe Pro Thr Ile Pro Gly Asp Pro Thr Ser Ala
    850                 855                 860

Asp Thr Pro Val Arg Ile Thr Ile Thr Phe Tyr Val Thr Ala Leu Pro
865                 870                 875                 880

Gln Ile Gln Ser Arg Ser Leu Leu Asp Met Ser Thr
                885                 890

<210> SEQ ID NO 94
<211> LENGTH: 807
<212> TYPE: PRT
<213> ORGANISM: Polypodium musifolium

<400> SEQUENCE: 94

Met Ala Asp Leu Asp Tyr Ser Lys Leu Tyr Gln Asp Leu Asn Gln Ile
1               5                   10                  15

Ser Val Arg Leu Glu Lys Thr Glu Phe Ser Glu Val Met Val Val His
            20                  25                  30

Arg Met Phe Val Arg Met Asp Asp Leu Asp Val Ser Ser Gly Ser Gly
        35                  40                  45

Leu Leu Ser Gly Ala Glu Lys Val Lys Arg Leu Tyr Val Phe Ala Asp
    50                  55                  60

Val Val Glu Leu Pro Ser Lys Gln Val Arg Leu Ala Gly Thr Asp Met
65                  70                  75                  80

Ile Val Val Phe Cys Arg Ile Phe Val Pro Glu Gly Arg His Tyr Ala

-continued

```
                85                  90                  95

Glu Leu Phe Leu Pro Ser Met Asn Met Ser Met Val Gly Ala Asp Gly
            100                 105                 110

Glu Gly Ser Ile Arg Gly Val Ile Leu Ser Pro Thr Val Leu Thr Thr
        115                 120                 125

Leu Ser Asn Ala Leu Gln Phe Arg Leu Glu Cys Gly Ser Met Thr Ser
    130                 135                 140

Val Met Arg Leu Asn Asp Val Ser Ala Gly Ala Thr Leu Thr Cys Asn
145                 150                 155                 160

Val Gln Ala Ala Ser Ala Cys Val Pro Leu Lys Val Lys Thr Thr Gly
                165                 170                 175

Thr Ser Pro Gly Asn Ile Cys Val Leu Gly Leu Ser Thr Ala Ala Val
            180                 185                 190

Val Pro Glu Ser Val Val Ala Val Ile Thr Asp Ala Asn Ile Leu Leu
        195                 200                 205

Gly Met Gln Val Thr Val Leu Ile Ala Glu Leu Val Lys Ile Ala His
    210                 215                 220

Asn Ser Asp Gly Val Ile Ala Ala Val Thr Arg His Val Glu Trp Leu
225                 230                 235                 240

Asn His Leu Leu Val Gln Ala Gln Ala Ala Ala Pro Ser Glu Asp Val
                245                 250                 255

Val Ala Leu Leu Tyr Arg Thr Gln Ala Phe Ile Lys Leu Arg Lys Glu
            260                 265                 270

Gly Leu Ile Val Pro Arg Leu Gln Tyr His Met Tyr Lys Asp Leu Ile
        275                 280                 285

Asp Arg Met Val Gln Val Ala Gln Ser Tyr Asp Gln Asp Phe Lys Gln
    290                 295                 300

Met Lys Leu Tyr Val Glu Gln Asn Lys Ile Leu Gly Ser Tyr Leu Leu
305                 310                 315                 320

Glu Gln Asn Lys Ala Phe Ala Glu Lys Glu Lys Asp Met Asp Ala Ser
                325                 330                 335

His Ser Gln Val Ile Ala Leu Arg Thr Ser Glu Leu Gln Ser Thr Ile
            340                 345                 350

Glu Arg Met Asp Asp Leu Ser Lys Gln Met Glu Val Gln Ser Thr Ala
        355                 360                 365

Met Glu Lys Ala Lys Ala Asp Met Asp Ala Gly Leu Ile Val Tyr Gln
    370                 375                 380

Asn Lys Gln Val Ala Asp Ala Val Phe Ala Val Met Glu Ala Ile Ala
385                 390                 395                 400

Ser Ile Gly Leu Ala Phe Ala Thr Gly Gly Ala Thr Ala Pro Gly Ala
                405                 410                 415

Val Ala Ser Ala Gly Ala Ala Val Ser Ala Ala Gly Lys Ala Gly Glu
            420                 425                 430

Gly Leu Lys Lys Val Val Glu Ile Leu Glu Gly Leu Gln Ala Ile Met
        435                 440                 445

Glu Val Ile Ala Ala Ile Lys Gly Leu Val Gln Ser Leu Gln Lys Ile
    450                 455                 460

Gly Gln Leu Val Asn Ala Pro Glu Met Pro Asp Leu Pro Ser Glu Ala
465                 470                 475                 480

Glu Trp Glu Met Phe Val Lys Glu Val Glu Ala Val Ala Ala Gln Met
                485                 490                 495

Pro Thr Glu Val Thr Gln Val Pro Ala Trp Thr Ala Lys Cys Lys Asn
            500                 505                 510
```

```
Val Ala Ala Leu Gly Arg Glu Met Ser Thr Thr Ala Ala His Ile Ala
        515                 520                 525

Glu Leu Gln Tyr Glu Ile Gln Val Gln Gly Met Leu Gln Gln Ile Ala
    530                 535                 540

Lys Lys Gln Ala Asp Arg Leu Ser Ser Ile Lys Pro Ala Asp Leu Thr
545                 550                 555                 560

Asn Tyr Phe Glu Met Val Ser Glu Met Asp Met Arg Thr Thr Arg Met
                565                 570                 575

Leu Leu Glu Leu Ile Gln Val Leu Asn Ile Gln Asn Gly Ala Leu Arg
            580                 585                 590

Tyr Glu Tyr Leu Gln Pro Ala Ala Pro Leu Asn Ala Trp Pro Val Thr
        595                 600                 605

Met Gln Thr Val Trp Gly Leu Leu Val Gln Gln Glu Ala Ala Ala Ile
    610                 615                 620

Asn Gly Leu Leu Gln Leu Gly Ala Pro Ser Asp Phe Thr Arg Glu Tyr
625                 630                 635                 640

Val Val Gly Asp Ile Pro Val Lys Leu Leu Leu Gly Gly Gly Asp Trp
                645                 650                 655

Glu Phe Glu Leu Pro Val Thr Asp Ala Asp Phe Pro Leu Thr Trp Cys
            660                 665                 670

Arg Val Arg Ile Gln His Val Asp Met Gln Phe Asp Ala Ala Ala Glu
        675                 680                 685

His Leu Pro Thr Thr Ser Thr Gly Glu Val Tyr Met Leu Leu Gln Ser
    690                 695                 700

Ser Arg Phe Phe Glu Asp Arg Ala Gln His Glu Asp Glu Phe Ile Ser
705                 710                 715                 720

Tyr Glu Ala Gly Thr Gly Leu Gln Tyr Gln Tyr Ala Tyr Arg Leu Ala
                725                 730                 735

Thr Gly Glu Ala Thr Val Thr Asn Val Pro Ser Glu Ala Tyr Val Asn
            740                 745                 750

Thr Phe Met Leu Leu Ala Pro Phe Thr Arg Trp Arg Leu Arg Leu Ser
        755                 760                 765

Ser Ser Ala Pro Glu Asn Lys Gly Leu Ala Phe Pro Thr Ala Thr Ser
    770                 775                 780

Ala Asp Ala Thr Thr Arg Ile Lys Ile Thr Phe His Val Ser Ala Ile
785                 790                 795                 800

Arg Arg Ile Ser Leu Ala Arg
                805
```

<210> SEQ ID NO 95
<211> LENGTH: 806
<212> TYPE: PRT
<213> ORGANISM: Polypodium punctatum 'Serratum'

<400> SEQUENCE: 95

```
Met Ala Asp Val Asp Tyr Ser Lys Leu Tyr His Asp Leu Asn Gln Ile
1               5                   10                  15

Ser Ile Arg Leu Gly Asn Val Glu Phe Ser Glu Val Met Val Val His
            20                  25                  30

Arg Met Phe Val Arg Leu Asp Asp Leu Asp Val Ser Ser Gly Ser Gly
        35                  40                  45

Leu Leu Ser Gly Ala Glu Lys Val Lys Arg Leu Tyr Val Phe Ala Asp
    50                  55                  60

Val Val Glu Leu Pro Ser Lys Gln Val Arg Leu Ala Gly Thr Asp Met
```

-continued

```
65                  70                  75                  80

Ile Val Val Phe Cys Arg Ile Phe Val Ile Asn Gly His His Gly Thr
                85                  90                  95

Glu Leu Phe Leu Pro Ser Thr Ser Met Ser Met Val Ala Ala Gly Glu
            100                 105                 110

Gly Ser Ile Arg Gly Val Ile Leu Ser Pro Thr Thr Leu Thr Pro Leu
        115                 120                 125

Ser His Ala Leu Gln Phe Lys Leu Glu Ser Gly Ser Met Thr Ser Val
    130                 135                 140

Met Arg Leu Asn Asp Val Ser Val Ala Ala Thr Leu Ala Cys Asn Val
145                 150                 155                 160

Gln Ala Ala Ser Ala Ser Met Pro Leu Lys Val Lys Thr Thr Gly Thr
                165                 170                 175

Ser Pro Gly Asn Ile Cys Val Leu Gly Met Ser Thr Asp Ala Val Val
            180                 185                 190

Pro Glu Asn Val Lys Ala Val Met Val Asp Val Asn Ile Leu Met Gly
        195                 200                 205

Met Lys Leu Thr Val Leu Ile Ala Glu Leu Val Lys Ile Ala Asn Asn
    210                 215                 220

Ser Asp Ala Val Ile Ala Ala Val Thr Arg His Val Glu Trp Leu Asn
225                 230                 235                 240

Tyr Leu Leu Val Gln Ala Leu Val Ala Ala Pro Ser Asp Asp Val Val
                245                 250                 255

Met Leu Leu Tyr Arg Thr Gln Ala Leu Ile Lys Leu Gln Lys Glu Gly
            260                 265                 270

Leu Ile Val Pro Arg Leu Gln Tyr His Lys Tyr Lys Asp Leu Ile Asp
        275                 280                 285

Arg Met Val Gln Val Ala Gln Ser Tyr Asp His Asp Phe Lys Gln Leu
    290                 295                 300

Lys Leu Tyr Val Glu Gln Asn Lys Ile Leu Gly Ser Tyr Leu Leu Asp
305                 310                 315                 320

Gln Asn Lys Ala Phe Ala Glu Lys Glu Lys Asp Met Asp Ala Ser His
                325                 330                 335

Ser Gln Leu Ile Ala Leu Arg Thr Ser Glu Leu Glu Ser Thr Ile Glu
            340                 345                 350

Arg Met Ser Asp Leu Ser Lys Gln Met Glu Val Gln Ser Lys Ala Met
        355                 360                 365

Lys Gln Ala Lys Ala Asp Met Asp Ala Gly Leu Val Glu Tyr Gln Asp
    370                 375                 380

Lys Gln Val Ala Asp Ala Val Phe Ala Val Leu Glu Ala Val Ala Ser
385                 390                 395                 400

Ile Gly Leu Ala Val Ala Thr Gly Gly Ala Ser Ala Pro Glu Ala Val
                405                 410                 415

Ala Ser Ala Gly Ala Ala Val Ser Ala Ala Gly Lys Ala Ala Glu Gly
            420                 425                 430

Leu Lys Lys Val Val Glu Val Leu Glu Gly Leu Lys Ala Val Met Glu
        435                 440                 445

Val Ile Ala Ala Ile Asn Lys Leu Val Gln Ser Ile Gln Lys Ile Gly
    450                 455                 460

Gln Leu Val Ser Ala Pro Glu Met Pro Asp Leu Pro Ser Asp Ala Lys
465                 470                 475                 480

Trp Glu Ile Phe Val Asn Glu Val Glu Ala Val Ala Ala Gln Met Pro
                485                 490                 495
```

Lys Glu Val Ser Gln Val Pro Ala Trp Thr Ala Lys Cys Lys Asn Val
500 505 510

Ala Ala Leu Gly Arg Glu Met Ser Thr Thr Ala Val His Ile Ser Glu
515 520 525

Leu Gln Tyr Glu Ile Gln Val Gln Gly Met Leu Gln Glu Ile Ala Lys
530 535 540

Lys Gln Ala Glu Arg Leu Ser Ser Ile Lys Pro Ala Asp Leu Thr Asn
545 550 555 560

Tyr Leu Glu Met Val Ser Glu Met Asp Met Arg Thr Thr Arg Met Leu
565 570 575

Val Glu Leu Ile Arg Val Leu Asn Ile Gln Asn Gly Ala Leu Arg Tyr
580 585 590

Glu Tyr Leu Gln Pro Ala Ala Pro Leu Asn Ala Trp Pro Val Thr Met
595 600 605

Gln Thr Val Trp Gly Leu Leu Val Gln Gln Glu Thr Ala Ala Ile Asn
610 615 620

Gly Leu Leu Gln Leu Gly Ala Pro Ser Asp Tyr Thr Arg Glu Tyr Val
625 630 635 640

Val Arg Asp Ile Pro Val Arg Leu Leu Leu Gly Gly Gly Asp Trp Glu
645 650 655

Phe Glu Leu Pro Val Thr Asp Asp Asp Phe Pro Leu Thr Trp Cys Arg
660 665 670

Val Arg Ile His Tyr Val Asp Met Gln Phe Asp Ala Ala Ala Glu His
675 680 685

Leu Pro Thr Thr Ser Thr Gly Glu Val Tyr Met Leu Leu Gln Ser Ser
690 695 700

Arg Phe Phe Asp Asp Arg Ala Lys His Glu Asp Glu Phe Val Ser Tyr
705 710 715 720

Glu Ala Gly Thr Gly Leu Gln Tyr Gln Tyr Ala Tyr Arg Leu Asp Thr
725 730 735

Gly Glu Ala Thr Val Thr Asn Val Pro Ser Asp Ala Tyr Val Asn Thr
740 745 750

Phe Met Leu Leu Ala Pro Phe Thr Arg Trp Arg Leu Arg Leu Ser Thr
755 760 765

Ser Ala Pro Glu Asn Lys Asp Leu Ala Phe Pro Thr Ala Thr Ser Asp
770 775 780

Asp Ala Thr Thr His Ile Lys Ile Thr Phe His Val Ser Ala Ile Arg
785 790 795 800

Arg Ile Ser Leu Ser Arg
805

<210> SEQ ID NO 96
<211> LENGTH: 854
<212> TYPE: PRT
<213> ORGANISM: Polypodium punctatum ‘Serratum’

<400> SEQUENCE: 96

Met Glu Arg Ala Val Pro Asp Tyr Ser His Met Tyr Arg Glu Leu Asn
1 5 10 15

Gln Val Ser Glu Arg Ile Arg Met Asp Gln Met Glu Phe Ser Glu Val
20 25 30

Met Val Ile His Arg Met Phe Ile Arg Leu Pro Asp Leu Ser Ile Ala
35 40 45

His Leu Asp Gly Ala Asp Lys Val Lys Arg Leu Tyr Val Phe Ala Asp

-continued

```
    50                  55                  60

Val Val Glu Leu Gly Ser Val Gln Gln Thr Ser Ser Leu Pro Gly Ser
65                  70                  75                  80

Ile Met Val Val Ile Met Cys Arg Val Leu Thr Leu His Val Asp Pro
                85                  90                  95

Ile Ala Thr Ala Tyr Gln Cys Asp Phe Pro His Met Arg Leu His Ala
            100                 105                 110

Phe Phe Gly Ser Asn Gly Val Arg Ile Asp Arg Arg Asn Ser Asp Ser
        115                 120                 125

Val His Asp Asp Tyr Pro Val Ile Thr Val Ser Ala Asn Val Ile Glu
    130                 135                 140

Phe Ser Gly Thr Arg Ala Glu Thr Leu Phe Ala Ile Ala Pro Leu Arg
145                 150                 155                 160

Asp Pro Ser Met Ile Ile Ser Ser Asp Leu Ile Ser Asn Thr Val Glu
                165                 170                 175

Arg Pro Ala Ser Gly Phe Phe Cys Asn Val Val Pro Asn Trp Gly Gln
            180                 185                 190

Pro Ser Pro Ile Thr Val Asp Pro Leu Arg Ile Arg Phe Gln Thr Gly
        195                 200                 205

Ala Thr Met Val Gly Gly Gly Ser Leu Thr Phe Pro Leu Gly Pro Glu
    210                 215                 220

Gly Phe Ser Ile Leu Gln Arg Asn Leu Pro Asp Leu Leu Leu Ile Asp
225                 230                 235                 240

Pro Asn Ile Leu Leu Cys Met Gln Thr Ser Met Leu Val Ala Glu Leu
                245                 250                 255

Val Glu Phe Ser His Pro Ser Ser Asp Ile His Ala Ala Val Thr Asp
            260                 265                 270

His Val Ala Trp Leu Asn Thr His Leu Leu Gln Ala Ser Ala Lys Ala
        275                 280                 285

Gln Gly Thr Ser Ser His Asp Asp Tyr Leu Ala Leu Ile Phe Arg Ala
    290                 295                 300

Gln Tyr Leu Leu Lys Gly Met Gly Arg Ala Arg Ser Leu Val Val Pro
305                 310                 315                 320

Gln Leu Gln Tyr Asp Val Tyr Arg Asn Leu Ile Ser Gln Met Ala Arg
                325                 330                 335

Val Ala Glu Ser Tyr Asp Gln Ser Leu Lys Gln Leu Gln Leu Phe Val
            340                 345                 350

Ala Gln Asn Lys Ile Leu Gly Gly Tyr Leu Leu Glu Gln Asn Arg Ala
        355                 360                 365

Phe Ala Ala Lys Glu Arg Asp Met Glu Val Phe His Ser Glu Leu Ile
    370                 375                 380

Ala Gln Lys Glu Leu Glu Leu Lys Asn Thr Met Val Lys Met Glu Gln
385                 390                 395                 400

Leu Ser Leu Gln Met Glu Thr Gln Ile Ala Asp Met Asp Gln Ala Lys
                405                 410                 415

Glu Asp Met Asp Ala Gly Leu Arg Arg Phe Gln Asn Arg Gln Val Ala
            420                 425                 430

Asn Ala Met Phe Ala Val Phe Arg Ala Ile Gly Ala Ile Ala Leu Thr
        435                 440                 445

Val Val Thr Ala Gly Ala Ala Ala Pro Ala Ala Met Ala Ala Ala Lys
    450                 455                 460

Gly Ala Val Thr Thr Ala Gly Gln Ala Ala Arg Gly Leu Val Arg Val
465                 470                 475                 480
```

```
Leu Glu Ile Leu Asp Asp Leu Gln Ala Ala Met Glu Val Phe Lys Leu
                485                 490                 495

Ile Lys Asp Leu Val Glu Ser Leu Arg Glu Val Gly Gln Leu Val Asp
            500                 505                 510

Ala Pro Asp Met Pro Asp Met Pro Thr Glu Ala Asp Trp Ser Ile Phe
        515                 520                 525

Val Asn Glu Ile Glu Gly Val Ala Glu Gln Met Pro Glu Glu Val Ser
    530                 535                 540

Glu Val Ser Ala Trp Lys Thr Ser Cys Lys Asn Val Ala Ala Val Gly
545                 550                 555                 560

Arg Glu Leu Met Thr Thr Ser Ala Tyr Ile Ser Gln Leu Gln Tyr Asp
                565                 570                 575

Ile Lys Val Gln Ala Leu Leu Gln Asp Ile Ala Asn Arg Gln Ala Asp
            580                 585                 590

Arg Leu Ser Ser Ile Gln Ala Ala Asp Leu Thr Ser Tyr Thr Glu Met
        595                 600                 605

Val Thr Gln Met Asp Met Arg Thr Thr Arg Leu Leu Met Glu Leu Ile
    610                 615                 620

Lys Val Leu Asp Met Gln Asn Val Ala Leu Met Tyr Gln Phe Leu Thr
625                 630                 635                 640

Pro Pro Thr Pro Met Asn Ala Trp Pro Val Thr Met Glu Thr Val Trp
                645                 650                 655

Gly Met Leu Val Gln His Glu His Ala Ala Val Leu Gly Leu Met Arg
            660                 665                 670

Leu Gly Pro Ala Phe Asp Phe Lys Arg Thr Phe Ile Val Lys Glu Ile
        675                 680                 685

Pro Val Asp Leu Leu Leu His Gly Glu Asp Trp Gln Phe Glu Ile Pro
    690                 695                 700

Val Asn Glu Arg Thr Val Phe Pro Ser Thr Trp Ser Gln Val Arg Ile
705                 710                 715                 720

His His Leu Glu Met Lys Phe Val Gly Ser Asn Asn Ile Asp His Glu
                725                 730                 735

Gly Ser His Gln Pro Ile Thr Glu Ser Gly Glu Val Tyr Ile Leu Leu
            740                 745                 750

Gln Gly Ser Arg Val Phe His Asp Arg Asn Lys Ser Glu Leu Leu His
        755                 760                 765

Tyr Glu Ala Ala Val Pro Leu Asp Tyr His Tyr Ala Tyr His Leu Glu
    770                 775                 780

Thr Gly Glu Thr Thr Leu Ser Asn Ser Pro Ser Asn Glu Phe Ile Arg
785                 790                 795                 800

Thr Phe Met Arg Met Thr Pro Phe Thr Thr Trp Arg Leu Arg Val Ser
                805                 810                 815

Ala Ser Ala Gln Glu Asn Gln Gly Leu Ala Phe Pro Thr Thr Thr Val
            820                 825                 830

Gly Ala Gly Asp Thr Thr Gln Ile Ala Val Thr Phe Ser Val Ser Ala
        835                 840                 845

Ile Arg Glu Ile Ser Leu
    850
```

<210> SEQ ID NO 97
<211> LENGTH: 896
<212> TYPE: PRT
<213> ORGANISM: Polypodium punctatum ‘Serratum’

<400> SEQUENCE: 97

Met His Pro Thr Gly His Asp Gly Ile Ser Asn Ile Pro Leu Glu Gln
1 5 10 15

Cys His Asp Asp Tyr Ala Glu Glu Arg Gln Met Lys Pro Arg Phe Glu
20 25 30

Thr Asn Gly Leu Glu Leu Asp Tyr Glu Lys Ile Tyr Ala Gly Ser Asn
35 40 45

Ser Ile Ala Arg Glu Val Gly Leu Asp Lys Val Asn Cys Gly Glu Val
50 55 60

Met Ala Ile His Gln Met Phe Phe Arg Leu Asp Thr Leu Ser Gln Glu
65 70 75 80

Leu Leu Arg Arg Pro Glu Leu Val Lys Arg Leu Ile Val Val Ala Asp
85 90 95

Val Val Glu Ile Glu Gly Ser Asn Ala Thr Leu Ser Leu Pro Gly Ser
100 105 110

Ser Leu Val Leu Ile Phe Cys Arg Ile Leu Ile Leu Lys Ser Arg Asn
115 120 125

Leu Val Leu Asp Leu Asp Asn Trp Asn Leu Arg Ala Ala Ser Thr Thr
130 135 140

Pro Leu His Arg Cys Ser Ile Arg Ala Gln Arg Val Val Ile Ala Ser
145 150 155 160

Gly Phe Ser Leu Tyr Ser Ser Leu Leu Ile Gln Val Lys His Lys Phe
165 170 175

Glu Trp Ser Asp Gly Thr His Leu Asp Gln Tyr Phe Gly Arg Pro Phe
180 185 190

Tyr Phe Thr Ala Ile Gly Ile Asn Ser Ser Ala Thr Ile Thr Thr Thr
195 200 205

Ala Thr Ser Ala Met Arg Ser Ile Asn Thr Trp Pro Gly Thr Ala Pro
210 215 220

Val Ser Asn Phe Ile Arg Val Asn Ser Glu Lys Phe Asn Val Leu Val
225 230 235 240

Asn Ala Val Pro Trp Lys Gly Val Ile Asp Cys Gln Ala Ala Leu Pro
245 250 255

Ser Leu Asp Asp Leu Leu His Pro Asp Val Ile Ser Gly Phe Gln Ser
260 265 270

Thr Leu Leu Ile Val Glu Thr Ile Leu Asn Phe Gln Thr Asp Asn Pro
275 280 285

Ala Ile Ile Ser Leu Ala Arg Gln His Ala Glu Trp Ile Leu Asp Ser
290 295 300

Leu Leu Gln Val Val Pro Leu Pro Asp Ser Thr Leu Gly Val Pro Glu
305 310 315 320

Ala Lys Thr Leu Leu Ala Arg Ala Gln Ile Leu Met Lys Leu Pro Thr
325 330 335

Asp Gly Ser Gln His Leu Arg Val Pro Leu Leu Ala Tyr Gly Glu Tyr
340 345 350

Gln Glu Asp Ile Glu Arg Leu Leu Arg Asn Ala Glu Ala Tyr Asp Gln
355 360 365

Glu Tyr Arg Glu Leu Thr Arg Phe Val Gln Leu Val Glu Ile Ile Gly
370 375 380

Ser Glu Phe Leu Gln Leu Ser Arg Ser Leu Ala Gln Arg Glu Arg Asp
385 390 395 400

Ile Glu Ala Phe Glu Ser Leu Ala Val Ile Arg Lys Gln Ser Glu Leu
405 410 415

```
Asp Gln Ala Ile Arg Arg Met Asn Ser Leu Met Pro Glu Ile Glu Arg
            420                 425                 430

Arg Ser Phe Glu Met Ala Asp Ala Lys Ala Arg Met Glu Glu Gly Leu
        435                 440                 445

Glu Asp Tyr Asn Arg Arg Gln Leu Thr Arg Ala Ile Phe Gly Ile Leu
    450                 455                 460

Gly Ala Leu Leu Gln Leu Cys Ala Ser Leu Lys Phe Gly Gly Gly Ala
465                 470                 475                 480

Asp Ile Ala Gly Gly Ile Ala Thr Thr Val Pro Ala Ala Ile Asp Leu
                485                 490                 495

Ile His Ala Val Gln Asp Thr Ser Ala Ser Thr Lys Leu Leu Ala Ile
            500                 505                 510

Ser Gln Thr Leu Met Asp Leu Glu Lys Ile Val Asp Val Val Asn Ala
        515                 520                 525

Val Asn Thr Leu Ala Glu Ser Ala Thr Glu Leu Glu Asp Ile Val His
    530                 535                 540

Ala Pro Glu Leu Pro Leu Ile Pro Pro Tyr Thr Trp Asp Ile Leu Glu
545                 550                 555                 560

Asn Asp Ile Glu Glu Phe Ala Ala Leu Met Pro Leu Glu Val Ser Glu
                565                 570                 575

Val Val Thr Trp Lys Ala Lys Cys Arg Asn Leu Val Ala Val Cys Arg
            580                 585                 590

Glu Ile Cys Ile Ala Ala Ser Phe Ala Cys Glu Val Gln Tyr Glu Leu
        595                 600                 605

Phe Val His Ala Arg Gln Gln Glu Met Ala Arg Arg Gln Ala Glu Arg
    610                 615                 620

Leu Glu Gly Met Gln Thr Ala Ala Asp Leu Ser Ser Tyr Ile Glu Leu
625                 630                 635                 640

Ala Thr Gln Ala Asp Met Arg Thr Ala Arg Leu Leu Leu Ser Leu Leu
                645                 650                 655

Asn Val Leu Ala Gly His Gln Gly Ala Leu His Tyr His Tyr Leu Met
            660                 665                 670

Glu Leu Glu Val Phe Thr Ser Ser Trp Pro Thr Val Asp Ser Val Arg
        675                 680                 685

Thr His Leu Leu Gln Leu Asn Gln Arg Ala Arg Ala Arg Glu Asn Ala
    690                 695                 700

Leu Phe Gly Asp Gly Val Leu Thr Val Asp Leu Gln His Asp Tyr Val
705                 710                 715                 720

Leu Asp Ala Ile Pro Val Ser Leu Leu Leu Ser Gly Glu Asp Trp Asn
                725                 730                 735

Phe Thr Ile Asn Pro Glu Arg Asn Ala Ser Ser Phe Pro Thr Pro Trp
            740                 745                 750

Asp Tyr Val Arg Ile Arg Tyr Val Glu Met Arg Phe Thr Gly Glu His
        755                 760                 765

Leu Pro Val Ser Glu Thr Gly Glu Ile Tyr Leu Leu Leu Arg Ser Ser
    770                 775                 780

Ala Asn Phe Gln Asp Arg Leu Glu Glu Gln Val Leu Glu Tyr Glu Ala
785                 790                 795                 800

Ala Val Pro Leu Val Tyr Gln Tyr Ala Tyr Asn Leu Ser Thr Gly Ala
                805                 810                 815

Thr Thr Leu Pro Asn Gln Pro Ser Glu Ser Gly Lys Phe Phe Arg Met
            820                 825                 830
```

Thr Pro Phe Thr Arg Trp Arg Leu Arg Leu Ser Ala Ser Ala Tyr Gln
835 840 845

Asn Gln Gly Val Ser Phe Pro Thr Leu Pro Gly Asp Pro Asn Ser Asp
850 855 860

Ser Pro Val Gln Ile Thr Ile Thr Phe Phe Val Thr Ala Leu Pro Gln
865 870 875 880

Ile Gln Ser Arg Ser Leu Asp Met Ser Asp Gly Asp Pro Thr Glu Glu
885 890 895

<210> SEQ ID NO 98
<211> LENGTH: 907
<212> TYPE: PRT
<213> ORGANISM: Polypodium punctatum 'Serratum'

<400> SEQUENCE: 98

Met Ala Ser Ile Thr Ser Gly Ala Gly Ala Asp Trp Arg Glu Leu Tyr
1 5 10 15

Ser Glu Met Asn Gln Val Ser Glu Arg Leu Arg Leu Asp Gln Leu Glu
20 25 30

Phe Ser Glu Val Met Ile Ile His Arg Met His Ile Lys Leu Ser Glu
35 40 45

Leu Asp Leu Gly His Leu Glu Gly Ala Asp Lys Val Lys His Leu Tyr
50 55 60

Val Phe Ala Asp Val Val Glu Leu Asp Asn Ala Ala Asp Pro Ser Thr
65 70 75 80

Pro Val Asp Val Arg Leu Pro Gly Ser Ile Ser Val Val Phe Leu Cys
85 90 95

Arg Val Trp His Val Ser Arg Arg Leu Thr Val Gly Val Asn Ser Pro
100 105 110

Gln Tyr Trp Leu Pro Thr Phe Asp Gly Arg Pro Val Arg Ile Gln Leu
115 120 125

Pro His Val Lys Trp His Met Asn Thr Leu Thr Arg Ser Met His Arg
130 135 140

Ile Asp Pro Glu Thr Leu Gln Asp Leu Ser Gly Pro Leu Leu Cys Val
145 150 155 160

Tyr Ala Asp Leu Leu Arg Thr Ser Leu His Pro Pro Val Gly His Ser
165 170 175

Asn Trp Asp Ala Ala Leu Ala Phe Pro Ser Met Thr Val Leu Arg Glu
180 185 190

Val Glu Val Leu Pro Cys Phe Asp His Ser Thr Pro Arg Gln Gly Leu
195 200 205

Leu Thr Leu Thr Ser Asn Ala Ala Pro Gln Trp Val Asn Gln Leu Arg
210 215 220

Ala Ala Phe Ile Phe Thr Asp Gln Asp Ala Met Thr Glu Ile Leu Ser
225 230 235 240

Leu Pro Ala Asp Ala Ser Val Ile Leu Asn Lys Asn Arg Pro Ser Ile
245 250 255

Ile Leu Thr Ala Gly Gln Ser Gly Gly Tyr Thr Asp Arg Asn Val Ser
260 265 270

Ala Pro Ala Phe Ser Val Leu Arg Glu Gly Ala Glu Thr Pro Ile Asp
275 280 285

Ser Leu Thr Asp Pro Asn Phe Leu Pro Ala Met Gln Thr Ser Met Leu
290 295 300

Ile Ala Glu Leu Val Glu Val Gly Arg Pro Ser Ala Ala Ile Ile Glu
305 310 315 320

```
Val Met His Lys His Val Glu Trp Leu Asn Asn Leu Leu Leu Gln Val
                325                 330                 335

Ile Glu Ala Lys Lys Gly Lys Asp Asp Val Glu Asp Tyr Ile Gln Leu
            340                 345                 350

Ser Tyr Arg Ser Gln Tyr Ile Leu Lys Asn Val Gly Arg Ile Asp Arg
        355                 360                 365

Phe Val Val Pro Gln Leu Gln Tyr Asp Thr Tyr Ser Pro Leu Ile Asn
    370                 375                 380

Arg Met Ala Gln Val Ala Glu Ser Tyr Asp Gln Ala Leu Arg Gln Phe
385                 390                 395                 400

Arg Leu Phe Ile Gln Gln Thr Gln Gln Asn Lys Ile Leu Gly Ala Phe
                405                 410                 415

Leu Leu Asp Gln Asn Arg Ala Phe Ala Asp Lys Glu Lys Asp Met Asp
            420                 425                 430

Ile Phe Tyr Ser Glu Leu Ile Ala Gln Arg Gln Ile Glu Leu His Asn
        435                 440                 445

Thr Leu Gln Lys Met Glu Gln Leu Ser Leu Gln Met Glu Thr Gln Ser
    450                 455                 460

Ala Asp Met Glu Gln Ala Gln Ala Asp Met Glu Ala Gly Leu Arg Arg
465                 470                 475                 480

Phe Gln Asn Glu Arg Val Ala Arg Ala Val Phe Gly Val Leu Gly Ala
                485                 490                 495

Ile Ala Ala Val Ala Leu Ala Phe Val Thr Gly Gly Ala Thr Ala Gly
            500                 505                 510

Ala Ala Ile Gly Ala Ala Lys Thr Ala Val Thr Leu Ala Gly Ala Ala
        515                 520                 525

Ala Arg Gly Leu Gln Gln Val Leu Glu Ile Leu Asp Gly Leu Gln Ala
    530                 535                 540

Val Met Glu Val Val Gly Met Ile Lys Glu Leu Phe Glu Ser Leu Gln
545                 550                 555                 560

Glu Leu Gly Gln Ala Val Asp Leu Pro Glu Met Pro Glu Met Pro Leu
                565                 570                 575

Glu Ser Asp Trp His Ile Phe Val Asn Glu Val Glu Ala Val Ala Glu
            580                 585                 590

Gln Met Pro Thr Glu Val Ser Glu Val Val Ala Trp Lys Thr Lys Cys
        595                 600                 605

Lys Asn Val Ala Val Leu Gly Arg Glu Met Ile Thr Leu Ala Thr Tyr
    610                 615                 620

Ile Ser Gln Leu Gln Tyr Asp Ile Gln Met Gln Asp Met Leu Gln Gln
625                 630                 635                 640

Ile Ala Arg Lys Gln Ala Asp Arg Leu Ser Ala Ile Gln Leu Ser Ile
                645                 650                 655

Pro Asn Thr Gly Tyr Thr Glu Met Leu Met Gln Met Asp Met Arg Thr
            660                 665                 670

Thr Arg Leu Leu Val Ala Leu Ile Arg Ala Val His Ile Gln Asn Ala
        675                 680                 685

Ala Leu Met Tyr Gln Tyr Leu Ser Glu Pro Ile Pro Val Ser Ala Trp
    690                 695                 700

Pro Val Asn Met Asp Ala Val Trp Arg Ile Leu Val Gln His Glu Gln
705                 710                 715                 720

Ser Ala Ile Gln Gly Leu Leu Arg Leu Gly Pro Ala Phe Asp Ile Glu
                725                 730                 735
```

Arg Val Phe Val Val Glu Asp Ile Pro Val Ser Leu Leu Leu Glu Gly
740 745 750

Asp Asp Tyr Glu Phe Asp Ile Pro Val Glu Asp Asn Ile Thr Phe Pro
755 760 765

Leu Ser Leu Ser Arg Val Arg Ile His His Leu Glu Met Lys Phe Val
770 775 780

Ala Ser Gly Gly Gln Lys Gln Val His Met Pro Val Thr Asp Ser Gly
785 790 795 800

Ser Val Tyr Ile Leu Leu Gln Ser Ser Arg Asn Phe His Asp Arg Asn
805 810 815

Glu Arg Ala Val Val His Tyr Glu Ala Ala Thr Ser Leu Asp Tyr His
820 825 830

Tyr Ala Tyr Asn Leu Glu Thr Gly Gln Ile Lys Val Thr Asn Gln Pro
835 840 845

Ser Ala Glu Phe Arg Lys Thr Phe Met Arg Ser Thr Pro Phe Thr Asn
850 855 860

Trp Arg Leu Arg Leu Ser Ala Ser Ala Glu Glu Asn Lys Gly Leu Ala
865 870 875 880

Phe Pro Thr Ala Thr Ser Ala Asp Ala Thr Thr Gln Ile Val Val Thr
885 890 895

Phe His Ile Ser Ala Val Arg Gln Val Ala Phe
900 905

<210> SEQ ID NO 99
<211> LENGTH: 902
<212> TYPE: PRT
<213> ORGANISM: Polypodium punctatum 'Serratum'

<400> SEQUENCE: 99

Met Ala Asn Asp Thr Ser Ser Gly Ile Val Asp Trp Arg Glu Leu Tyr
1 5 10 15

Arg Asp Met Asn Gln Ala Ser Asp Arg Ile Arg Phe Asn Gln Leu Glu
20 25 30

Phe Ser Glu Val Met Val Ile Tyr Arg Met His Ile Lys Met Ser Glu
35 40 45

Leu Asp Met Gly His Leu Glu Gly Ser Glu Lys Val Lys Arg Leu Tyr
50 55 60

Val Phe Ala Asp Val Val Glu Tyr Asp Ala Asn Gly Ile Ala Arg Leu
65 70 75 80

Pro Gly Ser Ile Ser Val Val Phe Leu Cys Arg Glu Trp His Val Ser
85 90 95

Tyr His Leu Val Ala Arg Met Asp Arg Asn Pro Pro Arg Tyr Gln Leu
100 105 110

Asp Leu Ala Gln Gly Val Ile Ile Ser Leu Pro His Met Ala Trp His
115 120 125

Leu Asp Val Arg Arg Gln Ser Met His Arg Leu Asp Pro Glu Thr Leu
130 135 140

Gln Glu Phe Leu Glu Pro Ser Phe Cys Val Tyr Ala Asp Asp Ile Ser
145 150 155 160

Val Ala Tyr Tyr Ser Leu Asn Gly Ala Ser Trp Asp Pro Ala Leu Gln
165 170 175

Phe Pro Asp Thr Ala Glu Leu Ala Lys Cys Ala Leu Leu Ile Tyr Ser
180 185 190

Asn Ser Asn Pro Thr Pro Asn His Val Leu Leu Thr Ser Asn Arg Phe
195 200 205

```
Asn Gly Thr Arg Trp Ala Phe Arg Phe Glu Phe Ser Met Tyr Tyr Ile
    210                 215                 220

Asp Asn Glu Asp Val Ala Lys Asp Ile Ala Leu Gln Pro Pro Gly Thr
225                 230                 235                 240

Arg Val Ile Phe Lys Arg Glu Gly Leu His Leu Val Val Leu Ala Met
                245                 250                 255

Asp Ser Ala Asn Arg Ile Ile Ser Phe Asp Pro Glu Arg Gly Asp Leu
            260                 265                 270

Asp Ala Tyr Met Pro Ala Phe Ser Leu Leu Arg Gln Asp Ala Lys Phe
        275                 280                 285

Pro Ile Glu Leu Leu Thr Asp Pro Asn Ile Leu Ser Ala Met Gln Thr
    290                 295                 300

Ser Met Leu Ile Gly Glu Leu Val Glu Val Gly Asn Pro Ser Thr Ala
305                 310                 315                 320

Val Thr Glu Val Val His Lys His Val Lys Trp Leu Ser Lys Leu Leu
                325                 330                 335

His Gln Val Ile Glu Glu Lys Asn Gly Lys Asp Val Glu Asp Tyr Ile
            340                 345                 350

Gly Leu Ser Phe Arg Ala Gln Tyr Val Ile Lys Lys Val Gly Arg Ile
        355                 360                 365

Arg Gly Leu Val Val Pro Gln Leu Gln Tyr Asp Val Tyr Ser Asn Leu
    370                 375                 380

Ile Asn Arg Met Ala Gln Val Ala Glu Ser Tyr Asp Gln Ala Leu Arg
385                 390                 395                 400

Gln Phe Arg Leu Phe Ile Gln Asn Asn Lys Ile Leu Gly Gly Phe Leu
                405                 410                 415

Leu Glu Gln Asn Arg Ala Phe Ala Glu Lys Glu Lys Asp Met Asp Val
            420                 425                 430

Phe Tyr Ser Glu Leu Ile Thr Gln Arg Gln Ile Glu Leu Asp Asn Thr
        435                 440                 445

Leu Gln Lys Leu Lys Arg Leu Ser Leu Gln Met Glu Thr Gln Gln Ala
    450                 455                 460

Asp Met Glu Gln Ala Gln Ala Asp Met Glu Ala Gly Leu Arg Arg Phe
465                 470                 475                 480

Gln Asn Arg Gln Ala Ala Arg Ala Leu Phe Ala Val Leu Gly Ala Ile
                485                 490                 495

Ala Ala Val Gly Leu Ala Phe Leu Thr Gly Gly Ala Thr Ala Pro Ala
            500                 505                 510

Ala Leu Gly Ala Ala Arg Thr Ala Val Thr Val Ala Gly Ser Val Val
        515                 520                 525

Ser Gly Leu Gln Arg Val Leu Glu Val Leu Glu Gly Leu Gln Ala Val
    530                 535                 540

Met Glu Ile Val Val Ile Ile Lys Asp Leu Phe Ser Ala Leu Gln Asp
545                 550                 555                 560

Leu Thr Gln Ala Val Asp Leu Pro Asp Met Pro Glu Met Pro Leu Gln
                565                 570                 575

Ser Asp Trp Leu Ile Phe Val Asn Glu Val Glu Ala Val Ala Gln Gly
            580                 585                 590

Met Pro Thr Glu Val Ser Glu Val Val Ala Trp Lys Thr Lys Cys Lys
        595                 600                 605

Asn Val Ala Val Leu Gly Gln Glu Met Thr Thr Thr Ala Ala Tyr Ile
    610                 615                 620
```

Ser Gln Leu Gln Tyr Asp Ile Met Met Gln Asp Met Leu Gln Gln Ile
625 630 635 640

Ala Arg Arg Gln Ala Asp Arg Leu Ser Ala Ile Gln Leu Pro Asp Leu
645 650 655

Thr Asn Phe Thr Glu Met Val Ile Gln Met Asp Met Arg Thr Thr Arg
660 665 670

Ile Leu Val Ala Leu Ile Lys Val Met Tyr Ile Gln Asn Ala Ala Leu
675 680 685

Met Tyr Gln Tyr Leu Ser Glu Pro Thr Pro Val Ser Ala Trp Pro Val
690 695 700

Asn Met Asp Thr Val Trp Arg Met Leu Val Gln His Glu Gln Leu Ala
705 710 715 720

Ile Gln Gly Leu Leu Arg Leu Gly Pro Ala Phe Asp Ile Val Arg Thr
725 730 735

Phe Val Val Lys Ser Ile Pro Val Arg Leu Leu Leu Asp Gly Asp Asp
740 745 750

Tyr Gln Phe Glu Ile Pro Val Glu Asp Pro Leu Thr Phe Pro Leu Ser
755 760 765

Leu Ser Arg Val Arg Ile His His Leu Glu Met Lys Ile Val Gln Gly
770 775 780

Ala His Val His Thr Pro Ile Thr Ala Thr Gly Lys Ile Tyr Ile Leu
785 790 795 800

Leu Gln Gly Ser Arg Asn Phe His Asp Arg Asn Glu Gly Lys Ile Met
805 810 815

His Tyr Glu Ala Ala Thr Ala Leu Asp Tyr Gln Tyr Ala Tyr Gln Leu
820 825 830

Asp Thr Gly Glu Thr Thr Val Thr Asn Leu Pro Ser Ala Glu Phe Leu
835 840 845

Arg Thr Phe Thr Arg Met Thr Pro Phe Thr Asn Trp Arg Leu Arg Leu
850 855 860

Ser Ala Ser Ala Asp Glu Asn Glu Gly Leu Ala Phe Pro Thr Ala Thr
865 870 875 880

Ser Ala Asp Ala Thr Thr Glu Ile Ala Ile Thr Phe His Ile Ser Ala
885 890 895

Ile Arg Arg Ile Ser Asp
900

<210> SEQ ID NO 100
<211> LENGTH: 886
<212> TYPE: PRT
<213> ORGANISM: Polypodium punctatum ‘Serratum’

<400> SEQUENCE: 100

Met Glu Tyr Ser Ser Leu Tyr Gly Asp Val Asn Gln Val Ser Leu Arg
1 5 10 15

Phe Gln Asn Met Glu Phe Ser Glu Val Met Val Val His Arg Met His
20 25 30

Val Arg Leu Glu Glu Leu Asp Met Thr Gly Leu Glu Gly Ile Glu Lys
35 40 45

Val Lys Arg Leu Tyr Val Leu Ala Asp Val Val Glu Leu Pro Ser Thr
50 55 60

Ala Thr Gln Val Phe Gln Tyr Leu Arg Leu Pro Ala Ser Ile Ser Ala
65 70 75 80

Ile Ile Leu Cys Arg Val Leu Tyr Ile Pro Glu Val Asp Gln Arg Pro
85 90 95

```
His Met Ala Gln Cys Ser Leu Asp Phe Pro Phe Met Arg Leu His Val
            100                 105                 110

Val Gly Ser Ala His Glu Asn Gly Gly Gly Val Met Gln Ala Phe Ser
        115                 120                 125

Ser Asp Ala Thr Pro Ser Asn Ile Gly Ile Tyr Phe His Ala Asp Arg
    130                 135                 140

Phe Ile Tyr Arg Gln Ala Thr Ser Ser Ala Ser Asn Phe Val Leu Pro
145                 150                 155                 160

Leu Asp Val Arg Val Ser Phe Gly Ser Ser Thr Phe Ser Ala Pro Thr
                165                 170                 175

Leu Arg Pro Asp Trp Gln Asn Leu Asn Val Ser Asn Ile Gln Tyr Gly
            180                 185                 190

Pro Gln His Leu Ser Arg Gly Pro Pro Leu Thr Ser Ser Asp Ser Asp
        195                 200                 205

Leu Gln Arg Ser Asp Glu Ile Glu Leu Leu Ala Gln Gln Asp Val Trp
    210                 215                 220

Ser Pro Leu Leu His Val Ala Phe Ser Pro Asn Ala Pro Pro Gly Asn
225                 230                 235                 240

Ile Pro Gly Thr Gln Gly Ile Phe Arg Pro Ser Ser Ala Cys Ser Phe
                245                 250                 255

Phe His Val Pro Pro Pro Asp Val Pro Ala Asn Val Leu Thr Asp Pro
            260                 265                 270

Ser Ile Ile Leu Gly Met Gln Met Asn Met Leu Ile Ala Glu Leu Val
        275                 280                 285

Leu Ala Ala His Asn Ser Pro Gln Val Met Asn Val Ile Thr Lys His
    290                 295                 300

Val Leu Trp Leu Asn Lys Ile Leu Leu Gln Val Ala Ser Pro Asn Asp
305                 310                 315                 320

Asp Ile Leu Ala Leu Leu Phe Arg Ile Gln Ala Phe Met Lys Met Ala
                325                 330                 335

Lys Glu Pro Arg Phe Val Val Pro Arg Leu Gln Tyr His Met Tyr Gly
            340                 345                 350

Ser Leu Ile Asn Arg Met Val Gln Val Ala Gln Asn Tyr Asp Gln Glu
        355                 360                 365

Phe Lys Gln Leu Lys Leu Phe Ile Ala Gln Asn Lys Ile Leu Gly Ser
    370                 375                 380

Tyr Leu Leu Gln Gln Asn Arg Ala Phe Ala Glu Arg Glu Arg Glu Met
385                 390                 395                 400

Ser Ala Phe His Ser Gln Val Val Ser Met Arg Arg Ser Glu Leu Gln
                405                 410                 415

Ser Ala Ile Gln Thr Met Asp Asn Leu Ser Leu Gln Met Glu Ser Glu
            420                 425                 430

Ser Glu Ala Met Asn Glu Ala Gln Glu Asn Met Val Glu Ala Ile Gln
        435                 440                 445

Glu Tyr Glu Arg Lys Leu Leu Ala Arg Ala Leu Phe Ser Val Ile Gly
    450                 455                 460

Ala Ile Ala Ser Val Ala Leu Ala Phe Ala Thr Gly Gly Ala Thr Ala
465                 470                 475                 480

Pro Gly Ala Val Ala Ala Ala Gly Gly Ala Val Ala Ala Ala Gly Arg
                485                 490                 495

Leu Ala Ala Gly Leu Gln Lys Val Val Asp Ile Leu Gln Gly Leu Gln
            500                 505                 510
```

```
Ala Val Met Glu Val Val Val Ala Ile Arg Asp Ile Val Glu Ser Leu
        515                 520                 525

Lys Asn Met Gly Gln Leu Val Glu Ala Pro Glu Met Pro Glu Met Pro
    530                 535                 540

Thr Asp Ala Asp Trp Leu Ile Phe Val Asn Glu Val Glu Ala Val Ala
545                 550                 555                 560

Glu Gln Val Pro Thr Glu Val Ala Glu Val Pro Val Trp Lys Ala Lys
                565                 570                 575

Cys Lys Asn Val Ala Val Leu Gly Gln Ala Met Cys Thr Thr Ala Ala
            580                 585                 590

Tyr Ile Ser Glu Leu Gln Tyr Gln Ile Thr Val Glu Glu Met Leu Gln
        595                 600                 605

Glu Ile Ala Gln Arg Gln Ala Asp Arg Leu Val Gly Ile Ser Ala Ala
    610                 615                 620

Asp Leu Ser Ser Tyr Thr Glu Met Ala Ser Gln Ile Asp Met Arg Thr
625                 630                 635                 640

Thr Arg Ile Leu Leu Glu Leu Ile Lys Met Leu Tyr Ile Gln Asn Ala
                645                 650                 655

Ala Ile Lys Tyr Glu Tyr Leu Tyr Asp Ala Asn Glu Lys Leu Asn Ser
            660                 665                 670

Trp Pro Val Ser Met Glu Thr Val Trp Thr Met Leu Leu Gln Gln Glu
        675                 680                 685

Asn Ala Ala Leu Leu Gly Leu Leu Asp Leu Gly Pro Thr Asn Asp Phe
    690                 695                 700

Thr Val Thr Tyr Ala Val Lys Asp Ile Pro Thr Lys Leu Leu Val Asp
705                 710                 715                 720

Gly Phe Asp Trp Asn Phe Glu Ile Ala Val Glu Asp Phe Ala Ile Phe
                725                 730                 735

Pro Ser Gly Leu Ser Arg Val Arg Ile Arg Tyr Val Glu Leu Lys Phe
            740                 745                 750

Asp Gln Gln Gly Ala Asp Ser Ser Asn Ile Val Ile His Gln Pro Ser
        755                 760                 765

Thr Asn Thr Gly Leu Val Tyr Met Leu Leu Gln Gly Ser Arg Phe Val
    770                 775                 780

His Asp Arg Lys Arg Gln Glu Val Met Asp Tyr Glu Ala Ser Thr Gly
785                 790                 795                 800

Pro Val Tyr Ala Tyr Ala Tyr Asp Leu Asn Thr Gly Ala Thr Thr Leu
                805                 810                 815

Asn Asn Ile Pro Ser Gln Gln Gln Ala Asn Thr Phe Met Gln Met Thr
            820                 825                 830

Pro Phe Asn Ala Trp Arg Leu Arg Leu Ser Ala Ser Ala Ala Glu Asn
        835                 840                 845

Gln Gly Leu Val Phe Pro Thr Ala Thr Ser Pro Asp Asn Thr Thr Gln
    850                 855                 860

Ile Ser Ile Thr Phe Tyr Val Thr Ala Ile Arg Arg Ile Asp Leu Arg
865                 870                 875                 880

Gln Glu Gly Asp Val Glu
                885
```

<210> SEQ ID NO 101
<211> LENGTH: 813
<212> TYPE: PRT
<213> ORGANISM: Adiantum pedatum

<400> SEQUENCE: 101

```
Met Ala Asp Ile Asp Tyr Ser Val Leu Tyr Asn Asp Val Asn Gln Ile
1               5                   10                  15

Ser Ile Arg Leu Glu Arg Met Asp Phe Ser Glu Val Met Ala Val His
            20                  25                  30

Arg Met Phe Val Arg Met Asp Asp Leu Asp Val Ser Ser Gly Thr Gly
        35                  40                  45

Val Leu Glu Gly Ala Gln Asn Val Lys Arg Leu Tyr Val Phe Ala Asp
    50                  55                  60

Val Val Glu Leu Pro Ser Lys Gln Val Arg Leu Pro Gly Ser Asp Met
65                  70                  75                  80

Ile Val Ile Leu Cys Arg Ile Phe Val Arg Asn Gly Arg His Asn Thr
                85                  90                  95

Glu Leu Phe Leu Pro Ser Met Asn Met Ser Met Val Ala Ala Gly Asn
            100                 105                 110

Gly Thr Ile Arg Gly Val Asn Leu Ser Thr Thr Met Ser Ser Ser Ser
        115                 120                 125

Ser Asn Ala Leu Gln Phe Asn Leu Arg Ser Gly Ser Met Thr Ser Thr
    130                 135                 140

Val Arg Leu Lys Asp Val Asp Val Ala Ala Ala Leu Thr Cys Asp Val
145                 150                 155                 160

Gln Ala Ala Ser Ala Ser Met Pro Leu Thr Val Met Thr Thr Gly Thr
                165                 170                 175

Ser Pro Gly Asn Ile Trp Val Leu Gly Met Thr Thr Ala Val Val Ile
            180                 185                 190

Pro Glu Ser Ala Val Ala Val Ile Thr Asp Ala Asn Ile Leu Leu Gly
        195                 200                 205

Met Gln Val Thr Val Leu Ile Ala Glu Leu Val Lys Thr Ala His Asn
    210                 215                 220

Ser Asp Val Ile Ile Ala Ala Ile Thr Arg His Val Glu Trp Leu Asn
225                 230                 235                 240

His Leu Leu Val Gln Ala His Ala Ala Ala Pro Asn Glu Asp Val Ile
                245                 250                 255

Thr Leu Leu Tyr Arg Thr Gln Ala Phe Ile Lys Leu Lys Arg Glu Gly
            260                 265                 270

Leu Val Val Pro Arg Leu Gln Tyr His Met Tyr Lys Asn Leu Ile Asp
        275                 280                 285

Arg Met Val Gln Val Ala Gln Asn Tyr Asp Gln Asp Phe Arg Gln Leu
    290                 295                 300

Lys Leu Phe Val Glu Gln Asn Lys Ile Leu Gly Ser Tyr Leu Leu Glu
305                 310                 315                 320

Gln Asn Lys Ala Phe Ala Glu Lys Glu Lys Asp Met Asp Ala Phe His
                325                 330                 335

Ser Gln Ile Ile Ala Leu Arg Thr Thr Glu Leu Asn Asn Thr Ile Glu
            340                 345                 350

Arg Met Gly Glu Leu Ser Lys Gln Met Asp Gln Glu Asn Glu Ala Met
        355                 360                 365

Glu Gln Ala Lys Ala Asp Met Asp Ala Gly Leu Ile Glu Tyr Gln Asn
    370                 375                 380

Arg Gln Val Ala Asn Ala Leu Phe Ala Val Leu Gly Ala Ile Ala Ser
385                 390                 395                 400

Ile Gly Leu Ala Phe Ala Thr Gly Gly Ala Thr Ala Pro Gly Ala Val
                405                 410                 415
```

```
Ser Ala Ala Gly Ala Ala Val Thr Ala Ala Gly Lys Ala Ala Glu Gly
            420                 425                 430

Leu Lys Lys Val Val Glu Ile Leu Glu Gly Leu Gln Val Val Met Glu
        435                 440                 445

Val Val Ala Ala Ile Lys Glu Leu Val Gln Ser Leu Gln Gln Ile Gly
    450                 455                 460

Gln Leu Val Asp Ala Pro Glu Met Pro Asp Leu Pro Ser Asn Ala Asp
465                 470                 475                 480

Trp Glu Ile Phe Val Asn Glu Val Glu Ala Val Ala Glu Gln Met Pro
                485                 490                 495

Thr Glu Val Thr Gln Val Ala Ala Trp Lys Ala Lys Cys Lys Asn Val
            500                 505                 510

Ala Ala Leu Gly Arg Glu Met Ser Thr Met Ala Ala His Ile Ala Glu
        515                 520                 525

Leu Gln Tyr Gln Ile Gln Val Gln Glu Met Leu Arg Glu Ile Ala Gln
    530                 535                 540

Lys Gln Ala Asp Arg Leu Ser Ser Ile Ser Pro Ala Asp Leu Thr Asn
545                 550                 555                 560

Tyr Leu Glu Met Val Ser Gln Met Asp Met Arg Thr Thr Arg Met Leu
                565                 570                 575

Leu Glu Leu Ile Arg Val Leu Tyr Ile Gln Asn Ala Ala Leu Gln Tyr
            580                 585                 590

Glu Tyr Leu Gln Thr Pro Ala Pro Leu Asn Ala Trp Pro Val Ala Met
        595                 600                 605

Gln Thr Val Trp Gly Leu Leu Ile Gln Gln Glu Thr Thr Ala Ile Thr
    610                 615                 620

Gly Leu Leu Gln Leu Gly Ala Pro Ser Asp Phe Thr Gln Glu Tyr Val
625                 630                 635                 640

Val Lys Asp Ile Pro Val Ser Leu Leu Leu Glu Gly Arg Asp Trp Glu
                645                 650                 655

Phe Glu Leu Pro Val Leu Asn Ala Asp Phe Pro Ser Thr Trp Ser Arg
            660                 665                 670

Val Arg Ile His His Val Asp Met Gln Phe Asp Ala Ala Ala Thr Ser
        675                 680                 685

Ile His Ile Pro Thr Thr Asn Thr Gly Val Val Tyr Leu Leu Leu Gln
    690                 695                 700

Ser Ser Arg Phe Phe Asp Asp Arg Ala Arg Arg Ala Asn Glu Phe Ile
705                 710                 715                 720

Ser Tyr Glu Ala Gly Thr Gly Leu Phe Tyr Gln Tyr Ala Tyr Arg Leu
                725                 730                 735

Ala Thr Gly Glu Ala Thr Val Thr Asn Ile Pro Thr Asp Glu Tyr Ala
            740                 745                 750

Asn Thr Phe Met Arg Leu Thr Pro Phe Thr Arg Trp Arg Leu Arg Leu
        755                 760                 765

Ser Leu Ser Ala Glu Glu Asn Ala Gly Leu Ala Phe Pro Thr Ala Thr
    770                 775                 780

Ser Ala Asp Asp Thr Thr Gln Ile Lys Ile Thr Phe His Val Ser Ala
785                 790                 795                 800

Ile Arg Arg Ile Ser Thr Arg Ser Asp Gly Val Ser Ser
                805                 810
```

<210> SEQ ID NO 102
<211> LENGTH: 882
<212> TYPE: PRT

```
<213> ORGANISM: Adiantum pedatum

<400> SEQUENCE: 102

Met Ala Ala Ala Ala Arg Glu Tyr Ser Glu Leu Tyr Lys Asp Leu Asn
1               5                   10                  15

Gln Ile Ser Glu Arg Ile Arg Leu Asp Gln Met Glu Phe Ser Glu Val
            20                  25                  30

Met Val Ile His Arg Met Phe Ile Arg Leu Glu Glu Leu Asp Leu Gly
        35                  40                  45

His Leu Glu Gly Ala Glu Arg Val Lys Arg Leu Tyr Val Phe Ala Asp
    50                  55                  60

Val Val Glu Val Glu Glu Gly Gly Asn Phe Ile Glu Thr Gly Pro Leu
65                  70                  75                  80

Ala Arg Leu Pro Gly Ser Ile Met Val Val Ile Leu Cys Arg Val Leu
                85                  90                  95

Ser Val Arg Val Leu Met Phe Asp Asn Gly Asn Asn Ala Met Arg Leu
            100                 105                 110

Gln Leu Pro His Met Lys Leu Arg Val Val Glu Ile Thr Thr Gln Pro
        115                 120                 125

Thr Thr Lys Leu Gln Ile His Arg Ala Asp Ala Glu Asp Tyr Gln Tyr
    130                 135                 140

Pro Ala Leu Cys Ile His Ala Asp Val Ile Gln Ala Ser Ile Arg Leu
145                 150                 155                 160

Ser Ser Ser Ser Asn Arg Pro Pro Met Asp Leu Arg Phe Phe Asn Phe
                165                 170                 175

Arg Pro Asn Arg Gly Ser Asp Asn Val Val Phe Ser Ser Glu Ser Arg
            180                 185                 190

Ser Leu Ile Asp Glu Pro Val Glu Ile Phe Tyr Val Tyr Ser His Ile
        195                 200                 205

Pro Arg Phe Ile His Ala Leu Pro Ile Pro Glu Ala Ala Thr Val Asp
    210                 215                 220

Pro Ala Ser Arg Ser Asn Asp Trp Tyr Tyr Val Ser Leu Arg Arg Val
225                 230                 235                 240

Asn Ser Thr Leu Ser Ser Ser Val Ala Ala Glu Gly Glu Leu Glu Pro
                245                 250                 255

Ala Phe Ser Leu Leu Lys Pro Lys Ile Pro Val Val Val Leu Thr Asp
            260                 265                 270

Pro Asn Ile Leu Leu Ala Met Gln Thr Ser Leu Leu Ile Ala Glu Leu
        275                 280                 285

Val Glu Val Ala His Pro Ser Ala Glu Thr Ala Asp Ala Val Ala Lys
    290                 295                 300

His Val Glu Trp Leu Asn Lys Ile Leu Leu Gln Ala Thr Lys Val Glu
305                 310                 315                 320

Gly Ile Leu Asn Ser Ser His Asp Glu His Leu Ala Leu Leu Phe Arg
                325                 330                 335

Ala Gln Tyr Leu Met Lys Met Arg Pro Gly Arg Thr Arg Asn Leu Val
            340                 345                 350

Val Pro Gln Leu Gln Tyr Asp Val Tyr Ser Asn Leu Val Asn Arg Met
        355                 360                 365

Ala Gln Val Ala Glu Ser Tyr Asp Gln Ser Leu Arg Gln Phe Lys Leu
    370                 375                 380

Phe Ile Asp Gln Asn Lys Ile Leu Gly Ser Tyr Leu Leu Gln Gln Asn
385                 390                 395                 400
```

```
Lys Ala Phe Ala Asp Lys Glu Arg Asp Met Asp Val Phe His Ser Glu
                405                 410                 415

Leu Ile Ser Gln Arg Lys Ile Glu Leu Asp Asn Thr Ile Leu Lys Met
            420                 425                 430

Asp Gln Leu Ser Leu Gln Met Glu Ser Gln Arg Glu Asp Met Asp Gln
        435                 440                 445

Ala Lys Lys Asp Met Asp Ala Gly Leu Arg Glu Phe Gln Asn Arg Gln
    450                 455                 460

Val Ala Asn Ala Met Phe Ala Val Ile Gly Ala Ile Ala Ala Ile Gly
465                 470                 475                 480

Leu Ala Phe Ile Thr Gly Gly Ala Thr Ala Pro Ala Ala Val Gly Ala
                485                 490                 495

Ala Lys Thr Ala Val Thr Ala Ala Gly Ala Ala Ala Arg Ala Leu Glu
            500                 505                 510

Arg Val Val Glu Ile Leu Asp Ser Leu Gln Ala Val Met Glu Ile Val
        515                 520                 525

Ser Ile Ile Lys Glu Leu Val Ser Ser Leu Gln Glu Ile Gly Gln Leu
    530                 535                 540

Val Glu Ala Pro Asp Met Pro Pro Met Pro Thr Glu Ala Asp Trp Phe
545                 550                 555                 560

Ile Phe Glu Asn Glu Ile Glu Gly Val Ala Glu Gln Met Pro Thr Glu
                565                 570                 575

Val Ser Glu Val Ser Ala Trp Lys Thr Lys Cys Lys Asn Val Ala Val
            580                 585                 590

Leu Gly Arg Glu Met Ile Thr Thr Ala Thr Tyr Ile Ser Glu Leu Gln
        595                 600                 605

Tyr Asp Ile Lys Val Gln Gly Met Leu Gln Glu Ile Ala Thr Ser His
    610                 615                 620

Ala Asn Arg Leu Ser Ser Ile Gln Ala Thr Asp Leu Ser Asn Tyr Thr
625                 630                 635                 640

Glu Met Val Thr Gln Met Asp Met Arg Thr Thr Arg Met Leu Val Ala
                645                 650                 655

Leu Ile Asn Val Val His Met Gln Asn Ala Ala Leu Met Tyr Gln Cys
            660                 665                 670

Leu Ser Pro Pro Thr Tyr Val Asn Ala Trp Pro Val Thr Met Glu Thr
        675                 680                 685

Val Trp Ser Met Leu Val Gln His Glu His Ala Ala Val Leu Gly Leu
    690                 695                 700

Met Arg Leu Gly Pro Ser Phe Asp Phe Met Arg Thr Tyr Val Val Glu
705                 710                 715                 720

Gly Ile Pro Val Gln Leu Leu Leu Asp Gly Glu Asp Trp Glu Phe Glu
                725                 730                 735

Ile Ser Val Glu Asp Tyr Thr Thr Phe Pro Ser Thr Trp Ser Arg Val
            740                 745                 750

Arg Ile His His Leu Glu Met Lys Phe Val Gln Ala Ala Asp Val His
        755                 760                 765

Gln Pro Ile Thr Asp Thr Gly Lys Val Tyr Met Leu Leu Gln Gly Ser
    770                 775                 780

Arg Ile Phe Arg Asp Arg Asn Arg Ala Asp Ala Ile Arg Tyr Glu Ala
785                 790                 795                 800

Ala Met Ser Leu Asp Tyr His Tyr Ala Tyr Arg Leu Asp Thr Gly Glu
                805                 810                 815

Thr Thr Leu Ser Asn Leu Pro Ser Gln Asp Phe Thr Arg Thr Phe Met
```

```
            820                 825                 830

Arg Met Thr Pro Phe Thr Asn Trp Arg Leu Arg Leu Ser Ala Ser Ala
        835                 840                 845

Glu Glu Asn Lys Gly Leu Gly Phe Pro Thr Ala Thr Ser Ala Gly Ser
    850                 855                 860

Thr Thr Gln Ile Ala Ile Ile Phe Tyr Ile Ser Ala Ile Arg Arg Ile
865                 870                 875                 880

Ser Leu


<210> SEQ ID NO 103
<211> LENGTH: 888
<212> TYPE: PRT
<213> ORGANISM: Adiantum pedatum

<400> SEQUENCE: 103

Met Glu Tyr Ser Ala Leu Tyr Gly Asp Val Asn Gln Val Ser Leu Arg
1               5                   10                  15

Phe Glu Lys Thr Glu Phe Ser Glu Val Val Val Val His Arg Met His
            20                  25                  30

Val Arg Leu Ala Glu Leu Asn Val Thr Leu Gly Asp Asn Asn Ile Leu
        35                  40                  45

Leu Gln Gly Ser Asp Arg Val Lys Arg Leu Tyr Val Leu Ala Asp Val
    50                  55                  60

Val Glu Leu Pro Pro Ile Phe Ser Thr Ser Met Ser Leu Pro Gly Thr
65                  70                  75                  80

Val Ser Val Val Ile Leu Cys Arg Ile Leu Tyr Leu Pro Tyr Leu Glu
                85                  90                  95

Asp Ala Ser Ser Ala Ser Gly Trp Ala Val His Ala Ala Leu Leu Arg
            100                 105                 110

Leu Arg Val Val Glu Met His Ala Gly Phe Ala Gln Val Phe Thr Ile
        115                 120                 125

Pro Ala Asn Asp Ser Ser Ala Ala Ala Pro Ala Asp Ile Gly Leu Tyr
    130                 135                 140

Ile His Ala Asp Arg Ile Ile Tyr Arg Asp Asp Pro Gly Arg Ser Ile
145                 150                 155                 160

Pro Val Ile Glu Val Arg Val Gly Gly Asp Ser Arg Phe Ser Pro Phe
                165                 170                 175

Leu Pro Gly Ser Pro Glu Ile Arg Leu Ser Ser Val Gln Tyr Val Arg
            180                 185                 190

Glu Phe Ser Lys Gly Gln Pro Val Ala Pro Glu Asp Ser Glu Leu Gln
        195                 200                 205

Arg Ser Asp Glu Ile Glu Leu Ile Ala Pro Ser Gly Ser Glu Gln Gln
    210                 215                 220

Leu Arg Ala Ala Phe Gly Ala Ser Val Gly Met Asn Leu Leu Phe His
225                 230                 235                 240

Phe Ser Ser Ser Phe Asp Ile Leu Ser Leu Asp Pro Val Pro Ala Ala
                245                 250                 255

Leu Leu Thr Asp Pro Asn Ile Ile Thr Gly Met Gln Met Asn Met Leu
            260                 265                 270

Ile Ala Glu Leu Val Leu Thr Ala Ala His Asn Ser Pro Gln Leu Ile
        275                 280                 285

Lys Val Val Thr Arg His Val Glu Trp Leu Asn Lys Met Phe Leu Gln
    290                 295                 300

Leu Ala Ser Pro Asn Asp Asp Ile Leu Ala Leu Leu Phe Arg Val Gln
```

-continued

```
305                 310                 315                 320

Ala Tyr Gln Lys Met Ala Lys Gln Pro His Pro Val Val Pro Arg Met
                325                 330                 335

Arg Tyr Ser Arg Tyr Glu Gly Leu Ile Asn Gln Met Val Gln Ile Ala
            340                 345                 350

Gln Ser Tyr Asp Gln Asp Leu Lys Gln Leu Lys Leu Phe Ile Ala Gln
        355                 360                 365

Asn Glu Ile Leu Gly Ser Tyr Leu Leu Glu Gln Asn Lys Ala Phe Ala
    370                 375                 380

Ala Lys Glu Lys Ser Met Ser Glu Phe His Leu Gln Val Ser Asp Leu
385                 390                 395                 400

Arg Arg Ser Glu Leu Asn Asp Ala Ile Gln Lys Met Thr Gly Leu Gly
                405                 410                 415

Glu Glu Met Glu Val Glu Lys Glu Ala Met Asp Gln Ala Tyr Lys Asp
            420                 425                 430

Met Glu Gln Gly Leu Gln Glu Tyr Glu Lys Arg Gln Ile Val Thr Ala
        435                 440                 445

Val Phe Ala Val Ile Ser Ala Ile Ser Leu Cys Ala Leu Gly Phe Val
    450                 455                 460

Thr Gly Gly Ala Thr Val Ala Ala Val Pro Gly Ala Val Ala Asn Ala
465                 470                 475                 480

Ala Gln Ala Val Ser Ala Ala Val Ser Leu Ala Asn Lys Leu Gln Lys
                485                 490                 495

Val Met Gly Ile Leu Glu Ile Ile Asn Gln Val Val Gln Thr Ala Ala
            500                 505                 510

Ala Ile Lys Glu Val Ile Glu Leu Phe Asp Asn Met Gly Gln Leu Leu
        515                 520                 525

Glu Ala Pro Glu Met Pro Glu Met Pro Ser Asn Tyr Asp Trp Leu Ile
    530                 535                 540

Phe Val Asn Glu Val Glu Ala Met Ala Glu Gln Leu Pro Val Glu Val
545                 550                 555                 560

Asn Glu Arg Ile Val Trp Lys Ala Lys Cys Lys Asn Val Ala Val Leu
                565                 570                 575

Gly Gln Glu Met Cys Thr Thr Gly Ser His Ile Ala Asp Leu Gln Tyr
            580                 585                 590

Gln Ile Lys Val Glu Glu Met Leu Arg Glu Ile Ala Gln Ser Gln Ala
        595                 600                 605

Glu Arg Leu Glu Gly Ile Ser Ser Ala Asp Leu Ser Ser Tyr Thr Glu
    610                 615                 620

Met Val Ser Gln Ile Asp Met Arg Thr Thr Arg Leu Leu Phe Gln Leu
625                 630                 635                 640

Ile Lys Val Leu His Ile Gln Asn Ala Ala Leu Lys Tyr Glu Tyr Leu
                645                 650                 655

Tyr Ala Ala Asp Glu His Leu Val Ser Trp Pro Val Ser Met Glu Thr
            660                 665                 670

Val Trp Thr Met Leu Leu Gln Gln Gln Arg Leu Ser Leu Leu Gly Trp
        675                 680                 685

Glu Asn Leu Val Gly Thr Asn Asn Leu Pro Asn Asp Asp Thr Arg Thr
    690                 695                 700

Tyr Val Val Lys Asp Ile Pro Val Glu Val Leu Leu Ser Gly Arg Asp
705                 710                 715                 720

Trp Pro Phe Val Ile His Glu Glu Asp Tyr Thr Ala Phe Pro Ser Gly
                725                 730                 735
```

```
Trp Tyr Tyr Val Arg Ile Asn His Val Glu Leu Lys Phe Glu Gln Gln
            740                 745                 750

Thr Ala Gly Ser Thr Asp Ile Val Ile His Gln Pro Ser Thr Asn Thr
        755                 760                 765

Gly Arg Leu Tyr Met Leu Leu Gln Ser Ser Arg Phe Phe His Asp Arg
    770                 775                 780

Asn Gln Gly Val Lys Met Glu Tyr Glu Gly Ser Arg Gly Leu Ser Tyr
785                 790                 795                 800

Pro Tyr Ala Tyr Asn Leu Asn Thr Gly Glu Thr Thr His Asn Asn Ile
                805                 810                 815

Pro Ser Asp Gln Phe Lys Asn Ile Phe Met Gln Met Thr Pro Phe Thr
            820                 825                 830

Thr Trp Arg Leu Arg Leu Ser Ala Ser Ala Glu Glu Asn Glu Gly Leu
        835                 840                 845

Val Phe His Pro Pro Ser Thr Ser Pro Thr Ser Thr Thr Gln Val Ser
    850                 855                 860

Ile Thr Phe His Val Thr Arg Ile Arg Arg Ile Asp Arg Phe Thr Ser
865                 870                 875                 880

Thr Val His Gln Lys His Ala Ser
                885


<210> SEQ ID NO 104
<211> LENGTH: 897
<212> TYPE: PRT
<213> ORGANISM: Platycerium bifurcatum

<400> SEQUENCE: 104

Met Ala Ala Ala Arg Ser Ala Gly Ala Asn Glu Ala Trp Arg Glu Val
1               5                   10                  15

Tyr His Asp Leu Asn Gln Val Ser Asp Arg Ile Arg Leu Asp Gln Leu
            20                  25                  30

Glu Phe Ser Glu Val Met Val Val His Arg Met His Ile Lys Met Ser
        35                  40                  45

Glu Leu Asp Leu Gly His Leu Glu Gly Ala Glu Lys Val Glu Arg Leu
    50                  55                  60

Tyr Val Phe Ala Asp Met Val Glu Cys Asp Val Pro Pro His Ala Ser
65                  70                  75                  80

Ser Ser Asp Gly Asp Leu Val Ile Arg Leu Pro Gly Ser Leu Ser Val
                85                  90                  95

Ile Phe Ile Cys Arg Val Trp His Ile Asn Val Gly Val Val Gln Leu
            100                 105                 110

Thr Ser Thr Val Gln Met Ser Arg Thr Leu Ile Val Gln Leu Pro His
        115                 120                 125

Met Arg Trp His Val Asn Ala Thr Thr Gly Ser Met His Arg Leu His
    130                 135                 140

Pro Gln Thr Ser Gln Glu Gly Pro Asp Thr Ser Phe Cys Val Tyr Ala
145                 150                 155                 160

Glu Val Val Gln Val Ala Tyr Tyr Pro Asp Val Thr Phe Ser Glu Phe
                165                 170                 175

Asp Gly Ser Pro Thr Leu Arg Phe Leu Arg Leu Glu Phe Glu Ser Asp
            180                 185                 190

Gln Leu Arg Val Thr Thr Gln Thr Glu Gly Pro Ile Trp Ala Ile Arg
        195                 200                 205

Ala Ser Leu Asp Thr Thr Met Thr Pro Asp Asn Asp Gly Leu Leu Asn
```

```
    210                 215                 220

Glu Ile Ser Ala Gln Pro Ala Gly Thr Ile Phe Lys Leu Asn Ile Leu
225                 230                 235                 240

Pro Asp Asn Leu Ile Val Ser Leu Phe Gly Ser Leu Arg Pro Asn Ser
                245                 250                 255

Ser Thr Ser Leu Thr Arg Val Pro Asp Asn Leu Leu Pro Ala Phe Ser
            260                 265                 270

Ile Phe Arg Glu Lys Ala Val Glu Leu Leu Thr Asp Pro Asp Val Leu
        275                 280                 285

Ser Ala Met Gln Thr Ser Met Leu Ile Gly Glu Leu Val Glu Val Gly
    290                 295                 300

Gln Pro Pro Glu Ala Thr Thr Glu Val Val Arg Lys His Ile Glu Trp
305                 310                 315                 320

Leu Asn Asn Leu Leu Leu Lys Val Ile Glu Ala Lys Gln Gly Gln His
                325                 330                 335

Val Glu Asp Tyr Val Glu Leu Ser Phe Arg Ala Gln Tyr Val Ile Lys
            340                 345                 350

Asn Val Gly Lys Ile Gln Arg Met Val Val Pro Gln Leu Gln Tyr Ser
        355                 360                 365

Ala Tyr Ser Asn Leu Ile Asn Arg Met Ala Gln Val Ala Glu Ser Tyr
    370                 375                 380

Asp Gln Ala Leu Arg Gln Phe Lys Leu Phe Ile Gln Gln Asn Lys Ile
385                 390                 395                 400

Leu Gly Gly Phe Leu Leu Glu Gln Asn Arg Ala Phe Ala Glu Lys Glu
                405                 410                 415

Gln Asp Met Asp Val Phe Tyr Ser Glu Leu Ile Thr Gln Arg Gln Ile
            420                 425                 430

Glu Leu Asp Asn Thr Leu Gln Lys Met Lys His Leu Gly Thr Gln Met
        435                 440                 445

Asp Thr Gln Thr Ala Asp Met Glu Gln Ala Gln Ala Asp Met Glu Ala
    450                 455                 460

Gly Val Arg Lys Phe Gln Asn Glu Gln Val Ala Arg Gly Leu Phe Ala
465                 470                 475                 480

Val Leu Gly Ala Ile Gly Ala Val Gly Leu Thr Phe Leu Thr Gly Gly
                485                 490                 495

Ala Ala Ala Pro Leu Ala Ile Ser Thr Ala Arg Arg Ala Val Ser Val
            500                 505                 510

Ala Gly Ala Val Ala Gln Gly Leu Gln Thr Val Leu Asp Ile Leu Glu
        515                 520                 525

Gly Leu Gln Ala Val Met Glu Ile Val His Leu Ile Asn Asp Leu Ile
    530                 535                 540

Ser Ala Leu Gln Glu Leu Gly Gln Pro Val Glu Leu Pro Glu Met Ala
545                 550                 555                 560

Asp Met Pro Thr Glu Ala Asp Trp Leu Ile Phe Val Asn Glu Val Glu
                565                 570                 575

Gly Val Ala Glu Gln Met Pro Thr Glu Val Ser Glu Val Val Ala Trp
            580                 585                 590

Lys Thr Lys Cys Lys Asn Val Ala Val Leu Gly Arg Glu Met Thr Thr
        595                 600                 605

Leu Ala Ala Tyr Ile Ser Gln Leu Gln Tyr Asp Ile Glu Met Gln His
    610                 615                 620

Met Leu Gln Gln Ile Ala Arg Lys Gln Ala Asp Arg Leu Ser Ala Ile
625                 630                 635                 640
```

Gln Leu Pro Asp Leu Arg Asn Tyr Ala Glu Leu Val Thr Gln Met Asp
645 650 655

Met Arg Thr Thr Arg Leu Leu Val Ala Leu Ile Lys Val Val Asn Ile
660 665 670

Gln Asn Ala Ala Leu Met Tyr Gln Tyr Leu Ser Glu Pro Thr Pro Val
675 680 685

Tyr Ala Trp Pro Val Asn Met Asp Ser Val Trp Arg Met Leu Val Gln
690 695 700

His Glu Gln Phe Ala Ile Gln Gly Leu Met Arg Leu Gly Pro Ala Phe
705 710 715 720

Asp Ile Val Arg Thr Tyr Val Val Lys Ser Ile Pro Val Ser Leu Leu
725 730 735

Leu Asp Gly Asp Asp Tyr Glu Phe Glu Ile Pro Val Glu Asn His Ile
740 745 750

Thr Phe Pro Leu Ser Leu Ser Arg Val Arg Ile His His Leu Glu Met
755 760 765

Arg Phe Val Gln Asp Gly Asp Thr Ala Gln Gly Ala His Val His Met
770 775 780

Pro Ile Thr Asp Thr Gly Ser Ile Tyr Ile Leu Leu Gln Gly Ser Arg
785 790 795 800

Asn Phe Arg Asp Arg Asn Glu Gly Ala Ile Leu His Tyr Glu Ala Ala
805 810 815

Thr Pro Leu Asp Tyr His Phe Ala Tyr Arg Leu Asp Thr Gly Glu Thr
820 825 830

Thr Val Thr Asn Leu Pro Ser Ala Glu Phe Leu Thr Thr Phe Met Arg
835 840 845

Met Thr Pro Phe Thr Asn Trp Gly Leu Arg Val Ser Ala Ser Ala Glu
850 855 860

Glu Asn Lys Gly Leu Ala Phe Ser Thr Ala Thr Ser Ala Asp Ala Thr
865 870 875 880

Thr Gln Ile Ala Ile Thr Phe Phe Ile Ser Ala Ile Arg Gln Ile Ala
885 890 895

Leu

<210> SEQ ID NO 105
<211> LENGTH: 895
<212> TYPE: PRT
<213> ORGANISM: Platycerium bifurcatum

<400> SEQUENCE: 105

Met His Pro Arg Ala His Asp Gly Ile Ser Ile Pro Leu Gln Gln Gly
1 5 10 15

Asp Asp His Asp Ala Glu Glu Arg Gln Ile Ser Gln Met Arg Pro Arg
20 25 30

Phe Lys Ala Asn Val Val Glu Asp Tyr Glu Glu Ile Tyr Arg Gly Ser
35 40 45

Asn Ser Ile Ala Arg Glu Val Gly Val Ser Lys Val Asn Cys Gly Glu
50 55 60

Val Met Ala Ile His Arg Met Phe Phe Arg Leu Asp Thr Leu Ser Gln
65 70 75 80

Glu Leu Leu Arg Gln Pro Glu Arg Val Gln Arg Leu Ile Val Val Ala
85 90 95

Asp Val Val Glu Ile Glu Gly Ser Asn Asp Thr Leu Ser Leu Pro Gly
100 105 110

-continued

```
Ser Ser Leu Val Leu Val Leu Cys Arg Ile Leu Ile Leu Lys Ser Lys
        115                 120                 125

Asp Val Val Leu Asp Leu Thr Ser Trp Asp Leu Thr Val Ala Thr Thr
    130                 135                 140

Thr Pro Leu His Arg Cys Ser Ile His Ala Gln Arg Val Val Val Ala
145                 150                 155                 160

Ser Gly Ser Leu Ser Ala Ser Leu Leu Ile Gln Val Lys His Lys Phe
                165                 170                 175

Glu Trp Ser Asp Gly Thr His Leu Asp Gln Tyr Phe Gly Arg Pro Phe
            180                 185                 190

Ser Phe Ile Ala Ser Glu Ile Asn Ser Ser Ala Thr Ala Thr Thr Arg
        195                 200                 205

Thr Asn Ser Ala Met Arg Ser Ile Ser Thr Trp Pro Gly Thr Ala Pro
    210                 215                 220

Val Ser Asn Phe Ile Arg Val Asn Ser Glu Lys Phe Asn Val Leu Val
225                 230                 235                 240

Asn Ala Val Pro Trp Lys Gly Val Val Asp Cys Gln Ala Ser Leu Pro
                245                 250                 255

Ser Leu Asp Asp Leu Leu His Pro Asp Val Ile Ser Gly Ile Gln Ser
            260                 265                 270

Thr Leu Leu Ile Val Glu Thr Ile Leu Asn Phe Gln Thr Asp Asn Pro
        275                 280                 285

Ala Ile Ile Ile Leu Ala Gln Gln His Ala Glu Trp Ile Val Asp Ser
    290                 295                 300

Leu Leu Gln Val Val His Leu Pro Asp Ser Thr Phe Gly Val Ala Glu
305                 310                 315                 320

Val Lys Thr Leu Leu Ala Arg Ala Gln Met Leu Met Lys Leu Pro Thr
                325                 330                 335

Asp Gly Ser Gln His Leu Gln Val Pro Leu Leu Ala Tyr Gly Glu Tyr
            340                 345                 350

Gln Glu Asp Ile Asp Gln Leu Leu Arg Asn Ala Glu Ala Tyr Asp Gln
        355                 360                 365

Glu Tyr Arg Glu Leu Thr Arg Phe Val Gln Gln Val Glu Ile Ile Gly
    370                 375                 380

Asn Glu Phe Leu Gln Leu Ser Arg Ser Leu Ala Glu Lys Glu Arg Gln
385                 390                 395                 400

Ile Glu Ile Phe Glu Ser Leu Val Val Ile Arg Lys Gln Ser Glu Leu
                405                 410                 415

Asp Gln Ala Ile Arg Arg Met Asn Ser Leu Met Thr Glu Ile Glu Arg
            420                 425                 430

Arg Ser Tyr Glu Met Ala Asp Ala Arg Ser Glu Met Glu Gln Gly Leu
        435                 440                 445

Glu Asp Tyr His Arg Arg Gln Leu Thr Arg Ala Ile Phe Gly Ile Leu
    450                 455                 460

Gly Ala Leu Leu Gln Leu Cys Ala Ser Leu Lys Phe Gly Gly Gly Ala
465                 470                 475                 480

Asp Ile Ala Gly Gly Ile Ala Thr Thr Val Pro Ala Ala Ile Asp Met
                485                 490                 495

Ile His Ala Val Glu Asp Ala Ser Ala Asn Thr Lys Leu Leu Ala Ile
            500                 505                 510

Ser Gln Ser Leu Met Asp Leu Glu Lys Ile Val Asp Val Val Asn Ala
        515                 520                 525
```

```
Val Asn Ala Leu Val Glu Ser Ala Thr Glu Leu Glu Asp Ile Ile His
    530                 535                 540

Ala Pro Glu Leu Pro Leu Ile Pro Pro Tyr Thr Trp Asp Ile Met Glu
545                 550                 555                 560

Asn Asp Ile Glu Glu Phe Ala Ala Leu Met Pro Ser Glu Val Ser Glu
                565                 570                 575

Val Val Thr Trp Lys Ala Lys Cys Arg Asn Leu Val Ala Val Cys Arg
            580                 585                 590

Glu Ile Cys Ile Ala Ala Ser Phe Ala Cys Glu Val Gln Tyr Glu Leu
        595                 600                 605

Phe Val His Ala Arg Gln Gln Glu Met Ala Arg Arg Gln Ala Glu Arg
    610                 615                 620

Leu Glu Gly Met Gln Ile Ala Ala Asp Leu Ser Ser Tyr Ile Glu Leu
625                 630                 635                 640

Ala Thr Gln Ala Asp Met Arg Thr Thr Arg Leu Leu Leu Ser Leu Leu
                645                 650                 655

Asn Val Leu Ala Gly His Gln Gly Ala Leu His Tyr His Tyr Leu Met
            660                 665                 670

Glu Leu Glu Val Phe Thr Phe Ser Trp Pro Ser Val Asp Ser Val Arg
        675                 680                 685

Met His Leu Leu Gln Leu Asn Gln Arg Ala Arg Ala Arg Glu Ser Gly
    690                 695                 700

Leu Phe Gly Asn Gly Val Leu Thr Val Asp Leu Glu His Asn Tyr Val
705                 710                 715                 720

Leu Asp Ala Ile Pro Val Ser Leu Leu Leu Ser Gly Glu Asp Tyr Asn
                725                 730                 735

Phe Thr Ile Asn Pro Glu Arg Asn Ala Ser Ser Phe Pro Thr Pro Trp
            740                 745                 750

Asp Tyr Val Arg Ile Arg Tyr Val Glu Val Lys Phe Thr Gly Glu His
        755                 760                 765

Gln Pro Val Thr Lys Thr Gly Glu Ile Tyr Leu Val Leu Arg Ser Ser
    770                 775                 780

Ala Asn Phe Gln Asp Arg Leu Glu Glu Gln Val Phe Glu Tyr Glu Ala
785                 790                 795                 800

Ala Val Pro Leu Val Tyr Gln Tyr Ala Tyr Asn Leu Ser Thr Gly Ala
                805                 810                 815

Thr Thr Leu Pro Asn Leu Pro Ser Gln Ser Gly Lys Phe Phe Arg Met
            820                 825                 830

Thr Pro Phe Thr Arg Trp Arg Leu Arg Leu Ser Ala Ser Ala Tyr Gln
        835                 840                 845

Asn Glu Gly Val Ser Phe Pro Thr Leu Pro Asp Leu Pro Gly Ala Ala
    850                 855                 860

Asp Ser Pro Val Gln Ile Thr Ile Thr Phe Tyr Val Thr Ala Leu Pro
865                 870                 875                 880

Gln Ile Gln Thr Ser Ser Thr Asp Gln Asp Pro Ala Ser Thr Thr
                885                 890                 895


<210> SEQ ID NO 106
<211> LENGTH: 906
<212> TYPE: PRT
<213> ORGANISM: Nephrolepis falcate

<400> SEQUENCE: 106

Glu Ile Glu Thr Glu Lys Val Leu Ile Val Cys Glu Arg Val Ala Tyr
1               5                   10                  15
```

```
Leu Phe Leu Gly Gly Trp Gly Ala Cys Ser Glu Ala Pro Tyr Arg Ala
            20                  25                  30

Ile Gly Ile Leu Ser Ala Asp Gln Asn Pro His Glu Ile Phe Thr Met
        35                  40                  45

Gly Gly Ala Val Pro Asp Tyr Ser His Leu Tyr Arg Glu Leu Asn Gln
    50                  55                  60

Val Ser Glu Arg Ile Arg Leu Asp Gln Met Glu Phe Ser Glu Val Met
65                  70                  75                  80

Val Ile His Arg Met Phe Ile Arg Leu Pro Asp Leu Asn Ile Ala His
                85                  90                  95

Leu Glu Gly Ala Gly Gln Val Lys Arg Leu Tyr Ile Phe Ala Asp Val
            100                 105                 110

Val Glu Leu Gly Gly His Leu Val Thr Thr Gln Leu Pro Gly Thr Val
        115                 120                 125

Met Val Val Ile Leu Cys Arg Val Leu Ser Leu Arg Ser Pro Thr Ala
    130                 135                 140

Arg Tyr Gly Leu Asn Phe Pro His Met Arg Leu His Ala Val Phe Gln
145                 150                 155                 160

Ser Ala Ser Arg Ile Leu His Met His Arg Leu Ile Pro Asp Ser Ala
                165                 170                 175

Gln Tyr Asp Ala Tyr Pro Val Val Cys Val His Ala Asp Ala Leu Glu
            180                 185                 190

Phe Ser Gly Thr Ser Thr Gly Gly Ile Phe His Ile Gly Pro Leu Arg
        195                 200                 205

Tyr Pro Ser Met Ile Val Thr Ser Glu Ser His Ser Ala Val Asp Ala
    210                 215                 220

Gln Ile Ser Ser Phe Ser Cys Asn Val Ser Leu Arg Ser Ala Ser Ala
225                 230                 235                 240

Ser Ser Pro Leu Lys Ile Asn Pro Asp Asn Val Ser Phe Gln Ser Met
                245                 250                 255

Phe Asn Leu Val Thr Gly Gly Gly Phe Gly Phe Ala Val Arg Pro Glu
            260                 265                 270

Glu Phe Trp Leu Leu Arg Arg Asp Leu Pro Asp Ala Leu Leu Asn Asp
        275                 280                 285

Ser Ser Ile Leu Leu Cys Met Gln Thr Ser Met Leu Val Ala Glu Leu
    290                 295                 300

Val Glu Phe Ser His Pro Ser Ser Asp Leu His Ala Ala Ile Ile Leu
305                 310                 315                 320

His Ala Glu Trp Leu Asn Thr Leu Leu Leu Gln Ala Ser Ala Ala Ser
                325                 330                 335

Gln Gly Thr Ser His His Asp Asp Tyr Leu Ala Leu Ile Phe Arg Ala
            340                 345                 350

Gln Tyr Leu Ile Lys Gly Val Gly Arg Ala Arg Gly Ala Val Val Pro
        355                 360                 365

Gln Leu Gln Tyr Asp Met Tyr Ser Asn Leu Ile Asn Gln Met Ala Arg
    370                 375                 380

Ala Ala Asp Thr Tyr Asp Gln Ser Leu Lys Gln Phe Gln Leu Phe Val
385                 390                 395                 400

Ala Gln Asn Lys Ile Leu Gly Gly Tyr Leu Leu Glu Gln Asn Arg Ala
                405                 410                 415

Phe Ala Ala Lys Glu Arg Asp Met Glu Val Phe His Ser Glu Leu Ile
            420                 425                 430
```

```
Ala Gln Lys Lys Thr Glu Leu Gln Thr Val Met Val Lys Ile Asp Lys
        435                 440                 445

Leu Ser Leu Gln Met Asp Thr Gln Val Ala Asp Met Glu Gln Ala Arg
    450                 455                 460

Glu Asp Met Glu Ala Gly Leu Arg Arg Phe Arg Asp Arg Gln Val Ala
465                 470                 475                 480

Asn Ala Leu Phe Ser Val Phe Arg Ala Ile Gly Ala Val Ala Leu Thr
                485                 490                 495

Val Leu Thr Gly Gly Ala Ala Ala Pro Leu Ala Ile Ser Ala Ala Lys
            500                 505                 510

Gly Ala Val Ser Ile Ala Gly Gln Ala Ala Arg Gly Leu Glu Arg Val
        515                 520                 525

Leu Gln Ile Leu Asp Asp Leu Gln Ala Ala Met Glu Leu Leu Lys Ile
    530                 535                 540

Ile Lys Asp Leu Val Glu Ser Leu Gln Glu Val Gly Gln Leu Val Asp
545                 550                 555                 560

Ala Pro Glu Met Pro Asp Met Pro Thr Glu Val Asp Trp Ala Ile Phe
                565                 570                 575

Val Asn Glu Val Glu Gly Val Ala Glu Gln Met Pro Glu Glu Val Ser
            580                 585                 590

Glu Val Ser Ala Trp Lys Thr Ser Cys Lys Asn Val Ala Val Val Gly
        595                 600                 605

Arg Glu Leu Thr Thr Thr Ser Ala Tyr Met Ser Gln Leu Gln Tyr Asp
    610                 615                 620

Val Gln Val Gln Ala Met Leu Gln Asp Ile Ala Arg Lys Gln Ala Asp
625                 630                 635                 640

Arg Leu Ser Ser Ile Gln Ala Val Asp Leu Ser Ser Phe Thr Glu Met
                645                 650                 655

Val Thr Gln Met Asp Met Arg Thr Thr Arg Leu Leu Val Glu Leu Ile
            660                 665                 670

Lys Val Leu Asp Met Gln Asn Val Ala Leu Met Tyr Gln Ser Leu Ile
        675                 680                 685

Met Pro Glu Pro Ile Asn Ala Trp Pro Val Thr Met Glu Thr Val Trp
    690                 695                 700

Gly Leu Leu Ile Gln His Glu His Ala Ala Val Leu Gly Leu Ile Arg
705                 710                 715                 720

Leu Gly Pro Ser Phe Asp Phe Arg Arg Thr Phe Thr Val Lys Asp Ile
                725                 730                 735

Pro Val Asp Leu Leu Leu His Gly Glu Asp Trp Glu Phe Glu Ile Pro
            740                 745                 750

Val Asp Asp Phe Thr Val Phe Pro Val Thr Trp Ser Arg Val Arg Ile
        755                 760                 765

His His Leu Glu Met Lys Phe Val Gly Thr Asp Glu Ala Ala Pro Ala
    770                 775                 780

Pro Gly Leu Gln Gly Thr His Gln Pro Thr Thr Lys Thr Gly Glu Ile
785                 790                 795                 800

Tyr Ile Leu Leu Gln Ser Ser Arg Val Phe His Asp Arg Asn Asn Thr
                805                 810                 815

Lys Pro Leu His Tyr Glu Ala Gly Val Pro Leu Asp Tyr His Tyr Ala
            820                 825                 830

Tyr Asn Leu Glu Thr Gly Glu Thr Thr Leu Ser Asn Leu Pro Ser Tyr
        835                 840                 845

Asp Phe Ile Arg Ala Phe Met Arg Met Thr Pro Phe Thr Thr Trp Arg
```

```
    850                 855                 860

Leu Arg Val Ser Ala Ser Ala Gln Glu Asn Glu Gly Leu Ala Phe Pro
865                 870                 875                 880

Thr Ala Thr Ala Gly Asn Gly Asp Thr Thr Gln Ile Ala Val Thr Phe
                885                 890                 895

His Val Ser Ala Ile Arg Glu Ile Ala Leu
            900                 905


<210> SEQ ID NO 107
<211> LENGTH: 872
<212> TYPE: PRT
<213> ORGANISM: Nephrolepis falcate

<400> SEQUENCE: 107

Met Glu Tyr Ser Asp Leu Tyr His Asp Val Asn Met Leu Ser Leu Pro
1               5                   10                  15

Leu His Arg Thr Glu Leu Ser Glu Val Met Val Val His Arg Met His
            20                  25                  30

Val Lys Leu Arg Asp Leu Asn Leu Glu Thr Ala Val Ser Asp Lys Val
        35                  40                  45

His Arg Leu Tyr Val Val Ala Asp Val Val Glu Val Thr Leu Asp Thr
    50                  55                  60

Val Ser Leu Pro Cys Lys Val Ser Val Val Ile Leu Cys Arg Val Leu
65                  70                  75                  80

His Val Glu Gln Ser Ser Val Leu Phe Ser Ser Leu Leu Leu Pro Asn
                85                  90                  95

Met Asn Val Arg Val Val Leu Ser Asn Asn Arg Met Gln Val Tyr Pro
            100                 105                 110

Met Ala Thr Asp Gly Ser Ala Asp Asp Val Ala Leu Tyr Ile His Ala
        115                 120                 125

Asp Arg Val Ile Arg Arg Gln Gly Ala Trp Thr Leu Val Arg Val Met
    130                 135                 140

His Met Ser Ile Thr Gly Pro Glu Ser Thr Phe Ser Val Pro His Leu
145                 150                 155                 160

Pro Asp Pro Ala Leu Phe Asn Arg Val Met Val Asn Val Gln Met Asp
                165                 170                 175

Ala Gly Pro Ser Ile Pro Ala Ser Glu Ser Asp Leu Gln Arg Ser Asp
            180                 185                 190

Glu Thr Glu Leu Val Ser Arg Val Ser Asn Gly Val Thr Val Ser Ala
        195                 200                 205

Ser Ile Ala Gly Ser Ala Trp Thr Met Pro Ala Asp Asn Pro Ser Ala
    210                 215                 220

Thr Phe Thr Val Phe Pro Asn Pro Pro Ala Gln Pro Val Ala Arg Gly
225                 230                 235                 240

Val Leu Thr Asn Pro Tyr Val Ile Ile Gly Leu Gln Met Asn Met Leu
                245                 250                 255

Thr Ala Glu Leu Val Gln Ala Ala His Asn Ala Pro Leu Leu Ile Arg
            260                 265                 270

Ala Val Thr Arg His Val Glu Trp Leu Asn Lys Ile Leu Val Glu Ala
        275                 280                 285

Leu Gln Val Val Ser Gly Asn Glu Asp Leu Leu Ala Leu Leu Phe Arg
    290                 295                 300

Thr Glu Thr Tyr Leu Lys Met Ala Thr Glu Ser Arg Ser Val Val Pro
305                 310                 315                 320
```

-continued

```
Arg Leu Gln Tyr His Met Tyr Ser Asp Leu Ile His Arg Met Val Gln
                325                 330                 335

Val Ala Gln Ala Tyr Asp Asp Glu Phe Gln Arg Leu Arg Leu Phe Ile
            340                 345                 350

Ala Gln Asn Glu Ile Leu Gly Ser Tyr Leu Leu Glu Gln Asn Lys Ala
        355                 360                 365

Leu Ala Ser Arg Glu Arg Glu Met Ser Ala Phe His Ser Gln Val Val
    370                 375                 380

Ser Leu Arg Arg Thr Glu Leu Asp Asn Cys Leu Gln Arg Met Asp Gln
385                 390                 395                 400

Leu Asn Val Gln Met Glu Arg Glu Asn Lys Ala Met Glu Glu Ala Gln
                405                 410                 415

Glu Lys Met Asn Glu Ala Leu Glu Ala His Gln Arg Arg Gly Leu Ala
            420                 425                 430

Arg Ala Leu Phe Ala Val Leu Gly Ala Ile Ala Ala Val Ala Leu Thr
        435                 440                 445

Val Ala Thr Gly Gly Ala Ala Ala Pro Ala Ala Val Ala Ala Ala Gly
    450                 455                 460

Gln Ala Val Thr Ala Ala Gly Thr Leu Ala Gln Gly Leu Lys Thr Val
465                 470                 475                 480

Val Glu Ile Leu Glu Gly Leu Gln Ala Leu Met Asp Leu Val Val Ile
                485                 490                 495

Ile Arg Glu Leu Val Glu Asn Leu Gln Thr Ile Gly Gln Leu Ile Asp
            500                 505                 510

Ala Pro Glu Met Gln Glu Met Pro Ser Asn Ala Asp Trp Leu Ile Phe
        515                 520                 525

Val Asn Glu Val Glu Ala Val Ala Ala Gln Met Pro Glu Glu Val Phe
    530                 535                 540

Gly Ser Val Ala Val Trp Lys Ala Lys Cys Arg Asn Val Ala Val Leu
545                 550                 555                 560

Gly Gln Glu Met Cys Thr Met Ala Ala His Ile Ala Glu Leu Gln Gln
                565                 570                 575

Gln Ile Lys Leu Glu Glu Leu Leu Gln Glu Ile Ala Asp Arg Gln Ala
            580                 585                 590

Asp Arg Leu Leu Gly Ile Ser Ala Ala Asp Leu Ser Ser Phe Thr Glu
        595                 600                 605

Met Leu Thr Gln Ile Asp Met Arg Thr Thr Arg Leu Leu Leu Gln Leu
    610                 615                 620

Ile Lys Leu Leu His Ile Gln Asn Val Ala Ile Asn Tyr Glu Tyr Leu
625                 630                 635                 640

Phe Pro Ala Asn Gly Arg Leu Ser Ser Trp Pro Val Thr Met His Thr
                645                 650                 655

Val Trp Glu Met Leu Leu Gln Gln Glu Ser Ser Ala Ile Thr Gly Leu
            660                 665                 670

Leu Ala Leu Gly Pro Ser Thr Asp Phe Ala Arg Thr Phe Val Val His
        675                 680                 685

Asp Ile Pro Val Gly Leu Leu Val Asp Gly Phe Asp Trp Gln Phe Ala
    690                 695                 700

Ile Pro Val Met Asp Asp Ser Ser Ala Phe Pro Ile Gly Phe Ser Arg
705                 710                 715                 720

Val Arg Ile Arg His Val Glu Leu Lys Phe Ser Ala Ile Asp Ile Asp
                725                 730                 735

Ala Ser Ala Thr Val His Gln Pro Arg Thr Asp Asn Gly Phe Ile Tyr
```

```
            740                 745                 750

Ile Leu Leu Gln Ser Ala Arg Ser Phe Ser Asp Arg Arg Val Arg Gln
        755                 760                 765

Ala Met Asp Tyr Glu Ala Ser Glu Gly Leu Ala Tyr Pro Tyr Ala Tyr
    770                 775                 780

Asn Leu Thr Thr Gly Val Pro Ser Leu Thr Asn Leu Pro Ser Gln Glu
785                 790                 795                 800

His Ala Asn Thr Phe Met Arg Met Thr Pro Phe Thr Glu Trp Arg Leu
                805                 810                 815

Arg Leu Ser Ser Ser Ala Glu Glu Asn Arg Gly Leu Thr Phe Pro Thr
            820                 825                 830

Ala Thr Ser Pro Asp Asp Ser Thr Gln Ile Ser Ile Thr Phe His Ile
        835                 840                 845

Thr Ala Ile Arg Ala Ile Asp Phe Arg Gly Met Asp Asp Glu Glu Arg
    850                 855                 860

Ser Lys Ser Asp Ser Ser Gln Lys
865                 870


<210> SEQ ID NO 108
<211> LENGTH: 895
<212> TYPE: PRT
<213> ORGANISM: Nephrolepis falcate

<400> SEQUENCE: 108

Met Glu Tyr Ser Asp Leu Tyr Ala Asp Val Asn Gln Val Ser Leu Arg
1               5                   10                  15

Phe Gln Gln Thr Glu Phe Ser Glu Val Met Val Val His Arg Met Tyr
            20                  25                  30

Val Arg Leu Leu Asp Leu Asp Met Thr Thr Glu Pro His Leu Gln Met
        35                  40                  45

Leu Ala Gly Ser Glu Lys Val Arg Arg Leu Tyr Val Val Ala Asp Val
    50                  55                  60

Val Glu Leu Pro Ala Thr Ala Thr Asn Met Arg Leu Pro Ala Thr Ala
65                  70                  75                  80

Ser Val Val Ile Leu Cys Arg Val Leu Tyr Val Gln Asp Val Asn Ser
                85                  90                  95

Pro Tyr Leu Ala Cys Gly Leu His Phe Pro Leu Met Pro Leu Arg Val
            100                 105                 110

Val Glu Asp Thr Gln Gln Gly Arg Val His Val Phe Pro Val Val Gly
        115                 120                 125

Gly Glu Ser Ala Ser Val Asp Lys Ile Gly Leu Tyr Ile His Ala Asp
    130                 135                 140

Arg Val Val Tyr Arg Gln Asp Thr Ser Thr Ala Asn Pro Leu Gln Pro
145                 150                 155                 160

Leu Gln Leu Arg Val Ile Gly Asn Gly Ser Thr Phe Ser Thr Glu Val
                165                 170                 175

Arg Pro Asp Trp Pro Lys Thr Leu Glu Val Ser Ser Leu Leu Met Trp
            180                 185                 190

Leu Thr Leu Ser Lys Gly Gln Pro Ile Pro Ala Ala Glu Ser Asp Leu
        195                 200                 205

Gln Arg His Asp Glu Val Glu Leu Leu Ser Pro Pro Ser Pro Asp Arg
    210                 215                 220

Leu Ser Val Val Phe Ala Tyr Leu Ala Pro Gly Asn Leu Phe Ser Ile
225                 230                 235                 240
```

```
Ala Val Asp Val Glu Tyr Ile Gly Ala Gly Phe Cys Tyr Phe Arg Ile
                245                 250                 255

Pro Pro Ala Asp Pro Val Pro Thr Glu Val Leu Thr Asp Pro Tyr Val
            260                 265                 270

Ile Ile Gly Leu Gln Met Asn Met Leu Ile Ala Glu Leu Val Leu Ala
        275                 280                 285

Ala His Asn Ser Pro Pro Val Ile Ser Val Val Thr Lys His Val Glu
    290                 295                 300

Trp Leu Asn Lys Ile Leu Pro Asn Asp Asp Ile Leu Ala Leu Leu Phe
305                 310                 315                 320

Arg Val Gln Leu Ser Leu Pro Asn Asp Asp Ile Leu Ala Leu Leu Phe
                325                 330                 335

Arg Val Gln Ala Phe Leu Lys Met Ala Lys Gln Pro Arg Ser Val Val
            340                 345                 350

Pro Arg Leu Gln Tyr His Met Tyr Ser Pro Leu Ile Asn Arg Met Val
        355                 360                 365

Gln Val Ala Gln Val Tyr Asp Gln Glu Phe Lys Gln Leu Lys Leu Phe
    370                 375                 380

Ile Val Gln Asn Gln Ile Leu Gly Ser Tyr Leu Leu Glu Gln Asn Lys
385                 390                 395                 400

Ala Phe Ala Ser Arg Glu Thr Glu Met Ser Ser Phe His Ser Gln Val
                405                 410                 415

Val Ser Leu Arg Arg Thr Glu Leu Asn Asn Ala Ile Asp Arg Ile Asp
            420                 425                 430

Gln Leu Ser Val Gln Met Glu Asn Glu Asn Glu Ala Met Asp Gln Ala
        435                 440                 445

Lys Glu Asp Met Met Gln Ala Ile Ala Glu Tyr Glu Lys Lys Gln Leu
    450                 455                 460

Ala Asn Ala Leu Phe Ala Val Leu Gly Ala Ile Ala Ser Val Ala Leu
465                 470                 475                 480

Ala Phe Ala Thr Ala Gly Ala Thr Ala Pro Gly Ala Val Ala Ala Ala
                485                 490                 495

Gly Ala Ala Val Ser Ala Ala Gly Arg Leu Ala Glu Gly Leu Lys Lys
            500                 505                 510

Val Val Glu Ile Leu Glu Gly Leu Ala Ala Val Met Glu Ile Val Ala
        515                 520                 525

Ala Ile Arg Asp Leu Val Glu Ser Leu Gln Asn Leu Gly Gln Leu Val
    530                 535                 540

Glu Thr Pro Glu Met Pro Asp Met Pro Ser Asn Ala Asp Trp Leu Ile
545                 550                 555                 560

Phe Val Asn Glu Val Glu Ala Val Ala Glu Gln Met Pro Ala Glu Val
                565                 570                 575

Val Gly Ser Val Ala Val Trp Lys Ala Lys Cys Arg Asn Val Ala Val
            580                 585                 590

Leu Gly Gln Glu Met Cys Thr Thr Ala Ala His Ile Gly Glu Leu Thr
        595                 600                 605

Tyr Gln Ile Lys Val Glu Glu Met Leu Gln Glu Ile Ala Gln Arg Gln
    610                 615                 620

Ala Asn Arg Leu Glu Ser Leu Thr Pro Ala Asn Leu Ser Ser Tyr Thr
625                 630                 635                 640

Glu Met Leu Ser Glu Ile Asp Met Arg Thr Thr Arg Leu Leu Leu Gln
                645                 650                 655

Leu Ile Arg Leu Leu His Ile Gln Asn Ala Ala Ile Lys Tyr Glu Tyr
```

```
            660                 665                 670

Leu Tyr Ala Ala Gly Glu Gln Leu Asn Ser Trp Pro Val Ser Met Asp
        675                 680                 685

Thr Val Trp Ser Met Leu Leu Gln Gln Glu Asn Ser Ala Leu Val Gly
    690                 695                 700

Leu Leu Asp Leu Gly Pro Ser Asn Asp Phe Thr Arg Ser Phe Val Ile
705                 710                 715                 720

Gln Gly Ile Pro Ile Gly Leu Leu Val Asp Gly Asn Asp Trp Gln Phe
                725                 730                 735

Ser Ile Pro Val Glu Asp Ser Pro Thr Phe Pro Ile Gly Tyr Ser Arg
            740                 745                 750

Val Arg Ile Arg Tyr Val Glu Leu Arg Phe Asp Gln Gly Thr Ser Asp
        755                 760                 765

Glu Gly Arg Met Ile His Gln Pro Ser Thr Ser Ser Gly Leu Thr Tyr
    770                 775                 780

Met Leu Leu Gln Ser Ser Pro Val Phe Arg Asp Arg Arg Arg Arg Glu
785                 790                 795                 800

Val Leu Glu Tyr Glu Ala Ser Met Gly Leu Ala Tyr Ala Phe Ala Tyr
                805                 810                 815

Asn Leu Thr Thr Gly Val Pro Thr Leu Thr Asn Val Pro Ser Pro Glu
            820                 825                 830

Phe Ala Asn Thr Phe Met Arg Met Thr Pro Phe Asn Ser Asn Trp Arg
        835                 840                 845

Leu Arg Leu Ser Ser Ser Ala Met Glu Asn Gln Gly Leu Met Phe Pro
    850                 855                 860

Thr Ala Ser Ser Ala Asp Asp Thr Thr Gln Ile Thr Ile Thr Phe Phe
865                 870                 875                 880

Ile Ser Ala Ile Arg Gly Ile Asp Thr Arg Ala Ala Val Glu Ile
                885                 890                 895


<210> SEQ ID NO 109
<211> LENGTH: 893
<212> TYPE: PRT
<213> ORGANISM: Nephrolepis falcate

<400> SEQUENCE: 109

Met Gln Gln Ser Val His Ile Ala Ala Arg Met Pro Gly Asp Gly Glu
1               5                   10                  15

Lys Gly Arg Phe Ser Ser Asp Glu Glu His Gln Met Met Met Arg Pro
            20                  25                  30

Arg Leu Thr Ser Asn Val Pro Glu Asp Tyr Glu Ala Ile Tyr Ala Gly
        35                  40                  45

Ser Asn Ser Ile Thr Arg Glu Val Gly Val Asn Lys Val Arg Cys Gly
    50                  55                  60

Glu Leu Met Ala Ile His Gln Met Phe Phe Arg Leu Asp Thr Leu Ser
65                  70                  75                  80

Gln Glu Leu Leu Gln Gln Pro Gln Leu Val Lys His Leu Ile Val Val
                85                  90                  95

Ala Asp Val Val Glu Ile Glu Gly Ser Arg Gly Thr Leu Val Leu Pro
            100                 105                 110

Gly Ser Ser Leu Val Leu Ile Phe Cys Arg Ile Leu Val Leu Lys Ser
        115                 120                 125

Lys Asp Val Val Leu Asp Leu Gly Ser Trp Asp Leu Ser Val Ala Thr
    130                 135                 140
```

```
Thr Ser Ser Pro Leu Val Arg Cys Ser Ile Arg Ala Gln Gln Val Val
145                 150                 155                 160

Ile Ser Ser Gly Ser Leu Ser Ala Ser Leu Leu Ile Gln Ala Lys His
                165                 170                 175

Arg Leu Arg Trp Ser Asp Gly Ser His Leu Asp Gln Tyr Phe Gly Arg
            180                 185                 190

Pro Phe Ser Phe Ala Ser Ser Lys Ile Asn Ser Phe Ala Thr Thr Thr
        195                 200                 205

Thr Gln Thr Ser Tyr Ala Lys Gln Ser Ile Ser Thr Trp Pro Gly Val
    210                 215                 220

Pro Pro Thr Ser Asn Leu Ile Val Val Asn Ser Glu Thr Phe Asn Val
225                 230                 235                 240

Arg Val Asn Ala Val Pro Trp Lys Gly Val Val Asp Cys Gln Thr Ala
                245                 250                 255

Leu Pro Ser Ser Asp Asp Leu Leu His Pro His Val Ile Ser Gly Ile
            260                 265                 270

Gln Ser Thr Leu Leu Ile Val Glu Thr Ile Leu Asn Phe Gln Thr Ser
        275                 280                 285

Asn Pro Ser Ile Ile Val Leu Ala Gln Gln His Ala Gln Trp Ile Val
    290                 295                 300

Asp Ser Leu Leu Gln Ala Val His Leu Pro Asn Ser Thr Thr Gly Val
305                 310                 315                 320

Pro Glu Leu Lys Thr Leu Leu Ala Arg Ser Gln Met Val Val Lys Leu
                325                 330                 335

Pro Ile Asp Gly Ser Gln His Leu Lys Val Pro Leu Leu Val Tyr Gly
            340                 345                 350

Glu Phe Gln Glu Asp Ile Asp Gln Leu Leu Arg Asn Ala Glu Ala Tyr
        355                 360                 365

Asp Gln Glu Tyr Arg Gln Leu Thr Arg Phe Val Gln Gln Val Gln Ile
    370                 375                 380

Ile Gly Ser Glu Phe Leu Gln Leu Ser Met Ser Leu Ala Gln Lys Glu
385                 390                 395                 400

Arg Gln Ile Glu Thr Phe Gln Ser Leu Leu Val Ile Arg Lys Gln Ser
                405                 410                 415

Glu Leu Asp Gln Thr Met Arg Arg Ile Asp Ser Leu Met Arg Glu Ile
            420                 425                 430

Glu Arg Arg Ser Phe Glu Met Ala Asp Ala Arg Tyr Arg Met Glu Glu
        435                 440                 445

Gly Val Leu Asp His Tyr Arg Arg Gln Val Asn Arg Ala Val Phe Gly
    450                 455                 460

Met Leu Gly Ala Leu Leu Gln Leu Phe Ala Ser Leu Lys Phe Gly Gly
465                 470                 475                 480

Gly Ala Asp Ile Ala Gly Ala Met Glu Thr Thr Val Ser Ala Ala Ile
                485                 490                 495

Asp Ile Ile His Ala Val Glu Asp Ala Ser Ala Ser Ser Lys Leu Leu
            500                 505                 510

Pro Met Thr Lys Asn Leu Ile Asp Leu Glu Lys Met Ile Glu Val Val
        515                 520                 525

Asn Ala Val Asn Glu Leu Val Glu Asn Ala Thr Glu Leu Glu Asp Ile
    530                 535                 540

Ile His Ala Pro Glu Leu Pro Ile Ile Ser Ser Tyr Thr Trp Asp Ile
545                 550                 555                 560

Leu Glu Asn Asp Ile Asp Glu Leu Ala Ala Leu Met Pro Ser Glu Val
```

```
                565                 570                 575

Ser Glu Val Val Thr Trp Lys Ala Lys Cys Arg Asn Leu Val Ala Val
            580                 585                 590

Cys Arg Glu Ile Cys Ile Ala Ala Asn Phe Ala Ala Glu Val Gln Tyr
        595                 600                 605

Glu Leu Phe Val His Ala Arg Gln Gln Glu Met Ala Arg Arg Gln Ala
    610                 615                 620

Glu Arg Leu Glu Gly Met Gln Leu Ala Thr Asp Leu Ser Ser Tyr Ile
625                 630                 635                 640

Glu Leu Ala Thr Gln Ala Asp Met Arg Thr Thr Arg Leu Leu Leu Ser
                645                 650                 655

Leu Leu Asn Val Leu Ala Asp His Gln Gly Ala Leu His Tyr His Tyr
            660                 665                 670

Leu Met Glu Leu Gln Val Phe Thr Phe Thr Trp Pro Ser Val Asp Ser
        675                 680                 685

Val Arg Met His Leu Leu Arg Leu Asn Gln Trp Ala Arg Ala Arg Glu
    690                 695                 700

Asn Met Leu Phe Gly Pro Gly Val Leu Thr Val Glu Val Gln Gln Asp
705                 710                 715                 720

Tyr Val Val Asp Ala Ile Pro Met Ser Leu Leu Leu Ser Gly Glu Asp
                725                 730                 735

Trp Ser Phe Thr Ile Asn Pro Gly Gln Asn Ala Ser Val Phe Pro Ala
            740                 745                 750

Pro Trp Asp Tyr Val Arg Ile Arg Tyr Val Glu Met Lys Phe Thr Gly
        755                 760                 765

Glu His His Pro Val Ser Gln Thr Gly Glu Val Tyr Leu Leu Leu Gln
    770                 775                 780

Ser Ser Ala Asn Phe Gln Asp Arg Phe Glu Gly Gln Val Leu Glu Tyr
785                 790                 795                 800

Glu Ala Ala Val Pro Leu Val Tyr Gln Tyr Ala Tyr Asn Leu Thr Thr
                805                 810                 815

Gly Ala Thr Thr Leu Pro Asn Leu Pro Phe Glu Ser Gly Lys Phe Phe
            820                 825                 830

Arg Met Thr Pro Phe Thr Arg Trp Arg Leu Arg Leu Ser Ala Ser Ala
        835                 840                 845

Tyr Gln Asn Glu Gly Ile Ser Phe Pro Thr Ala Asn Ser Ser Asp Thr
    850                 855                 860

Ser Ile Gln Ile Thr Ile Thr Phe Tyr Val Thr Ala Leu Pro Gln Ile
865                 870                 875                 880

Gln Ser Leu Ser Glu Asp Pro Ala Val Ala Thr Thr Leu
                885                 890


<210> SEQ ID NO 110
<211> LENGTH: 858
<212> TYPE: PRT
<213> ORGANISM: Colysis wrightii 'Monstifera'

<400> SEQUENCE: 110

Met Glu Arg Ala Ile Pro Asp Tyr Ser His Leu Tyr Arg Glu Leu Asn
1               5                   10                  15

Gln Val Ser Glu Arg Ile Arg Met Asp Gln Met Glu Phe Ser Glu Val
            20                  25                  30

Met Val Ile His Arg Met Phe Ile Lys Phe Pro Asp Leu Gly Ile Ala
        35                  40                  45
```

```
His Leu Glu Gly Ala Asp Lys Val Lys Cys Leu Tyr Val Phe Ala Asp
    50                  55                  60

Val Val Glu Leu Gly Ser Val Arg Gln Thr Ser Ser Leu Pro Gly Ser
65                  70                  75                  80

Ile Met Val Val Ile Met Cys Arg Val Leu Thr Leu His Leu Asp Ser
                85                  90                  95

Ala Ala Gln Ala Tyr Arg Ile Asp Leu Pro His Met Arg Leu His Ala
            100                 105                 110

Ile Asn Asp Ala Gln Arg Leu Arg Ile His Arg Arg Asn Ser Asp Ser
        115                 120                 125

Leu His Asp Asp Tyr Pro Val Ile Thr Ile Ser Ala Asn Val Ile Glu
    130                 135                 140

Phe Ser Gly Thr Arg Ser Leu Arg Asp Ile Phe Gly Ile Gly Pro Leu
145                 150                 155                 160

Gln Asp Pro Ser Met Ile Ile Thr Asn Thr Glu Thr Gln Pro Pro Val
                165                 170                 175

Val Glu Arg Pro Ser Ile Asn Ser Leu Cys Thr Val Gly Leu Val Gln
            180                 185                 190

Gly Gln Ser Ser Ser Pro Val Thr Val Asp Pro Asp Arg Ile Ser Arg
        195                 200                 205

His Phe Trp Phe Gln Ser Val Gly Gly Gly Ala Leu Gly Thr Leu Arg
    210                 215                 220

Ala Ala Glu Gly Phe Ser Leu Phe Gln Arg Asp Leu Pro Asp Val Leu
225                 230                 235                 240

Leu Ile Asp Pro Asn Ile Leu Leu Cys Met Gln Thr Ser Met Leu Val
                245                 250                 255

Ala Glu Leu Val Glu Phe Ser His Pro Ser Ser Asp Ile His Ser Ala
            260                 265                 270

Val Thr Glu His Val Val Trp Leu Asn Thr His Leu Leu Gln Ala Ser
        275                 280                 285

Thr Lys Ala Gln Gly Thr Ser Ser His Asp Asp Tyr Leu Ala Leu Ile
    290                 295                 300

Phe Arg Ala Gln Tyr Leu Leu Lys Gly Met Gly Arg Ala Arg Ser Leu
305                 310                 315                 320

Val Val Pro Gln Leu Gln Tyr Asp Val Tyr Arg Asn Leu Ile Asn Gln
                325                 330                 335

Met Ala Arg Val Ala Glu Ser Tyr Asp Gln Ser Leu Lys Gln Leu Gln
            340                 345                 350

Leu Phe Leu Ala Gln Asn Lys Ile Leu Gly Gly Tyr Leu Leu Glu Gln
        355                 360                 365

Asn Arg Ala Phe Ala Ala Lys Glu Arg Asp Met Glu Val Phe His Ser
    370                 375                 380

Glu Leu Ile Ala Gln Lys Glu Leu Glu Leu Gln Asn Thr Met Phe Lys
385                 390                 395                 400

Met Glu Gln Leu Ser Ser Gln Met Glu Thr Gln Ile Ala Asp Met Asp
                405                 410                 415

Gln Ala Glu Lys Asp Met Glu Ala Gly Leu Arg Arg Phe Gln Asn Arg
            420                 425                 430

Gln Val Ala Arg Ala Met Phe Ala Val Phe Arg Ala Ile Gly Ala Val
        435                 440                 445

Ala Leu Thr Val Val Thr Gly Gly Ala Ala Ala Pro Ala Ala Met Thr
    450                 455                 460

Ala Ala Lys Gly Ala Val Ser Ile Ala Gly Gln Ala Ala Arg Gly Leu
```

-continued

```
465                 470                 475                 480

Glu Arg Val Leu Glu Ile Leu Asp Asn Leu Gln Ala Ala Met Glu Val
                485                 490                 495

Phe Lys Ile Ile Lys Asp Leu Val Glu Ser Leu Arg Glu Val Gly Gln
            500                 505                 510

Leu Val Asp Ala Pro Glu Met Pro Asp Met Pro Thr Glu Ala Asp Trp
        515                 520                 525

Ser Ile Phe Val Asn Glu Val Glu Ala Val Ala Glu Gln Met Pro Glu
    530                 535                 540

Glu Val Ser Glu Val Ser Ala Trp Lys Thr Ser Cys Lys Asn Val Ala
545                 550                 555                 560

Ala Val Gly Arg Glu Leu Thr Thr Thr Ser Ala Tyr Ile Ser Gln Leu
                565                 570                 575

Gln Tyr Asp Ile Lys Val Gln Ala Met Leu Gln Asp Ile Ala Ser Arg
            580                 585                 590

Gln Ala Asp Arg Leu Leu Ser Ile Gln Ala Ala Asp Leu Ser Ser Tyr
        595                 600                 605

Thr Glu Met Val Thr Gln Met Asp Met Arg Thr Thr Arg Leu Leu Met
    610                 615                 620

Glu Leu Ile Lys Val Leu Asp Met Gln Asn Ala Ala Leu Met Tyr Gln
625                 630                 635                 640

Phe Leu Ser Leu Pro Ala Pro Met Asn Ala Trp Pro Val Thr Met Glu
                645                 650                 655

Thr Val Trp Gly Met Leu Val Gln His Glu His Ala Ala Val Leu Gly
            660                 665                 670

Leu Met Arg Leu Gly Pro Ala Phe Asp Phe Arg Arg Thr Phe Val Val
        675                 680                 685

Lys Glu Ile Pro Val Asp Leu Leu Leu His Gly Glu Asp Trp Gln Phe
    690                 695                 700

Glu Ile Pro Val Asn Glu Leu Thr Val Phe Pro Gly Thr Trp Ser Gln
705                 710                 715                 720

Val Arg Ile His His Leu Glu Met Lys Phe Val Gly Thr Ala Glu Gly
                725                 730                 735

Ser Ala Pro Asn Gly Ala His Gln Pro Ile Thr Glu Ser Gly Glu Val
            740                 745                 750

Tyr Ile Leu Leu Gln Gly Ser Arg Val Phe His Asp Arg Asn Lys Thr
        755                 760                 765

Glu Pro Leu His Tyr Glu Ala Ala Val Pro Leu Asp Tyr His Tyr Ala
    770                 775                 780

Tyr His Leu Lys Thr Gly Glu Thr Thr Leu Ser Asn Ser Pro Ser Asn
785                 790                 795                 800

Asp Phe Ile Arg Thr Phe Met Arg Met Thr Pro Phe Thr Thr Trp Arg
                805                 810                 815

Leu Arg Val Ser Ala Ser Ala Gln Glu Asn Gln Gly Leu Ala Phe Pro
            820                 825                 830

Thr Thr Thr Val Gly Ala Gly Asp Thr Thr Gln Ile Ala Val Thr Leu
        835                 840                 845

Tyr Val Ser Ala Ile Arg Glu Ile Ser Leu
    850                 855
```

<210> SEQ ID NO 111
<211> LENGTH: 824
<212> TYPE: PRT
<213> ORGANISM: Colysis wrightii

<400> SEQUENCE: 111

```
Met Val Ile His Arg Met Phe Phe Lys Leu Pro Asp Leu Asp Ile Ala
1               5                   10                  15

His Leu Asp Gly Ala Asp Lys Val Lys Cys Leu Tyr Val Phe Ala Asp
            20                  25                  30

Val Val Glu Leu Gly Ser Ala Gly Gln Thr Ser Asn Leu Pro Gly Ser
        35                  40                  45

Ile Met Val Val Ile Met Cys Arg Val Leu Thr Leu His Ala Asp Trp
    50                  55                  60

Ser Arg Thr Ser Tyr Arg Phe Val Phe Pro His Met Arg Leu His Ala
65                  70                  75                  80

Ile Phe Asp Leu Gln Gln Ala Arg Ile His Arg Arg Asn Ser Asp Ser
                85                  90                  95

Val His Asp Asp Tyr Pro Val Ile Thr Ile Ser Ala Asn Val Ile Glu
            100                 105                 110

Phe Ser Gly Thr Arg Ser Ser Ser Val Leu Phe Gly Ile Gly Val Phe
        115                 120                 125

Leu Asp Pro Ser Met Val Leu Ser Ser Asp Arg His Ser Ile Val Glu
    130                 135                 140

Arg Pro Ser Ser His Thr Leu Cys Asn Val Asn Pro Val Glu Gln Ser
145                 150                 155                 160

Ser Pro Ile Met Val Asp Pro Asp Thr Ile Arg Phe Gln Ser Ile Phe
                165                 170                 175

Asn Trp Val Gly Ser Asn Ile Met Ser Pro Gln Val Ala Arg Ala Pro
            180                 185                 190

Glu Gly Phe Ser Leu Phe Arg Arg Asp Leu Pro Asp Leu Leu Leu Ile
        195                 200                 205

Asp Pro Asn Ile Leu Leu Cys Met Gln Thr Ser Met Leu Ile Ala Glu
    210                 215                 220

Leu Val Glu Phe Ser His Pro Ser Ser Asp Ile His Ala Ala Val Thr
225                 230                 235                 240

Glu His Leu Ile Trp Leu Asn Thr His Leu Leu Gln Ala Ser Thr Lys
                245                 250                 255

Ala Gln Gly Thr Ser Ser Tyr Asp Asp Tyr Leu Ala Leu Ile Phe Arg
            260                 265                 270

Ser Gln Tyr Leu Leu Lys Gly Met Gly Arg Ala Arg Ser Leu Val Val
        275                 280                 285

Pro Gln Leu Gln Tyr Asp Val Tyr Arg Asn Leu Ile Asn Gln Met Ala
    290                 295                 300

Arg Val Ala Glu Ser Tyr Asp Gln Ser Leu Lys Gln Leu Gln Leu Phe
305                 310                 315                 320

Leu Ala Gln Asn Lys Val Leu Gly Gly Tyr Leu Leu Glu Gln Asn Arg
                325                 330                 335

Ala Phe Ala Ala Lys Glu Arg Asp Met Glu Val Phe His Ser Glu Leu
            340                 345                 350

Ile Ala Gln Lys Glu Leu Glu Leu Gln Asn Thr Met Phe Lys Met Glu
        355                 360                 365

Gln Leu Ser Ser Gln Met Glu Thr Gln Ile Ala Asp Met Asp Gln Ala
    370                 375                 380

Glu Lys Asp Met Glu Ala Gly Leu Arg Arg Phe Gln Asn Arg Gln Val
385                 390                 395                 400

Ala Arg Ala Ile Phe Ala Val Phe Arg Ala Ile Gly Ala Val Ala Leu
```

```
                405                 410                 415

Thr Val Val Thr Gly Gly Ala Ala Ala Pro Ala Ala Met Ser Ala Ala
            420                 425                 430

Lys Gly Ala Val Ser Ile Ala Gly Gln Ala Ala Arg Gly Leu Glu Arg
        435                 440                 445

Val Leu Glu Ile Leu Asp Asn Leu Gln Ala Ala Met Glu Val Phe Lys
    450                 455                 460

Ile Ile Lys Asp Leu Val Glu Ser Leu Arg Glu Val Gly Gln Leu Val
465                 470                 475                 480

Asp Ala Pro Glu Met Pro Asp Met Pro Thr Glu Ala Asp Trp Ser Ile
                485                 490                 495

Phe Val Asn Glu Val Glu Ala Val Ala Glu Gln Met Pro Glu Glu Val
            500                 505                 510

Ser Glu Val Ser Ala Trp Lys Thr Ser Cys Lys Asn Val Ala Ala Val
        515                 520                 525

Gly Arg Glu Leu Thr Thr Thr Ser Ala Tyr Ile Ser Gln Leu Gln Tyr
    530                 535                 540

Asp Ile Lys Val Gln Ala Met Leu Gln Asp Ile Ala Asn Lys Gln Ala
545                 550                 555                 560

Asp Arg Leu Ser Ser Ile Gln Ala Ala Asp Leu Ser Ser Tyr Thr Glu
                565                 570                 575

Met Val Thr Gln Met Asp Met Arg Thr Thr Arg Leu Leu Met Glu Leu
            580                 585                 590

Ile Lys Val Leu Asp Met Gln Asn Ala Ala Leu Met Tyr Gln Phe Leu
        595                 600                 605

Thr Leu Pro Ala Pro Met Asn Ala Trp Pro Val Thr Met Glu Thr Val
    610                 615                 620

Trp Gly Met Leu Val Gln His Glu His Ala Ala Val Leu Gly Leu Met
625                 630                 635                 640

Arg Leu Gly Pro Ala Phe Asp Phe Arg Arg Thr Phe Ile Val Lys Glu
                645                 650                 655

Ile Pro Val Asp Leu Leu Leu His Gly Glu Asp Trp Gln Phe Glu Ile
            660                 665                 670

Pro Val Asn Glu Leu Thr Val Phe Pro Gly Thr Trp Ser Gln Val Arg
        675                 680                 685

Ile His His Leu Glu Met Lys Phe Val Gly Thr Ala Glu Gly Ser Ala
    690                 695                 700

Pro Asn Gly Ala His Leu Pro Ile Thr Glu Ser Gly Glu Val Tyr Ile
705                 710                 715                 720

Leu Leu Gln Gly Ser Arg Val Phe His Asp Arg Asn Lys Thr Glu Pro
                725                 730                 735

Leu His Tyr Glu Ala Ala Val Pro Leu Asp Tyr His Tyr Ala Tyr His
            740                 745                 750

Leu Lys Thr Gly Glu Thr Thr Leu Ser Asn Ser Pro Ser Asn Asp Phe
        755                 760                 765

Ile Arg Thr Phe Met Arg Met Thr Pro Phe Thr Thr Trp Arg Leu Arg
    770                 775                 780

Val Ser Ala Ser Ala Gln Glu Asn Gln Gly Leu Ala Phe Pro Thr Thr
785                 790                 795                 800

Thr Val Gly Ala Gly Asp Thr Thr Gln Ile Ala Val Thr Phe Tyr Val
                805                 810                 815

Ser Ala Ile Arg Glu Ile Ser Leu
            820
```

<210> SEQ ID NO 112
<211> LENGTH: 884
<212> TYPE: PRT
<213> ORGANISM: Colysis wrightii

<400> SEQUENCE: 112

```
Val Asn Gln Val Ser Leu Arg Phe Gln Asn Met Glu Phe Ser Glu Val
1               5                   10                  15

Met Val Val His Arg Met His Val Arg Leu Glu Glu Leu Asp Met Thr
            20                  25                  30

Gly Val Glu Gly Ile Glu Lys Val Lys His Leu Tyr Val Leu Ala Asp
        35                  40                  45

Val Val Glu Leu Pro Pro Lys Ala Thr Ser Val Phe Glu Tyr Val Arg
    50                  55                  60

Leu Pro Ala Thr Ile Ser Ala Ile Ile Leu Cys Arg Val Leu Tyr Ile
65                  70                  75                  80

Pro Glu Val Gln Arg Leu Ser Gly Ala Gly Phe Arg Gly Gln Cys Ser
                85                  90                  95

Leu Asp Phe Pro Phe Met Arg Leu His Val Val Gly Ala Ala His Glu
            100                 105                 110

Ser Gly Gly Gly Val Met Gln Ala Phe Ser Ser Asp Ala Thr Ala Gly
        115                 120                 125

Asn Ile Gly Val Tyr Leu His Ala Asp Arg Phe Ile Tyr Arg Glu Ala
    130                 135                 140

Ala Ser Pro Ala Ser Asp Phe Val Trp Pro Leu Asp Val Arg Val Ser
145                 150                 155                 160

Phe Gly Ser Ser Thr Phe Ser Asn Thr Ala Val Pro Asp Trp Gln Asn
                165                 170                 175

Leu Asn Val Ser Ser Ile Arg Tyr Asp Ser Gln Arg Leu Ser Lys Gly
            180                 185                 190

Pro Pro Leu Thr Ser Ser Asp Ser Asp Leu Gln Arg Ser Asp Glu Ile
        195                 200                 205

Glu Leu Leu Ala Gln Gln Asp Ile Trp Ser Pro Ile Leu His Val Ser
    210                 215                 220

Phe Asn Pro Asn Ala Pro Pro Gly Asn Val Pro Gly Thr Gln Gly Leu
225                 230                 235                 240

Phe Arg Pro Ser Ser Ala Cys Ser Phe Phe His Val Pro Pro Pro Asp
                245                 250                 255

Val Pro Ala Asn Val Leu Thr Asp Pro Ser Ile Ile Leu Gly Met Gln
            260                 265                 270

Met Asn Met Leu Ile Ala Glu Leu Val Leu Ala Ala His Asn Ser Pro
        275                 280                 285

Gln Val Met Asn Val Val Thr Lys His Val Leu Trp Leu Asn Lys Ile
    290                 295                 300

Leu Leu Gln Val Ala Ser Pro Asn Asp Asp Ile Leu Ala Leu Leu Phe
305                 310                 315                 320

Arg Ile Gln Ala Phe Met Lys Met Ala Lys Gln Pro Arg Phe Val Pro
                325                 330                 335

Arg Phe Val Val Pro Arg Leu Gln Tyr His Met Tyr Gly Ser Leu Ile
            340                 345                 350

Asn Arg Met Val Gln Val Ala Gln Asn Tyr Asp Gln Glu Phe Lys Gln
        355                 360                 365

Leu Lys Leu Phe Ile Ala Gln Asn Glu Ile Leu Gly Ser Tyr Leu Leu
```

-continued

```
    370                 375                 380

Gln Gln Asn Lys Ala Phe Ala Glu Arg Glu Lys Glu Met Ser Ala Phe
385                 390                 395                 400

His Ser Gln Val Val Ser Met Arg Arg Ser Glu Leu Thr Thr Ala Ile
                405                 410                 415

Glu Thr Met Asn Gln Leu Ser Leu Gln Met Glu Thr Glu Ser Glu Ala
            420                 425                 430

Met Asn Glu Ala Gln Glu Asn Met Val Glu Ala Ile Gln Glu Tyr Glu
        435                 440                 445

Arg Lys Leu Leu Ala Arg Ala Leu Phe Ser Val Ile Gly Ala Ile Ala
    450                 455                 460

Ser Val Ala Leu Ala Val Ala Thr Gly Gly Ala Thr Ala Pro Gly Ala
465                 470                 475                 480

Val Ala Ala Ala Arg Gly Ala Val Thr Ala Ala Gly Arg Leu Ala Gln
                485                 490                 495

Gly Leu Gln Lys Val Val Asp Ile Leu Gln Gly Leu Gln Ala Val Met
            500                 505                 510

Glu Val Val Val Ala Ile Arg Asp Ile Val Glu Ser Leu Lys Asn Met
        515                 520                 525

Gly Gln Leu Val Glu Ala Pro Glu Met Pro Glu Met Pro Thr Asp Ala
    530                 535                 540

Asp Trp Leu Ile Phe Val Asn Glu Val Glu Ala Val Ala Glu Gln Val
545                 550                 555                 560

Pro Thr Glu Val Ala Glu Val Pro Val Trp Lys Ala Lys Cys Lys Asn
                565                 570                 575

Val Ala Val Leu Gly Gln Ala Met Cys Thr Thr Ala Ala Tyr Met Ser
            580                 585                 590

Glu Leu Gln Tyr Gln Ile Thr Val Glu Glu Met Leu Gln Glu Ile Ala
        595                 600                 605

Gln Arg Gln Ala Asp Arg Leu Val Gly Ile Ser Ala Ala Asp Leu Ser
    610                 615                 620

Ser Tyr Thr Glu Met Ala Ser Gln Ile Asp Met Arg Thr Thr Arg Ile
625                 630                 635                 640

Leu Leu Glu Leu Ile Lys Met Leu Tyr Ile Gln Asn Ala Ala Ile Lys
                645                 650                 655

Tyr Glu Tyr Leu Tyr Asp Ala Asn Glu Lys Leu Asn Ser Trp Pro Val
            660                 665                 670

Ser Met Glu Thr Val Trp Thr Met Leu Leu Arg Gln Glu Asn Ala Ala
        675                 680                 685

Leu Leu Gly Leu Leu Asn Leu Gly Pro Ser Asn Asp Phe Thr Val Thr
    690                 695                 700

Tyr Ala Val Lys Asp Ile Pro Val Lys Leu Leu Val Asp Gly Tyr Asp
705                 710                 715                 720

Trp Asn Phe Glu Ile Ala Val Glu Asp Phe Ser Ile Phe Pro Ser Gly
                725                 730                 735

Trp Ser Arg Val Arg Ile Arg Tyr Val Glu Leu Lys Phe Asp Gln Gln
            740                 745                 750

Gly Thr Asp Ser Ser Asn Ile Val Ile His Gln Pro Ser Thr Asn Thr
        755                 760                 765

Gly Leu Val Tyr Met Leu Leu Gln Gly Ser Arg Phe Leu His Asp Arg
    770                 775                 780

Lys Arg Glu Glu Val Met Asp Tyr Glu Ala Ser Met Gly Ala Val Phe
785                 790                 795                 800
```

```
Ala Tyr Ala Tyr Asp Leu Asn Thr Gly Ala Thr Thr Leu Ser Asn Ile
                805                 810                 815

Pro Ser Gln Gln His Ala Asn Thr Phe Met Gln Met Thr Pro Phe Asn
            820                 825                 830

Ala Ala Trp Arg Leu Arg Leu Ser Ala Ser Ala Met Glu Asn Gln Gly
        835                 840                 845

Leu Val Phe Pro Thr Ala Thr Ser Pro Asp Asn Thr Thr Gln Ile Ser
    850                 855                 860

Ile Thr Phe Tyr Val Thr Ala Ile Arg Arg Ile Asp His Arg Gln Glu
865                 870                 875                 880

Gly Asp Glu Glu


<210> SEQ ID NO 113
<211> LENGTH: 810
<212> TYPE: PRT
<213> ORGANISM: Bolbitis cladorrhizans

<400> SEQUENCE: 113

Met Ala Gly Ile Asp Tyr Ser Val Leu Tyr Gln Asp Val Asn Gln Ile
1               5                   10                  15

Ser Ile Arg Leu Glu Lys Met Asp Phe Ser Glu Val Met Ala Val His
            20                  25                  30

Arg Met Phe Val Arg Met Asp Asp Leu Asp Val Ser Ser Gly Thr Gly
        35                  40                  45

Leu Leu Ala Gly Ala Glu Lys Val Lys Arg Leu Tyr Val Phe Ala Asp
    50                  55                  60

Val Val Glu Leu Pro Ser Lys Arg Val Arg Leu Pro Gly Thr Asp Met
65                  70                  75                  80

Ile Ile Ile Leu Cys Arg Ile Phe Val Val Asn Gly Arg His Ser Thr
                85                  90                  95

Glu Leu Phe Leu Pro Ser Met Asn Leu Asn Met Val Ala Ala Gly Thr
            100                 105                 110

Gly Ser Ile Arg Gly Ala Tyr Leu Ser Thr Thr Ala Phe Ser Leu Ser
        115                 120                 125

Ser Asn Ala Leu Gln Phe Lys Leu Gln Ser Gly Ser Met Thr Ser Ala
    130                 135                 140

Ile Gln Leu Lys Asp Val Asp Leu Ala Ala Thr Leu Thr Cys Asp Val
145                 150                 155                 160

Gln Ala Ala Ser Ala Ser Met Pro Ile Val Val Lys Thr Thr Gly Thr
                165                 170                 175

Ser Pro Gly Asn Ile Leu Val Leu Gly Met Ser Thr Ala Val Val Ile
            180                 185                 190

Pro Glu Ser Ala Val Ala Val Ile Thr Asp Ala Asn Ile Leu Leu Gly
        195                 200                 205

Met Gln Val Thr Val Leu Ile Ala Glu Leu Val Lys Thr Ala His Asn
    210                 215                 220

Ser Asp Val Val Ile Ala Ala Val Thr Arg His Val Glu Trp Leu Asn
225                 230                 235                 240

His Leu Leu Val Gln Ala His Ala Ala Ala Pro Ser Asp Asp Val Val
                245                 250                 255

Ala Leu Leu Tyr Arg Thr Gln Gly Phe Ile Lys Leu Gln Arg Glu Asp
            260                 265                 270

Leu Val Val Pro Gly Leu Gln Tyr Arg Met Tyr Lys Asp Leu Ile Asn
        275                 280                 285
```

```
Arg Met Val Gln Val Ala Gln Ser Tyr Asp Gln Asp Phe Lys Gln Leu
    290                 295                 300

Lys Leu Tyr Val Glu Gln Asn Lys Ile Leu Gly Ser Tyr Leu Leu Glu
305                 310                 315                 320

Gln Asn Lys Ala Phe Ala Glu Lys Glu Lys Asp Met Asp Ala Phe His
                325                 330                 335

Ser Gln Val Ile Ala Leu Arg Thr Thr Glu Leu Asn Asn Thr Ile Glu
            340                 345                 350

Arg Met Asp Asp Leu Ser Lys Gln Met Glu Glu Gln Asn Ala Ala Met
        355                 360                 365

Glu Gln Ala Lys Ala Asp Met Asp Ala Gly Leu Ile Glu Tyr Gln Asn
    370                 375                 380

Lys Gln Val Ala Asn Ala Val Phe Ala Val Leu Gly Ala Ile Ala Ser
385                 390                 395                 400

Ile Gly Leu Ala Phe Ala Thr Gly Gly Ala Thr Ala Pro Gly Ala Val
                405                 410                 415

Ala Ala Ala Gly Thr Ala Val Thr Ala Ala Gly Lys Ala Ala Glu Gly
            420                 425                 430

Leu Lys Lys Val Val Glu Ile Leu Glu Gly Leu Gln Ala Val Met Glu
        435                 440                 445

Val Val Ala Ala Ile Lys Glu Leu Val Gln Ser Leu Gln Glu Ile Gly
    450                 455                 460

Gln Leu Val Asn Ala Pro Glu Met Pro Asp Leu Pro Ser Asn Ala Glu
465                 470                 475                 480

Trp Asp Ile Phe Val Asn Glu Val Glu Ala Val Ala Glu Gln Met Pro
                485                 490                 495

Thr Glu Val Thr Glu Val Pro Ala Trp Lys Ala Lys Cys Lys Asn Val
            500                 505                 510

Ala Ala Leu Gly Arg Glu Met Ser Thr Met Ala Ala His Ile Ser Glu
        515                 520                 525

Leu Gln Phe Glu Ile Lys Val Gln Glu Met Leu Arg Glu Ile Ala Gln
    530                 535                 540

Lys Gln Ala Asp Arg Leu Ser Ser Ile Lys Pro Ala Asp Leu Thr Asn
545                 550                 555                 560

Tyr Leu Glu Met Val Ser Glu Met Asp Met Arg Thr Thr Arg Met Leu
                565                 570                 575

Leu Glu Leu Ile Lys Val Leu Tyr Ile Gln Asn Ala Ala Leu Gln Tyr
            580                 585                 590

Glu Tyr Leu Gln Thr Pro Ala Arg Leu Asn Ala Trp Pro Val Thr Met
        595                 600                 605

Gln Thr Val Trp Thr Leu Leu Val Gln Gln Glu Thr Thr Ala Ile Thr
    610                 615                 620

Gly Leu Leu Gln Leu Gly Ala Pro Ser Asp Tyr Thr Gln Gly Tyr Val
625                 630                 635                 640

Val Glu Asn Ile Pro Val Ser Leu Leu Leu Glu Gly Arg Asp Trp Glu
                645                 650                 655

Phe Glu Leu Pro Val Met Asn Ala Asp Phe Pro Thr Thr Trp Cys Arg
            660                 665                 670

Val Arg Ile His His Val Glu Met Gln Phe Asp Ala Gly Ala Lys His
        675                 680                 685

Leu Pro Ser Thr Ser Thr Gly Gln Val Tyr Met Leu Leu Gln Ser Ser
    690                 695                 700
```

```
Arg Phe Phe Ala Asp Arg Ala Lys Arg Ala Asn Glu Tyr Ile Asn Tyr
705                 710                 715                 720

Gln Ala Gly Thr Gly Leu Tyr Tyr Gln Tyr Ala Tyr Arg Leu Ala Thr
                725                 730                 735

Gly Glu Ala Thr Val Thr Asn Ile Pro Ser Glu Glu Tyr Ala Asn Thr
            740                 745                 750

Phe Met Arg Leu Ala Pro Phe Thr Arg Trp Arg Leu Arg Leu Ser Ala
        755                 760                 765

Ser Ala Asp Glu Asn Lys Gly Leu Ala Phe Pro Thr Ala Thr Ser Ala
    770                 775                 780

Asp Ala Thr Thr Gln Ile Lys Ile Thr Phe His Val Ser Ala Ile Arg
785                 790                 795                 800

Arg Ile Ser Thr Phe Val Ala Asp Pro Lys
                805                 810


<210> SEQ ID NO 114
<211> LENGTH: 851
<212> TYPE: PRT
<213> ORGANISM: Bolbitis cladorrhizans

<400> SEQUENCE: 114

Met Ala Ser Leu Pro Asp Tyr Tyr Glu Ile Tyr Lys Asn Val Asn Gln
1               5                   10                  15

Val Ser Arg Pro Val Ala Ser Arg Gln Ala Ser Glu Val Thr Ser Ile
            20                  25                  30

His Arg Met Tyr Phe Lys Leu Asn Leu Leu Glu Val Ala Leu Leu Thr
        35                  40                  45

Lys Ala Asp Glu Val Lys Glu Leu Val Val Phe Ala Asp Val Val Glu
    50                  55                  60

Met Glu Gly Gly Lys Val Glu Leu Pro Ala Ser Arg Ile Val Thr Ile
65                  70                  75                  80

Val Cys Arg Ile Leu Ser Leu Lys Arg Glu Asp Val Glu Leu Gly Phe
                85                  90                  95

Lys Phe Leu Gly Pro Val Glu Cys Glu Glu Gly Trp Gln Val Gly Leu
            100                 105                 110

Asn Ser Glu Met Ala Tyr Ile Arg Arg Thr Ser Pro Gln Val Arg Leu
        115                 120                 125

Ser Ile Tyr Ala Gln Glu Val Val His Asn Ser Thr Gly Ala Ile Leu
    130                 135                 140

Arg Val Thr His Pro Val Thr Val Arg Gln Arg Val Ser Pro His Arg
145                 150                 155                 160

Pro Ser Gln Tyr Thr Pro Gly Thr Met Lys Trp Gln Ile Asn Ile Ser
                165                 170                 175

Ser Ala His Ala Asp Leu Ser Thr Ala Gln Arg Ser His Glu Leu Arg
            180                 185                 190

Thr Gln Arg Phe Trp Ser Glu Pro Glu Arg Thr Trp Leu Ile Asn Pro
        195                 200                 205

Gln Glu Trp Ser Pro Phe Thr Phe Phe Leu Pro Pro Gly Leu Leu Pro
    210                 215                 220

Leu Ala Ile Leu Gly Asp Ser Asn Ile Met Leu Gly Met Gln Ser Thr
225                 230                 235                 240

Leu Leu Ile Ala Glu Leu Val Leu Ser Tyr Gln Thr His Ala Gln Ala
                245                 250                 255

Thr Val Ser Ala Ala His Arg His Leu Gln Trp Leu Thr Thr Asn Leu
            260                 265                 270
```

```
Val Gln Val Leu Asp Asp Asp Ser Leu Glu Asn Glu Ile Arg Glu Gln
        275                 280                 285

Leu Leu Ala Leu Leu Ala Arg Ala Glu Leu Ala Ser Lys Leu Pro Leu
    290                 295                 300

Asp Gly Ser Gln Asn Leu Ile Val Pro Arg Leu Glu Tyr Gly Gln Tyr
305                 310                 315                 320

Arg Gly Leu Ile Ser Ser Met Ala Ala Val Ala Glu Ala Tyr Asn Ser
                325                 330                 335

Glu Phe Thr Ala Val Asn Leu Phe Ile Gln Gln Asn Glu Ile Leu Gly
            340                 345                 350

Ser Tyr Leu Leu Gln Gln Asn Lys Ala Phe Ala Ala Arg Glu Lys Asp
        355                 360                 365

Met Glu Ala Phe His Gly Leu Val Val Glu Arg Lys Arg Gln Glu Leu
    370                 375                 380

Ser Ser Ala Gln Glu Thr Met Glu Glu Leu Asn Val Gln Leu Thr Gln
385                 390                 395                 400

Gln Thr Glu Ala Met Asp Gln Ala Lys Glu Asp Met Glu Ala Gly Leu
                405                 410                 415

Lys Lys Tyr Arg Asp Ala Gln Ala Ala Arg Ala Phe Phe Ala Val Met
            420                 425                 430

Lys Gly Val Leu Glu Ile Gly Ala Ala Ile Phe Thr Gly Gly Ala Thr
        435                 440                 445

Met Gly Leu Ala Val Gln Gly Gly Ile Asn Ala Val Lys Ala Val Ser
    450                 455                 460

Ser Leu Ala Gly Lys Leu Asp Met Val Leu Gln Ile Met Glu Gly Met
465                 470                 475                 480

Glu Lys Val Met Glu Val Leu Asn Ala Ile Asp Asp Leu Val Ala Ala
                485                 490                 495

Val Ser Glu Ile Asn Lys Met Val Glu Ala Pro Glu Met Pro Ser Met
            500                 505                 510

Pro Ser Thr His Glu Trp Asp Ile Phe Glu Asn Glu Ile Glu Glu Val
        515                 520                 525

Ala Glu Ser Met Pro Glu Glu Val Thr Glu Ala Arg Thr Trp Arg Thr
    530                 535                 540

Lys Cys Arg Asn Val Ala Ala Val Cys Arg Ala Ile Ser Thr Thr Ala
545                 550                 555                 560

Ser Tyr Ile Gly Gln Leu Gln Tyr Glu Leu Phe Val His Ser Asn Gln
                565                 570                 575

Glu Leu Ile Ala Arg Arg Gln Ala Glu Arg Leu Glu Ala Ile Gln Pro
            580                 585                 590

Ala Asp Leu Thr Asn Ser Leu Glu Met Ala Thr Gln Leu Asp Met Arg
        595                 600                 605

Thr Ser Arg Met Leu Leu Asn Leu Leu Lys Val Leu Thr Leu Gln Ser
    610                 615                 620

Gly Ala Leu Gln Phe His Phe Leu Leu Pro Pro Thr Pro Phe Thr Gly
625                 630                 635                 640

Trp Val Asn Met Gly Met Val Arg Asn Ala Leu Val Lys His Glu Ala
                645                 650                 655

Asp Ala Val Ala Ala Gln Glu Arg Leu Gly Pro Ser Thr Asp Tyr Val
            660                 665                 670

Arg Thr Tyr Val Met Ser Gly Ile Pro Val Ser Leu Leu Leu Asp Gly
        675                 680                 685
```

Asp Asp Trp Ile Phe Thr Ile Asn Pro Leu Asp Gly Ser Thr Phe Pro
    690                 695                 700

Leu Ser Trp Ser Arg Val Arg Ile Arg Tyr Leu Glu Met Lys Phe Thr
705                 710                 715                 720

Gly Gly Glu Glu Phe His Lys Pro Thr Thr Asp Ser Gly Lys Val Tyr
                725                 730                 735

Met Leu Leu Gln Ala Ser Arg Asn Phe Gln Asp Arg Leu Arg Arg Glu
            740                 745                 750

Val Leu His Tyr Glu Ala Ala Val Pro Leu Gln Tyr Gln Tyr Ala Tyr
        755                 760                 765

His Leu Thr Thr Gly Glu Thr Thr Val Glu Asn Arg Pro Ser Gln Gln
    770                 775                 780

His His Gly Glu Tyr Met Gln Met Thr Pro Phe Gly Gln Trp Arg Leu
785                 790                 795                 800

Arg Leu Ser Ala Ser Ala Phe Glu Asn Arg Asn Leu Ala Phe Pro Thr
                805                 810                 815

Ala Ala Asn Thr Asp Leu Asp Ala Ala Thr Thr Gln Ile Ser Ile Thr
            820                 825                 830

Phe Phe Val Thr Ala Val Arg Ala Val Asp Phe Arg Ser Leu Asp Asp
        835                 840                 845

Gln Asp Met
    850

<210> SEQ ID NO 115
<211> LENGTH: 899
<212> TYPE: PRT
<213> ORGANISM: Blechnum brasiliense 'Crispum'

<400> SEQUENCE: 115

Met Gln Gly Arg Leu Ala Ser Met Ala Gly Ser Ala Gly Ala Ala Asp
1               5                   10                  15

Ala Trp Arg Glu Val Tyr Arg Asp Leu Asn Gln Val Ser Asp Arg Ile
            20                  25                  30

Arg Leu Asp Gln Leu Glu Phe Ser Glu Val Met Val Ile His Arg Met
        35                  40                  45

His Ile Lys Met Ser Glu Leu Asp Leu Gly His Leu Glu Gly Ala Glu
    50                  55                  60

Lys Val Glu Arg Leu Tyr Val Phe Ala Asp Val Val Glu Leu Asp Val
65                  70                  75                  80

Val Pro His Glu Ser Ser Ser Asp Gly Asp Val Val Val Arg Leu Pro
                85                  90                  95

Gly Ser Lys Ser Val Thr Phe Val Cys Arg Val Trp His Ile Asn Tyr
            100                 105                 110

Ala Leu Val Gln Ile Ser Ser Phe Ala Arg Ile Ser Arg Ser Val Val
        115                 120                 125

Leu Glu Leu Arg His Met Arg Trp His Phe Asn Ala Ile Thr Gly Arg
    130                 135                 140

Met His Leu Leu Asp Pro Gln Thr Leu Gln Asp Gly Met Asp Leu Cys
145                 150                 155                 160

Phe Cys Val His Ala Glu Val Val Gln Ile Ala Tyr Tyr Pro Asp Val
                165                 170                 175

Thr Phe Pro Glu Ser Asn Asp Ser Pro Ser Phe Leu Arg Phe Leu Arg
            180                 185                 190

Leu Glu Ile Val Pro Asp Gln Leu Arg Val Thr Thr Gln Thr Asp Gly
        195                 200                 205

```
Pro Val Trp Ala Leu Arg Gly Ala Leu Glu Tyr Phe Met Ala Pro Asp
    210                 215                 220

Asn Asp Gly Leu Leu Asn Glu Val Ser Ser Gln Pro Ala Gly Thr Ser
225                 230                 235                 240

Phe Val Leu Asn Ile Leu Pro Asp Asn Leu Asp Val Gln Leu Phe Ala
                245                 250                 255

Asn Leu Arg Pro Asn Ser Gly Thr Thr Leu Thr Arg Asp Pro Asn Thr
            260                 265                 270

Ile Val Pro Ala Phe Ser Val Tyr Lys Glu Lys Glu Gly Glu Leu Leu
        275                 280                 285

Ser Asp Pro Asn Ile Leu Pro Ala Met Gln Thr Ser Met Leu Ile Gly
    290                 295                 300

Glu Leu Val Glu Val Gly Gln Pro Pro Ser Val Thr Thr Glu Val Val
305                 310                 315                 320

Arg Lys His Val Glu Trp Leu Asn Asn Leu Leu Leu Gln Val Ile Glu
                325                 330                 335

Ala Lys Arg Gly Glu His Val Glu Asp Tyr Val Glu Leu Ser Phe Arg
            340                 345                 350

Ala Gln Tyr Val Ile Lys Lys Val Gly Arg Ile Gln Arg Leu Val Val
        355                 360                 365

Pro Gln Leu Gln Tyr Ser Ala Tyr Ser Asn Leu Ile Asn Arg Leu Ala
    370                 375                 380

Gln Val Ala Glu Ser Tyr Asp Gln Ala Leu Arg Gln Phe Arg Leu Phe
385                 390                 395                 400

Ile Gln Gln Asn Lys Ile Leu Gly Gly Phe Leu Leu Glu Gln Asn Arg
                405                 410                 415

Ala Phe Ala Glu Lys Glu Gln Asp Met Asp Val Phe Tyr Ser Glu Leu
            420                 425                 430

Ile Ala Gln Arg Gln Ile Glu Leu Asp Asn Thr Leu Gln Lys Met Lys
        435                 440                 445

His Leu Gly Ala Gln Met Glu Thr Gln Thr Ala Asp Met Glu Gln Ala
    450                 455                 460

Gln Ala Asp Met Glu Ala Gly Ile Arg Glu Phe Gln Asn Arg Gln Val
465                 470                 475                 480

Ala Arg Gly Leu Phe Ala Val Leu Gly Ala Ile Ala Ala Val Gly Leu
                485                 490                 495

Thr Leu Leu Thr Gly Gly Ala Ala Ala Pro Leu Ala Met Ser Ala Ala
            500                 505                 510

Arg Ser Ala Val Ser Leu Ala Gly Ala Val Ala Gln Gly Leu Gln Arg
        515                 520                 525

Val Leu Asp Ile Leu Glu Gly Leu Gln Val Val Met Glu Val Val Glu
    530                 535                 540

Leu Ile Asn Asp Leu Ile Ser Ser Leu Gln Glu Leu Gly Gln Pro Val
545                 550                 555                 560

Glu Leu Pro Glu Met Ala Glu Met Pro Thr Glu Ala Asp Trp Leu Ile
                565                 570                 575

Phe Val Asn Glu Val Glu Gly Val Ala Glu Gln Met Pro Thr Glu Val
            580                 585                 590

Ser Glu Val Val Ala Trp Lys Thr Lys Cys Lys Asn Val Ala Val Leu
        595                 600                 605

Gly Arg Glu Met Thr Thr Leu Ala Ala Tyr Ile Ser Gln Leu Gln Tyr
    610                 615                 620
```

-continued

| | | | | | | | | | | | | | | | |
|---|---|---|---|---|---|---|---|---|---|---|---|---|---|---|---|
| Asp | Ile | Asn | Met | Gln | His | Met | Leu | Gln | Gln | Ile | Ala | Arg | Lys | Gln | Ala |
| 625 | | | | | 630 | | | | | 635 | | | | | 640 |
| Asp | Arg | Leu | Ser | Ala | Ile | Glu | Leu | Pro | Asp | Leu | Arg | Asn | Tyr | Gly | Glu |
| | | | | 645 | | | | | 650 | | | | | 655 | |
| Leu | Val | Thr | Gln | Met | Asp | Met | Arg | Thr | Thr | Arg | Leu | Leu | Val | Ala | Leu |
| | | | 660 | | | | | 665 | | | | | 670 | | |
| Ile | Lys | Val | Val | Asn | Ile | Gln | Asn | Ala | Ala | Leu | Met | Tyr | Gln | Tyr | Leu |
| | | 675 | | | | | 680 | | | | | 685 | | | |
| Ser | Glu | Pro | Thr | Pro | Val | Tyr | Ala | Trp | Pro | Val | Asn | Met | Asp | Ser | Val |
| | 690 | | | | | 695 | | | | | 700 | | | | |
| Trp | Arg | Met | Leu | Val | Gln | His | Glu | Gln | Phe | Ala | Ile | Gln | Gly | Leu | Met |
| 705 | | | | | 710 | | | | | 715 | | | | | 720 |
| Arg | Leu | Gly | Pro | Ala | Phe | Asp | Ile | Val | Arg | Thr | Tyr | Glu | Val | Lys | Gly |
| | | | | 725 | | | | | 730 | | | | | 735 | |
| Ile | Pro | Val | Ser | Leu | Leu | Leu | Asp | Gly | Asp | Asp | Tyr | Glu | Phe | Glu | Ile |
| | | | 740 | | | | | 745 | | | | | 750 | | |
| Pro | Ala | Gln | Asp | His | Val | Thr | Phe | Pro | Leu | Ser | Leu | Ser | Arg | Val | Arg |
| | | 755 | | | | | 760 | | | | | 765 | | | |
| Ile | His | His | Leu | Glu | Met | Lys | Phe | Val | Gln | Gly | Glu | Gly | Asp | Gln | Leu |
| | 770 | | | | | 775 | | | | | 780 | | | | |
| His | Met | Pro | Val | Thr | Asp | Thr | Gly | Ser | Val | Tyr | Ile | Leu | Leu | Gln | Gly |
| 785 | | | | | 790 | | | | | 795 | | | | | 800 |
| Ser | Arg | Asn | Phe | His | Asp | Arg | Ser | Glu | Gly | Thr | Ile | Leu | His | Tyr | Glu |
| | | | | 805 | | | | | 810 | | | | | 815 | |
| Ala | Ala | Thr | Ser | Leu | Asp | Tyr | His | Phe | Ala | Tyr | Arg | Leu | Asp | Thr | Gly |
| | | | 820 | | | | | 825 | | | | | 830 | | |
| Glu | Thr | Thr | Val | Thr | Asn | Leu | Pro | Ser | Ala | Glu | Phe | Leu | Arg | Thr | Phe |
| | | 835 | | | | | 840 | | | | | 845 | | | |
| Met | Arg | Met | Thr | Pro | Phe | Thr | Asn | Trp | Arg | Leu | Arg | Val | Ser | Ala | Ser |
| | 850 | | | | | 855 | | | | | 860 | | | | |
| Ala | Glu | Glu | Asn | Lys | Gly | Leu | Ala | Phe | Pro | Thr | Ala | Thr | Ser | Ala | Asp |
| 865 | | | | | 870 | | | | | 875 | | | | | 880 |
| Ala | Thr | Thr | His | Ile | Ala | Ile | Thr | Phe | Phe | Ile | Ser | Ala | Ile | Arg | Gln |
| | | | | 885 | | | | | 890 | | | | | 895 | |
| Ile | Ala | Leu | | | | | | | | | | | | | |